(12) United States Patent
Okuno et al.

(10) Patent No.: US 9,139,518 B2
(45) Date of Patent: *Sep. 22, 2015

(54) AMINE DERIVATIVE HAVING NPY Y5 RECEPTOR ANTAGONISTIC ACTIVITY

(75) Inventors: Takayuki Okuno, Osaka (JP); Naoki Kouyama, Osaka (JP); Masahiro Sakagami, Sapporo (JP)

(73) Assignee: SHIONOGI & CO., LTD., Osaka-shi (JP)

( * ) Notice: Subject to any disclaimer, the term of this patent is extended or adjusted under 35 U.S.C. 154(b) by 648 days.

This patent is subject to a terminal disclaimer.

(21) Appl. No.: 12/823,568

(22) Filed: Jun. 25, 2010

(65) Prior Publication Data
US 2010/0267945 A1 Oct. 21, 2010

Related U.S. Application Data

(62) Division of application No. 12/226,516, filed as application No. PCT/JP2007/058938 on Apr. 25, 2007.

(30) Foreign Application Priority Data

| Apr. 28, 2006 | (JP) | 2006-124762 |
| Aug. 11, 2006 | (JP) | 2006-219606 |
| Feb. 26, 2007 | (JP) | 2007-045587 |

(51) Int. Cl.
C07C 311/05 (2006.01)
C07C 311/07 (2006.01)
(Continued)

(52) U.S. Cl.
CPC ............ *C07C 311/05* (2013.01); *C07C 311/07* (2013.01); *C07C 311/08* (2013.01); *C07C 311/20* (2013.01); *C07C 311/21* (2013.01); *C07C 311/37* (2013.01); *C07C 311/39* (2013.01); *C07C 311/43* (2013.01); *C07C 317/36* (2013.01); *C07D 207/27* (2013.01); *C07D 207/325* (2013.01); *C07D 211/14* (2013.01); *C07D 213/38* (2013.01); *C07D 213/74* (2013.01); *C07D 213/82* (2013.01); *C07D 215/38* (2013.01); *C07D 217/04* (2013.01); *C07D 217/14* (2013.01); *C07D 217/22* (2013.01); *C07D 219/10* (2013.01); *C07D 231/38* (2013.01); *C07D 233/58* (2013.01); *C07D 233/61* (2013.01); *C07D 235/30* (2013.01); *C07D 237/20* (2013.01); *C07D 237/22* (2013.01); *C07D 237/34* (2013.01); *C07D 239/42* (2013.01); *C07D 241/20* (2013.01); *C07D 261/14* (2013.01); *C07D 261/20* (2013.01); *C07D 263/58* (2013.01); *C07D 265/30* (2013.01); *C07D 265/36* (2013.01); *C07D 267/14* (2013.01); *C07D 275/02* (2013.01); *C07D 277/28* (2013.01); *C07D 277/62* (2013.01); *C07D 277/82* (2013.01); *C07D 295/12* (2013.01);
(Continued)

(58) Field of Classification Search
CPC ....................................................... C07C 311/05
See application file for complete search history.

(56) References Cited

U.S. PATENT DOCUMENTS

2006/0025433 A1* 2/2006 Barbosa et al. ................ 514/269
2006/0040965 A1* 2/2006 Farthing et al. ............. 514/265.1
(Continued)

FOREIGN PATENT DOCUMENTS

| EP | 1 249 233 | 10/2002 |
| EP | 1 719 765 | 11/2006 |

(Continued)

OTHER PUBLICATIONS

Vippagunta et al 'Crystalline Solids' Advanced Drug Delivery Reviews, vol. 48, p. 3-26, 2001.*
(Continued)

*Primary Examiner* — Paul Zarek
(74) *Attorney, Agent, or Firm* — Oblon, McClelland, Maier & Neustadt, L.L.P.

(57) ABSTRACT

A compound of the formula (I):

[Formula 14]

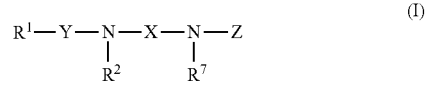

a pharmaceutically acceptable salt or solvate thereof, where $R^1$ is optionally substituted lower alkyl, Y is —S(O)$_2$—, $R^2$ is hydrogen or optionally substituted lower alkyl, $R^7$ is hydrogen or optionally substituted lower alkyl, X is a group of the formula:

[Formula 15]

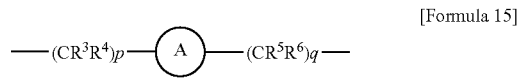

where $R^5$ and $R^6$ are each independently hydrogen, a group of the formula:

[Formula 16]

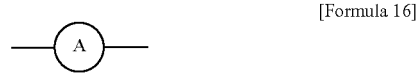

is optionally substituted cycloalkylene, p is 0, and q is 1 or 2, Z is optionally substituted carbocyclyl or optionally substituted heterocyclyl, and provided that a compound wherein Z is fused heterocyclyl consisting of three rings or optionally substituted pyrimidinyl is excluded.

12 Claims, No Drawings

(51) Int. Cl.

| | |
|---|---|
| *C07C 311/08* | (2006.01) |
| *C07C 311/20* | (2006.01) |
| *C07C 311/21* | (2006.01) |
| *C07C 311/37* | (2006.01) |
| *C07C 311/39* | (2006.01) |
| *C07C 311/43* | (2006.01) |
| *C07C 317/36* | (2006.01) |
| *C07D 207/27* | (2006.01) |
| *C07D 207/325* | (2006.01) |
| *C07D 211/14* | (2006.01) |
| *C07D 213/38* | (2006.01) |
| *C07D 213/74* | (2006.01) |
| *C07D 213/82* | (2006.01) |
| *C07D 215/38* | (2006.01) |
| *C07D 217/04* | (2006.01) |
| *C07D 217/14* | (2006.01) |
| *C07D 217/22* | (2006.01) |
| *C07D 219/10* | (2006.01) |
| *C07D 231/38* | (2006.01) |
| *C07D 233/58* | (2006.01) |
| *C07D 233/61* | (2006.01) |
| *C07D 235/30* | (2006.01) |
| *C07D 237/20* | (2006.01) |
| *C07D 237/22* | (2006.01) |
| *C07D 237/34* | (2006.01) |
| *C07D 239/42* | (2006.01) |
| *C07D 241/20* | (2006.01) |
| *C07D 261/14* | (2006.01) |
| *C07D 261/20* | (2006.01) |
| *C07D 263/58* | (2006.01) |
| *C07D 265/30* | (2006.01) |
| *C07D 265/36* | (2006.01) |
| *C07D 267/14* | (2006.01) |
| *C07D 275/02* | (2006.01) |
| *C07D 277/28* | (2006.01) |
| *C07D 277/62* | (2006.01) |
| *C07D 277/82* | (2006.01) |
| *C07D 295/12* | (2006.01) |
| *C07D 295/135* | (2006.01) |
| *C07D 295/18* | (2006.01) |
| *C07D 333/36* | (2006.01) |
| *C07D 333/40* | (2006.01) |
| *C07D 333/66* | (2006.01) |
| *C07D 333/72* | (2006.01) |
| *C07D 403/04* | (2006.01) |
| *C07D 409/04* | (2006.01) |
| *C07D 413/04* | (2006.01) |
| *C07D 417/12* | (2006.01) |
| *C07D 498/04* | (2006.01) |
| *C07D 513/04* | (2006.01) |

(52) U.S. Cl.
CPC .......... *C07D 295/135* (2013.01); *C07D 295/18* (2013.01); *C07D 333/36* (2013.01); *C07D 333/40* (2013.01); *C07D 333/66* (2013.01); *C07D 333/72* (2013.01); *C07D 403/04* (2013.01); *C07D 409/04* (2013.01); *C07D 413/04* (2013.01); *C07D 417/12* (2013.01); *C07D 498/04* (2013.01); *C07D 513/04* (2013.01); *C07C 2101/02* (2013.01); *C07C 2101/04* (2013.01); *C07C 2101/08* (2013.01); *C07C 2101/14* (2013.01); *C07C 2102/08* (2013.01); *C07C 2102/10* (2013.01); *C07C 2103/18* (2013.01)

(56) References Cited

U.S. PATENT DOCUMENTS

| | | |
|---|---|---|
| 2006/0258728 A1 | 11/2006 | Tani et al. |
| 2006/0293341 A1 | 12/2006 | Jubian et al. |
| 2007/0060598 A1 | 3/2007 | Albers et al. |
| 2007/0099938 A1 | 5/2007 | Ohmoto et al. |
| 2007/0213376 A1* | 9/2007 | Jubian et al. ............ 514/342 |
| 2008/0221082 A1 | 9/2008 | Geneste et al. |
| 2009/0203712 A1 | 8/2009 | Yano |
| 2010/0004295 A1 | 1/2010 | Kouyama |

FOREIGN PATENT DOCUMENTS

| | | | |
|---|---|---|---|
| EP | 1 736 467 | 12/2006 | |
| EP | 1 760 073 | 3/2007 | |
| EP | 1 787 657 A1 | 5/2007 | |
| JP | 2006-124387 | 5/2006 | |
| WO | WO 94/22835 | 10/1994 | |
| WO | WO 96/16542 | 6/1996 | |
| WO | WO 97/20823 | 6/1997 | |
| WO | WO 99/55667 | 11/1999 | |
| WO | WO 99/67203 | 12/1999 | |
| WO | WO 00/61562 | 10/2000 | |
| WO | WO 00/64880 | 11/2000 | |
| WO | WO 00/68197 | 11/2000 | |
| WO | WO 01/02379 | 1/2001 | |
| WO | WO 2004/103998 A1 * | 12/2004 | ............ C07D 417/12 |
| WO | WO 2005/121107 | 12/2005 | |
| WO | WO 2006/014482 | 2/2006 | |
| WO | WO 2007/002126 | 1/2007 | |
| WO | WO 2007/103295 A2 | 9/2007 | |
| WO | WO 2008/134228 A1 | 11/2008 | |
| WO | WO 2009/054434 A1 | 4/2009 | |

OTHER PUBLICATIONS

King, F.D. (Ed.), "Bioisosteres, conformational restriction and pro-drugs-case history: an example of a conformational restriction approach," Medical Chemistry: Principles and Practice, 1994, Chapter 14, 206-209.*

Yutaka Takebe et al., "SRα Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, vol. 8, No. 1, Jan. 1988, pp. 466-472.

Sumit Deswal et al., "A novel range based QSAR study of human neuropeptide Y (NPY) Y5 receptor inhibitors", European Journal of Medical Chemistry, vol. 42, 2007, pp. 463-470.

Lars Grundemar et al., "Neuropeptide Y effector systems: perspectives for drug development", Trends in Pharmacological Sciences, vol. 15, 1994, pp. 153-159.

Catalina Betancur et al., "Nonpeptide antagonists of neuropeptide receptors: tools for research and therapy", Trends in Pharmacological Sciences, vol. 18, 1997, pp. 372-386.

Ambikaipakan Balasubramaniam, "Neuropeptide Y Family of Hormones: Receptor Subtypes and Antagonists", Peptides, vol. 18, No. 3, 1997, pp. 445-457.

Akio Inui et al., "Evidence for Further Heterogeneity of the Receptors for Neuropeptide-Y and Peptide-YY in Tumor Cell Lines Derived from Neural Crest", Endocrinology, vol. 131, No. 5, 1992, pp. 2090-2096.

U.S. Appl. No. 12/767,641, filed Apr. 26, 2010, Okuno et al.
U.S. Appl. No. 12/766,458, filed Apr. 23, 2010, Okuno, et al.
U.S. Appl. No. 12/936,693, filed Oct. 7, 2010, Sakagami, et al.
U.S. Appl. No. 13/354,881, filed Jan. 20, 2012, Sakagami, et al.
U.S. Appl. No. 13/254,750, filed Sep. 2, 2011, Sakagami, et al.
U.S. Appl. No. 13/254,702, filed Sep. 2, 2011, Yoshida, et al.

* cited by examiner

AMINE DERIVATIVE HAVING NPY Y5 RECEPTOR ANTAGONISTIC ACTIVITY

CROSS-REFERENCE TO RELATED APPLICATIONS

This application is a divisional of and claims benefit of priority from U.S. application Ser. No. 12/226,516, filed Oct. 21, 2008, the entire contents of which are hereby incorporated by reference. U.S. application Ser. No. 12/226,516 is a national stage of International Application No. PCT/JP2007/058938, filed Apr. 25, 2007, which claims the benefit of priority from Japanese Patent Application Nos. 2006-124762, filed Apr. 28, 2006, 2006-219606, filed Aug. 11, 2006 and 2007-045587, filed Feb. 26, 2007.

FIELD OF THE INVENTION

This invention relates to a new compound having NPY Y5 receptor antagonistic activity. The compound is useful as a pharmaceutical composition, especially an anti-obesity agent.

BACKGROUND ART

Neuropeptide Y (hereinafter referred to as NPY) is a peptide which consists of 36 amino acid residues and was isolated from porcine brain in 1982. NPY is widely distributed in the central nervous system and peripheral tissues of humans and animals.

It has been reported that NPY possesses a stimulating activity of food intake, an anti-seizure activity, a learning-promoting activity, an anti-anxiety activity, an anti-stress activity etc. in central nervous system, and it may be pivotally involved in the central nervous system diseases such as depression, Alzheimer's disease and Parkinson's disease. NPY is thought to be associated with the cardiovascular diseases, since it induces a contraction of smooth muscles such as blood vessels or cardiac muscles in the peripheral tissues. Furthermore, NPY is also known to be involved in the metabolic diseases such as obesity, diabetes and hormone abnormalities (Non-patent Document 1). Therefore, an NPY receptor antagonist is expected as a medicine for preventing or treating various diseases involved in the NPY receptor like the above.

Subtypes of Y1, Y2, Y3, Y4, Y5, and Y6 have now been identified as the NPY receptor (Non-patent Document 2). It has been suggested that the Y5 receptor is at least involved in the feeding behavior and its antagonist is expected as an anti-obesity agent (Non-patent Document 3).

Amine derivatives having sulfonyl group and similar structures to compounds of the present invention and exhibiting NPY Y5 receptor antagonistic activity are disclosed in Patent Document 1, 2, 3, 4 and the like. Amide derivatives having sulfonyl group and exhibiting NPY Y5 receptor antagonistic activity are disclosed in Patent Document 5, 8, 9, 10 and 11. Derivatives having sulfonyl group and exhibiting NPY Y5 receptor antagonistic activity are disclosed in Patent Document 12. The structures of these compounds are different from those of the compounds of the present invention.

Furthermore, although compounds having similar structures to compounds of the present invention are disclosed in Patent Document 6, 7, 13, 14 and the like, the activities of their compounds are quite different from those of the compounds of the present invention and these documents do not suggest the present invention.

[Non-patent Document 1] Tends in Pharmacological Sciences, Vol. 15, 153 (1994)
[Non-patent Document 2] Trends in Pharmacological Sciences, Vol. 18, 372 (1997)
[Non-patent Document 3] Peptides, Vol. 18, 445 (1997)
[Patent Document 1] WO01/002379
[Patent Document 2] WO00/064880
[Patent Document 3] WO99/055667
[Patent Document 4] WO00/068107
[Patent Document 5] WO01/037826
[Patent Document 6] WO2006/014482
[Patent Document 7] WO2005/097738
[Patent Document 8] WO97/20823
[Patent Document 9] US2006/293341
[Patent Document 10] WO2007/002126
[Patent Document 11] WO2006/001318
[Patent Document 12] WO2005/080348
[Patent Document 13] US2007/060598
[Patent Document 14] WO2005/121107

DISCLOSURE OF INVENTION

Problems to be Solved by the Invention

The object of the present invention is to provide excellent new compounds having NPY Y5 receptor antagonistic activity. In our examination, compounds in Patent Document 1 or 2 showed the strong induction of a drug-metabolizing enzyme and some compounds in Patent Document 10 showed toxicity such as anemia induction.

Means for Solving the Problem

The present inventors have intensively studied to synthesize the following excellent new compounds having NPY Y5 receptor antagonistic activity. Patent Document 5 disclosed that amide derivatives having sulfonyl group are compounds having NPY Y5 receptor antagonistic activity. However, the present inventors found that transportability of compounds which the amide is substituted with the amine through the blood-brain barrier is much higher than that of the unsubstituted compounds. Furthermore, the inventors found that compounds of the present invention have less the induction of a drug-metabolizing enzyme compared to compounds described in Patent Document 1 or 2 to achieve the present invention.

The present invention includes the followings.
(1) A compound of the formula (I):

[Formula 1]

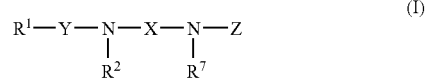

(I)

a pharmaceutically acceptable salt or solvate thereof,
wherein
$R^1$ is optionally substituted lower alkyl,
Y is —S(O)$_n$— wherein n is 1 or 2, or —CO—,
$R^2$ is hydrogen or optionally substituted lower alkyl,
$R^1$ and $R^2$ taken together may form lower alkylene,
$R^7$ is hydrogen or optionally substituted lower alkyl,
X is optionally substituted lower alkylene,
optionally substituted lower alkenylene,
optionally substituted —CO-lower alkylene,
optionally substituted —CO-lower alkenylene or a group of the formula:

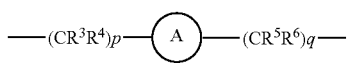
[Formula 2]

wherein $R^3$, $R^4$, $R^5$ and $R^6$ are each independently hydrogen or optionally substituted lower alkyl,
a group of the formula:

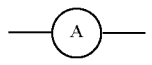
[Formula 3]

is optionally substituted cycloalkylene, optionally substituted cycloalkenylene, optionally substituted bicycloalkylene, optionally substituted arylene or optionally substituted heterocyclyldiyl,
p and q are each independently an integer between 0 and 2, either p or q is not 0, and provided that a group of the formula:

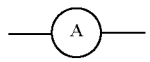
[Formula 4]

is not a group of the formula:

[Formula 5]

wherein $R^{14}$ is optionally substituted phenyl,
—$NR^2$—X— may be a group of the formula:

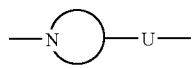
[Formula 6]

wherein a group of the formula:

[Formula 7]

is piperidinediyl, piperazinediyl, pyridinediyl, pyrazinediyl, pyrrolidinediyl or pyrrolediyl, and U is lower alkylene or lower alkenylene,
Z is optionally substituted lower alkyl, optionally substituted lower alkenyl, optionally substituted amino, optionally substituted lower alkoxy, optionally substituted carbocyclyl or optionally substituted heterocyclyl,
provided that Z is not fused heterocyclyl consisting of three rings, optionally substituted thiazolyl or optionally substituted quinazolinyl, and provided that a compound wherein X is a group of the formula:

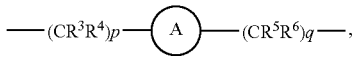
[Formula 8]

wherein a group of the formula:

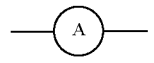
[Formula 9]

is optionally substituted cycloalkylene, p is 0, q is 1 and Z is optionally substituted pyrimidinyl is excluded.
(2) The compound, pharmaceutically acceptable salt or solvate thereof of (1), wherein $R^1$ is lower alkyl.
(3) The compound, pharmaceutically acceptable salt or solvate thereof of (1), wherein Y is —$S(O)_2$—.
(4) The compound, pharmaceutically acceptable salt or solvate thereof of (1), wherein Z is optionally substituted carbocyclyl or optionally substituted heterocyclyl.
(5) The compound, pharmaceutically acceptable salt or solvate thereof of (1),
wherein X is a group of the formula:

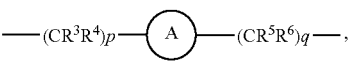
[Formula 10]

and
$R^1$ is optionally substituted C2 to C10 alkyl.
(6) The compound, pharmaceutically acceptable salt or solvate thereof of (5), wherein Z is optionally substituted heterocyclyl.
(7) The compound, pharmaceutically acceptable salt or solvate thereof of (5), wherein a group of the formula:

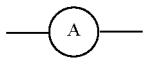
[Formula 11]

is optionally substituted cycloalkylene, optionally substituted cycloalkenylene, optionally substituted bicycloalkylene or optionally substituted piperidinylene.
(8) The compound, pharmaceutically acceptable salt or solvate thereof of (5),
wherein a group of the formula:

[Formula 12]

is optionally substituted cyclohexylene or optionally substituted piperidinylene, p and q are each independently 0 or 1, either p or q is not 0.
(9) The compound, pharmaceutically acceptable salt or solvate thereof of (7) or (8), wherein Z is optionally substituted lower alkyl, optionally substituted phenyl, optionally substituted pyridyl, optionally substituted pyrazolyl, optionally substituted isoxazolyl, optionally substituted oxadiazolyl, optionally substituted pyridazinyl, optionally substituted pyrazinyl, optionally substituted pyrimidinyl or optionally substituted fused heterocyclyl consisting of two rings.

(10) The compound, pharmaceutically acceptable salt or solvate thereof of (1),
wherein X is a group of the formula:

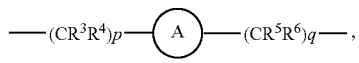
[Formula 13]

and
p+q is 1 or 2.

(11) The compound, pharmaceutically acceptable salt or solvate thereof of (10), wherein p+q is 1.

(12) A compound of the formula (I):

[Formula 14]

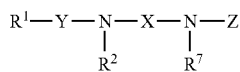
(I)

a pharmaceutically acceptable salt or solvate thereof,
wherein
$R^1$ is optionally substituted lower alkyl,
Y is $-S(O)_2-$,
$R^2$ is hydrogen or optionally substituted lower alkyl,
$R^7$ is hydrogen or optionally substituted lower alkyl,
X is a group of the formula:

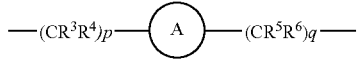
[Formula 15]

wherein $R^5$ and $R^6$ are each independently hydrogen,
a group of the formula:

[Formula 16]

is optionally substituted cycloalkylene,
p is 0, and
q is 1 or 2,
Z is optionally substituted carbocyclyl or optionally substituted heterocyclyl, and provided that a compound wherein Z is fused heterocyclyl consisting of three rings or optionally substituted pyrimidinyl is excluded.

(13) The compound, pharmaceutically acceptable salt or solvate thereof of (12), wherein Z is optionally substituted phenyl, optionally substituted indanyl, optionally substituted pyridyl, optionally substituted pyridazinyl, optionally substituted pyrimidinyl, optionally substituted pyrazolyl, optionally substituted isoxazolyl, optionally substituted oxadiazolyl or optionally substituted fused heterocyclyl consisting of two rings.

(14) The compound, pharmaceutically acceptable salt or solvate thereof of (12), wherein Z is optionally substituted isoquinolyl, optionally substituted benzothiazolyl, optionally substituted benzoxazolyl, optionally substituted benzopyridazinyl, optionally substituted benzopyridadiyl, optionally substituted benzimidazolyl, optionally substituted thiazolopyridyl, optionally substituted benzisoxazolinonyl, optionally substituted benzoxazolinonyl, optionally substituted benzoxadinonyl or optionally substituted benzoxyazepinonyl.

(15) A compound of the formula (I):

[Formula 17]

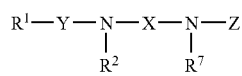
(I)

a pharmaceutically acceptable salt or solvate thereof,
wherein
$R^1$ is optionally substituted lower alkyl,
Y is $-S(O)_2-$,
$R^2$ is hydrogen or optionally substituted lower alkyl,
$R^7$ is hydrogen or optionally substituted lower alkyl,
X is a group of the formula:

[Formula 18]

wherein $R^3$ and $R^4$ are each independently hydrogen,
a group of the formula:

[Formula 19]

is optionally substituted cycloalkylene,
p is 1 or 2, and
q is 0,
provided that

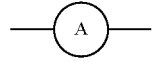
[Formula 20]

is not

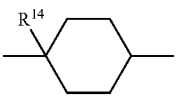
[Formula 21]

wherein $R^{14}$ is optionally substituted phenyl,
Z is optionally substituted carbocyclyl or optionally substituted heterocyclyl, and provided that a compound wherein Z is fused heterocyclyl consisting of three rings, optionally substituted thiazolyl or optionally substituted quinazolinyl is excluded.

(16) The compound, pharmaceutically acceptable salt or solvate thereof of (15), wherein Z is optionally substituted phenyl, optionally substituted pyridyl, optionally substituted pyridazinyl, optionally substituted pyrazinyl, optionally substituted pyrimidinyl, optionally substituted quinolyl, optionally substituted isoquinolyl, optionally substituted benzothiazolyl, optionally substituted benzimidazolyl, optionally substituted benzoxazolyl, optionally substituted thiazolopyridyl or optionally substituted oxazolopyridyl.

(17) A compound of the formula (I):

[Formula 22]

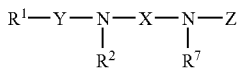

a pharmaceutically acceptable salt or solvate thereof, wherein $R^1$ is optionally substituted lower alkyl, Y is —S(O)$_2$—, $R^2$ is hydrogen or optionally substituted lower alkyl, $R^7$ is hydrogen or optionally substituted lower alkyl, X is a group of the formula:

[Formula 23]

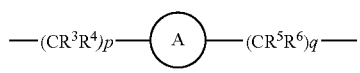

wherein $R^3$ and $R^4$ are each independently hydrogen, a group of the formula:

[Formula 24]

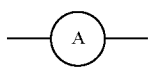

is optionally substituted cycloalkylene, p is 1 or 2, and q is 0, and

Z is optionally substituted phenyl, optionally substituted pyridyl, optionally substituted pyridazinyl, optionally substituted pyrazinyl, optionally substituted pyrimidinyl, optionally substituted quinolyl, optionally substituted isoquinolyl, optionally substituted benzothiazolyl, optionally substituted benzimidazolyl, optionally substituted benzoxazolyl, optionally substituted thiazolopyridyl or optionally substituted oxazolopyridyl.

(18) A pharmaceutical composition comprising the compound, pharmaceutically acceptable salt or solvate thereof of any one of (1) to (17) as an active ingredient.

(19) A NPY Y5 receptor antagonist comprising the compound, pharmaceutically acceptable salt or solvate thereof of any one of (1) to (17) as an active ingredient.

(20) A compound of the formula:

[Formula 25]

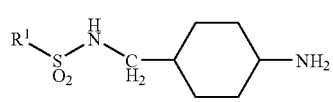

a salt or solvate thereof, wherein $R^1$ is ethyl or tert-butyl.

(21) A compound of the formula:

[Formula 26]

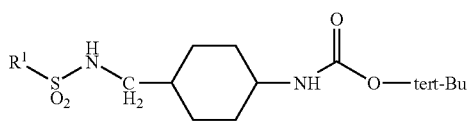

a salt or solvate thereof, wherein $R^1$ is ethyl, isopropyl or tert-butyl.

(22) A compound of the formula:

[Formula 27]

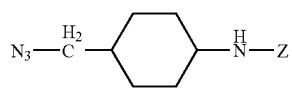

a salt or solvate thereof, wherein Z is optionally substituted carbocyclyl or optionally substituted heterocyclyl.

(23) A compound of the formula:

[Formula 28]

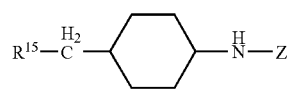

a salt or solvate thereof, wherein $R^{15}$ is NH$_2$ or OH, and

Z is optionally substituted pyridyl, optionally substituted pyridazinyl, optionally substituted pyrazinyl, optionally substituted pyrimidinyl, optionally substituted quinolyl, optionally substituted isoquinolyl, optionally substituted benzothiazolyl, optionally substituted benzoxazolyl, optionally substituted benzopyridyl, optionally substituted benzopyridazinyl, optionally substituted benzimidazolyl, optionally substituted benzoxazolyl, optionally substituted thiazolopyridyl optionally substituted benzisoxazolinonyl, optionally substituted benzoxazolinonyl, optionally substituted benzoxadinonyl or optionally substituted benzoxyazepinonyl.

Effect of the Invention

A compound of the present invention exhibits NPY Y5 receptor antagonistic activity and are very useful as a medicine especially for preventing and/or treating feeding disorder, obesity, hyperorexia, sexual disorder, impaired fertility, depression, epileptic seizure, hypertension, cerebral hemorrhage, congestive heart failure or sleep disorders.

BEST MODE FOR CARRYING OUT THE INVENTION

Each term used in this description is explained below. The each term has the same meaning in this description both when it is used alone each term and when it is used with the other term.

The term "halogen" includes fluorine, chlorine, bromine and iodine. Especially, fluorine or chlorine is preferable.

The term "protective group" in "optionally protected hydroxyl" and "optionally protected hydroxy lower alkyl" includes all of hydroxy protecting groups usually used. For example, acyl such as acetyl, trichloroacetyl and benzoyl, lower alkoxycarbonyl such as t-butoxycarbonyl, lower alkylsulfonyl such as methane sulfonyl, lower alkoxy(lower)alkyl such as methoxymethyl and trialkylsilyl such as t-butyldimethylsilyl are included.

The term "lower alkyl" includes C1 to C10 straight or branched alkyl. Examples are methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.

"Lower alkyl" represented by $R^1$ is preferably C2 to C10, more preferably C2 to C6 alkyl and most preferably ethyl, isopropyl or t-butyl.

"Lower alkyl" in other cases is preferably C1 to C6 and more preferably C1 to C4 alkyl.

The examples of substituents of "optionally substituted lower alkyl" represented by Z are, (1) halogen; (2) cyano;
(3) the following groups (i) to (xvi), which are optionally substituted with one or more substituents selected from "a substituents group β" defined below,
(i) hydroxy, (ii) lower alkoxy, mercapto, (iv) lower alkylthio, (v) acyl, (vi) acyloxy, (vii) carboxy, (viii) lower alkoxycarbonyl, (ix) imino, (x) carbamoyl, (xi) thiocarbamoyl, (xii) lower alkylcarbamoyl, (xiii) lower alkylthiocarbamoyl, (xiv) amino, (xv) lower alkylamino or (xvi) heterocyclylcarbonyl;
or
(4) a group of the formula:

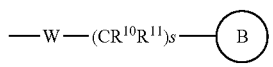

[Formula 29]

wherein $R^{10}$ and $R^{11}$ are each independently hydrogen or lower alkyl and when this group has two or more of $R^{10}$ and/or two or more of $R^{11}$, each $R^{10}$ and/or each $R^{11}$ may be different,
W is single bond, O, S or $NR^{12}$,
$R^{12}$ is hydrogen, lower alkyl or phenyl,
a group of the formula:

[Formula 30]

is cycloalkyl, bicycloalkyl, cycloalkenyl, aryl or heterocyclyl, each of which is optionally substituted with one or more of substituents selected from "a substituents group α" defined below and
s is an integer of 0 to 4.

In the present specification, "a substituents group α" is a group constituting of (1) halogen; (2) oxo; (3) cyano; (4) nitro; (5) imino optionally substituted with lower alkyl or hydroxy;
(6) the following groups (i) to (xxi), which are optionally substituted with one or more of groups selected from the substituents group β,
(i) hydroxy, (ii) lower alkyl, (iii) lower alkenyl, (iv) lower alkoxy, (v) carboxy, (vi) lower alkoxycarbonyl, (vii) acyl, acyloxy, (ix) imino, (x) mercapto, (xi) lower alkylthio, (xii) carbamoyl, (xiii) lower alkylcarbamoyl, (xiv) cycloalkylcarbamoyl, (xv) thiocarbamoyl, (xvi) lower alkylthiocarbamoyl, (xvii) lower alkylsulfinyl, (xviii) lower alkylsulfonyl, (xix) sulfamoyl, (xx) lower alkylsulfamoyl and (xxi) cycloalkylsulfamoyl;
(7) the following groups (i) to (v), which are optionally substituted with the substituents group β, lower alkyl, lower alkoxy(lower)alkyl, optionally protected hydroxy(lower) alkyl, halogeno(lower)alkyl, lower alkylsulfonyl and/or arylsulfonyl,
(i) cycloalkyl, (ii) cycloalkenyl, (iii) cycloalkyloxy, (iv) amino and (v) alkylenedioxy;
and
(8) the following groups (i) to (xii), which are optionally substituted with the substituents group β, lower alkyl, halogeno(lower)alkyl and/or oxo,
(i) phenyl, (ii) naphthyl, phenoxy, (iv) phenyl(lower)alkoxy, (v) phenylthio, (vi) phenyl(lower)alkylthio, (vii) phenylazo, heterocyclyl, (ix) heterocyclyloxy, (x) heterocyclylthio, (xi) heterocyclylcarbonyl and (xii) heterocyclylsulfonyl.

The preferable examples of the substituents group α as substituents for Ring B are halogen; nitro; hydroxy;
optionally substituted lower alkyl wherein the substituent(s) is halogen, cyano, phenyl, carboxy and/or lower alkoxycarbonyl; lower alkenyl; lower alkoxycarbonyl(lower)alkenyl;
optionally substituted lower alkoxy wherein the substituent(s) is halogen, hydroxy, lower alkoxy, carboxy, lower alkoxycarbonyl, lower alkylamino and/or cyano; acyl; hydroxyimino; lower alkylthio; lower alkylsulfinyl; sulfamoyl;
optionally substituted amino wherein the substituent(s) is lower alkyl, optionally protected hydroxy(lower)alkyl, phenyl and/or acyl; alkylenedioxy; cyanophenyl; heterocyclylphenyl; biphenylyl; phenoxy; phenylazo optionally substituted with lower alkyl; or
optionally substituted heterocyclyl wherein the substituent(s) is optionally protected hydroxy, mercapto, halogen, lower alkyl, cycloalkyl, lower alkoxycarbonyl, amino, lower alkoxycarbonyl amino, carbamoyl, oxo, phenyl, lower alkoxyphenyl or heterocyclyl. More preferable examples are halogen; lower alkyl optionally substituted with halogen; or lower alkoxy optionally substituted with halogen.

"A substituents group β" is a group consisting of halogen, optionally protected hydroxy, mercapto, lower alkoxy, lower alkenyl, amino, lower alkylamino, lower alkoxycarbonylamino, lower alkylthio, acyl, carboxy, lower alkoxycarbonyl, carbamoyl, cyano, cycloalkyl, phenyl, phenoxy, lower alkylphenyl, lower alkoxyphenyl, halogenophenyl, naphthyl and heterocyclyl.

Examples of the substituents for "optionally substituted lower alkyl" represented by any other than Z (e.g., $R^1$) are one or more substituents selected from the substituents group β. The lower alkyl may be substituted with these substituents at any possible positions.

The lower alkyl part in "lower alkoxy", "lower alkoxycarbonyl", "lower alkoxycarbonyl(lower)alkyl", "lower alkylphenyl", "lower alkoxyphenyl", "lower alkylcarbamoyl", "lower alkylthiocarbamoyl", "lower alkylamino", "halogeno (lower)alkyl", "hydroxy(lower)alkyl", "phenyl(lower) alkoxy", "lower alkylthio", "phenyl(lower)alkylthio", "lower alkoxycarbonylamino", "lower alkoxycarbonyl(lower)alkenyl", "lower alkylsulfinyl", "lower alkylsulfonyl", "aryl (lower)alkoxycarbonyl", "lower alkylbenzoyl" and "lower alkoxybenzoyl" is the same as defined in the above "lower alkyl".

Examples of the substituent(s) for "optionally substituted lower alkoxy" are one or more substituents selected from the substituents group β. Preferable examples are phenyl, lower alkylphenyl, lower alkoxyphenyl, naphthyl and heterocyclyl.

The term "cycloalkyl" includes C3 to C8 and preferably C5 to C6 cyclic alkyl. Examples are cyclopropyl, cyclobutyl, cyclopentyl, cyclohexyl, cycloheptyl and cyclooctyl.

Examples of the substituent(s) for "optionally substituted cycloalkyl" are one or more substituents selected from the substituents group α and the cycloalkyl may be substituted with these substituents at any possible positions.

The term "bicycloalkyl" includes a group which is formed by excluding one hydrogen atom from a C5 to C8 aliphatic cycle containing two rings which possess two or more of atoms in common. Examples are bicyclo[2.1.0]pentyl, bicyclo[2.2.1]heptyl, bicyclo[2.2.2]octyl and bicyclo[3.2.1]octyl.

The term "lower alkenyl" includes C2 to C10, preferably C2 to C8 and more preferably C3 to C6 straight or branched alkenyl having one or more double bonds at any possible positions. Examples are vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl and decenyl.

The "lower alkenyl" part in "lower alkoxycarbonyl(lower)alkenyl" is the same as the above "lower alkenyl".

Examples of the substituent(s) for "optionally substituted lower alkenyl" are halogen, lower alkoxy, lower alkenyl, amino, lower alkylamino, lower alkoxycarbonylamino, lower alkylthio, acyl, carboxy, lower alkoxycarbonyl, carbamoyl, cyano, cycloalkyl, phenyl, lower alkylphenyl, lower alkoxyphenyl, naphthyl and/or heterocyclyl.

The term "acyl" includes (1) C1 to C10, preferably C1 to C6 and more preferably C1 to C4 straight or branched alkylcarbonyl or alkenylcarbonyl, (2) C4 to C9 and preferably C4 to C7 cycloalkylcarbonyl and (3) C7 to C11 arylcarbonyl. Examples are formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl and benzoyl.

The "acyl" part in "acyloxy" is the same as the above.

The term "cycloalkenyl" includes a group having at least one double bond at any possible positions in the above cycloalkyl. Examples are cyclopropenyl, cyclobutenyl, cyclopentenyl, cyclohexenyl and cyclohexadienyl.

Examples of substituents for "optionally substituted cycloalkenyl" are one or more substituents selected from the substituents group β.

Examples of the substituent(s) for "optionally substituted amino" are the substituents group β, optionally substituted benzoyl and/or optionally substituted heterocyclylcarbonyl wherein the substituents is hydroxy, lower alkyl, lower alkoxy and/or lower alkylthio.

The term "aryl" includes a monocyclic of polycyclic aromatic carbocyclyl group and examples are phenyl, naphthyl, anthryl and phenanthryl. "Aryl" includes aryl fused with other a non-aromatic carbocyclyl group, for example, indanyl, indenyl, biphenylyl, acenaphthyl, tetrahydronaphthyl and fluorenyl. Phenyl is preferable.

The aryl part in "aryl(lower)alkoxycarbonyl" is the same as the above.

The term "optionally substituted aryl" and "optionally substituted phenyl" represented by Z include the above "aryl" and "phenyl" respectively, which may be substituted with the substituents group a or lower alkyl which may be substituted with one or more group selected from the substituents group α.

Examples of the substituent(s) for "optionally substituted aryl" and "optionally substituted phenyl" represented by any other than Z are one or more groups selected from the substituents group β.

The term "carbocyclyl" includes the above "cycloalkyl", "cycloalkenyl", "bicycloalkyl" and "aryl".

The term "non-aromatic carbocyclyl" includes the above "cycloalkyl", "cycloalkenyl" and "bicycloalkyl".

The term "optionally substituted carbocyclyl" includes the above "optionally substituted cycloalkyl", "optionally substituted cycloalkenyl", "optionally substituted bicycloalkyl" and "optionally substituted aryl".

The term "heterocyclyl" includes a heterocyclic group containing at least one heteroatom arbitrarily selected from O, S and N. For example, 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl and thienyl; fused heterocyclyl consisting of two rings such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazoropyridyl, imidazothiazolyl, pyrazinopyridazinyl, tetrahydroquinolyl, tetrahydrobenzothienyl, oxazolopyridyl, thiazolopyridyl (e.g., thiazolo[5,4-b]pyridin-2-yl, thiazolo[5,4-c]pyridin-2-yl, thiazolo[4,5-b]pyridin-2-yl and thiazolo[4,5-c]pyridin-2-yl), benzoxazolinonyl, benzisoxazolinonyl, benzoxazinonyl, benzoxyazepinonyl, oxazolopyridinonyl and benzodioxolyl; fused heterocyclyl consisting of three rings such as carbazolyl, acridinyl, xanthenyl, phenothiazinyl, phenoxathiinyl, phenoxazinyl and dibenzofuryl; and non-aromatic heterocyclyl such as dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydrofuryl, tetrahydropyranyl, tetrahydrothiazolyl and tetrahydroisothiazolyl.

"Fused heterocyclyl" fused with a ring other than a heterocycle (e.g., benzothiazolyl), may connect at any possible position.

The substituent(s) for "optionally substituted heterocyclyl" and "optionally substituted fused heterocyclyl consisting of two rings" are the same as those for the above "optionally substituted aryl".

Heterocyclyl parts in "heterocyclylcarbonyl", "heterocyclyloxy", "heterocyclylthio" and "heterocyclyl substituted phenyl" are the same as the above "heterocyclyl".

The term "lower alkylene" includes a bivalent group comprising 1 to 6 of methylene, preferably 2 to 6 of methylene and more preferably 3 to 6 of methylene. For example, methylene, ethylene, trimethylene, tetramethylene, pentamethylene and hexamethylene are included. Tetramethylene is preferable.

"$R^1$ and $R^2$ taken together may form lower alkylene" includes the case

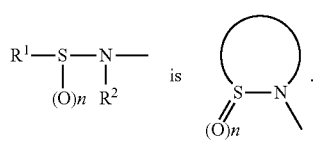

[Formula 31]

is

Preferable examples are

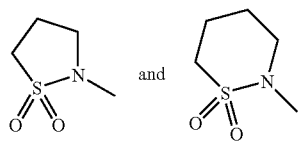

[Formula 32]

Lower alkylene part in "lower alkylenedioxy" is the same as the above "lower alkylene". Methylenedioxy or ethylenedioxy is preferable.

The term "lower alkenylene" includes a bivalent group comprising 2 to 6 of methylene, preferably 3 to 6 of methylene and more preferably 4 to 5 of methylene and including at least one double bond.

The term "cycloalkylene" includes a bivalent group which is formed by excluding one hydrogen atom from the above "cycloalkyl". A preferable example of cycloalkylene represented by X is 1,4-cyclohexanediyl.

The term "cycloalkenylene" includes a group containing at least one double bonds in the above cycloalkylene.

The term "bicycloalkylene" includes a group which is formed by excluding one hydrogen atom from the above "bicycloalkyl". Examples are bicyclo[2.1.0]pentylene, bicyclo[2.2.1]heptylene, bicyclo[2.2.2]octylene and bicyclo[3.2.1]octylene.

The term "heterocyclediyl" includes a bivalent group which is formed by excluding one hydrogen atom from the above "heterocyclyl". Piperidinediyl, piperazinediyl, pyridinediyl, pyrimidinediyl, pyrazinediyl, pyrrolidinediyl or pyrrolediyl is preferable. Piperidinediyl is more preferable.

The term "arylene" includes a bivalent group which is formed by excluding one hydrogen atom from the above "aryl". Phenylene is preferable.

The term "heteroarylene" includes aromatic groups in the above "heterocyclediyl". Examples are pyrrolediyl, imidazolediyl, pyrazolediyl, pyridinediyl, pyridazinediyl, pyrimidinediyl, pyrazinediyl, triazolediyl, triazinediyl, isoxazolediyl, oxazolediyl, oxadiazolediyl, isothiazolediyl, thiazolediyl, thiadiazolediyl, furandiyl and thiophenediyl.

One or more groups selected from the substituents group β are examples of substituents for "optionally substituted lower alkylene", "optionally substituted lower alkenylene", "optionally substituted cycloalkylene", "optionally substituted cyclohexylene", "optionally substituted bicycloalkylene", "optionally substituted cycloalkenylene", "optionally substituted phenylene", "optionally substituted heterocyclyldiyl" and "optionally substituted piperidinylene". Halogen, hydroxy, lower alkyl, halogeno(lower)alkyl, lower alkoxy, amino, lower alkylamino, acyl, carboxy or lower alkoxycarbonyl is preferable. These substituents may attach to any possible positions.

When —$NR^2$—X— is a group of the formula:

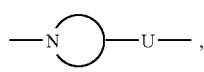

[Formula 33]

U is preferably methylene or ethylene. More preferred is a group of the formula:

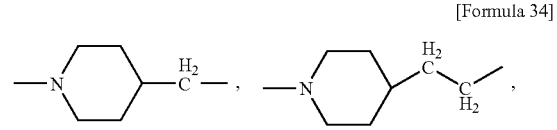

[Formula 34]

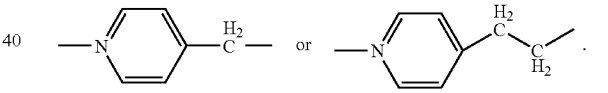

The compounds of the present invention include any formable and pharmaceutically acceptable salts thereof. Examples of "the pharmaceutically acceptable salt" are salts with mineral acids such as hydrochloric acid, sulfuric acid, nitric acid and phosphoric acid; salts with organic acids such as para-toluenesulfonic acid, methanesulfonic acid, oxalic acid and citric acid; salts with organic bases such as ammonium, trimethylammonium and triethylammonium; salts with alkaline metals such as sodium and potassium; and salts with alkaline earth metals such as calcium and magnesium.

The compounds of the present invention include solvates thereof. Hydrate is preferable and arbitrary numbers of water molecules may coordinate to the compound of the present invention.

When Compound (I) of the present invention has an asymmetric carbon atom, it includes racemates, all of enantiomers and all of stereoisomers such as diastereomer, epimer and enantiomer thereof. When Compound (I) of the present invention having one or more double bonds forms an E isomer or Z isomer, Compound (I) includes both isomers. When X is cycloalkylene, Compound (I) includes both of cis isomer and trans isomer.

For example, Compound (I) of the present invention can be synthesized by the following methods. Hereinafter, X will be described as —CH$_2$-G- or -G-CH$_2$—.
[Compounds Wherein Y=S(O)$_n$]

tion may be carried out at 0° C. to 50° C. Examples of solvents are tetrahydrofuran, dimethylformamide, diethyl ether, dichloromethane, toluene, benzene, xylene, cyclohexane, hexane, chloroform, ethyl acetate, butyl acetate, pentane,

[Formula 35]

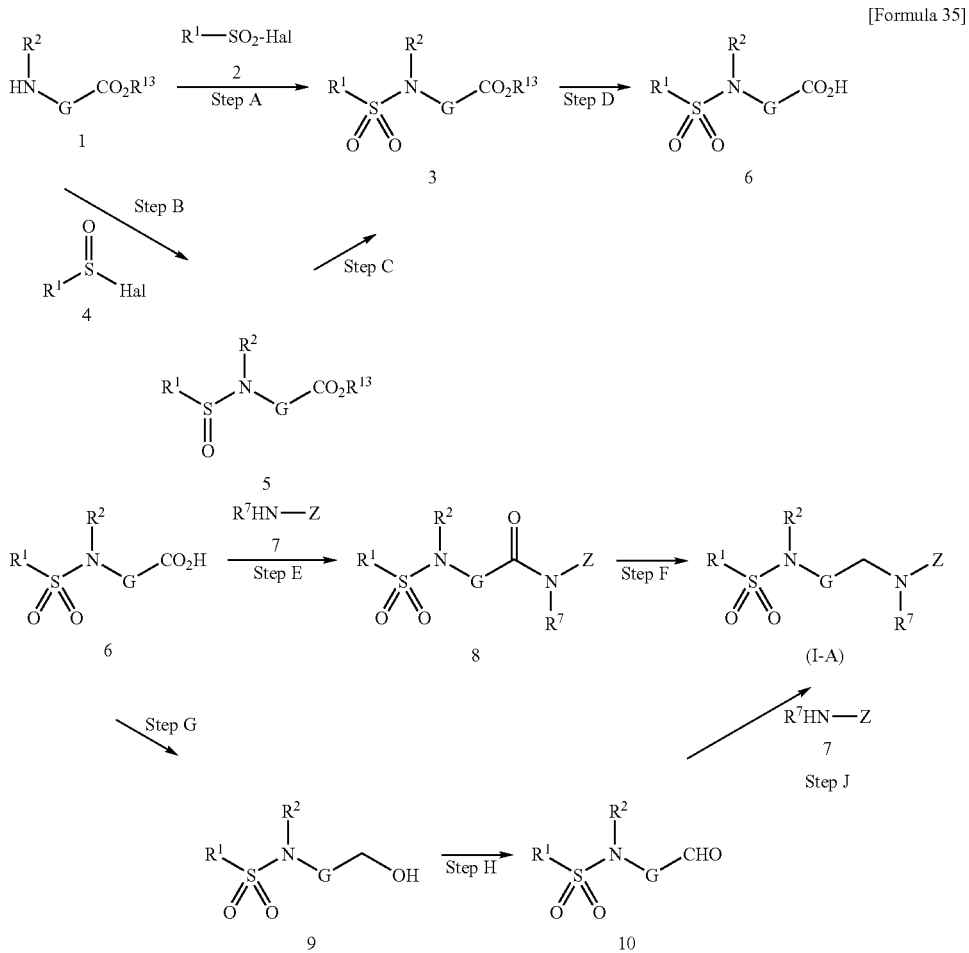

wherein Hal is halogen, -G-CH$_2$— is the same as —X— in the formula (I), R$^{13}$ is lower alkyl and the other symbols are the same as the above.

Step A

Compound 1 is reacted with Sulfonyl Halide 2 having the desired substituent R$^1$ in a suitable solvent at 0° C. to 50° C. for several minutes to several hours to give Compound 3 wherein n is 2. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water and a mixture thereof.

Step B

Compound 5 wherein n is 1 can be synthesized by reacting Compound 1 and Sulfinyl Halide 4 having substituent R$^1$. The conditions for the reaction are the same as those of the above Step A.

Step C

Compound 5 obtained in Step B is oxidized by the usual method to give Compound 3 wherein n is 2. Examples of an oxidizer are m-Chloroperbenzoic acid, peracetic acid, hydrogen peroxide, trifluoroperacetic acid, sodium periodate, sodium hypochlorite and potassium permanganate. The reacheptane, dioxane, acetone, acetonitrile, water, methanol, ethanol, isopropanol and mixture thereof.

Step D

Compound 3 obtained from Step A or C is treated in a suitable solvent and base to give Compound 6. Examples of the base are barium hydroxide, sodium hydroxide, potassium hydroxide, hydrazine, lithium salt of propanethiol. Examples of the solvent are tetrahydrofuran, dimethylformamide, dioxane, acetone, acetonitrile, methanol, ethanol, propanol, water and a mixed solvent thereof. The reaction may be carried out at 0° C. to 100° C. for several minutes to tens of hours.

Step E

Compound 6 obtained form Step D is reacted with Amino Compound 7 having the desired substituent Z and R$^7$ in a suitable solvent at 0° C. to 50° C. for several minutes to several hours to give Compound 8. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water and a mixed solvent thereof. An activator such as thionyl chloride, acid halide, acid anhydride and activated ester can be used, if necessary.

Step F

The obtained Compound 8 is treated in a suitable solvent with a suitable reducing agent to give Compound (I-A). Examples of the reducing agent are sodium borohydride, lithium boron hydride and lithium aluminum hydride. Examples of the solvent are tetrahydrofuran, dimethylformamide, dioxane, acetonitrile, methanol, ethanol, propanol, acetic acid and a mixed solvent thereof. The reaction may be carried out at 0° C. to 100° C. for several minutes to tens of hours.

Step G

Compound 6 obtained from Step D is treated in a suitable solvent with a reducing agent to give Compound 9. Examples of reducing agent are sodium borohydride, lithium boron hydride, lithium aluminum hydride and diborane. Examples of the solvent are tetrahydrofuran, dimethylformamide, dioxane, acetonitrile, methanol, ethanol, propanol and a mixed solvent thereof. The reaction may be carried out at 0° C. to 100° C. for several minutes to tens of hours. Compound 9 can be obtained through the intermediate such as acid halide, acid anhydride and activated ester, if necessary.

Step H

Compound 9 obtained from Step G is oxidized by the usual method to give Compound 10. Examples of an oxidizer are m-Chloroperbenzoic acid, peracetic acid, hydrogen peroxide, pertrifluoroacetic acid, sodium periodate, sodium hypochlorite, potassium permanganate, Dess-Martin periodinane, dimethylsulfoxide/oxalyl chloride (Swern oxidation) and ruthenium-catalyst. The reaction may be carried out at −80° C. to 50° C. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water, methanol, ethanol, isopropanol and a mixed solvent thereof.

Step J

The obtained Compound 10 and Amino Compound 7 having the desired substituent Z and $R^7$ are subjected to reductive amination reaction by a ordinary method to give Compound (I-A). Examples of the reducing agent are sodium borohydride, triacetoxy sodium borohydride and cyano sodium borohydride. The reaction may be carried out at 0° C. to 50° C. Examples of the solvent are tetrahydrofuran, dimethylformamide, dioxane, acetonitrile, methanol, ethanol, propanol, acetic acid, hydrochloric acid and a mixed solvent thereof.

[Compounds Wherein Y=CO]

[Formula 36]

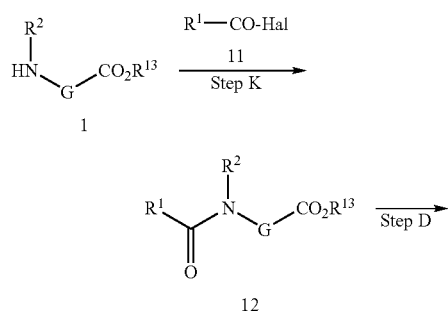

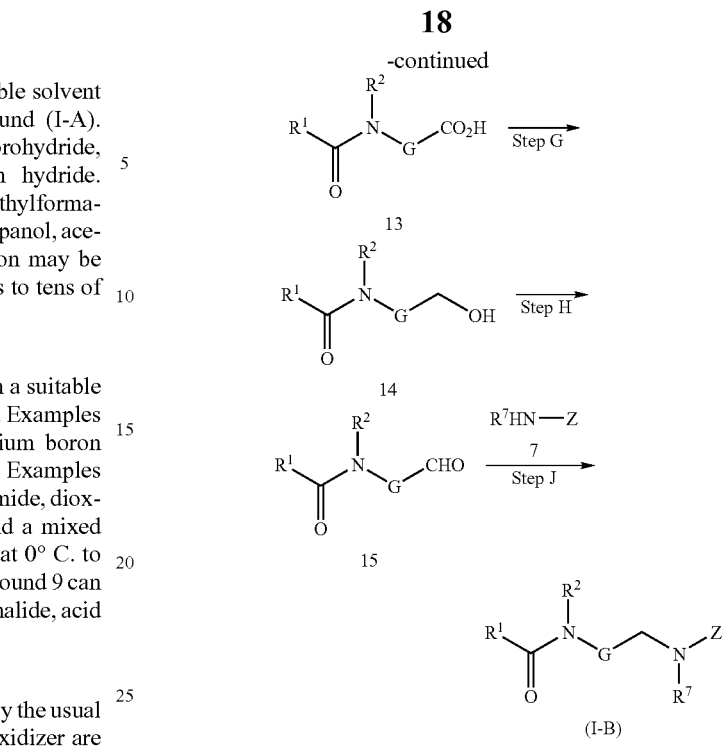

wherein each of the symbols is the same as the above and -G-CH$_2$— is the same as —X— in the formula (I).

Step K

Compound 1 is reacted with Acyl Halide 11 having the desired substituent $R^1$ in a suitable solvent at −20° C. to 50° C. for several minutes to several hours to give Compound 12. Examples of the solvent are tetrahydrofuran, dimethylformamide, diethyl ether, dichloromethane, toluene, benzene, xylene, cyclohexane, hexane, chloroform, ethyl acetate, butyl acetate, pentane, heptane, dioxane, acetone, acetonitrile, water and a mixed solvent thereof.

Step D, G, H and J

The obtained Compound 12 is subjected to the similar method to the above Step D, G, H and J to give Compound (I-B) of the present invention.

[Formula 37]

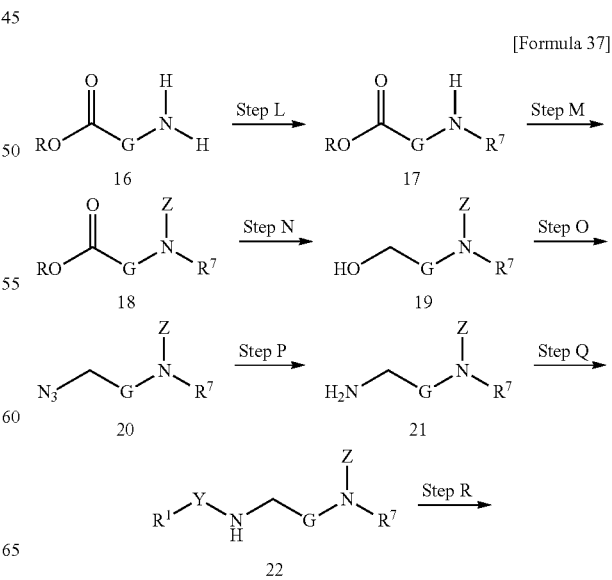

-continued

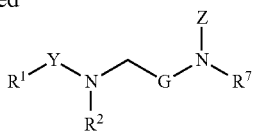

(I-C)

wherein each of the symbols is the same as the above, —CH$_2$-G- is the same as —X— in the formula (I) and R is alkyl.

Step L

This is the step to introduce substituent R$^7$ into Compound 16. For example, Compound 16 is reacted with R$^7$X$^1$ wherein X$^1$ is halogen under the presence of a base to give Compound 17. Examples of the solvent are tetrahydrofuran and dimethylformamide. The reaction may be carried out at a room temperature. Examples of the base are triethylamine, pyridin and dimethylamino pyridin. The compound wherein R$^7$ is hydrogen in formula (I-C) do not need this step.

Step M

This is the step to introduce substituent Z into Compound 17. For example, Compound 17 is reacted with ZX$^1$ wherein X$^1$ is halogen under the presence of a base to give Compound 18. Examples of the solvent are methanol, ethanol, isopropanol and dimethylformamide. The reaction may be carried out at a room temperature or under heating. For example, it can be carried out in a sealed tube by a microwave reactor. An example of the base is N,N-diisopropyl ethyl amine.

Step N

This is the step to reduce Compound 18 to give Compound 19. An example of reducing agent is lithium aluminum hydride. An example of the solvent is tetrahydrofuran. The reaction may be carried out at a room temperature.

Step O

This is the step to give Compound 20 by azidation of Compound 19. For example, methanesulfonyl chloride is reacted with Compound 19 by using triethylamine as a base to give mesylate. Chloroform can be used as the solvent for the mesylation. Sodium azide is reacted with the obtained compound and azidation is carried out in dimethylformamide or the like at room temperature or under warming to give Compound 20.

Step P

This is the step to reduce Compound 20 to give Compound 21. It can be carried out by catalytic reduction. An example of the catalyst is 10% palladium carbon. An example of the solvent is ethanol.

Step Q

This is the step to a compound of the formula: R$^1$—Y—X$^1$ wherein X$^1$ is halogen or the like, and Y is S, SO, SO$_2$ or CO is reacted with Compound 21 to give Compound 22. Examples of a compound of the formula: R$^1$—Y—X$^1$ are various sulfonyl chloride and acyl chloride. Examples of the solvent are tetrahydrofuran and dimethylamide. The reaction may be carried out at a room temperature or under heating. The reaction is preferably carried out under a base. Examples of the base are pyridin and triethylamine. A compound wherein R$^2$ is hydrogen in the formula (I-C) do not need the subsequent Step R and Compound 22 is a final target compound. This reaction can be carried out with a compound of the formula: R$^1$—Y—X$^1$ wherein Y=S or SO to give Compound 22, and then the oxidation can be carried out to transform to a compound wherein Y is SO$_2$ used for the next step.

Step R

This is the step to introduce substituent R$^2$ into Compound 22. R$^2$X$^1$ wherein X$^1$ is halogen or the like is reacted with Compound 22 under the presence of a base to give Compound (I-C). An example of base is sodium hydride. An example of the solvent is dimethylformamide.

The following intermediates are useful in the above steps.

[Formula 38]

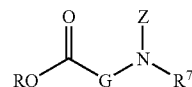
18

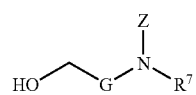
19

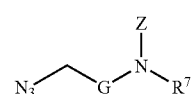
20

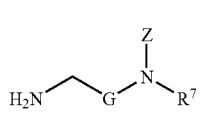
21 wherein

R is optionally substituted lower alkyl,

R$^7$ is hydrogen or optionally substituted lower alkyl,

G is 1,4-cycloalkylene, and

Z is optionally substituted carbocyclyl or optionally substituted heterocyclyl.

R is preferably lower alkyl and more preferably methyl and ethyl. Ethyl is especially preferable.

Preferable R$^7$ is hydrogen.

Preferable Z is optionally substituted heterocyclyl.

The following compounds are especially preferable.

A compound of the formula:

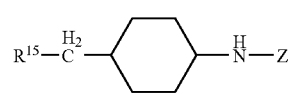

[Formula 39]

wherein

R$^{15}$ is NH$_2$ or OH, and

Z is optionally substituted pyridyl, optionally substituted pyridazinyl, optionally substituted pyrazinyl, optionally substituted pyrimidinyl, optionally substituted quinolyl, optionally substituted isoquinolyl, optionally substituted benzothiazolyl, optionally substituted benzoxazolyl, optionally substituted benzopyridyl, optionally substituted benzopyridazinyl, optionally substituted benzimidazolyl, optionally substituted benzoxazolyl, optionally substituted thiazolopyridyl optionally substituted benzisoxazolinonyl, optionally substituted benzoxazolinonyl, optionally substituted benzoxazinonyl or optionally substituted benzoxyazepinonyl.

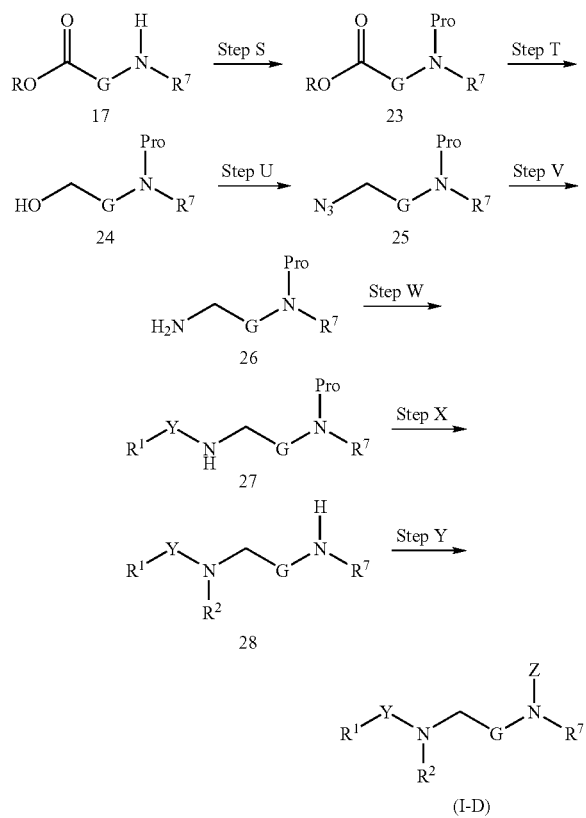

[Formula 40]

wherein each of the symbols is the same as the above, —CH$_2$-G- is the same as —X— in the formula (I), R is alkyl and Pro is amino protecting group.

Step S

This is the step to introduce a protecting group into Compound 17. As a protecting group, the protecting group described in Protective Groups in Organic Synthesis (Theodra W. Greene) or the like can be used. The amino protecting groups which can be removed under the acid condition are preferable. Examples are benzyloxycarbonyl and tert-butyloxycarbonyl. For example, ProX$^1$ wherein X$^1$ is halogen or the like and Pro is benzyloxycarbonyl, tert-butyloxycarbonyl or the like and Pro-O-Pro wherein Pro is benzyloxycarbonyl, tert-butyloxycarbonyl or the like are reacted under the presence of the base to give Compound 23. Examples of the solvent are tetrahydrofuran and dimethylformamide. The reaction may be carried out at a room temperature. Examples of the base are triethylamine, pyridin and dimethyl amino pyridin. The reaction also can be carried out with a compound wherein R$^7$ is hydrogen.

Step T

This is the step to reduce Compound 23 to give Compound 24. Lithium aluminum hydride can be used as the reducing agent. An example of the solvent is tetrahydrofuran. The reaction may be carried out at a room temperature.

Step U

This is the step to give Compound 25 by azidation of Compound 24. For example, methanesulfonyl chloride is reacted with Compound 24 by using triethylamine as a base to give mesylate. Chloroform can be used as the solvent for the mesylation. Sodium azide is reacted with the obtained compound and azidation is carried out in dimethylformamide or the like at room temperature or under warming to give Compound 25.

Step V

This is the step to reduce Compound 25 to give Compound 26. Compound 25 is reduced with triphenylphosphine and water to give Compound 26. The reaction may be carried out under heating. An example of the solvent is tetrahydrofuran. Except for the reduction method with triphenylphosphine, the catalytic reduction can be used. For the catalytic reduction, 10% palladium carbon or the like can be used as catalyst. An example of the solvent is ethanol. The reduction method can be suitably selected depending on the used protecting group.

Step W

This is the step to react a compound of the formula: R$^1$—Y—X$^1$ wherein X$^1$ is halogen or the like, Y is S, SO, SO$_2$ or CO with Compound 26 to give Compound 27. Examples of the compound of the formula: R$^1$—Y—X$^1$ wherein X$^1$ is halogen or the like are various sulfonyl chloride and acyl chloride. Examples of the solvent are tetrahydrofuran and dimethylamide. The reaction may carry out at a room temperature or under heating. The reaction is preferably carried out under a base. Examples of the base are pyridin and triethylamine. This reaction can be carried out with a compound of the formula: R$^1$—Y—X$^1$ wherein Y=S or SO to give Compound 27, and then the oxidation can be carried out to transform to a compound wherein Y is SO$_2$ used for the next step.

Step X

This is the step to remove the protecting group of Compound 27. The method for removing the protecting group can be used by selecting various conditions depending on the protecting group. For example, tert-butyloxycarbonyl can be removed with acid. Benzyloxycarbonyl can be removed by catalytic reduction or the like.

Step Y

This is the step to introduce substituent Z into Compound 28. For example, ZX$^1$ wherein X$^1$ is halogen is reacted under the presence of the base to give Compound (I-D). Examples of the solvent are methanol, ethanol, isopropanol and dimethylformamide. The reaction may carry out at a room temperature or under heating. For example, it can be carried out in a sealed tube by a microwave reactor. An example of the base is N,N-diisopropyl ethyl amine.

In the above steps, the following intermediates are useful.

A compound of the formula:

[Formula 41]

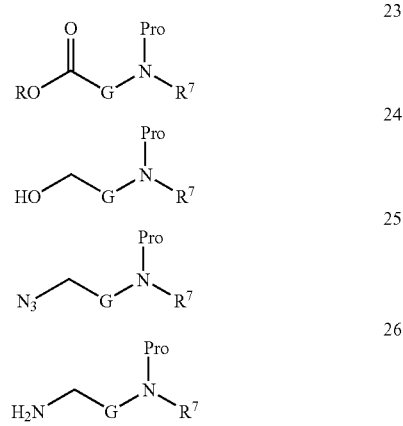

27

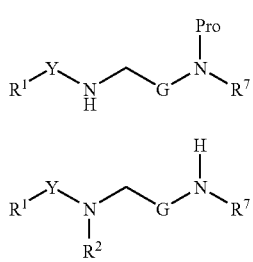

28 wherein
R is optionally substituted lower alkyl,
Pro is a protecting group,
$R^7$ is hydrogen or optionally substituted lower alkyl,
G is 1,4-cycloalkylene,
Y is $SO_2$ or SO,
$R^1$ is optionally substituted lower alkyl, and
$R^2$ is hydrogen or optionally substituted lower alkyl.

R is preferably lower alkyl and more preferably methyl and ethyl. Ethyl is especially preferable.

Preferable Pro is amino protecting group which can be removed under the acid condition. Examples of Pro are the formula: —(C=O)—O—R, wherein R is optionally substituted lower alkyl, optionally substituted lower alkenyl. Tert-butyloxycarbonyl is especially preferable.

Preferable $R^7$ is hydrogen.
Preferable Y is $SO_2$.
$R^1$ is preferably lower alkyl and more preferably isopropyl and ethyl. Ethyl is especially preferable.
Preferable $R^2$ is hydrogen.

The following compounds are especially preferable.
A compound of the formula:

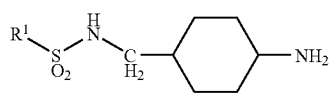

[Formula 42]

wherein $R^1$ is ethyl or tert-butyl.
A compound of the formula:

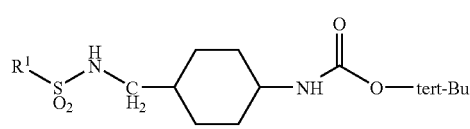

[Formula 43]

wherein $R^1$ is ethyl, isopropyl or tert-butyl.
A compound of the formula:

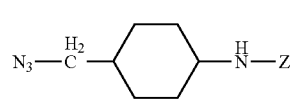

[Formula 44]

wherein Z is optionally substituted carbocyclyl or optionally substituted heterocyclyl.

All of the compounds of the present invention have an NPY Y5 antagonistic activity and the following compounds are especially preferable.

In the formula (I),
a compound wherein $R^1$ is optionally substituted lower alkyl (hereinafter referred to as "$R^1$ is R1-1"),
a compound wherein $R^1$ is C1 to C10 alkyl optionally substituted with halogen (hereinafter referred to as "$R^1$ is R1-2"),
a compound wherein $R^1$ is C1 to C10 alkyl optionally substituted with halogen (hereinafter referred to as "$R^1$ is R1-3"),
a compound wherein $R^1$ is isopropyl or t-butyl (hereinafter referred to as "$R^1$ is R1-4"),
a compound wherein $R^2$ is hydrogen or C1 to C3 alkyl (hereinafter referred to as "$R^2$ is R2-1"),
a compound wherein $R^2$ is hydrogen (hereinafter referred to as "$R^2$ is R2-2"),
a compound wherein X is optionally substituted lower alkylene, optionally substituted lower alkenylene or a group of the formula:

[Formula 45]

wherein a group of the formula:

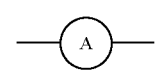

[Formula 46]

is optionally substituted cycloalkylene, optionally substituted cycloalkenylene, optionally substituted bicycloalkylene, optionally substituted phenylene or optionally substituted heterocyclediyl (hereinafter referred to as "X is X-1"), a compound wherein X is C2 to C6 alkylene, C3 to C6 alkenylene or a group of the formula:

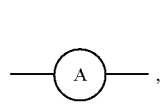

[Formula 47]

wherein a group of the formula:

[Formula 48]

is optionally substituted cycloalkylene, optionally substituted cycloalkenylene, optionally substituted bicycloalkylene, optionally substituted phenylene, optionally substituted piperidinylene, optionally substituted thiophenediyl or optionally substituted furandiyl (hereinafter referred to as "X is X-2"), a compound wherein X is C2 to C6 alkylene or a group of the formula:

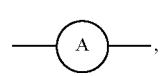

[Formula 49]

wherein a group of the formula:

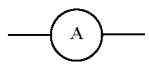

[Formula 50]

wherein is optionally substituted cycloalkylene, optionally substituted phenylene, optionally substituted piperidinylene, optionally substituted thiophenediyl or optionally substituted furandiyl (hereinafter referred to as "X is X-3"),
a compound wherein X is (i) C2 to C6 alkylene or (ii) cycloalkylene or phenylene, each of which is optionally substituted with halogen, hydroxy, lower alkyl or halogeno (lower)alkyl (hereinafter referred to as "X is X-4"),
a compound wherein X is C2 to C6 alkylene or to C5 to C6 cycloalkylene (hereinafter referred to as "X is X-5"),
a compound wherein X is C3 to C6 alkylene or 1,4-cyclohexylene (hereinafter referred to as "X is X-6"),
a compound wherein Y is —SO— (hereinafter referred to as "Y is Y-1"),
a compound wherein Y is —SO$_2$— (hereinafter referred to as "Y is Y-2"),
a compound wherein Y is —CO— (hereinafter referred to as "Y is Y-3"),
a compound wherein Z is optionally substituted lower alkyl, optionally substituted carbocyclyl or optionally substituted heterocyclyl (hereinafter referred to as "Z is Z-1"),
a compound wherein Z is a group of the formula: —(CR$^8$R$^9$)$_r$—W—(CR$^{10}$R$^{11}$)$_s$—V
wherein
R$^8$, R$^9$, R$^{10}$ and R$^{11}$ are each independently hydrogen or lower alkyl and when Z has two or more of R$^8$, two or more of R$^9$, two or more of R$^{10}$ and/or two or more of R$^{11}$, each of R$^8$, R$^9$, R$^{10}$ and R$^{11}$ may be different,
W is single bond, O, S or NR$^{12}$,
R$^{12}$ is hydrogen, lower alkyl or phenyl,
V is hydrogen, optionally substituted cycloalkyl, optionally substituted bicycloalkyl, optionally substituted aryl or optionally substituted heterocyclyl,
r is an integer of 1 to 4 and
s is an integer of 0 to 4
(hereinafter referred to as "Z is Z-2"),
a compound wherein Z is a group of the formula: —(CH$_2$)$_r$—W—(CH$_2$)$_s$—V
wherein
W is single bond, O, S or NR$^{12}$,
R$^{12}$ is hydrogen or lower alkyl,
V is optionally substituted aryl or optionally substituted heterocyclyl
wherein the substituent(s) is halogen, hydroxy, lower alkyl, halogeno(lower)alkyl, lower alkoxy, lower alkenyl, amino, lower alkylamino, acyl, carboxy, lower alkoxycarbonyl, phenyl or monocyclic heteroaryl,
r is an integer of 1 to 4 and
s is an integer of 0 to 4
(hereinafter referred to as "Z is Z-3"),
a compound wherein Z is a group of the formula: —(CH$_2$)$_r$—W—(CH$_2$)$_s$—V
wherein
W is single bond, O, S, NH or NMe,
V is optionally substituted phenyl or optionally substituted heteroaryl wherein the substituents is halogen, lower alkyl, halogeno(lower)alkyl, lower alkoxy, amino or lower alkylamino,
r is an integer of 1 to 3 and
s is an integer of 0 or 1
(hereinafter referred to as "Z is Z-4"),
a compound wherein Z is optionally substituted carbocyclyl, wherein the substituent is halogen; hydroxy;
optionally substituted lower alkyl wherein the substituent(s) is halogen, hydroxy, carboxy, lower alkoxycarbonyl, cyano and/or phenyl;
lower alkenyl optionally substituted with lower alkoxycarbonyl;
optionally substituted lower alkoxy wherein the substituent(s) is halogen, hydroxy, lower alkoxy, carboxy, lower alkoxycarbonyl, lower alkylamino, cycloalkyl, cyano and/or heterocyclyl;
cycloalkyl; cycloalkyloxy; acyl; lower alkylthio; carbamoyl; lower alkylcarbamoyl; cycloalkylcarbamoyl; hydroxy imino;
optionally substituted amino wherein the substituent(s) is lower alkyl, optionally protected hydroxy(lower)alkyl, lower alkoxy(lower)alkyl, acyl, lower alkylsulfonyl, arylsulfonyl and/or phenyl;
phenyl optionally substituted with halogen, cyano, phenyl and/or heterocyclyl; lower alkylsulfinyl; lower alkylsulfamoyl; cycloalkylsulfamoyl;
nitro; cyano; alkylenedioxy; phenylazo optionally substituted with lower alkyl; phenoxy; oxo;
optionally substituted heterocyclyl wherein the substituent(s) is optionally protected hydroxy, mercapto, halogen, lower alkyl, cycloalkyl, lower alkoxycarbonyl, acyl, amino, lower alkoxycarbonylamino, carbamoyl, oxo, phenyl, lower alkoxyphenyl, halogenophenyl, heterocyclyl and/or oxo;
heterocyclylsulfonyl optionally substituted with lower alkyl; heterocyclyloxy; heterocyclylcarbonyl optionally substituted with lower alkyl
(hereinafter referred to as "Z is Z-5"),
a compound wherein Z is optionally substituted phenyl
wherein the substituent(s) is halogen; hydroxy; lower alkyl optionally substituted with halogen, hydroxy, lower alkoxycarbonyl, cyano and/or phenyl; lower alkoxycarbonyl(lower)alkenyl; lower alkoxy optionally substituted with halogen, lower alkoxy, lower alkoxycarbonyl, cycloalkyl and/or heterocyclyl; cycloalkyl; cycloalkyloxy; acyl; lower alkylthio; carbamoyl; lower alkylcarbamoyl; amino optionally substituted with lower alkyl, hydroxy (lower)alkyl, acyl, lower alkylsulfonyl and/or phenyl; phenyl optionally substituted with halogen, cyano, phenyl and/or heterocyclyl; lower alkyl sulfamoyl; cycloalkylsulfamoyl; nitro; alkylenedioxy; phenylazo optionally substituted with lower alkyl; phenoxy; oxo;
heterocyclyl optionally substituted with hydroxy, halogen, lower alkyl, lower alkoxycarbonyl, amino, carbamoyl, phenyl, halogenophenyl, heterocyclyl and/or oxo; heterocyclyloxy; and/or heterocyclylsulfonyl optionally substituted with lower alkyl (hereinafter referred to as "Z is Z-6"),
a compound wherein Z is optionally substituted phenyl
wherein the substituent(s) is halogen; lower alkyl optionally substituted with halogen, hydroxy, lower alkoxycarbonyl and/or phenyl; lower alkoxy optionally substituted with halogen and/or cycloalkyl; cycloalkyl; cycloalkyloxy; acyl; lower alkylthio; lower alkylcarbamoyl; amino optionally substituted with lower alkyl, hydroxy(lower) alkyl, acyl and/or phenyl; phenyl optionally substituted with piperidyl; cycloalkylsulfamoyl; alkylenedioxy; phenoxy;

morpholinyl or morpholino, each of which is optionally substituted with lower alkyl; piperidyl optionally substituted with hydroxy, lower alkyl, lower alkoxycarbonyl, phenyl, halogenophenyl and/or oxo; pyrrolidinyl optionally substituted with hydroxy, carbamoyl and/or oxo; piperazinyl optionally substituted with phenyl or pyrimidinyl; dihydropyridyl; pyrrolyl; pyrrolinyl; imidazolyl optionally substituted with halogen and/or lower alkyl; pyrazolyl; thienyl; thiadiazolyl; furyl; oxazolyl; isoxazolyl; tetrazolyl optionally substituted with lower alkyl and/or phenyl; indolinyl; indolyl; tetrahydroquinolyl; benzothiazolyl optionally substituted with lower alkyl; tetrahydroisothiazolyl optionally substituted with oxo; benzopyranyl optionally substituted with oxo; tetrahydropyranyloxy; tetrahydrofuryloxy; morpholinosulfonyl optionally substituted with lower alkyl; and/or piperidylsulfonyl optionally substituted with lower alkyl
(hereinafter referred to as "Z is Z-7"),
a compound wherein Z is optionally substituted phenyl
wherein the substituent(s) is halogen, lower alkyl, halogeno(lower)alkyl, lower alkoxy, cycloalkyloxy, lower alkylcarbamoyl, phenyl, lower alkyl morpholino and/or tetrahydropyranyloxy
(hereinafter referred to as "Z is Z-8"),
a compound wherein Z is optionally substituted heterocyclyl
wherein the substituent(s) is halogen, hydroxy, lower alkyl, halogeno(lower)alkyl, lower alkoxy, mercapto, lower alkylthio, acyl, carboxy, lower alkoxycarbonyl, amino, lower alkylamino, phenyl, naphthyl, phenylthio optionally substituted with halogen, phenoxy optionally substituted with halogen, oxo, and/or heterocyclyl optionally substituted with lower alkyl
(hereinafter referred to as "Z is Z-9"),
a compound wherein Z is thienyl, pyrazolyl, thiazolyl, thiadiazolyl, pyridyl, pyrimidinyl, pyrazinyl, pyridazinyl, triazinyl, indolyl, isoindolyl, indolinyl, isoindolinyl, indazolyl, benzopyranyl, benzoxazolyl, benzothienyl, benzothiazolyl, benzothiazolinyl, benzothiadiazolyl, benzimidazolyl, quinolyl, isoquinolyl, dihydrobenzofuryl, carbazolyl, acridinyl, dibenzofuryl or thiazolopyridyl, each of which is optionally substituted with substituents selected from the group of lower alkyl; halogeno(lower)alkyl; lower alkoxy; lower alkoxycarbonyl; acyl; lower alkoxycarbonyl(lower)alkyl; mercapto; phenyl, naphthyl, phenylthio or phenoxy, each of which is optionally substituted with halogen; furyl; nitro; oxo; and morpholino optionally substituted with lower alkyl) (hereinafter referred to as "Z is Z-10"),
a compound wherein Z is thienyl, thiazolyl, thiadiazolyl, pyridyl, pyrazinyl, indolyl, isoindolinyl, benzopyranyl, quinolyl, carbazolyl, dibenzofuryl, benzopyranyl, benzothienyl or benzothiazolyl, each of which is optionally substituted with one or more substituent(s) selected from the group of lower alkyl, halogeno(lower)alkyl, lower alkoxy, lower alkoxycarbonyl, acyl, phenyl, naphthyl, phenylthio, lower alkyl morpholino and oxo) (hereinafter referred to as "Z is Z-11"),
a compound wherein $R^1$ is R1-2, $R^2$ is R2-2, n is 2 and a combination of X, Y and Z, i.e., (X, Y, Z), is any one of the followings.
(X,Y,Z)=(X-3,Y-2,Z-1), (X-3,Y-2,Z-2), (X-3,Y-2,Z-3), (X-3,Y-2,Z-4), (X-3,Y-2,Z-5), (X-3,Y-2,Z-6), (X-3,Y-2,Z-7), (X-3,Y-2,Z-8), (X-3,Y-2,Z-9), (X-3,Y-2,Z-10), (X-3,Y-2,Z-11), (X-3,Y-3,Z-1), (X-3,Y-3,Z-2), (X-3,Y-3,Z-3), (X-3,Y-3,Z-4), (X-3,Y-3,Z-5), (X-3,Y-3,Z-6), (X-3,Y-3,Z-7), (X-3,Y-3,Z-8), (X-3,Y-3,Z-9), (X-3,Y-3,Z-10), (X-3,Y-3,Z-11), (X-4,Y-2,Z-1), (X-4,Y-2,Z-2), (X-4,Y-2,Z-3), (X-4,Y-2,Z-4), (X-4,Y-2,Z-5), (X-4,Y-2,Z-6), (X-4,Y-2,Z-7), (X-4,Y-2,Z-8), (X-4,Y-2,Z-9), (X-4,Y-2,Z-10), (X-4,Y-2,Z-11), (X-4,Y-3,Z-1), (X-4,Y-3,Z-2), (X-4,Y-3,Z-3), (X-4,Y-3,Z-4), (X-4,Y-3,Z-5), (X-4,Y-3,Z-6), (X-4,Y-3,Z-7), (X-4,Y-3,Z-8), (X-4,Y-3,Z-9), (X-4,Y-3,Z-10), (X-4,Y-3,Z-11), (X-5,Y-2,Z-1), (X-5,Y-2,Z-2), (X-5,Y-2,Z-3), (X-5,Y-2,Z-4), (X-5,Y-2,Z-5), (X-5,Y-2,Z-6), (X-5,Y-2,Z-7), (X-5,Y-2,Z-8), (X-5,Y-2,Z-9), (X-5,Y-2,Z-10), (X-5,Y-2,Z-11), (X-5,Y-3,Z-1), (X-5,Y-3,Z-2), (X-5,Y-3,Z-3), (X-5,Y-3,Z-4), (X-5,Y-3,Z-5), (X-5,Y-3,Z-6), (X-5,Y-3,Z-7), (X-5,Y-3,Z-8), (X-5,Y-3,Z-9), (X-5,Y-3,Z-10) or (X-5,Y-3,Z-11)
the pharmaceutically acceptable salt or solvate thereof.

The NPY Y5 receptor antagonist of the present invention is effective for all of the diseases in which NPY Y5 is involved and it is especially useful for preventing and/or treating obesity and suppressing food intake. Moreover, the antagonist is effective for preventing and/or treating the diseases in which obesity acts as a risk factor, for example, diabetes, hypertension, hyperlipemia, atherosclerosis and acute coronary syndrome.

Furthermore, a compound of the present invention has not only NPY Y5 receptor antagonistic activity but also any or all good characters as a medicine selected from the followings.
a) weak CYP enzyme inhibition
b) less induction of a drug-metabolizing enzyme.
c) good drug disposition such as high bioavailability.
d) low toxicity of anemia-inducing activity or the like.
e) high metabolic stability.
f) high selectivity for Y5 receptor.
g) high water solubility.
h) high transportability through the blood-brain barrier.

In addition, the NPY Y5 receptor antagonist of the present invention has a low affinity for NPY Y1 and Y2 receptors, and has a high selectivity for NPY Y5 receptor. NPY causes a sustained vasoconstrictive action in the periphery and this action is mainly via Y1 receptor. Since Y5 receptor is not involved in this action at all, the NPY Y5 receptor antagonist has a low risk of inducing side effects based on the peripheral vasoconstriction, and is expected to be suitably used as a safe medicine.

The NPY Y5 receptor antagonist shows an anti-obesity effect by suppressing food intake. Therefore, it is one of the features of the present antagonist not to induce side effects such as dyspepsia caused by an anti-obesity agent which inhibits digestion and absorption, or central nervous system side-effects such as an antidepressant effect due to a serotonin transporter inhibitor that shows an anti-obesity effect.

A compound of the present invention can be administered orally or parenterally as an anti-obesity agent or anorectic agent. In the case of oral administration, it may be in any usual form such as tablets, granules, powders, capsules, pills, solutions, syrups, buccal tablets and sublingual tablets. When the compound is parenterally administered, any usual form is preferable, for example, injections (e.g., intravenous, intramuscular), suppositories, endermic agents and inhalations. Oral administration is especially preferable because the compounds of the present invention show a high oral absorbability.

A pharmaceutical composition may be manufactured by mixing an effective amount of a compound of the present invention with various pharmaceutical additives suitable for the administration form, such as excipients, binders, moistening agents, disintegrants, lubricants and diluents. When the composition is of an injection, an active ingredient together with a suitable carrier can be sterilized to give a pharmaceutical composition.

Examples of the excipients include lactose, saccharose, glucose, starch, calcium carbonate and crystalline cellulose. Examples of the binders include methylcellulose, carboxymethylcellulose, hydroxypropylcellulose, gelatin and polyvinylpyrrolidone. Examples of the disintegrants include carboxymethylcellulose, sodium carboxymethylcellulose, starch, sodium alginate, agar and sodium lauryl sulfate. Examples of the lubricants include talc, magnesium stearate and macrogol. Cacao oil, macrogol, methylcellulose or the like may be used as base materials of suppositories. When the composition is manufactured as solutions, emulsified injections or suspended injections, solubilizing agents, suspending agents, emulsifiers, stabilizers, preservatives, isotonic agents and the like which are usually used may be added. For oral administration, sweetening agents, flavors and the like which are usually used may be added.

Although the dosage of a compound of the present invention as an anti-obesity agent or anorectic agent should be determined in consideration of the patient's age and body weight, the type and degree of diseases, the administration route and the like, a usual oral dosage for an adult is 0.05 to 100 mg/kg/day and preferable is 0.1 to 10 mg/kg/day. For parenteral administration, although the dosage highly varies with administration routes, a usual dosage is 0.005 to 10 mg/kg/day and preferably 0.01 to 1 mg/kg/day. The dosage may be administered in one to several divisions per day.

The present invention is further explained by the following Examples, which are not intended to limit the scope of the present invention.

The abbreviations used in the present description stand for the following meanings.

Me: methyl
Et: ethyl
i-Pr: isopropyl
DMSO: dimethylsulfoxide
Pd—C: palladium carbon
THF: tetrahydrofuran
DMF: N,N-dimethylformamide
mCPBA: meta-Chloroperoxybenzoic acid

EXAMPLE

Example 1

Synthesis of Compound (Ii-1)

Step 1

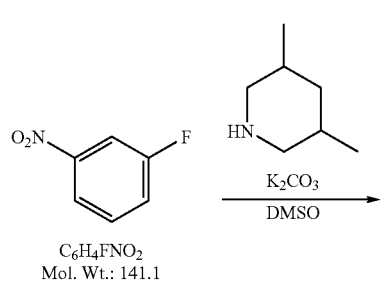

[Formula 51]

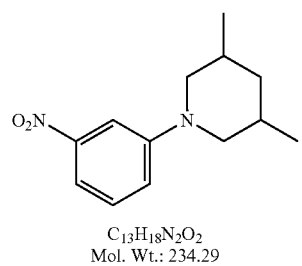

$C_{13}H_{18}N_2O_2$
Mol. Wt.: 234.29

3-fluoronitrobenzene (2.00 g, 14.2 mmol) was dissolved in dimethylsulfoxide (15 ml). 3,5-dimethylpiperidine (3.21 g, 28.4 mmol) and potassium carbonate (3.92 g, 28.4 mmol) were added thereto and the mixture was stirred for 3 hours at 150° C. The reactant was poured into water and extracted with ethyl acetate. The organic layer was washed with water and dried over sodium sulphate anhydrous. The solvent was removed under reduced pressure. Ethyl acetate and hexane were added to the residue. The precipitated crystals were collected with filtration to give the desired substituted nitrobenzene (2.05 g, 62% yield).

1H-NMR (CDCl3) δppm: 0.76 (q, 1H, J=12.0 Hz), 0.96 (d, 6H, J=6.3 Hz), 1.70-1.91 (m, 3H), 2.32 (t, 2H, J=12.0 Hz), 3.62-3.72 (m, 2H), 7.17-7.25 (m, 1H), 7.34 (t, 1H, J=8.1 Hz), 7.59 (d, 1H, J=8.1 Hz), 7.71 (s, 1H).

Step 2

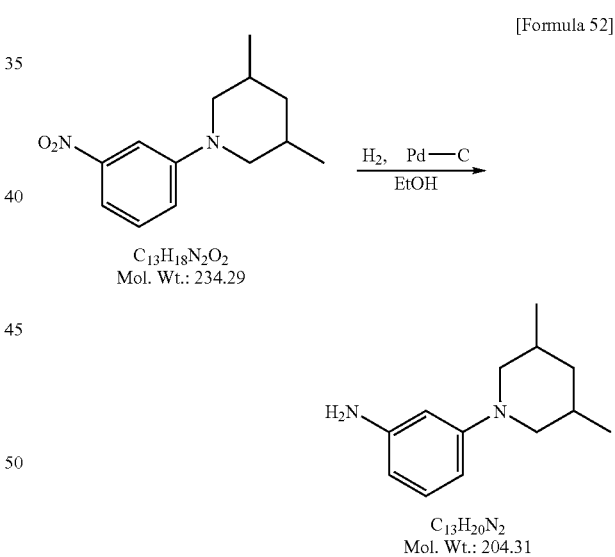

[Formula 52]

The compound obtained in Step 1 (2.05 g, 8.75 mmol) was dissolved in ethanol (25 ml) and 10% Pd—C (0.20 g) was added thereto to carry the hydrogenation reaction for 12 hours. Pd—C was removed by celite filtration and the filtrate was condensed under reduced pressure. The residue was purified by silica gel chromatography to give the desired aniline (1.62 g, 90% yield).

1H-NMR (CDCl3) δppm: 0.69 (q, 1H, J=12.0 Hz), 0.92 (d, 6H, J=6.3 Hz), 1.75-1.98 (m, 3H), 2.22 (t, 2H, J=12.0 Hz), 3.53-3.62 (m, 2H), 6.21 (d, 1H, J=7.5 Hz), 6.38 (s, 1H), 6.42 (d, 1H, J=8.1 Hz), 7.04 (t, 1H, J=8.1 Hz).

Step 3

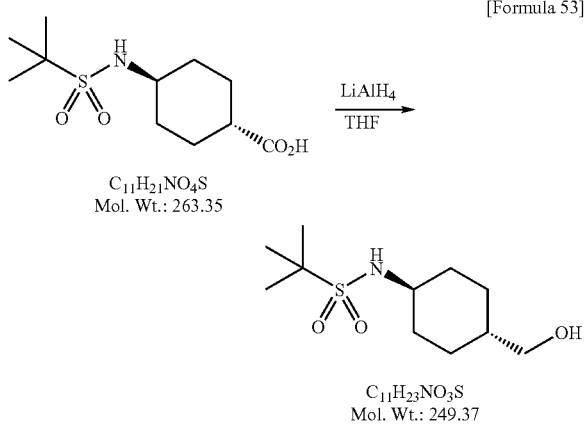

Carboxylic acid (the synthesis method was described in WO01/037826) (5.04 g, 19.1 mmol) was suspended in tetrahydrofuran (50 ml) and lithium aluminum hydride (0.726 g, 19.1 mmol) was added thereto under ice-cooling. The mixture was stirred at room temperature for 1 hour and under ice-cooling and water (1.5 mL) was carefully added dropwise. After that, the mixture was stirred at room temperature for 5 minutes and the generated deposit was removed by filtration. The filtrate was condensed under reduced pressure. Ethyl acetate and hexane were added to the residue. The precipitated crystals were collected with filtration to give the desired alcohol (3.15 g, 66% yield).

1H-NMR (DMSO-d6) δppm: 0.88 (q, 2H, J=11.6 Hz), 1.25 (s, 9H), 1.15-1.30 (m, 3H), 1.67-1.76 (m, 2H), 1.83-1.92 (m, 2H), 2.97 (m, 1H), 3.13-3.20 (m, 2H), 4.35 (t, 1H, J=5.2 Hz), 6.71 (d, 1H, J=8.8 Hz).

Step 4

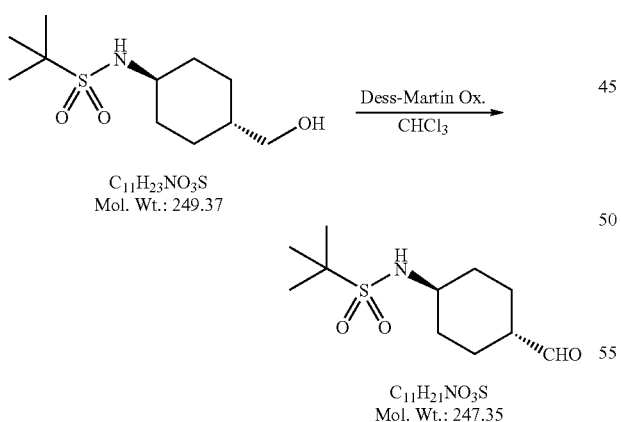

The compound obtained in Step 3 (500 mg, 2.01 mmol) was dissolved in chloroform (5 ml) and Dess-Martin periodinane (893 mg, 2.11 mmol) was added thereto. The mixture was stirred at room temperature for 1 hour. The deposit was removed by filtration, the filtrate was condensed under reduced pressure. The residue was purified by silica gel chromatography to give the desired aldehyde (385 mg, 77% yield).

1H-NMR (DMSO-d6) δppm: 1.26 (s, 9H), 1.13-1.38 (m, 4H), 1.85-1.98 (m, 4H), 2.16 (m, 1H), 3.01 (m, 1H), 6.80 (d, 1H, J=8.0 Hz), 9.54 (s, 1H).

Step 5

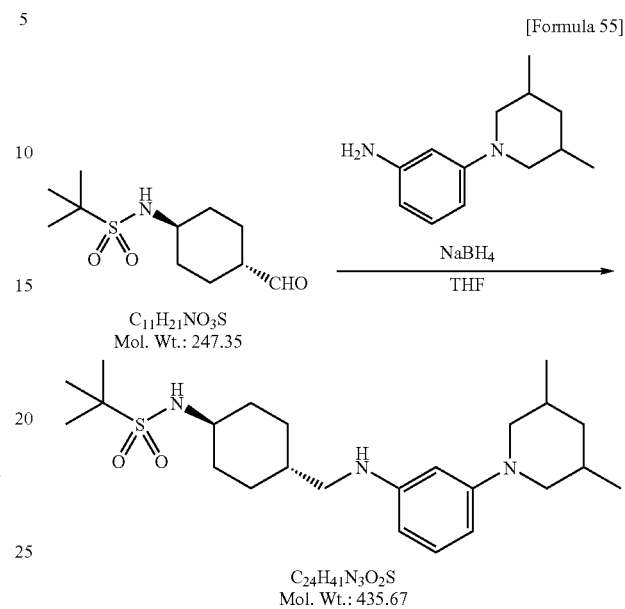

Aniline obtained in Step 2 (107 mg, 0.523 mmol) was dissolved in tetrahydrofuran (3 ml). Aldehyde obtained in Step 4 (130 mg, 0.523 mmol) was added thereto and the mixture was stirred at room temperature for 1 hour. To the reactant, was added sodium borohydride (23.7 mg, 0.628 mmol) and the mixture was stirred at room temperature for 3 hours. The reactant was poured into water and extracted with ethyl acetate. The organic layer was washed with water and dried over sodium sulphate anhydrous. The solvent was removed under reduced pressure and the residue was purified by silica gel chromatography to give the desired compound (99.3 mg, yield 43%).

1H-NMR (DMSO-d6) δppm: 0.64 (q, 1H, J=11.6 Hz), 0.87 (d, 6H, J=6.0 Hz), 0.92-1.08 (m, 2H), 1.25 (s, 9H), 1.15-1.32 (m, 2H), 1.41 (m, 1H), 1.58-1.95 (m, 7H), 2.08 (t, 2H, J=11.6 Hz), 2.75-2.82 (m, 2H), 3.00 (m, 1H), 3.48-3.55 (m, 2H), 5.31 (m, 1H), 5.94 (d, 1H, J=8.5 Hz), 6.08-6.13 (m, 2H), 6.71 (d, 1H, J=8.5 Hz), 6.85 (t, 1H, J=8.5 Hz). Melting point: 161 to 162° C.

Example 2

Synthesis of Compound (Ij-1)

Step 1

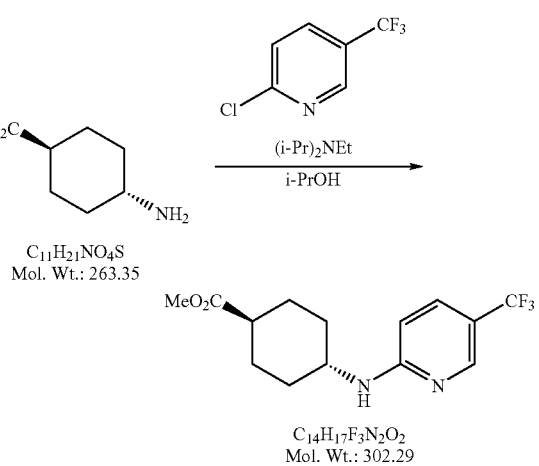

Amine (1.20 g, 3.64 mmol) and 2-chloro-5-trifluoromethylpyridin (727 mg, 4.01 mmol) was suspended in isopropanol (4 ml) and N,N-diisopropylethylamine (1.87 ml, 10.9 mmol) was added thereto. After the mixture was in sealed tubes and the reaction was carried out by a microwave reactor for 1 hour at 160° C. The reactant was poured into water and extracted with ethyl acetate. The organic layer was washed with water and dried over sodium sulphate anhydrous. The solvent was removed under reduced pressure and the residue was purified by silica gel chromatography to give the desired ester (222 mg, 20% yield).

Step 2

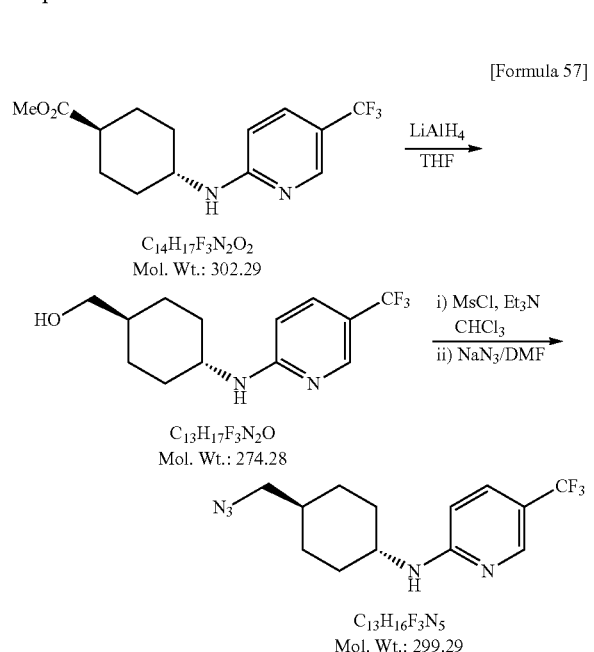

Ester obtained in Step 1 (207 mg, 0.685 mmol) was dissolved in tetrahydrofuran (3 ml). Lithium aluminum hydride (31.1 mg, 0.822 mmol) was added thereto under ice-cooling and the mixture was stirred at room temperature for 0.5 hour. The reactant was poured into iced water and extracted with ethyl acetate. The organic layer was washed with water and dried over sodium sulphate anhydrous. The solvent was removed under reduced pressure to give alcohol. The obtained alcohol was dissolved in chloroform (3 ml). Triethylamine (0.28 ml, 2.04 mmol) was added thereto and methanesulfonyl chloride (0.12 ml, 1.64 mmol) was added dropwise under ice-cooling. The mixture was stirred at room temperature for 1 hour. The reactant was poured into water and extracted with ethyl acetate. The organic layer was washed with water and dried over sodium sulphate anhydrous. The solvent was removed under reduced pressure to give mesylate. The obtained mesylate was dissolved in dimethylformamide (3 ml) and sodium azide (221 mg, 3.40 mmol) was added thereto. The mixture was stirred for 3 hours at 100° C. The reactant was poured into water and extracted with ethyl acetate. The organic layer was washed with water and dried over sodium sulphate anhydrous. The solvent was removed under reduced pressure. The residue was purified by silica gel chromatography to give the desired azide (178 mg, 87% yield).

Step 3

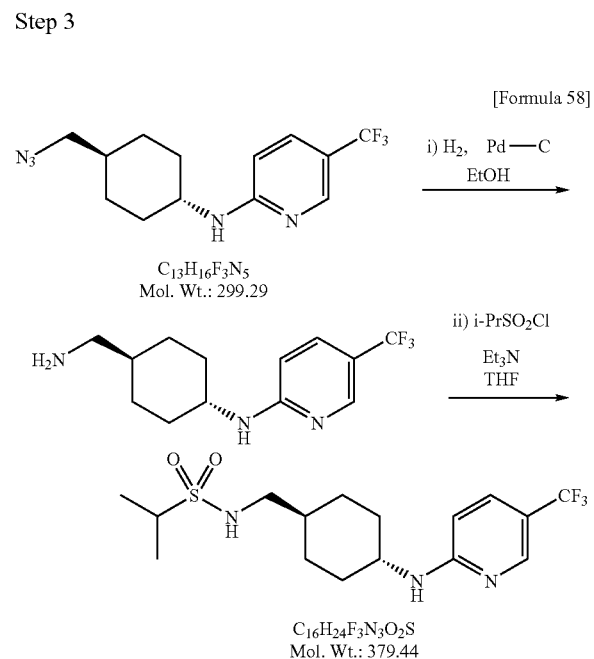

Azide (178 mg, 0.595 mmol) obtained in Step 2 was dissolved in ethanol (3 ml) and 10% Pd—C (30 mg) was added thereto to carry the hydrogenation reaction for 4 hours. Pd—C was removed by celite filtration and the filtrate was condensed under reduced pressure to give amine.

The obtained amine was dissolved in tetrahydrofuran (3 ml) and triethylamine (0.28 ml, 0.714 mmol) was added thereto. Isopropyl sulfonyl chloride (0.10 ml, 1.64 mmol) was added dropwise under ice-cooling and the mixture was stirred for 1 hour. The reactant was poured into water and extracted with ethyl acetate. The organic layer was washed with water and dried over sodium sulphate anhydrous. The solvent was removed under reduced pressure. The residue was purified by silica gel chromatography to give the desired compound (64.8 mg, 29% yield).

1H-NMR (DMSO-d6) δ: 0.92-1.06 (m, 2H), 1.10-1.25 (m, 2H), 1.22 (d, 6H, J=6.4 Hz), 1.38 (m, 1H), 1.76-1.84 (m, 2H), 1.93-2.02 (m, 2H), 2.81 (t, 2H, J=6.0 Hz), 3.08-3.19 (m, 1H), 3.69 (m, 1H), 6.53 (d, 1H, J=8.8 Hz), 6.95 (t, 1H, J=5.6 Hz), 7.16 (d, 1H, J=7.6 Hz), 7.58 (d, 1H, J=8.8 Hz), 8.26 (s, 1H)
Melting point: 155 to 156° C.

Example 3

Synthesis of Compound (Ij-1)

Step 1

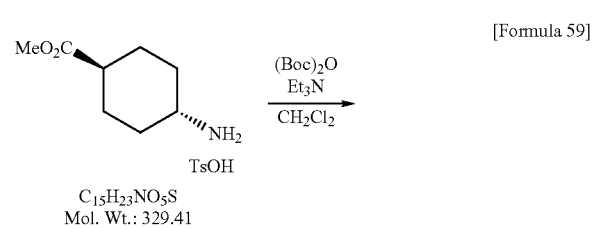

-continued

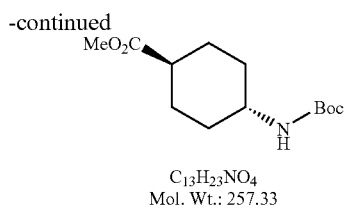

C₁₃H₂₃NO₄
Mol. Wt.: 257.33

Amine (132 g, 401 mmol) was suspended in dichloromethane (1000 ml) under ice-cooling. Triethylamine (123 ml, 882 mmol) and (Boc)2O (101 ml, 440 mmol) were sequentially added thereto and stirred for 10 minutes. After that, the mixture was stirred at room temperature for 2 hours and the solvent was removed. The residue was poured into aqueous citric acid (citric acid monohydrate 50 g in water 400 ml) to become pH4 and extracted with ethyl acetate. The organic layer was washed with water and dried over magnesium sulfate anhydrous. The solvent was removed under reduced pressure to quantitatively give the target compound.

1H-NMR (DMSO-d6) δppm: 1.06-1.25 (m, 2H), 1.25-1.43 (m, 2H), 1.37 (s, 9H), 1.75-1.94 (m, 4H), 2.19 (tt, 1H, J=11.7, 3.9 Hz), 3.07-3.24 (m, 1H), 3.58 (s, 3H), 6.74 (d, 1H, J=6.6 Hz).

Step 2

[Formula 60]

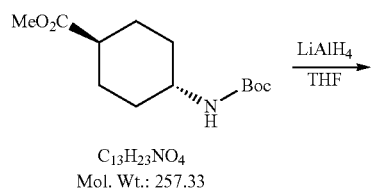

Lithium aluminum hydride (18.3 g, 483 mmol) was suspended in tetrahydrofuran (800 ml) and ester in tetrahydrofuran (300 ml) obtained in Step 1 was slowly added thereto under ice-cooling with stirring over 1 hour. The mixture was stirred under ice-cooling for 10 minutes and at room temperature for 2.5 hours. The reactant was ice-cooled and the mixture of water and tetrahydrofuran (1:1, 36 ml), 2N aqueous sodium hydroxide (18 ml) and water (18 ml) were sequentially added thereto. The mixture was stirred for 20 minutes and at room temperature for 1.5 hours. The deposit was removed by filtration, the filtrate was condensed under reduced pressure. Ethyl acetate and hexane was added to the residue. The precipitated crystals were collected with filtration to give the desired alcohol (79.5 g, 87% yield) (through Step 1 to 2).

1H-NMR (DMSO-d6) δppm: 0.78-1.00 (m, 2H), 1.00-1.32 (m, 3H), 1.37 (s, 9H), 1.65-1.84 (m, 4H), 3.04-3.24 (m, 3H), 4.32-4.42 (m, 1H), 6.66 (d, 1H, J=7.8 Hz).

Step 3

[Formula 61]

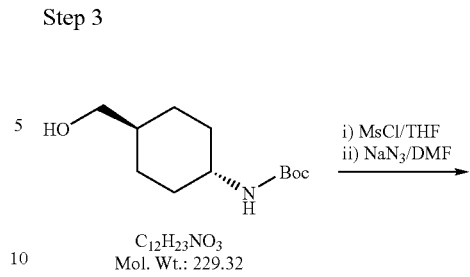

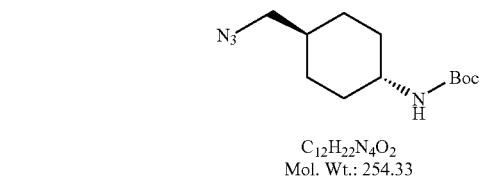

Alcohol (79.5 g, 347 mmol) was dissolved in tetrahydrofuran (800 ml). Triethylamine (72.5 ml, 520 mmol) and methanesulfonyl chloride (32.2 ml, 416 mmol) were sequentially added thereto under ice-cooling with stirring and the mixture was stirred for 1.5 hours. The reactant was poured into aqueous citric acid (citric acid monohydrate 30 g in water 500 ml) to become pH4 and extracted with ethyl acetate. The organic layer was washed with water and dried over magnesium sulfate anhydrous. The solvent was removed under reduced pressure. The crystal deposited in the removal process was collected by filtration and washed with hexane to give mesylate (100 g). The obtained mesylate was dissolved in dimethylformamide (100 ml) and sodium azide (63.7 g, 980 mmol) was added thereto and reacted at 80° C. for 2 hours. The reactant was poured into water and extracted with ethyl acetate. The organic layer was washed with water and dried over magnesium sulfate anhydrous and the solvent was removed under reduced pressure to quantitatively give the desired azide (the crude weight is 85.4 g).

1H-NMR (DMSO-d6) δppm: 0.90-1.21 (m, 4H), 1.32-1.50 (m, 1H), 1.37 (s, 9H), 1.65-1.84 (m, 4H), 3.06-3.24 (m, 3H), 6.71 (d, 1H, J=8.1 Hz).

Step 4

[Formula 62]

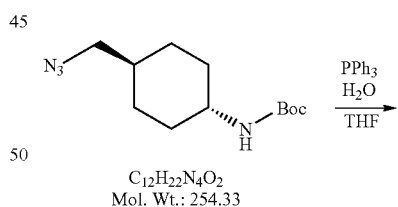

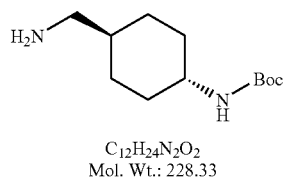

Azide obtained in Step 3 was dissolved in tetrahydrofuran (900 ml) at room temperature. Triphenylphosphine (103 g, 392 mmol) and water (90 ml) were sequentially added thereto and stirred at 80° C. for 1.5 hours. The solvent (770 ml) was removed and water (300 ml), ethyl acetate (400 ml) and 2N hydrochloric acid (150 ml) were sequentially added to become pH 2.5 and liquid-liquid extraction was carried out.

The organic layer was extracted with 2N hydrochloric acid and the water layer was added thereto. The mixture was washed with ethyl acetate and 2N sodium hydroxide was added to alkalinize and repeatedly extracted with ethyl acetate and chloroform. The organic layer was added thereto and dried over magnesium sulfate anhydrous. The solvent was removed under reduced pressure and hexane was added to the residue. The precipitated crystals were collected with filtration and washed with hexane to give the desired amine (41.7 g, 53% yield) (through Step 3 to 4).

1H-NMR (DMSO-d6) δppm: 0.77-0.96 (m, 2H), 1.00-1.18 (m, 3H), 1.37 (s, 9H), 1.67-1.82 (m, 4H), 2.30-2.38 (m, 2H), 2.90-3.60 (m, 2H), 3.05-3.22 (m, 1H), 6.66 (d, 1H, J=7.2 Hz).

Step 5

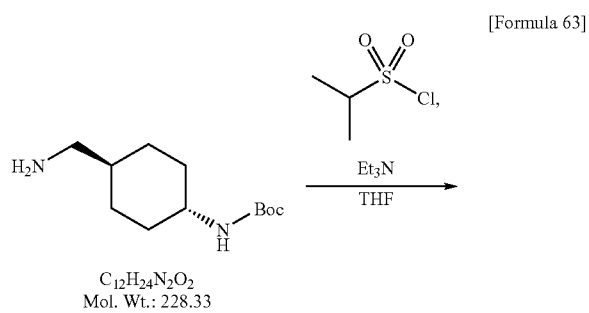

Amine (37.5 g, 164 mmol) was suspended in tetrahydrofuran (400 ml). Triethylamine (91.7 ml, 656 mmol) and isopropyl sulfonyl chloride (32.2 ml, 416 mmol) were slowly and sequentially added thereto at −55 to −40° C. with stirring. The mixture was stirred for 6 hours with gradually warming to 0° C. The reactant was poured into the ice-cooled dilute aqueous acid and extracted with ethyl acetate. The organic layer was washed with water and dried over magnesium sulfate anhydrous. The solvent was removed under reduced pressure and isopropyl ether was added to the residue. The precipitated crystals were collected with filtration and washed with isopropyl ether to give the desired sulfonamide (43.1 g, 79% yield).

1H-NMR (DMSO-d6) δppm: 0.79-0.98 (m, 2H), 1.00-1.36 (m, 3H), 1.20 (d, 6H, J=6.6 Hz), 1.37 (s, 9H), 1.70-1.84 (m, 4H), 2.72-2.80 (m, 2H), 3.04-3.22 (m, 2H), 6.68 (d, 1H, J=8.1 Hz), 6.94 (t, 1H, J=6.0 Hz).

Step 6

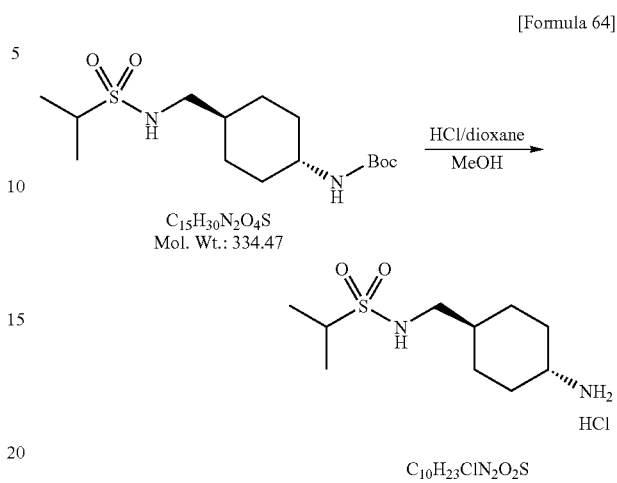

Boc-protected amine (43.0 g, 128 mmol) was suspended in methanol (200 ml) and 4N hydrochloric acid in dioxane (96 ml, 384 mmol) was added thereto under ice-cooling with stirring for 20 minutes and at room temperature for 3 hours. The reactant was ice-cooled and isopropyl ether (220 ml) was added thereto. After stirring for 30 minutes, the precipitated crystals were collected with filtration and washed with isopropyl ether to give the desired amine hydrochloride (30.8 g, 89% yield).

1H-NMR (DMSO-d6) δppm: 0.85-1.02 (m, 2H), 1.20 (d, 6H, J=6.6 Hz), 1.20-1.40 (m, 3H), 1.75-1.84 (m, 2H), 1.90-2.00 (m, 2H), 2.73-2.82 (m, 2H), 2.83-2.97 (m, 1H), 3.08-3.20 (m, 1H), 7.01 (t, 1H, J=5.7 Hz), 8.01 (s, 3H).

Step 7

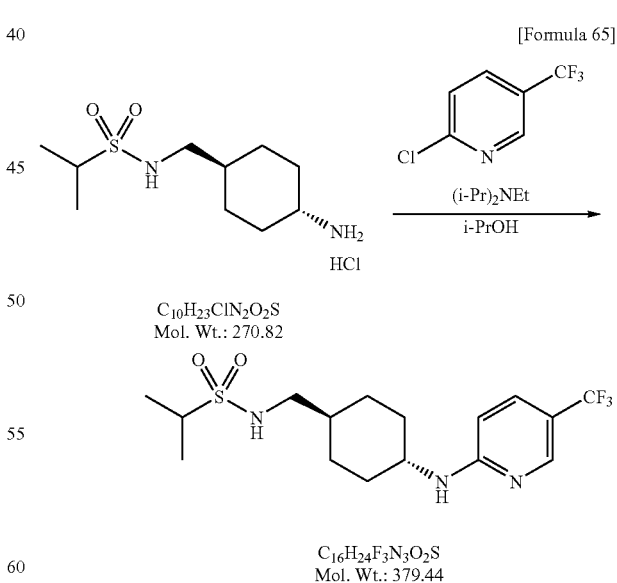

Amine (190 mg, 0.700 mmol) and 2-chloro-5-trifluoromethyl pyridin (1.27 g, 7.00 mmol) were suspended in N-methyl pyrrolidone (4 ml) and N,N-diisopropyl ethyl amine (1.25 ml, 7.00 mmol) was added thereto. After the mixture was in sealed tubes and the reaction was carried out by a microwave reactor for 20 minutes at 210° C. The reactant was poured into water and extracted with ethyl acetate. The organic layer was washed with water and dried over sodium sulphate anhydrous. The solvent was removed under reduced pressure and the residue was purified by silica gel chromatography to give the desired Compound (Ij-1) (158 mg, 60% yield).

In Step 5, ethanesulfonyl chloride instead of isopropyl sulfonyl chloride was reacted to give the following compound wherein $R^1$ is ethyl.

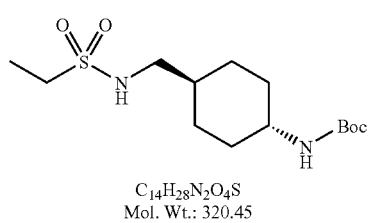

[Formula 66]

$C_{14}H_{28}N_2O_4S$
Mol. Wt.: 320.45

1H-NMR (DMSO-d6) δppm: 0.80-0.98 (m, 2H), 1.02-1.18 (m, 2H), 1.17 (t, 3H, J=7.2 Hz), 1.22-1.34 (m, 1H), 1.37 (s, 9H), 1.68-1.82 (m, 4H), 2.68-2.78 (m, 2H), 2.96 (q, 2H, J=7.2 Hz), 3.04-3.22 (m, 1H), 6.68 (d, 1H, J=8.1 Hz), 6.94 (t, 1H, J=6.0 Hz).

In Step 5, tert-butyl sulfinylchloride instead of isopropyl sulfonyl chloride was reacted and the oxidation with mCPBA was carried out to give the following compound wherein $R^1$ is tert-butyl (WO2001037826, Example 3).

[Formula 67]

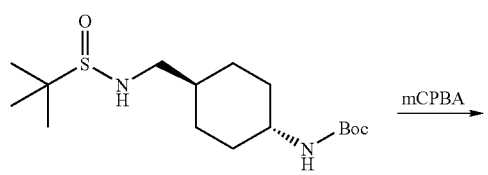

mCPBA →

$C_{16}H_{32}N_2O_4S$
Mol. Wt.: 348.5

1H-NMR (DMSO-d6) δppm: 0.79-1.00 (m, 2H), 1.01-1.20 (m, 2H), 1.22-1.34 (m, 1H), 1.25 (s, 9H), 1.37 (s, 9H), 1.70-1.86 (m, 4H), 2.81-2.90 (m, 2H), 3.04-3.22 (m, 1H), 6.68 (d, 1H, J=8.1 Hz), 6.83 (t, 1H, J=6.0 Hz).

The following compounds wherein $R^1$ is ethyl or tert-butyl was obtained in Step 6 by using the above compound.

A Compound Wherein $R^1$ is Ethyl.

[Formula 68]

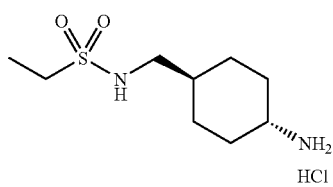

HCl $C_9H_{21}ClN_2O_2S$
Mol. Wt.: 256.79

H-NMR (DMSO-d6) δppm: 0.84-1.02 (m, 2H), 1.18 (t, 3H, J=7.5 Hz), 1.20-1.40 (m, 3H), 1.74-1.82 (m, 2H), 1.90-2.00 (m, 2H), 2.72-2.80 (m, 2H), 2.83-2.96 (m, 1H), 2.97 (q, 2H, J=7.5 Hz), 7.04 (t, 1H, J=6.0 Hz), 8.03 (s, 3H).

A Compound Wherein $R^1$ is Tert-Butyl

[Formula 69]

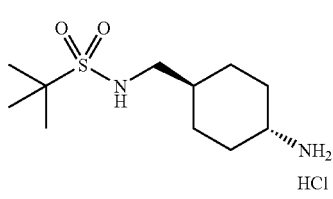

HCl $C_{11}H_{25}ClN_2O_2S$
Mol. Wt.: 284.85

H-NMR (DMSO-d6) δppm: 0.84-1.04 (m, 2H), 1.16-1.38 (m, 3H), 1.26 (s, 9H), 1.74-1.84 (m, 2H), 1.92-2.02 (m, 2H), 2.82-2.98 (m, 3H), 6.90 (d, 1H, J=6.0 Hz), 8.01 (s, 3H).

The following compounds synthesized in similar methods also include the present invention.

[Formula 70]

I-1

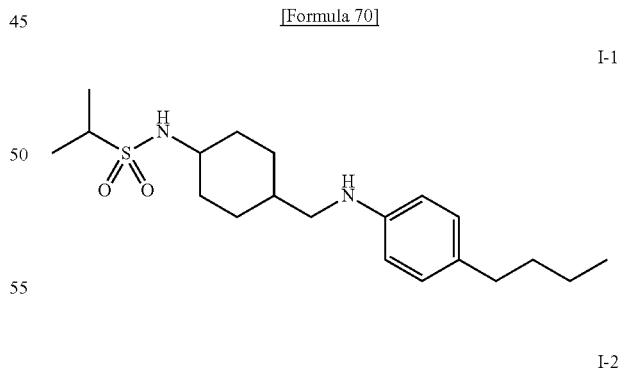

I-2

I-3
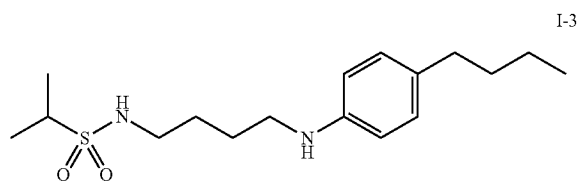
I-4
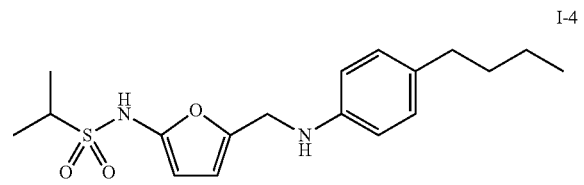
I-5

I-6
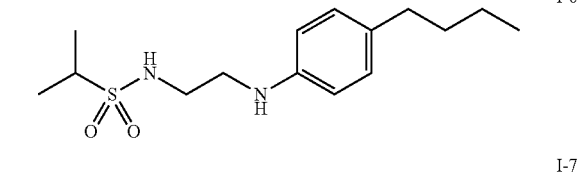
I-7
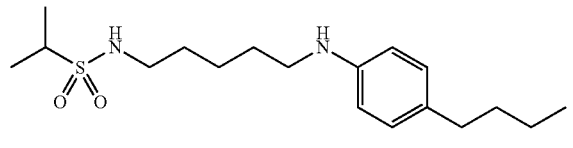
I-8
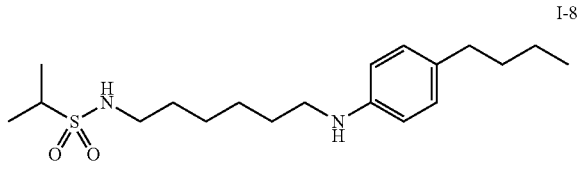
I-9
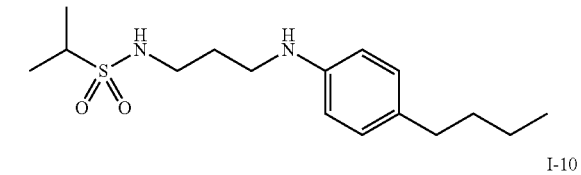
I-10
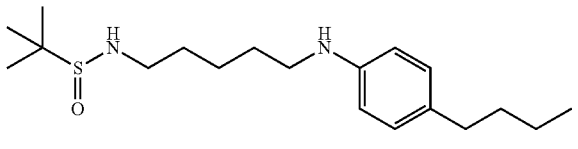
I-11
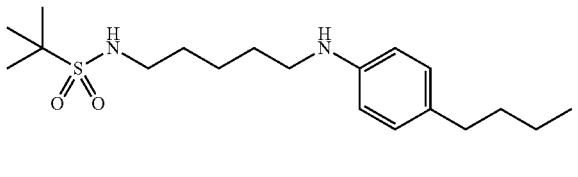
I-12
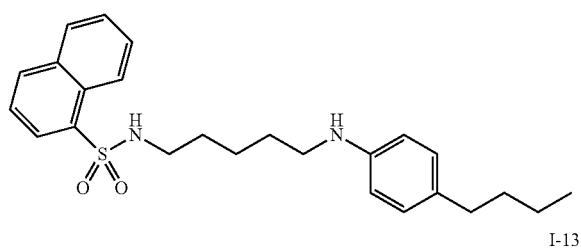
I-13
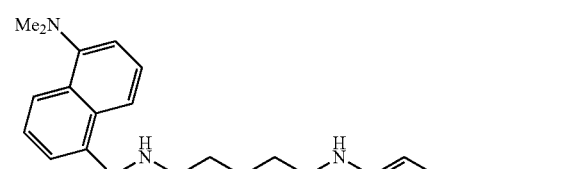
I-14

I-15
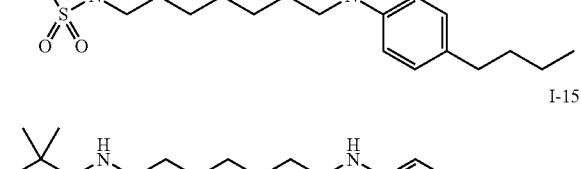
I-16

I-17
I-18

I-19

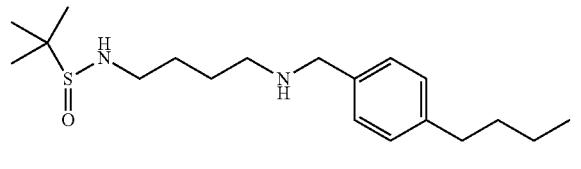

I-20 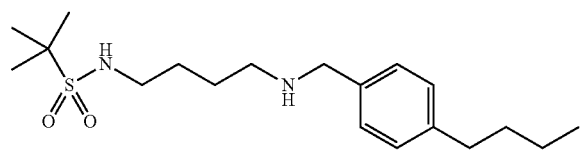
I-21 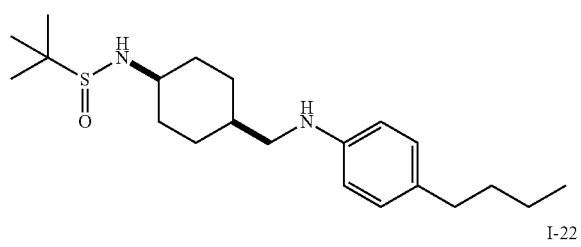
I-22 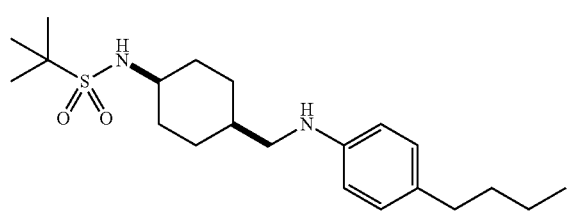
[Formula 71]
I-23 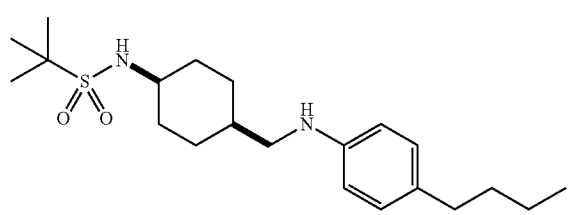
I-24 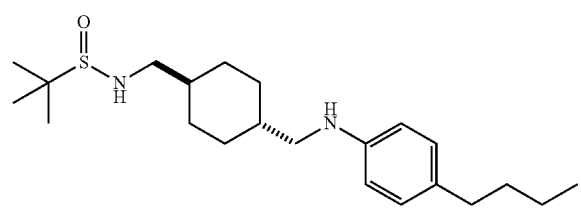
I-25 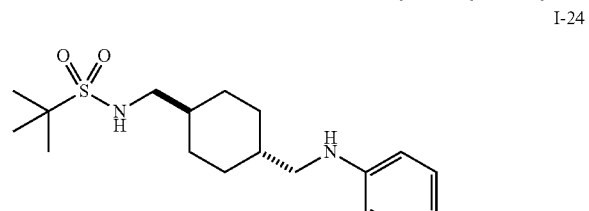
I-26 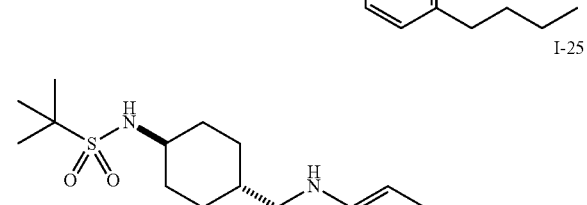
I-27 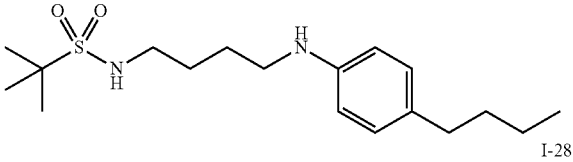
I-28 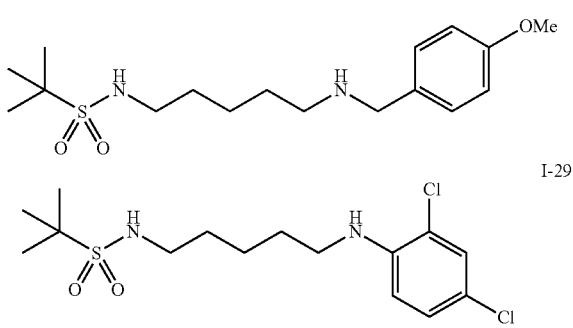
I-29 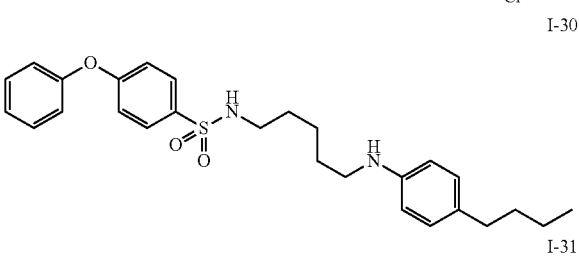
I-30 
I-31 
I-32 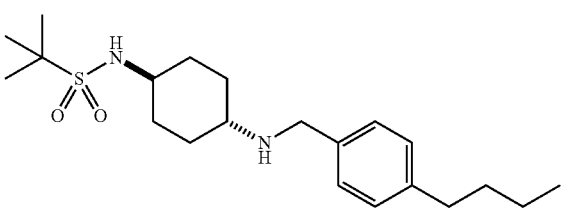
I-33 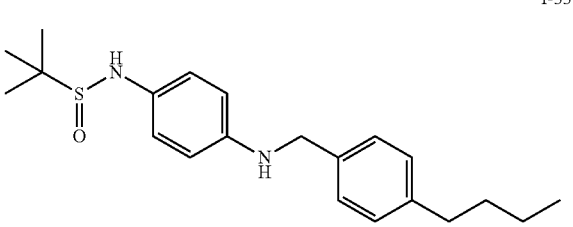
I-34 
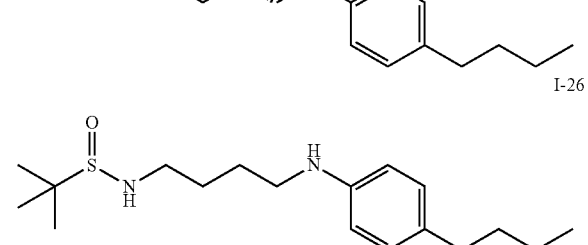

I-35
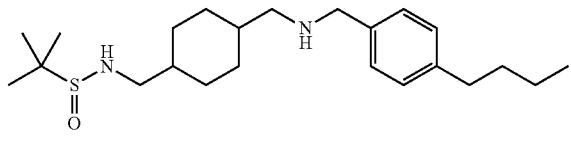
I-36
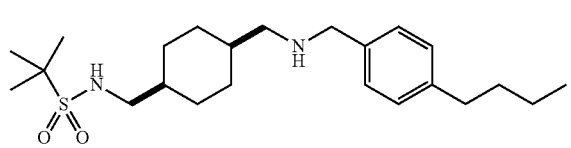
I-37
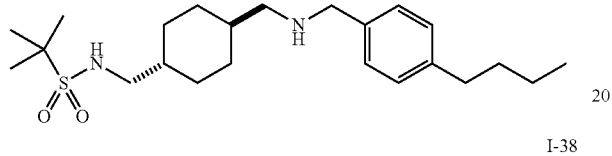
I-38

I-39
I-40
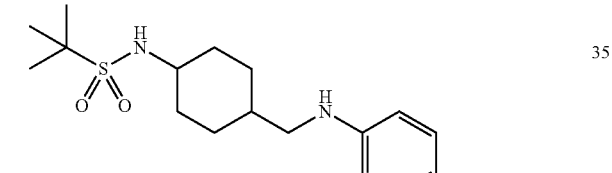
I-41

I-42
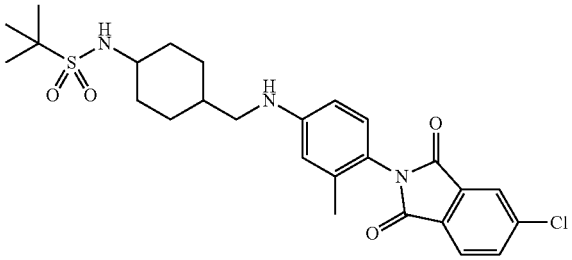
I-43
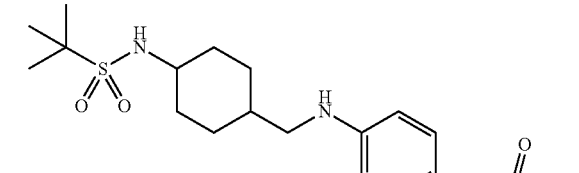
I-44
[Formula 72]
I-45
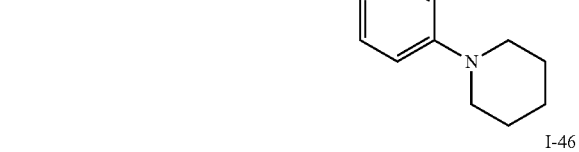
I-46
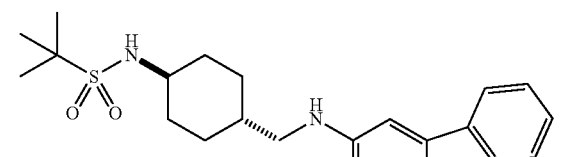

I-47
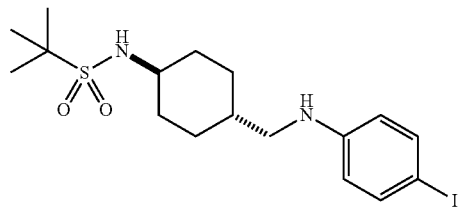
I-48
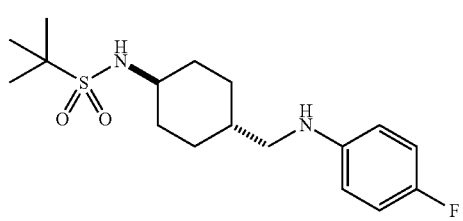
I-49
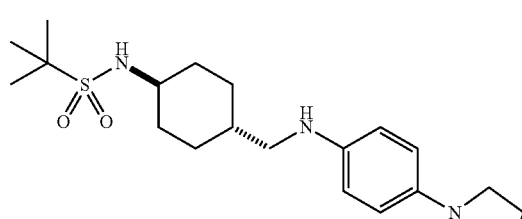
I-50
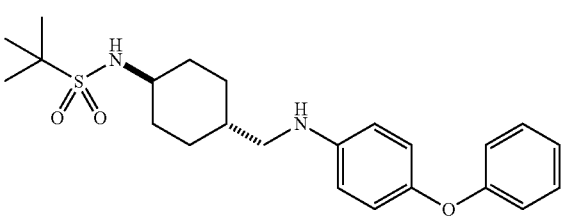
I-51
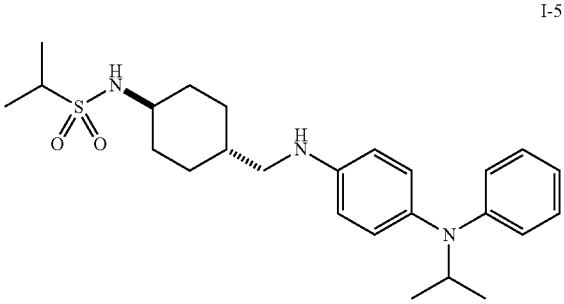
I-52
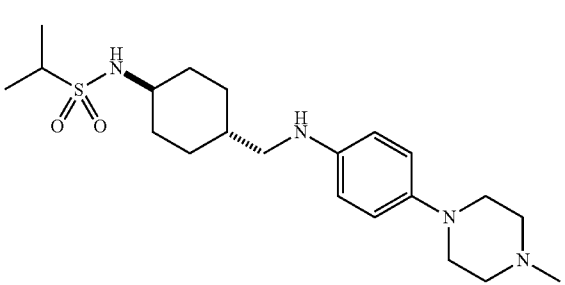
I-53
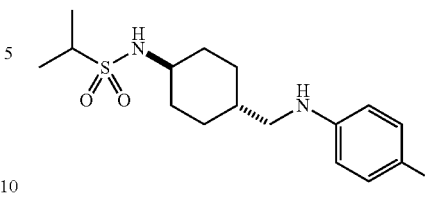
I-54
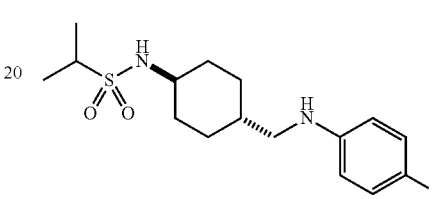
I-55

I-56
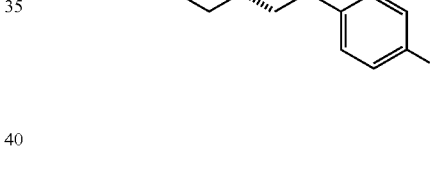
I-57
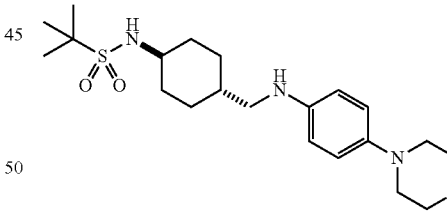
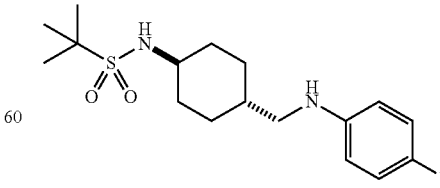

I-58
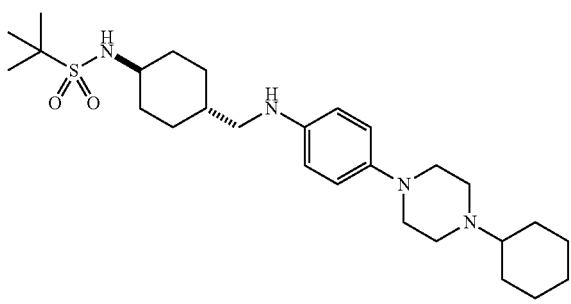
I-59
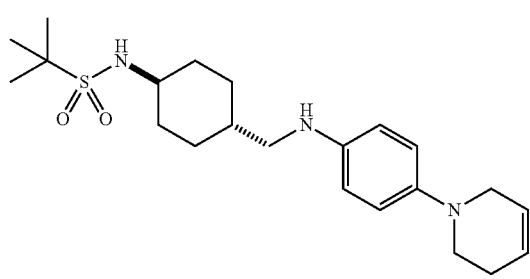
I-60
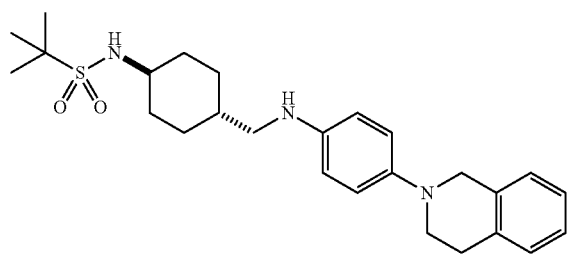
I-61
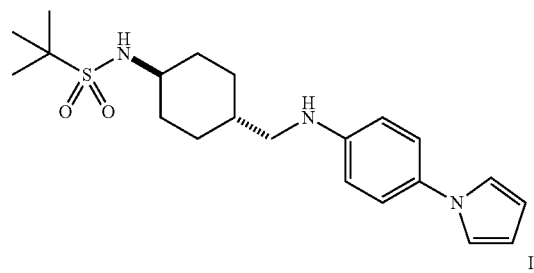
I-62
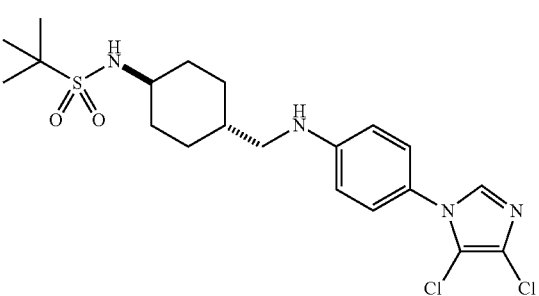
I-63
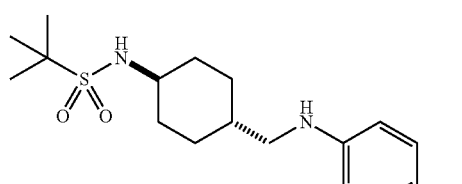
I-64
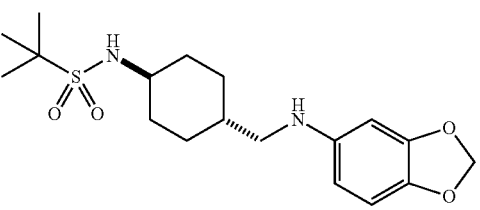
I-65
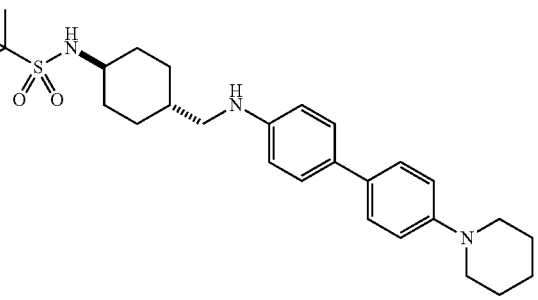
I-66
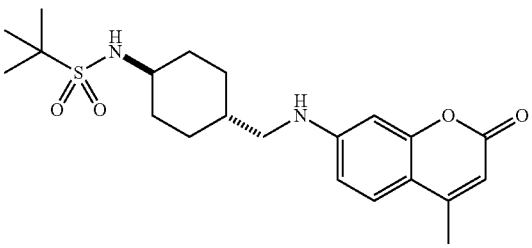
[Formula 73]
I-67
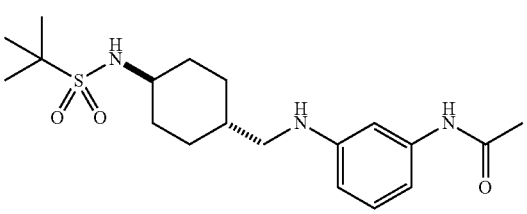
I-68
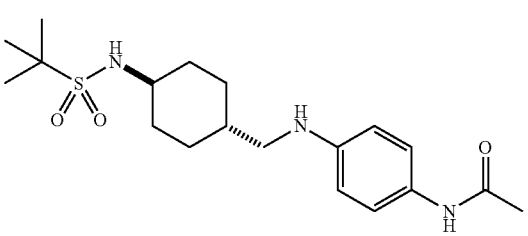

I-69
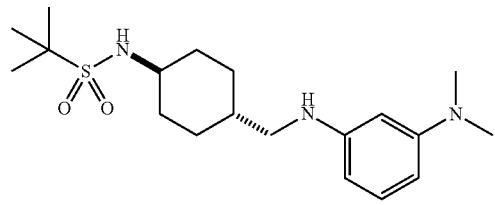
I-70
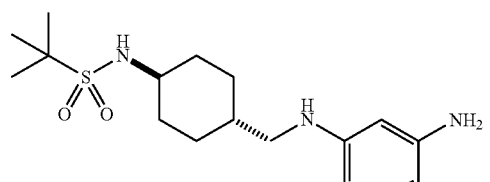
I-71
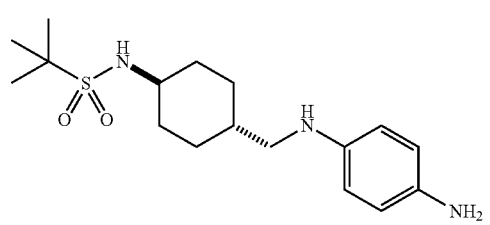
I-72
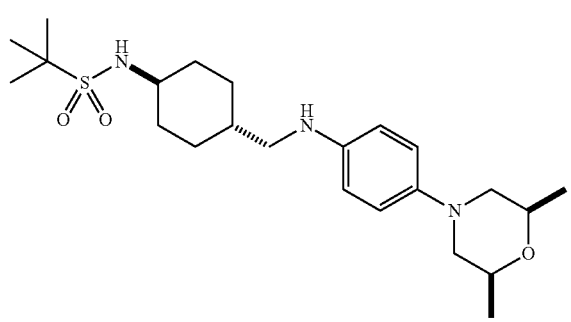
I-73
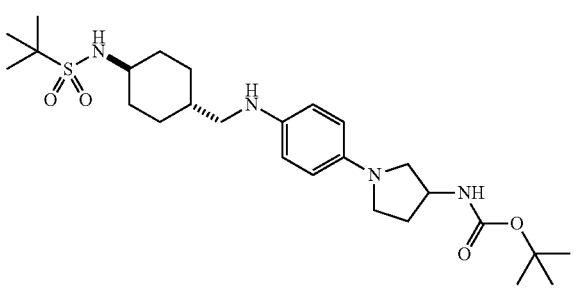
I-74
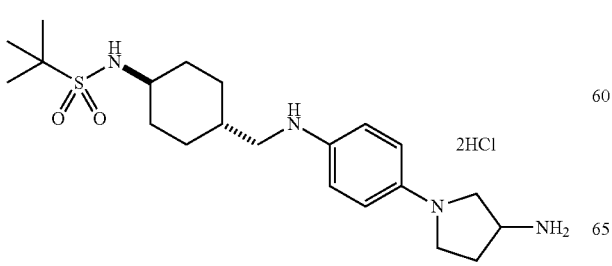
2HCl
I-75
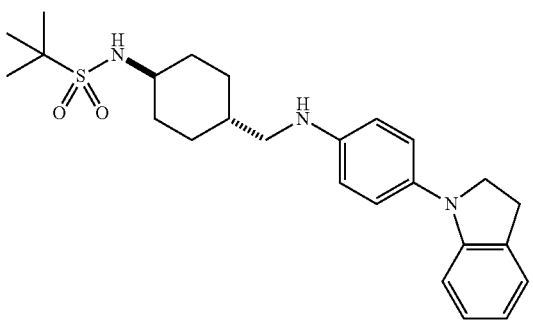
I-76
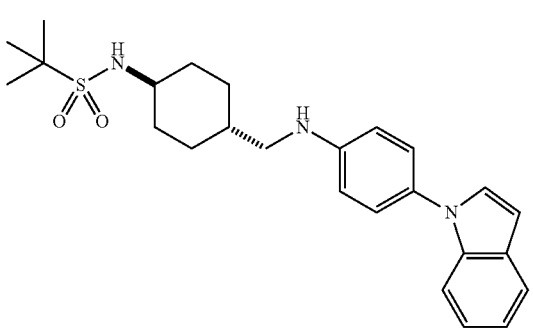
I-77
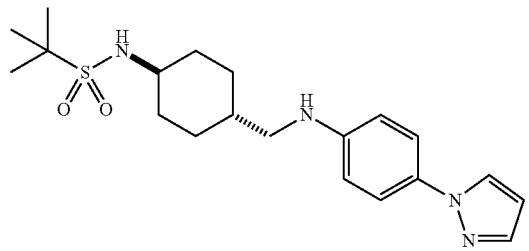
I-78
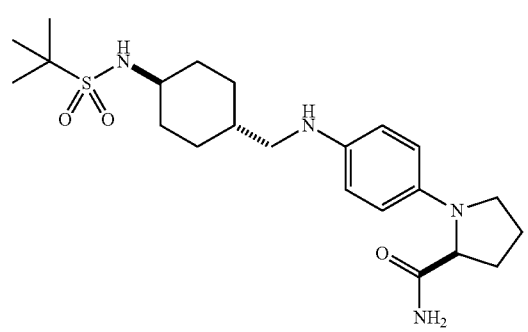
I-79
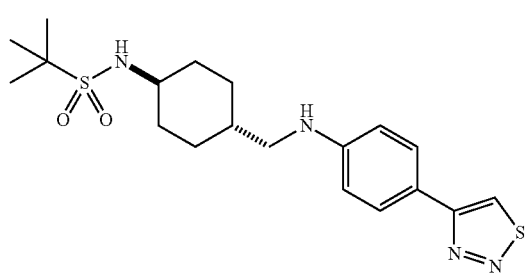

I-80
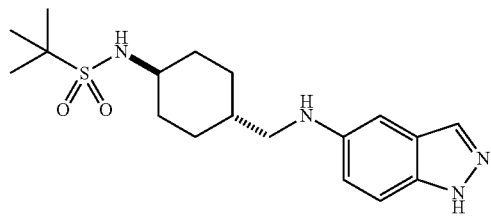
I-81
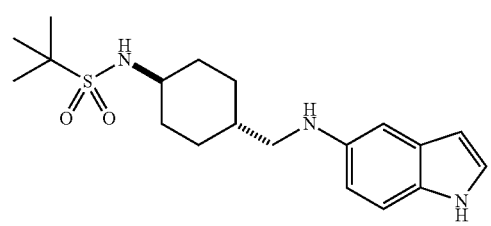
I-82
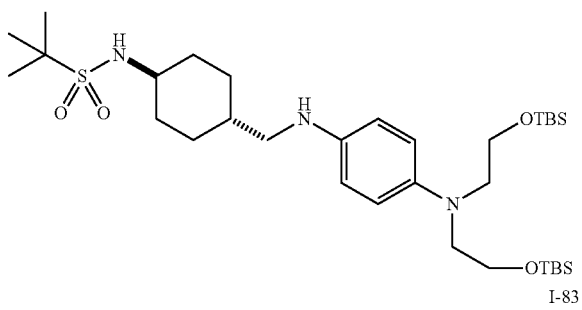
I-83
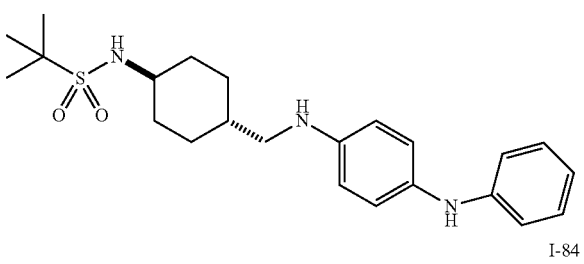
I-84
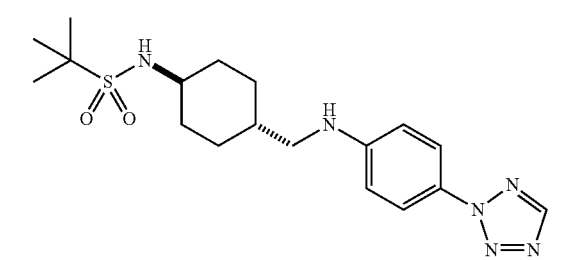
I-85
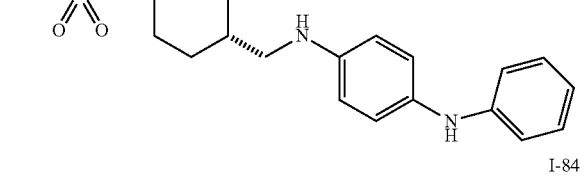
I-86
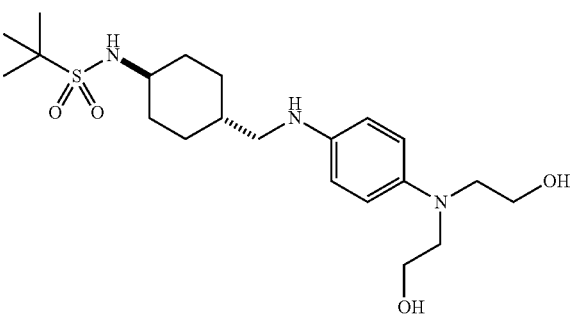
I-87
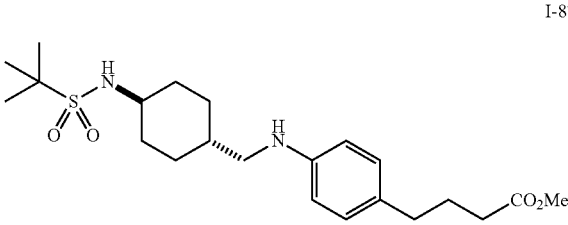
I-88
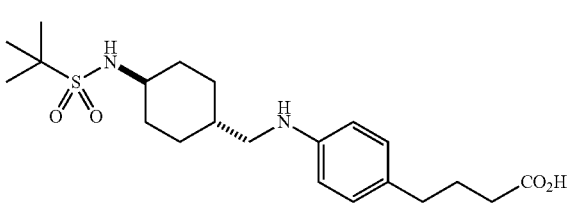
I-89
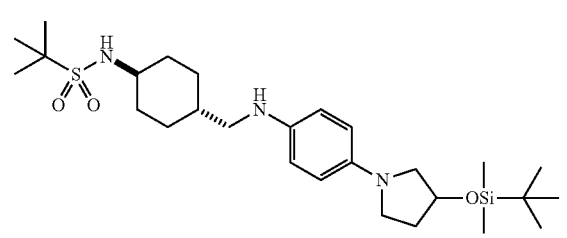
I-90
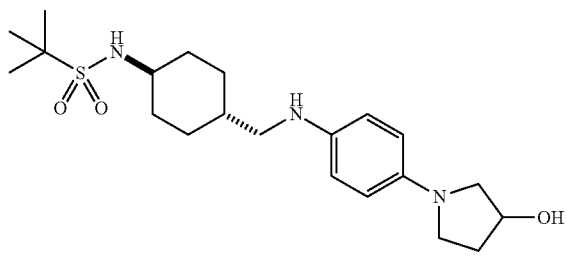
[Formula 74]
I-91
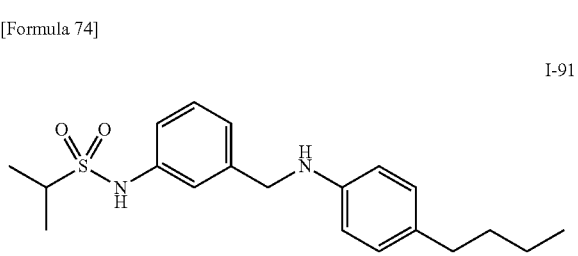

I-92
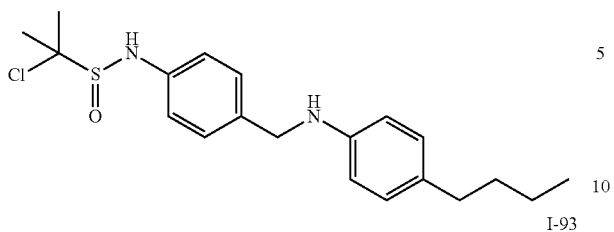
I-93
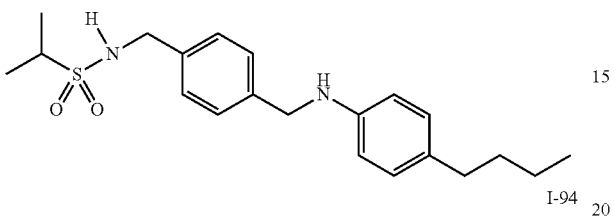
I-94

I-95

I-96

I-97
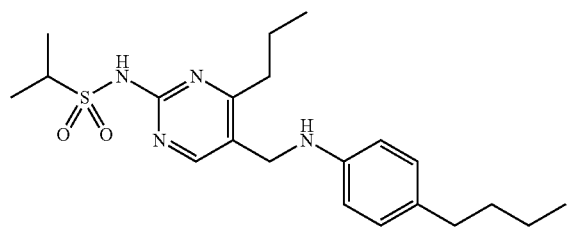
I-98
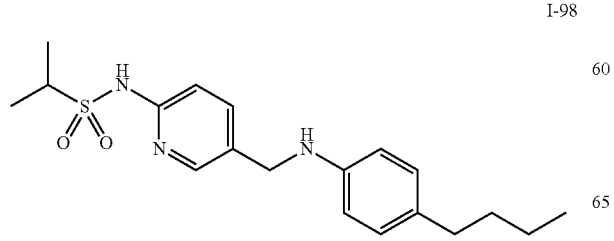
I-99
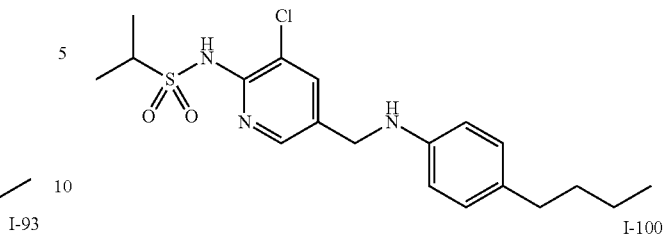
I-100
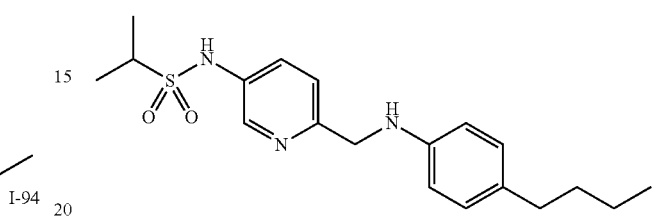
I-101

I-102
I-103

I-104

I-106
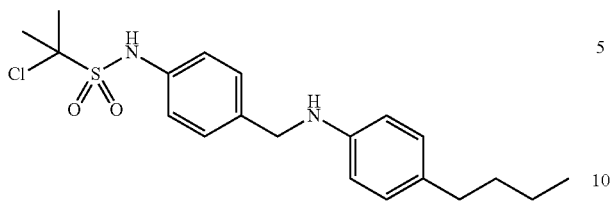
I-107
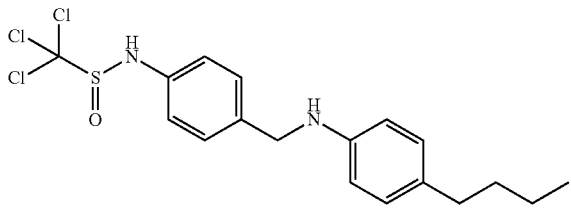
I-108
I-109
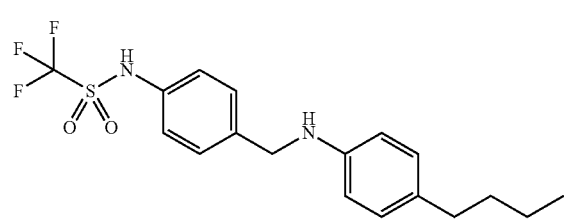
I-110
I-111
I-112
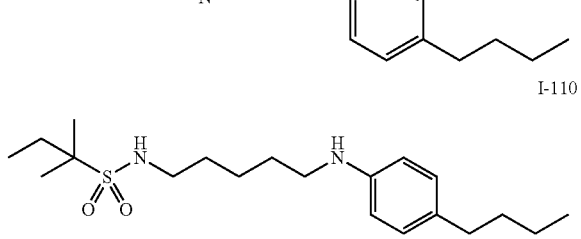
I-113
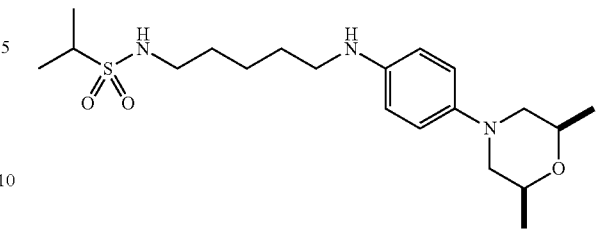
[Formula 75]
I-115
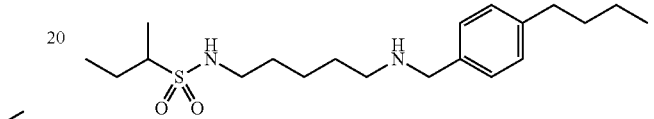
I-116
I-117
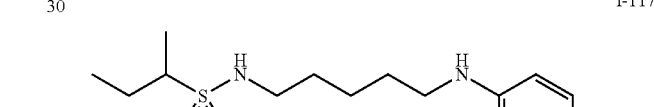
I-118
I-119
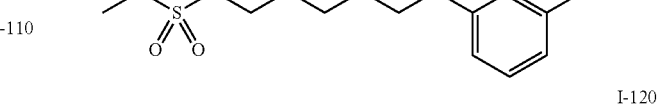
I-120
I-121
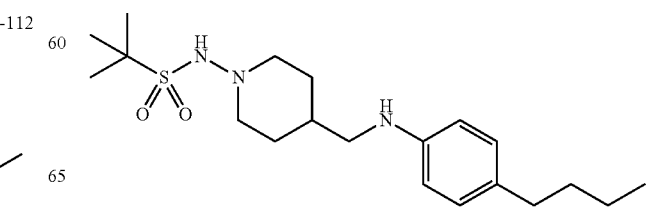

I-122
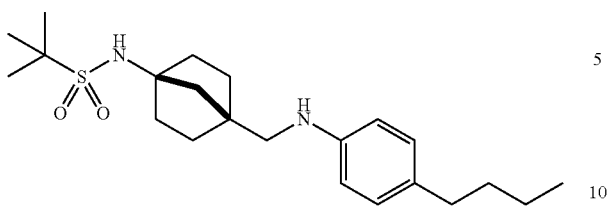
I-128
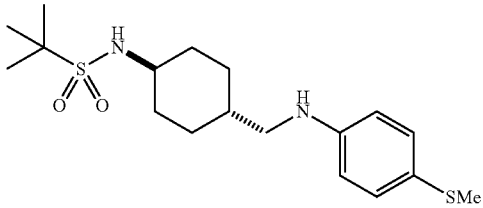
I-123
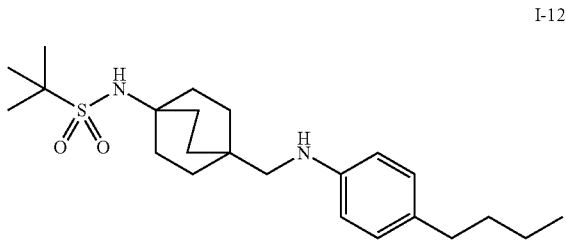
I-129
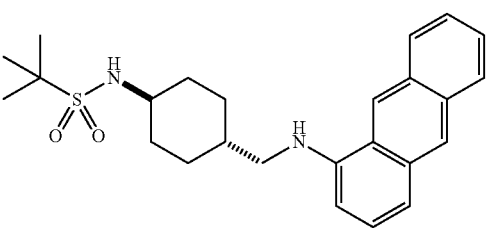
I-124
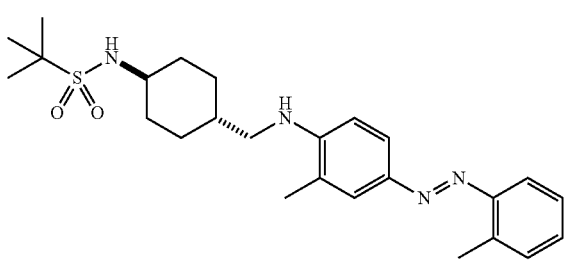
I-130
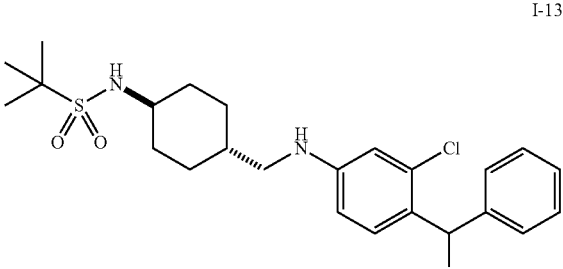
I-125
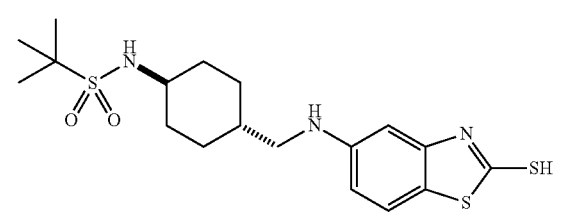
I-131
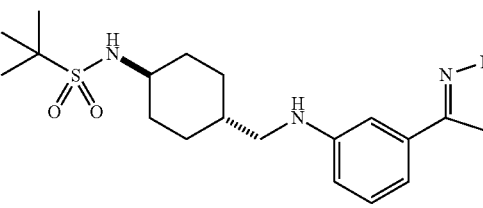
I-126
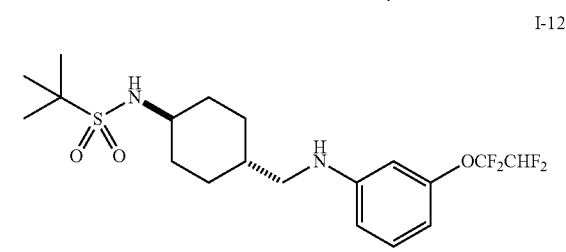
I-132
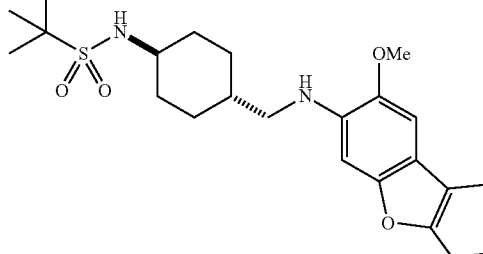
I-127
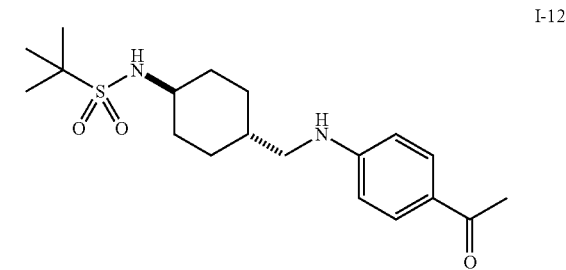
I-133
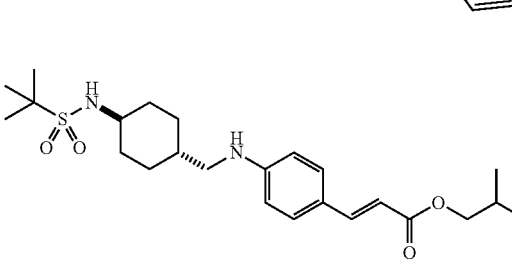

I-134
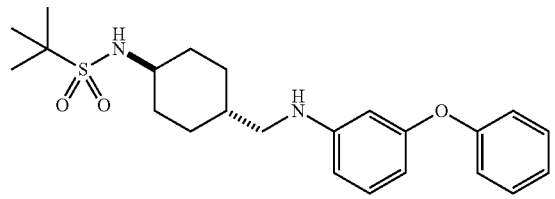
I-135
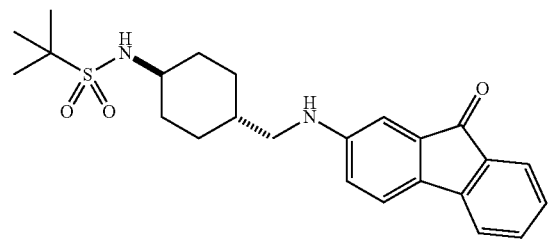
I-136
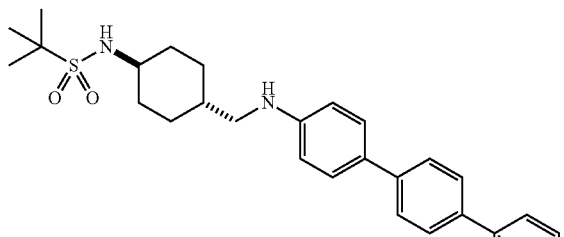
I-137
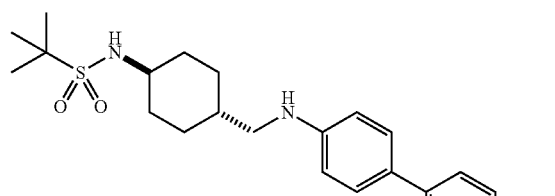
I-138
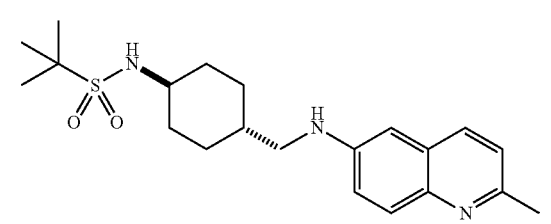
[Formula 76]
I-139
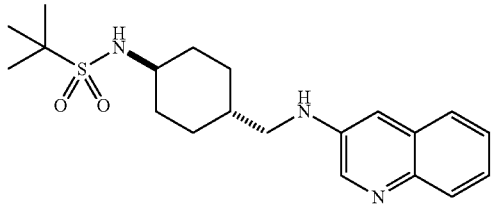
I-140
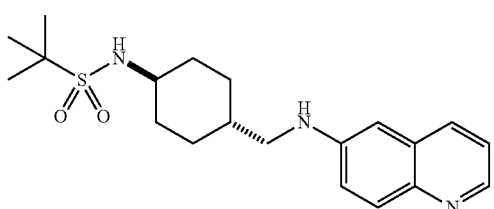
I-141
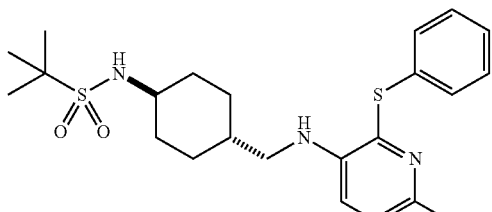
I-142
I-143
I-144
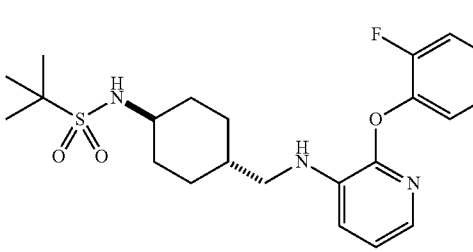

I-145 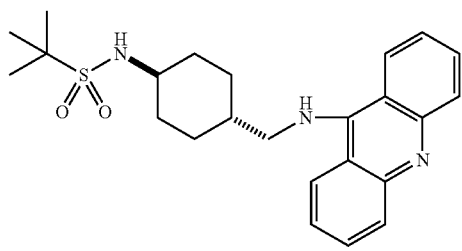
I-146 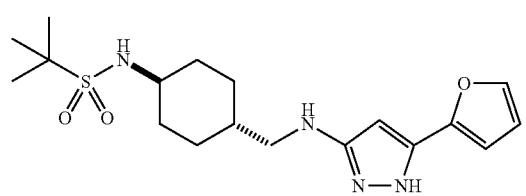
I-147 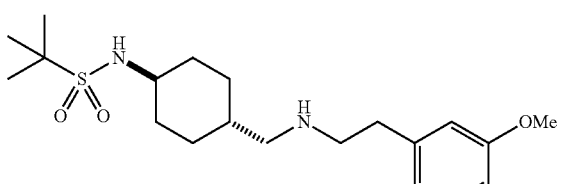
I-148 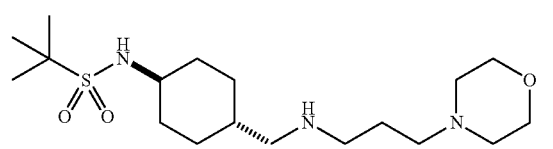
I-149 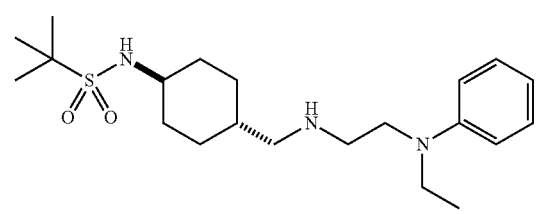
I-150 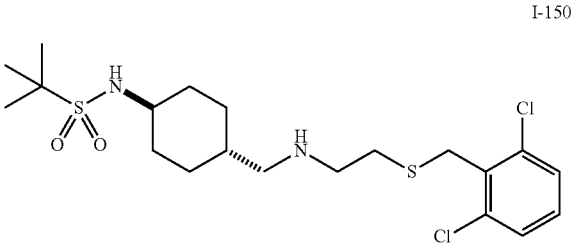
I-151 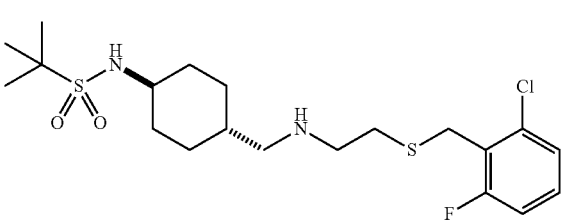
I-152 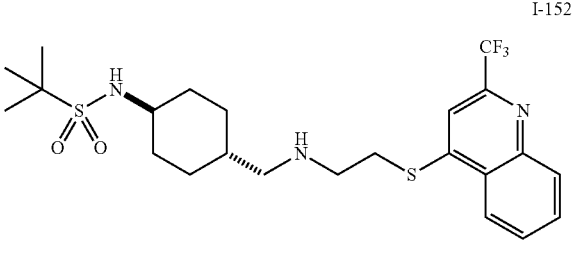
I-153 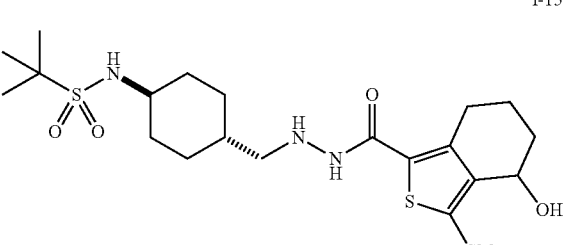
I-154 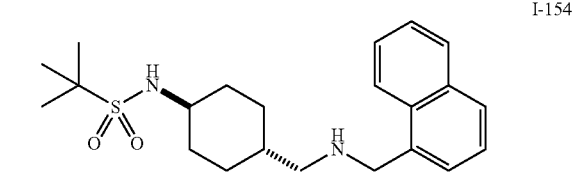
I-155 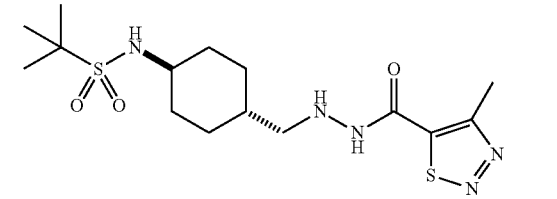
I-156 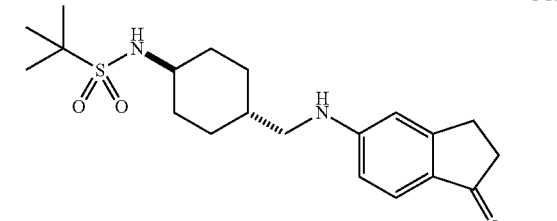
I-157 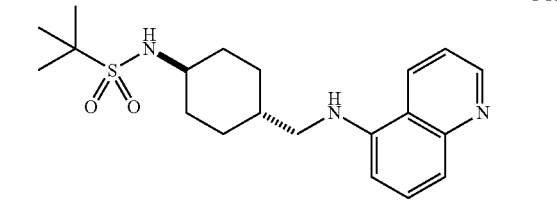
I-158 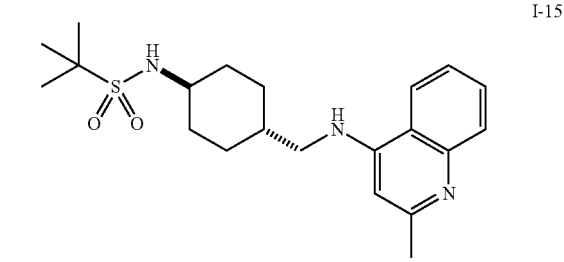

-continued
I-159
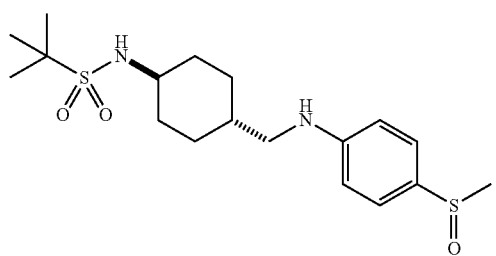
I-160
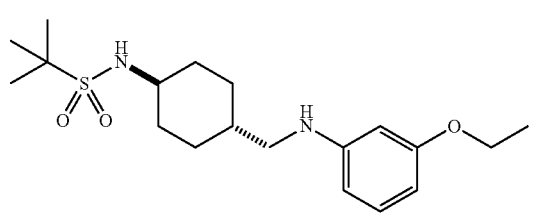
I-161
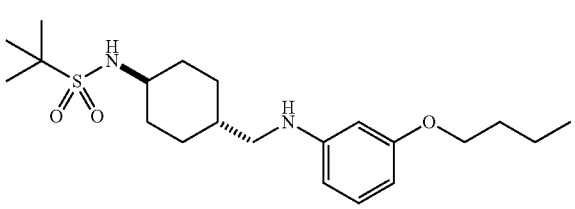
I-162
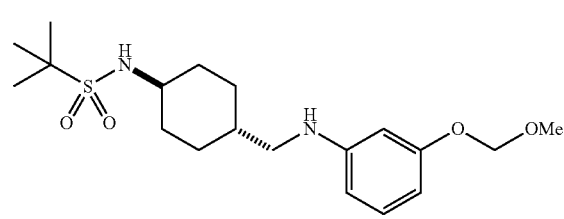
[Formula 77]
I-163
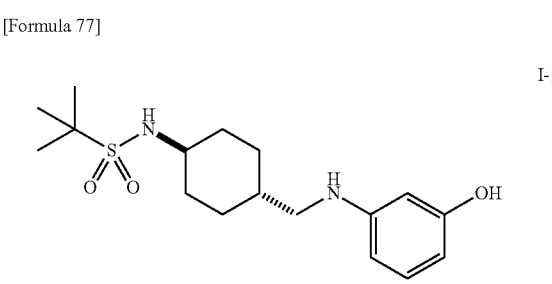
I-164
-continued
I-165
I-166
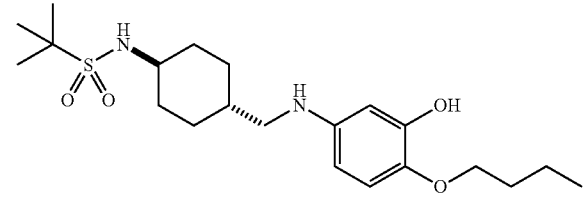
I-167
I-168
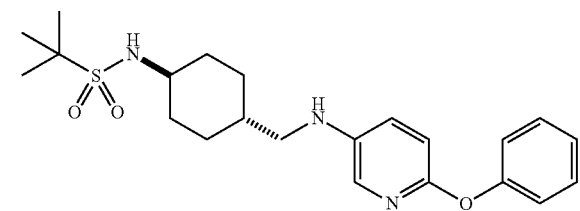
I-169
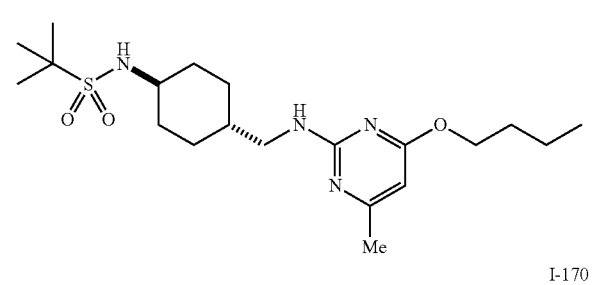
I-170
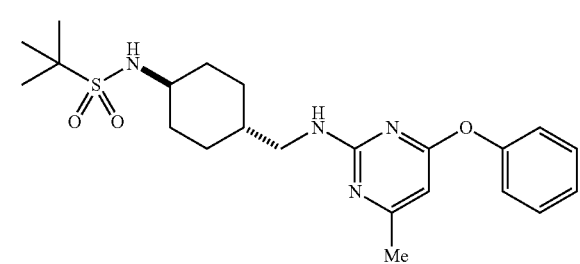

I-171
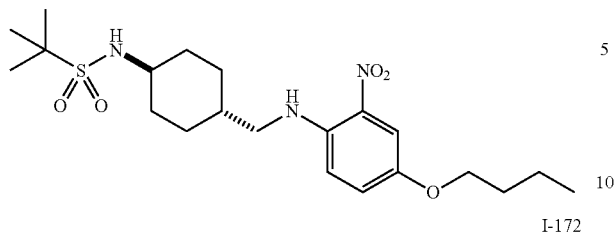
I-172
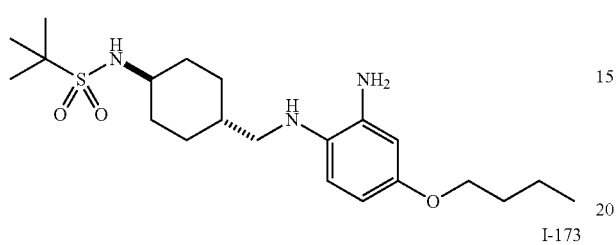
I-173
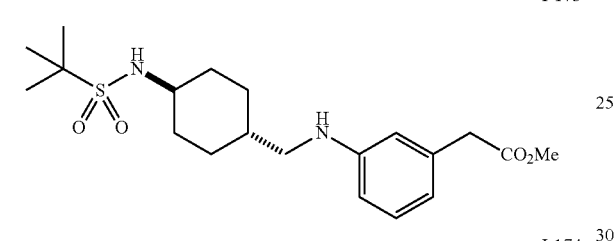
I-174
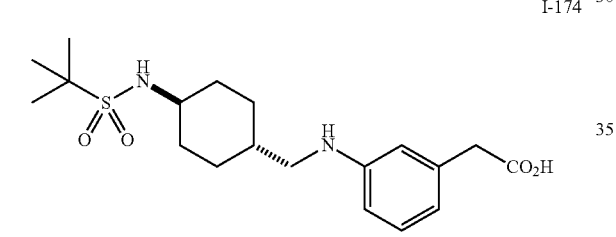
I-175

I-176

I-177
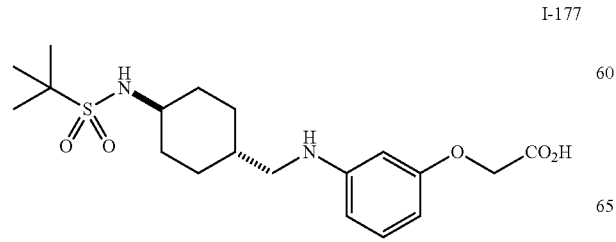
I-178
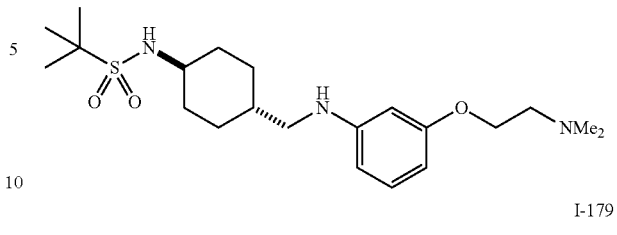
I-179
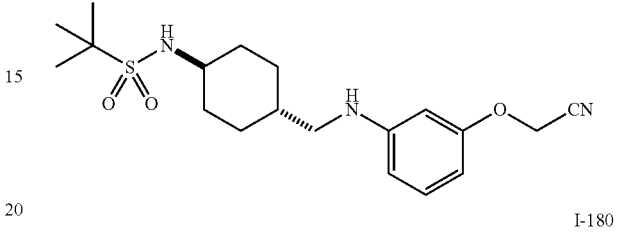
I-180
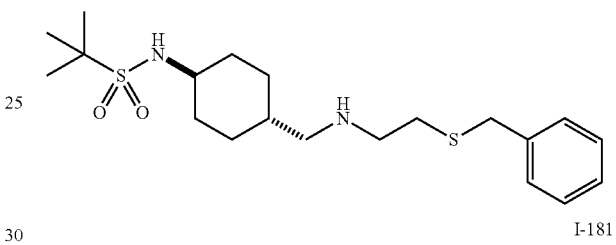
I-181
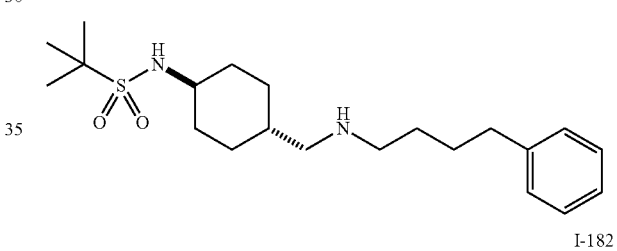
I-182

[Formula 78]
I-183

I-184
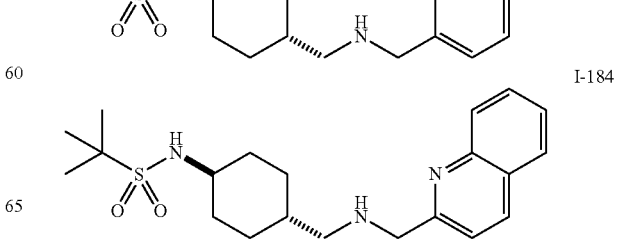

I-185 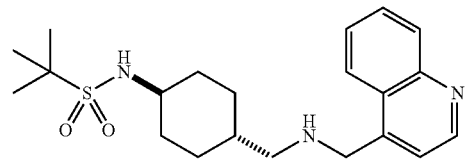
I-186 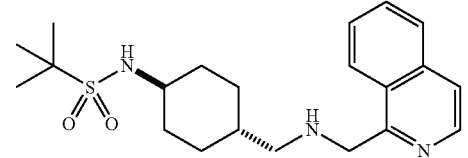
I-187 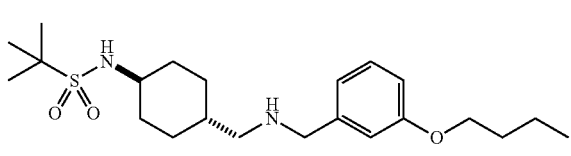
I-188 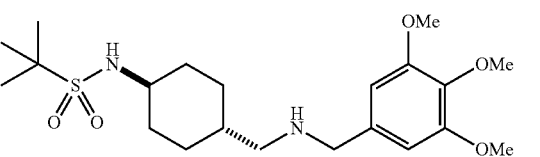
I-189 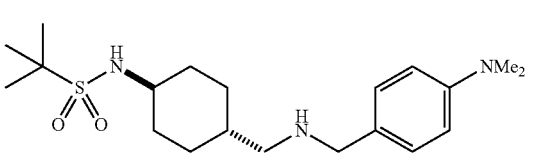
I-190 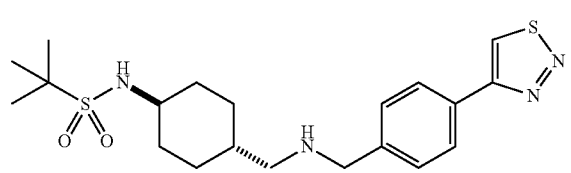
I-191 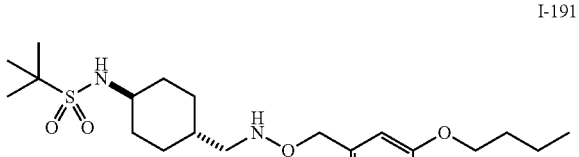
I-192 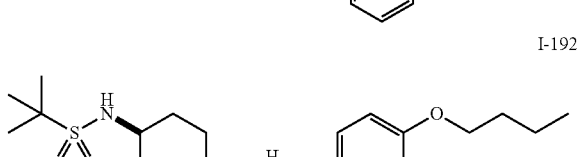
I-193 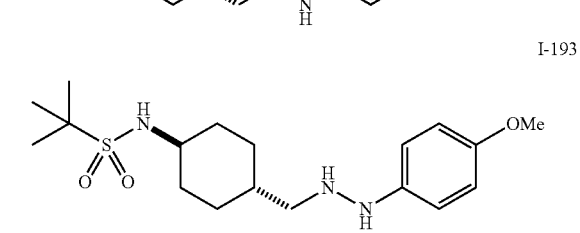
I-194 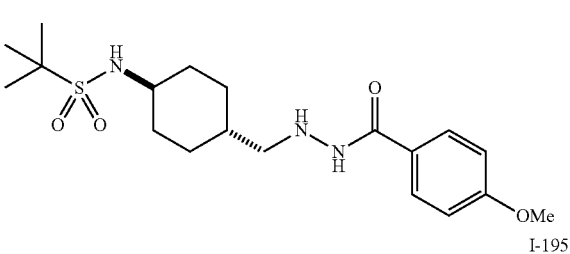
I-195 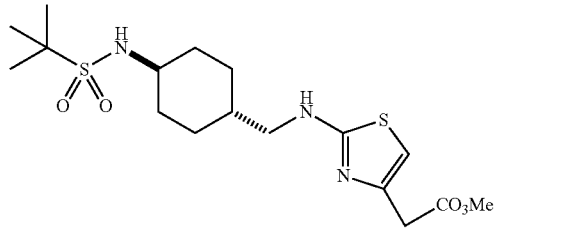
I-196 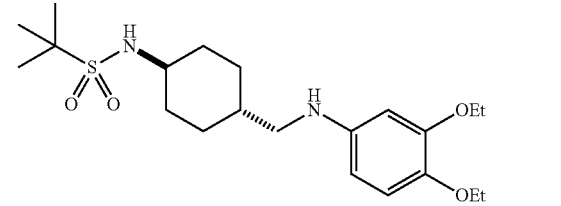
I-197 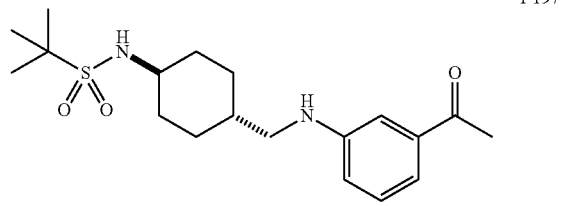
I-198 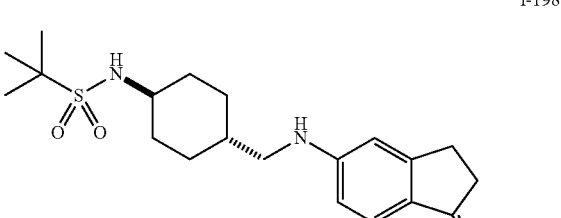
I-199 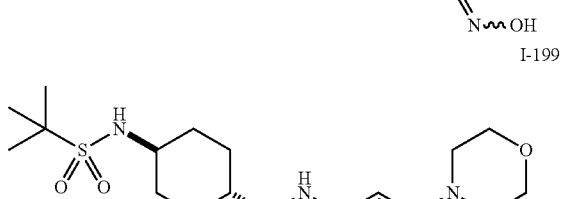
I-200 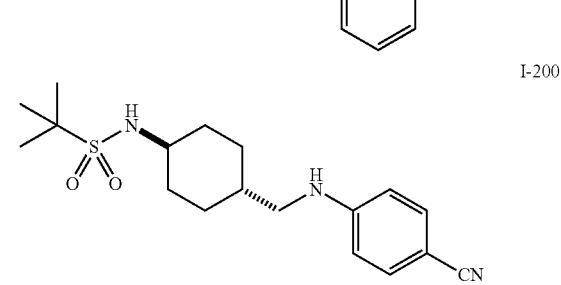

71
-continued
I-201
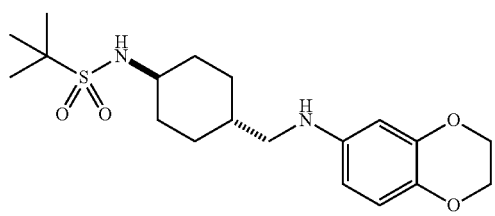
I-202
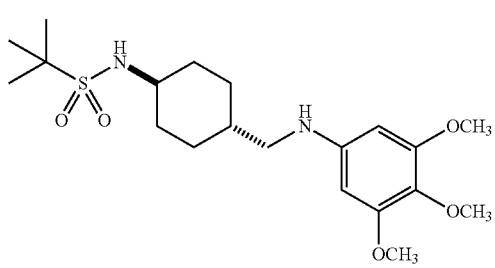
[Formula 79]
I-203
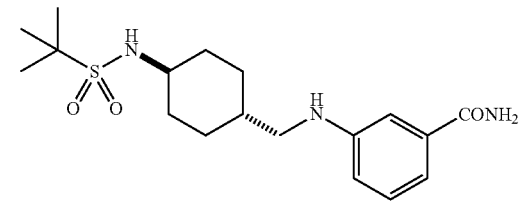
I-204
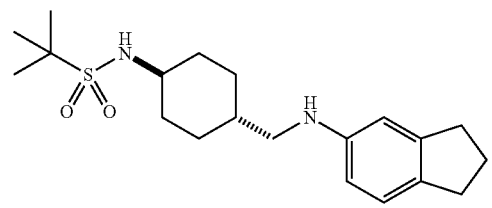
I-205
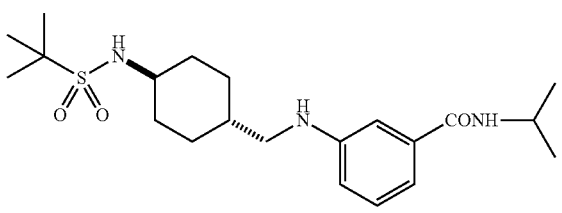
I-206
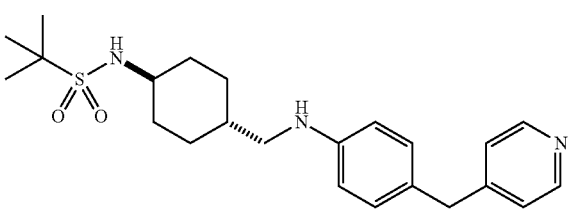
72
-continued
I-207
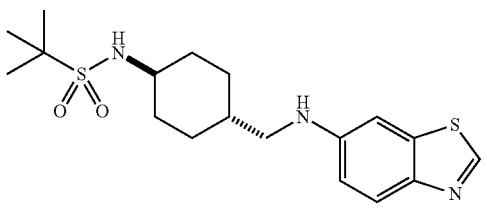
I-208
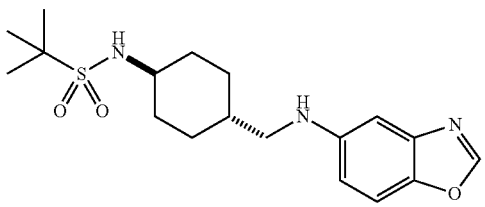
I-209
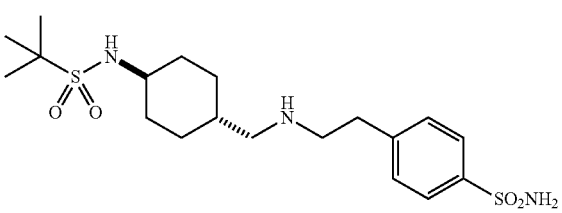
I-210
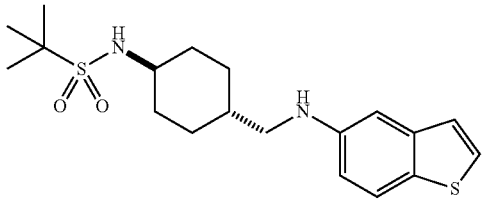
I-211
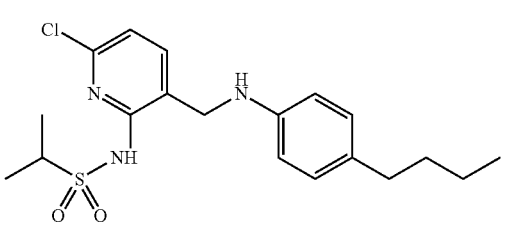
I-212
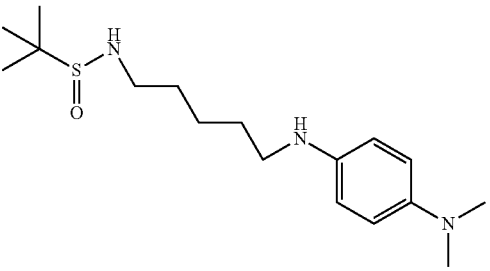

I-213
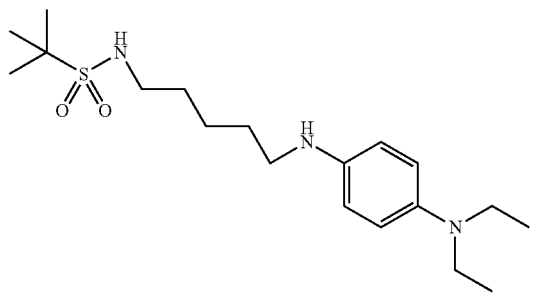
I-214
I-218
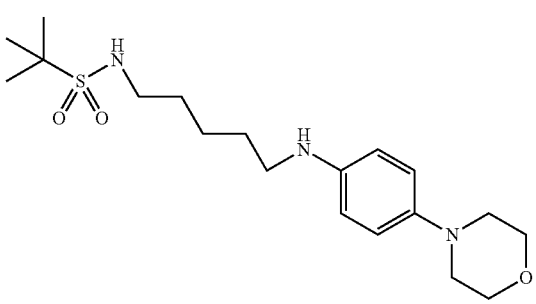
I-219
I-215
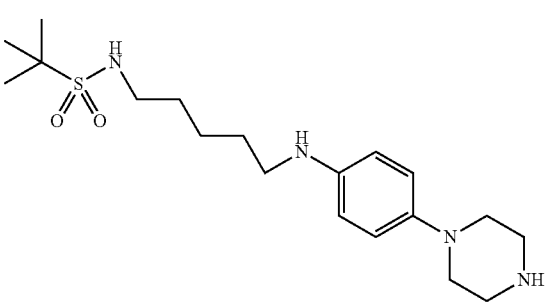
I-220
I-216
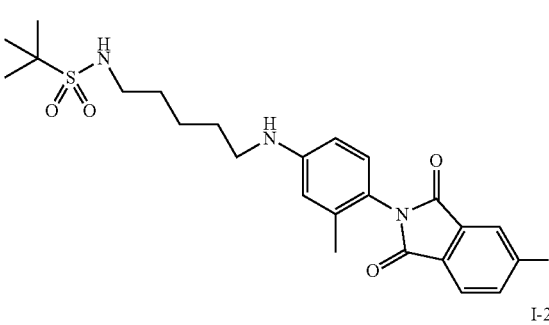
[Formula 80]
I-227
I-217
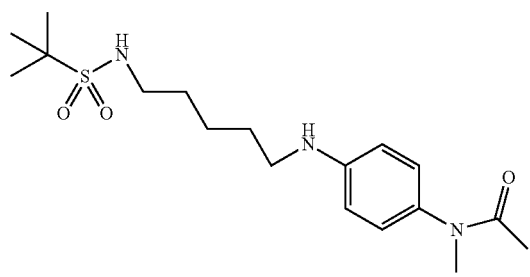
I-228
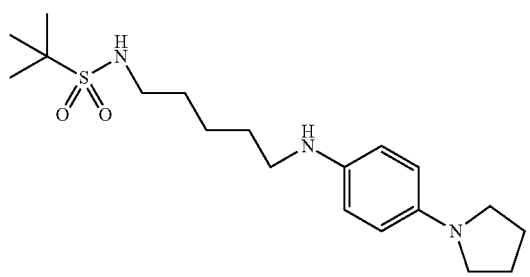

I-229
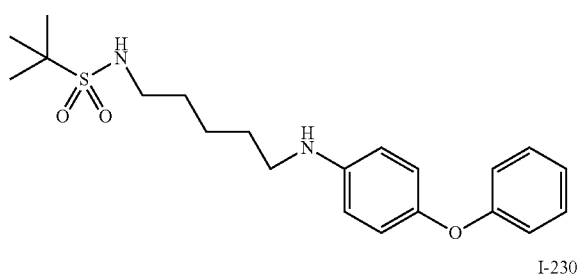
I-230
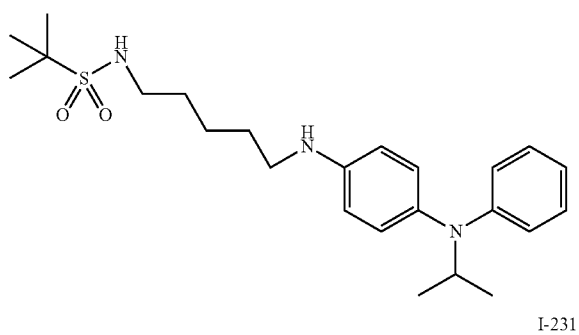
I-231
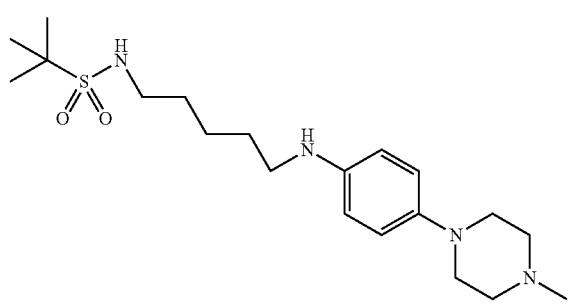
I-232
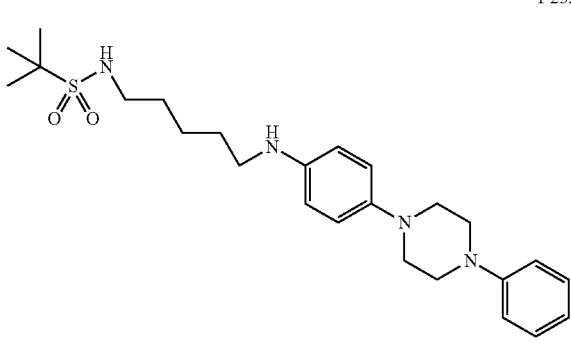
I-234
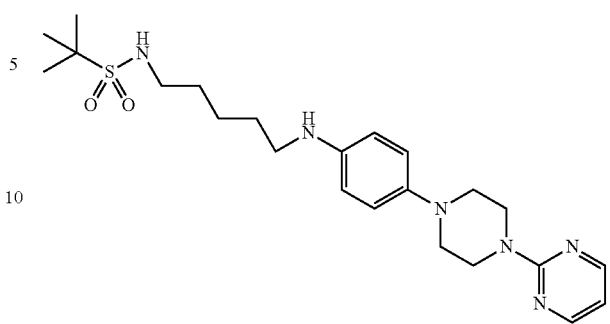
I-235
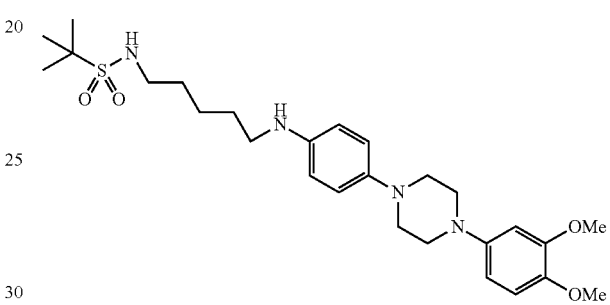
I-236
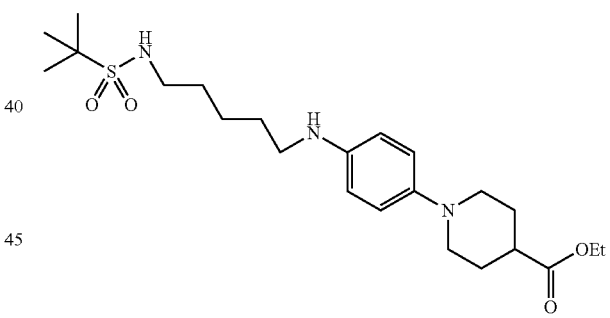
I-237
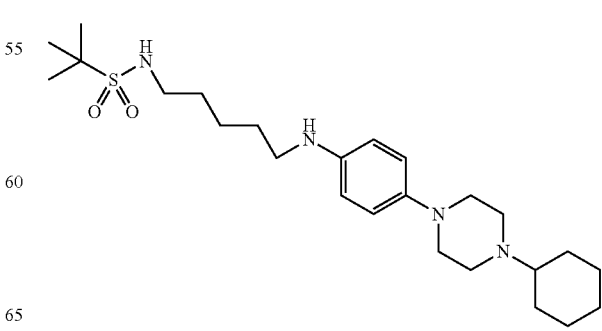

[Formula 81]
I-238
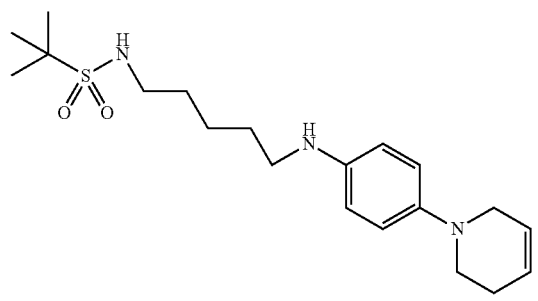
I-239
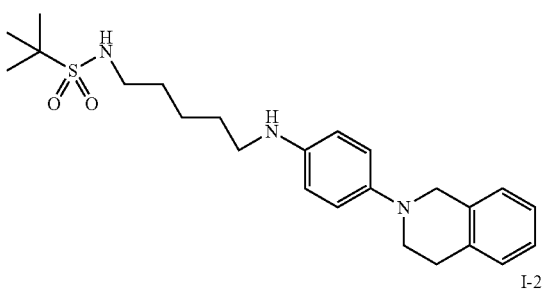
I-240

I-241
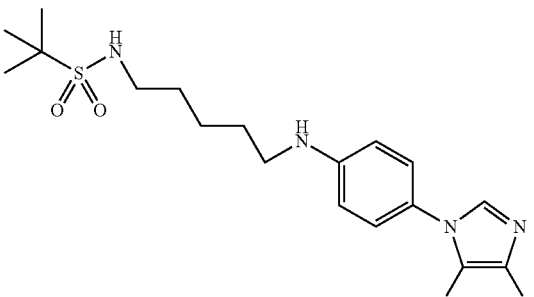
I-242
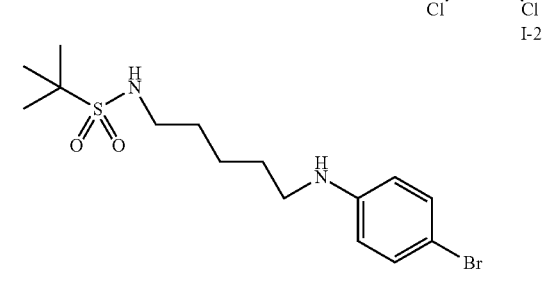
I-243
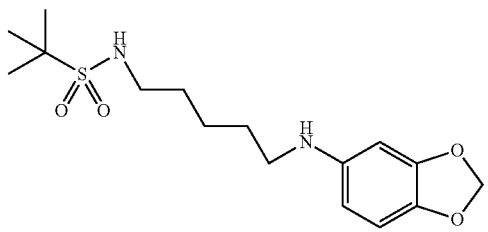
I-244
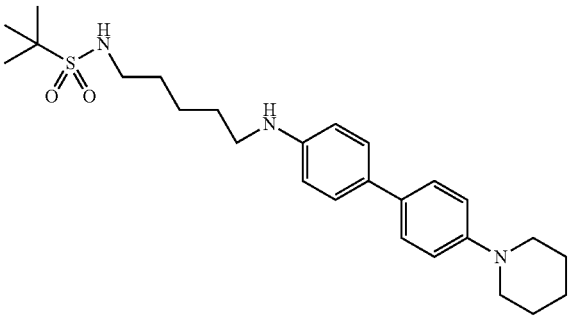
I-245
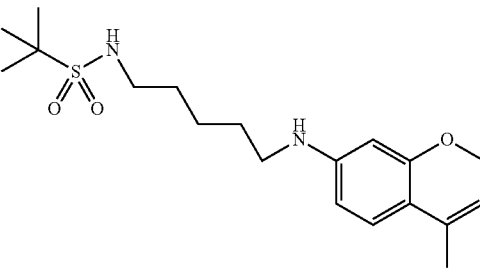
I-246
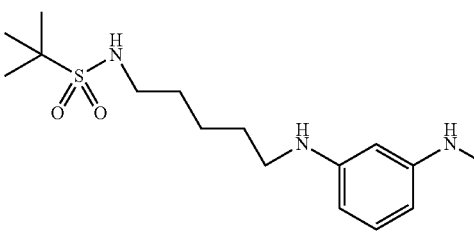
I-247
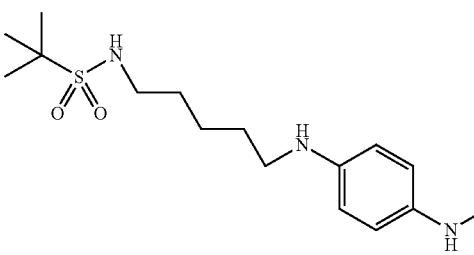
I-248
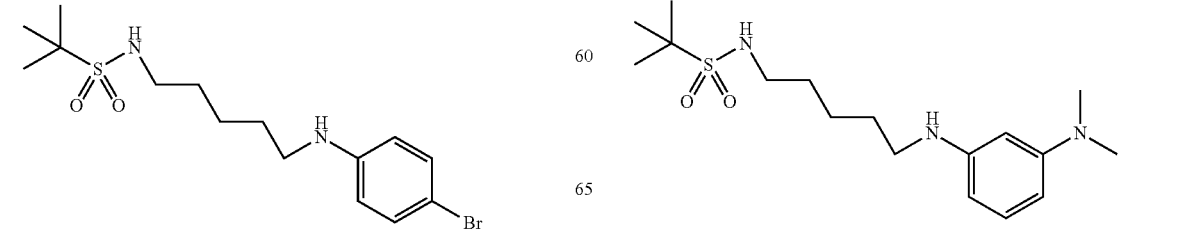

I-249
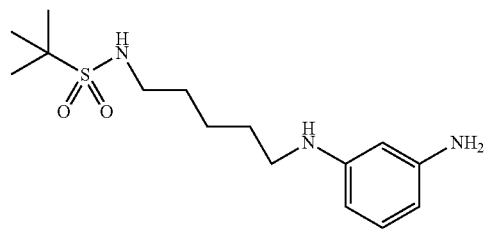
I-250
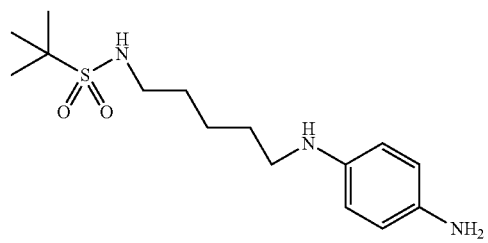
I-251
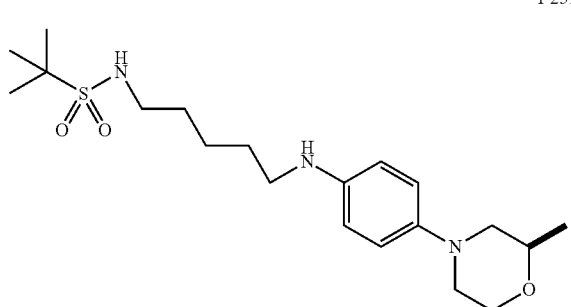
I-252
I-253
2HCl
I-254
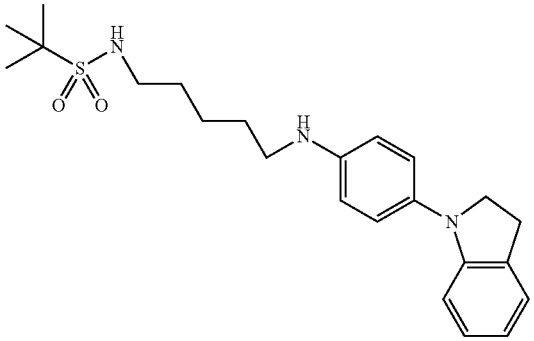
I-255
I-256
I-257
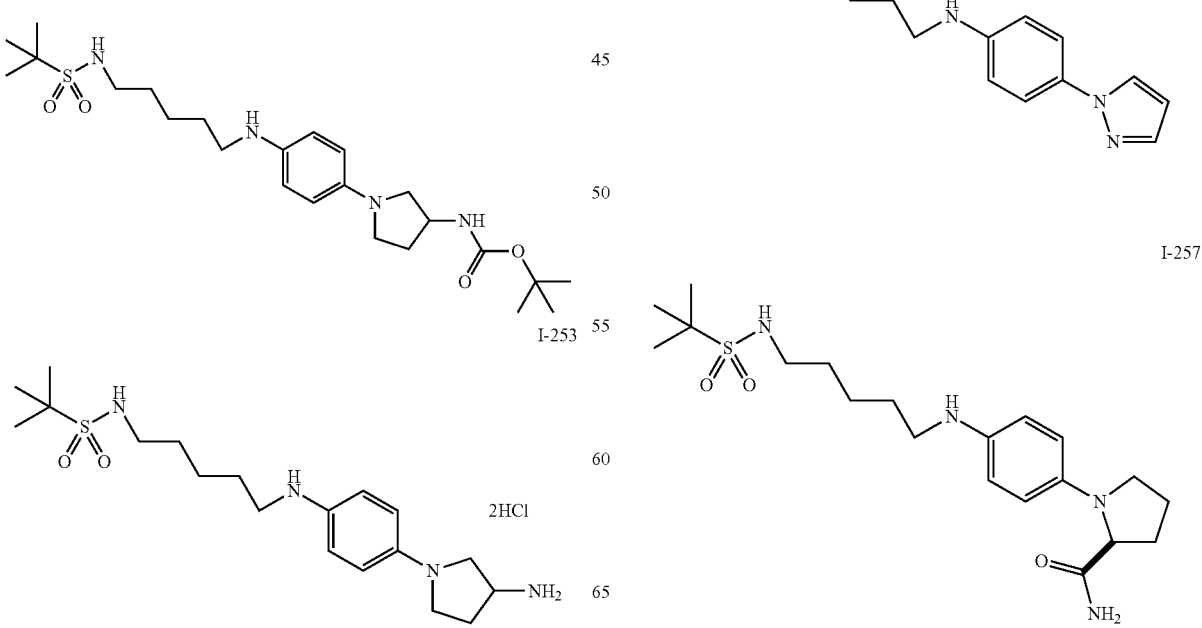

81
-continued
I-258
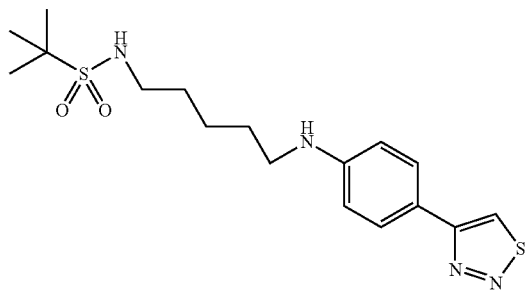
I-259
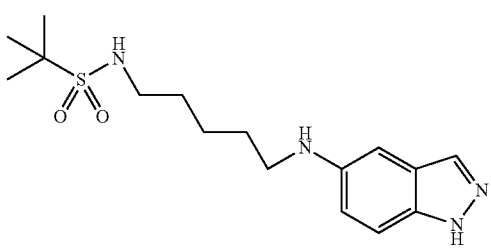
[Formula 82]
I-260
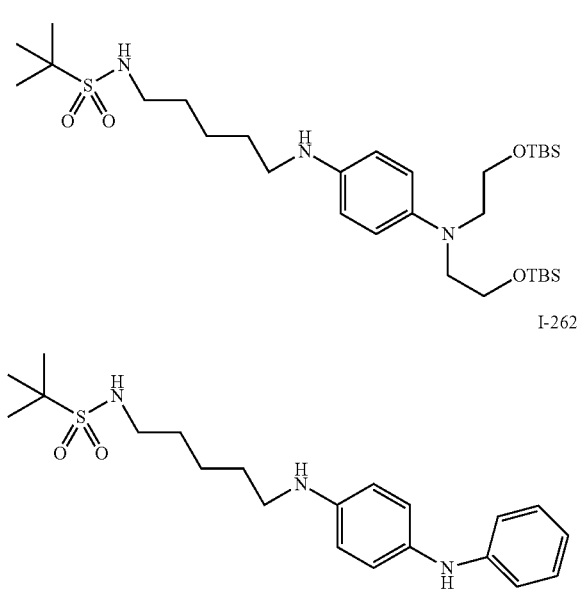
I-261
I-262
82
-continued
I-263
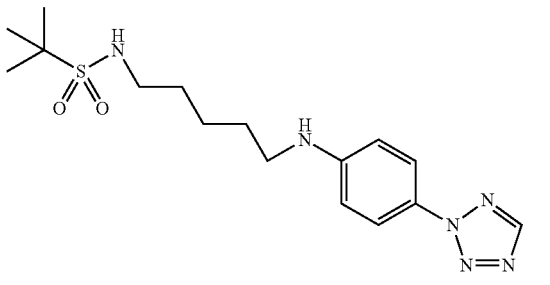
I-264
I-265
I-266
I-267
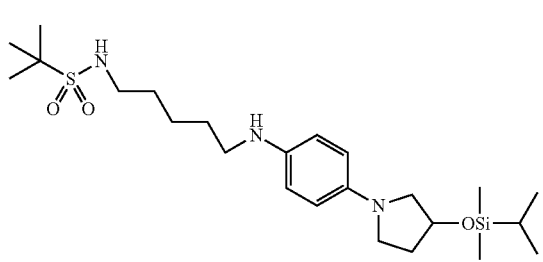
I-268

I-269
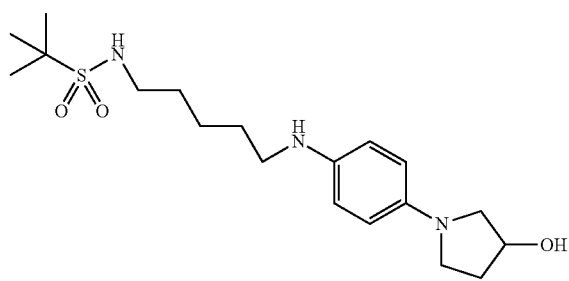
I-270
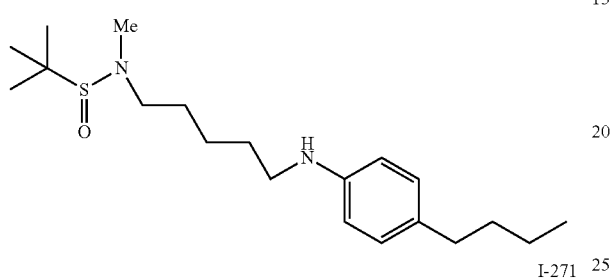
I-271
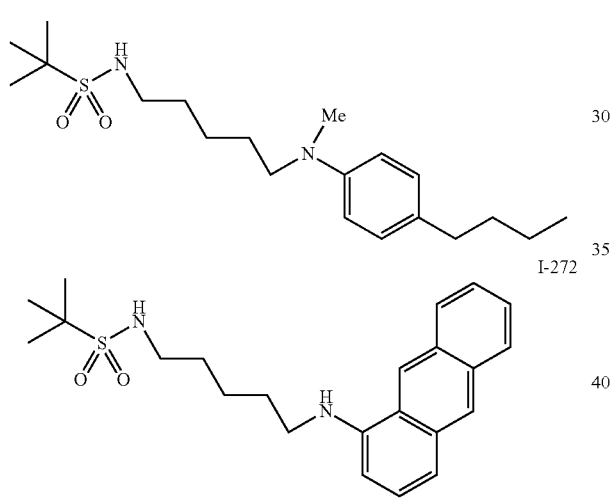
I-272
I-273
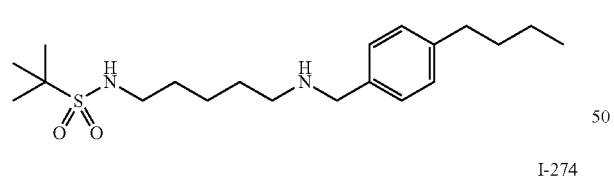
I-274
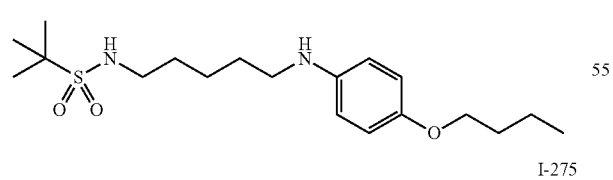
I-275
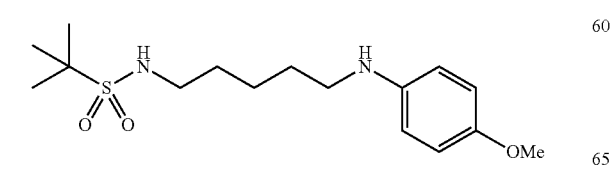
I-276
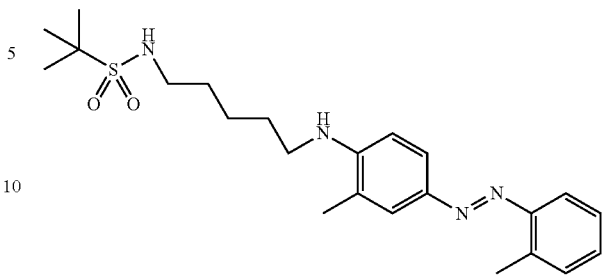
I-277
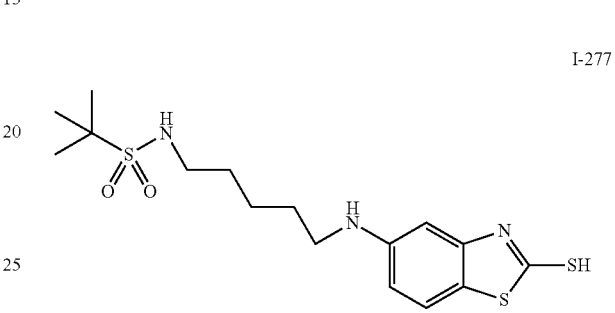
I-278
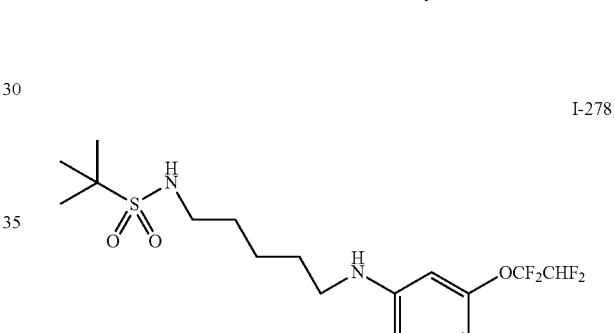
I-279
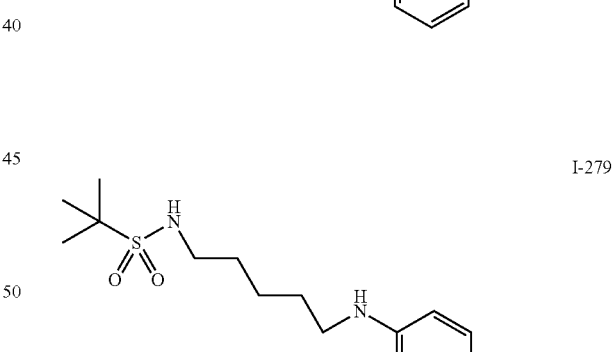
I-280
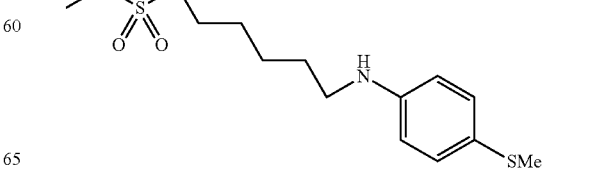

I-282
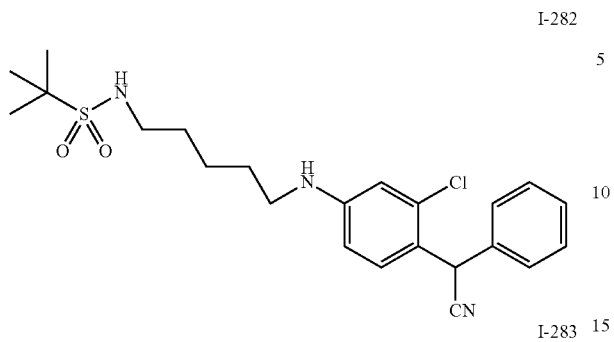
I-283
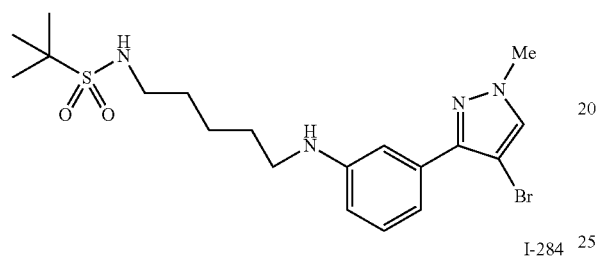
I-284
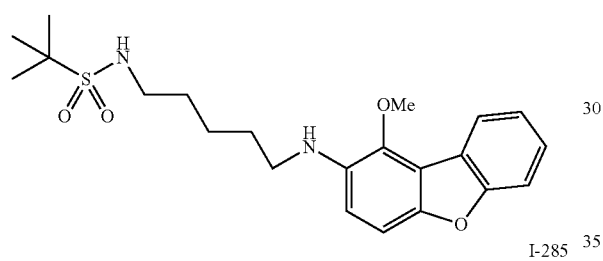
I-285
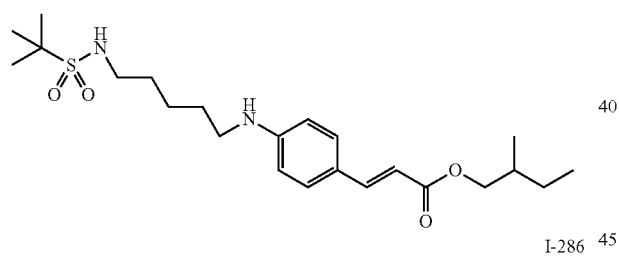
I-286
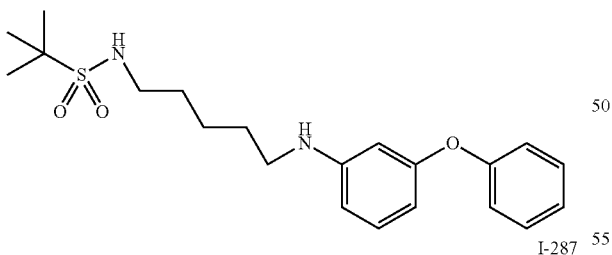
I-287
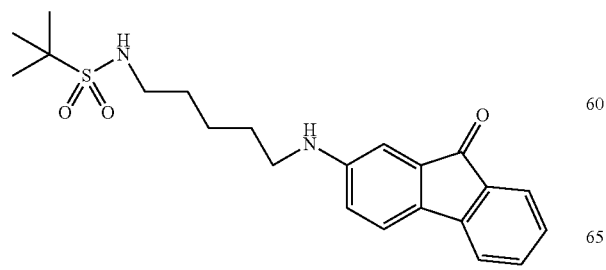
I-288
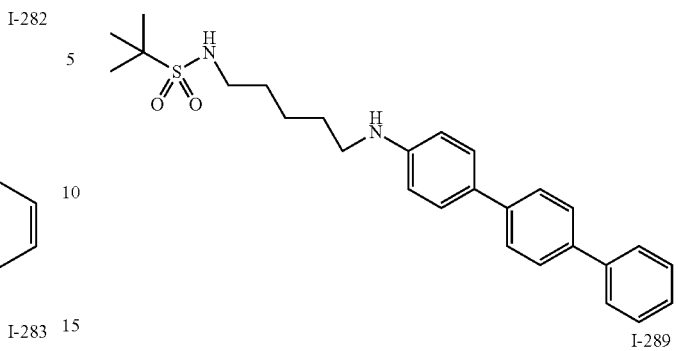
I-289
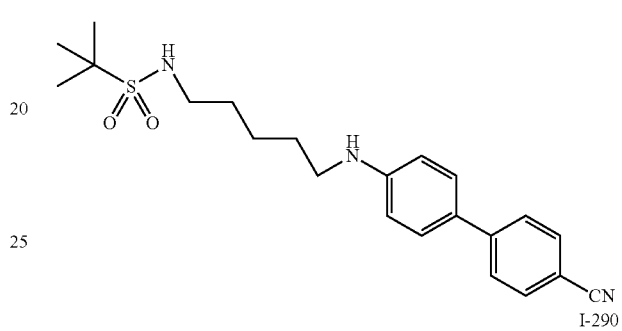
I-290
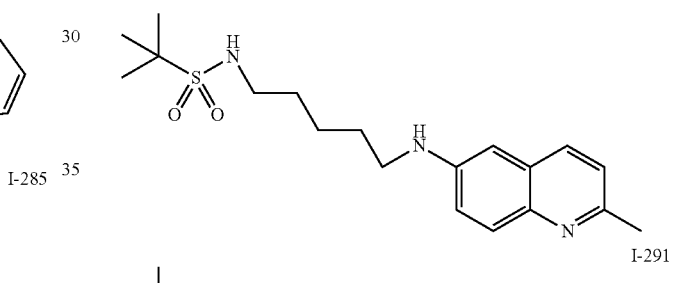
I-291
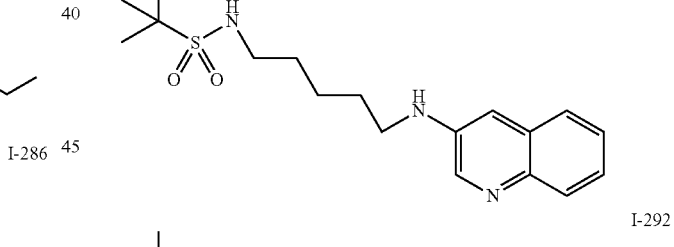
I-292
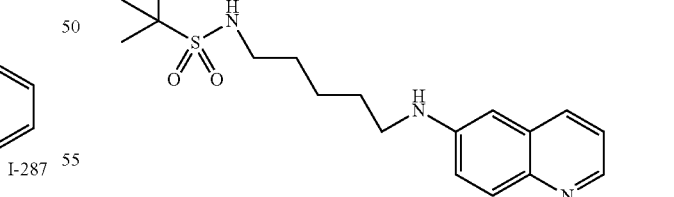
I-293
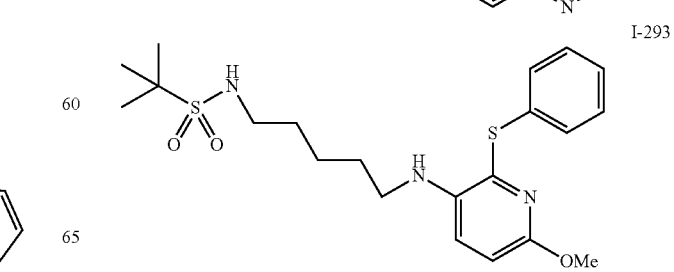

I-294
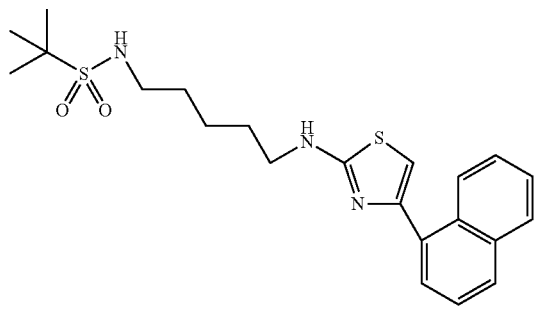
I-295
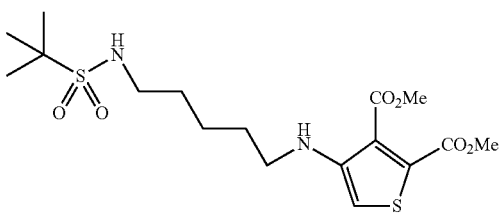
I-296
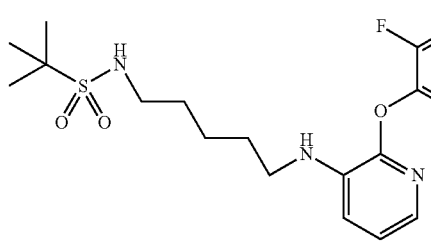
I-297
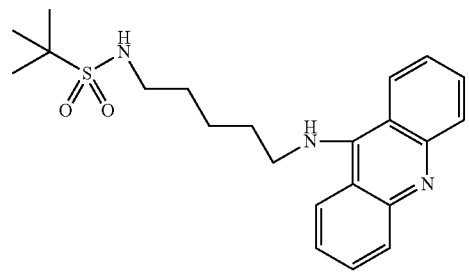
I-298
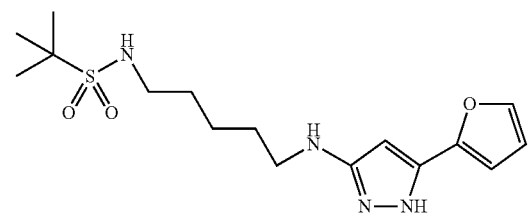
I-299
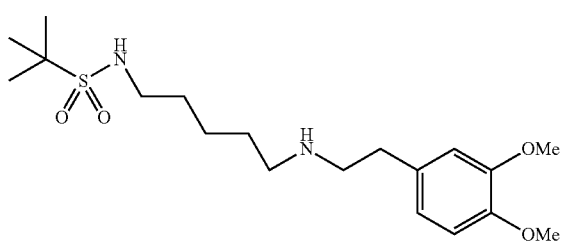
I-300
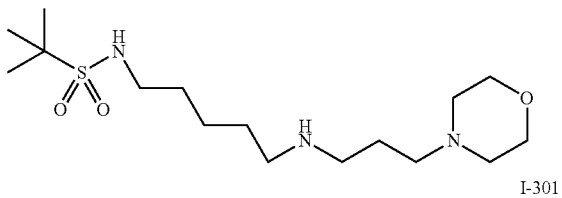
I-301
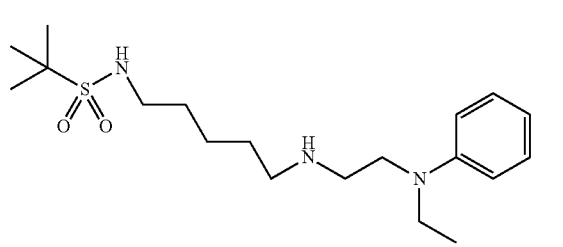
I-302
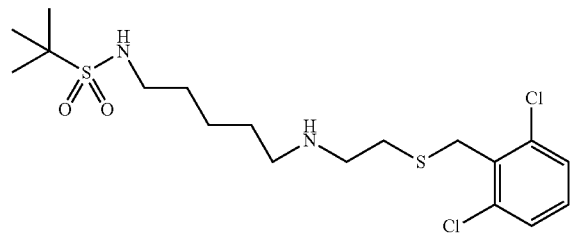
I-303
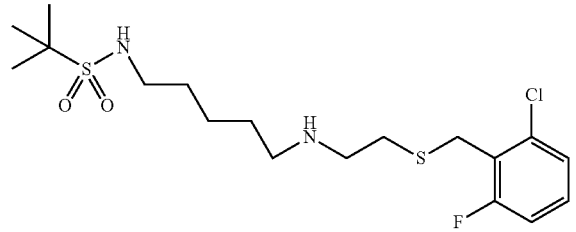
[Formula 84]
I-304
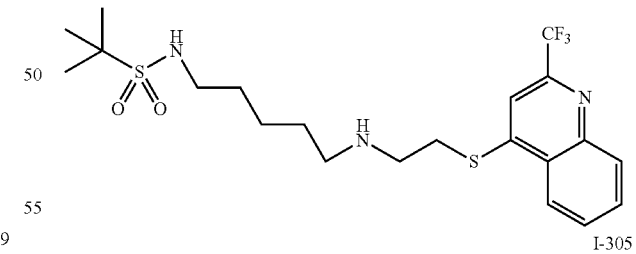
I-305
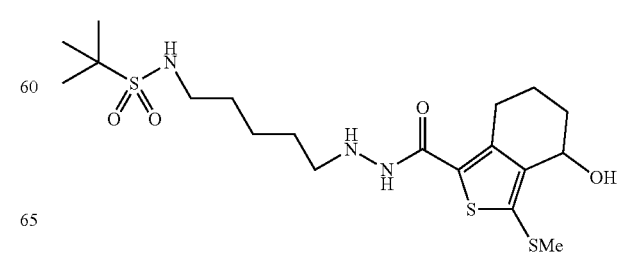

I-306
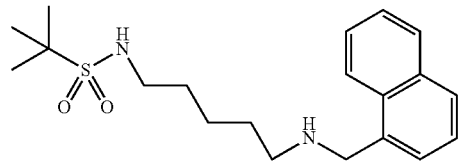
I-307
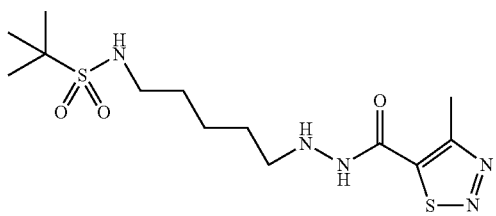
I-308
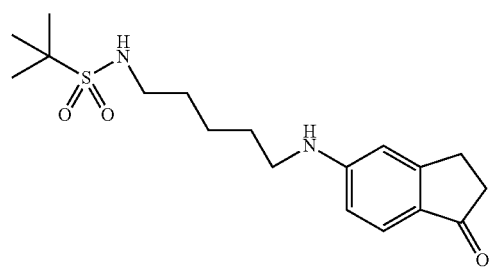
I-309
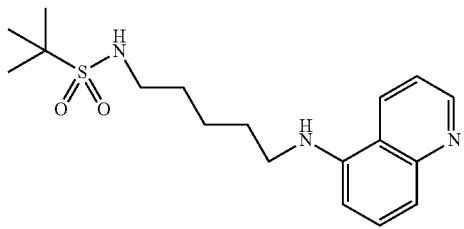
I-310
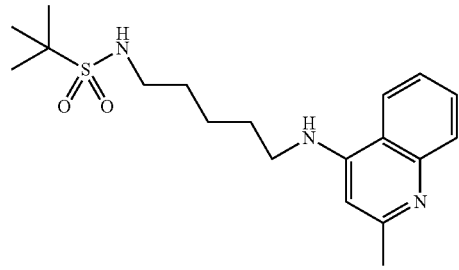
I-311
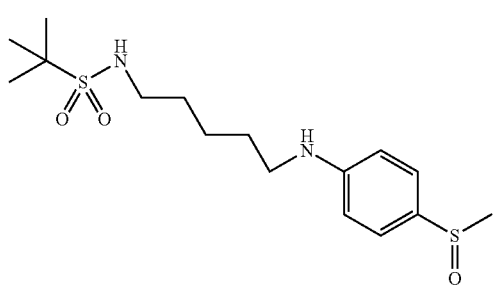
I-312
I-313
I-314
I-315
I-316
I-317
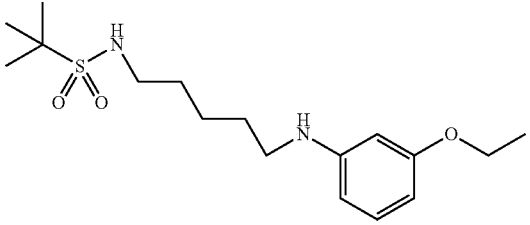

I-318
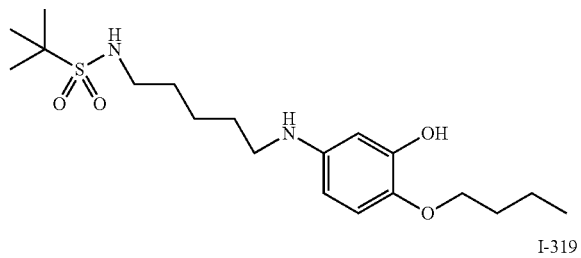
I-319
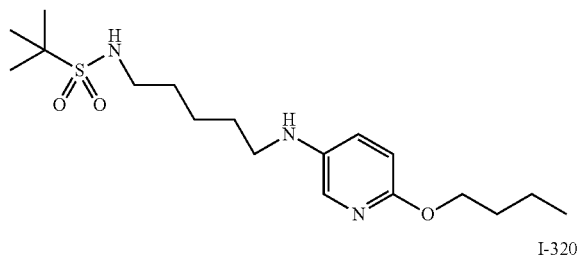
I-320
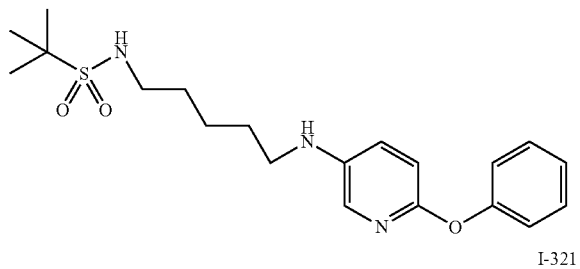
I-321
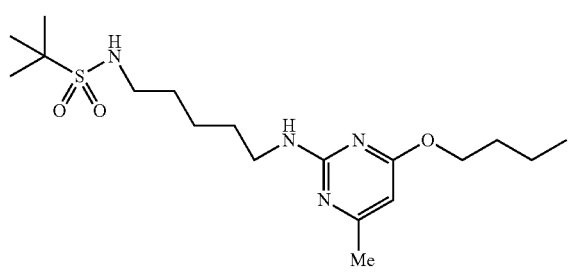
I-322
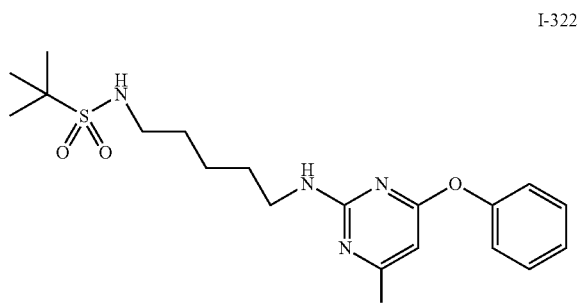
I-323
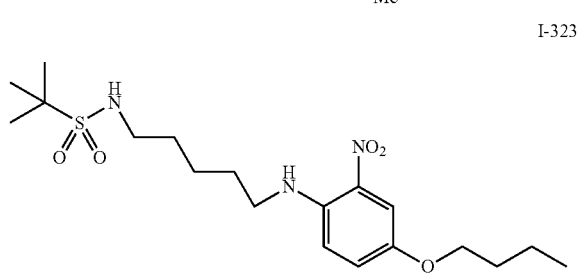
I-324
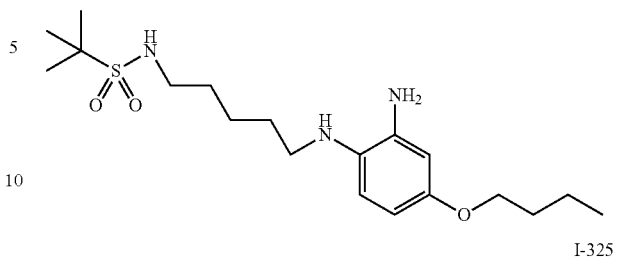
I-325
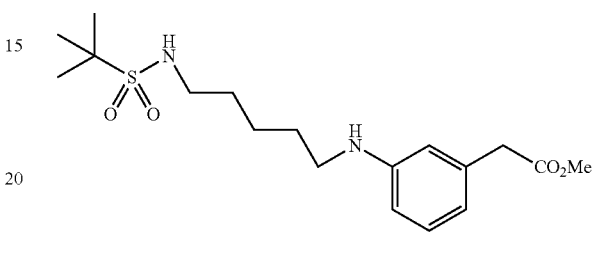
[Formula 85]
I-326
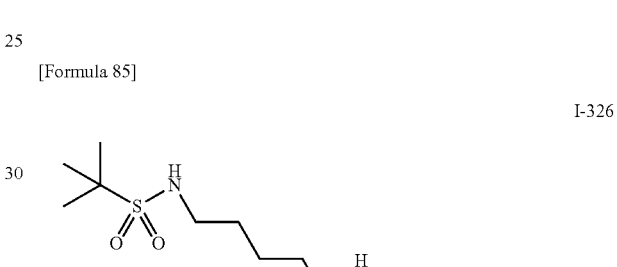
I-327

I-328
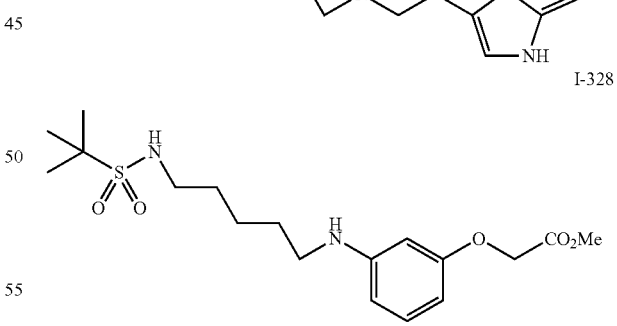
I-329
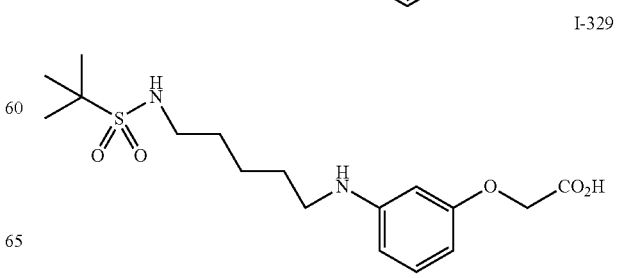

I-330
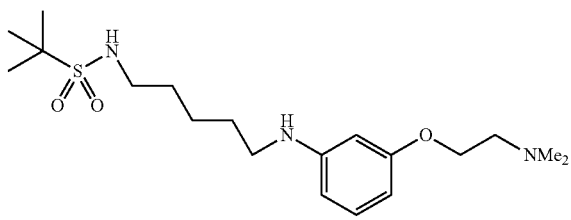
I-331
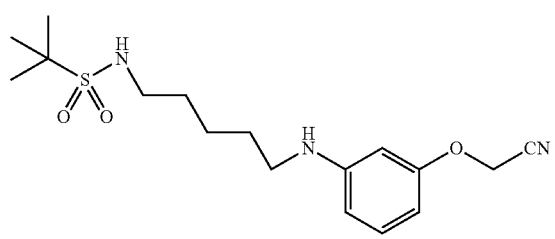
I-332
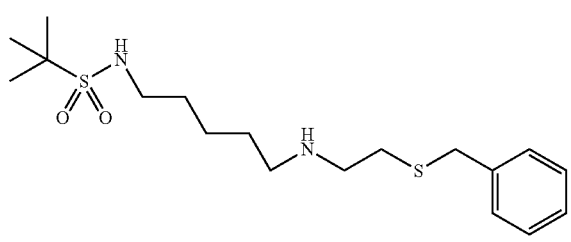
I-333
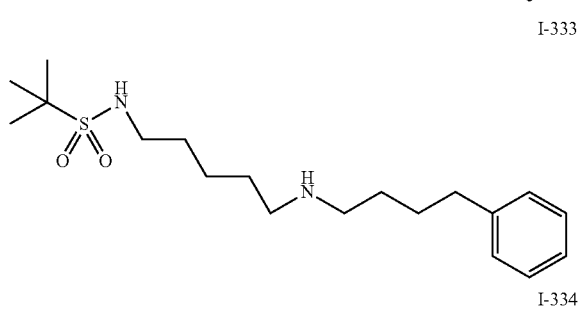
I-334
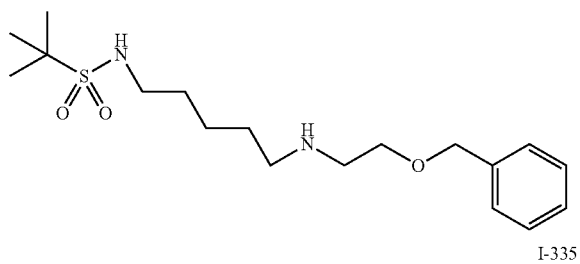
I-335
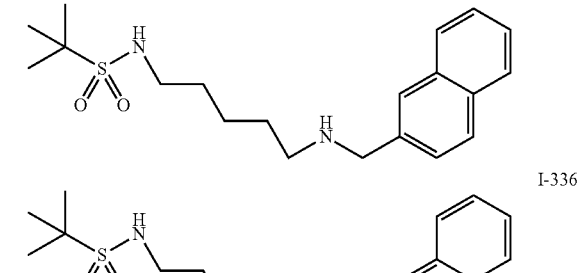
I-336
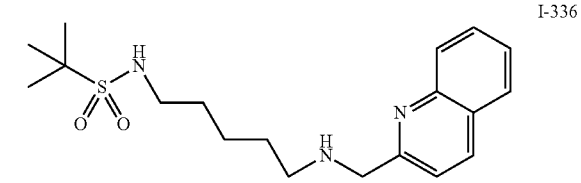
I-337
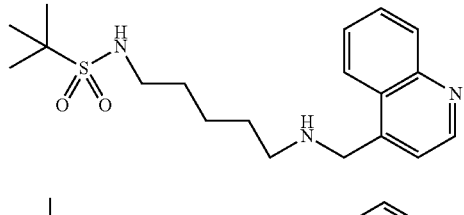
I-338
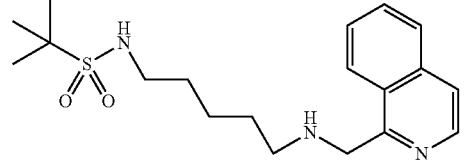
I-339
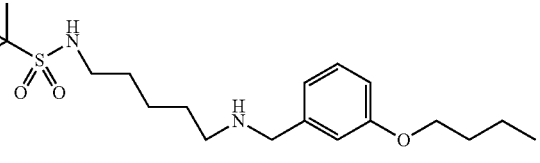
I-340
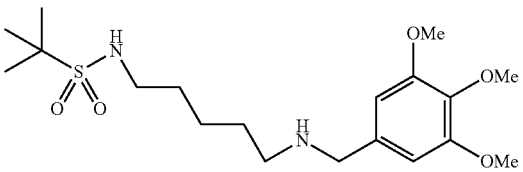
I-341
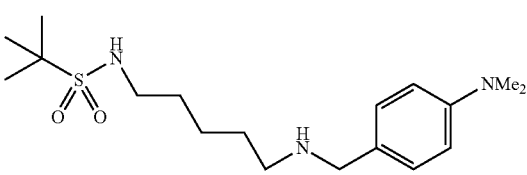
I-342
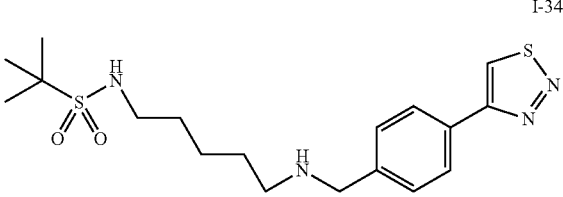
I-343
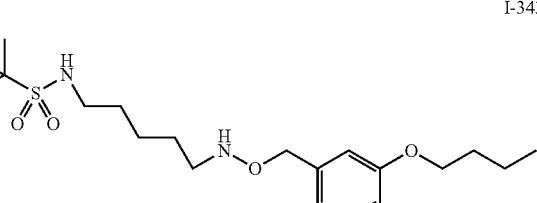
I-344
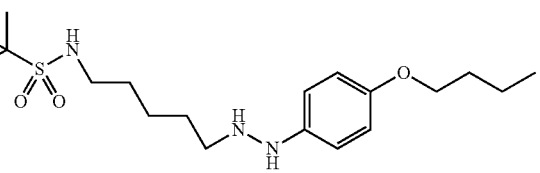

I-345
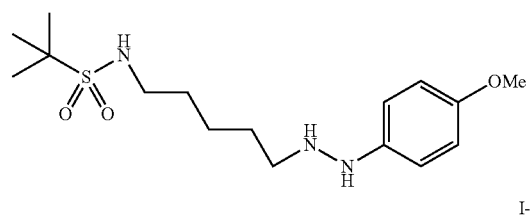
I-346
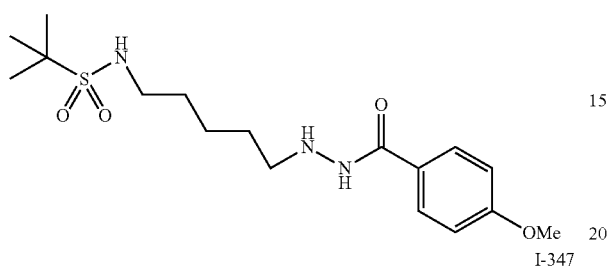
I-347
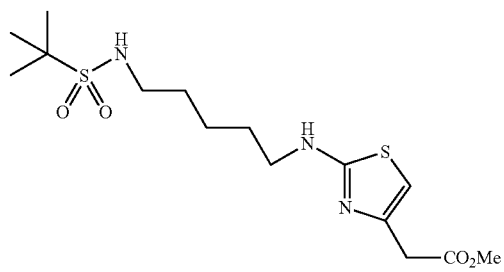
[Formula 86]
I-348
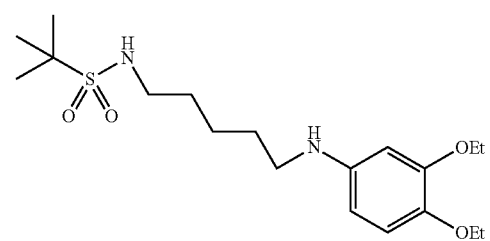
I-349
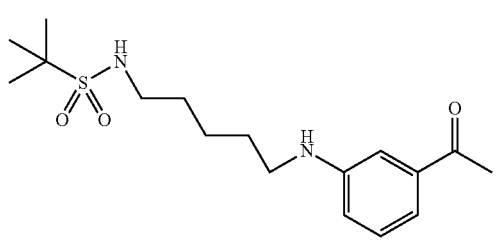
I-350
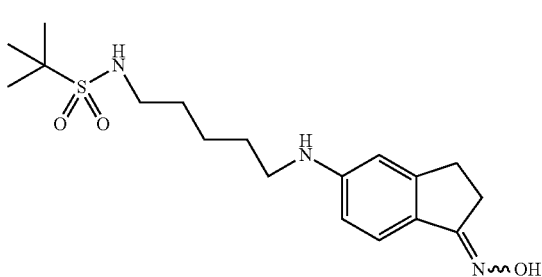
I-351
I-352
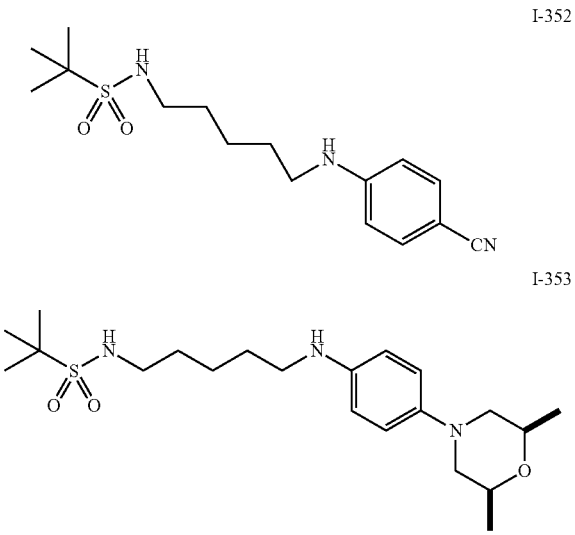
I-353
I-354
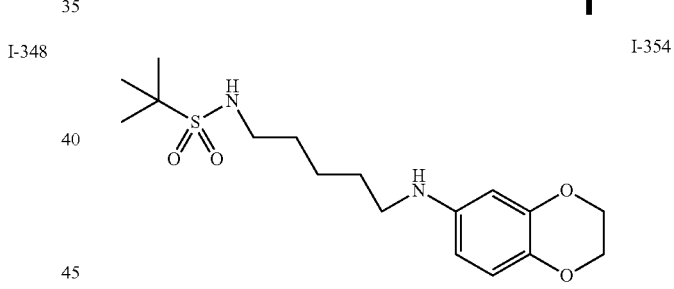
I-355
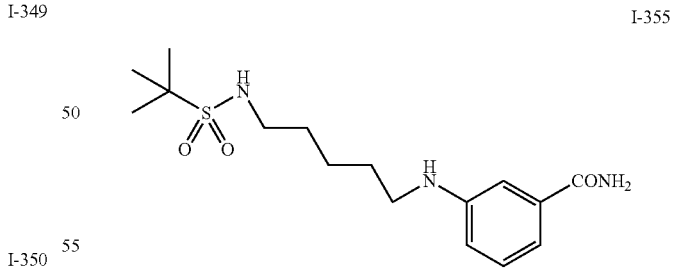
I-356
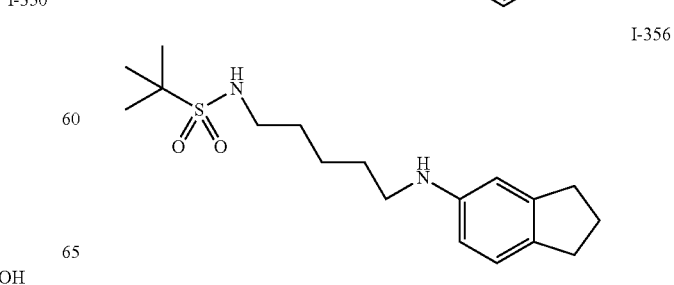

I-357
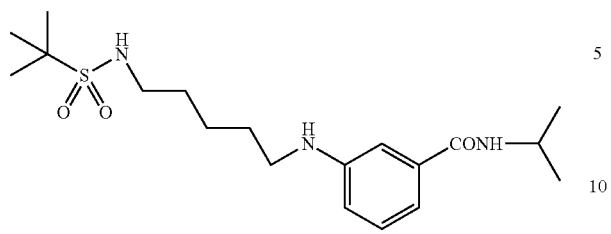
I-358
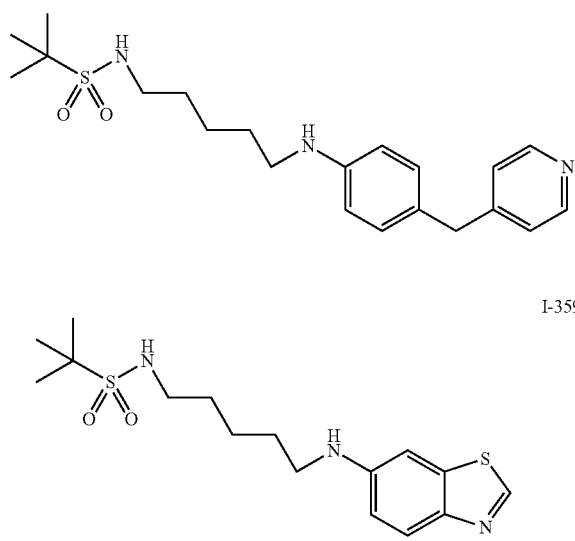
I-359
I-360
I-361
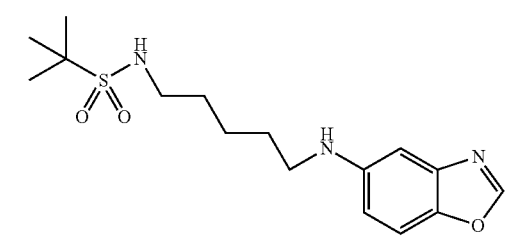
I-362
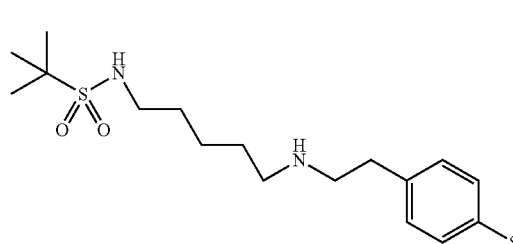
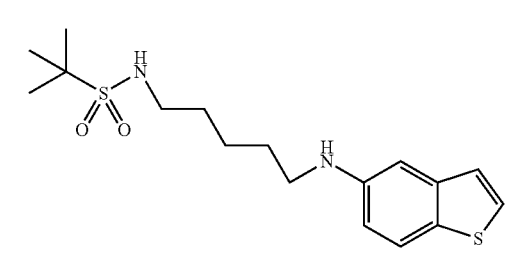
I-363
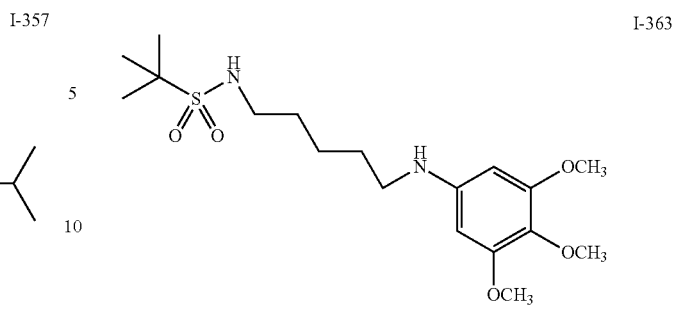
I-364
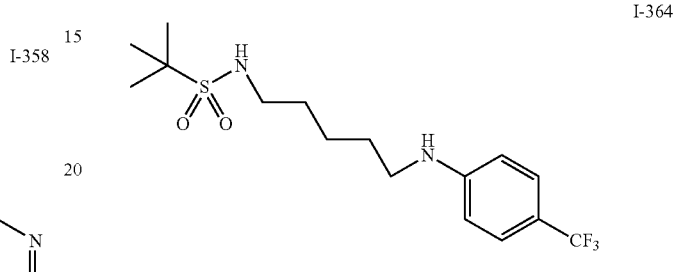
I-365
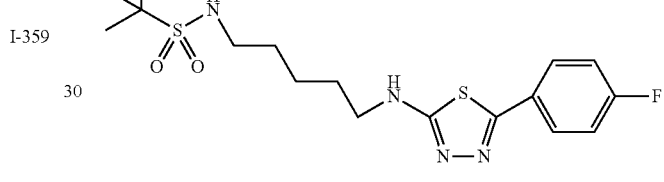
[Formula 87]
I-366
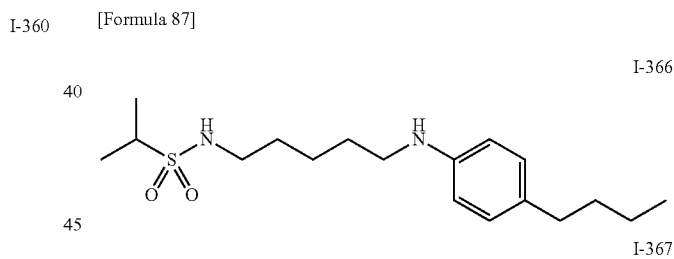
I-367
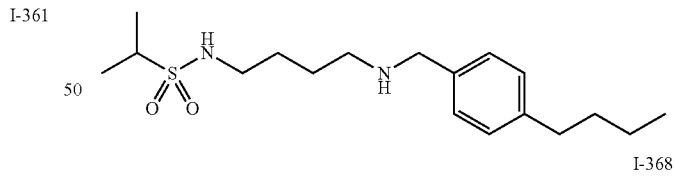
I-368
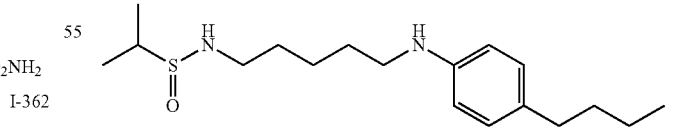
I-369
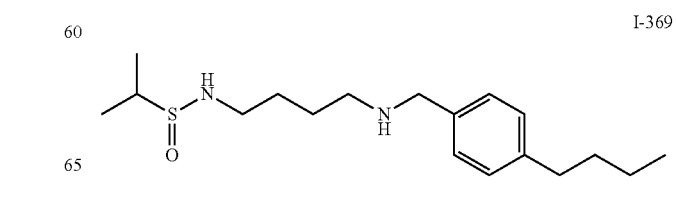

I-370
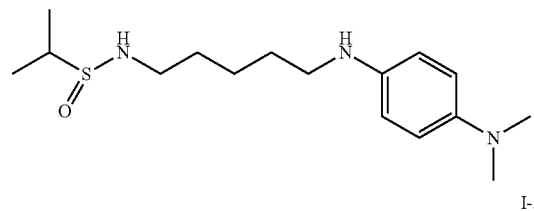
I-371
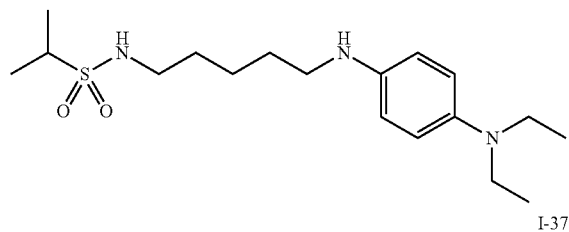
I-372
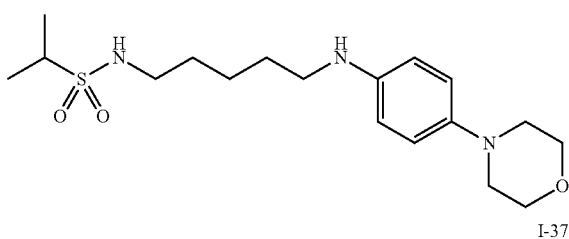
I-373
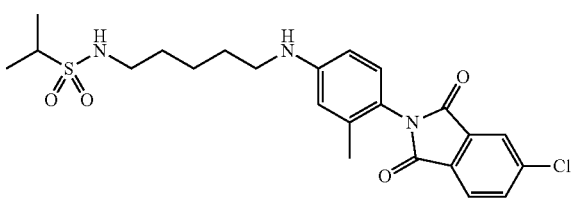
I-374
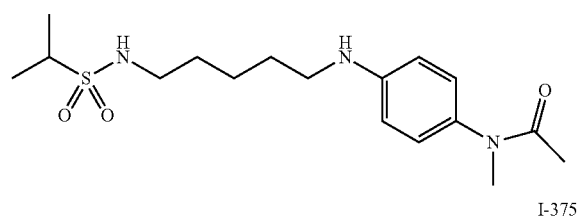
I-375
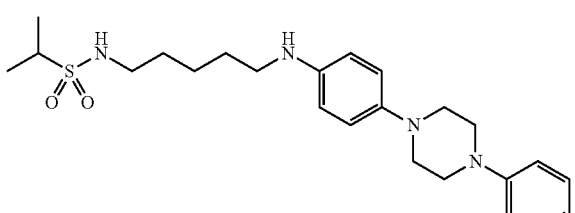
I-376
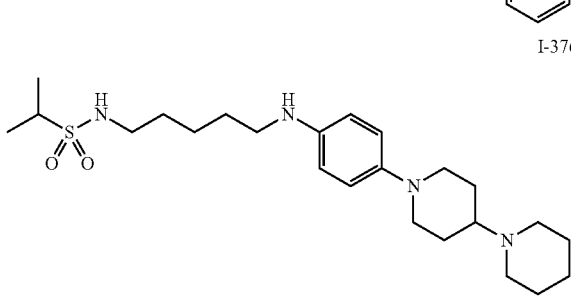
I-377
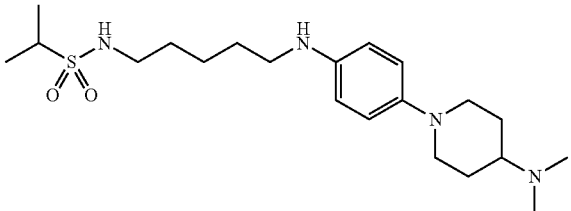
I-378
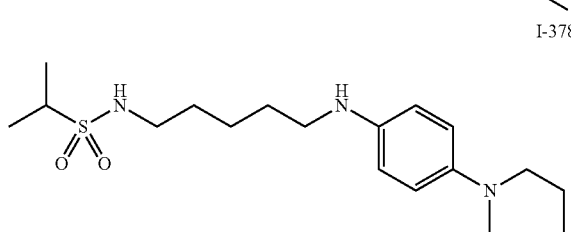
I-379
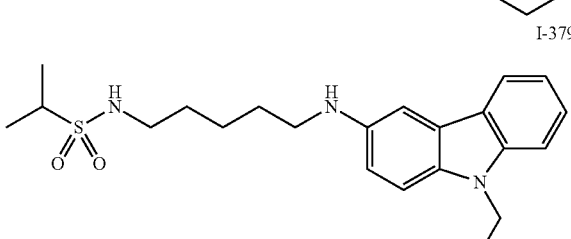
I-380
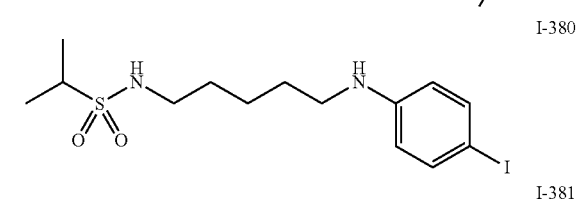
I-381
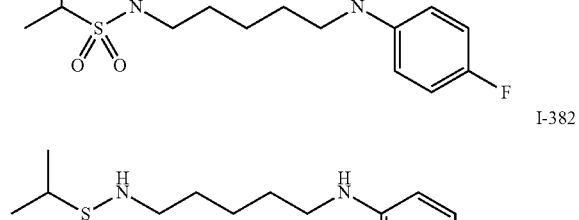
I-382
I-383
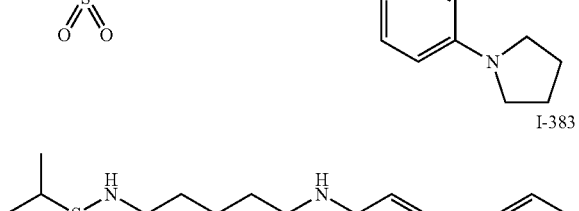
I-384

I-385
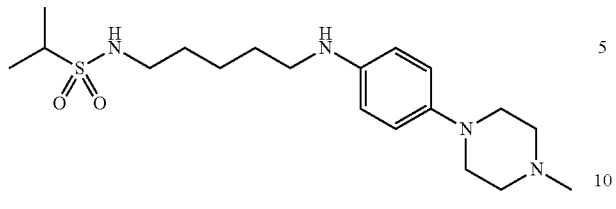
I-386

I-387
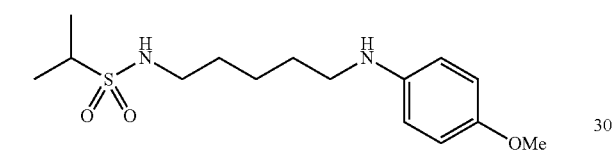
[Formula 88]
I-388

I-389
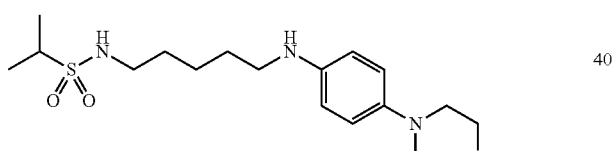
I-390
I-391
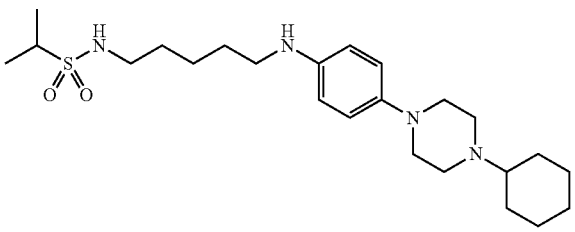
I-392
I-393
I-394
I-395
I-396
I-397

I-398
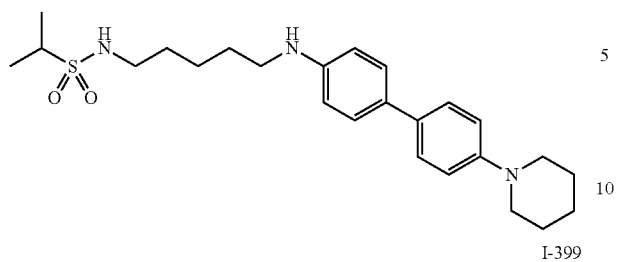
I-399
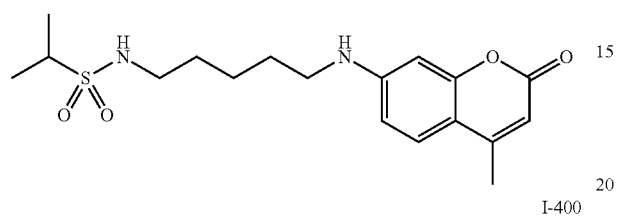
I-400
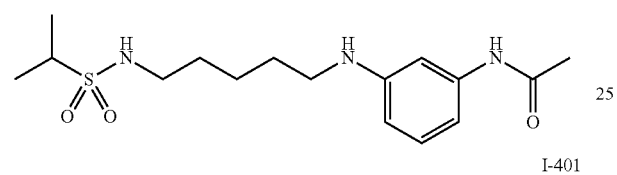
I-401
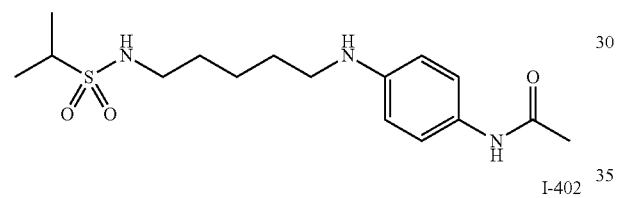
I-402
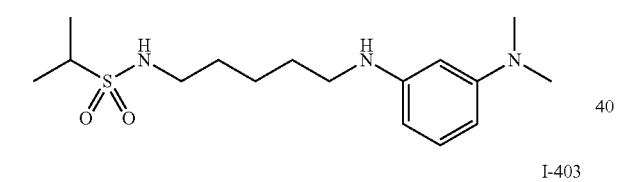
I-403
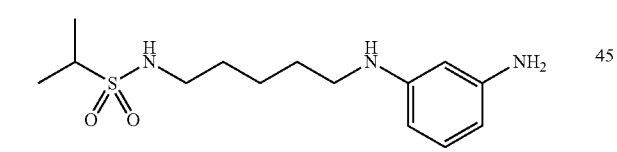
I-404
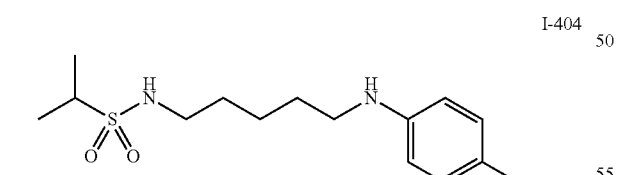
I-405
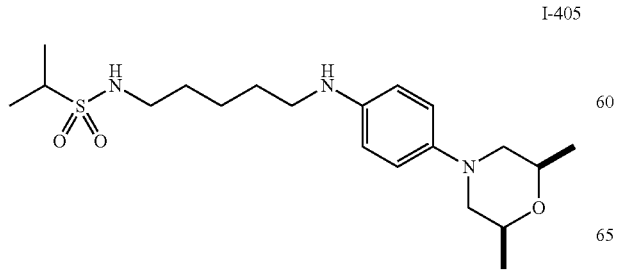
I-406
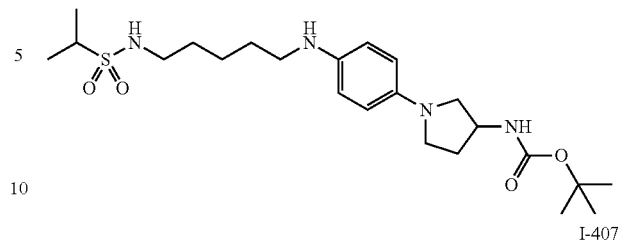
I-407
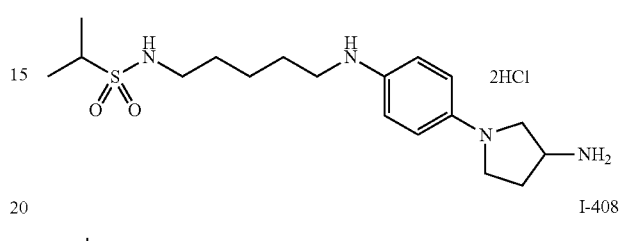
I-408
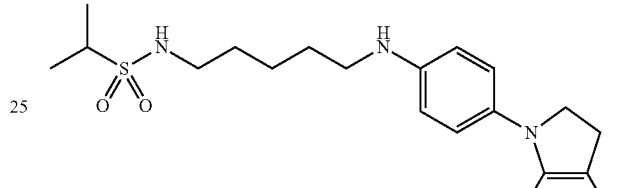
I-409
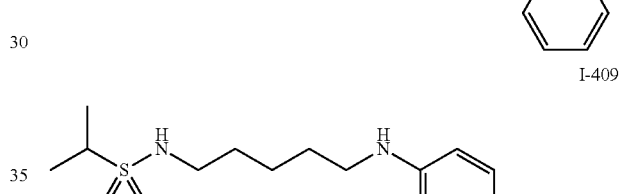
[Formula 89]
I-410
I-411

I-412
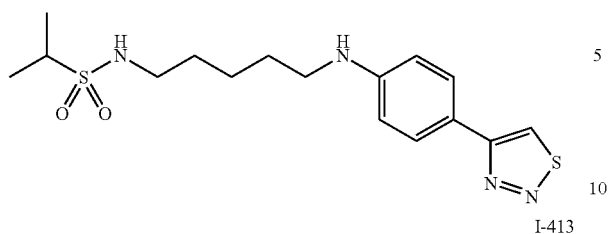
I-413
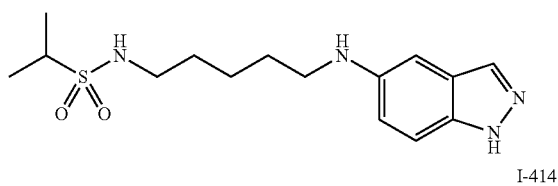
I-414
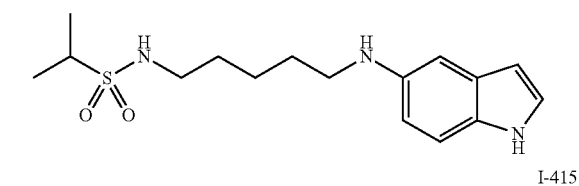
I-415
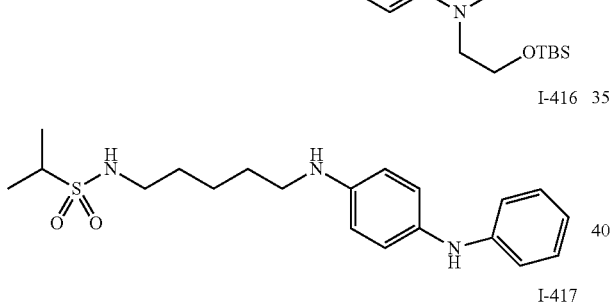
I-416
I-417
I-418
I-419
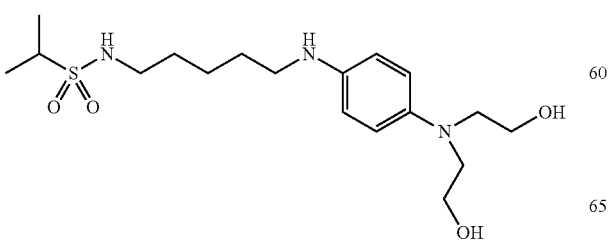
I-420
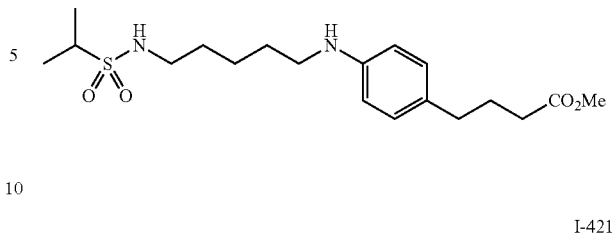
I-421
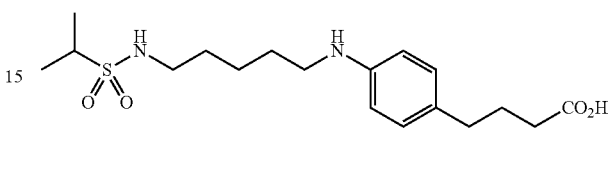
I-422
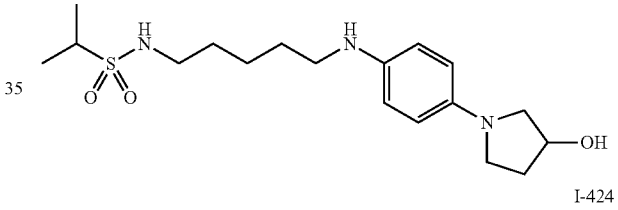
I-423
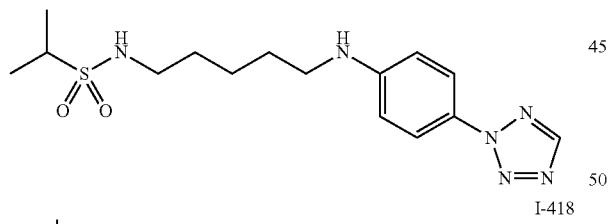
I-424
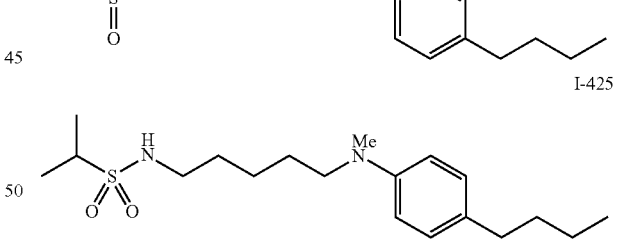
I-425
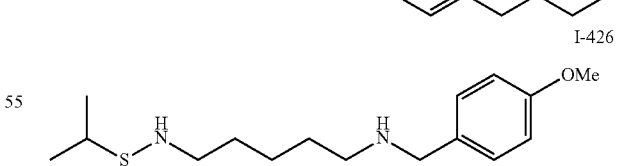
I-426
I-427
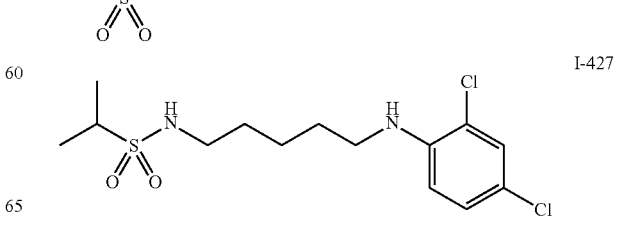

[Formula 90]
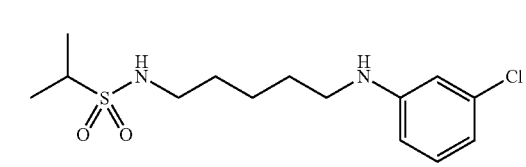
I-432
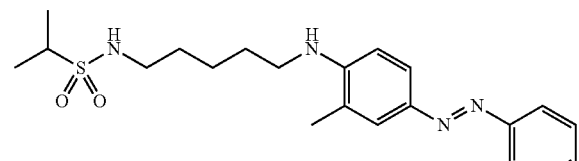
I-433
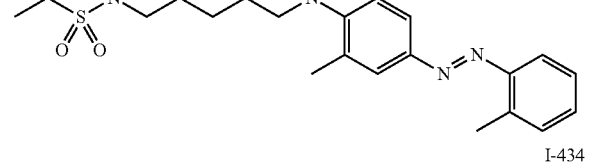
I-434
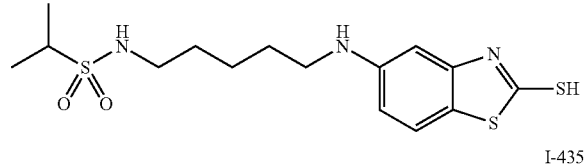
I-435
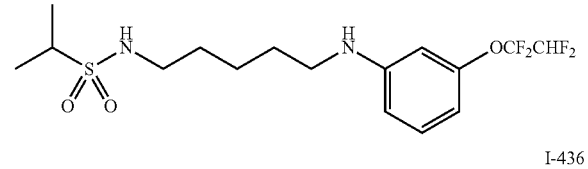
I-436
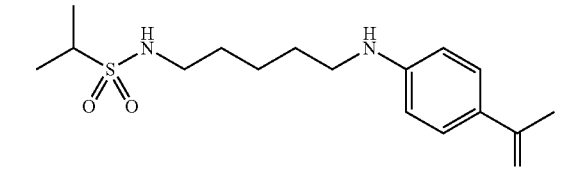
I-437
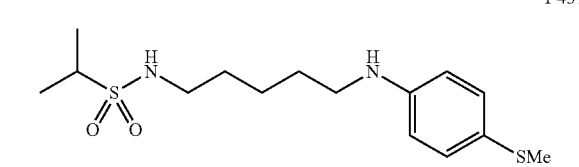
I-438
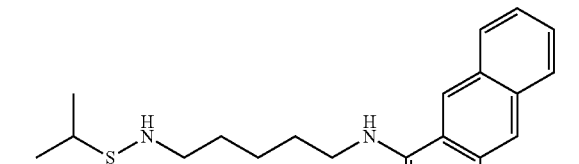
I-439
-continued
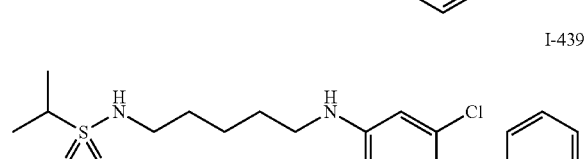
I-440
I-441
I-442
I-443
I-444
I-445
I-446
I-447

I-448
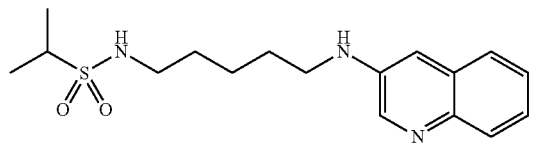
I-449
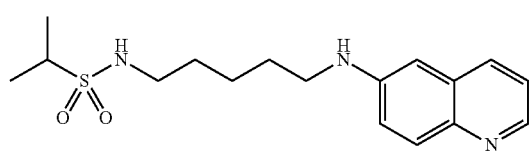
I-450
I-451
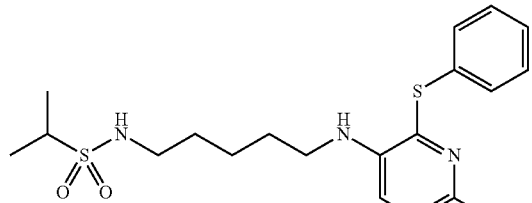
I-452
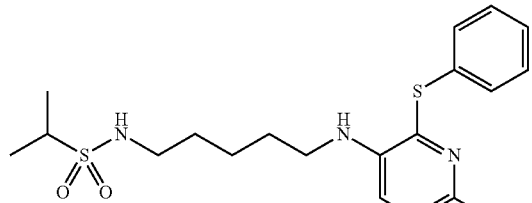
I-453
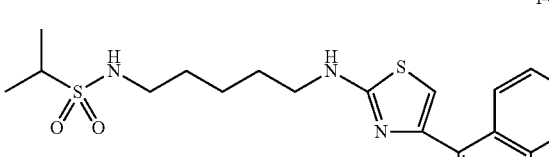
I-454
I-455
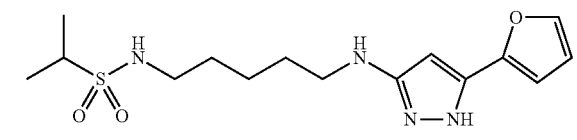
[Formula 91]
I-456
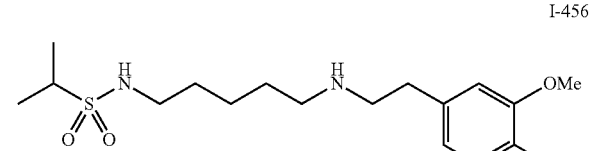
I-457
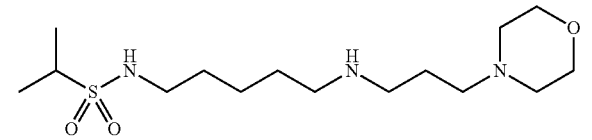
I-458
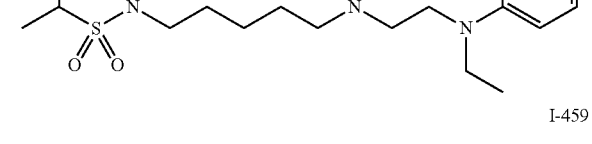
I-459
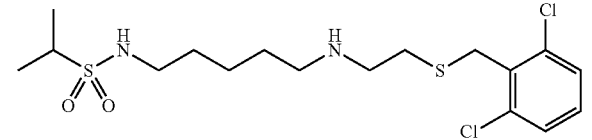
I-460
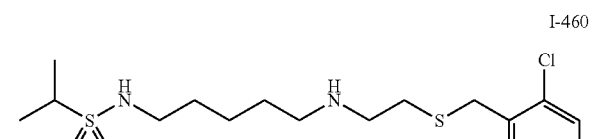
I-461
I-462

I-463
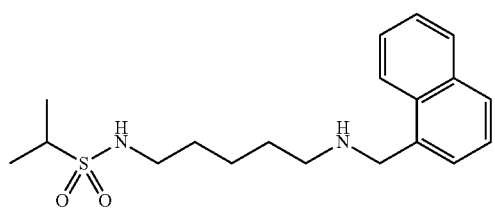
I-464
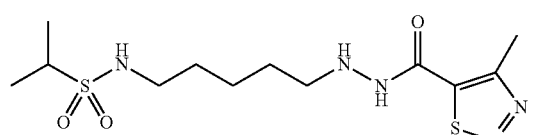
I-465
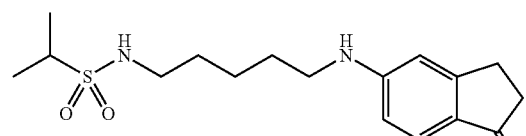
I-466
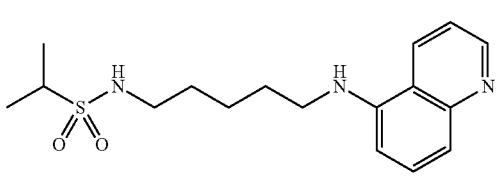
I-467
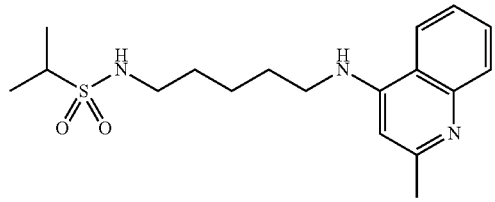
I-468
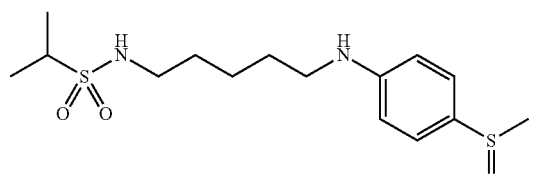
I-469
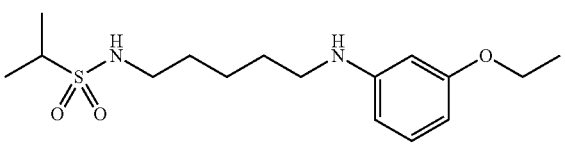
I-470
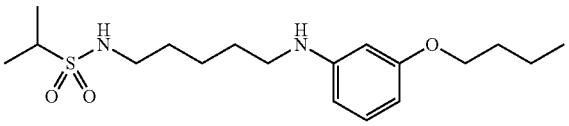
I-471
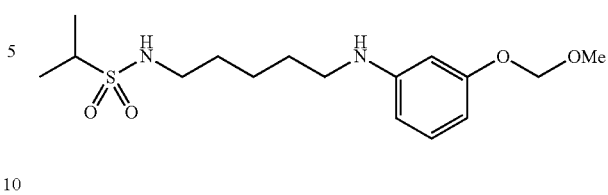
I-472
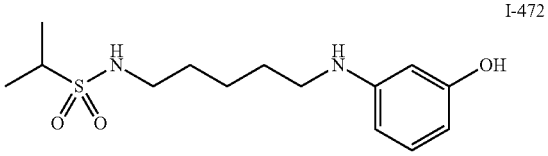
I-473
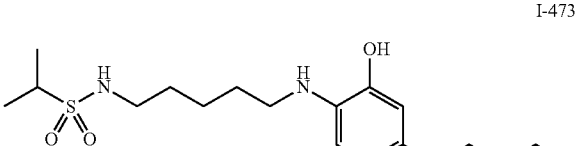
I-474
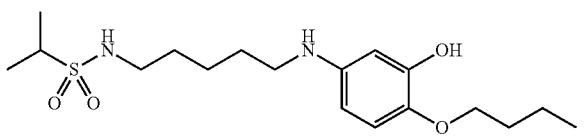
I-475
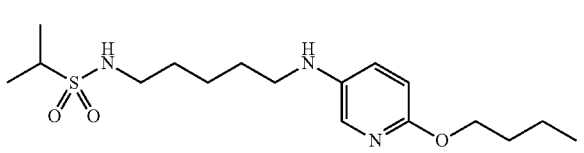
I-476
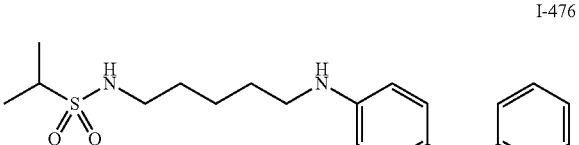
I-477
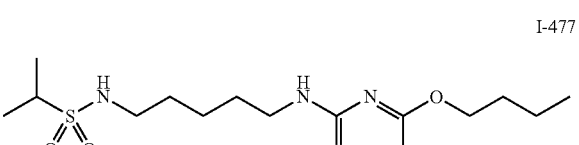
[Formula 92]
I-478
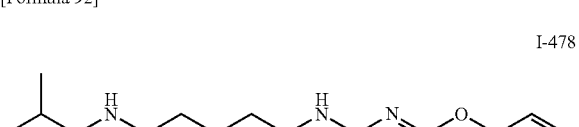

I-479
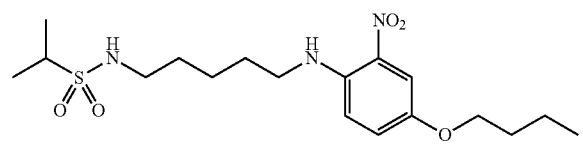
I-480
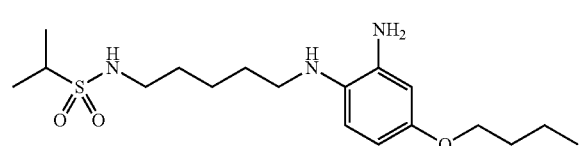
I-481
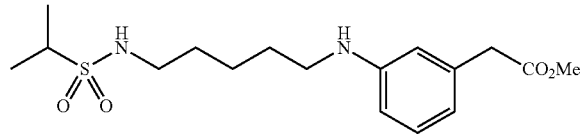
I-482
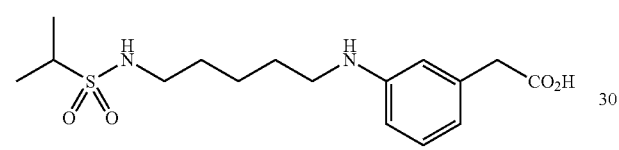
I-483
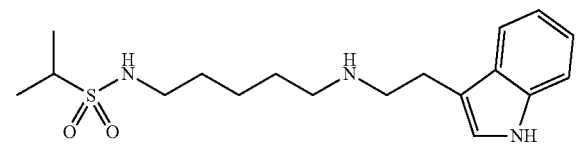
I-484
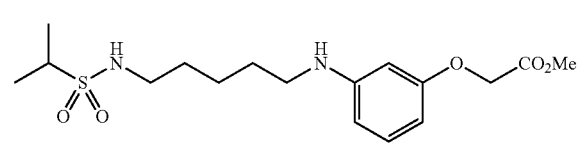
I-485
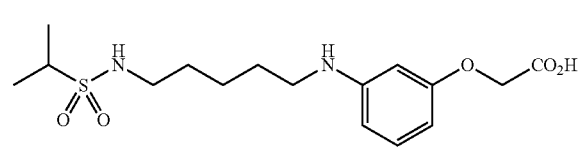
I-486
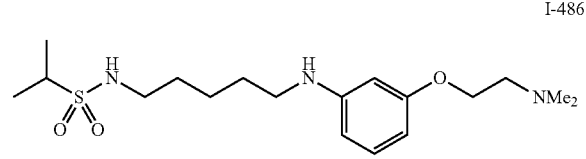
I-487
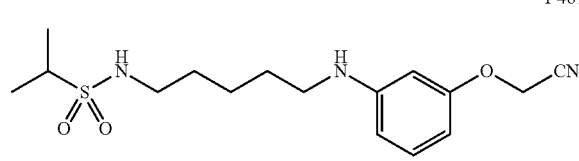
I-488
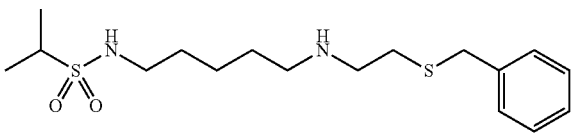
I-489
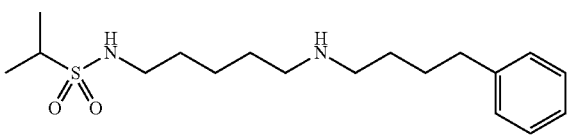
I-490
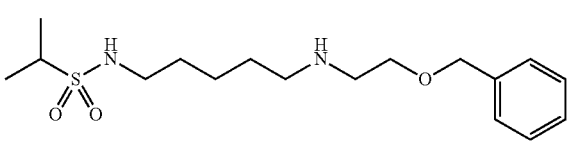
I-491
I-492
I-493
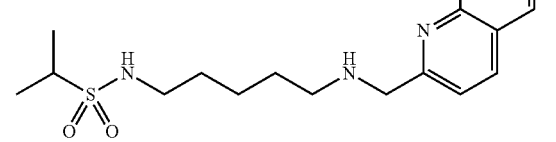
I-494
I-495
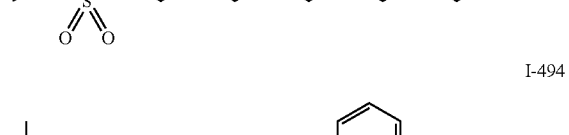

I-496 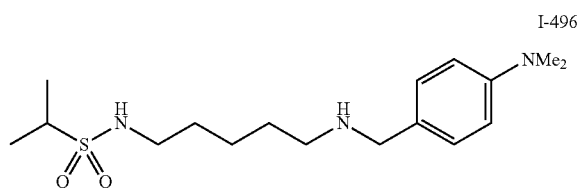
I-504 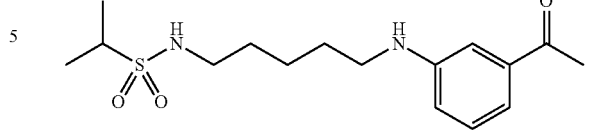
I-497 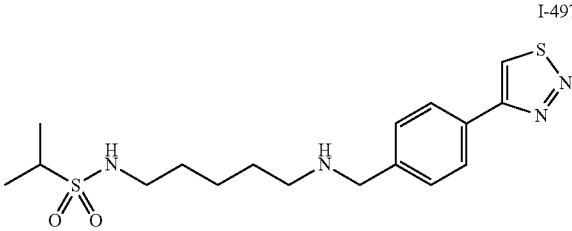
I-505 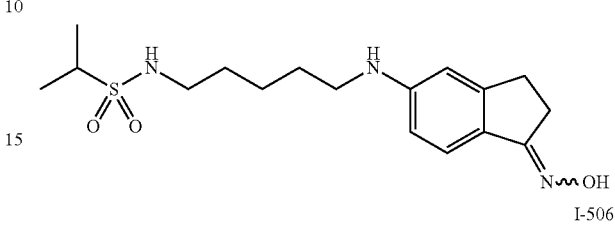
I-498 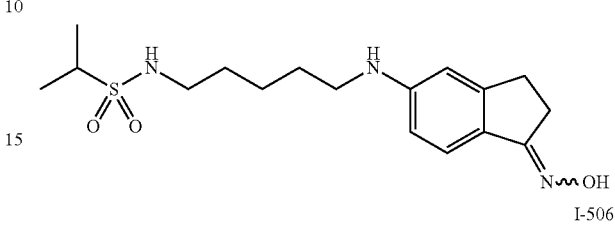
I-506 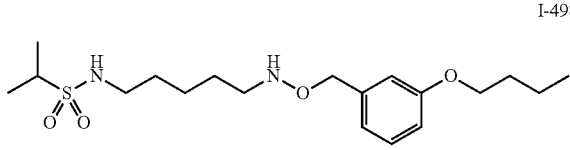
I-499 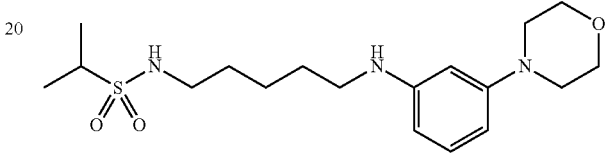
I-507 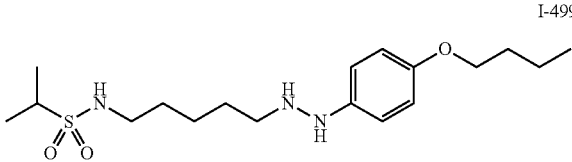
[Formula 93]
I-500 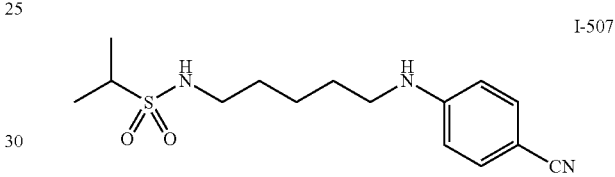
I-508 
I-501 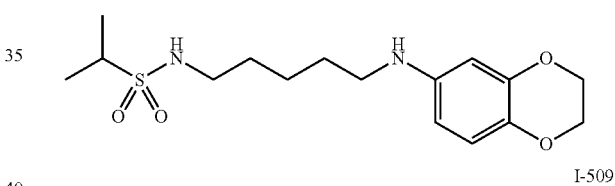
I-509 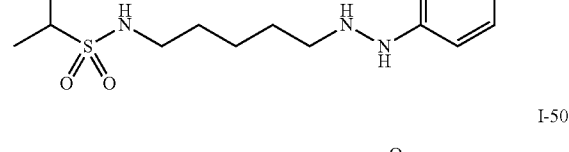
I-502 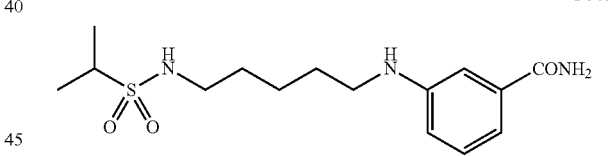
I-510 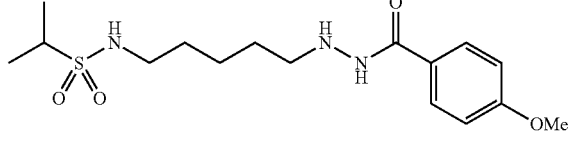
I-503 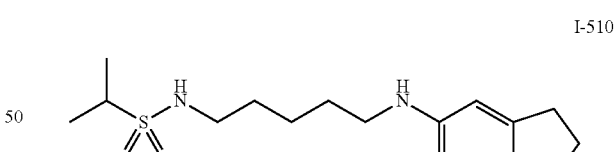
I-511 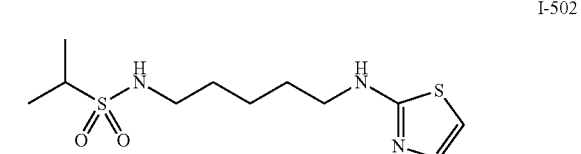
I-512 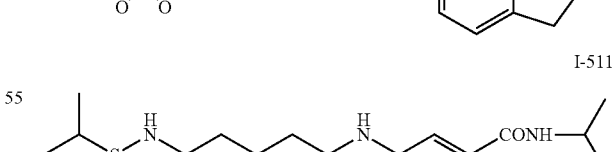

I-513
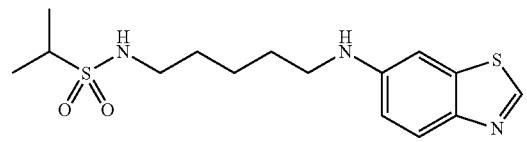
I-514
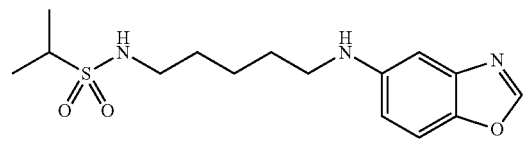
I-515
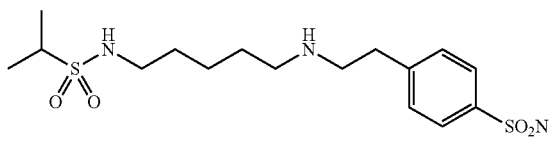
I-516
I-517
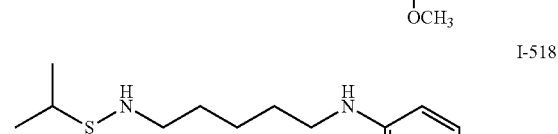
I-518
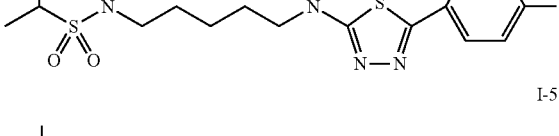
I-519
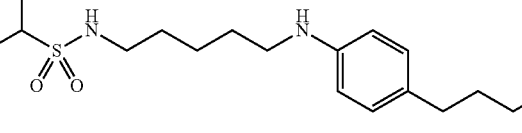
I-520
[Formula 94]
I-521
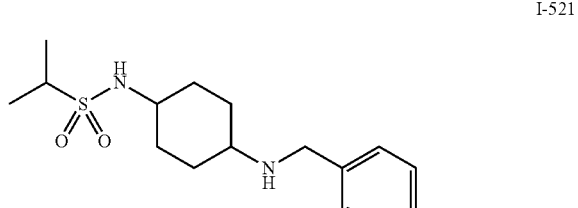
I-522
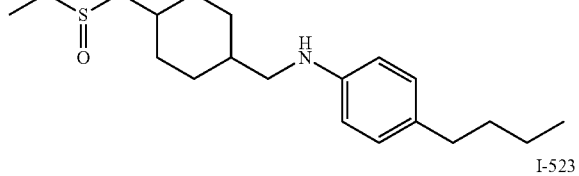
I-523
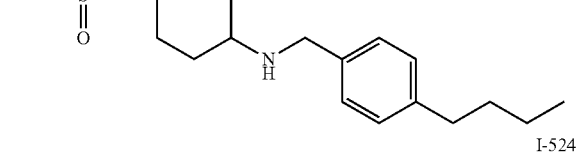
I-524
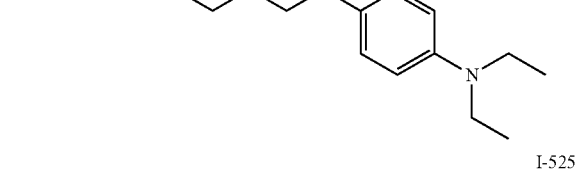
I-525
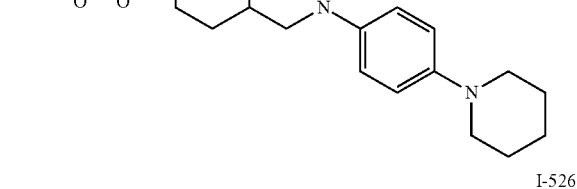
I-526
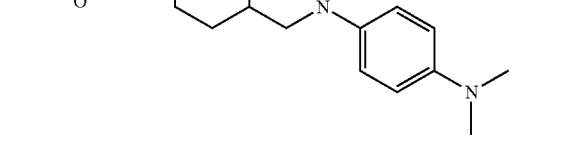

I-527
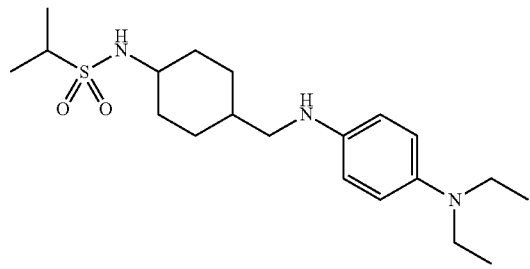
I-532
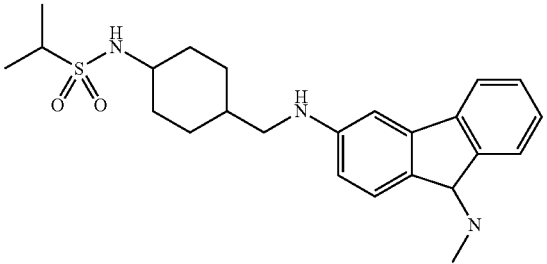
I-528
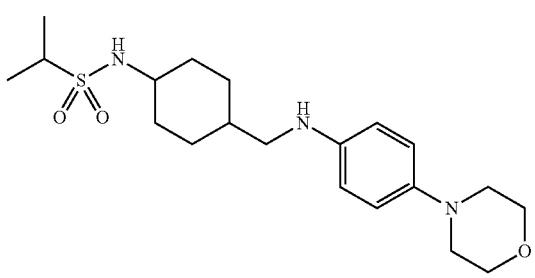
I-533
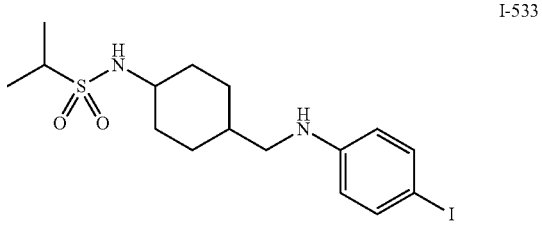
I-534
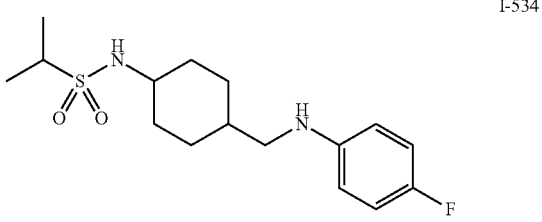
I-529
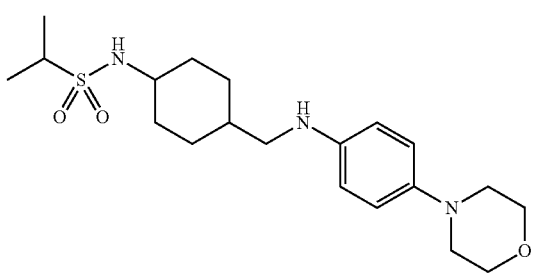
I-535
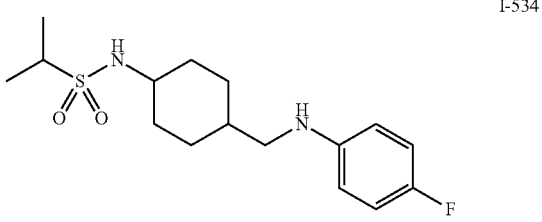
I-530
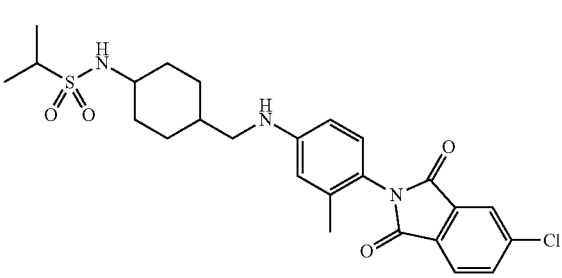
I-536
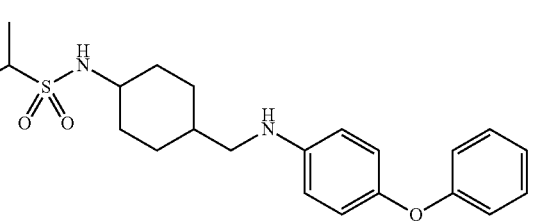
I-531
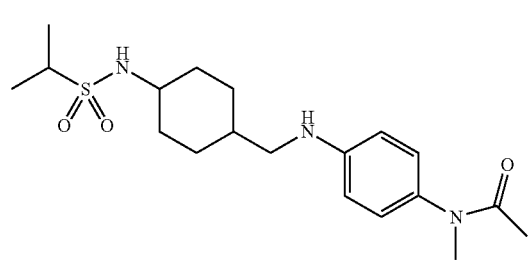
I-537
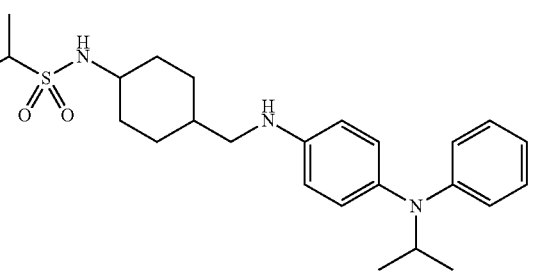

I-538
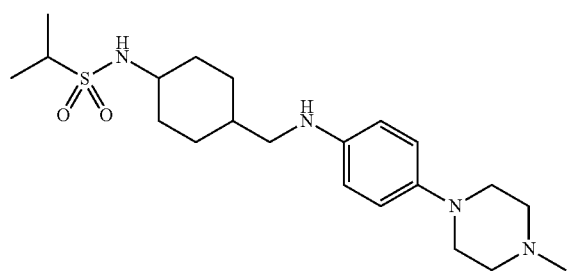
I-544
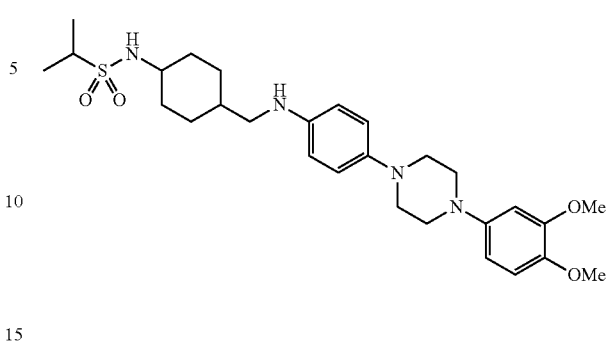
I-539
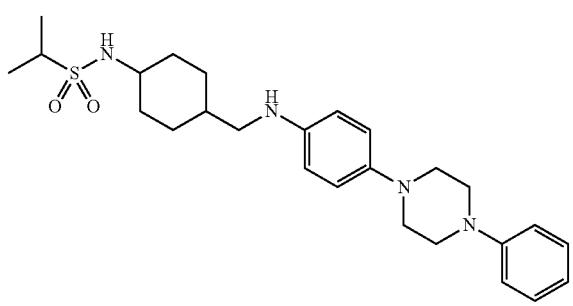
I-545
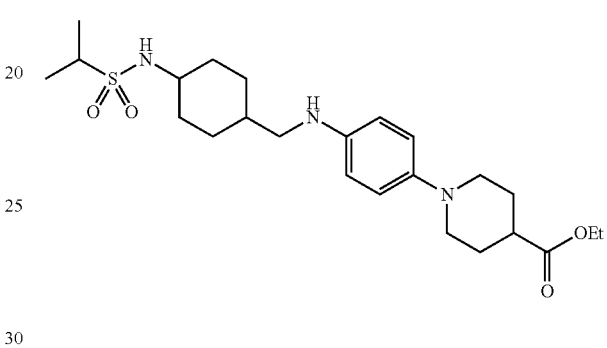
I-540
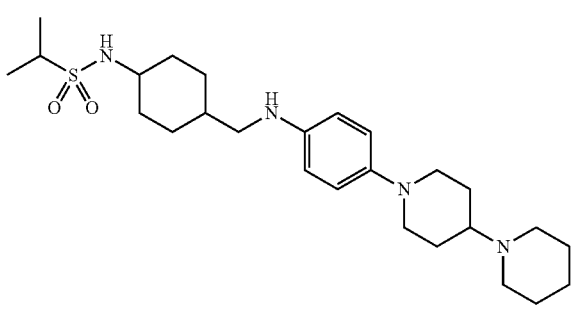
I-546
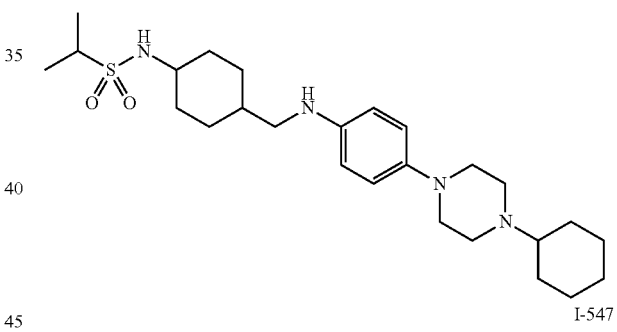
I-547
[Formula 95]
I-543
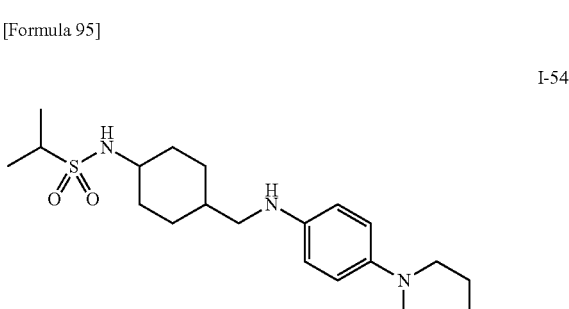
I-548
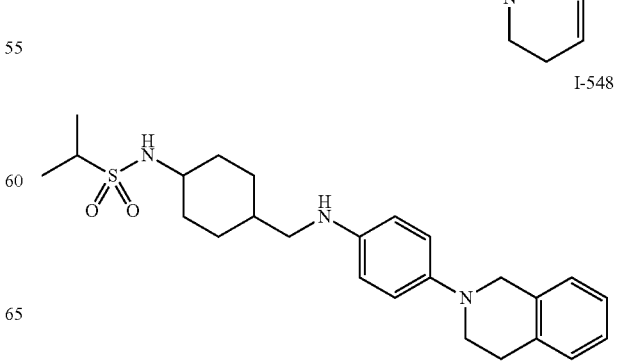

I-549
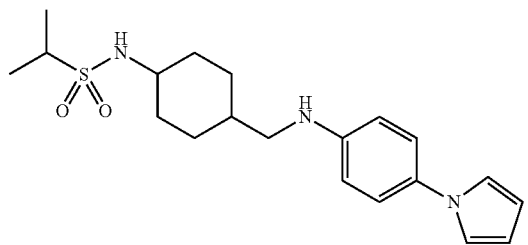
I-550
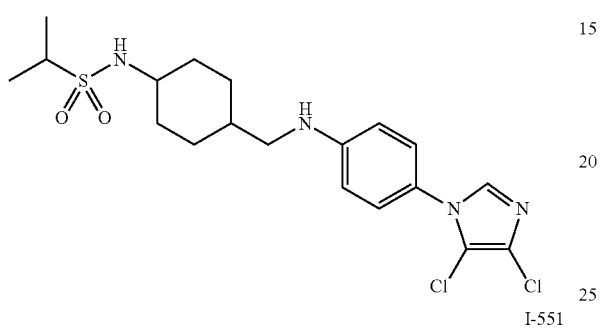
I-551
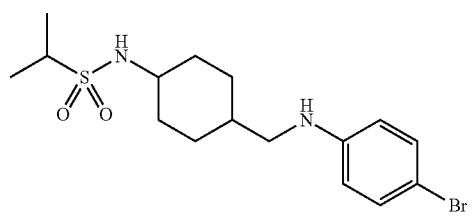
I-552
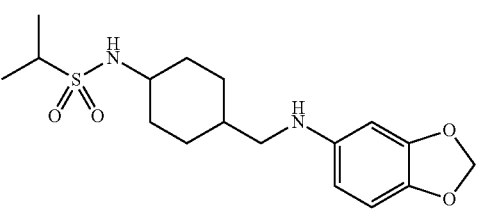
I-553
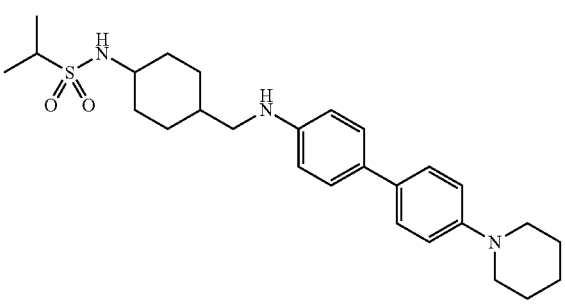
I-554
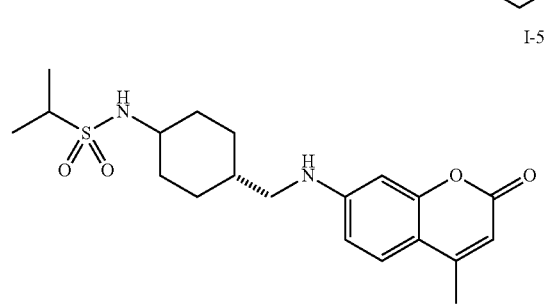
I-555
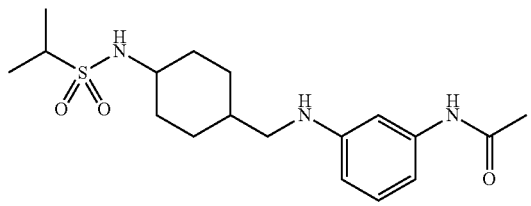
I-556
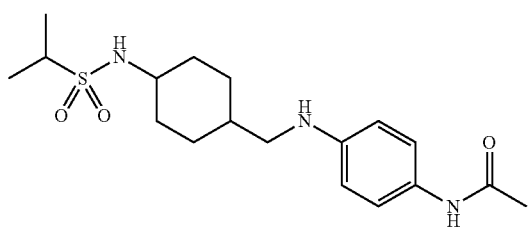
I-557
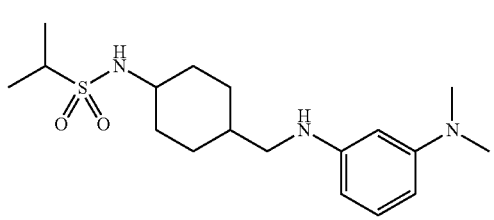
I-558
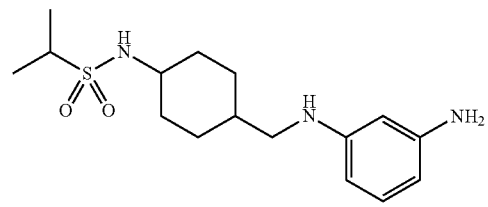
I-559
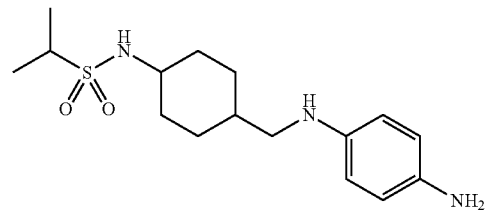
I-560

I-561
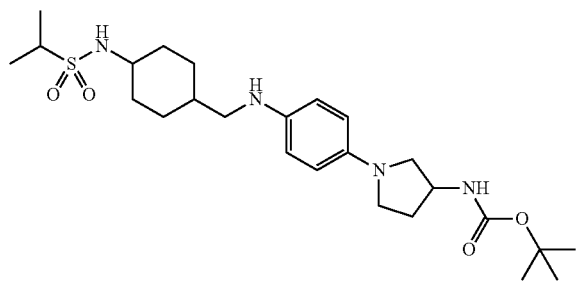
I-562
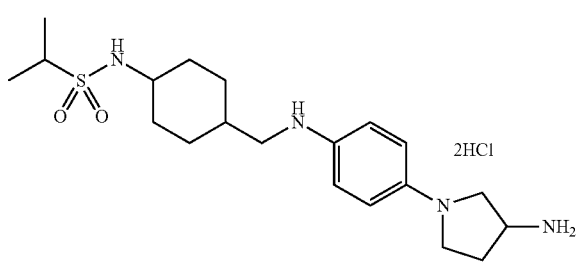
2HCl
I-563
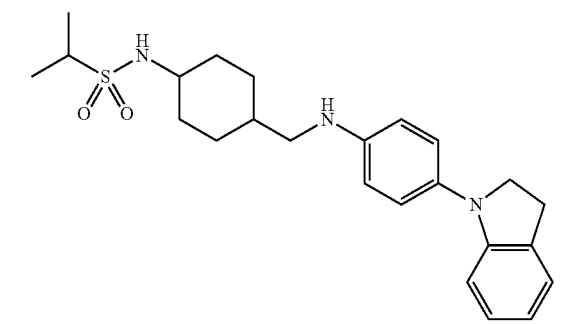
I-564
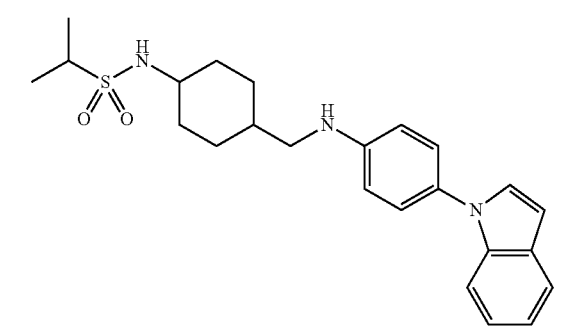
[Formula 96]
I-565
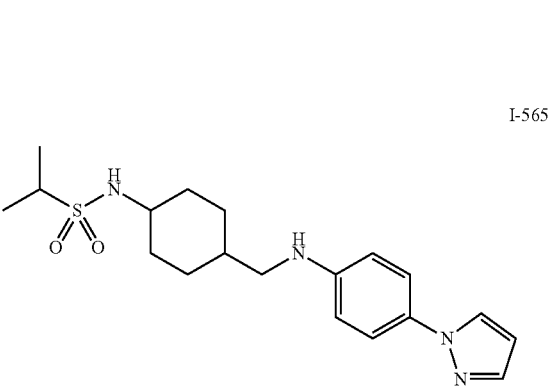
I-566
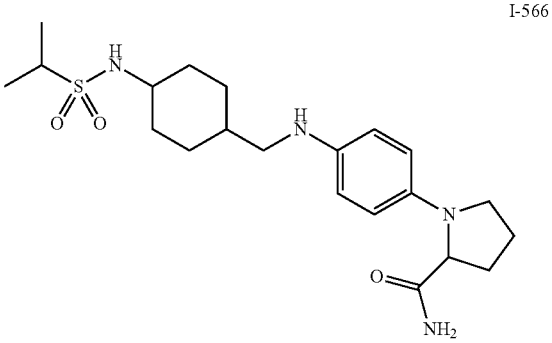
I-567
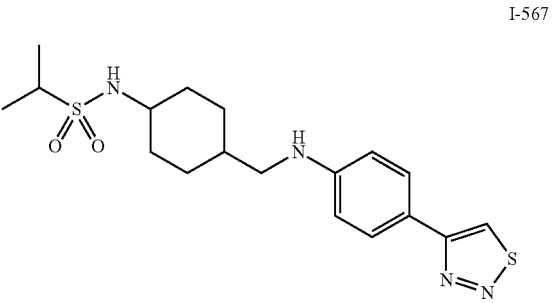
I-568
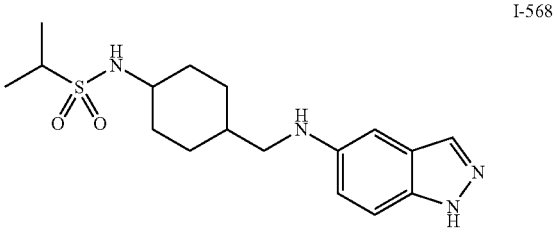
I-569
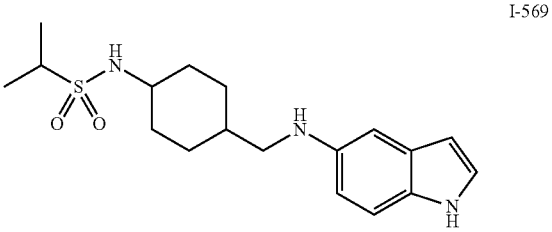

127
-continued
I-570
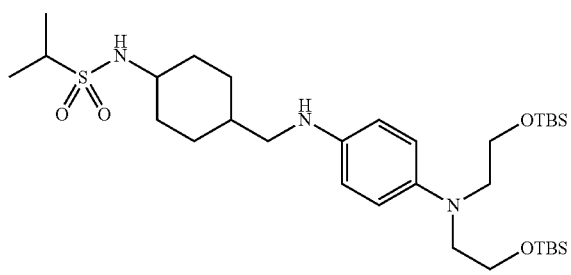
I-571
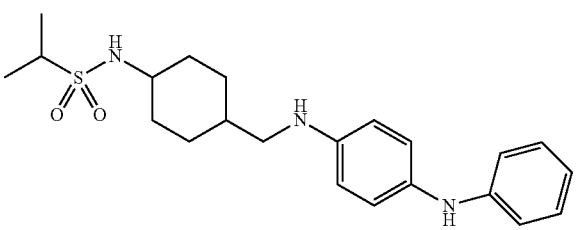
I-572
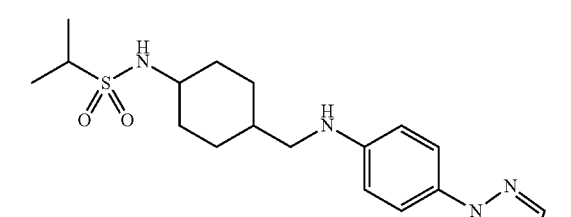
I-573
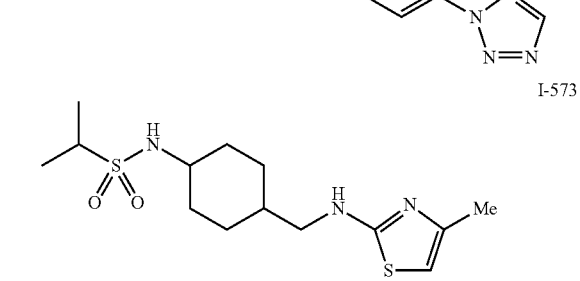
I-574
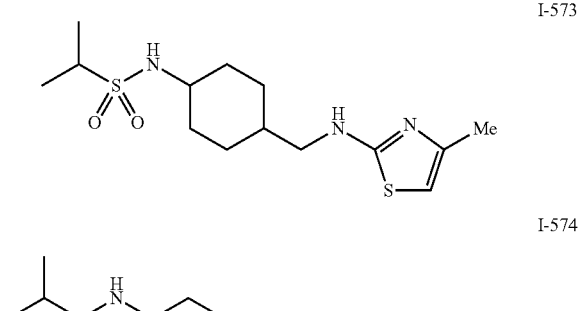
I-575
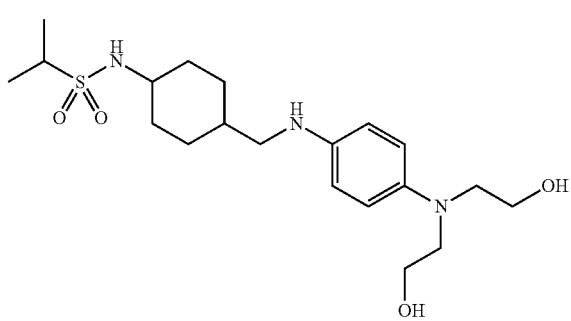
128
-continued
I-576
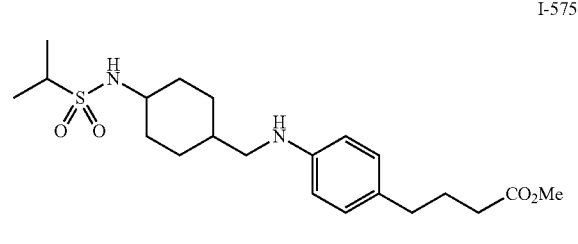
I-577
I-578
I-579
I-580
I-581
I-582
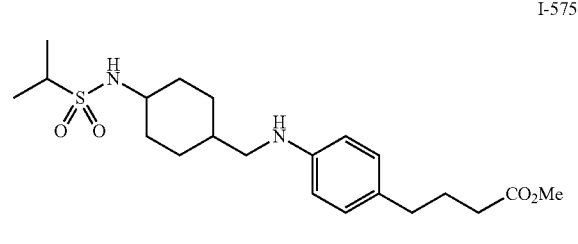

I-583
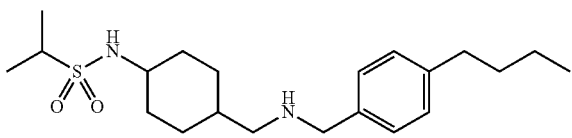
I-584
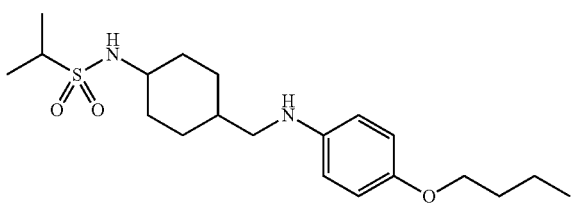
I-585
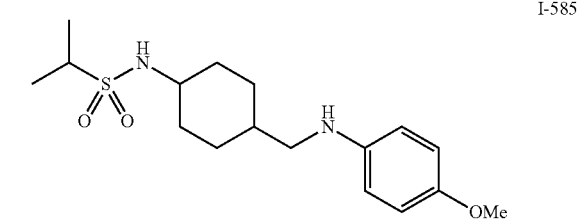
[Formula 97]
I-587
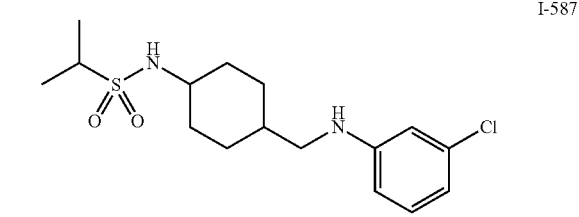
I-589
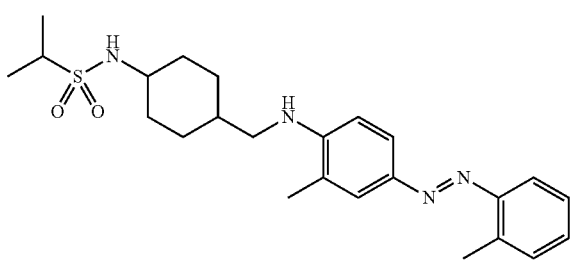
I-590
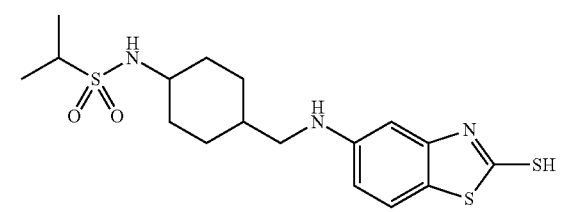
I-591
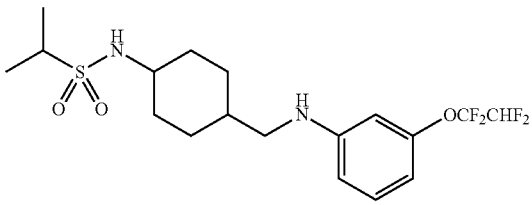
I-592
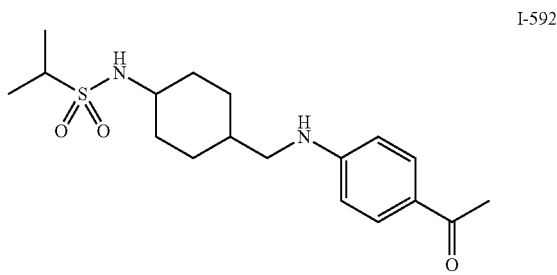
I-593
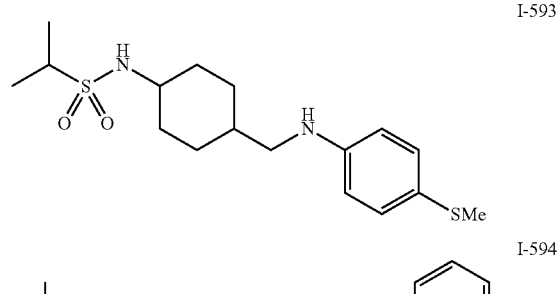
I-594
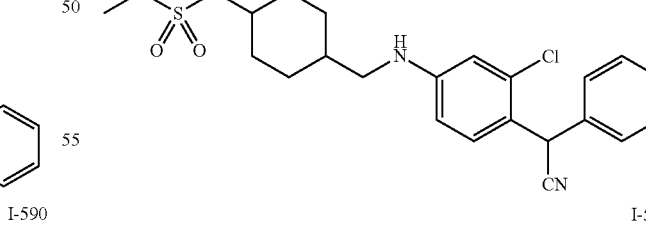
I-595
I-596
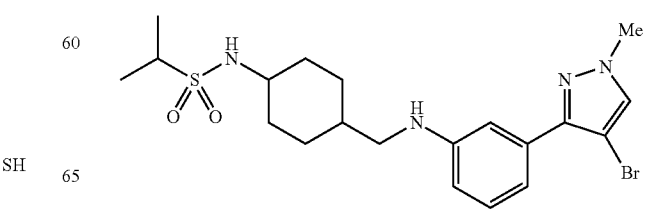

I-597
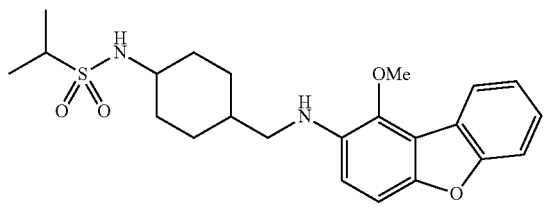
I-598
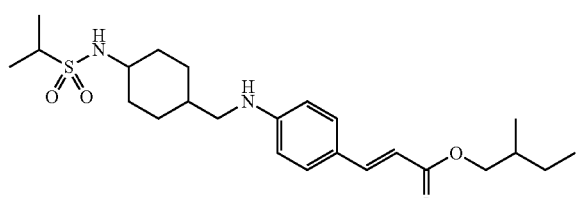
I-599
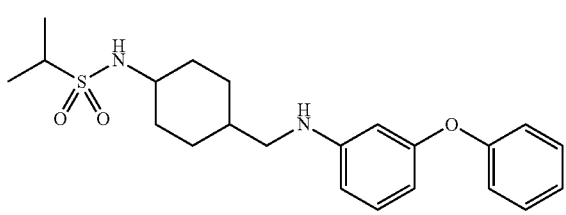
I-600
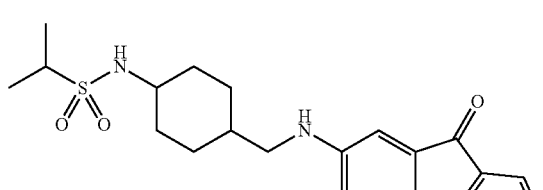
I-601
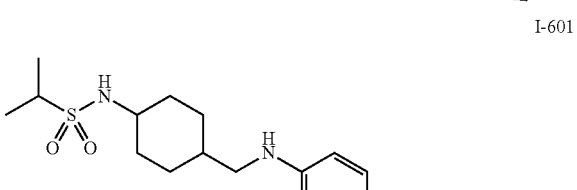
I-602
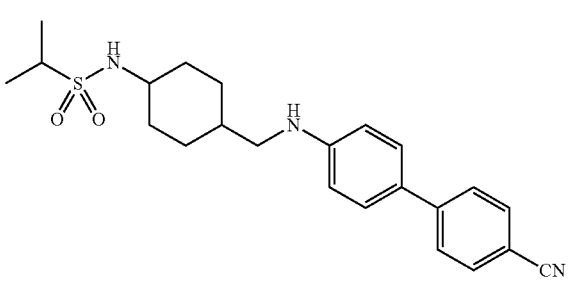
I-603
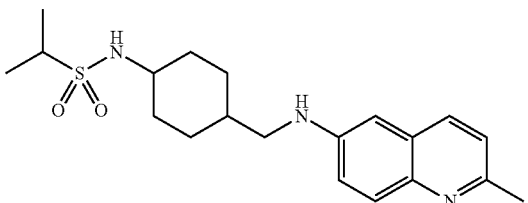
I-604
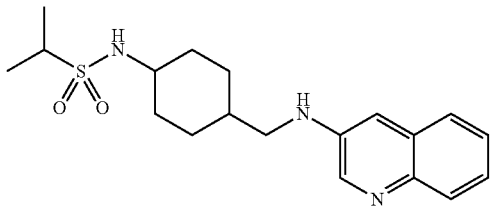
I-605
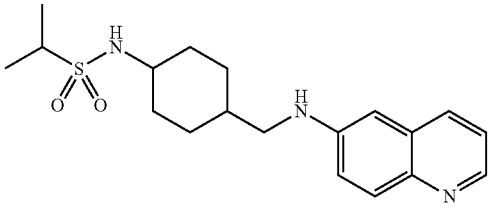
I-606
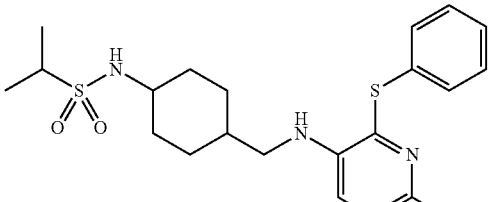
I-607
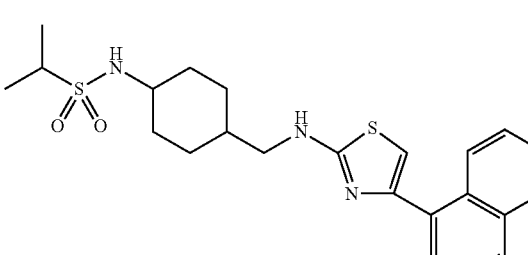
I-608

I-609
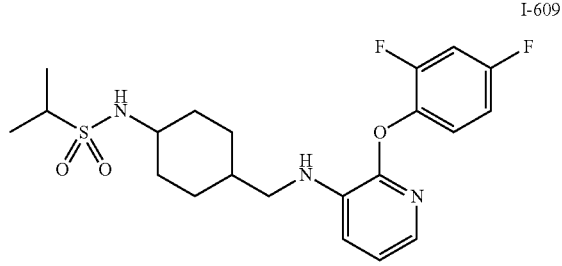
[Formula 98]
I-610
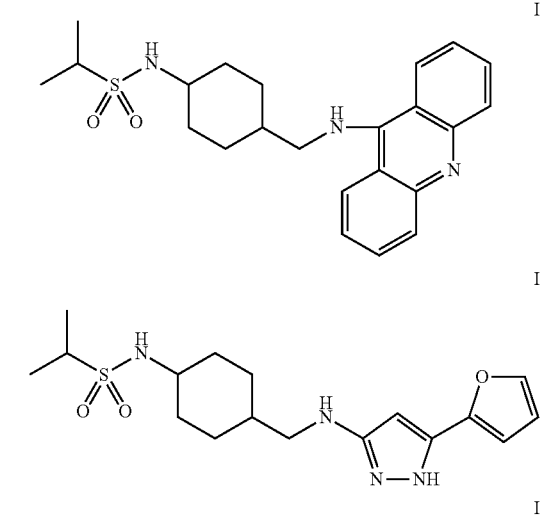
I-611
I-612
I-613
I-614
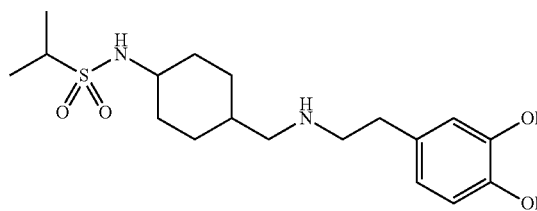
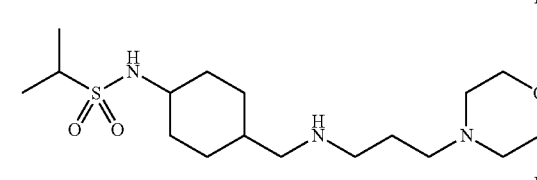
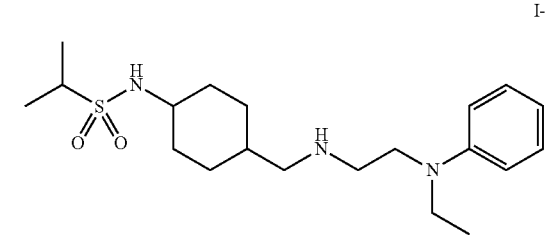
I-615
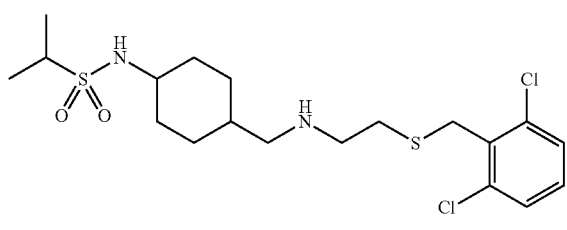
I-616
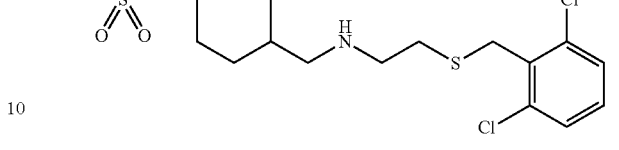
I-617
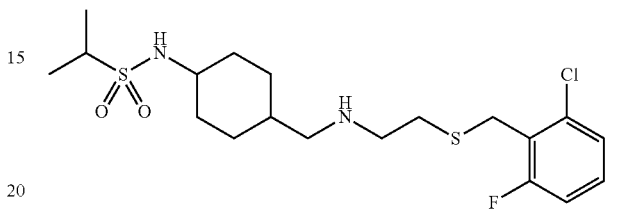
I-618
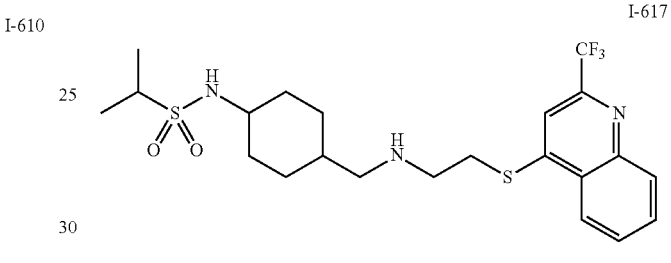
I-619
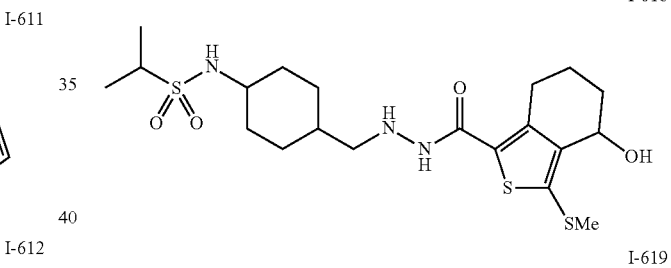
I-620
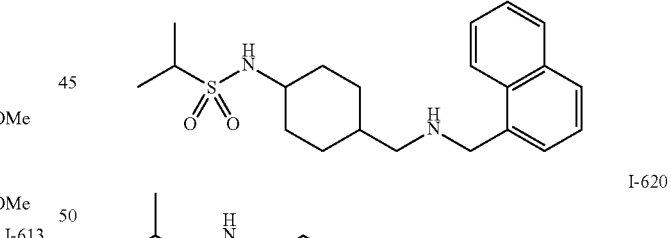
I-621
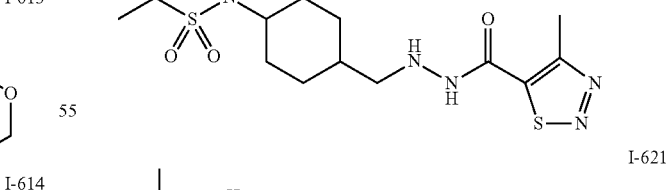

I-622 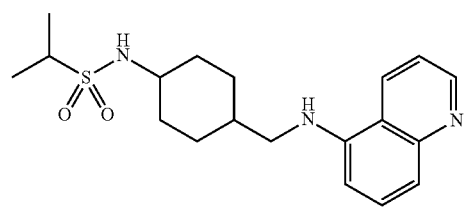
I-623 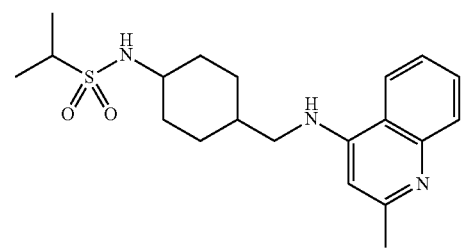
I-624 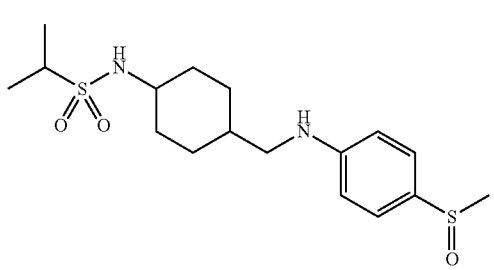
I-625 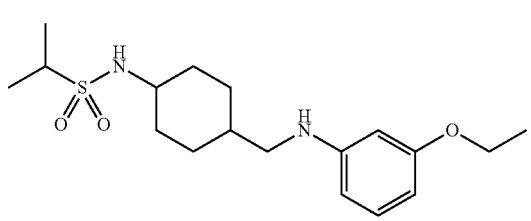
I-626 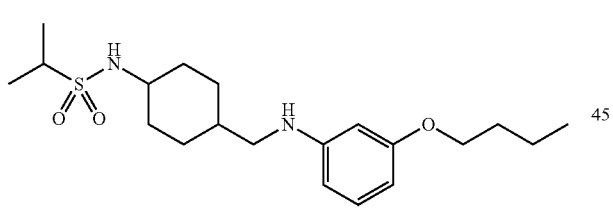
I-627 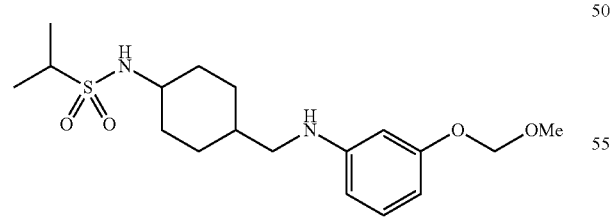
I-628 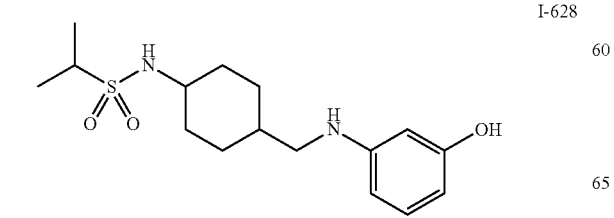
I-629 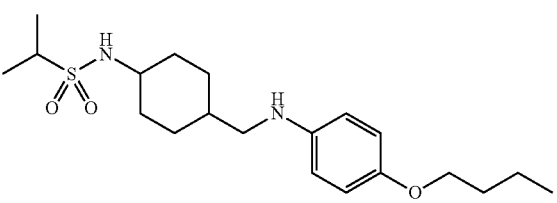
I-630 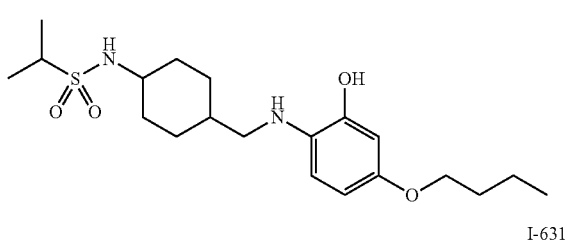
I-631 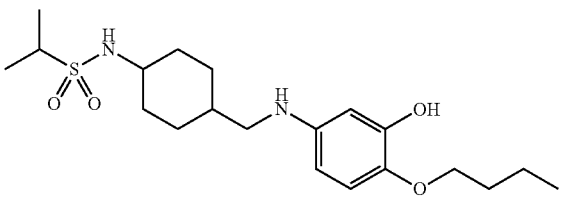
[Formula 99]
I-632 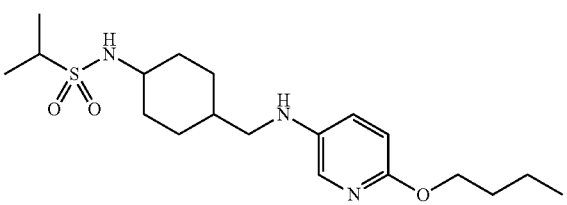
I-633 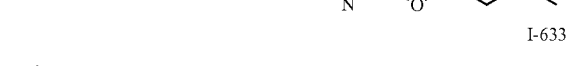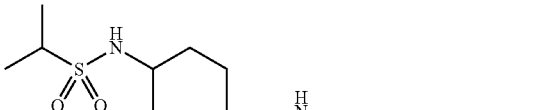
I-634 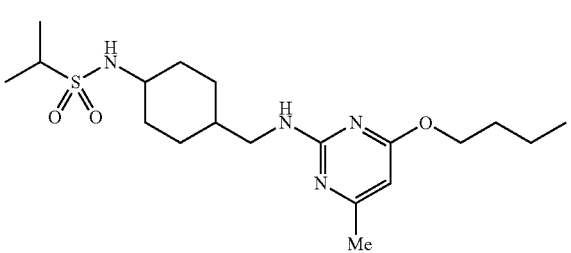

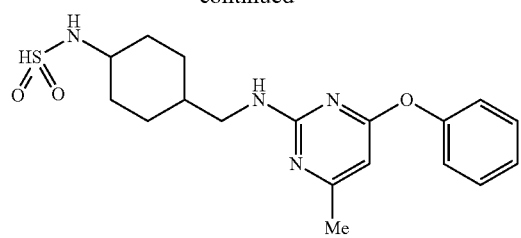
I-636
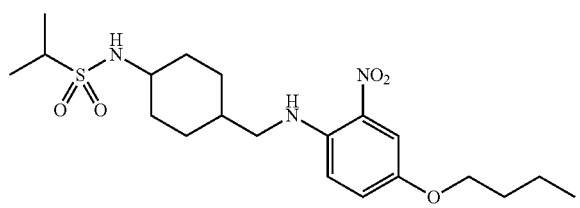
I-637
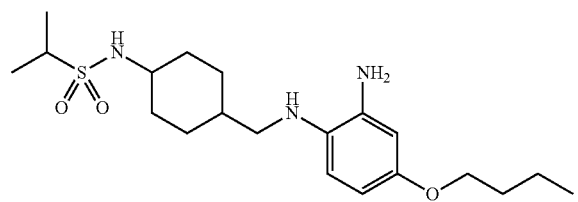
I-638
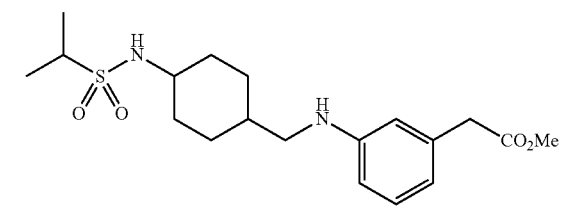
I-639
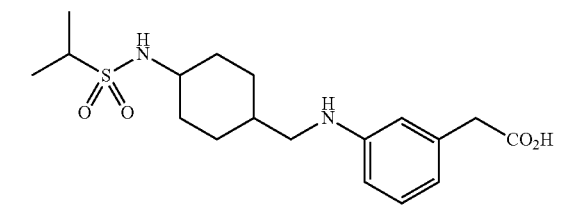
I-640
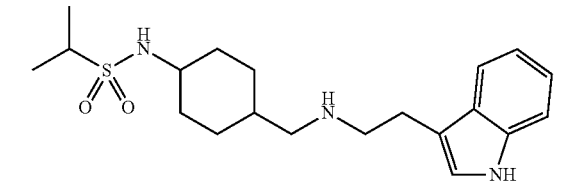
I-641
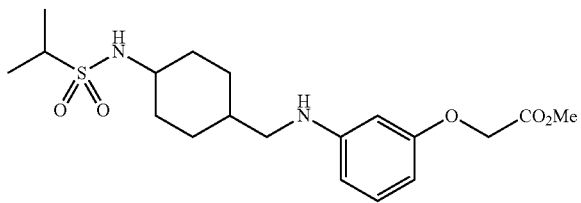
I-642
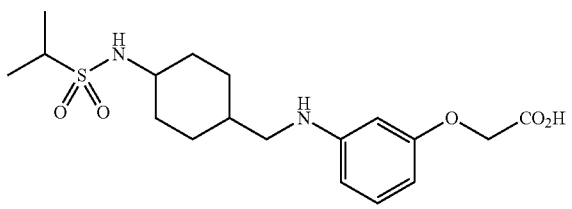
I-643
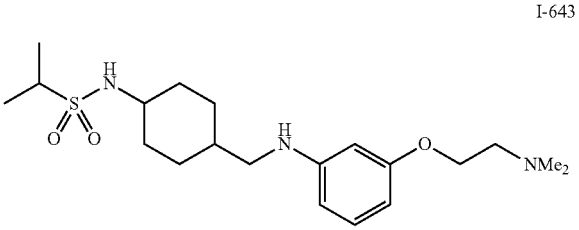
I-644
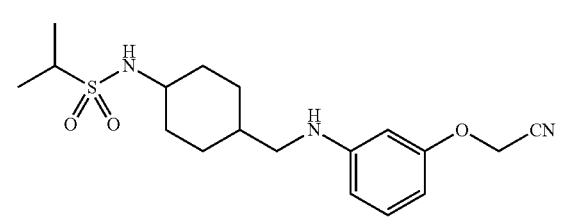
I-645
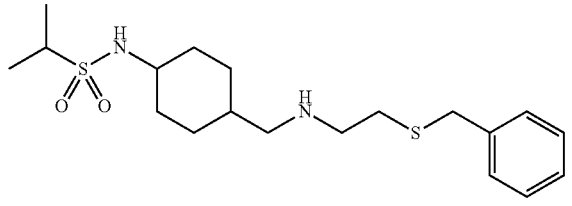
I-646
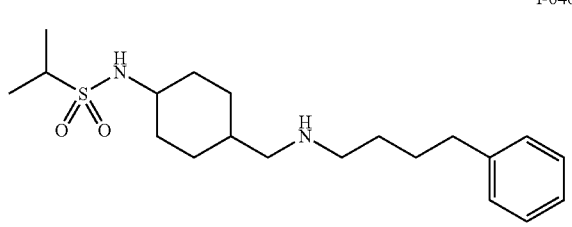
I-647
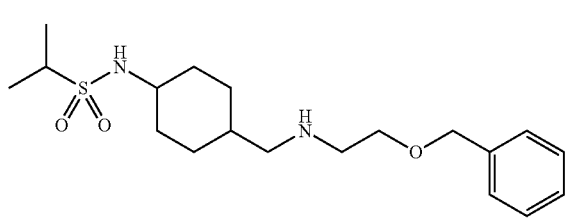
I-648

I-649 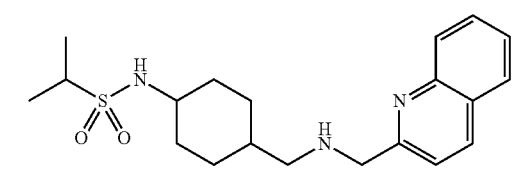
I-650 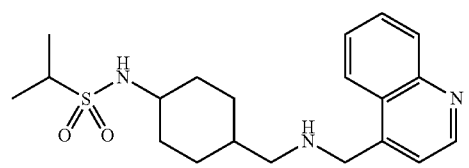
I-651 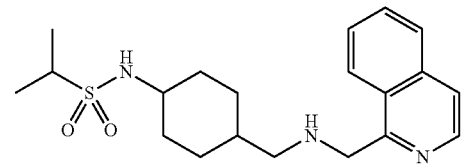
I-652 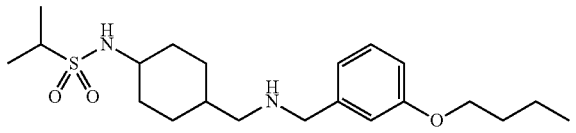
I-653 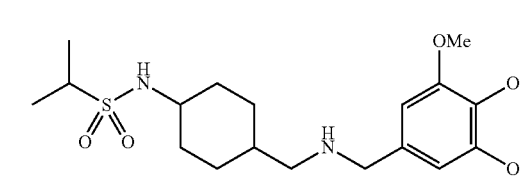
I-654 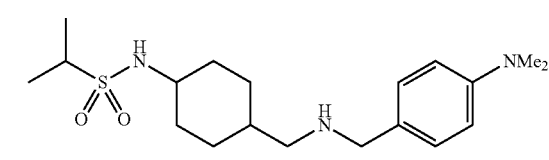
I-655 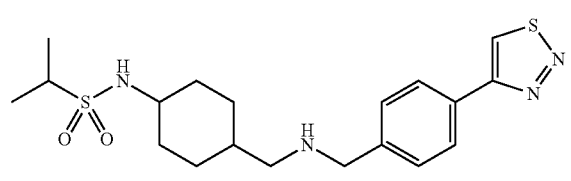
[Formula 100]
I-656 
I-657 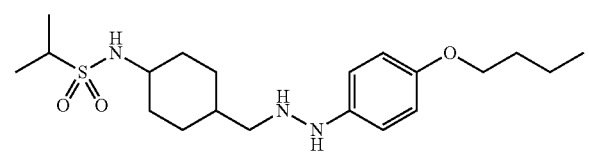
I-658 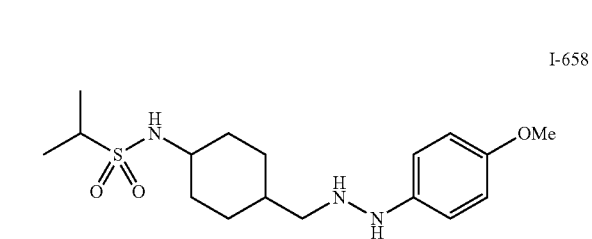
I-659 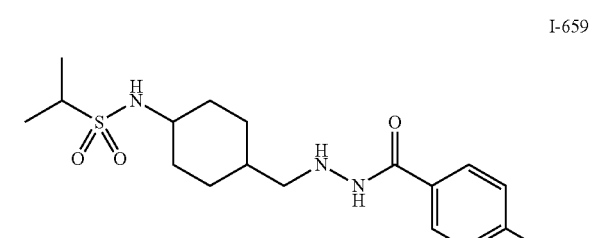
I-660 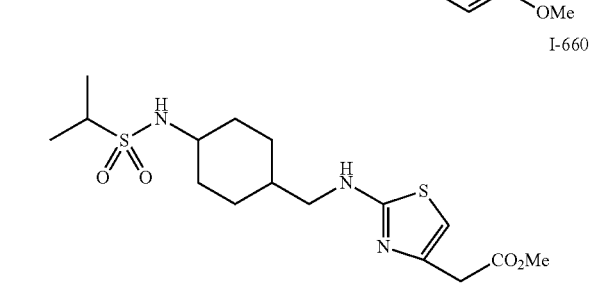
I-661 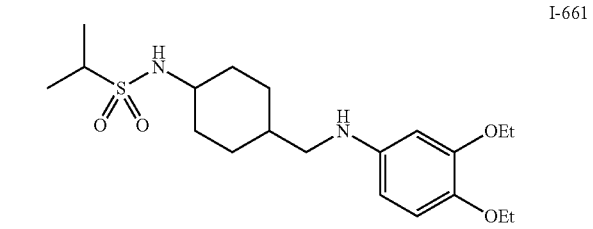
I-662 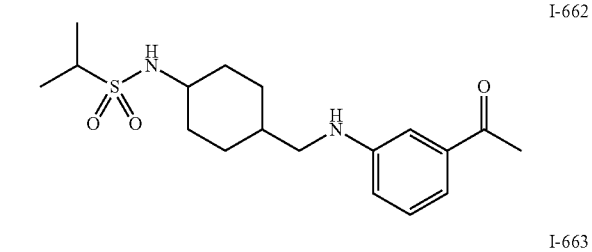
I-663 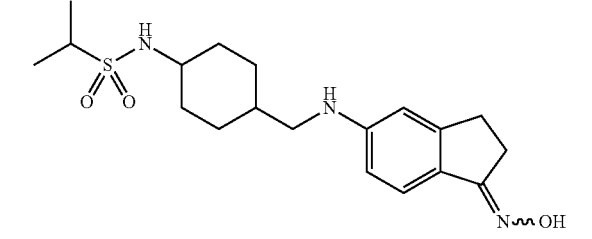

I-664
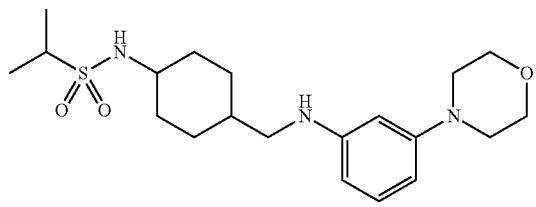
I-670
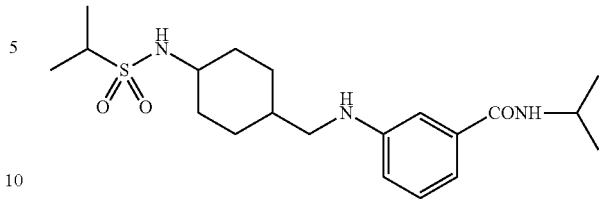
I-665
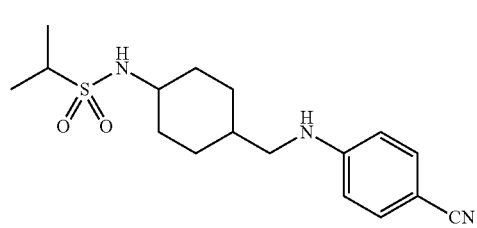
I-671
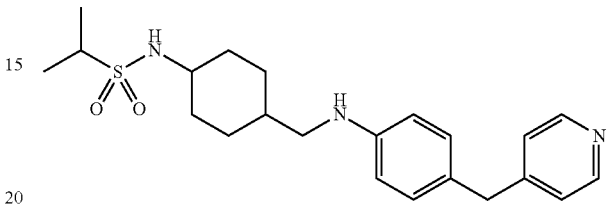
I-672
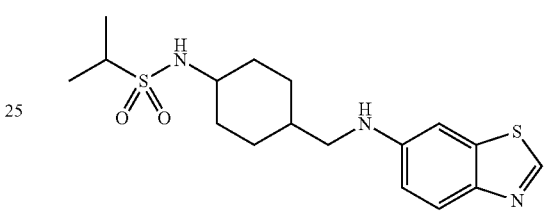
I-666
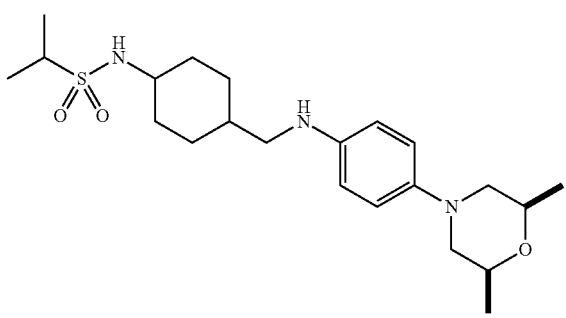
I-673
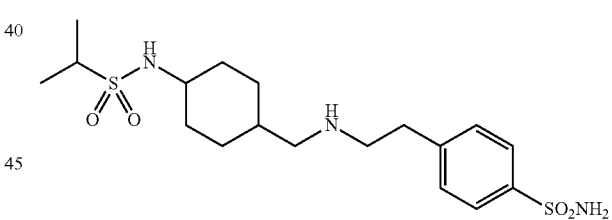
I-667
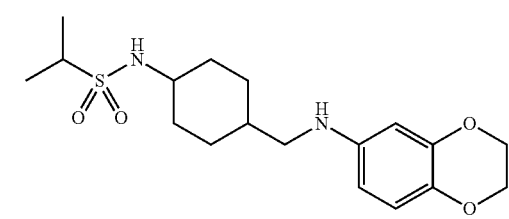
I-674
I-668
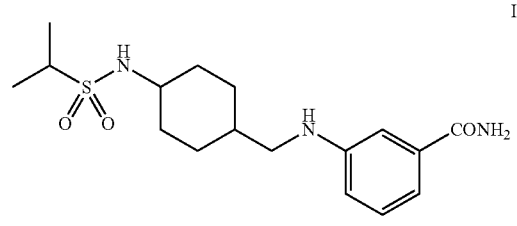
I-675
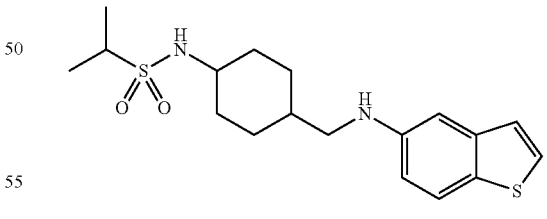
I-669
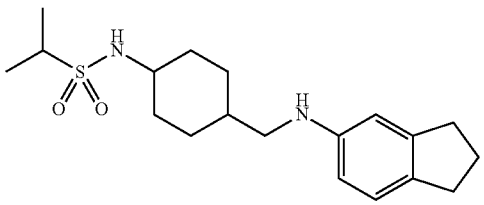
I-676
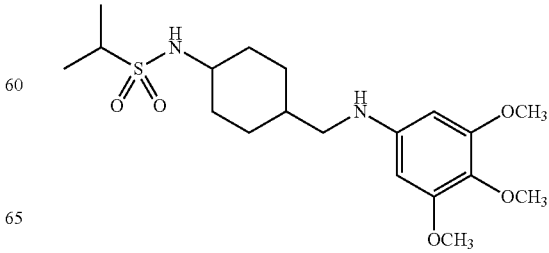

143
-continued
I-677
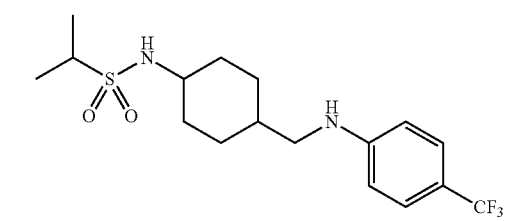
I-678
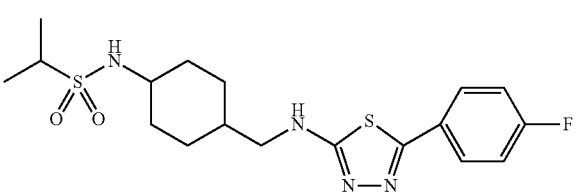
I-679
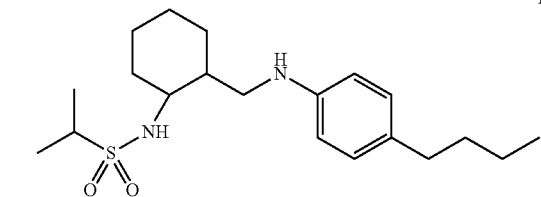
[Formula 101]
I-680
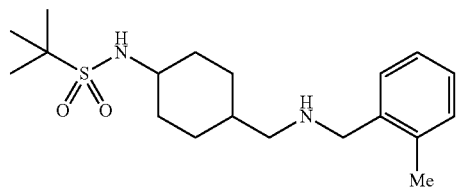
I-681
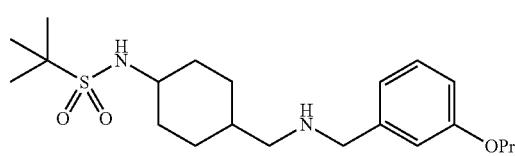
I-682
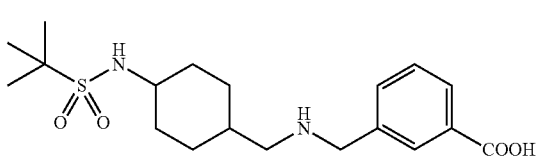
I-683
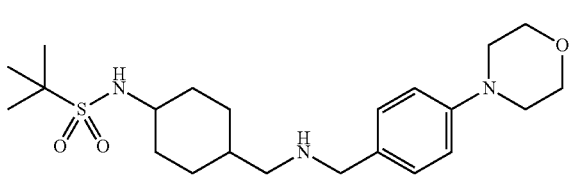
144
-continued
I-684
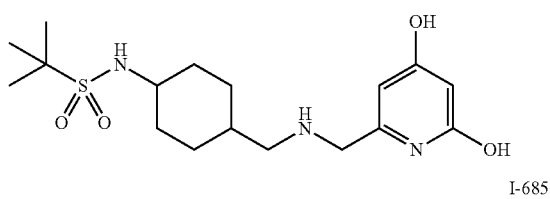
I-685
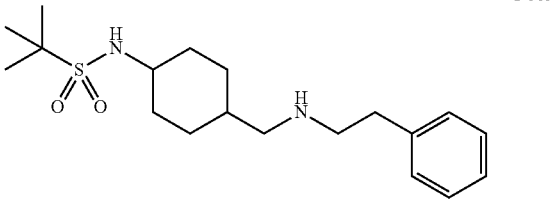
I-686
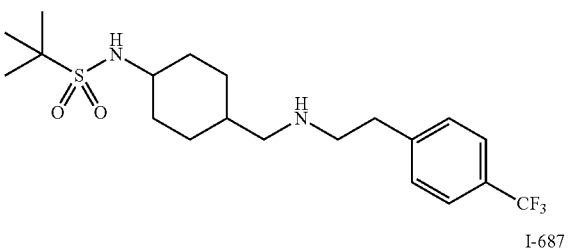
I-687
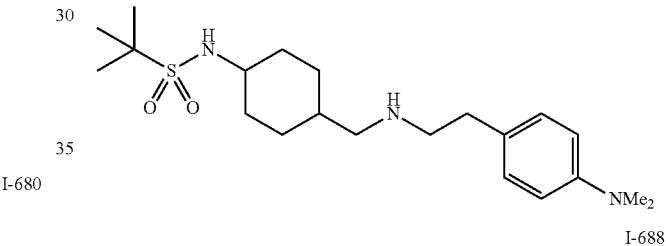
I-688
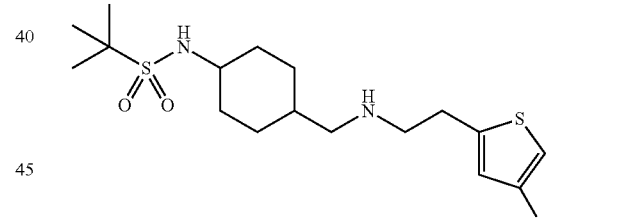
I-689
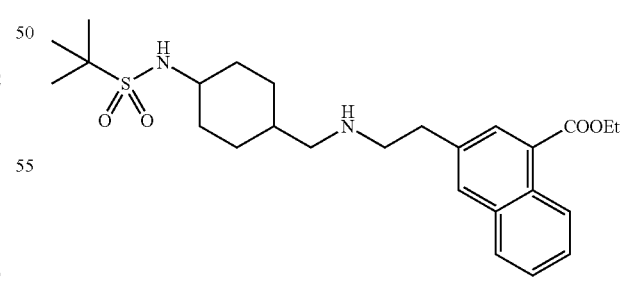
I-690
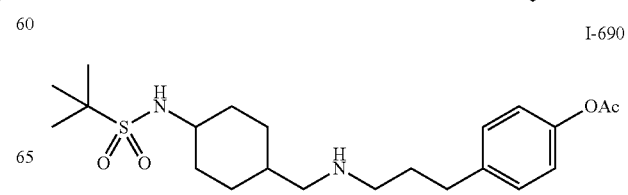

I-691
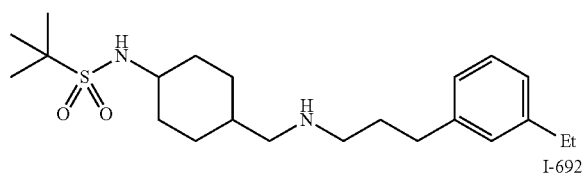
I-692
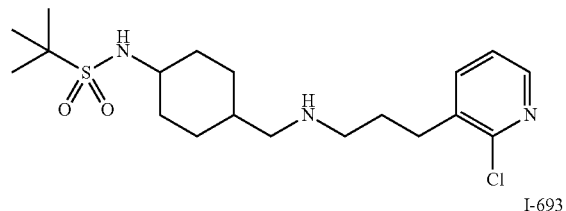
I-693
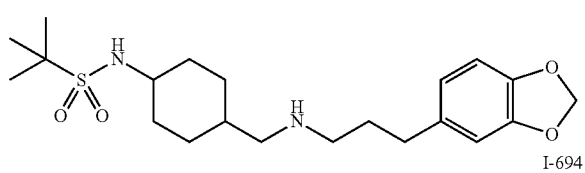
I-694
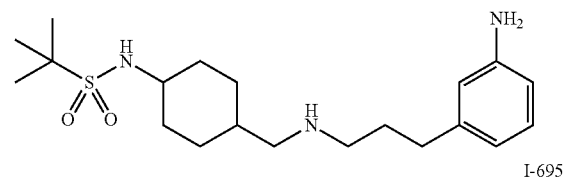
I-695
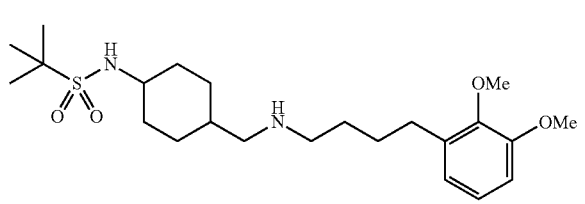
I-696
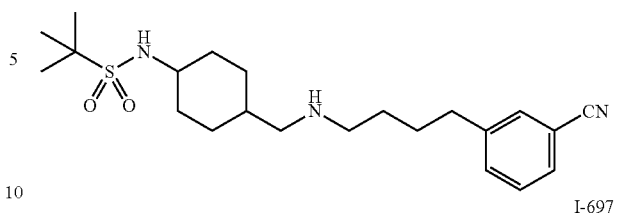
I-697
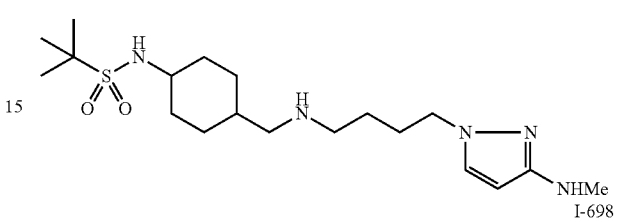
I-698
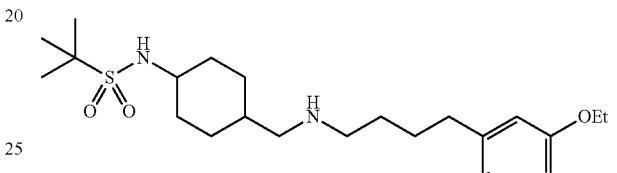
I-699
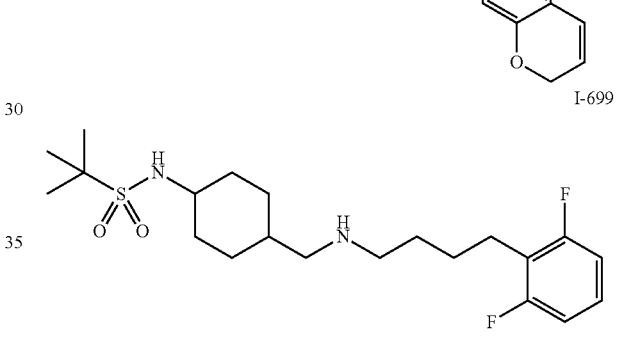
[Formula 102]
I-700
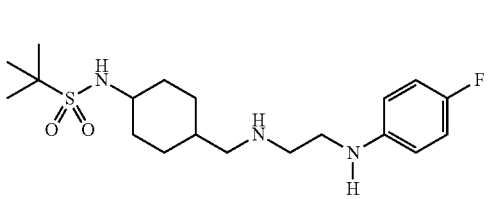
I-701
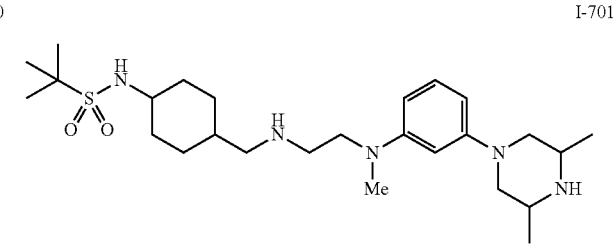
I-702
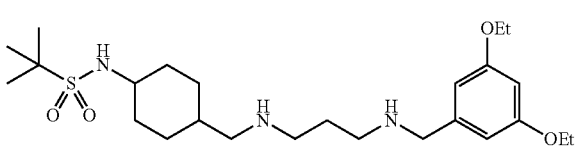
I-703

-continued
I-704
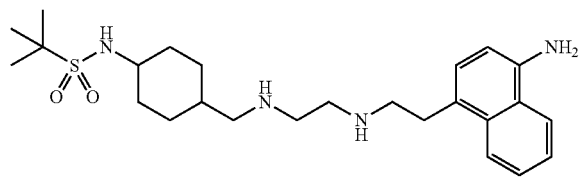
I-705
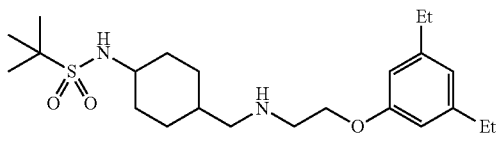
I-706
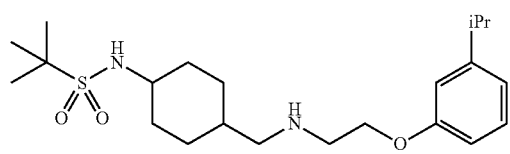
I-707
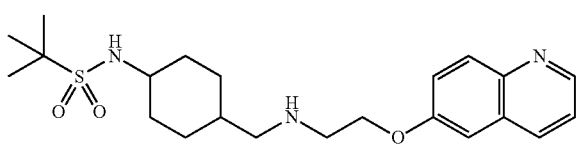
I-708
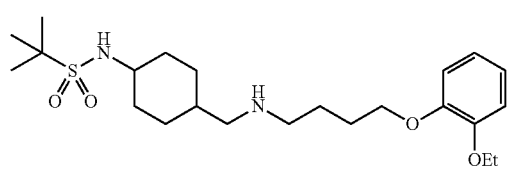
I-709
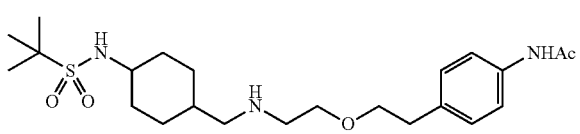
I-710
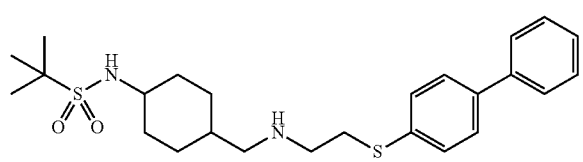
I-711
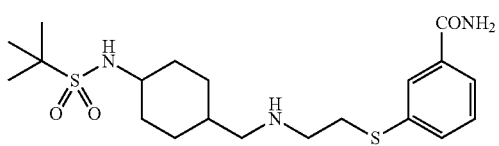
I-712
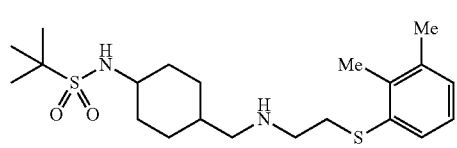
I-713
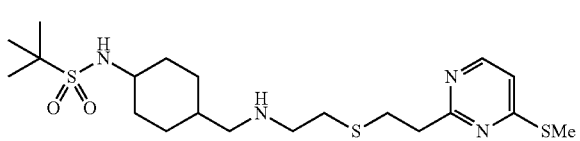
I-714
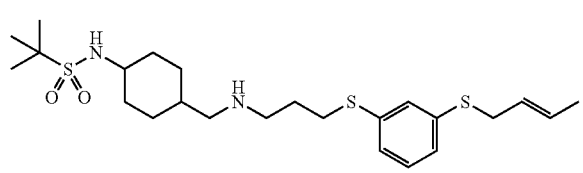
I-715
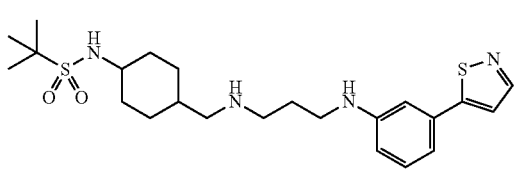
I-716
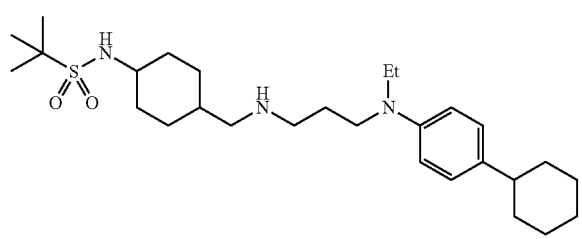
I-717
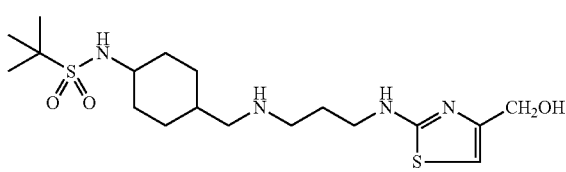
I-718
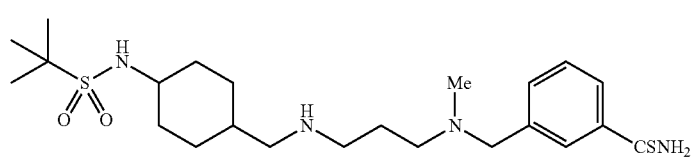

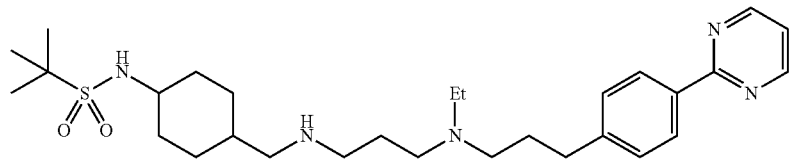
[Formula 103]
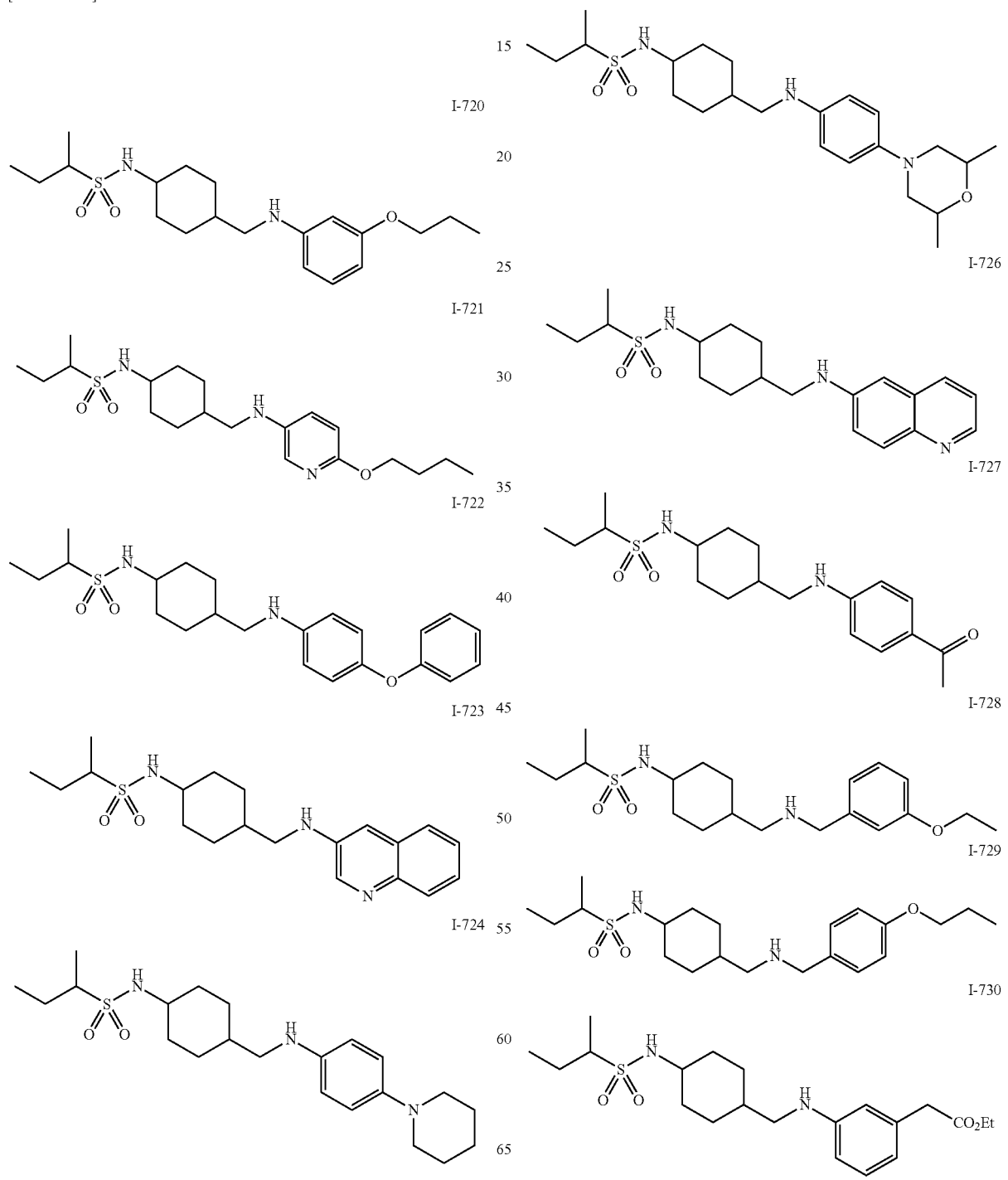

I-731
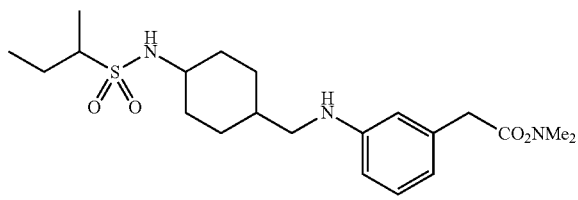
I-738
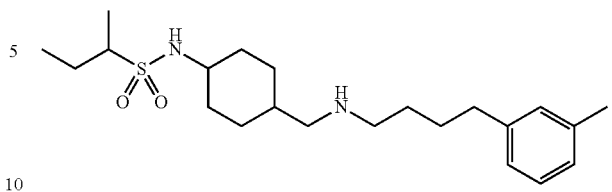
I-732
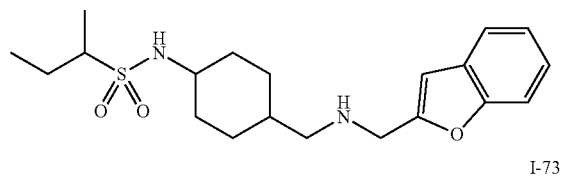
I-739
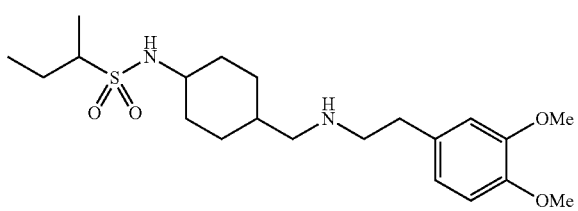
I-733
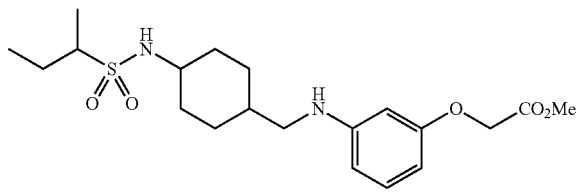
[Formula 104]
I-740
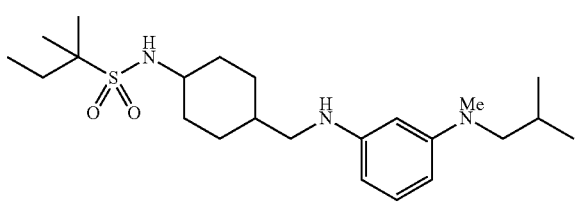
I-734
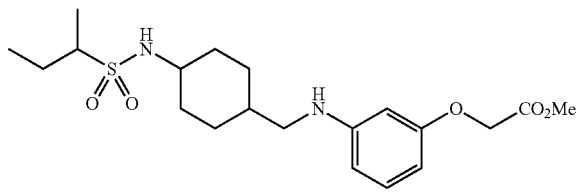
I-735
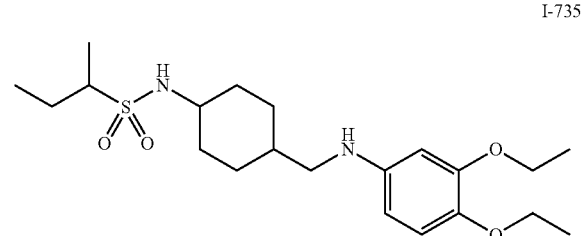
I-741
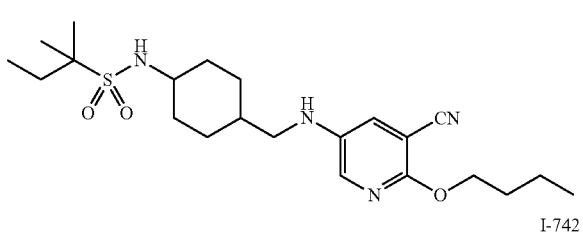
I-736
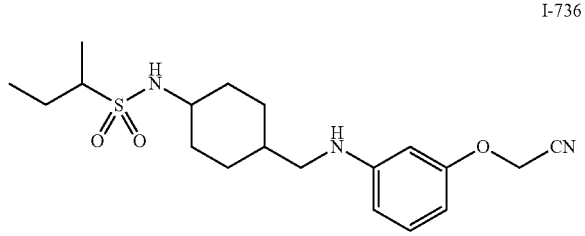
I-742
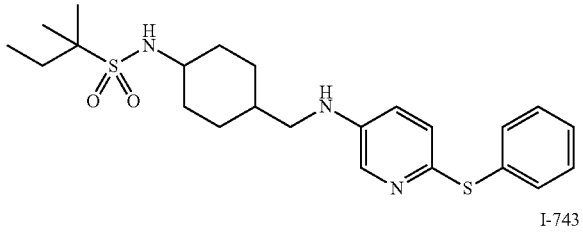
I-737
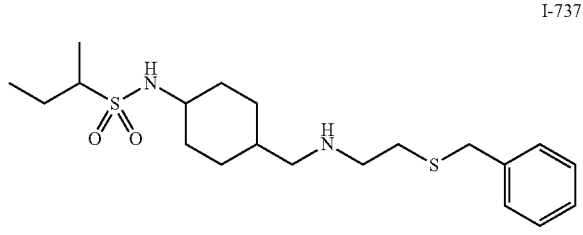
I-743

I-744
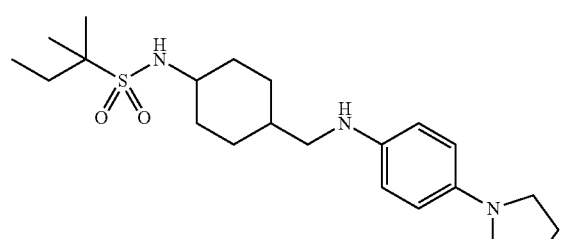
I-745
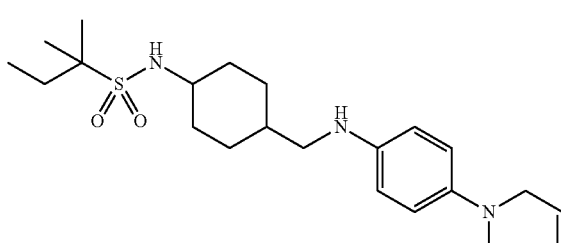
I-746
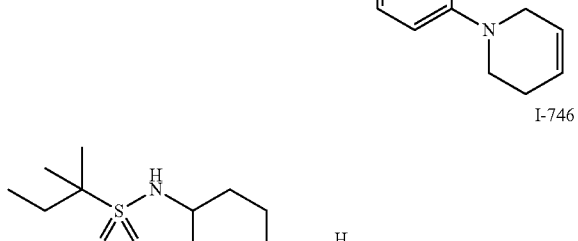
I-747
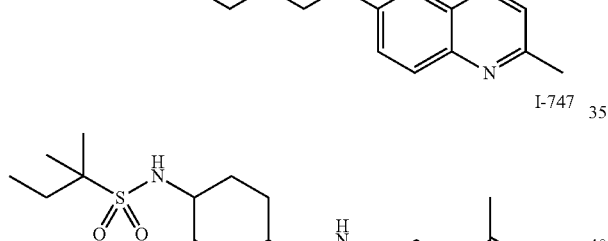
I-748
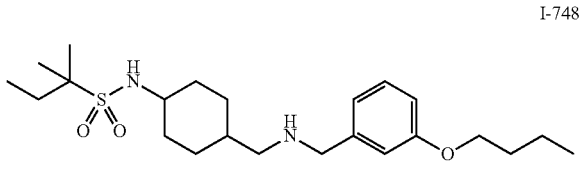
I-749

I-750
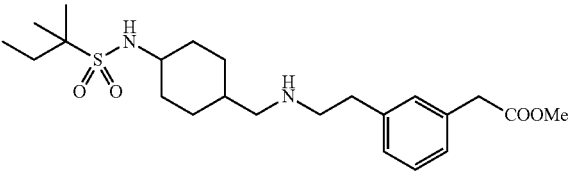
I-751

I-752
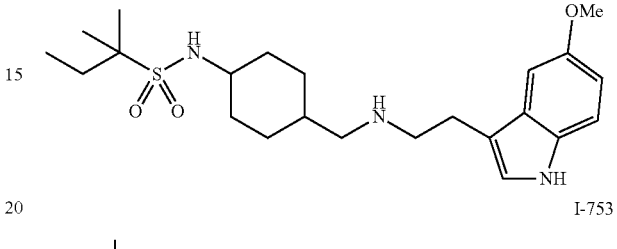
I-753

I-754
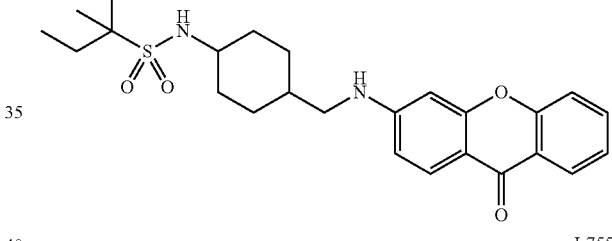
I-755
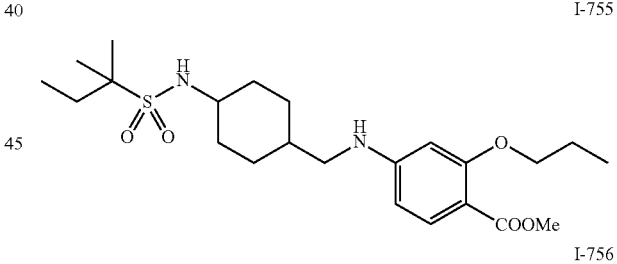
I-756
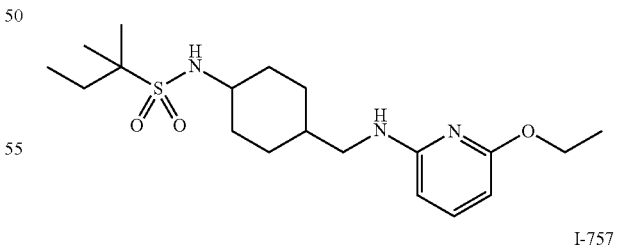
I-757
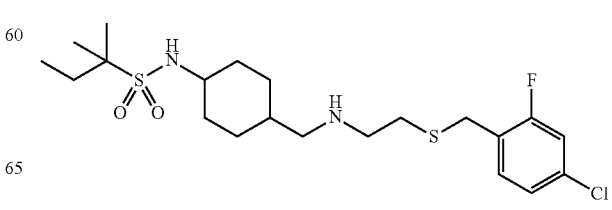

I-758
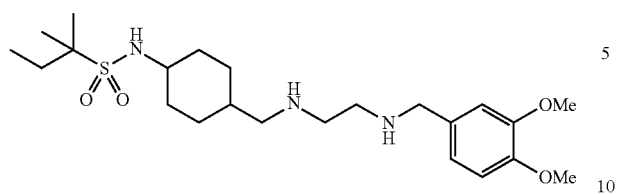
I-759
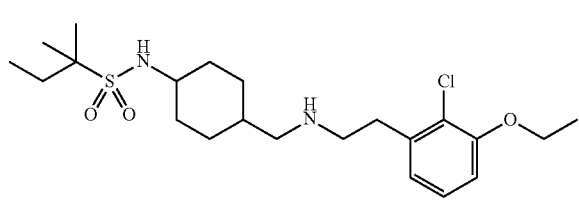
[Formula 105]
Ia-1
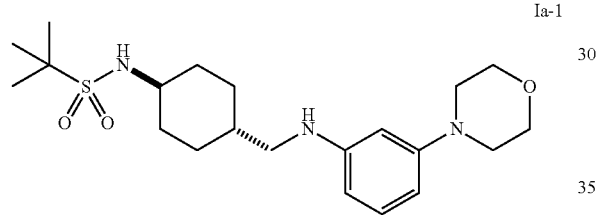
Ia-2
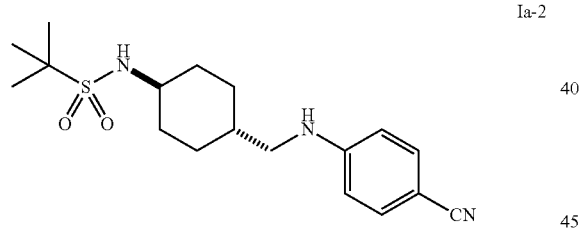
Ia-3
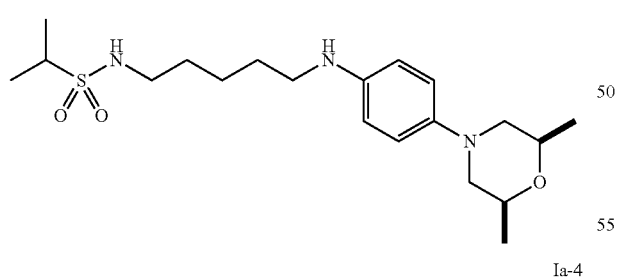
Ia-4
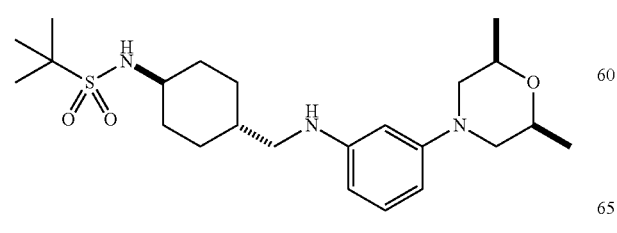
Ia-5
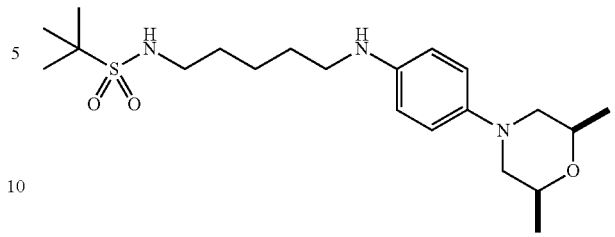
Ia-6
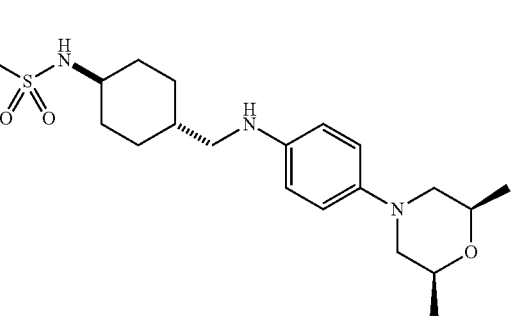
Ia-7
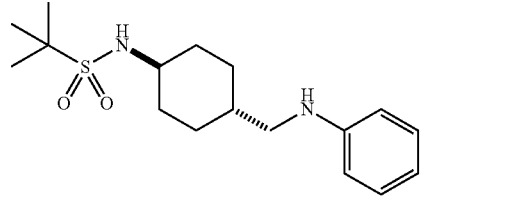
Ia-8
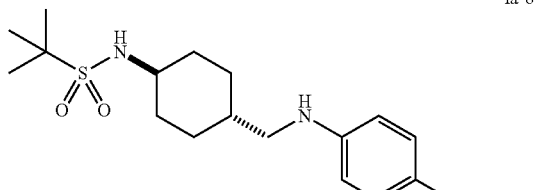
Ia-9
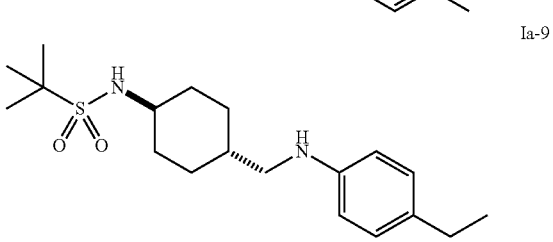
Ia-10
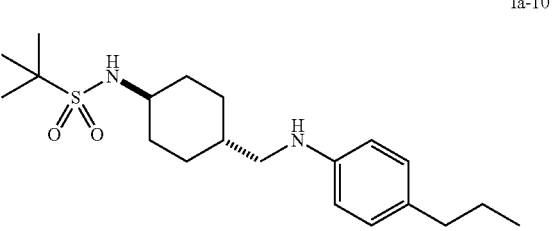

-continued
Ia-11
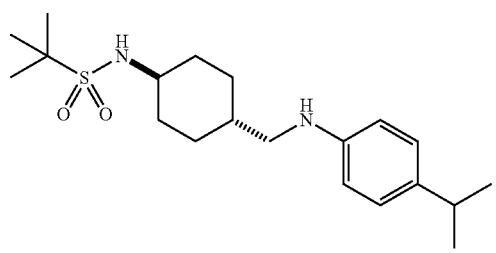
Ia-12
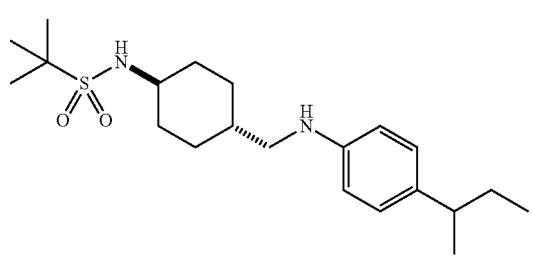
Ia-13
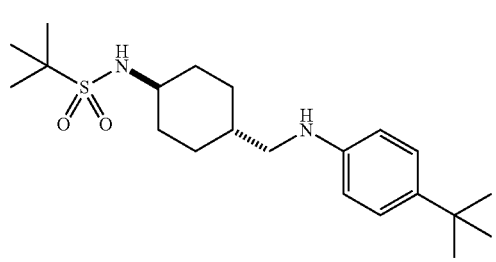
Ia-14
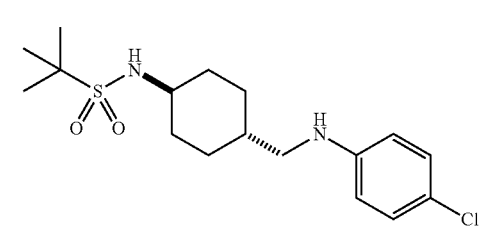
Ia-15
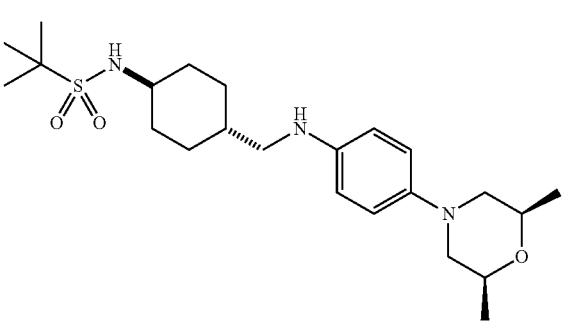
Ia-16
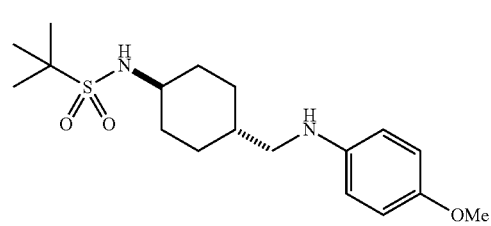
-continued
Ia-17
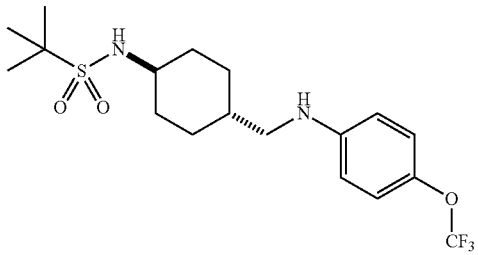
Ia-18
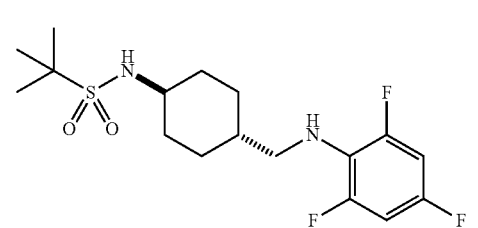
Ia-19
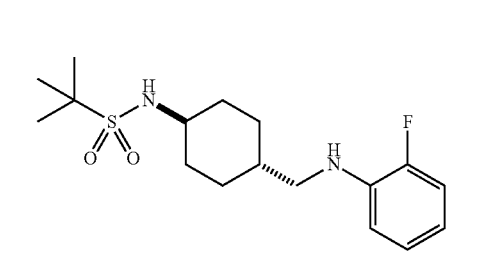
Ia-20
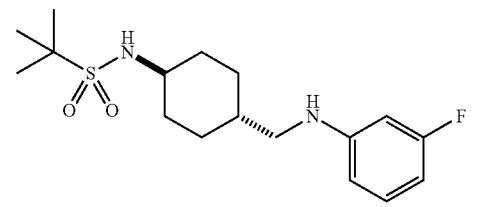
Ia-21
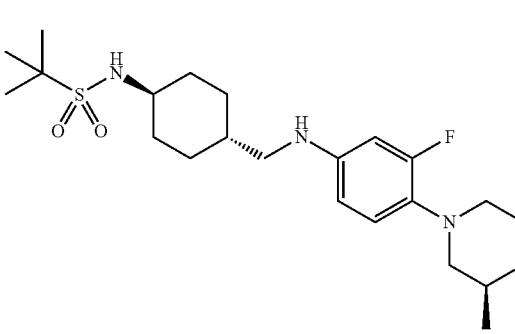
Ia-22
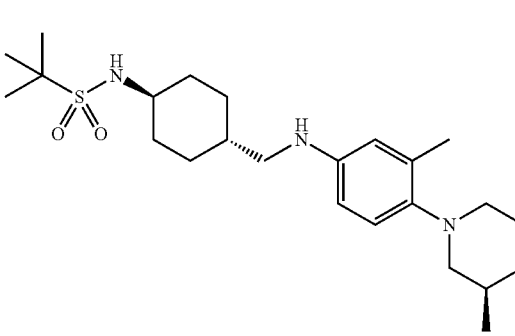

[Formula 106]
Ia-23
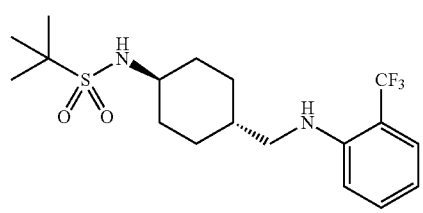
Ia-24
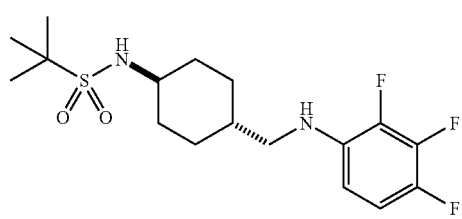
Ia-25
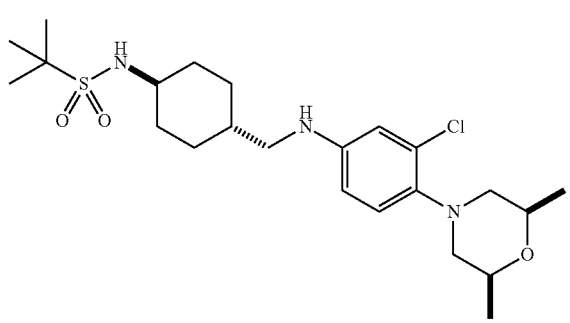
Ia-26
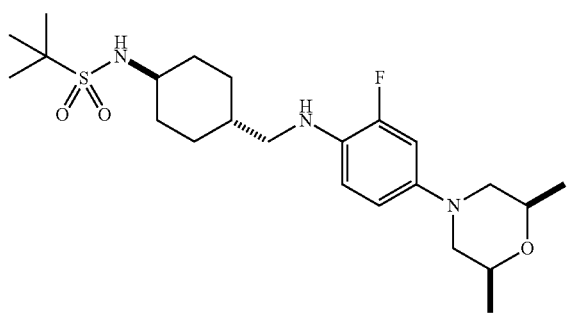
Ia-27
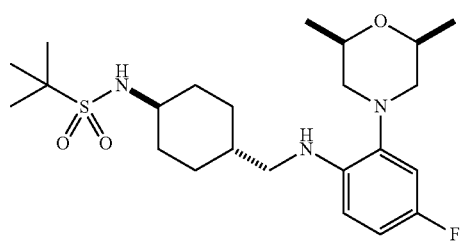
-continued
Ia-28
Ia-29
Ia-30
Ia-31
Ia-32
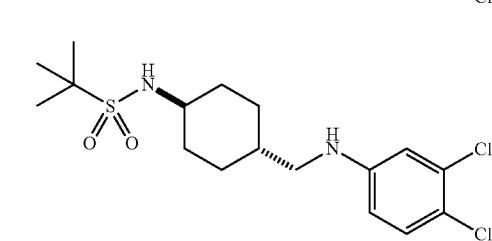

Ia-33
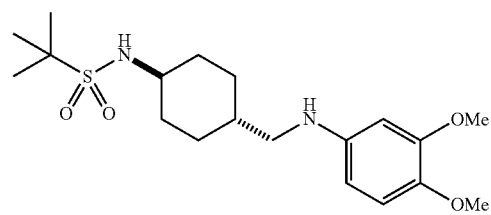
Ia-35
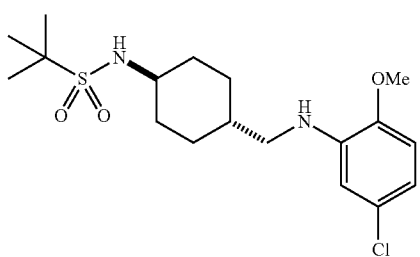
Ia-36
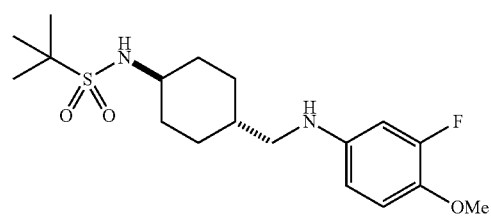
Ia-37
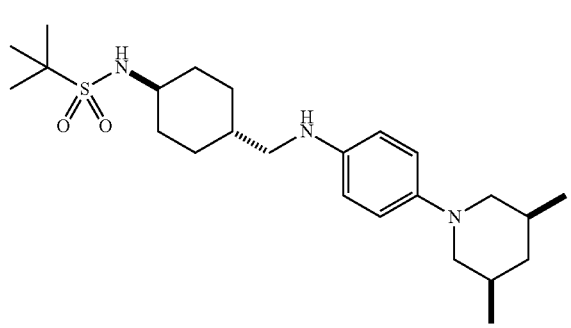
Ia-38
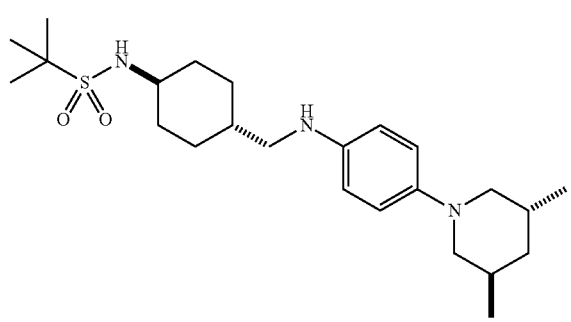
Ia-39
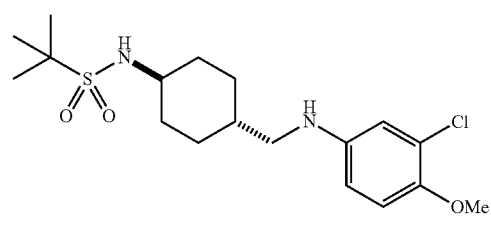
Ia-40
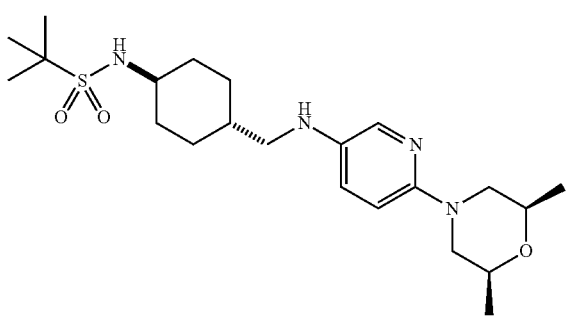
Ia-41
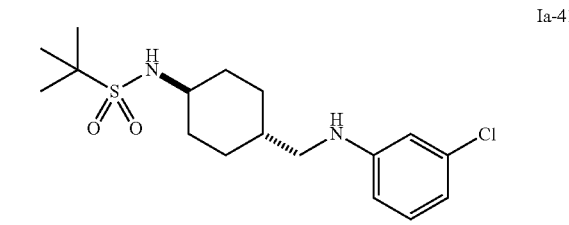
Ia-42
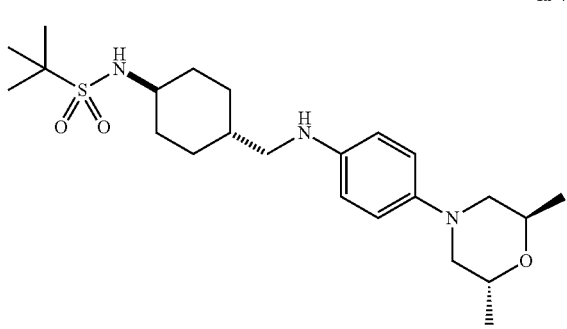
Ia-43
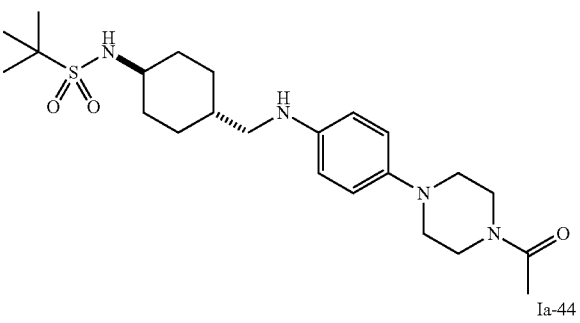
Ia-44
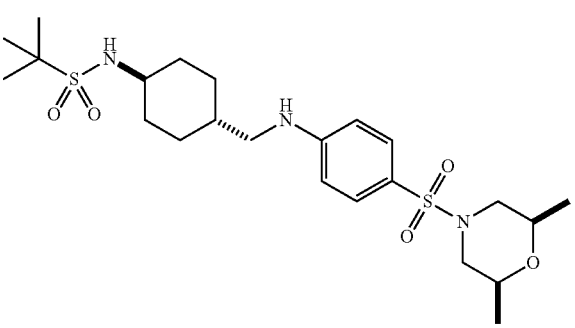

[Formula 107]
Ia-45
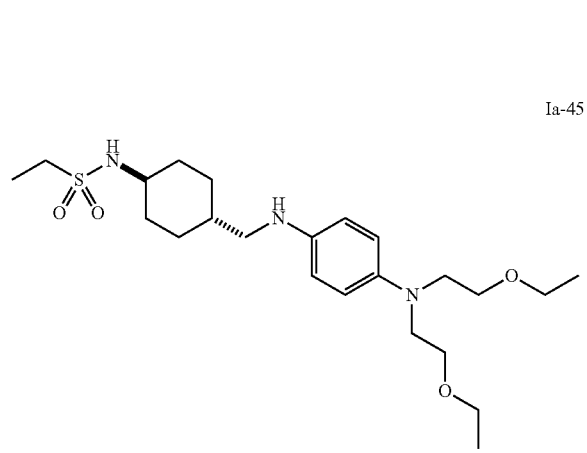
Ia-46
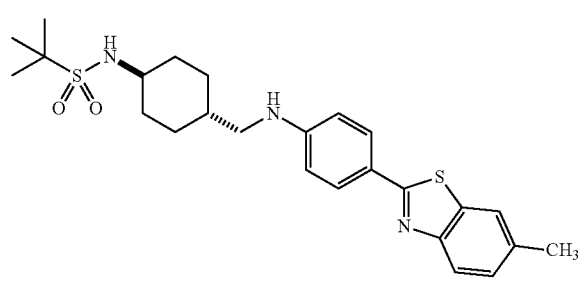
Ia-47
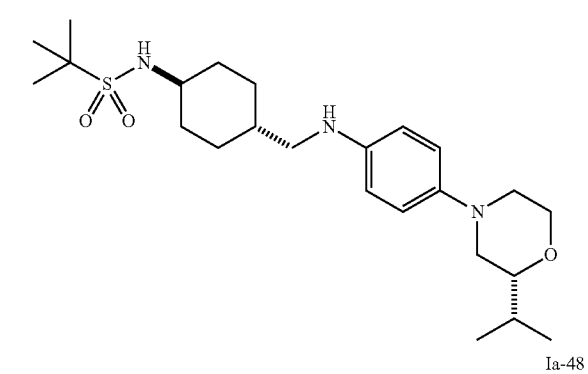
Ia-48
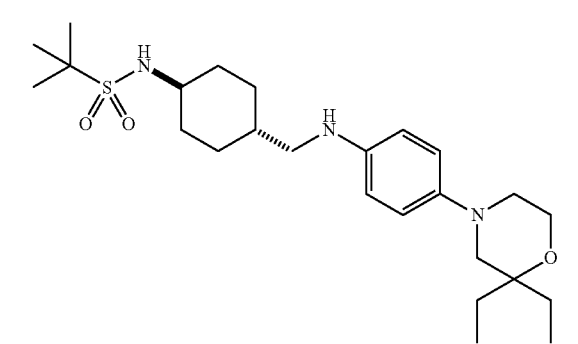
-continued
Ia-49
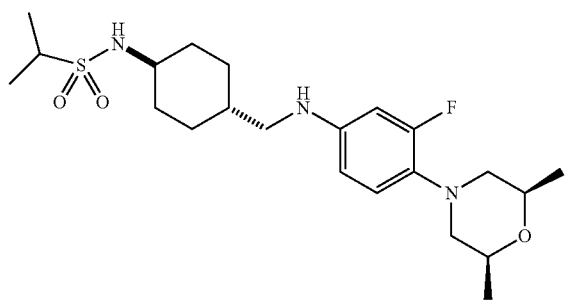
Ia-50
Ia-51
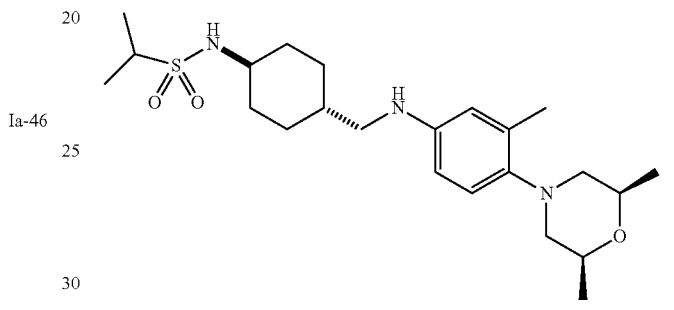
Ia-52
Ia-53
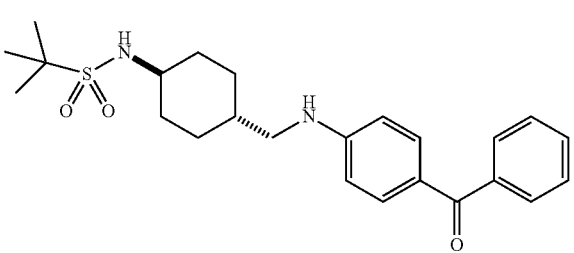

Ia-54
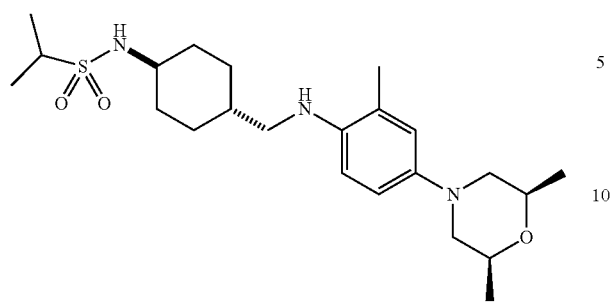
Ia-55
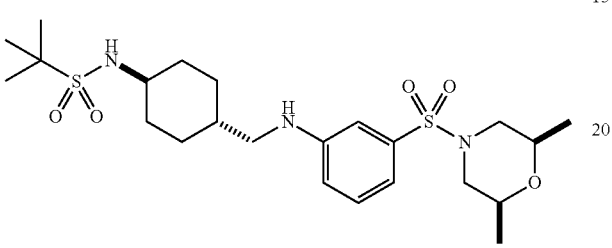
Ia-56
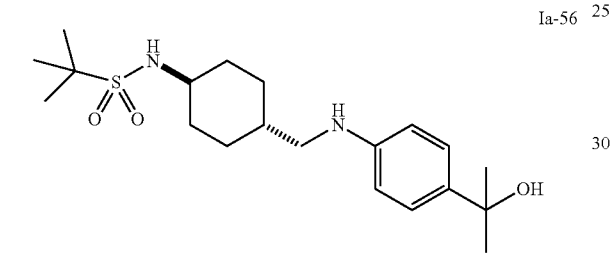
Ia-57
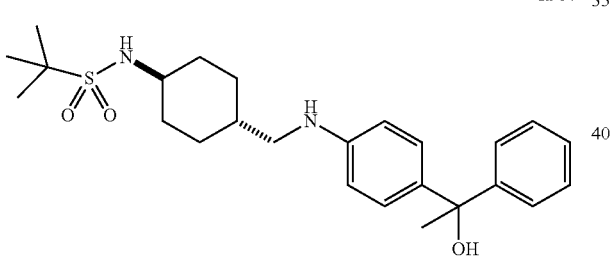
Ia-58
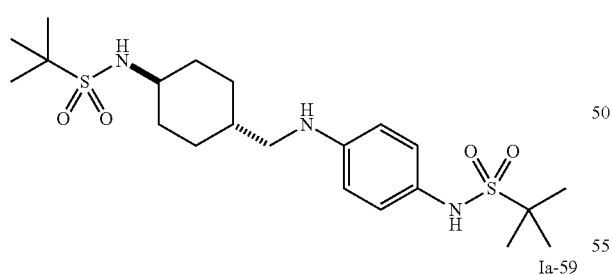
Ia-59
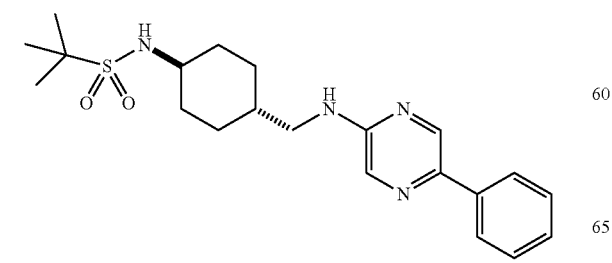
Ia-60
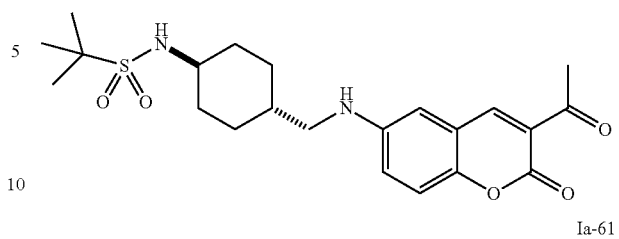
Ia-61
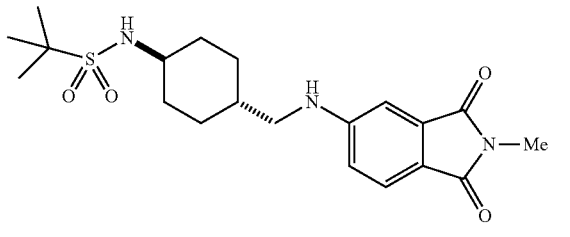
Ia-62
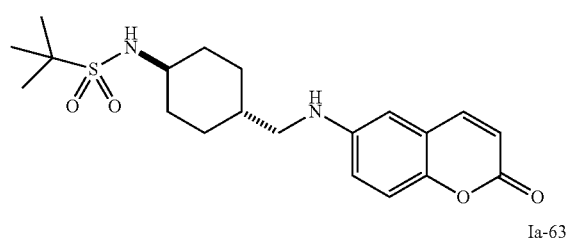
Ia-63
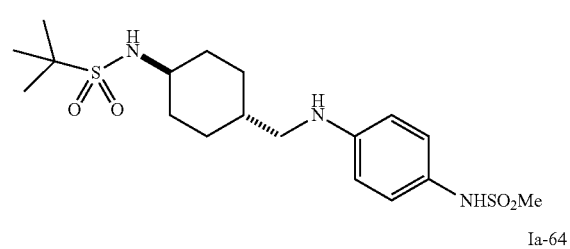
Ia-64
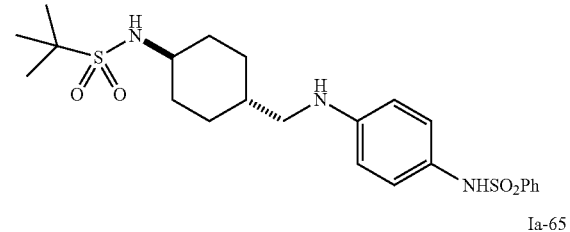
Ia-65
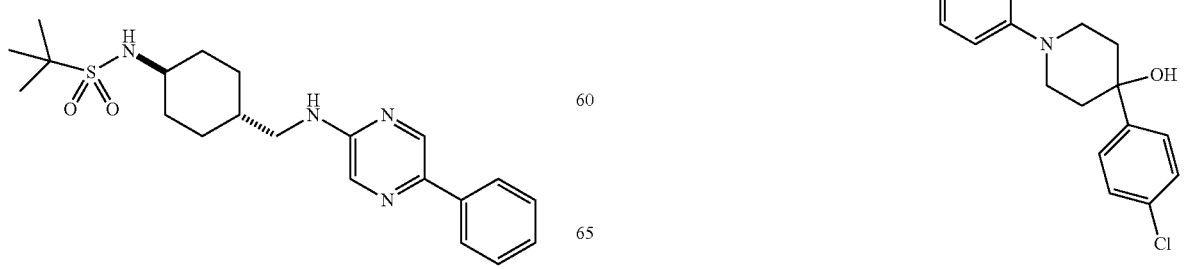

Ia-66
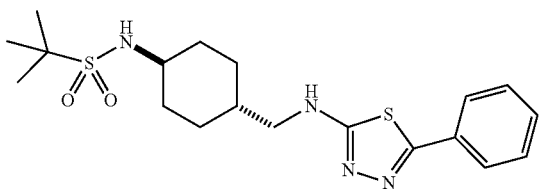
Ia-72
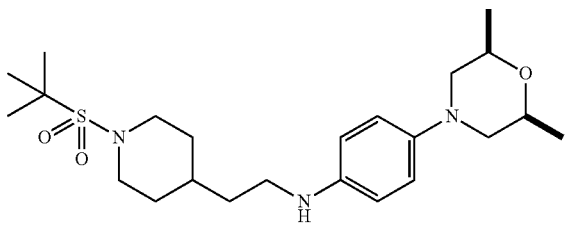
[Formula 108]
Ia-67
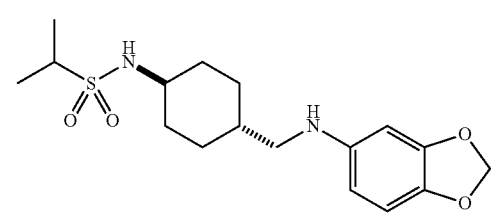
Ia-73
Ia-68
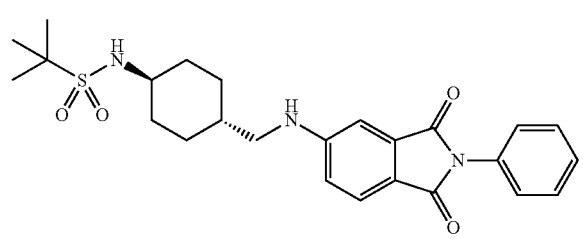
Ia-74
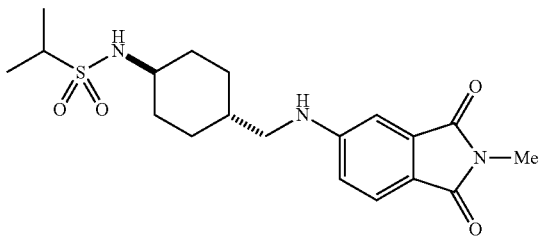
Ia-69
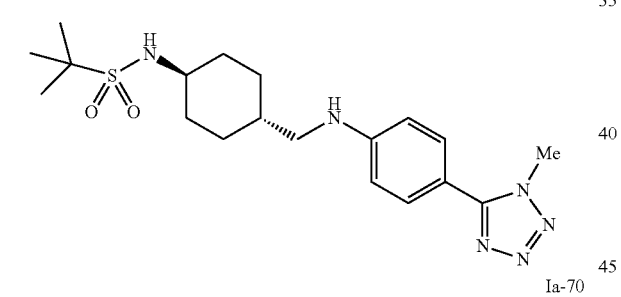
Ia-75
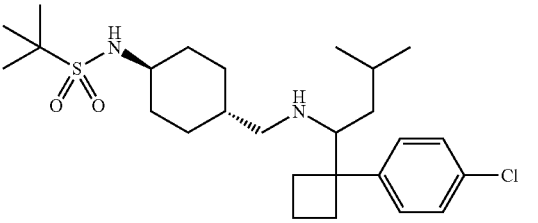
Ia-70
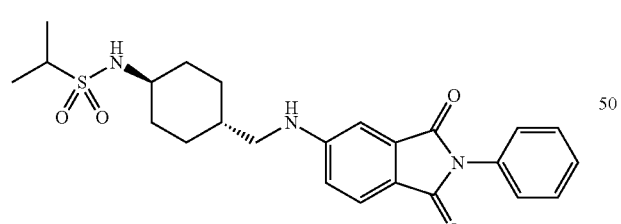
Ia-76
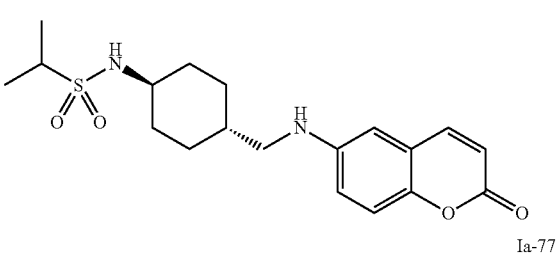
Ia-71
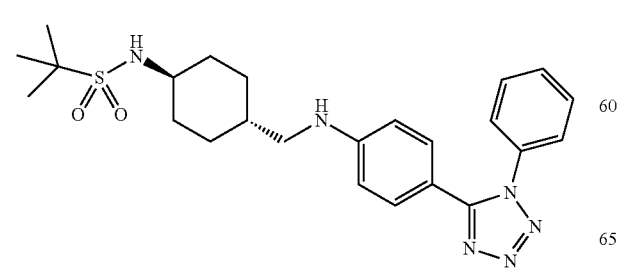
Ia-77
Ia-78
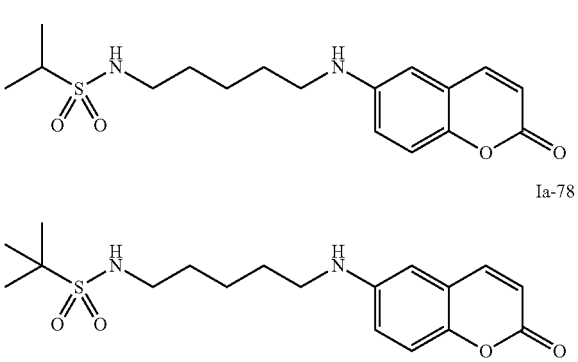

Ia-79
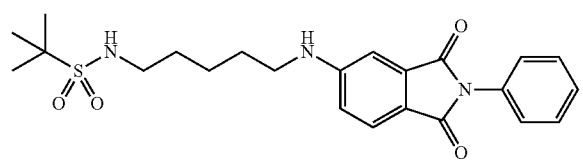
Ia-80
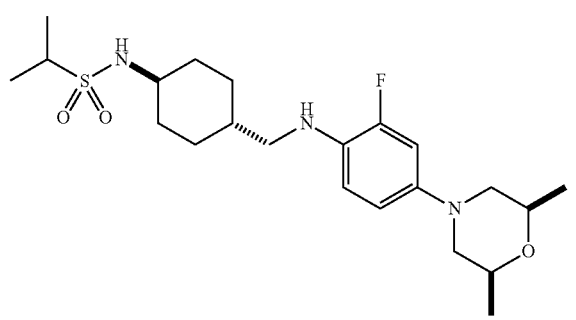
Ia-81
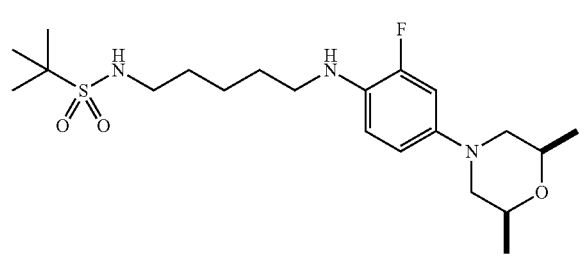
Ia-82
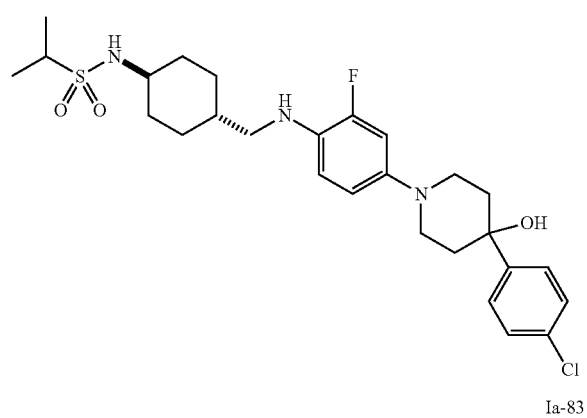
Ia-83
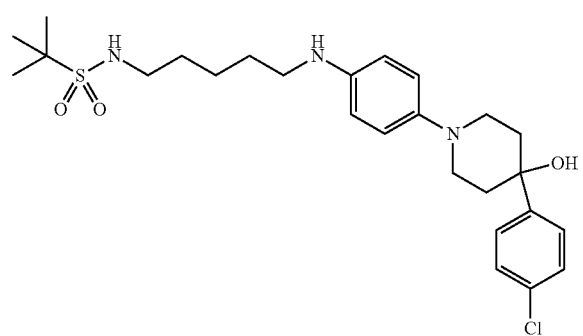
Ia-84
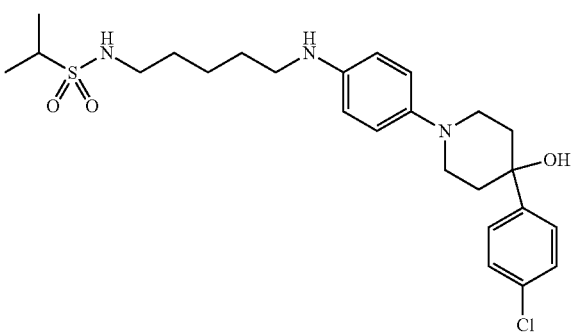
[Formula 109]
Ia-89
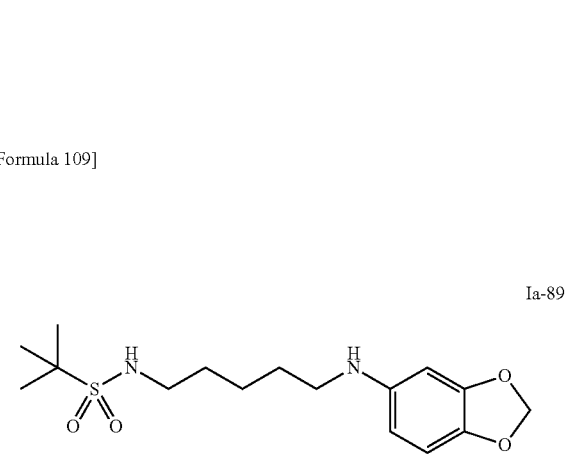
Ia-90
Ia-91
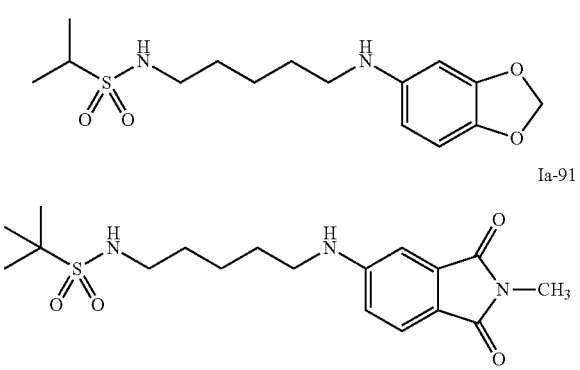
Ia-104
Ia-105
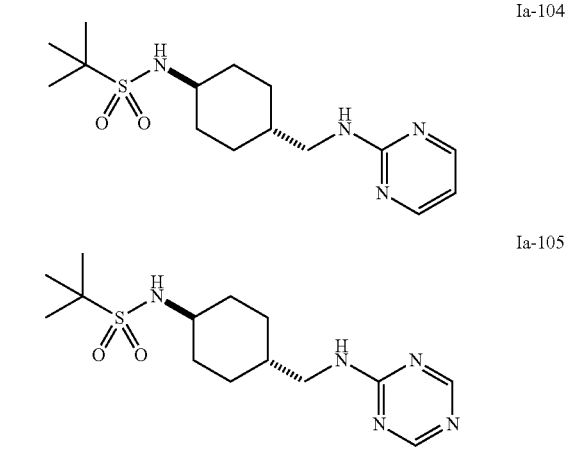

Ia-106 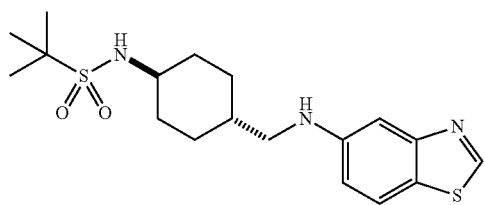
Ia-107 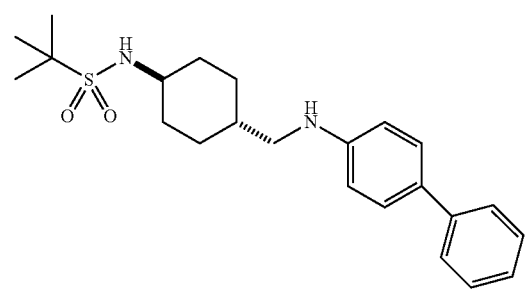
Ia-108 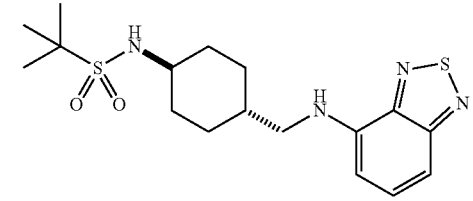
Ia-109 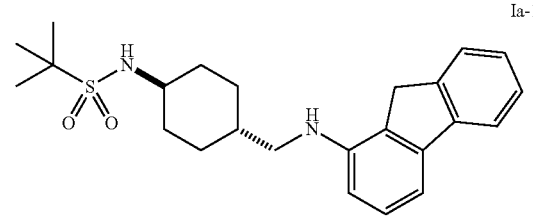
Ia-110 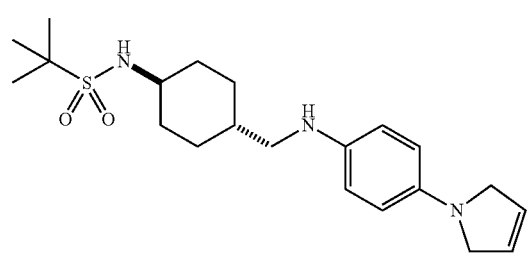
Ia-111 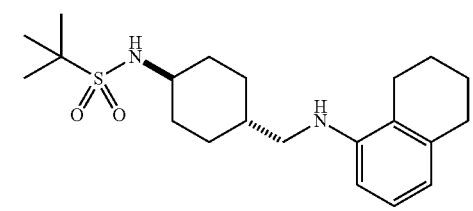
Ia-122 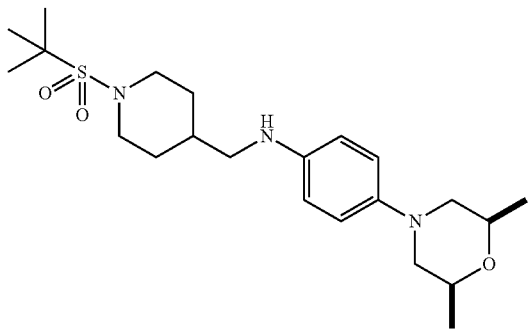
Ia-123 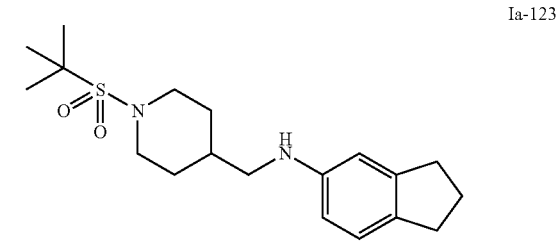
Ia-124 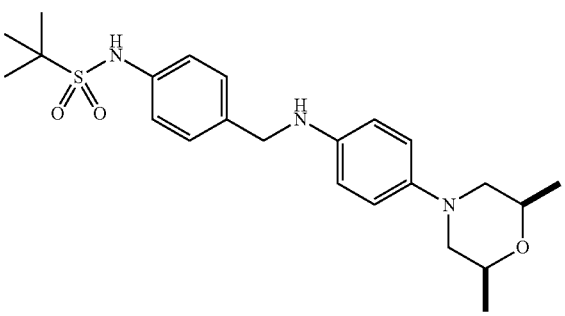
Ia-125 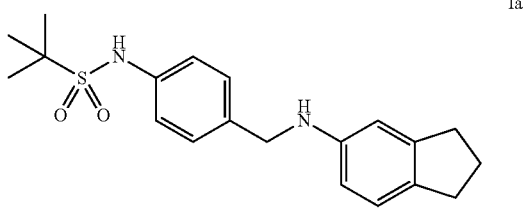
Ia-126 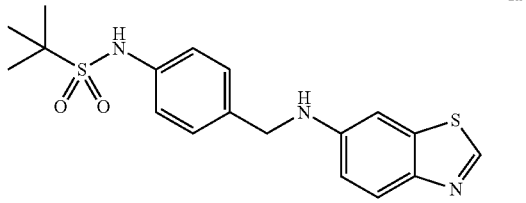
Ia-127 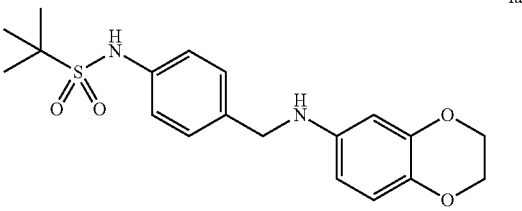

Ia-128
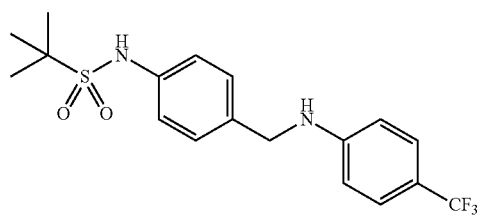
Ia-129
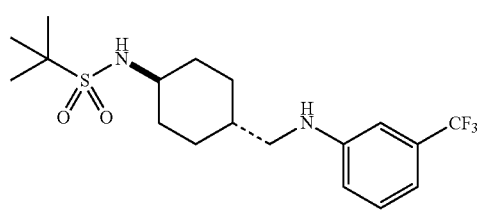
Ia-130
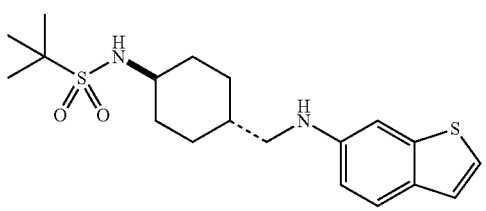
Ia-131
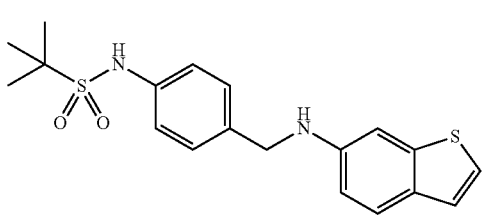
Ia-132
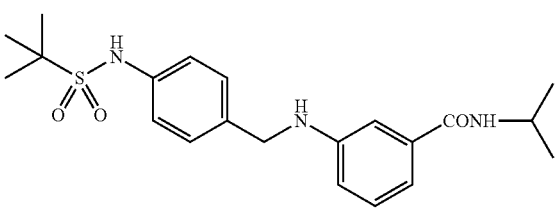
[Formula 110]
Ia-133
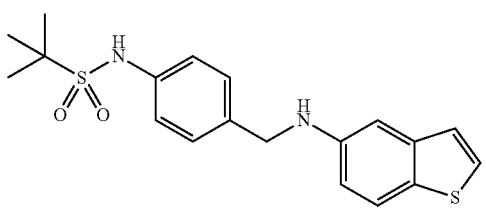
Ia-134
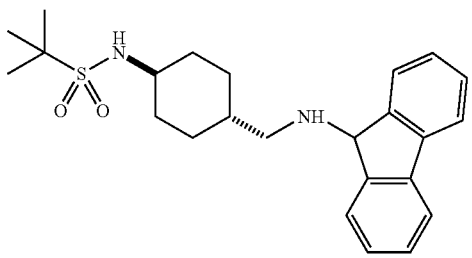
Ia-135
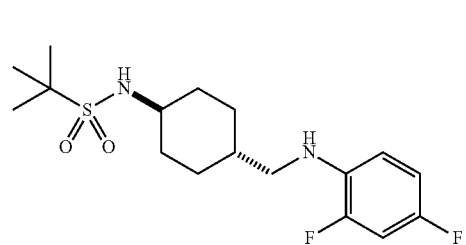
Ia-136
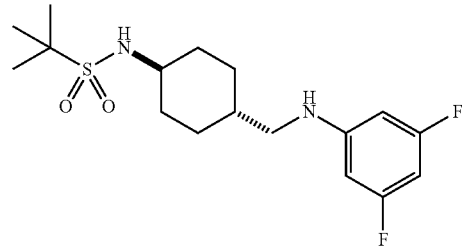
Ia-137
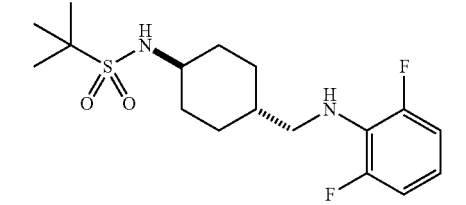
Ia-138
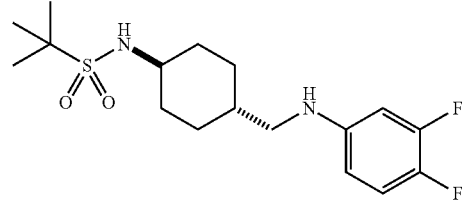
Ia-139
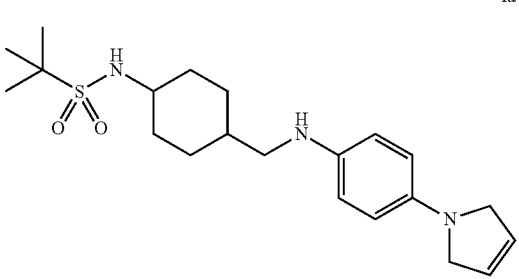

175
-continued
Ia-140
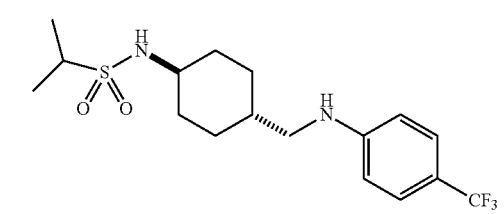
Ia-141
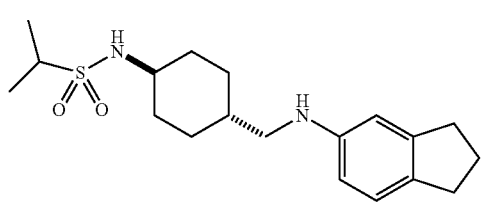
Ia-142
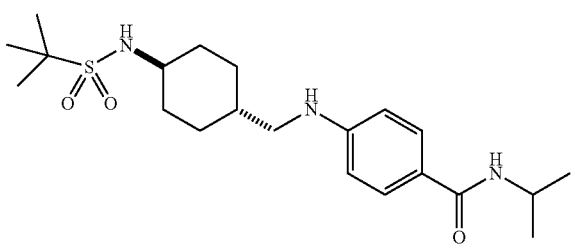
Ia-143
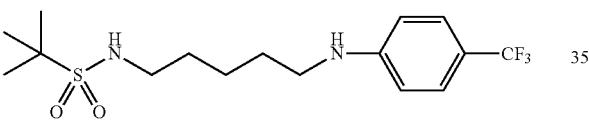
Ia-144
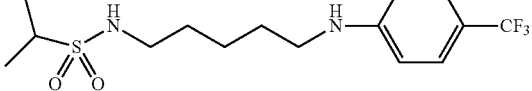
Ia-145
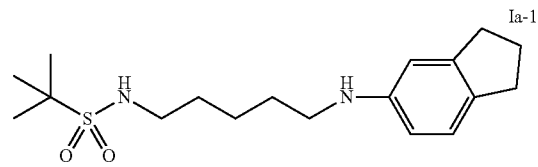
Ia-146
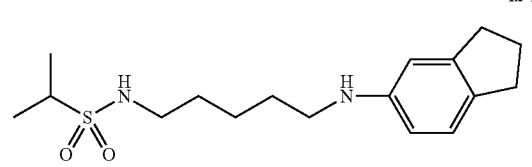
Ia-147
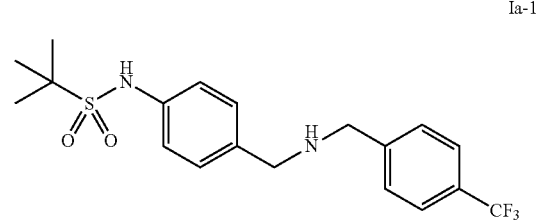
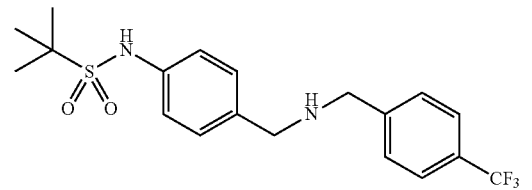
176
-continued
Ia-148
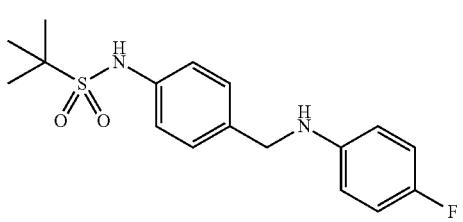
Ia-149
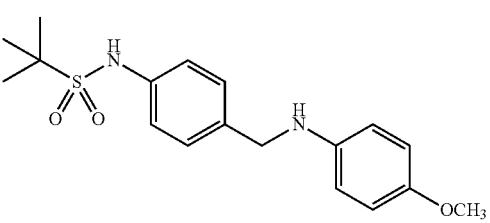
Ia-150
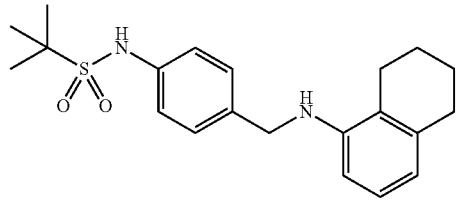
Ia-151
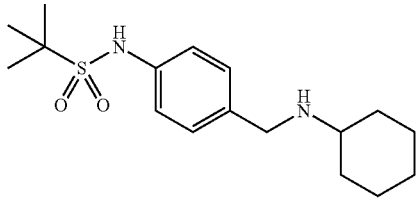
Ia-152
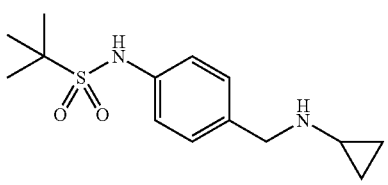
Ia-153
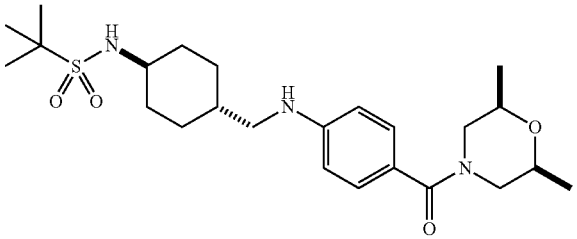
Ia-154
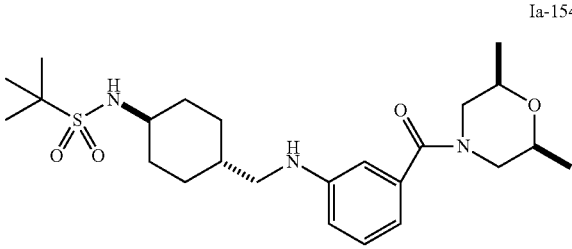

[Formula 111]
Ia-155
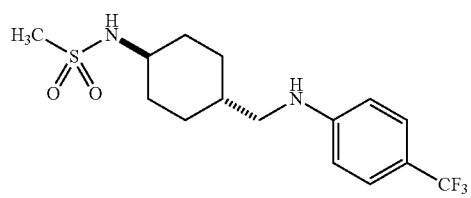
Ia-156
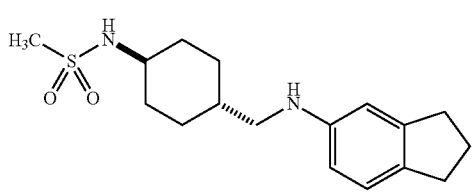
Ia-157
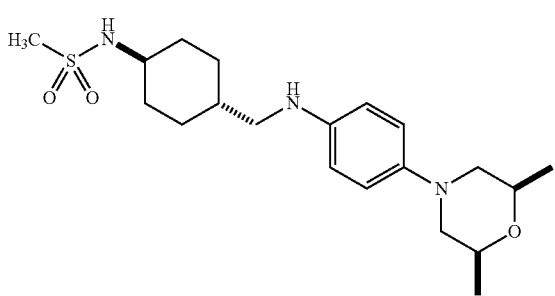
Ia-158
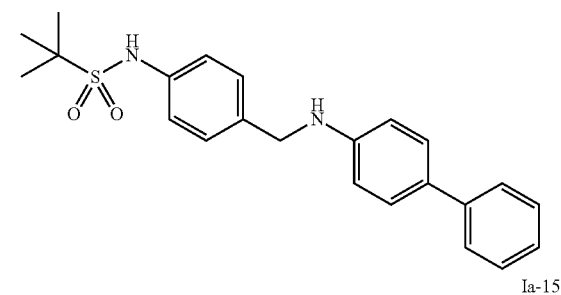
Ia-159
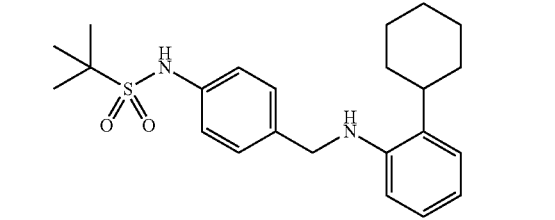
Ia-160
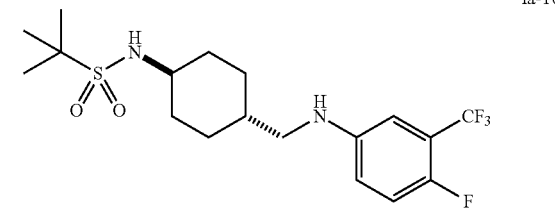
-continued
Ia-161
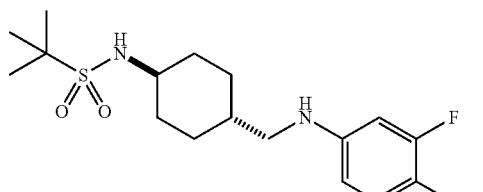
Ia-162
Ia-163
Ia-164
Ia-165
Ia-166

Ia-167
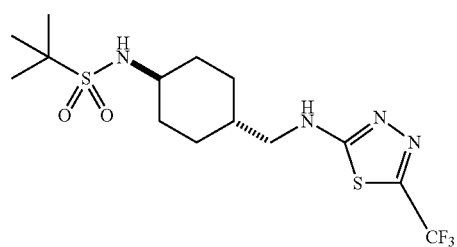
Ia-174
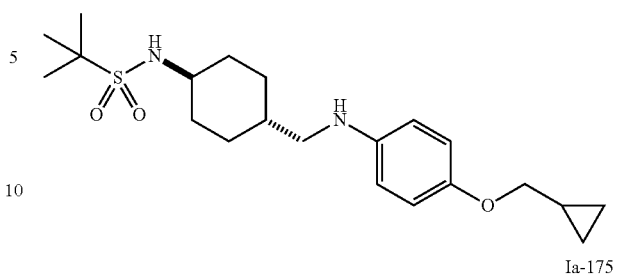
Ia-175
Ia-168
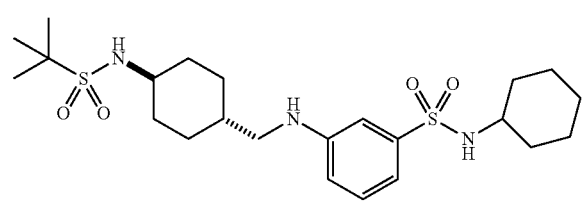
Ia-169
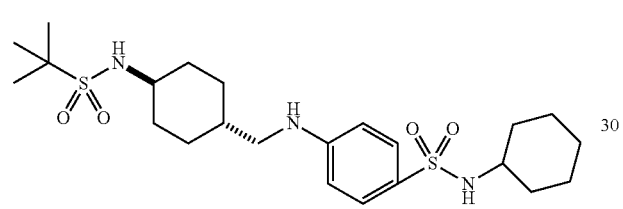
Ia-176
Ia-171
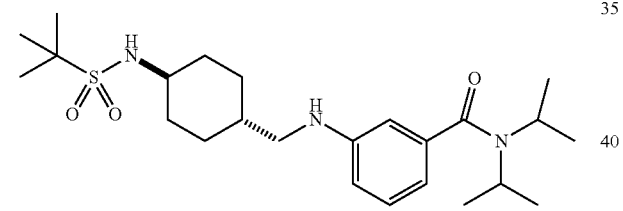
[Formula 112]
Ia-177
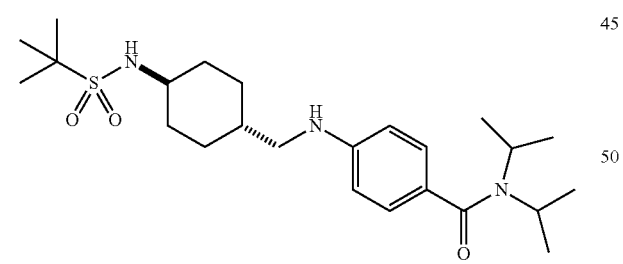
Ia-172
Ia-178
Ia-173
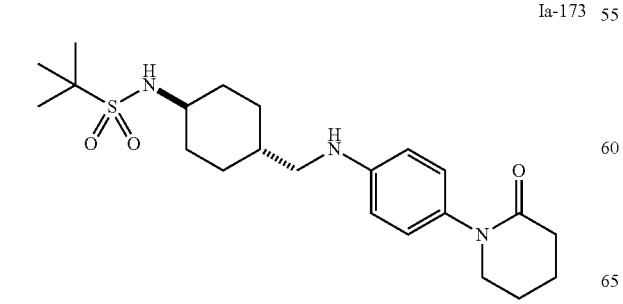
Ia-179
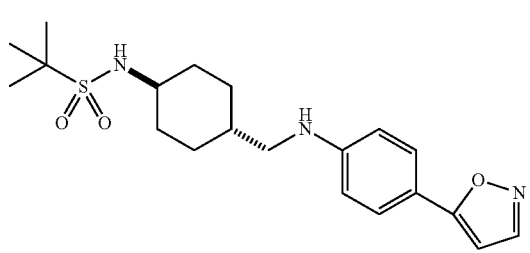

Ia-180
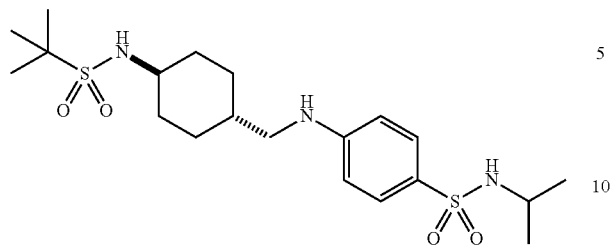
Ia-186
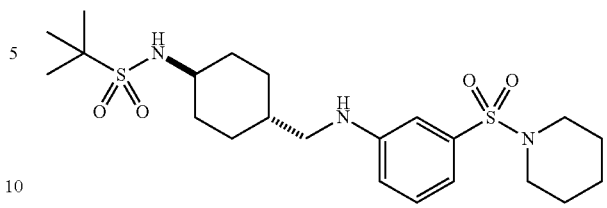
Ia-181
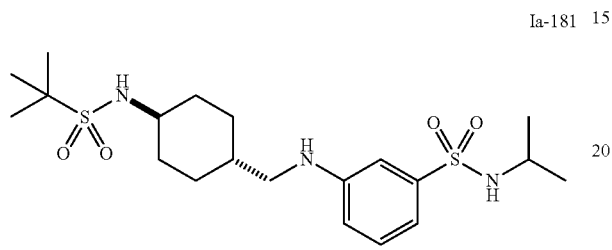
Ia-187
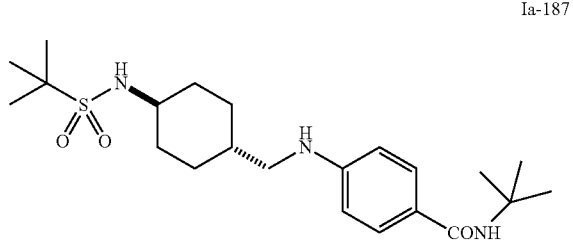
Ia-182
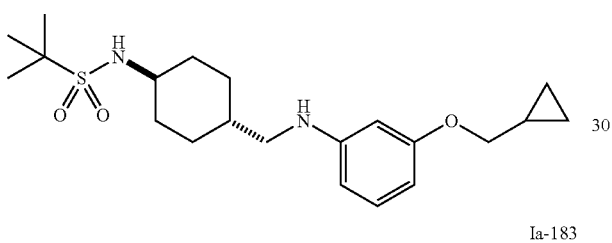
Ia-188
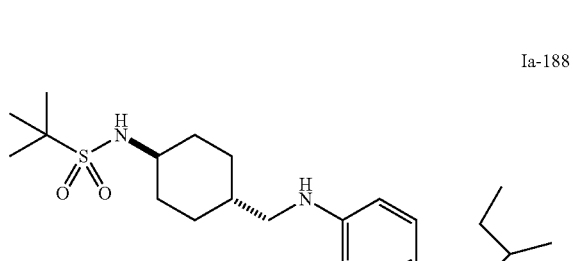
Ia-183
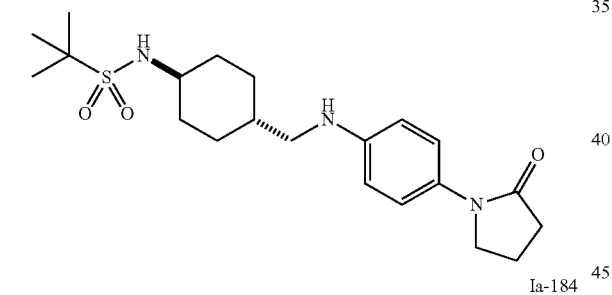
Ia-189
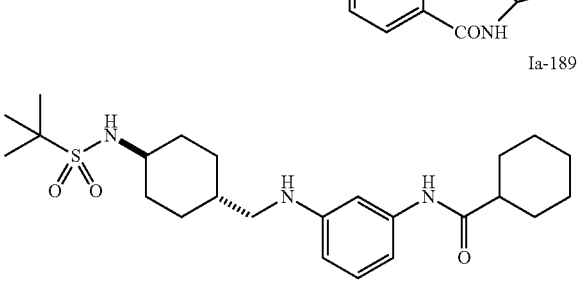
Ia-184
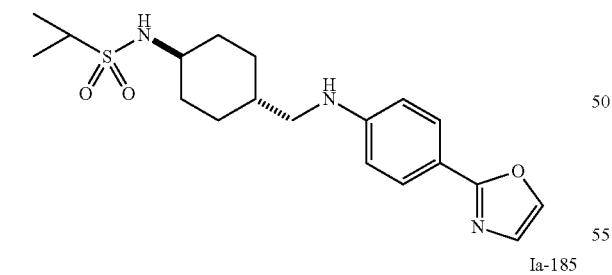
Ia-190
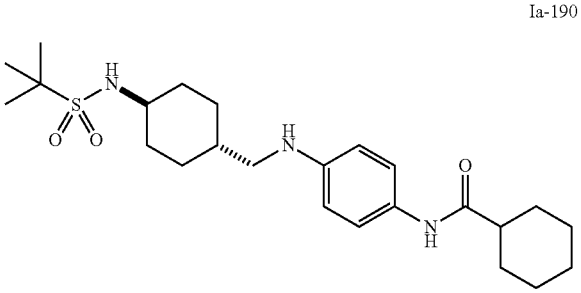
Ia-185
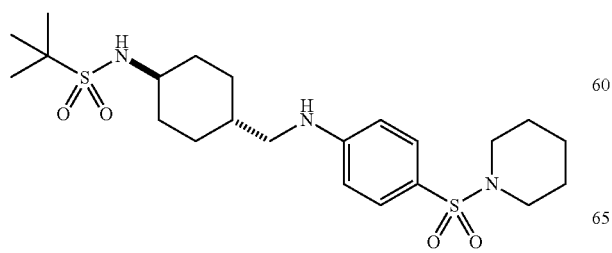
Ia-191

Ia-192
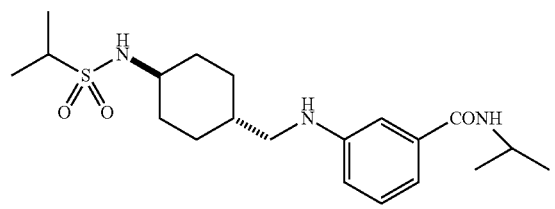
Ia-193
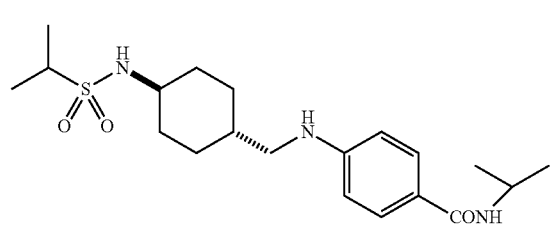
Ia-194
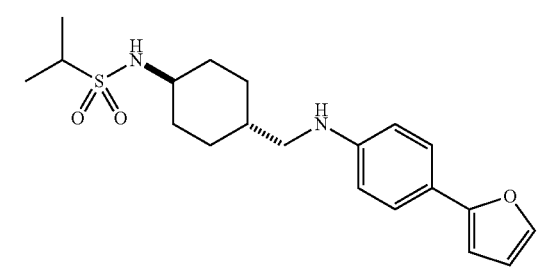
Ia-195
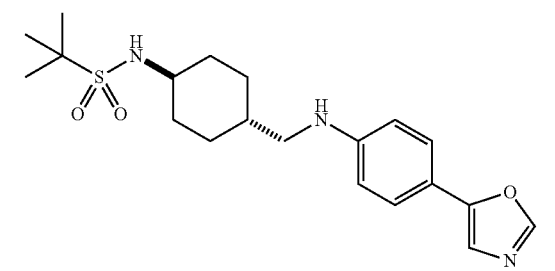
Ia-196
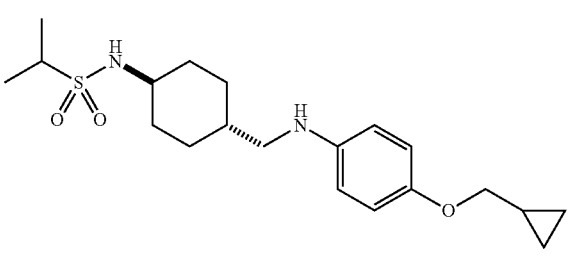
Ia-197
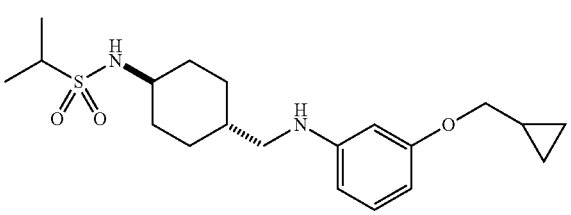
Ia-198
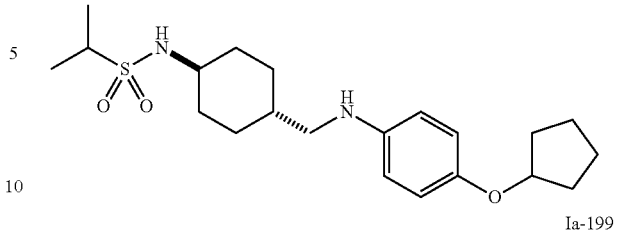
Ia-199
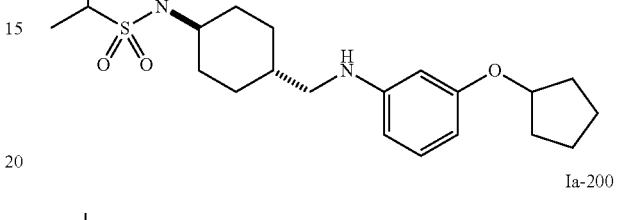
Ia-200
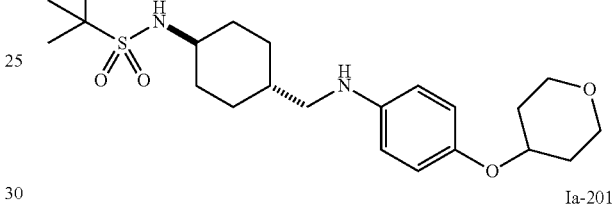
Ia-201
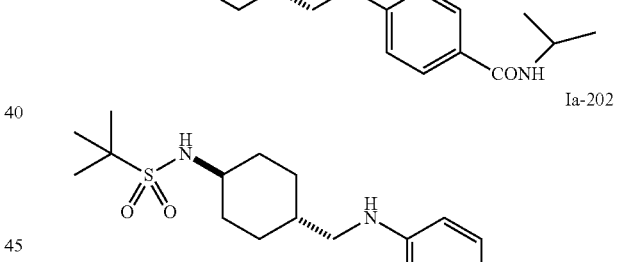
Ia-202
[Formula 113]
Ia-203
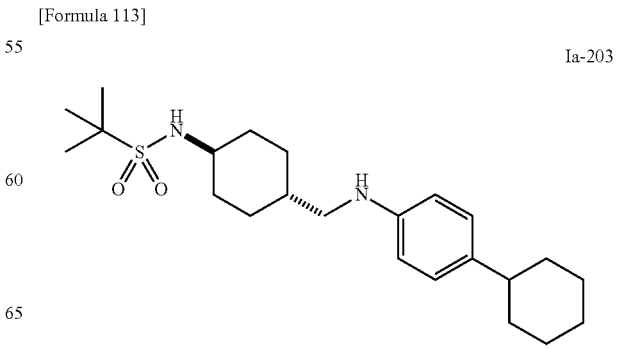

-continued
Ia-204
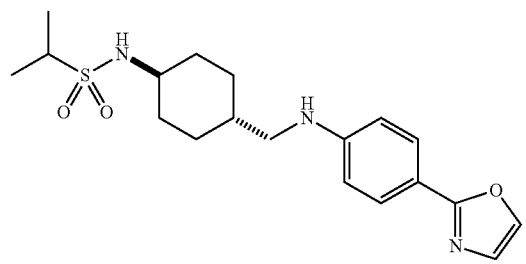
Ia-205
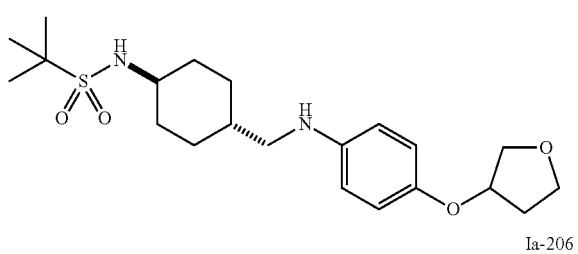
Ia-206
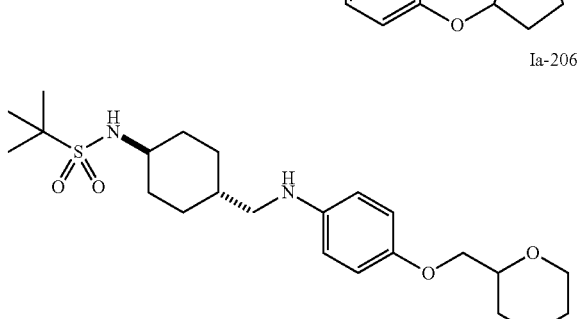
Ia-207
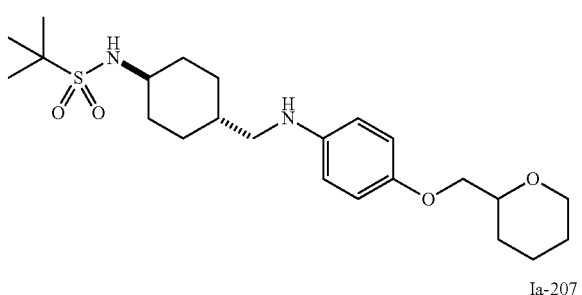
Ia-208
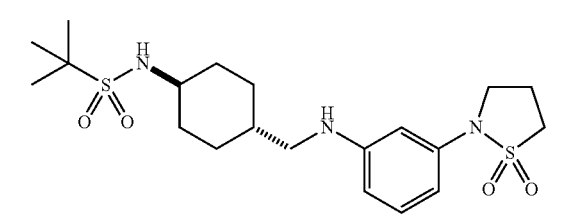
Ia-209
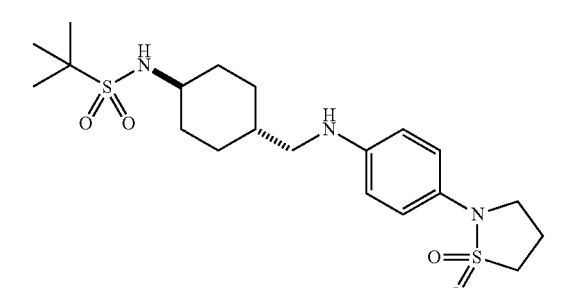
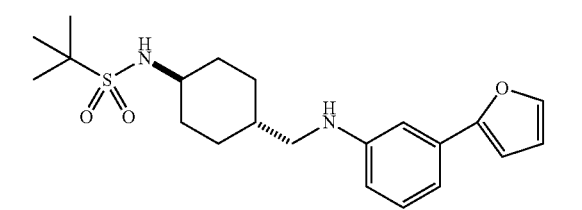
-continued
Ia-210
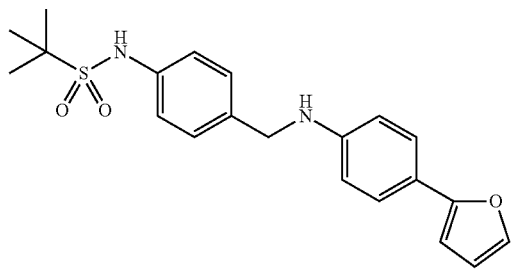
Ia-211
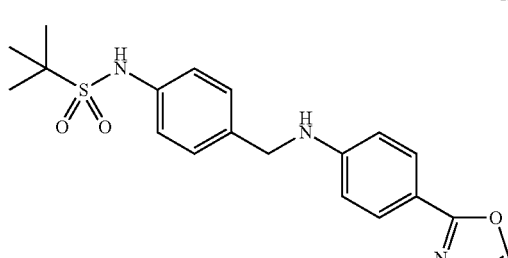
Ia-212
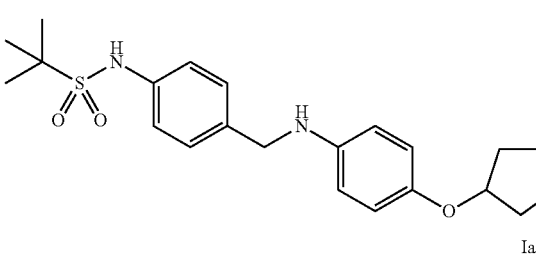
Ia-213
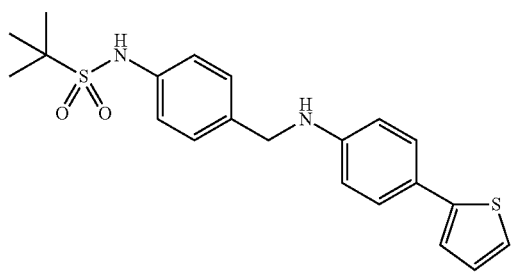
Ia-214
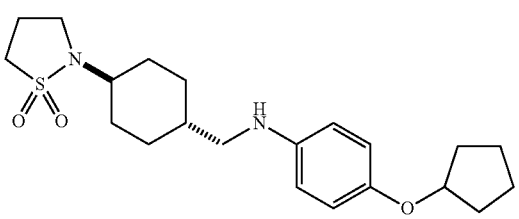
Ia-215
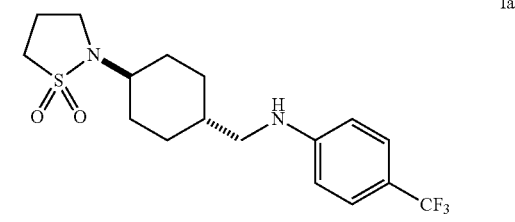

Ia-216
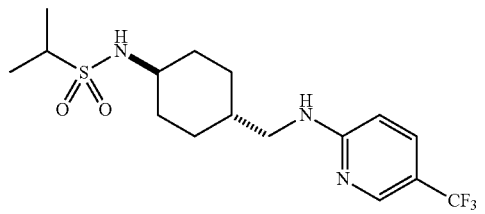
Ia-219
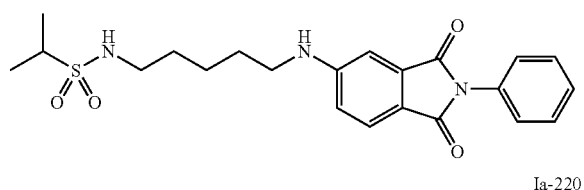
Ia-220
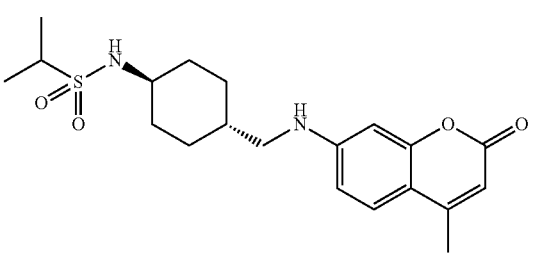
Ia-221
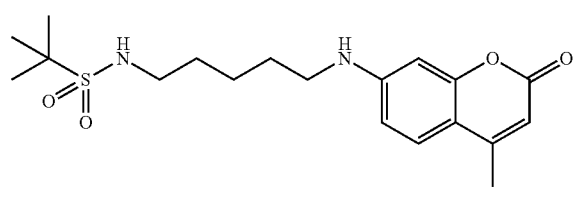
Ia-222
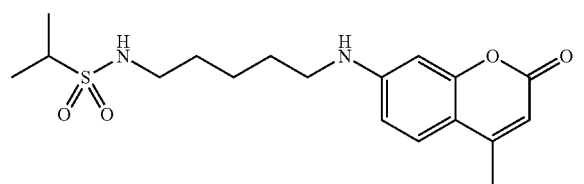
Ia-223
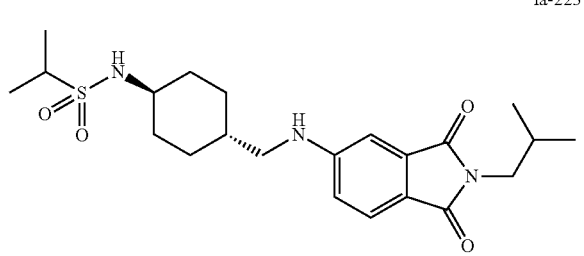
Ia-224
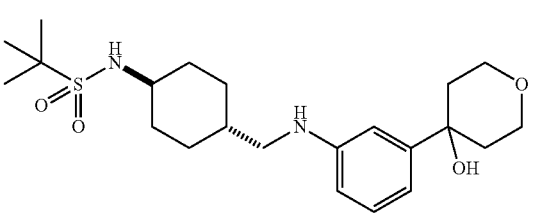
Ia-225
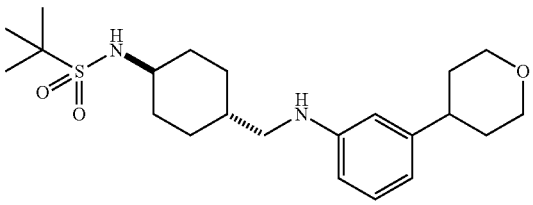
Ia-226
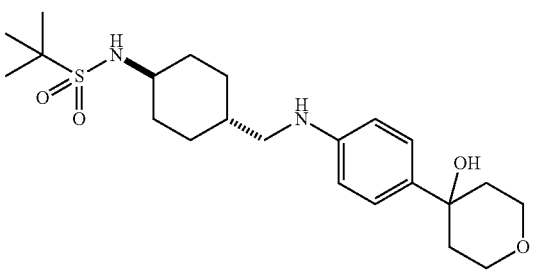
Ia-227
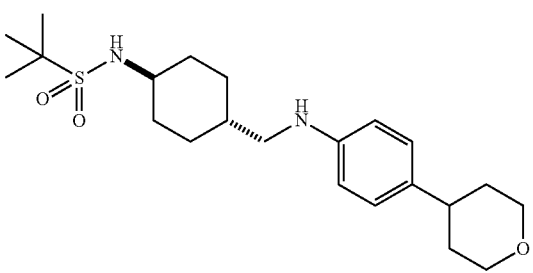
Ia-228
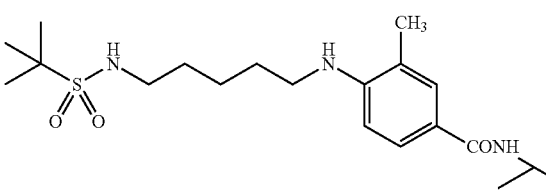
Ia-229
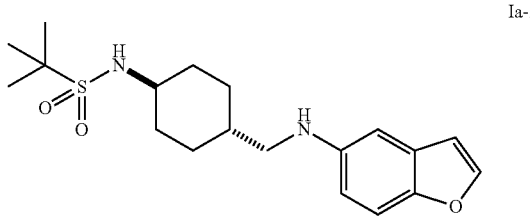
Ia-230
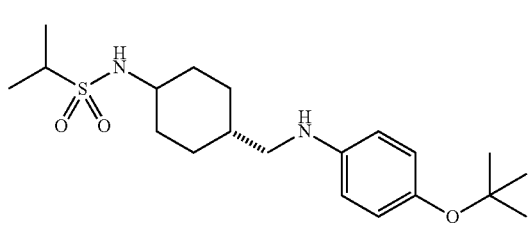

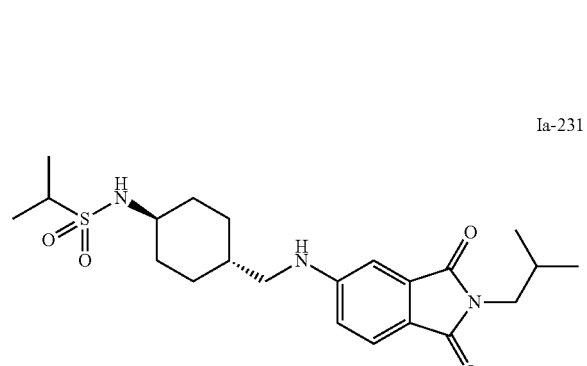

Ia-244
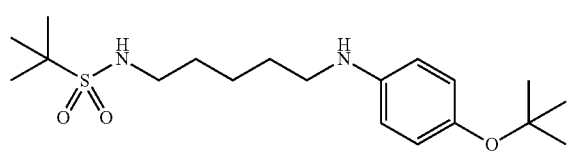
Ib-10
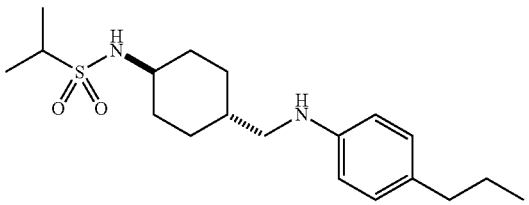
[Formula 115]
Ib-1
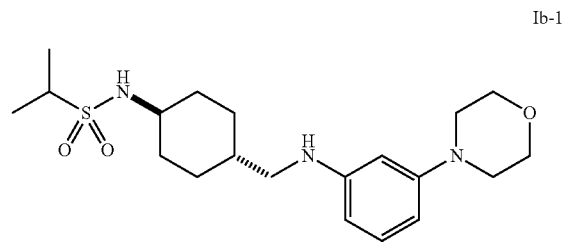
Ib-11
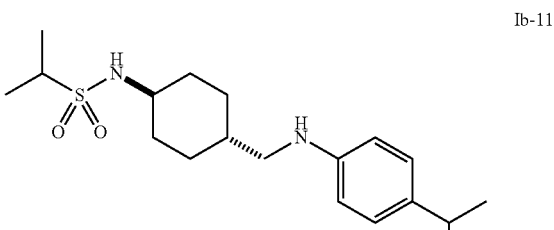
Ib-2
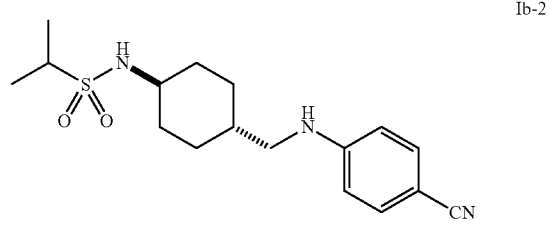
Ib-12
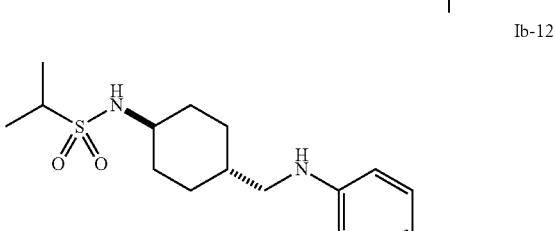
Ib-5
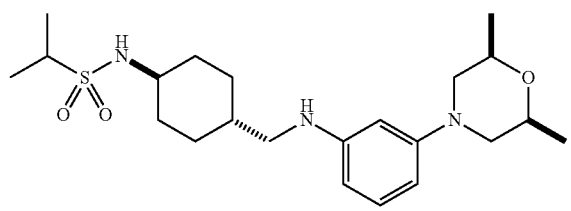
Ib-13
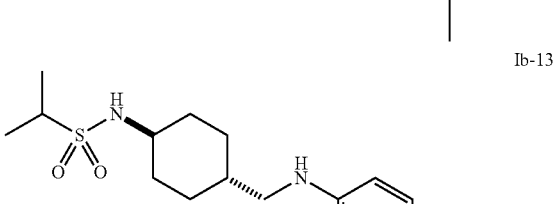
Ib-7
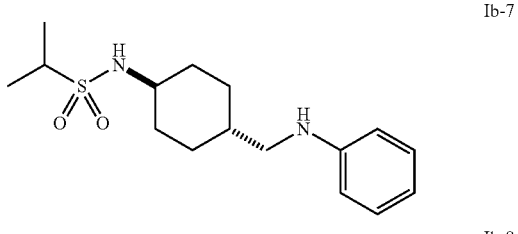
Ib-14
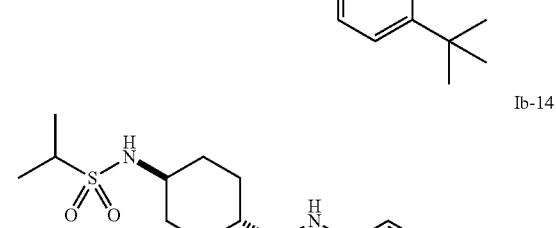
Ib-8
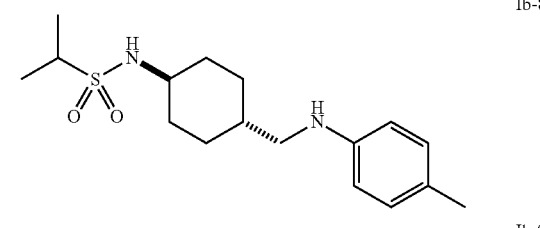
Ib-15
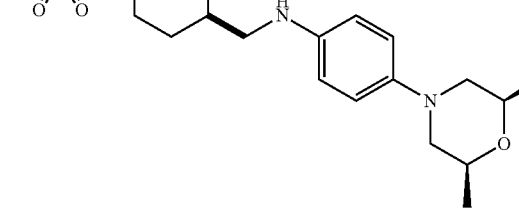
Ib-9
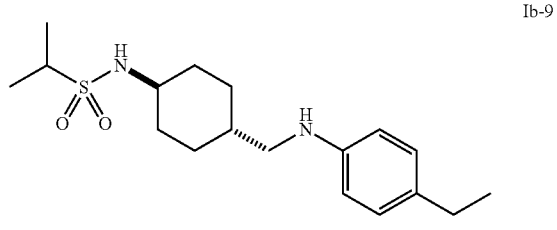

Ib-16
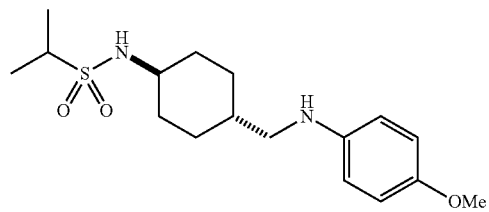
Ib-17
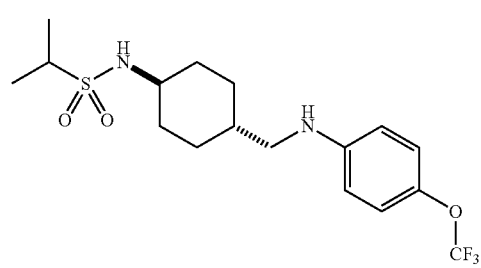
Ib-18
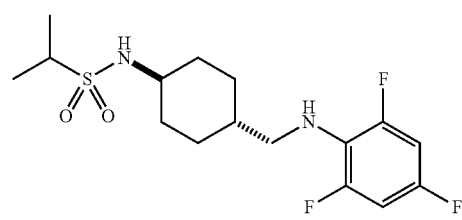
Ib-19
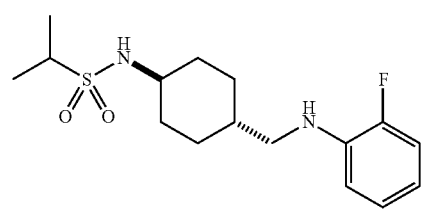
Ib-20
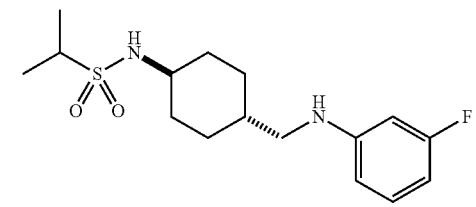
Ib-21
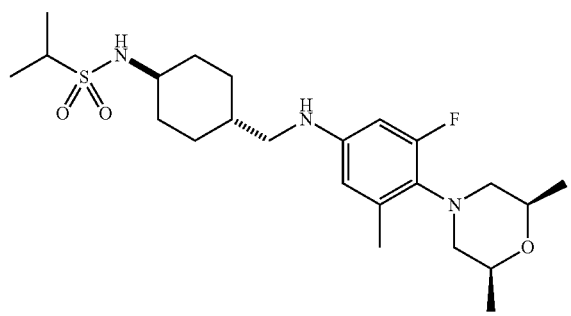
Ib-22
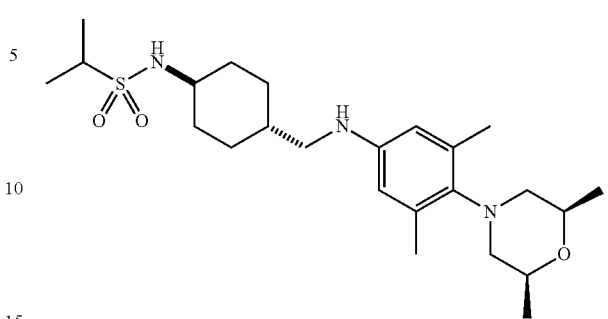
[Formula 116]
Ib-23
Ib-24
Ib-25
Ib-26

Ib-27
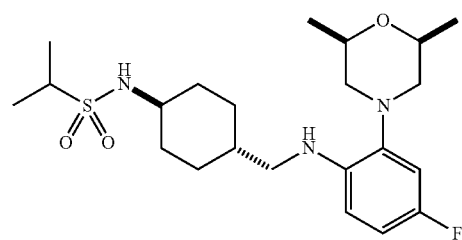
Ib-28
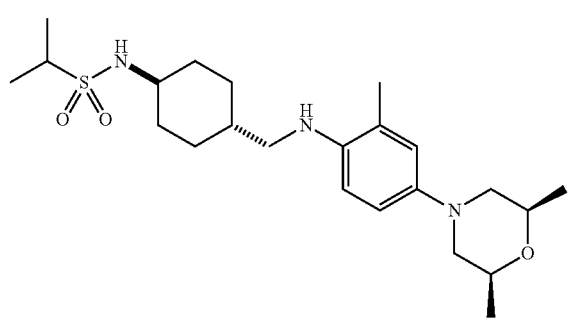
Ib-29
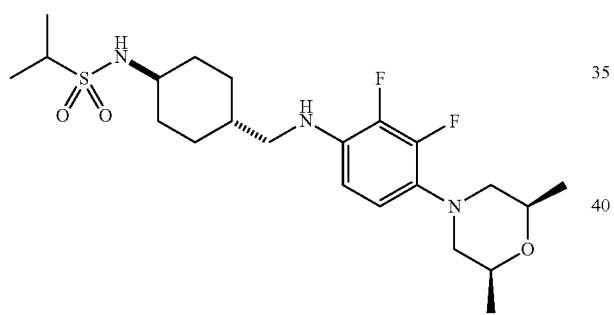
Ib-30
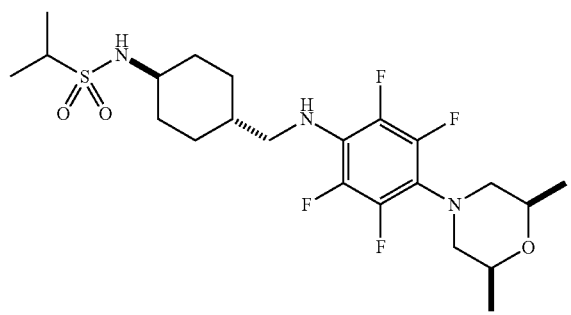
Ib-31
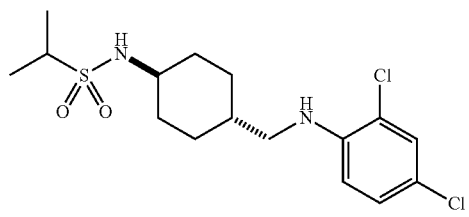
Ib-32
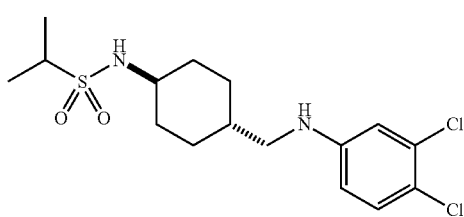
Ib-33
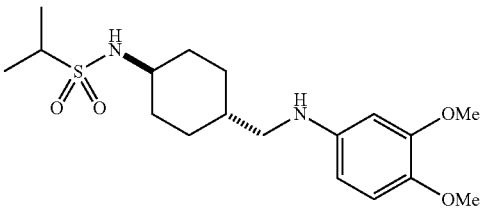
Ib-35
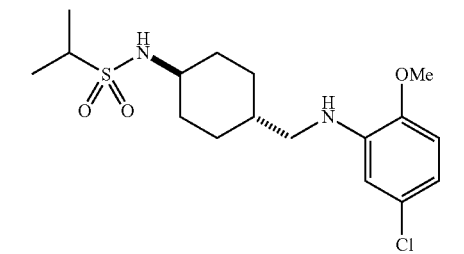
Ib-36
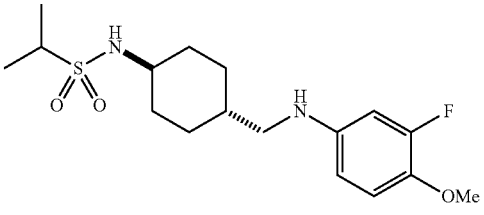
Ib-37
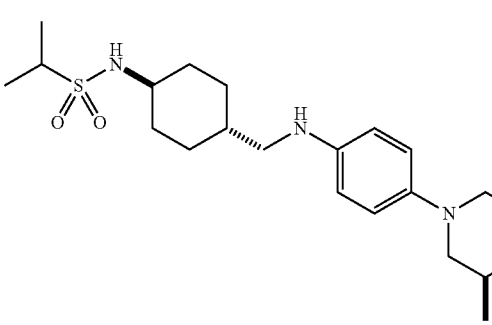
Ib-38
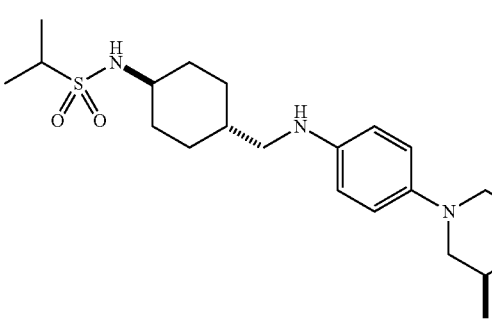

-continued
Ib-39
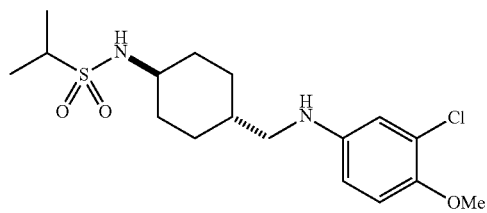
Ib-40
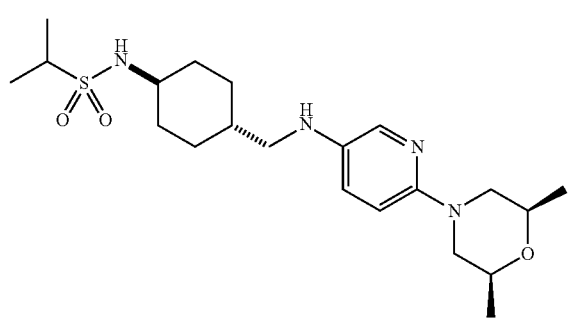
Ib-41
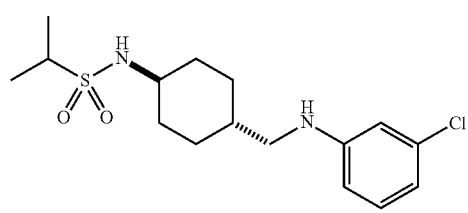
Ib-42
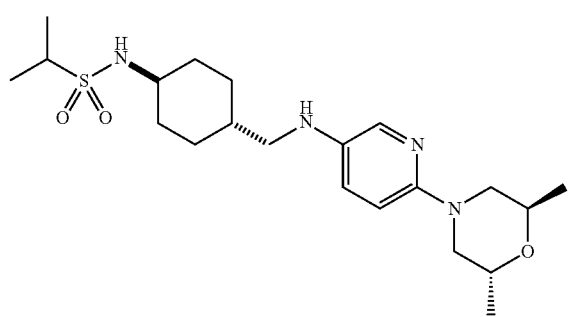
Ib-43
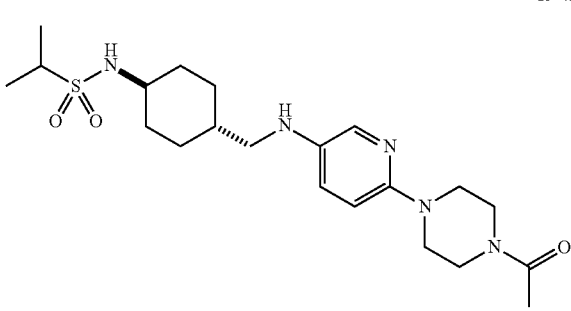
-continued
Ib-44
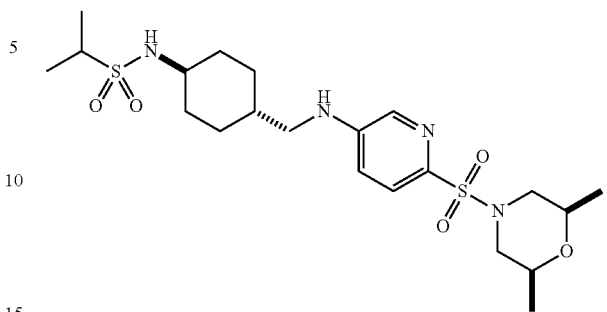
[Formula 117]
Ib-45
Ib-46
Ib-47
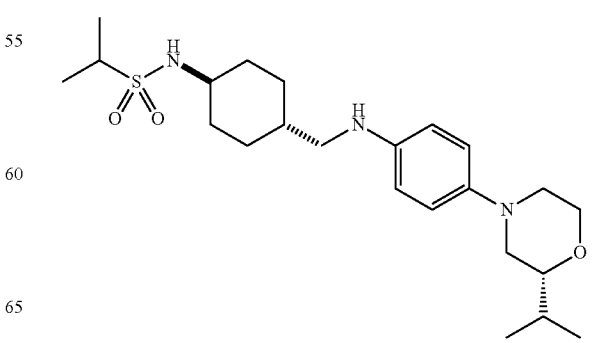

Ib-48
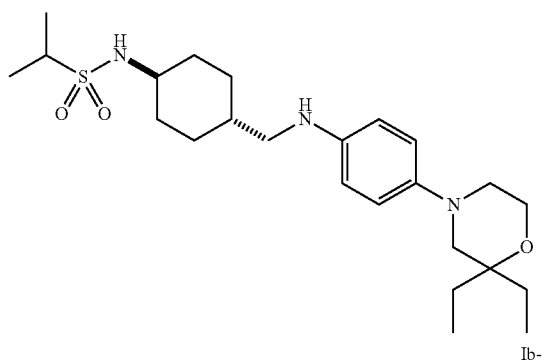
Ib-53
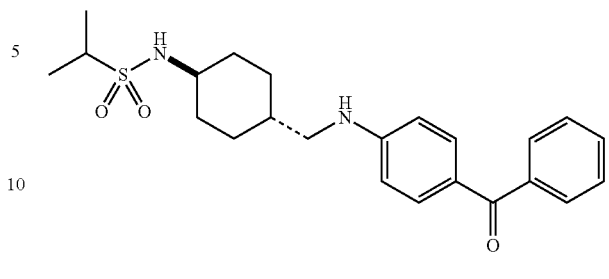
Ib-49
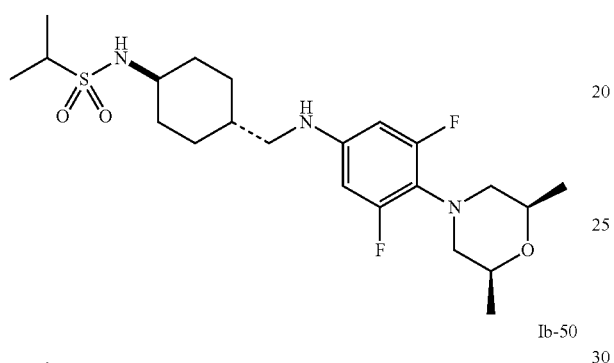
Ib-54
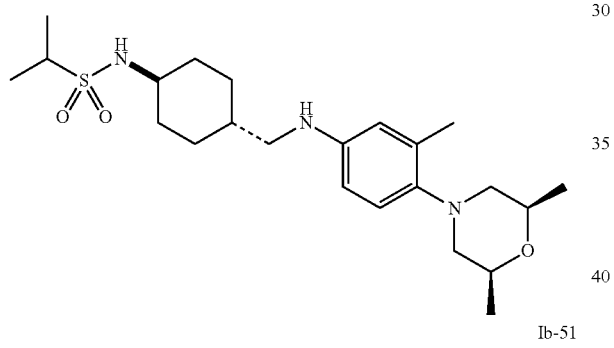
Ib-50
Ib-55
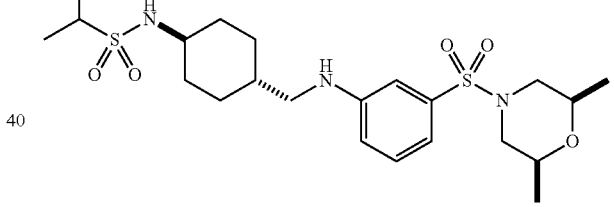
Ib-51
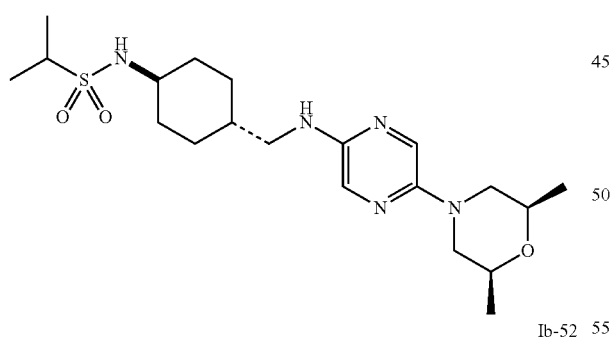
Ib-56
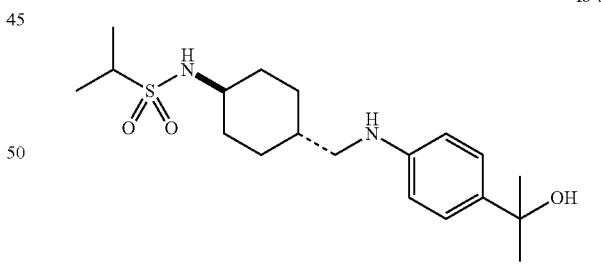
Ib-52
Ib-57
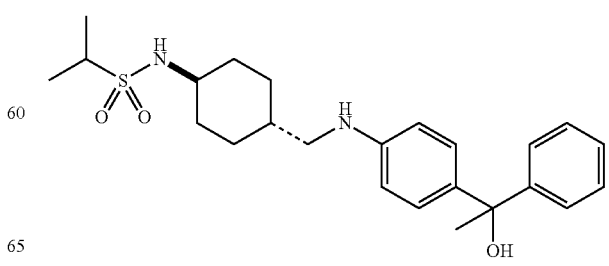
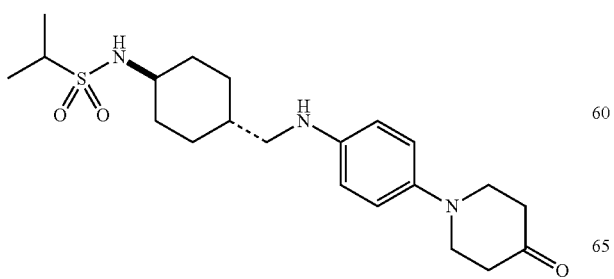

Ib-58
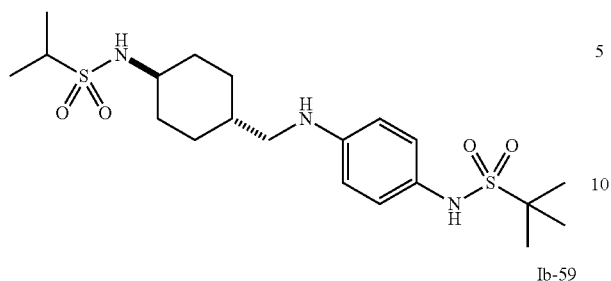
Ib-59
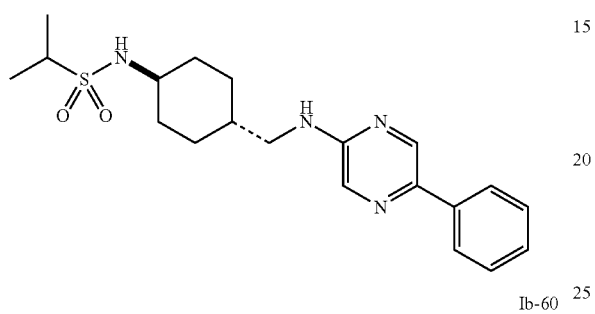
Ib-60
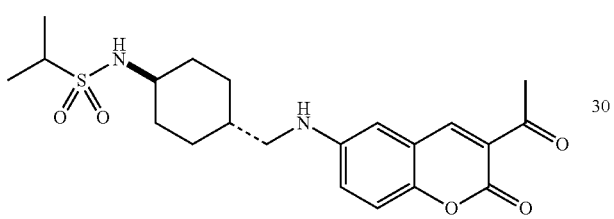
Ib-61
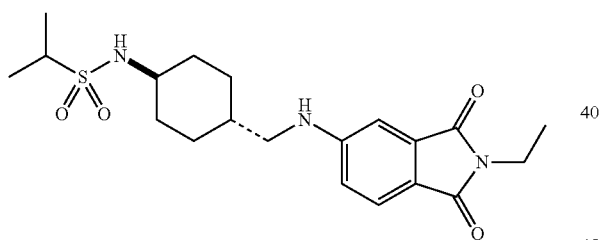
Ib-62
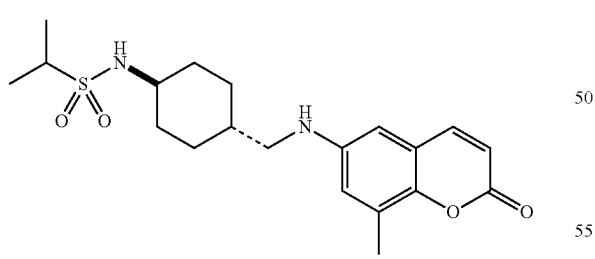
Ib-63
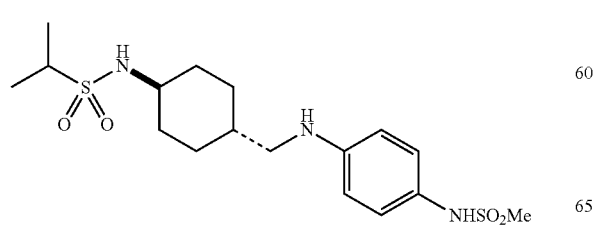
Ib-64
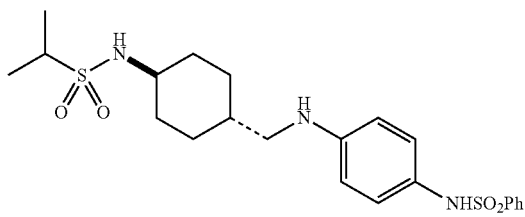
Ib-65
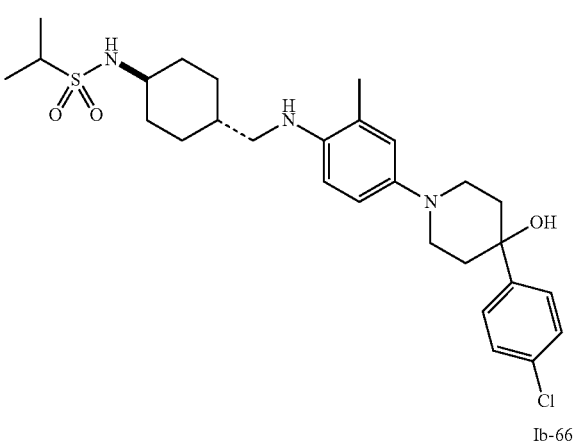
Ib-66
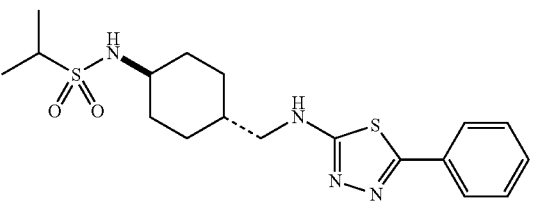
[Formula 118]
Ib-68
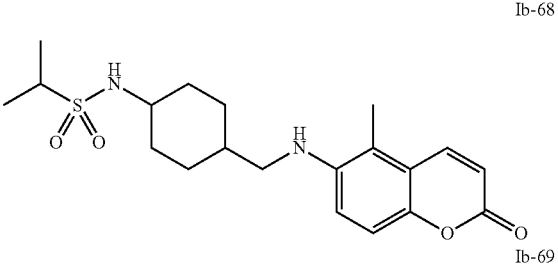
Ib-69
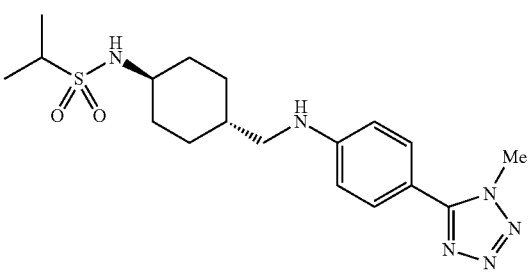

Ib-70
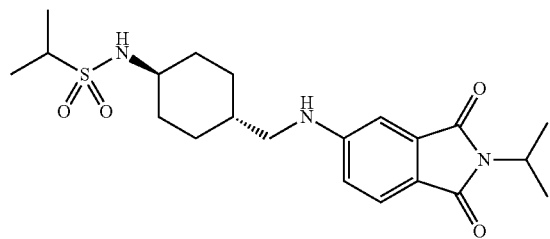
Ib-71
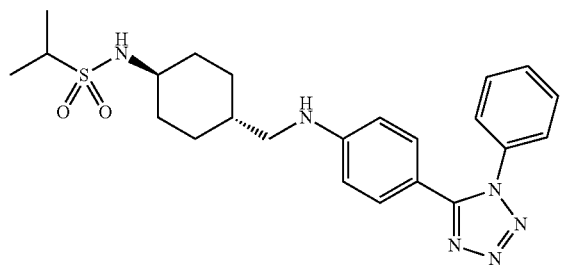
Ib-72
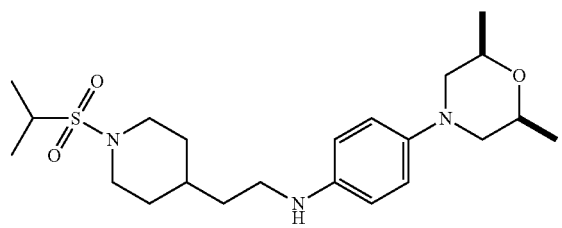
Ib-73
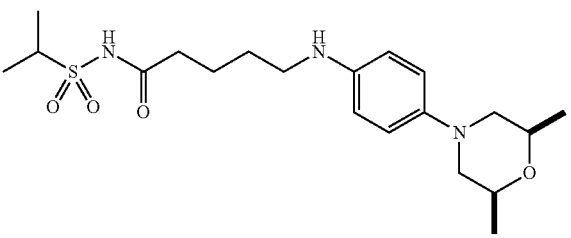
Ib-74
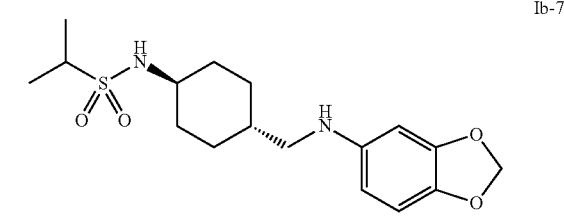
Ib-75
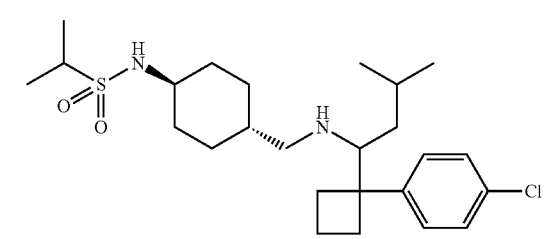
Ib-76
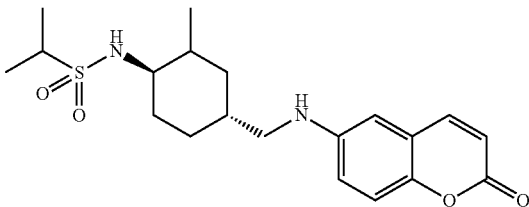
Ib-77
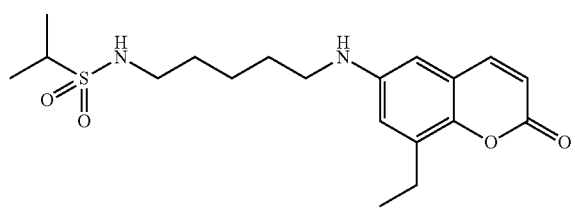
Ib-78
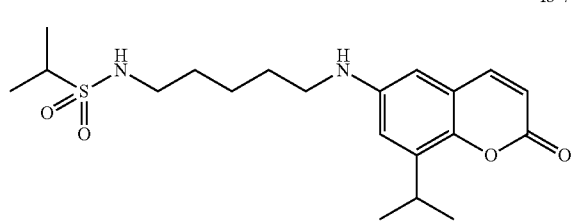
Ib-79
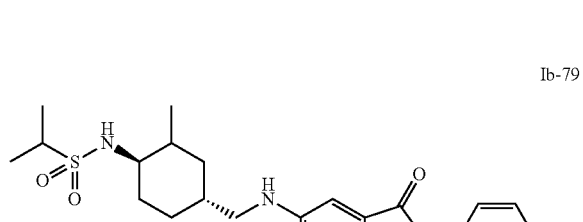
Ib-80
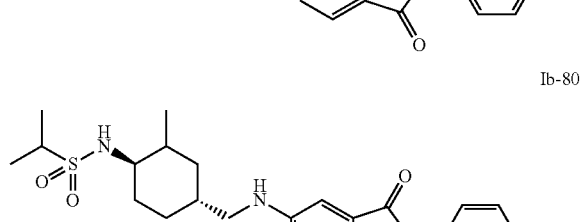
Ib-81
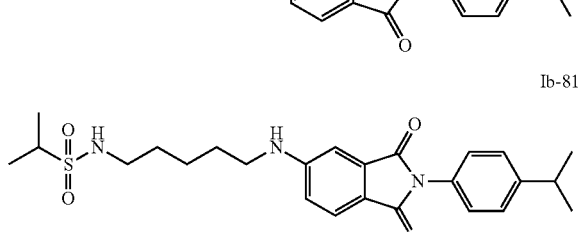

Ib-82
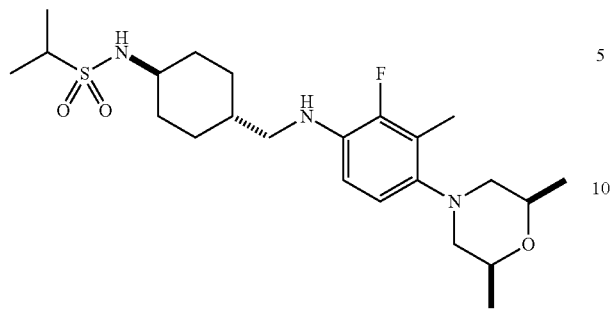
Ib-83
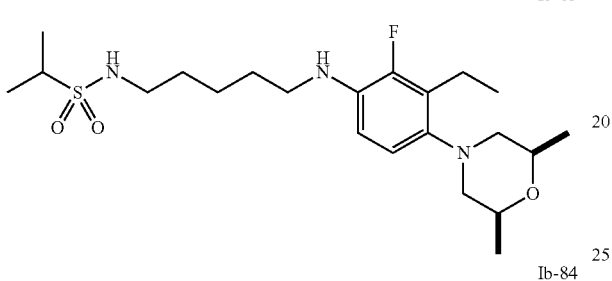
Ib-84
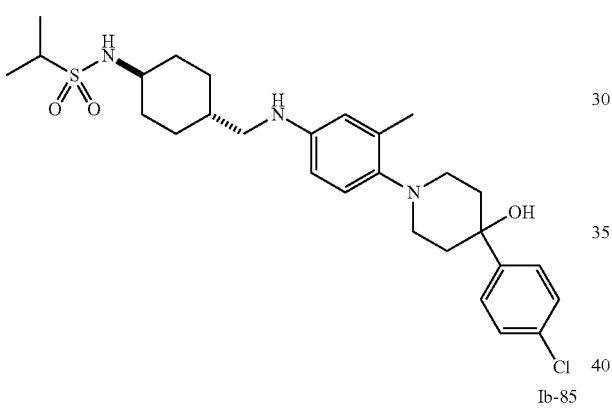
Ib-85
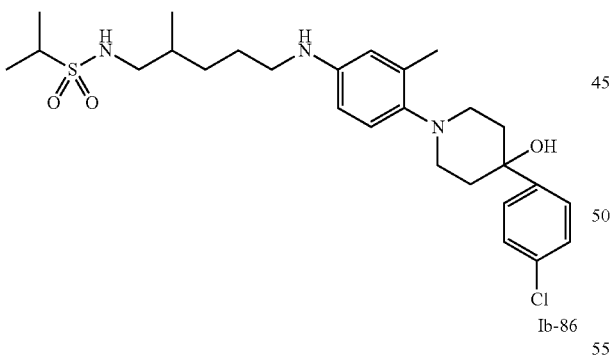
Ib-86
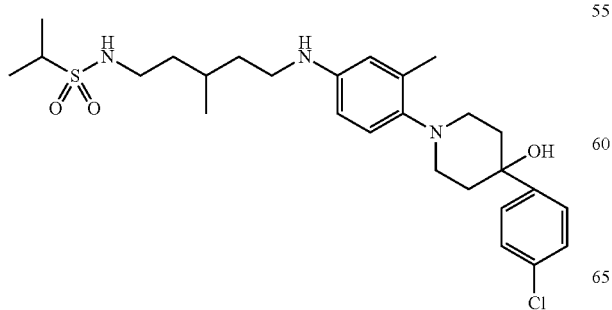
Ib-87
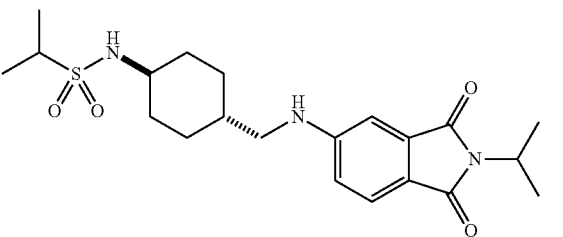
[Formula 119]
Ib-88
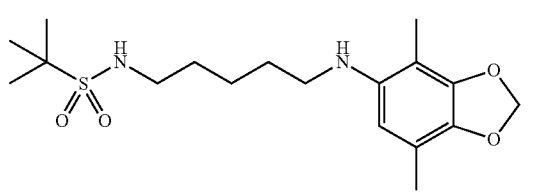
Ib-89
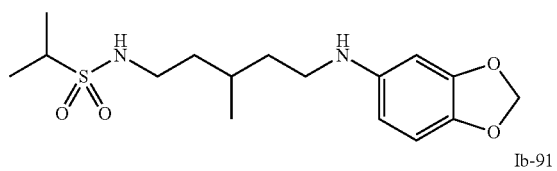
Ib-90
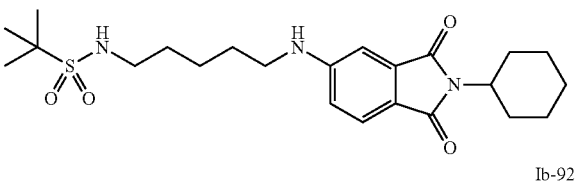
Ib-91
Ib-92
Ib-93
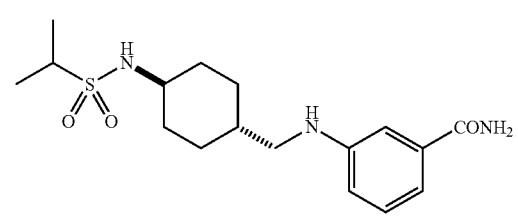

Ib-94
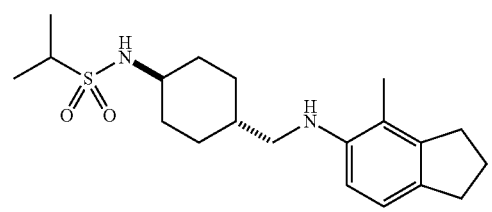
Ib-95
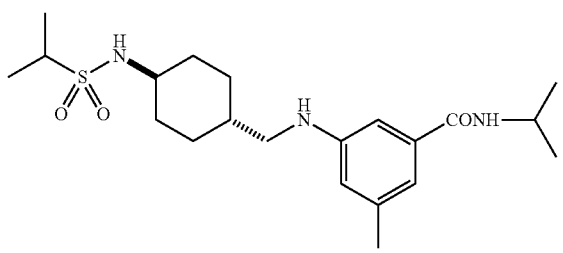
Ib-96
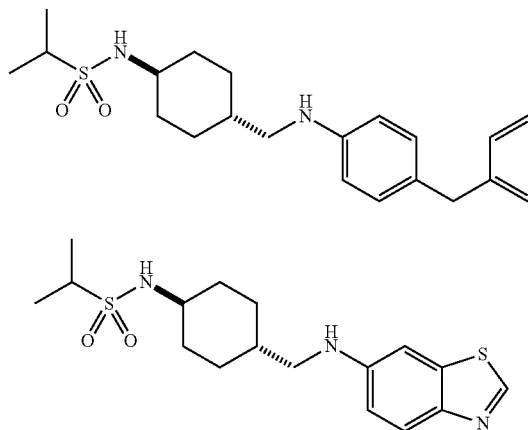
Ib-97
Ib-98
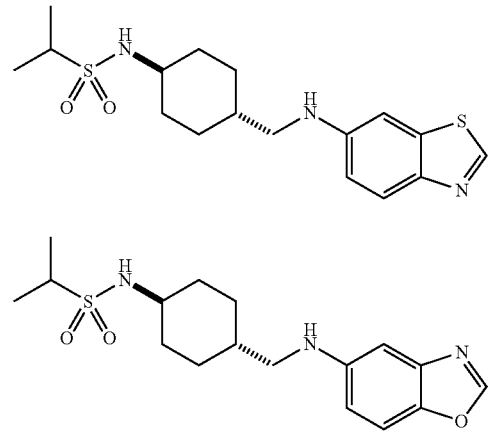
Ib-99
Ib-100
Ib-101
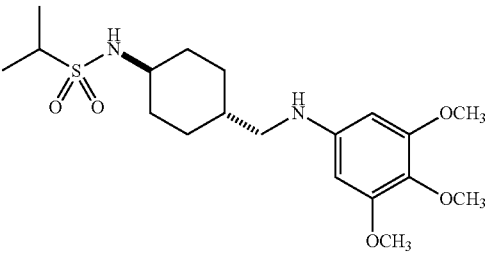
Ib-102
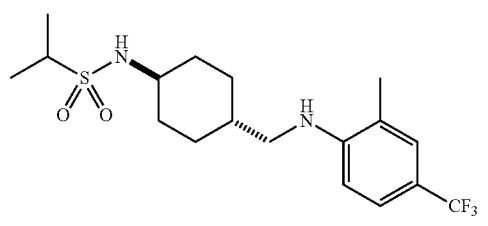
Ib-103
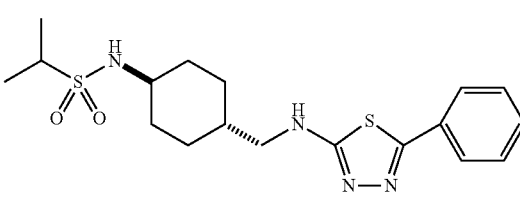
Ib-104
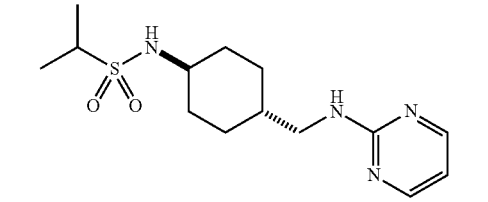
Ib-105
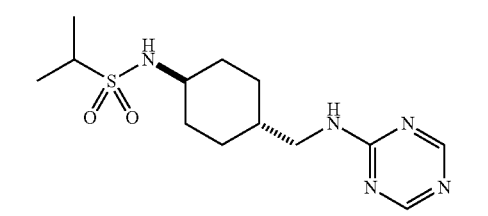
Ib-106
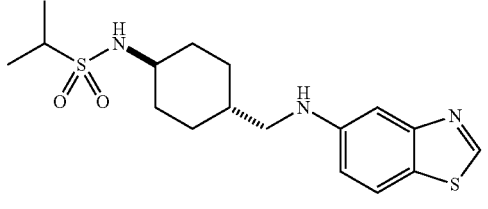
Ib-107

Ib-108 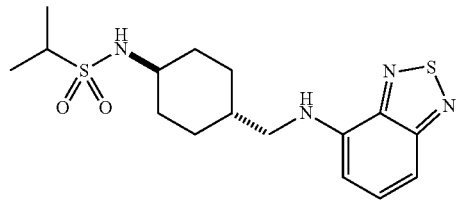
Ib-109 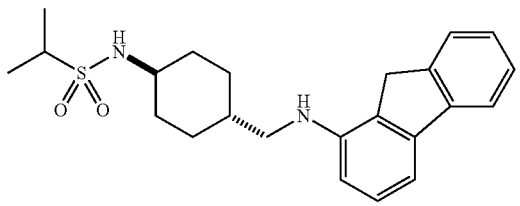
Ib-110 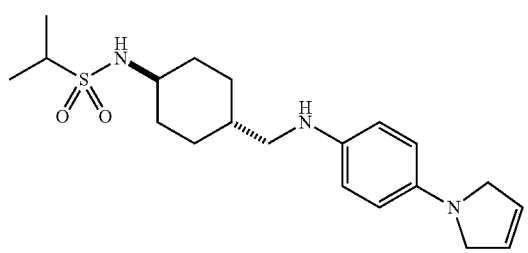
[Formula 120]
Ib-111 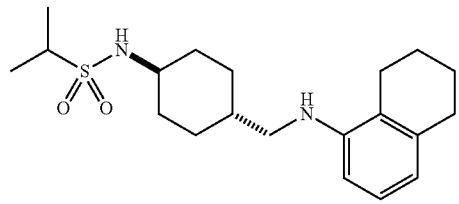
Ib-112 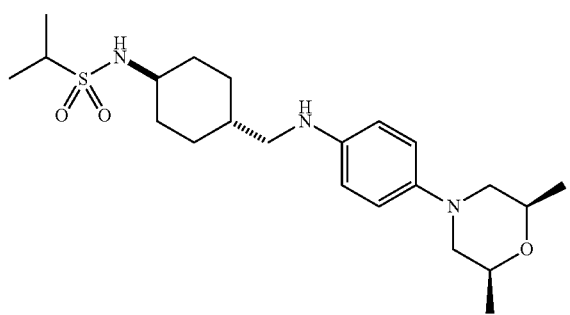
Ib-113 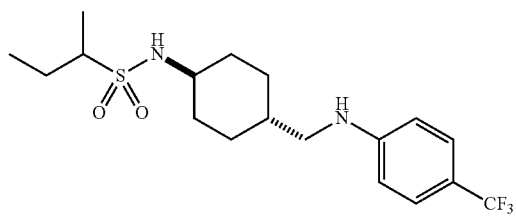
Ib-114 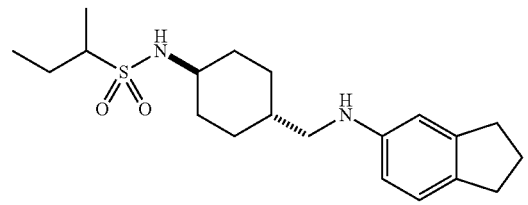
Ib-115 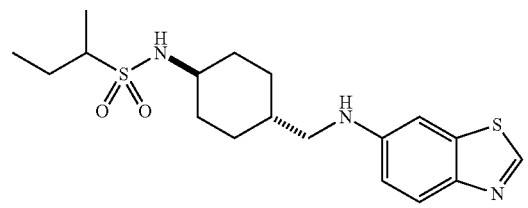
Ib-116 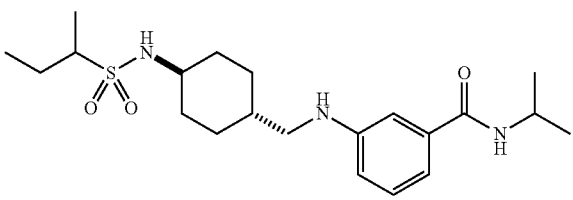
Ib-117 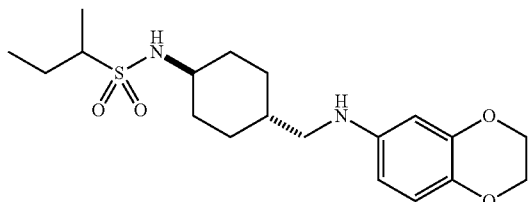
Ib-118 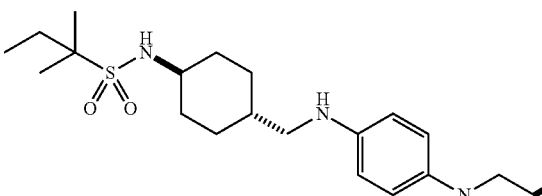
Ib-119 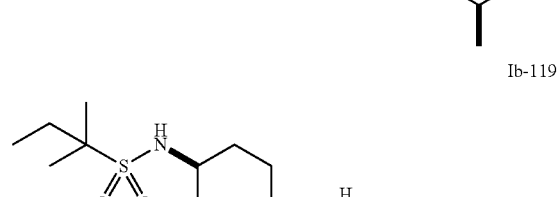

Ib-120
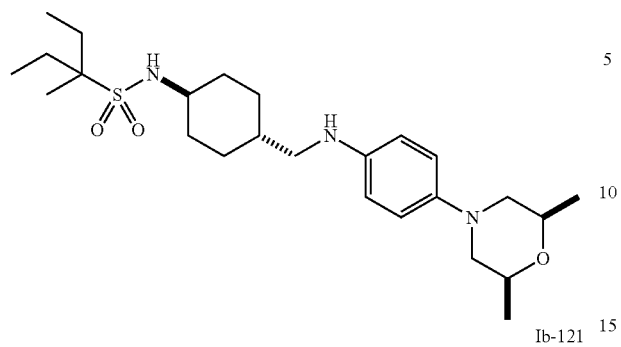
Ib-121
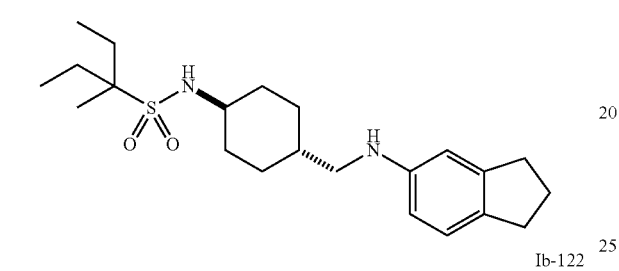
Ib-122
Ib-123
Ib-124
Ib-125
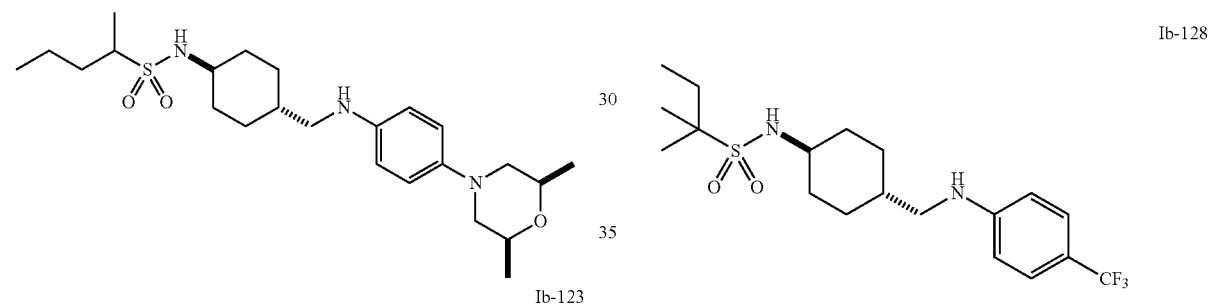
Ib-126
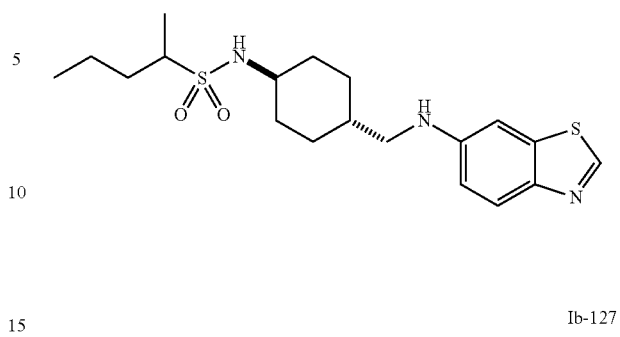
Ib-127
Ib-128
Ib-129
Ib-130
Ib-131
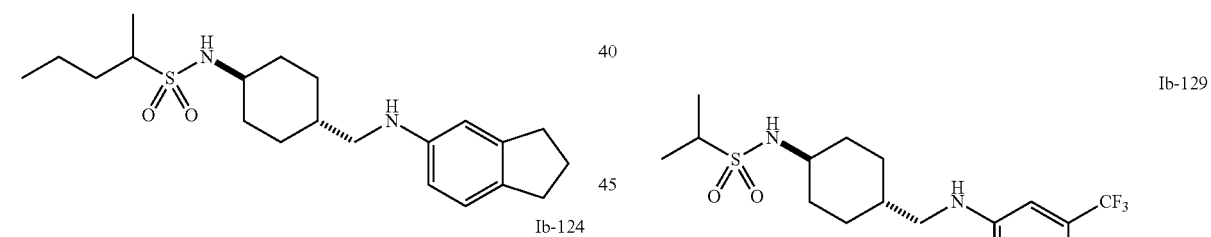
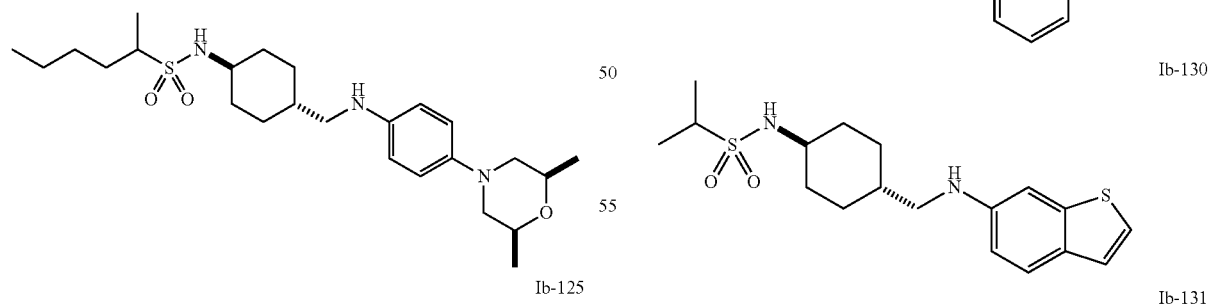
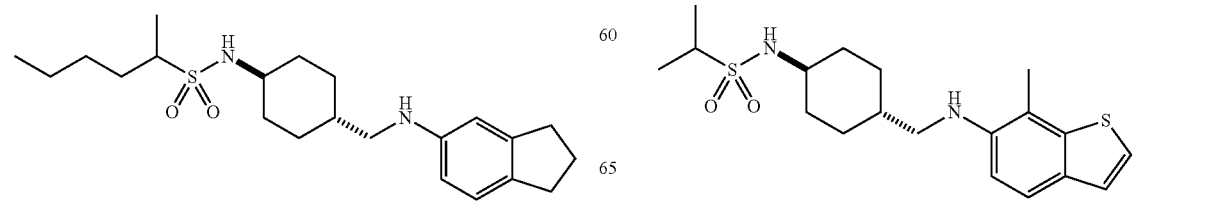

-continued
Ib-132
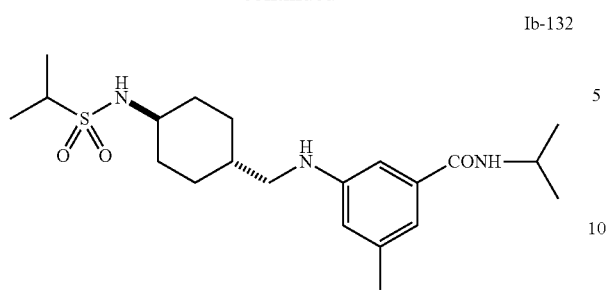
[Formula 121]
Ib-133
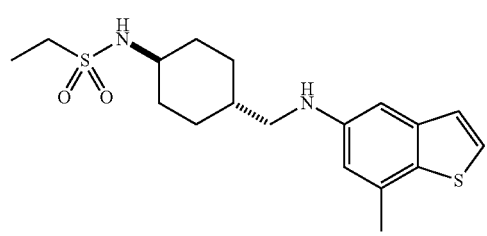
Ib-134
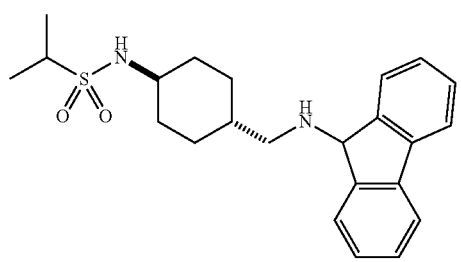
Ib-135
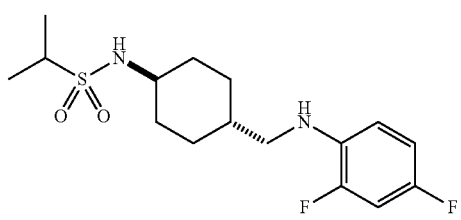
Ib-136
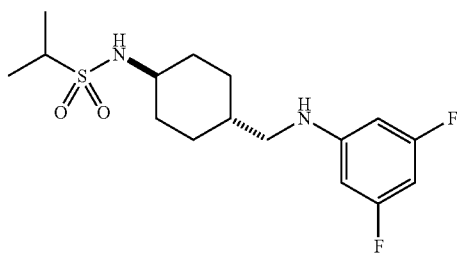
Ib-137
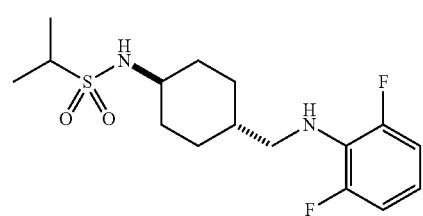
-continued
Ib-138
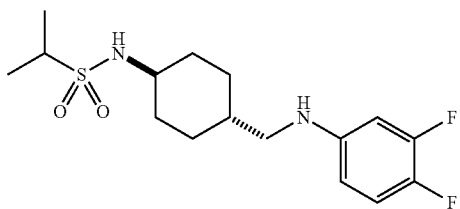
Ib-139
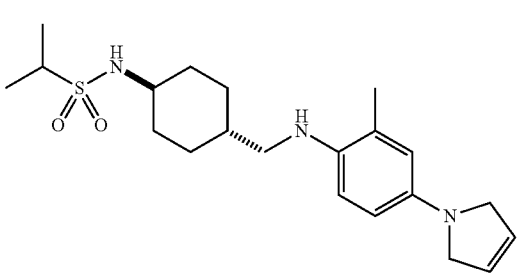
Ib-140
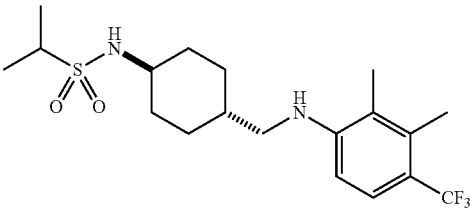
Ib-141
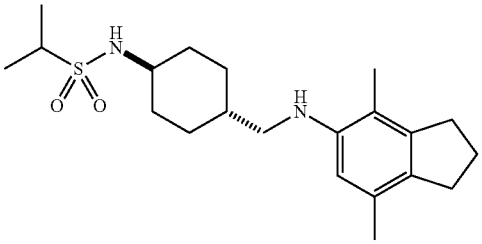
Ib-142
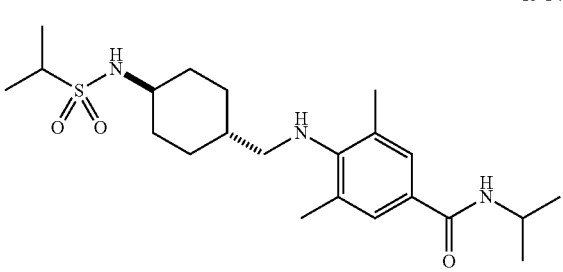
Ib-143
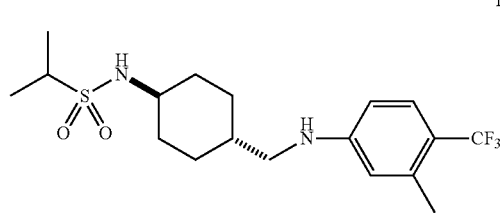

Ib-144
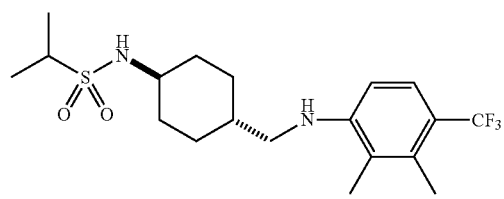
Ib-145
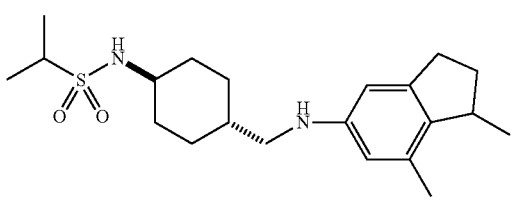
Ib-146
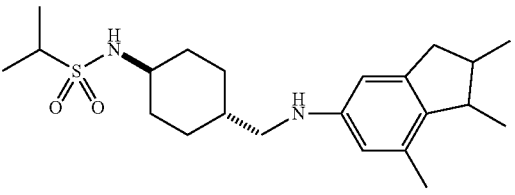
Ib-147
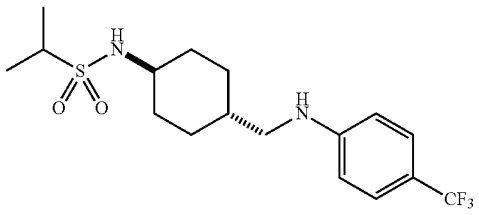
Ib-148
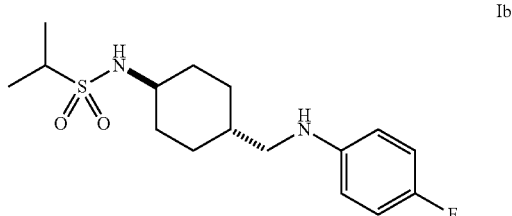
Ib-149
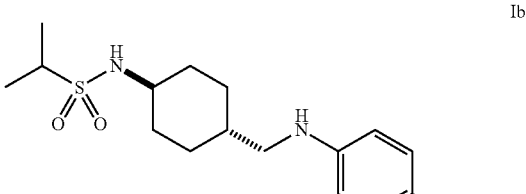
Ib-150
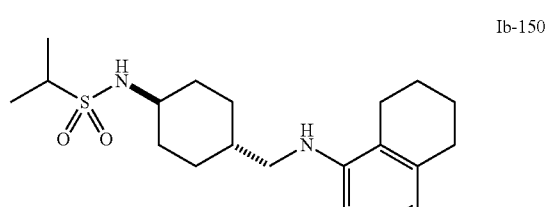
Ib-151
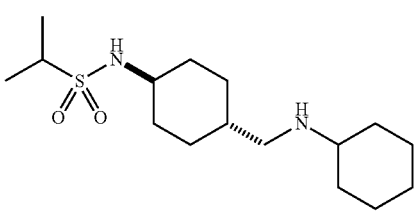
Ib-152
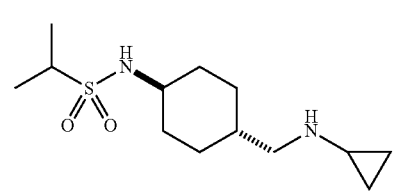
Ib-153
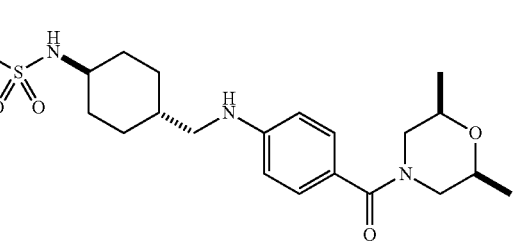
Ib-154
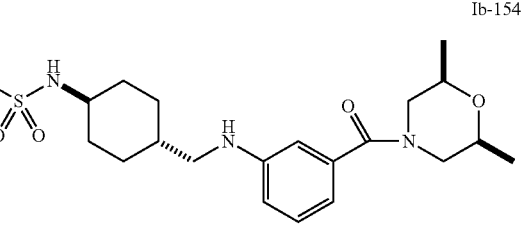
[Formula 122]
Ib-155
Ib-156
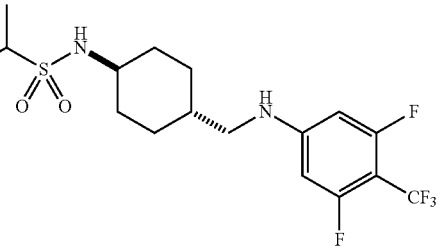
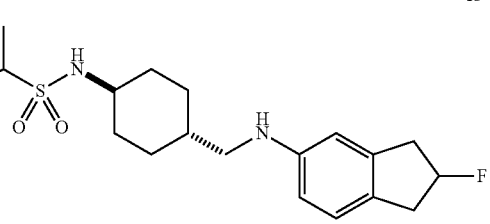

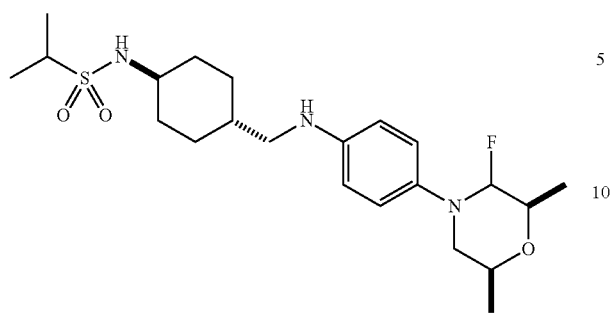
Ib-157
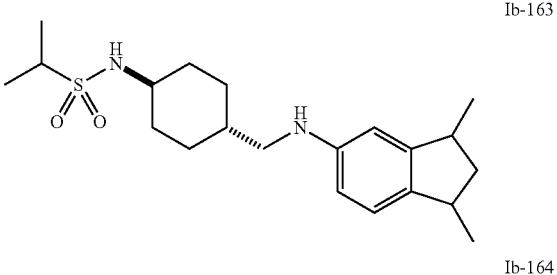
Ib-163
Ib-158
Ib-164
Ib-159
Ib-165
Ib-160
Ib-166
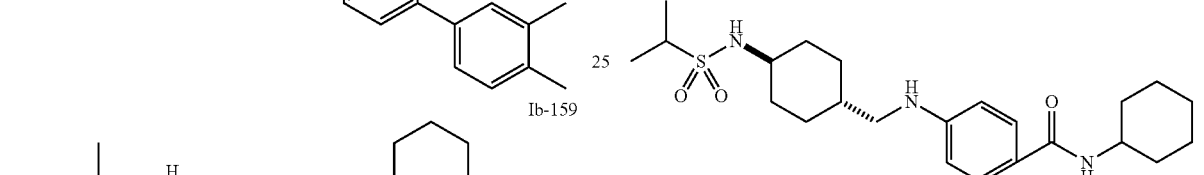
Ib-161
Ib-167
Ib-162
Ib-168
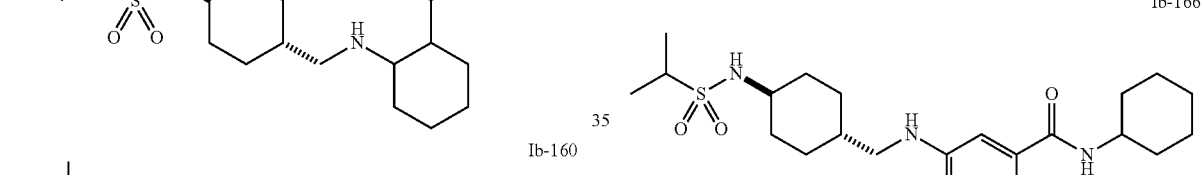
Ib-169

Ib-171
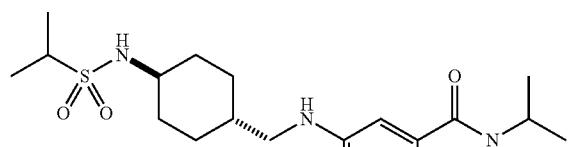
Ib-172
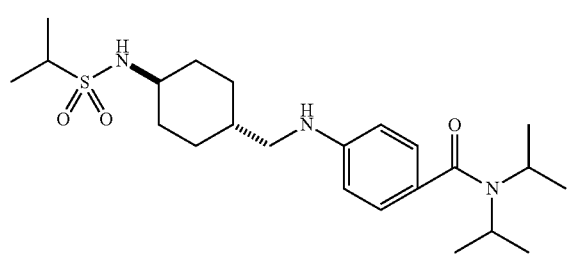
Ib-173
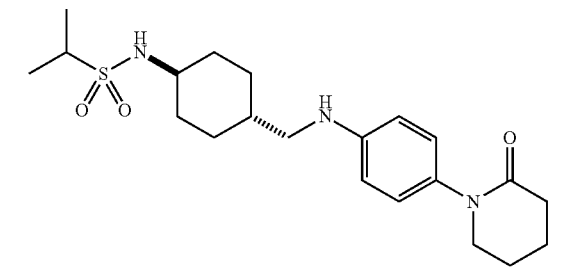
Ib-174
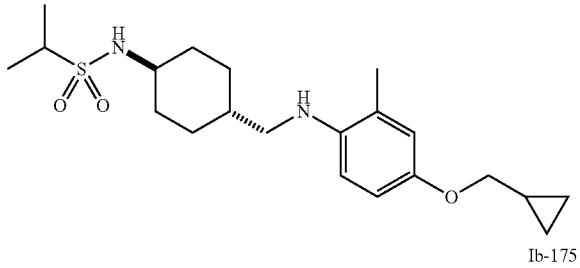
Ib-175
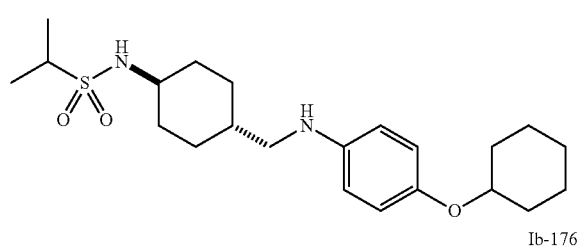
Ib-176
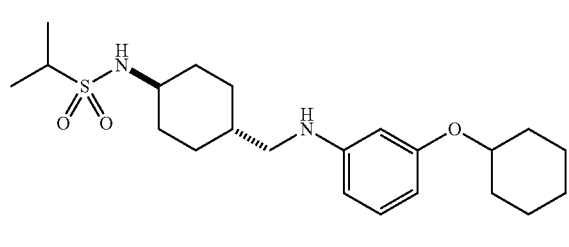
[Formula 123]
Ib-177
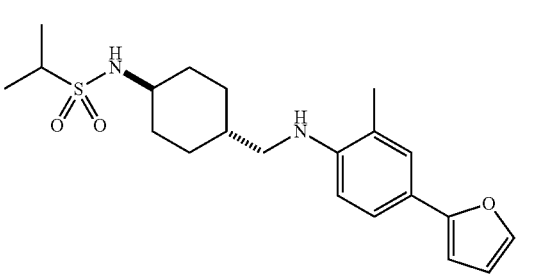
Ib-178
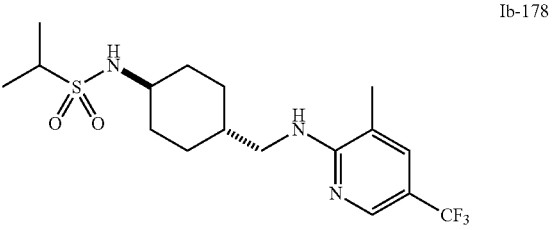
Ib-179
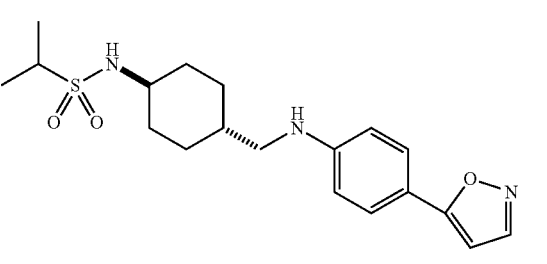
Ib-180
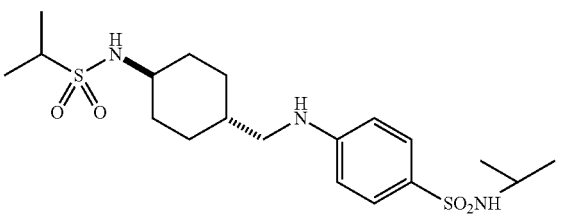
Ib-181
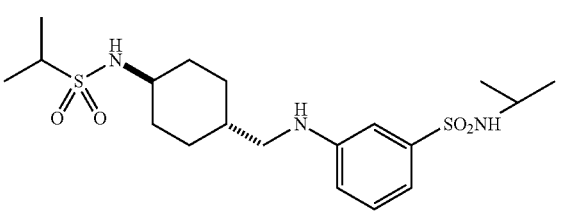
Ib-182
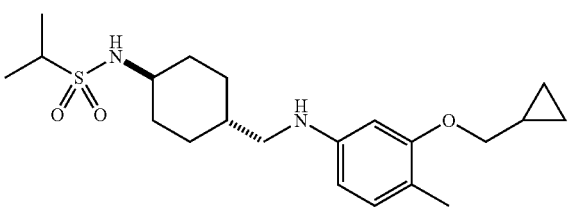

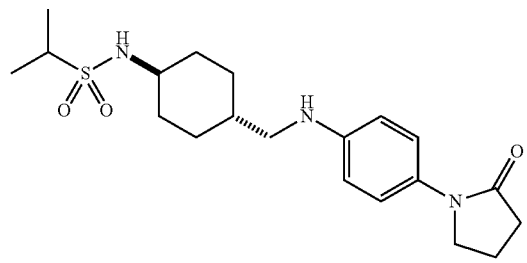
Ib-183
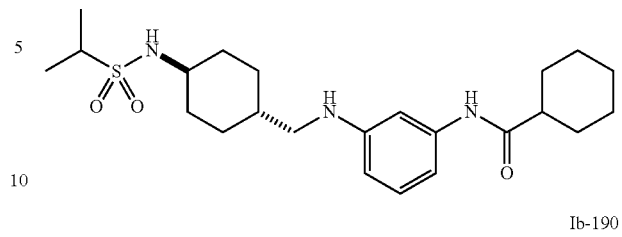
Ib-189
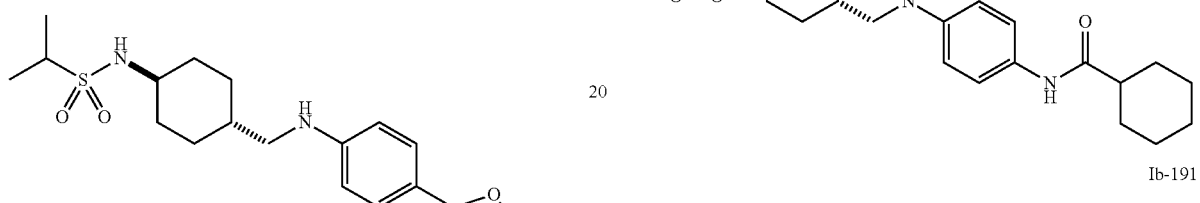
Ib-184
Ib-190
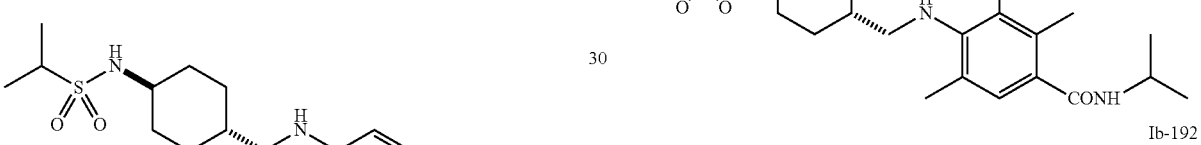
Ib-185
Ib-191
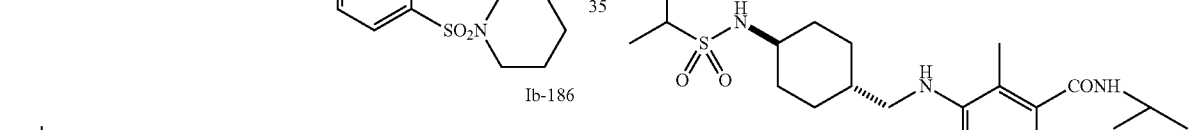
Ib-186
Ib-192

Ib-187
Ib-193
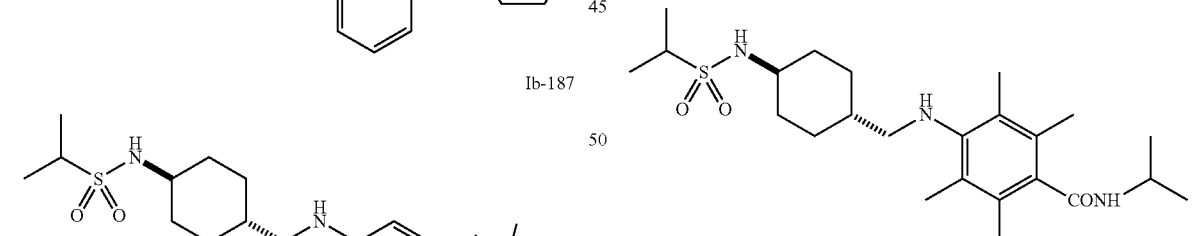
Ib-188
Ib-194
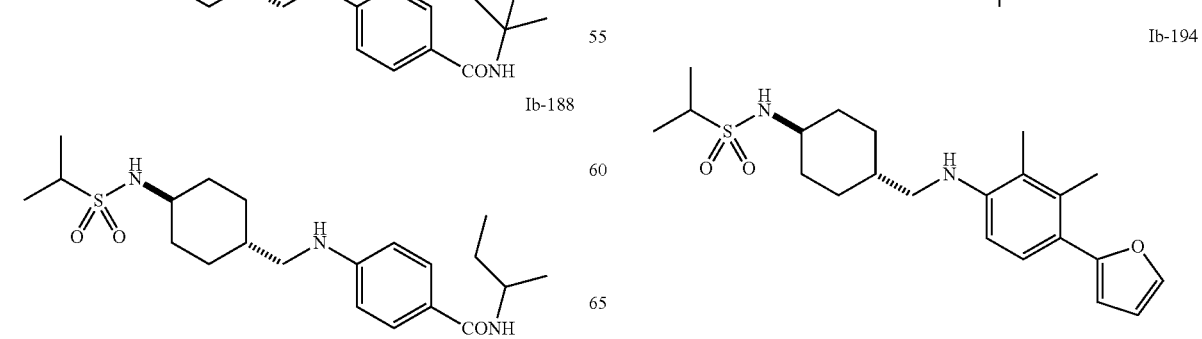

Ib-195
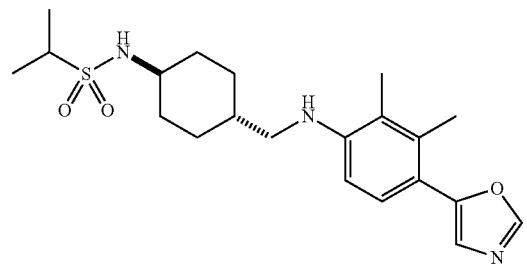
Ib-196
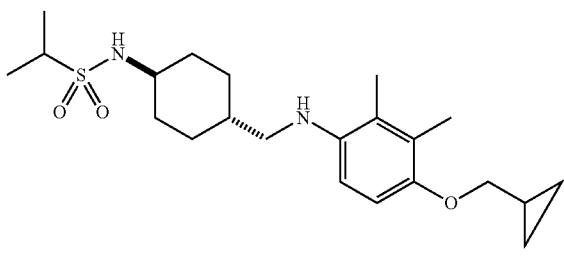
Ib-197
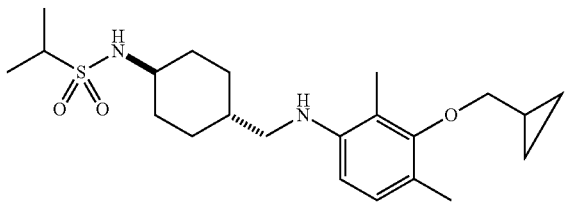
Ib-198
[Formula 124]
Ib-199
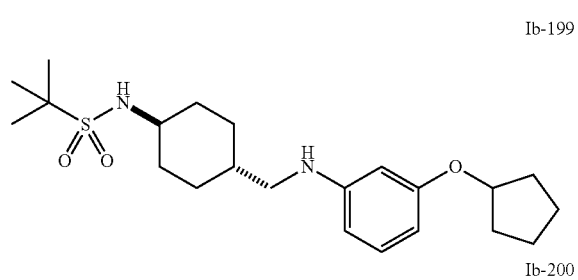
Ib-200
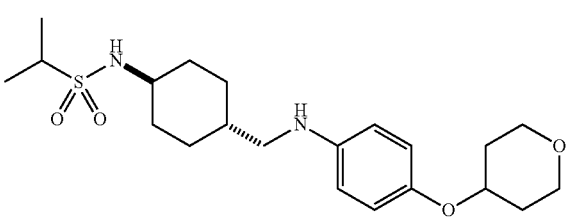
Ib-201
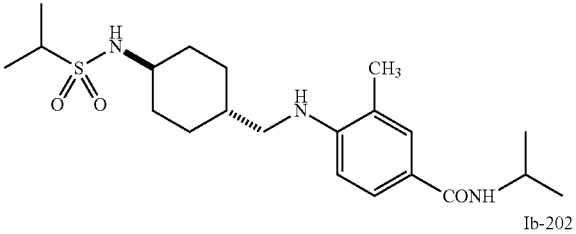
Ib-202
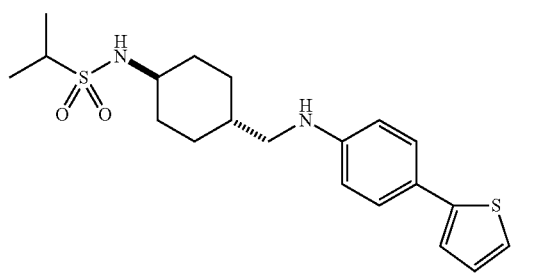
Ib-203
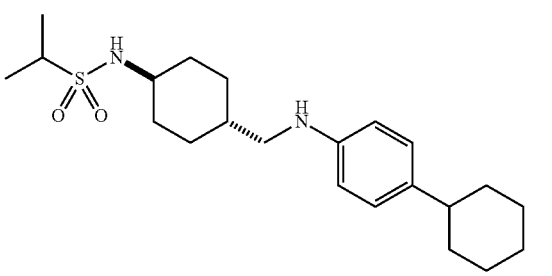
Ib-204
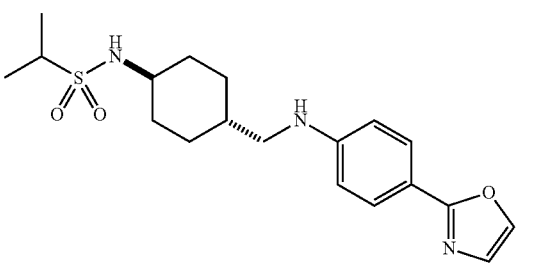
Ib-205
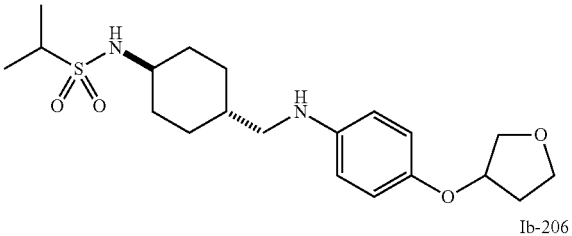
Ib-206

Ib-207
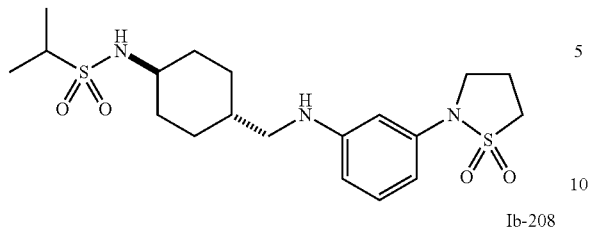
Ib-208
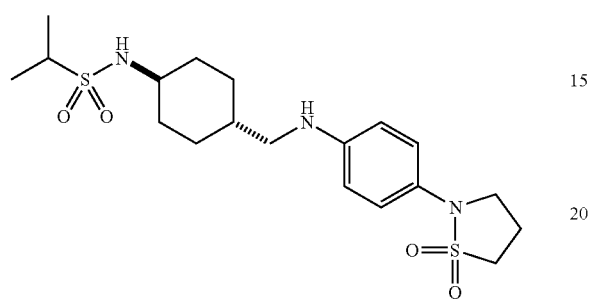
Ib-209
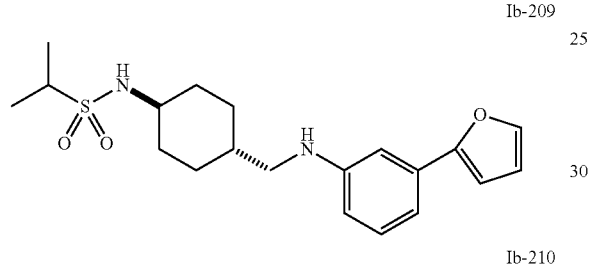
Ib-210
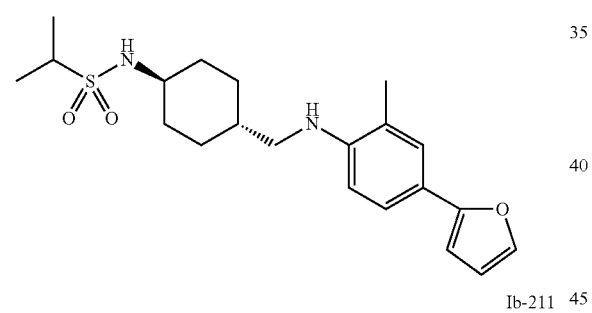
Ib-211
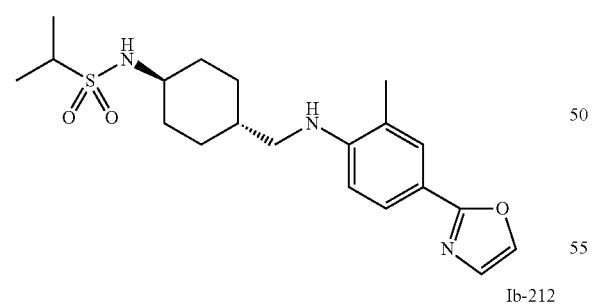
Ib-212
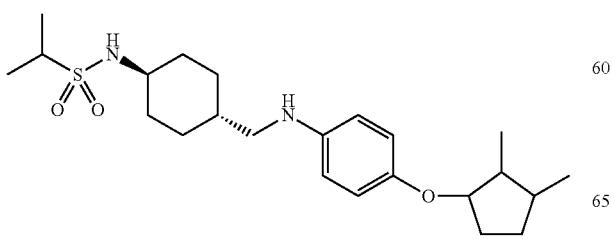
Ib-213
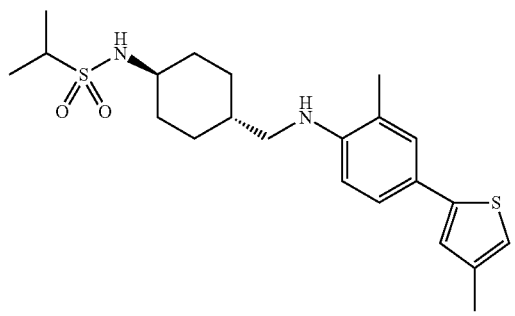
Ib-214
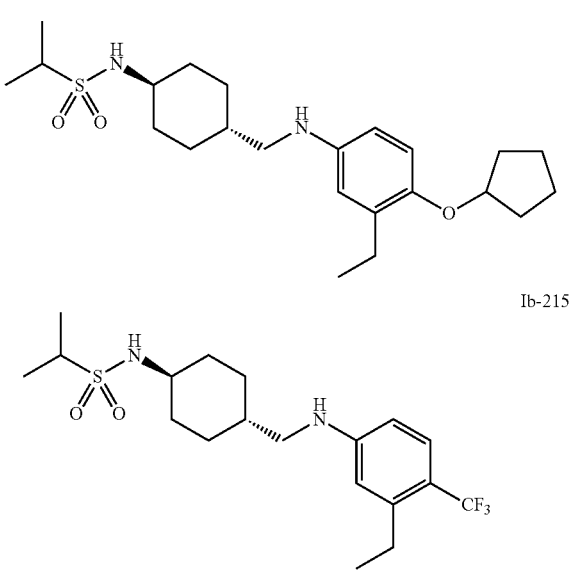
Ib-215
Ib-216
Ib-219
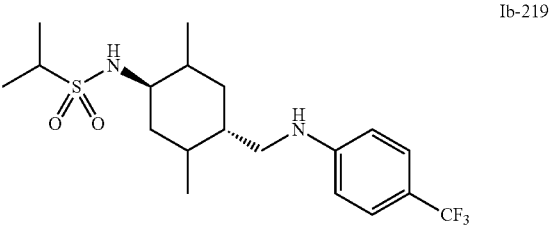
Ib-220
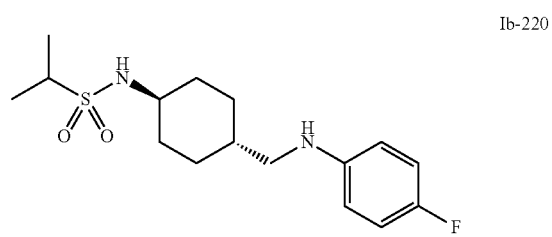

Ib-221
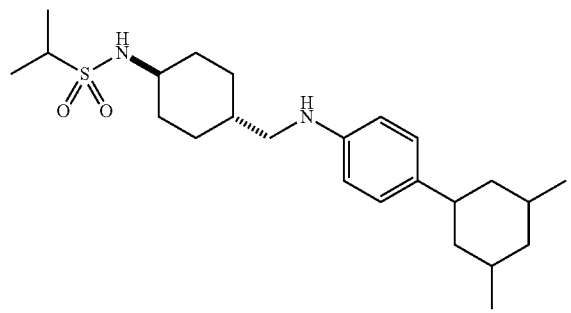
Ib-226
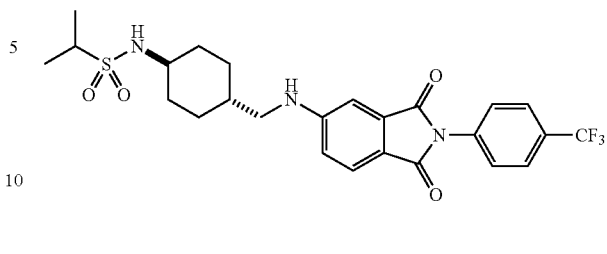
[Formula 125]
Ib-222
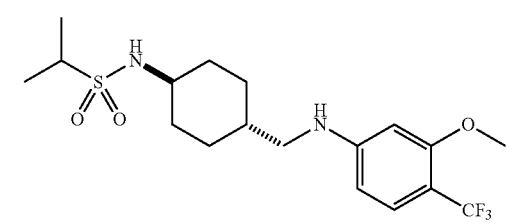
Ic-1
Ic-2
Ib-223
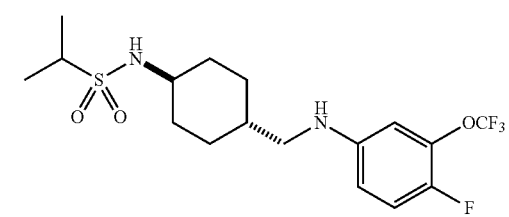
Ic-5
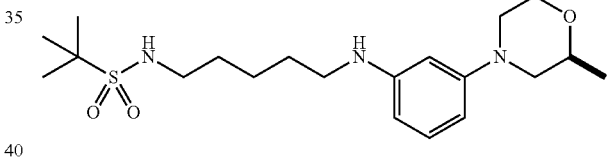
Ic-7
Ib-224
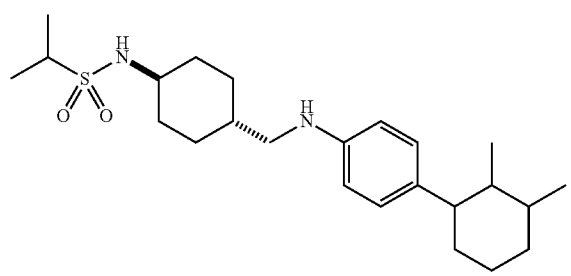
Ic-8
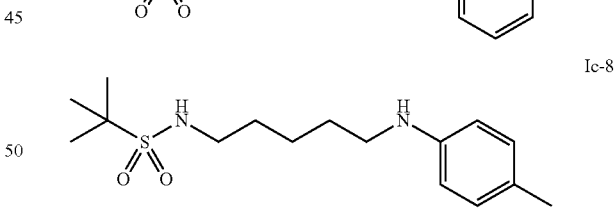
Ic-9
Ib-225
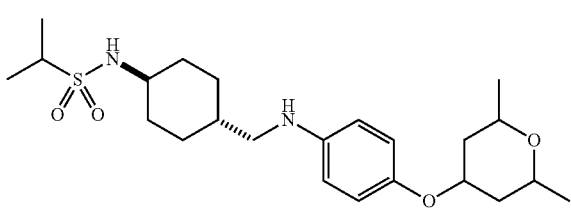
Ic-10
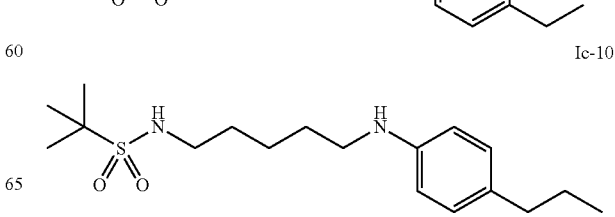

229
-continued
Ic-11
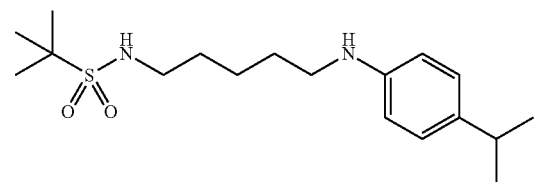
Ic-12
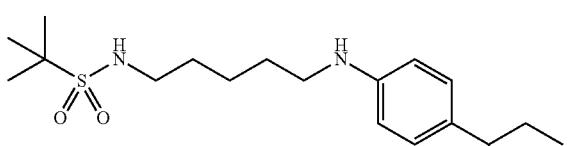
Ic-13
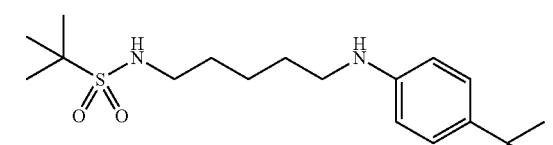
Ic-14
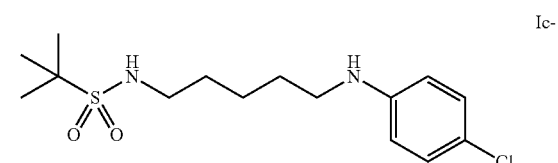
Ic-16
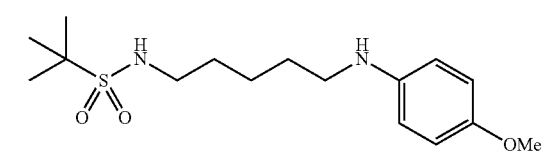
Ic-17
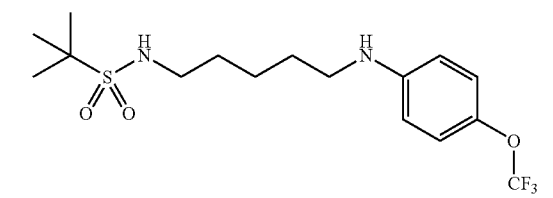
Ic-18
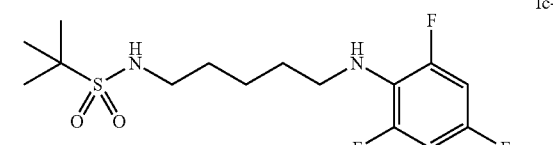
Ic-19
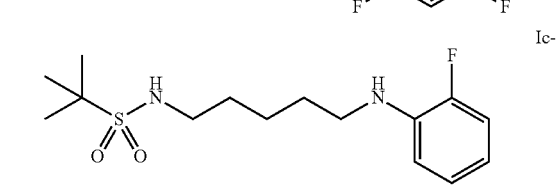
230
-continued
Ic-20
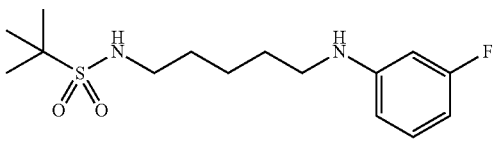
Ic-21
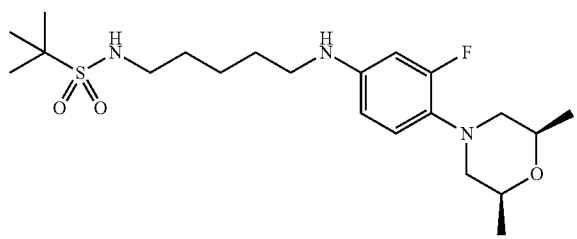
Ic-22
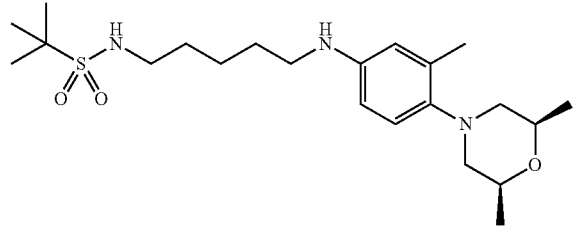
[Formula 126]
Ic-23
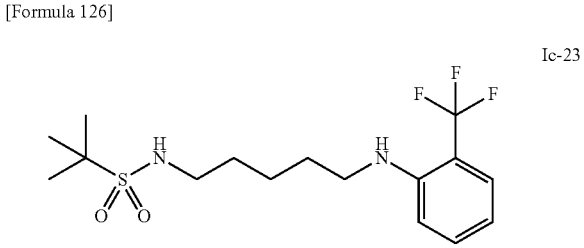
Ic-24
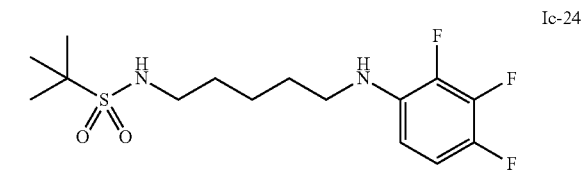
Ic-25
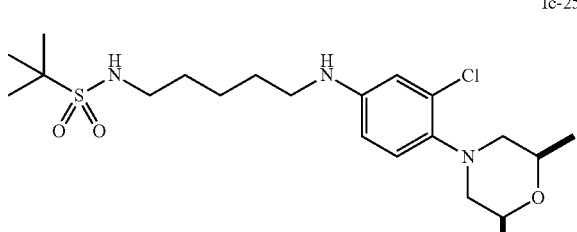
Ic-26
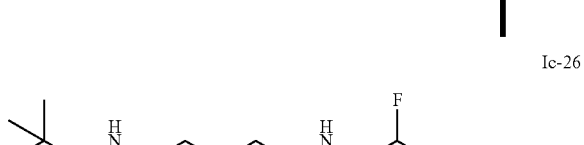

Ic-27
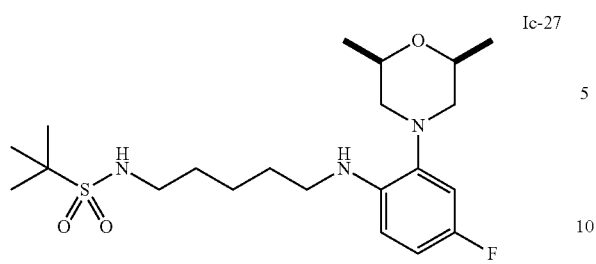
Ic-28
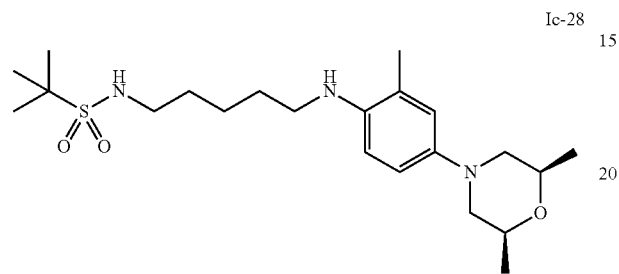
Ic-29
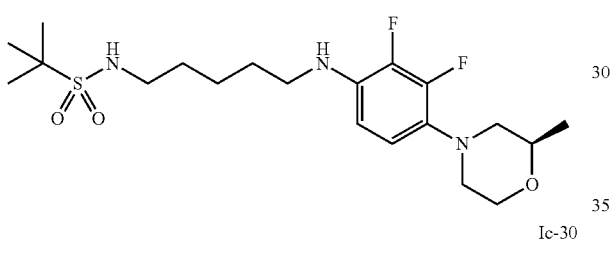
Ic-30
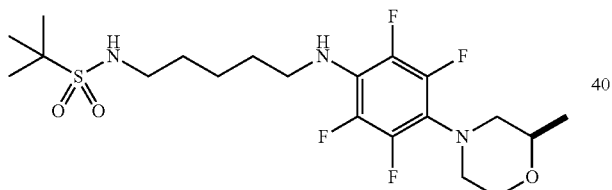
Ic-31
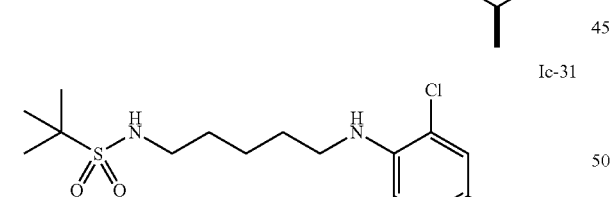
Ic-32
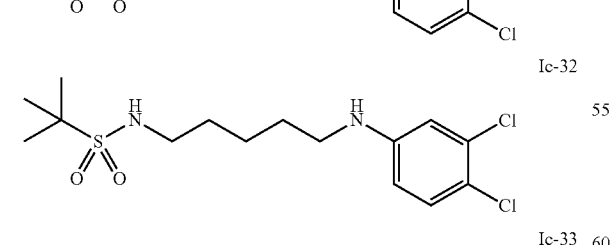
Ic-33
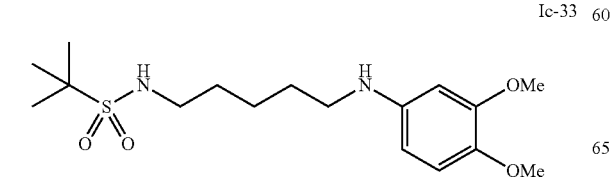
Ic-35
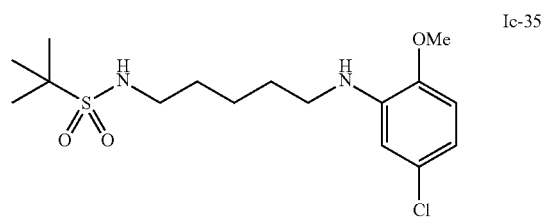
Ic-36
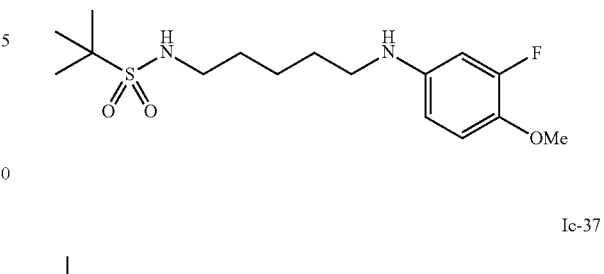
Ic-37
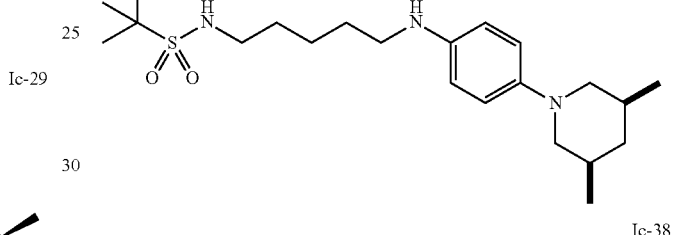
Ic-38
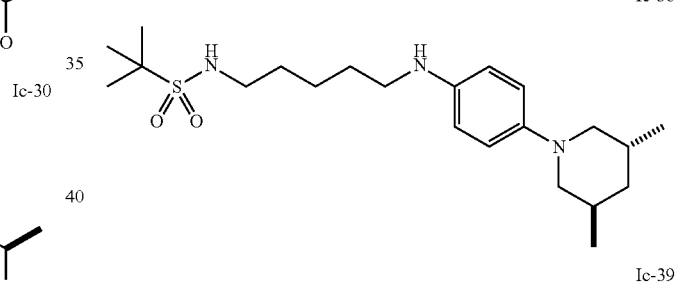
Ic-39
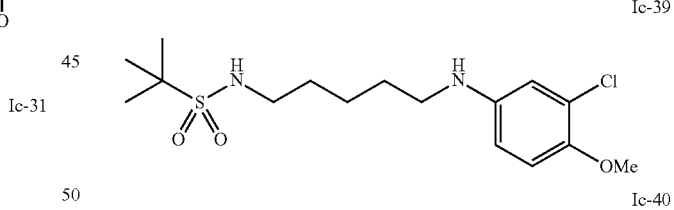
Ic-40
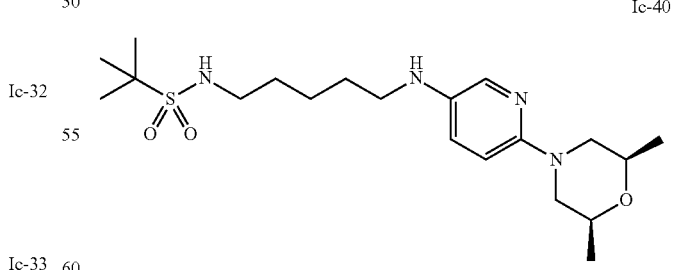
Ic-41
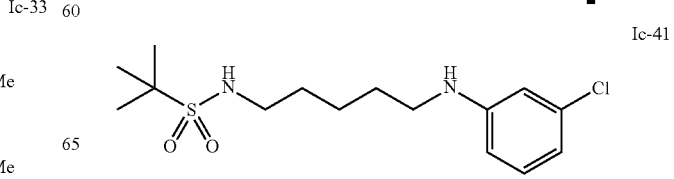

Ic-42
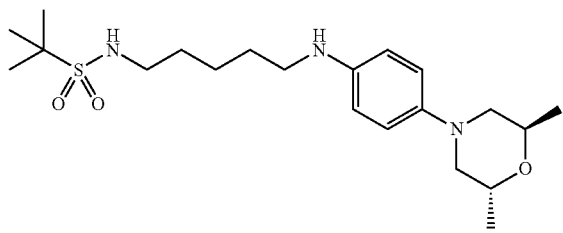
Ic-43
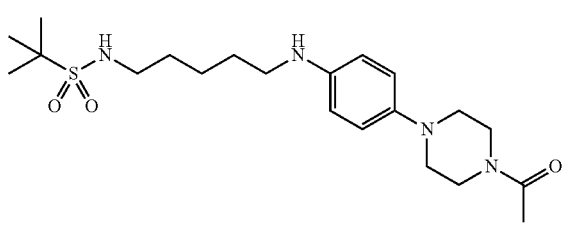
Ic-44
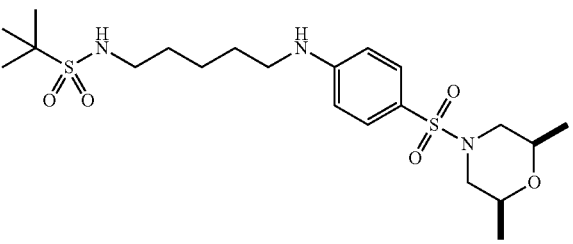
[Formula 127]
Ic-45
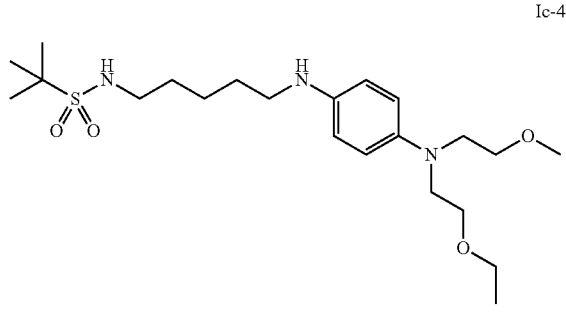
Ic-46
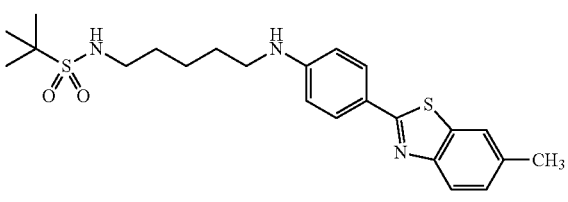
Ic-47
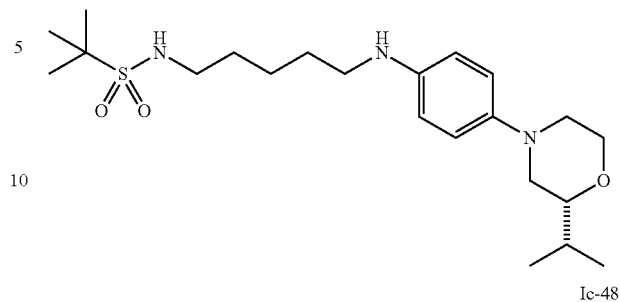
Ic-48
Ic-49
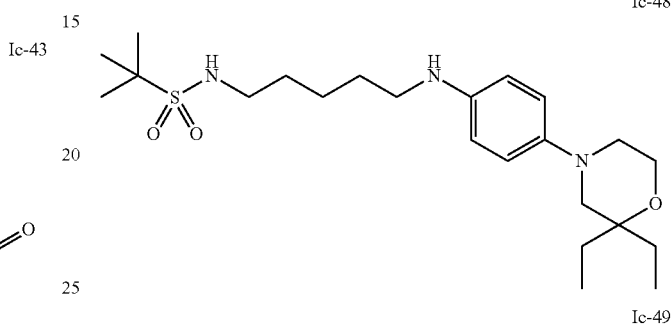
Ic-50
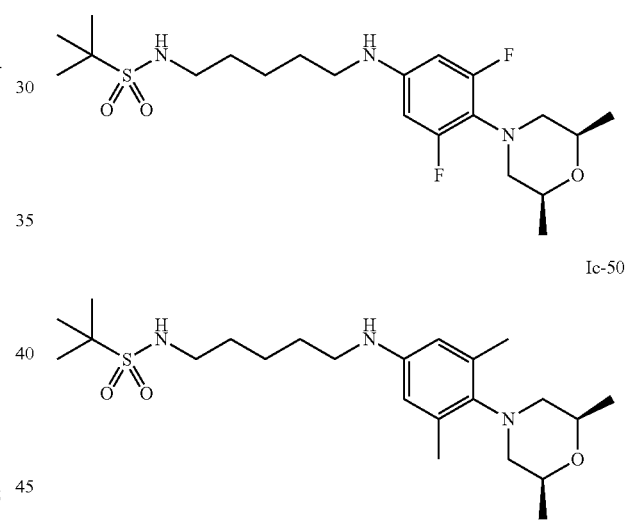
Ic-51
Ic-52
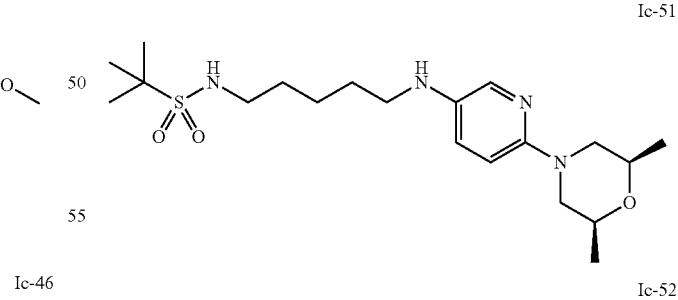
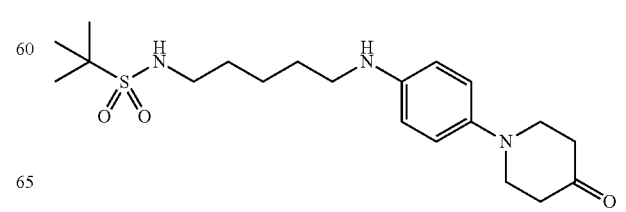

Ic-53
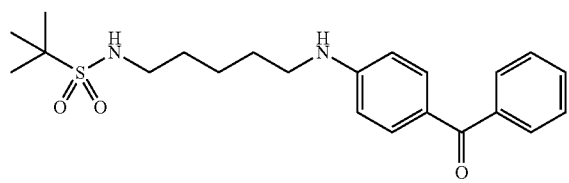
Ic-54
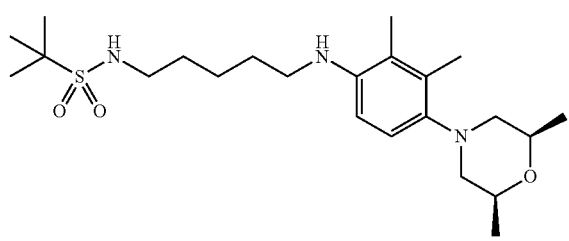
Ic-55
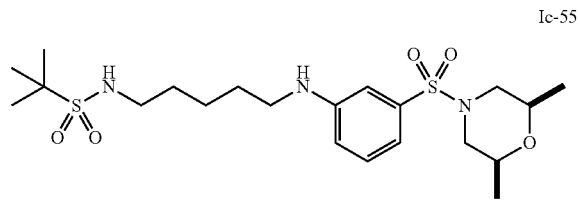
Ic-56
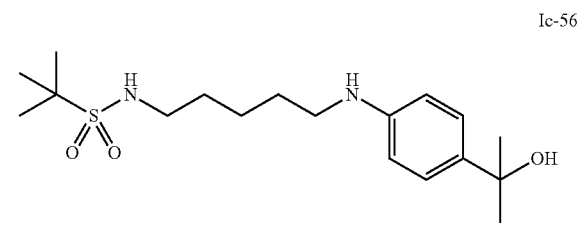
Ic-57
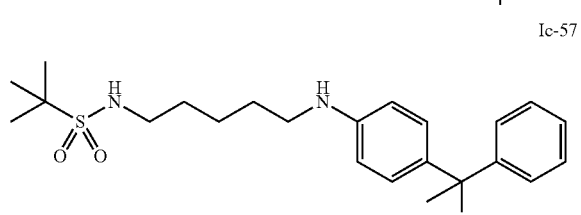
Ic-58
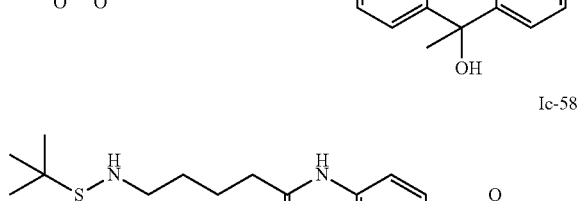
Ic-59
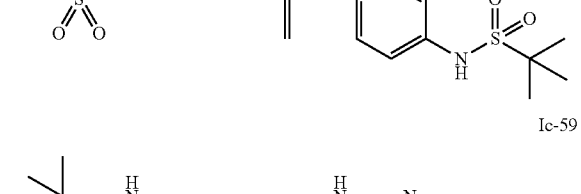
Ic-60
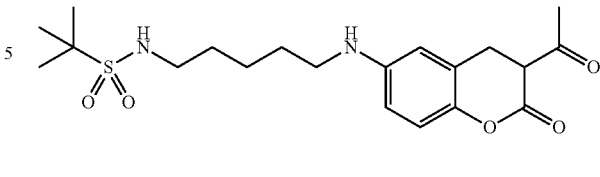
Ic-61
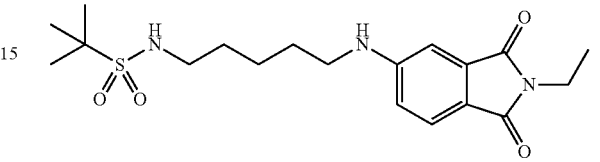
Ic-62
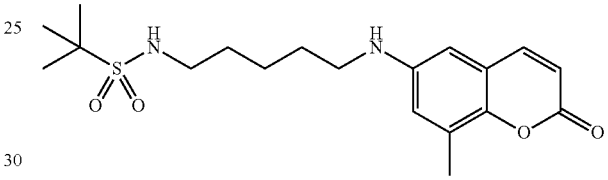
Ic-63
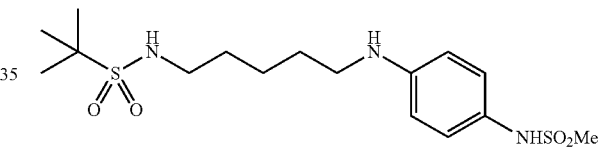
Ic-64
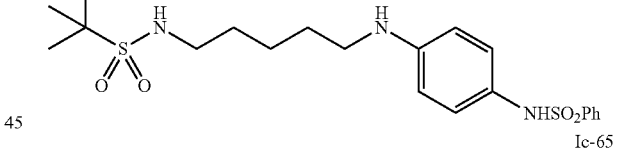
Ic-65
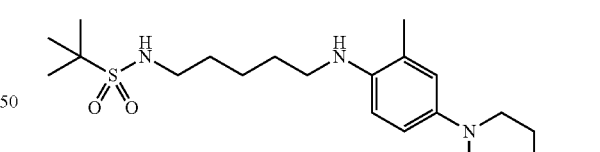
Ic-66

[Formula 128]
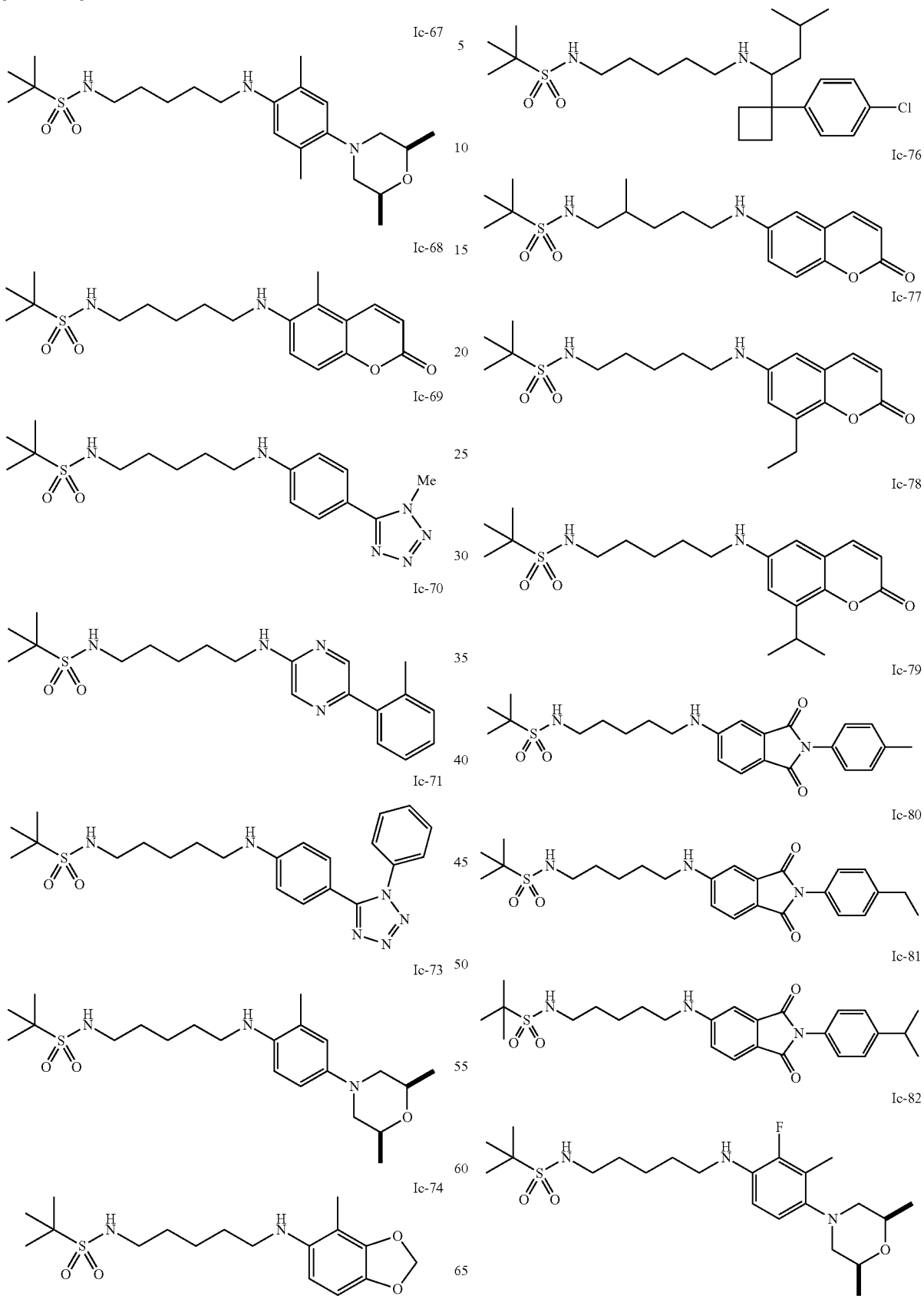

-continued

Ic-83

Ic-84

Ic-85

IC-86

Ic-87

[Formula 129]

Ic-89

Ic-90

Ic-91

Ic-92

Ic-93

Ic-94

Ic-95

Ic-96

Ic-97

Ic-98
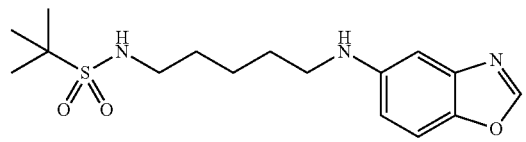
Ic-99
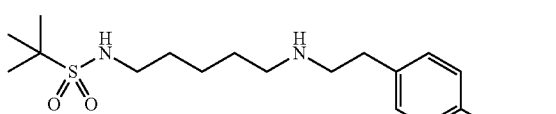
Ic-100
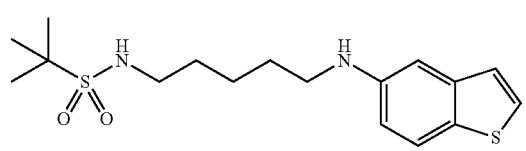
Ic-101
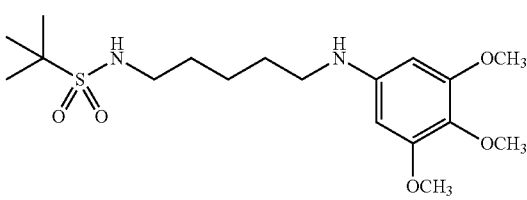
Ic-102
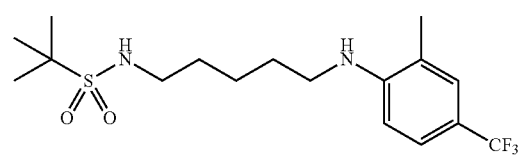
Ic-103
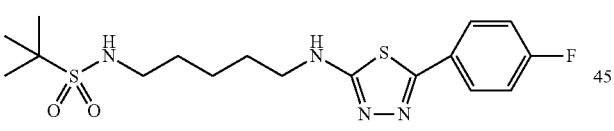
Ic-104
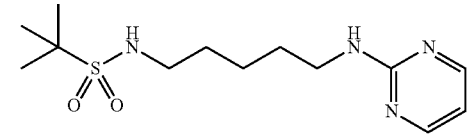
Ic-105
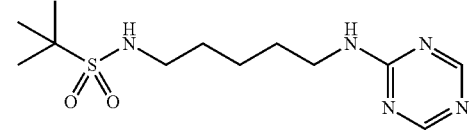
Ic-106
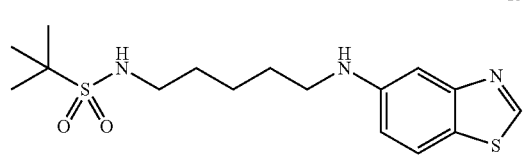
Ic-107
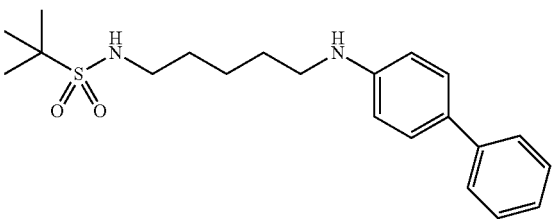
Ic-108
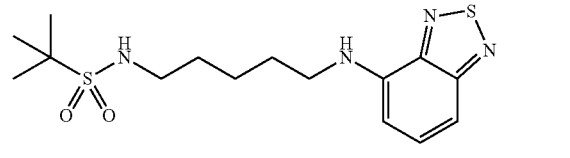
Ic-109
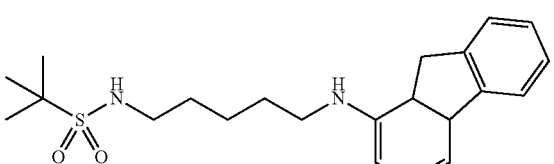
Ic-110
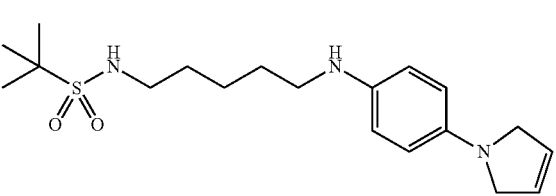
[Formula 130]
Ic-111
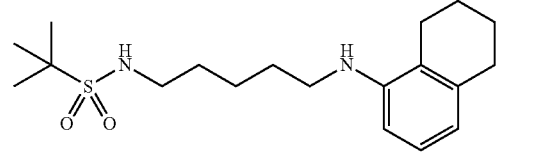
Ic-112
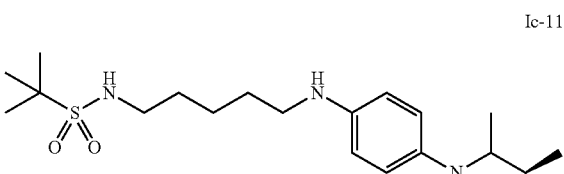
Ic-113
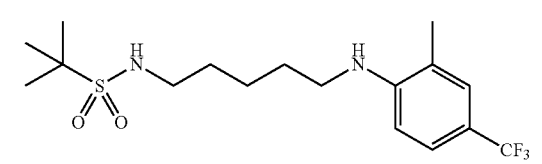

Ic-114
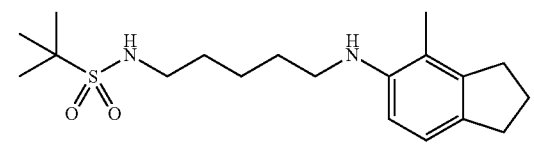
Ic-115
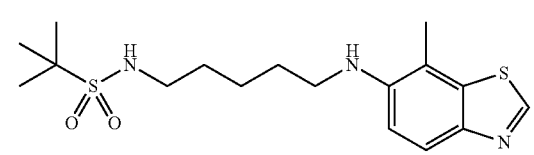
Ic-116

Ic-117
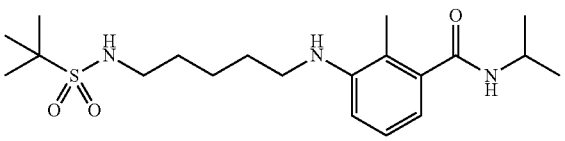
Ic-118
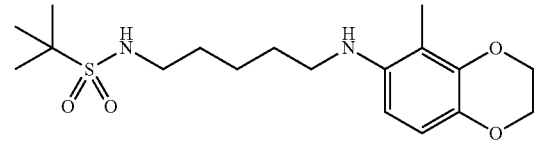
Ic-119
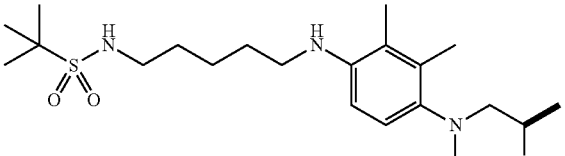
Ic-120
Ic-121
Ic-122
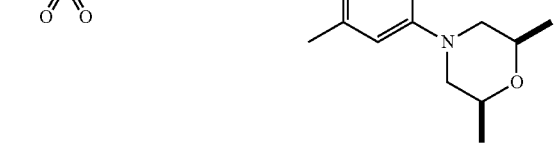
Ic-123
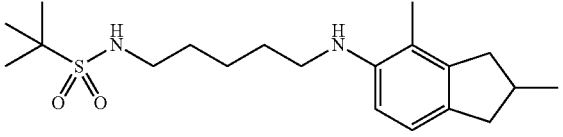
Ic-124
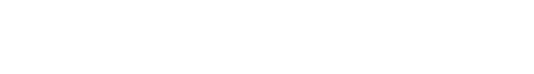
Ic-125
Ic-126
Ic-127
Ic-128
Ic-129

Ic-130
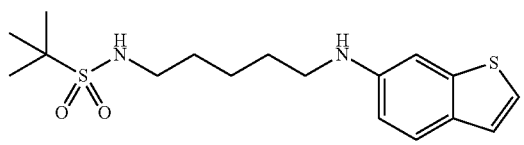
Ic-131
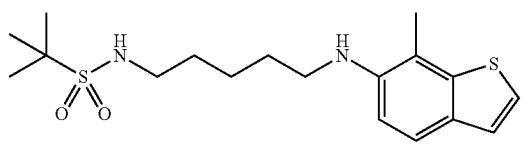
Ic-132
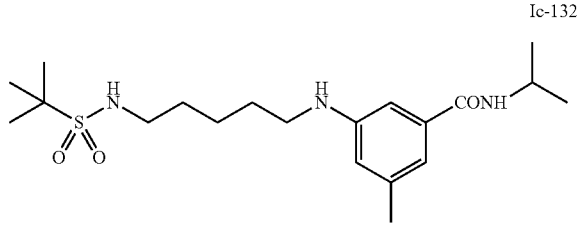
[Formula 131]
Ic-133
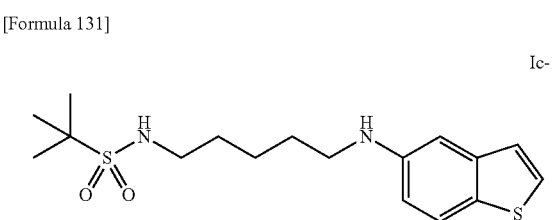
Ic-134
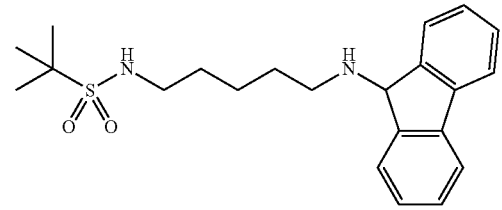
Ic-135
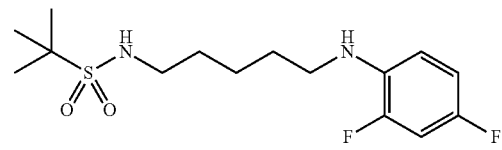
Ic-136
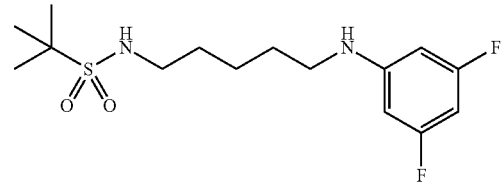
Ic-137
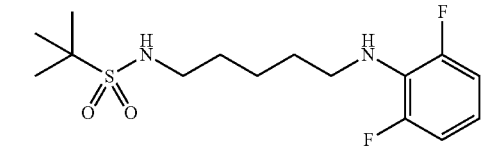
Ic-138
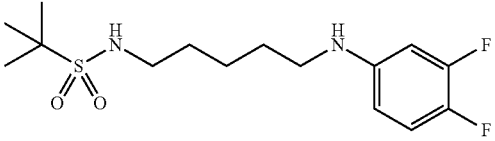
Ic-139
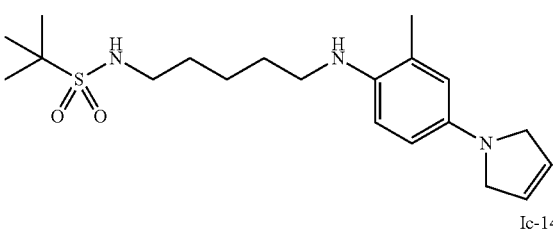
Ic-140
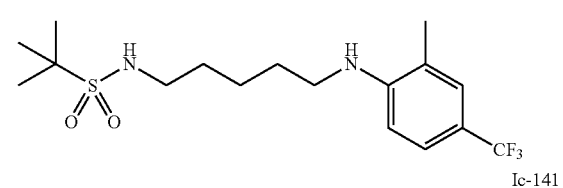
Ic-141
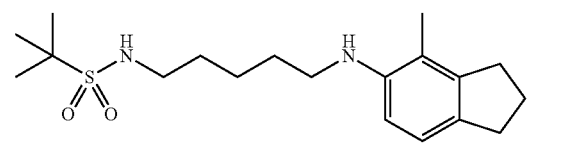
Ic-142
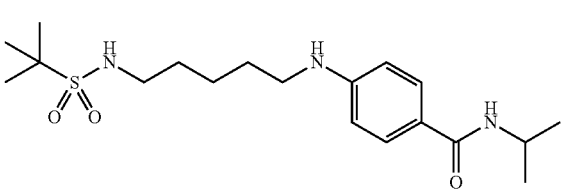
Ic-143
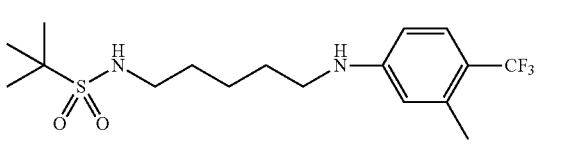
Ic-144
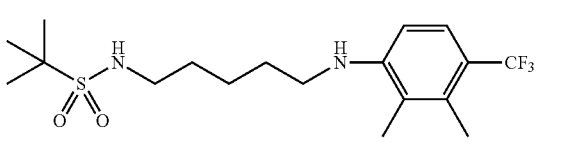
Ic-145
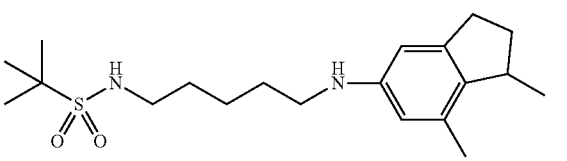
Ic-146
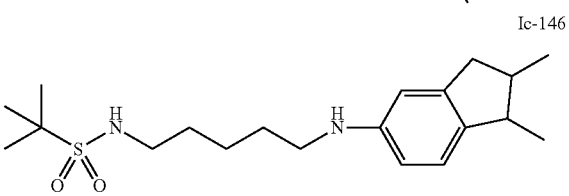

Ic-147
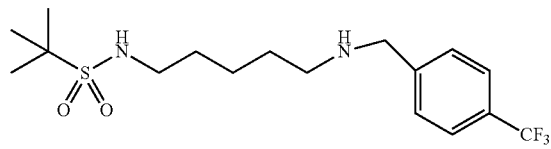
Ic-148
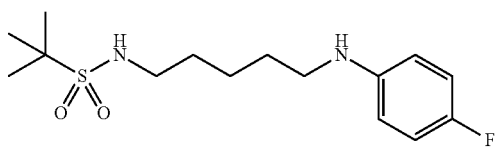
Ic-149
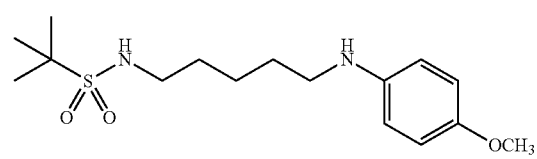
Ic-150
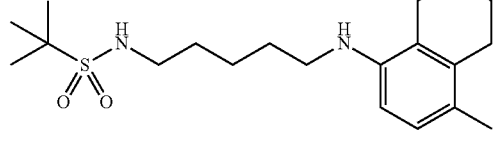
Ic-151
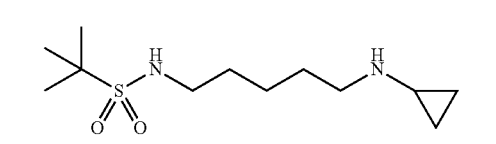
Ic-152
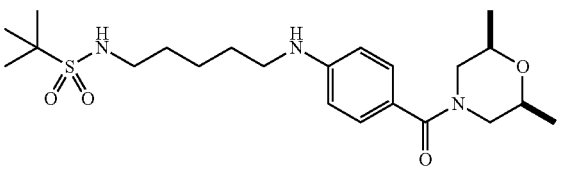
Ic-153
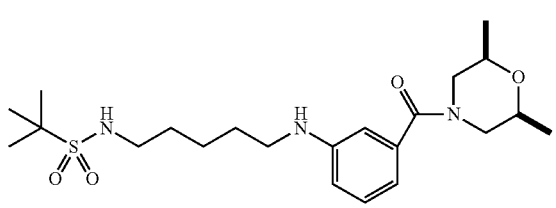
[Formula 132]
Ic-155
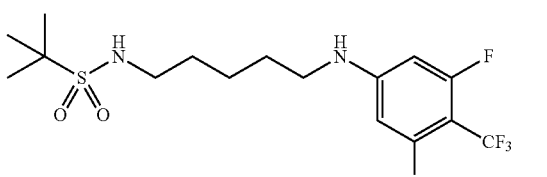
Ic-156
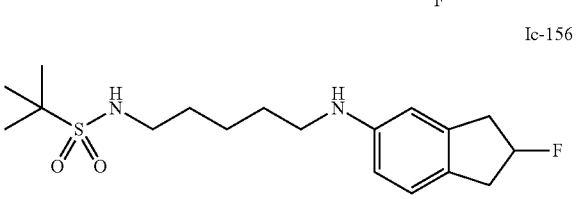
Ic-157
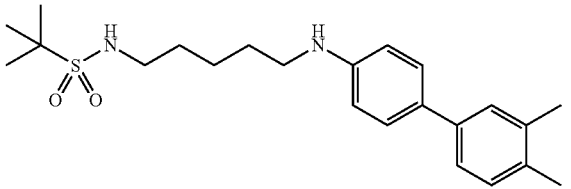
Ic-158
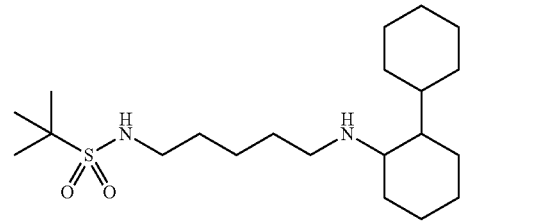
Ic-159
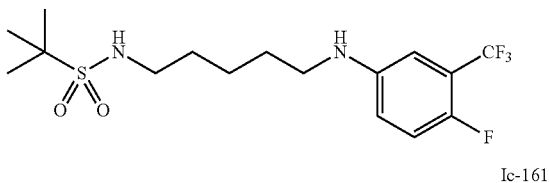
Ic-160
Ic-161

Ic-162
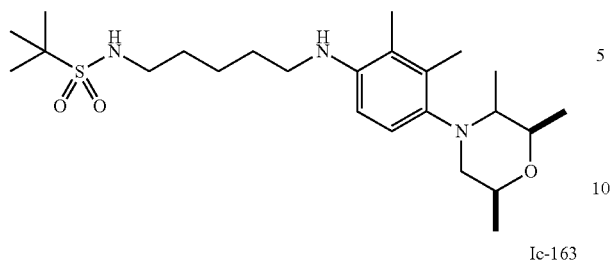
Ic-163
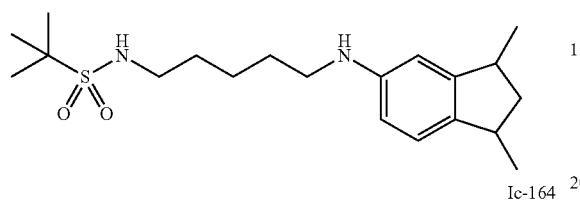
Ic-164
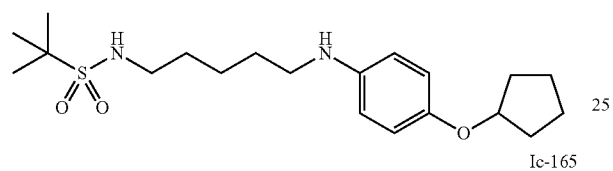
Ic-165
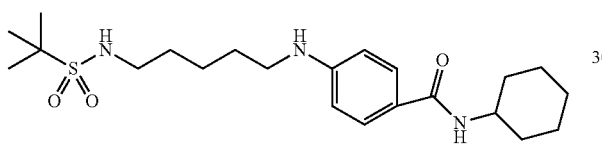
Ic-166
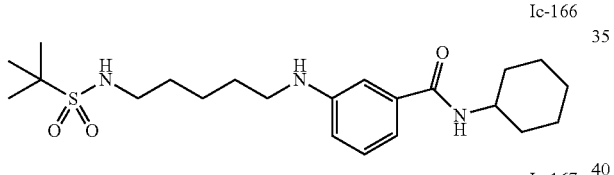
Ic-167
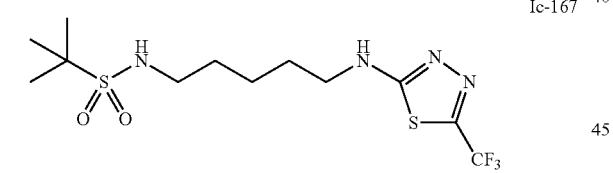
Ic-168
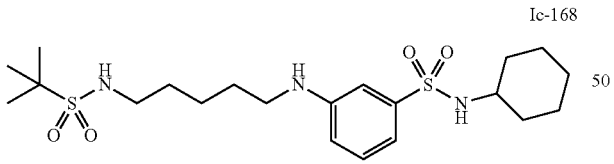
Ic-169
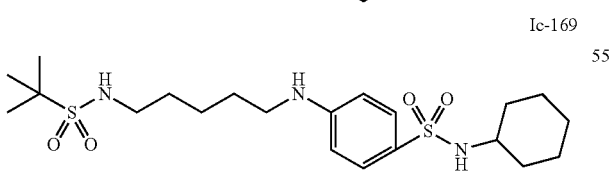
Ic-171
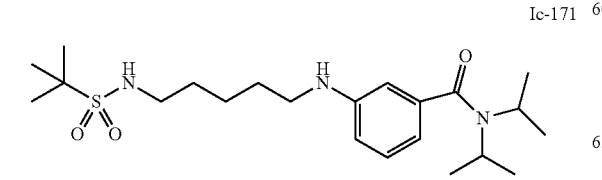
Ic-172
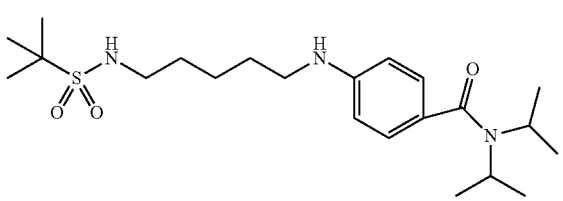
Ic-173
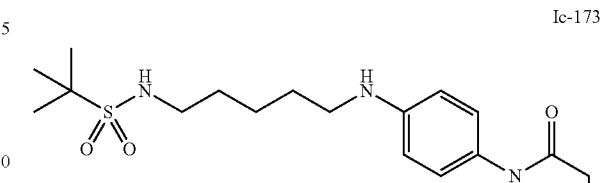
Ic-174

Ic-175
Ic-176

[Formula 133]
Ic-177
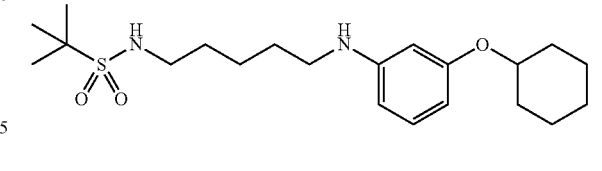
Ic-178

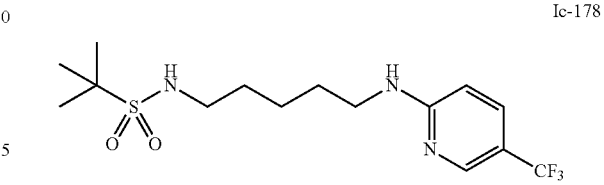

Ic-179
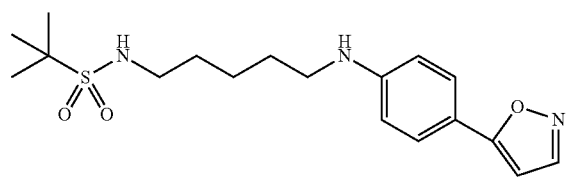
Ic-180
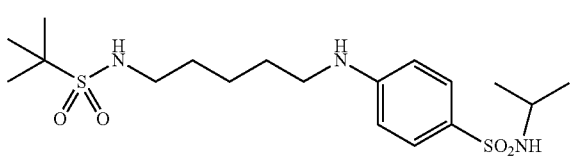
Ic-181
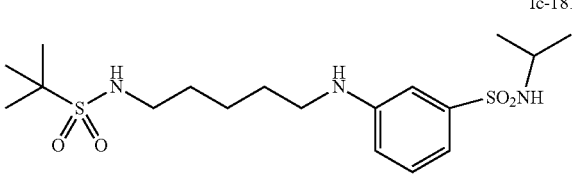
Ic-182
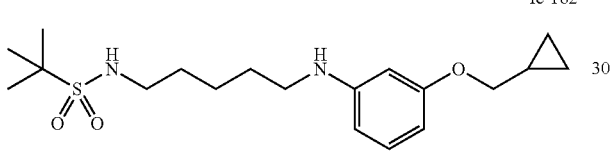
Ic-183
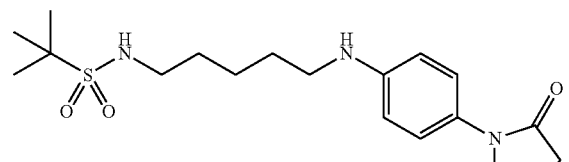
Ic-184
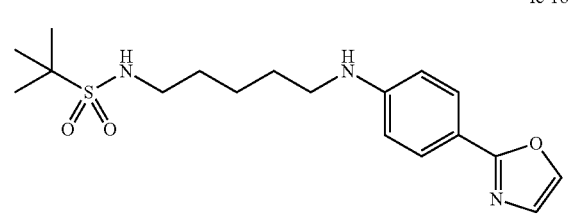
Ic-185
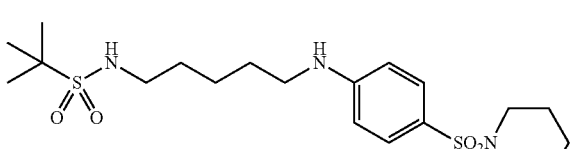
Ic-186
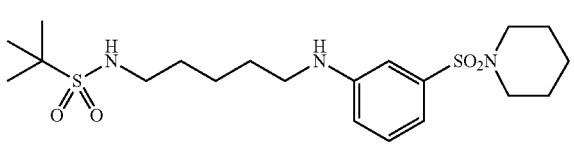
Ic-187
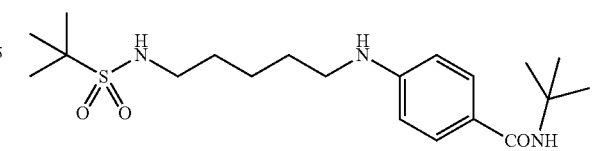
Ic-188
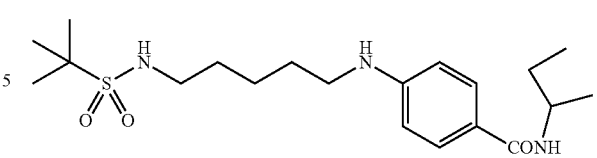
Ic-189
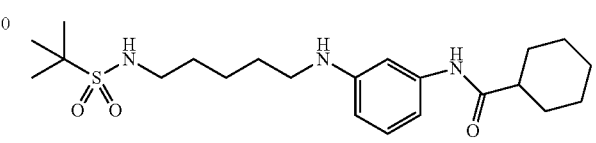
Ic-190
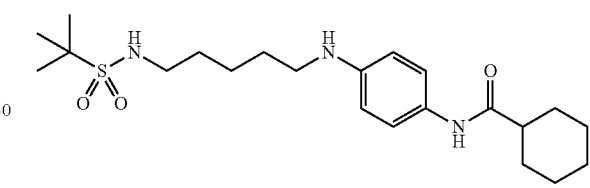
Ic-191
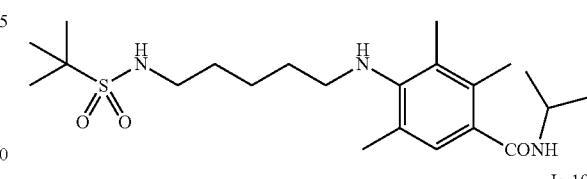
Ic-192
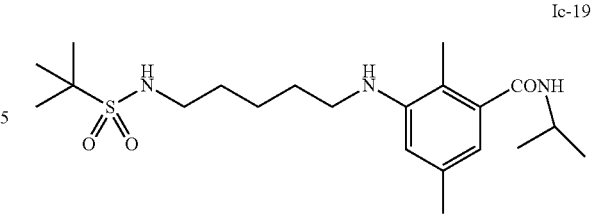
Ic-193
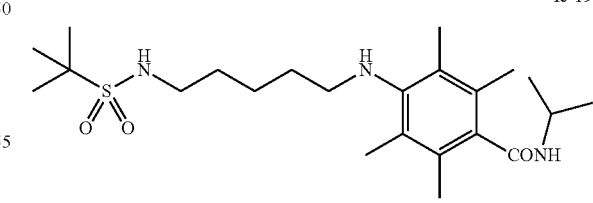
Ic-194
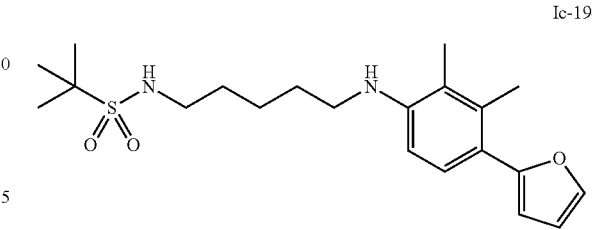

Ic-195
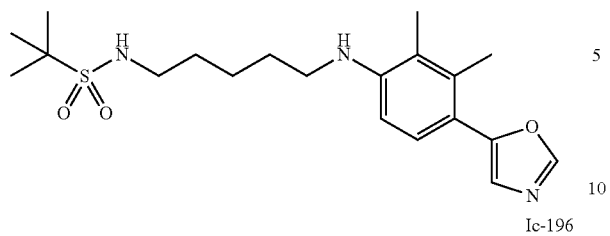
Ic-203
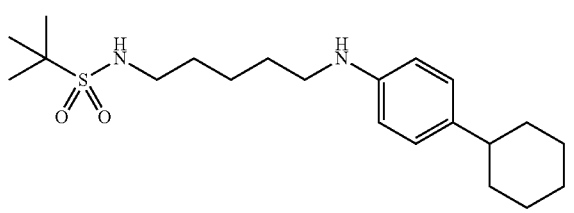
Ic-196
Ic-197
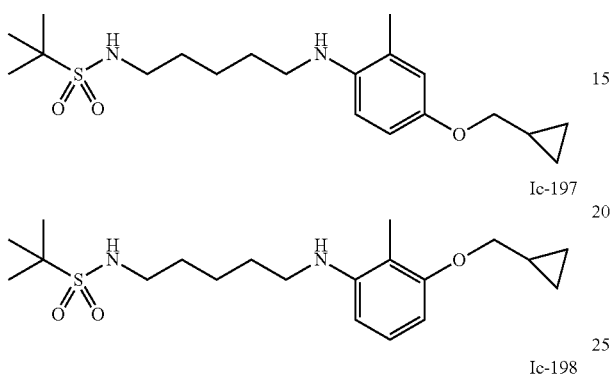
Ic-204
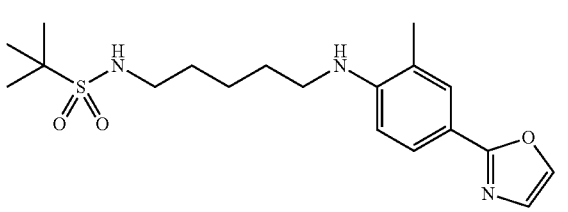
Ic-198
Ic-205
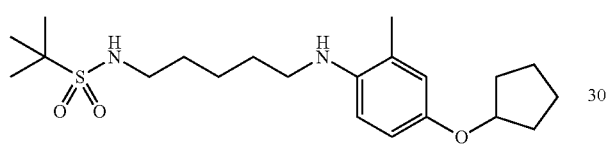
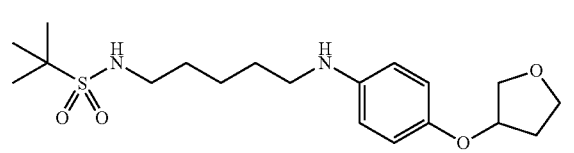
[Formula 134]
Ic-199
Ic-206
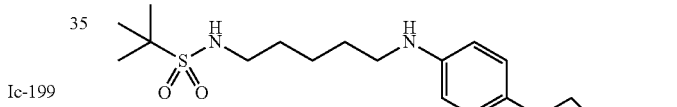
Ic-200
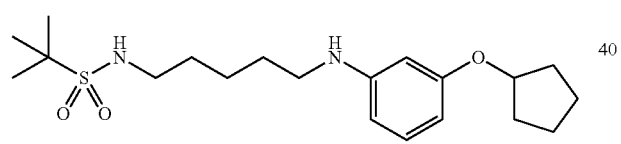
Ic-207
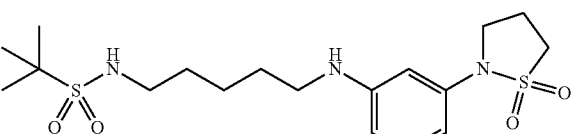
Ic-201
Ic-208
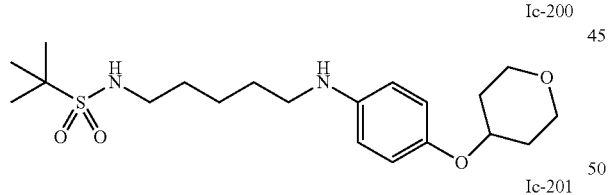
Ic-202
Ic-209
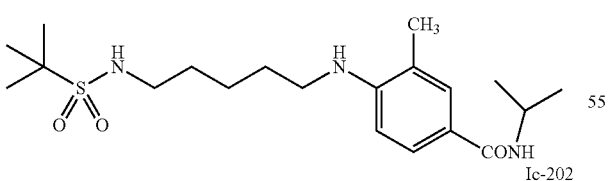
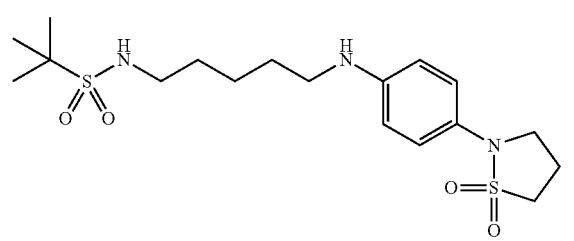
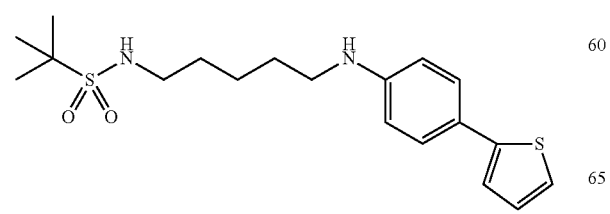
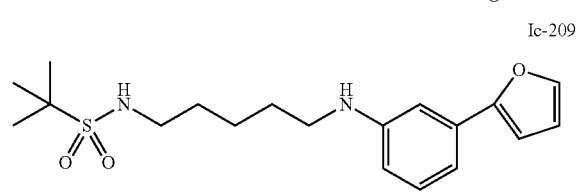

255
-continued
Ic-210
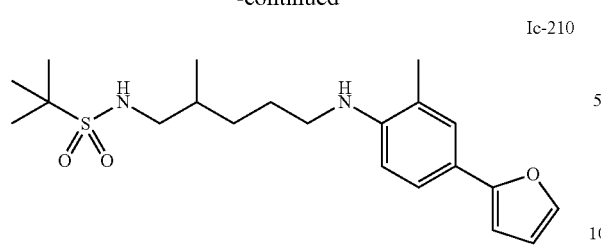
Ic-211
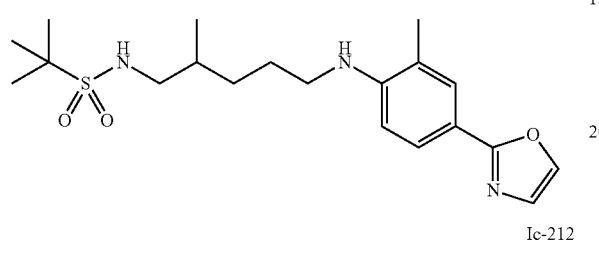
Ic-212
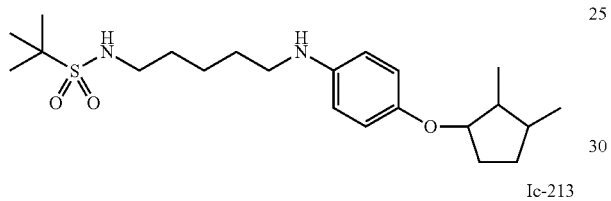
Ic-213
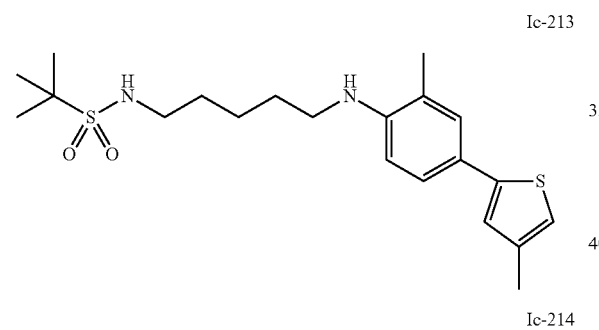
Ic-214
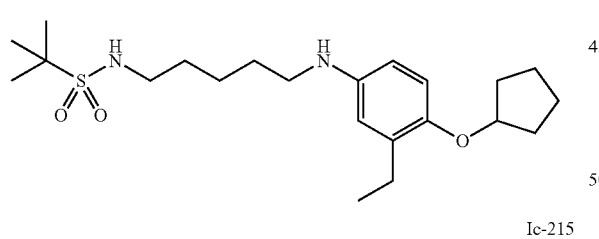
Ic-215
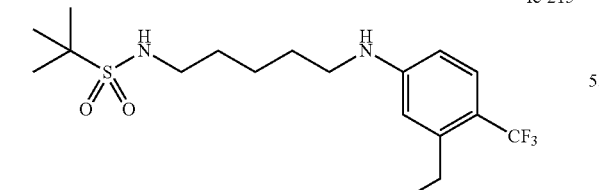
Ic-216
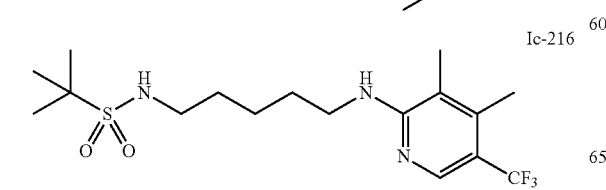
256
-continued
Ic-219
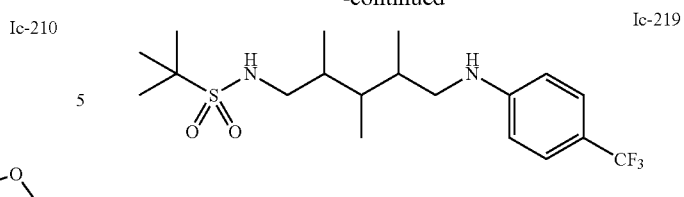
Ic-220
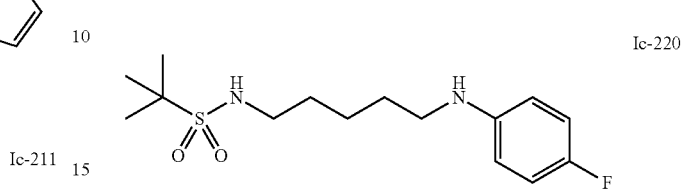
Ic-221
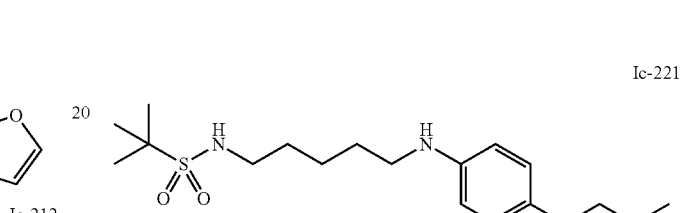
Ic-222
Ic-223
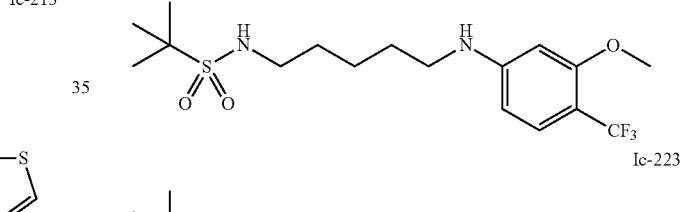
Ic-224

Ic-225
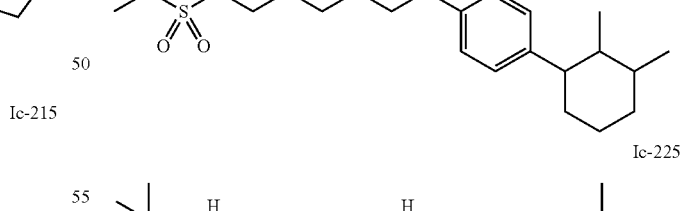
Ic-226
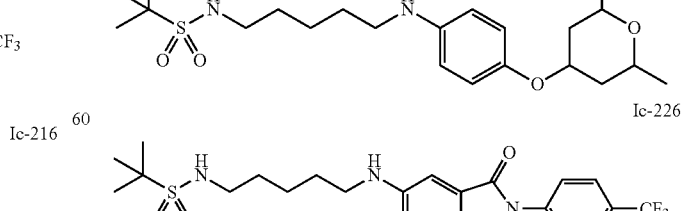

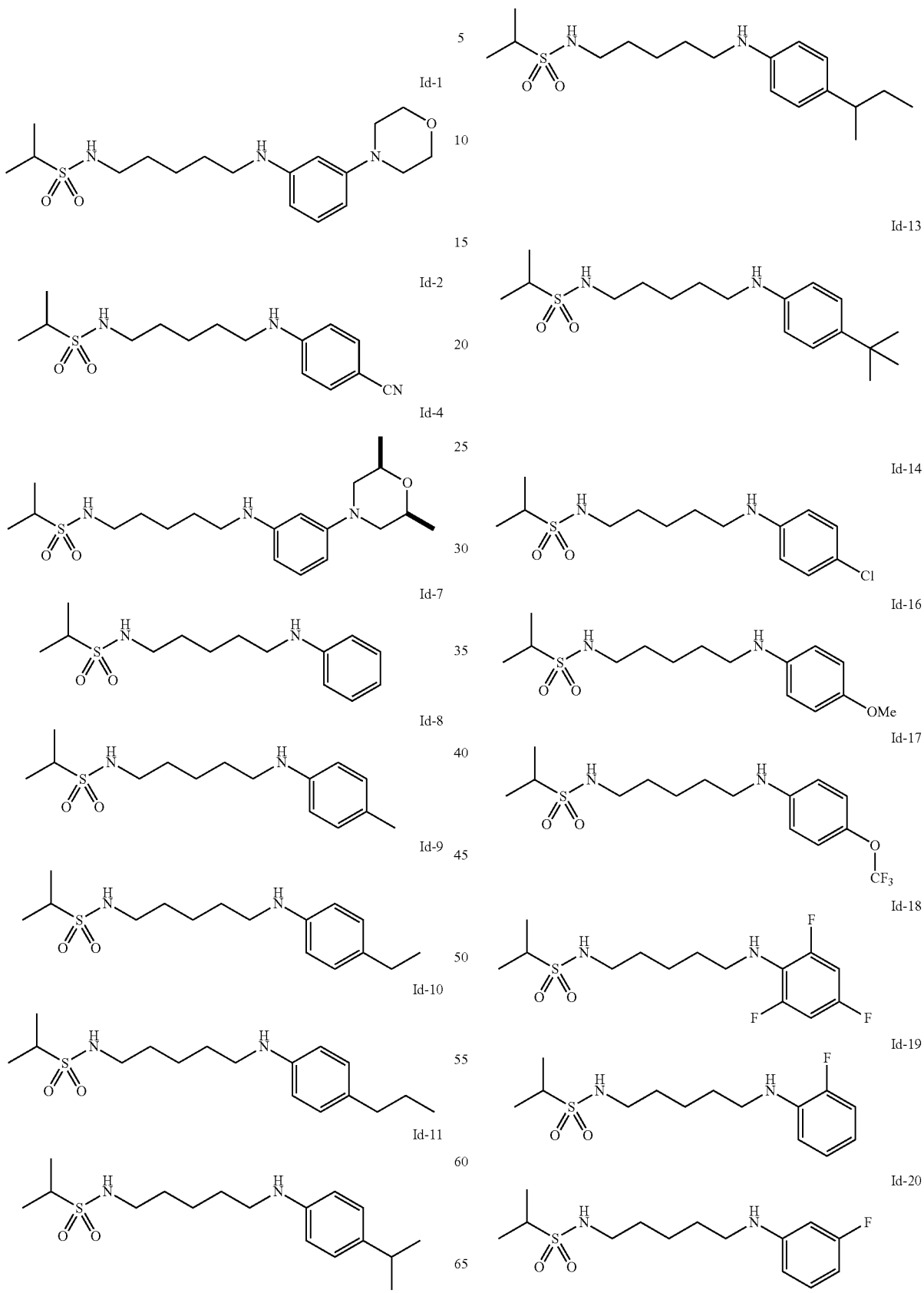

Id-21
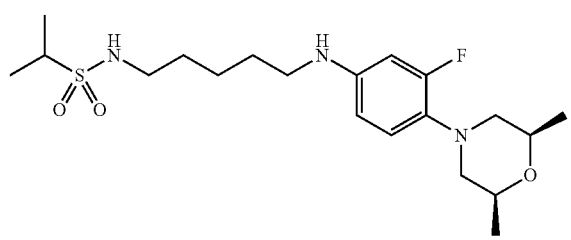
Id-27
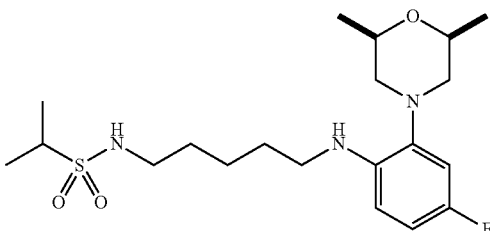
Id-22
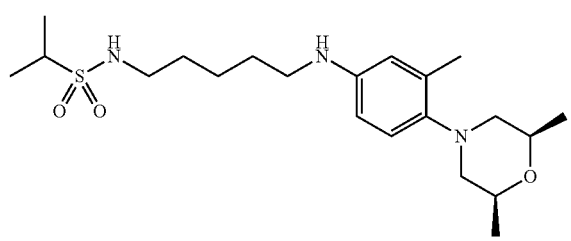
Id-28
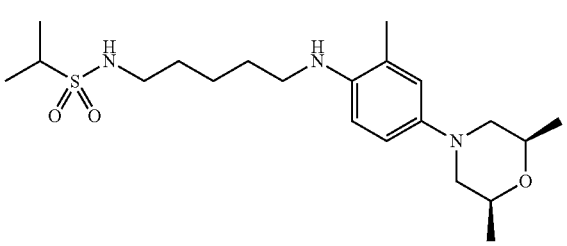
[Formula 136]
Id-23
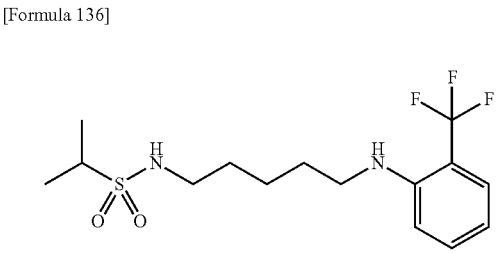
Id-29
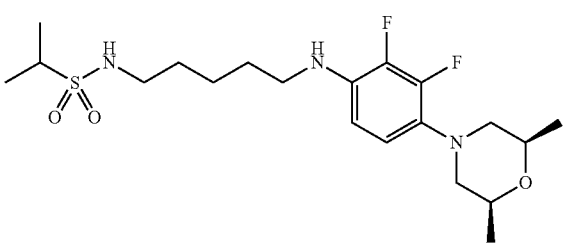
Id-24
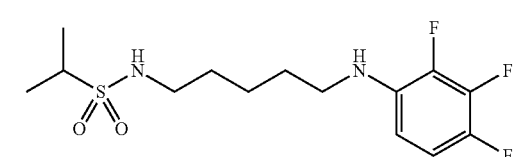
Id-30
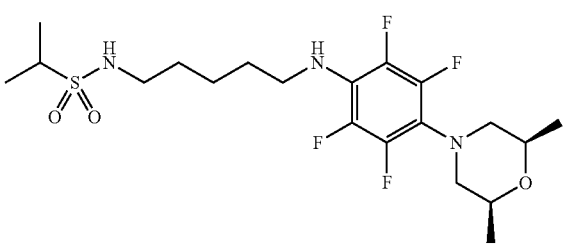
Id-25
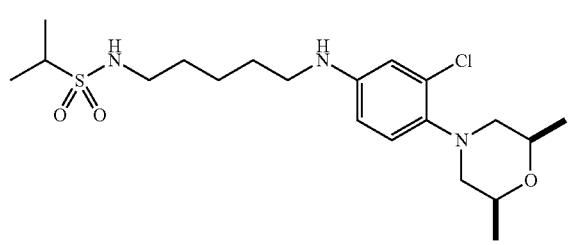
Id-31
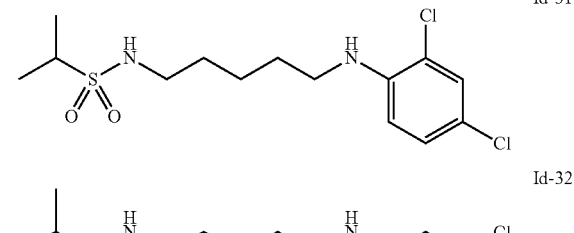
Id-32
Id-26
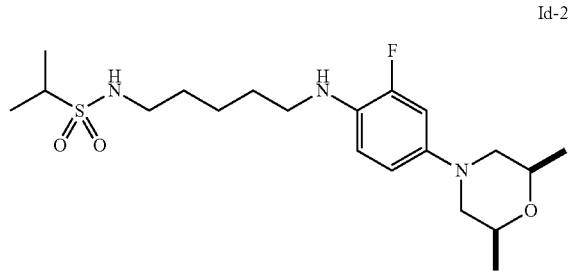
Id-33
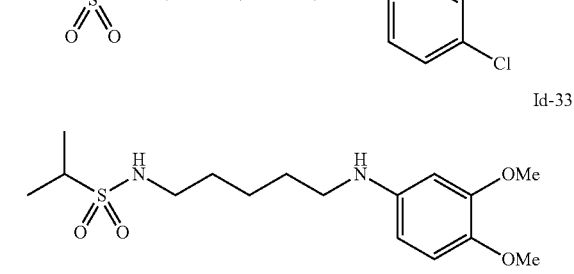

Id-35
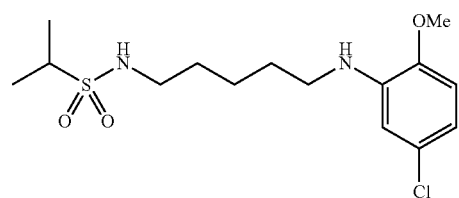
Id-36
Id-37
Id-38
Id-39
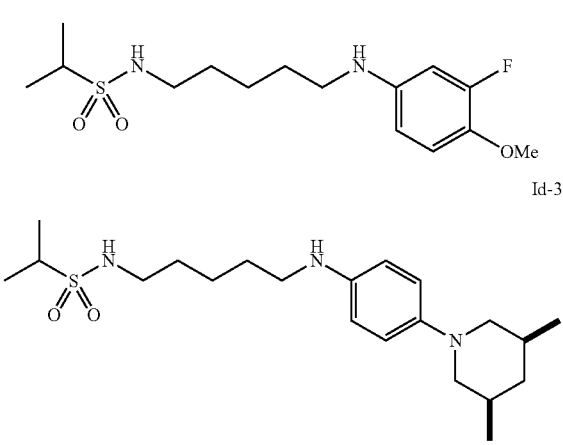
Id-40
Id-41
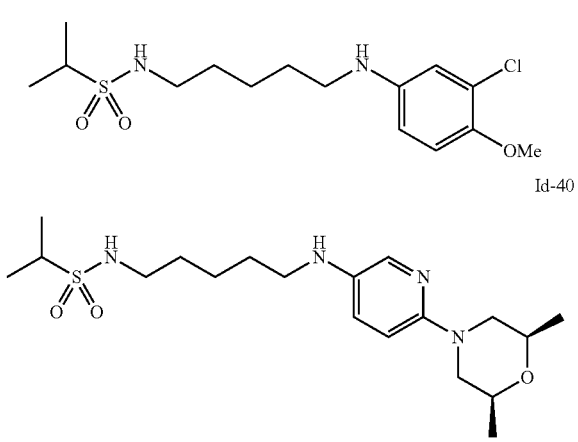
Id-42
Id-43
Id-44
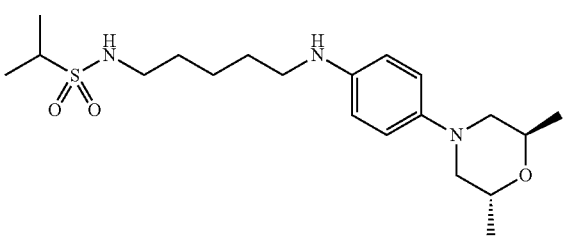
[Formula 137]
Id-45
Id-46

Id-47
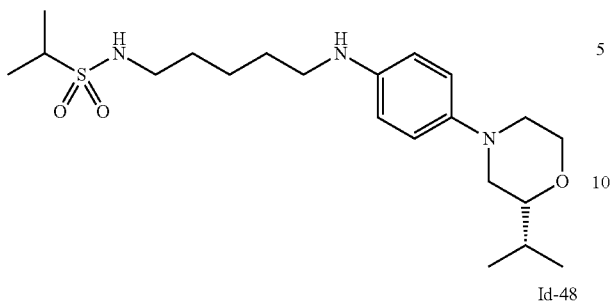
Id-48
Id-53
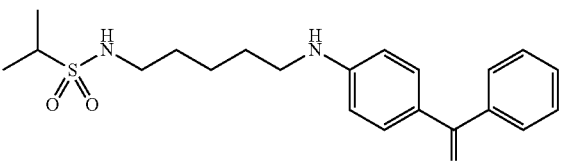
Id-54
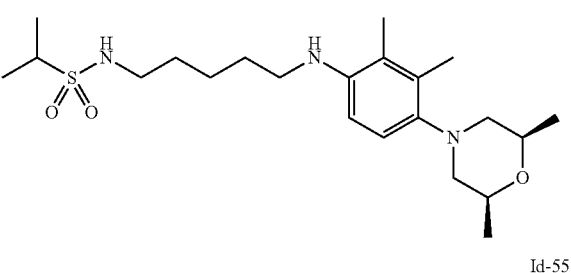
Id-49
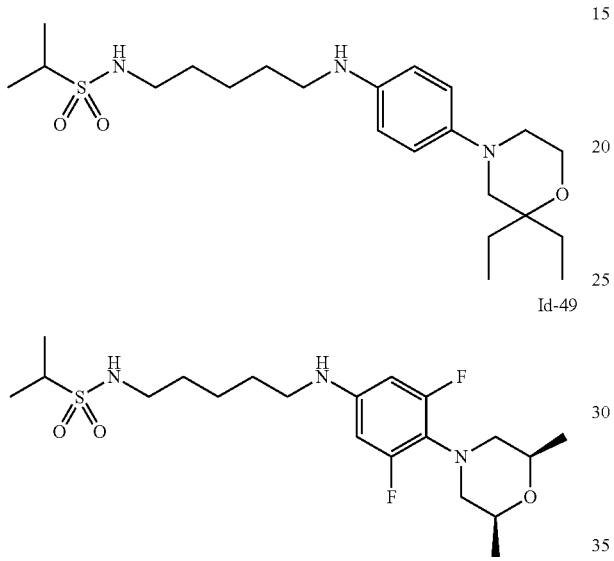
Id-50
Id-55
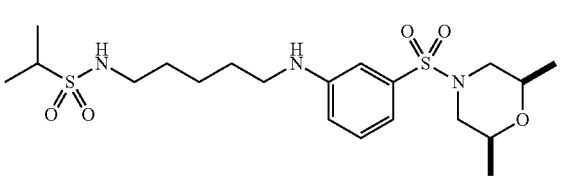
Id-56
Id-51
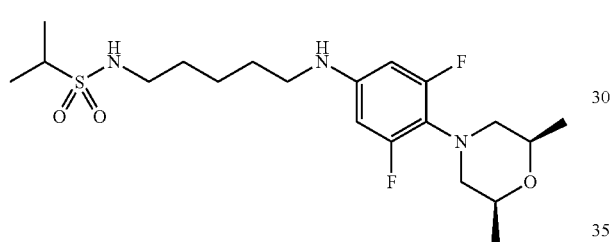
Id-57
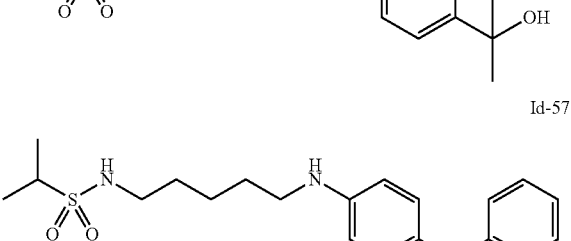
Id-52
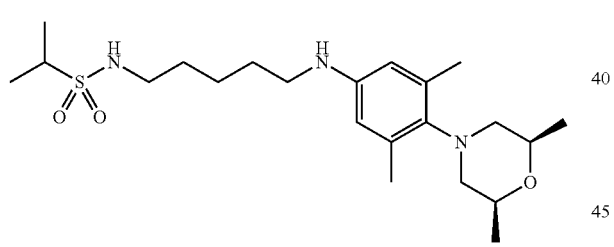
Id-58
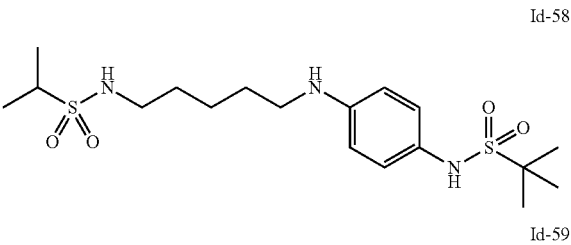
Id-59
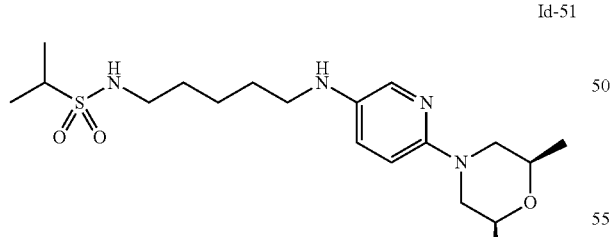
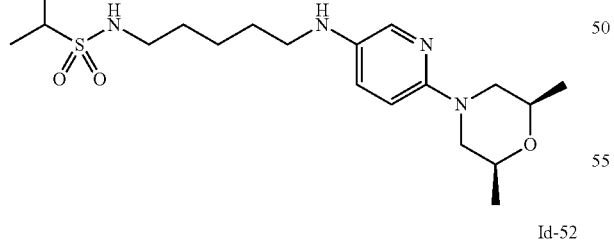
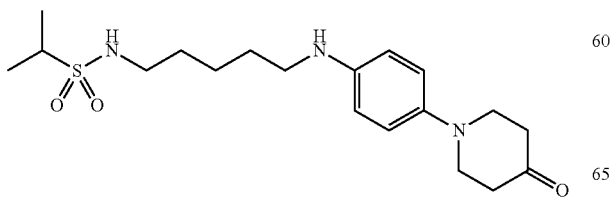
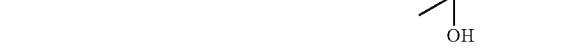
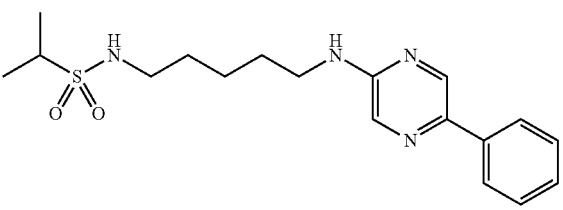

Id-60
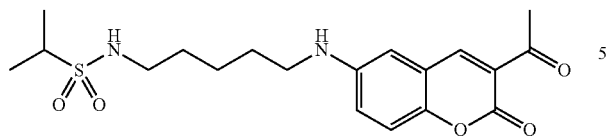
Id-61
Id-62
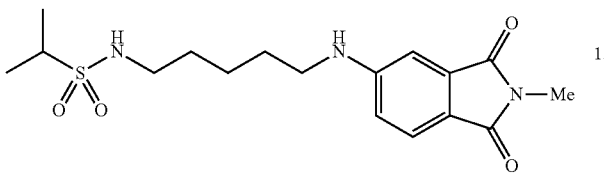
Id-63
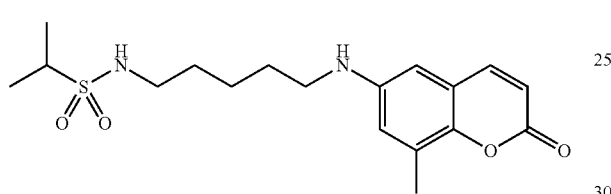
Id-64
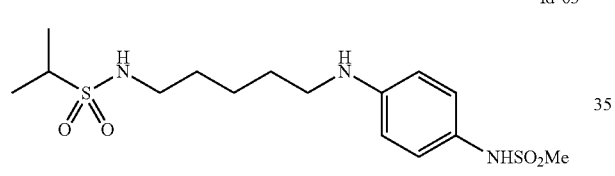
Id-65
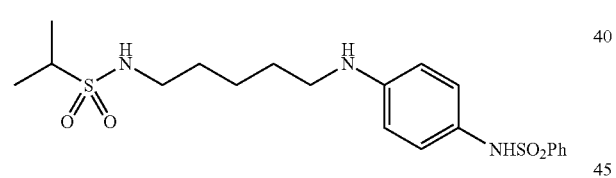
Id-66
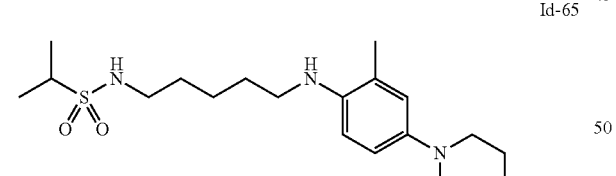
[Formula 138]
Id-67
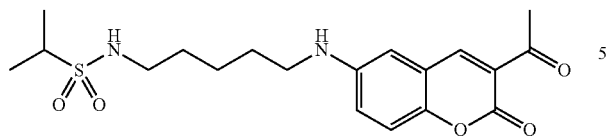
Id-68
Id-69
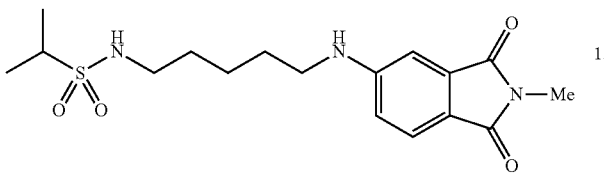
Id-70
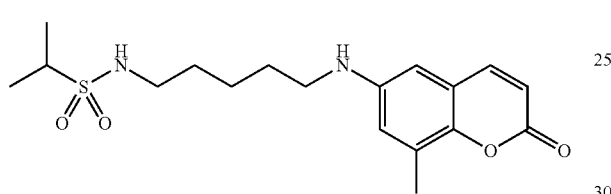
Id-71
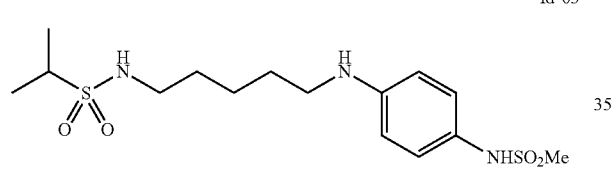
Id-73
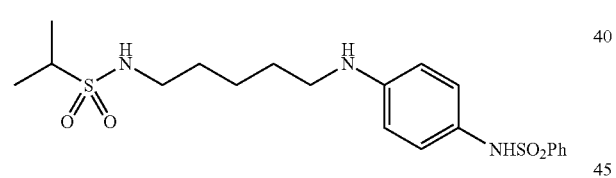
Id-74
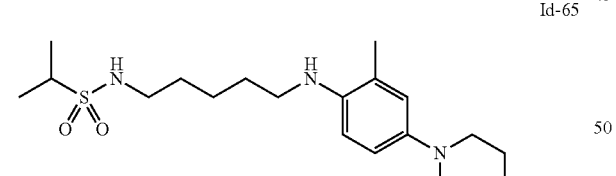

Id-75
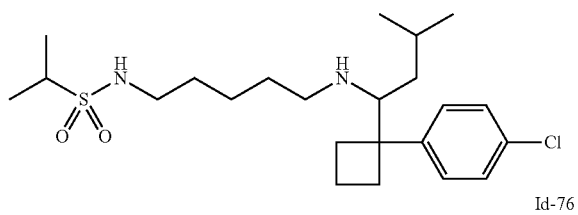
Id-76
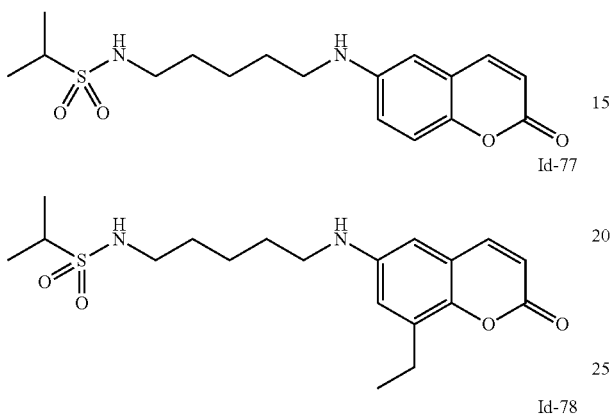
Id-77
Id-78
Id-79
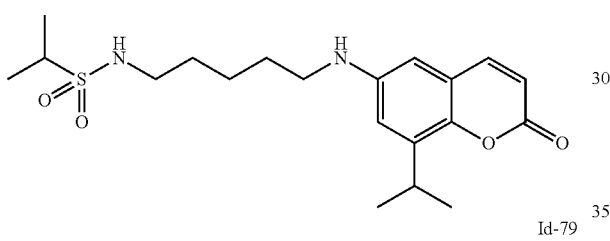
Id-80
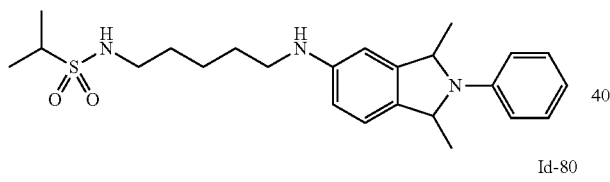
Id-81
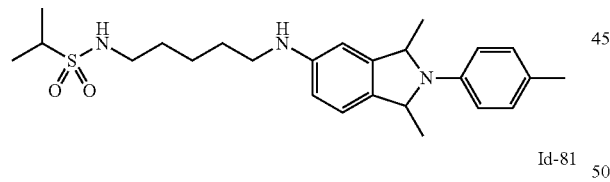
Id-82
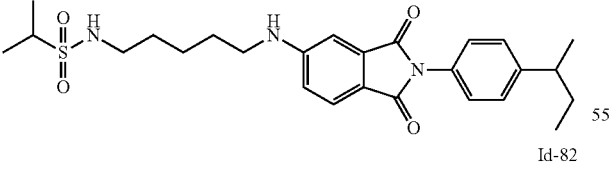
Id-83
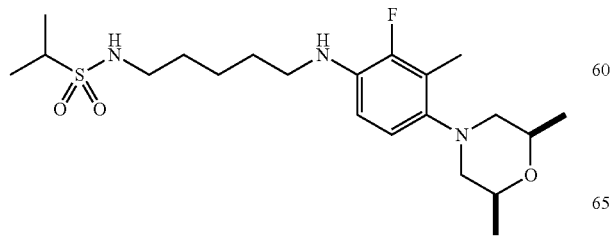
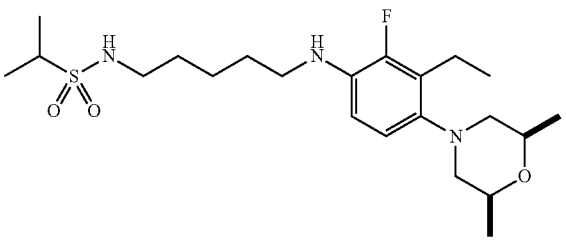
Id-84
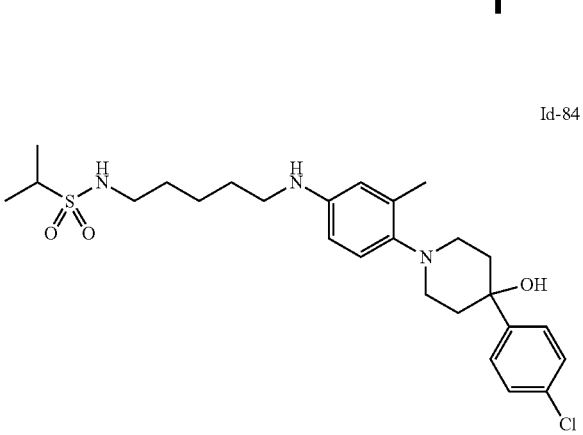
Id-85
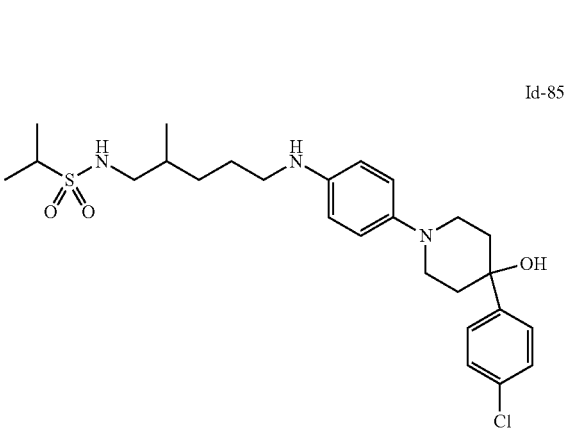
Id-86
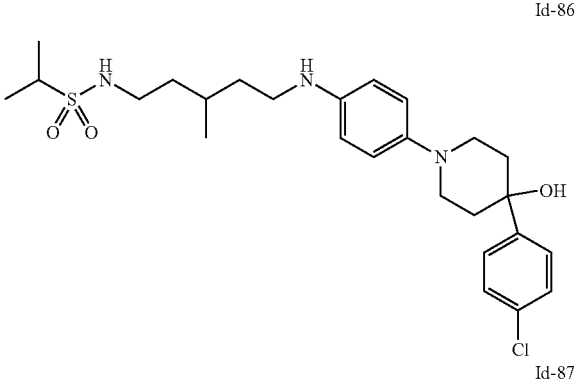
Id-87
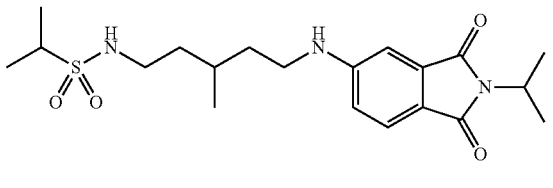

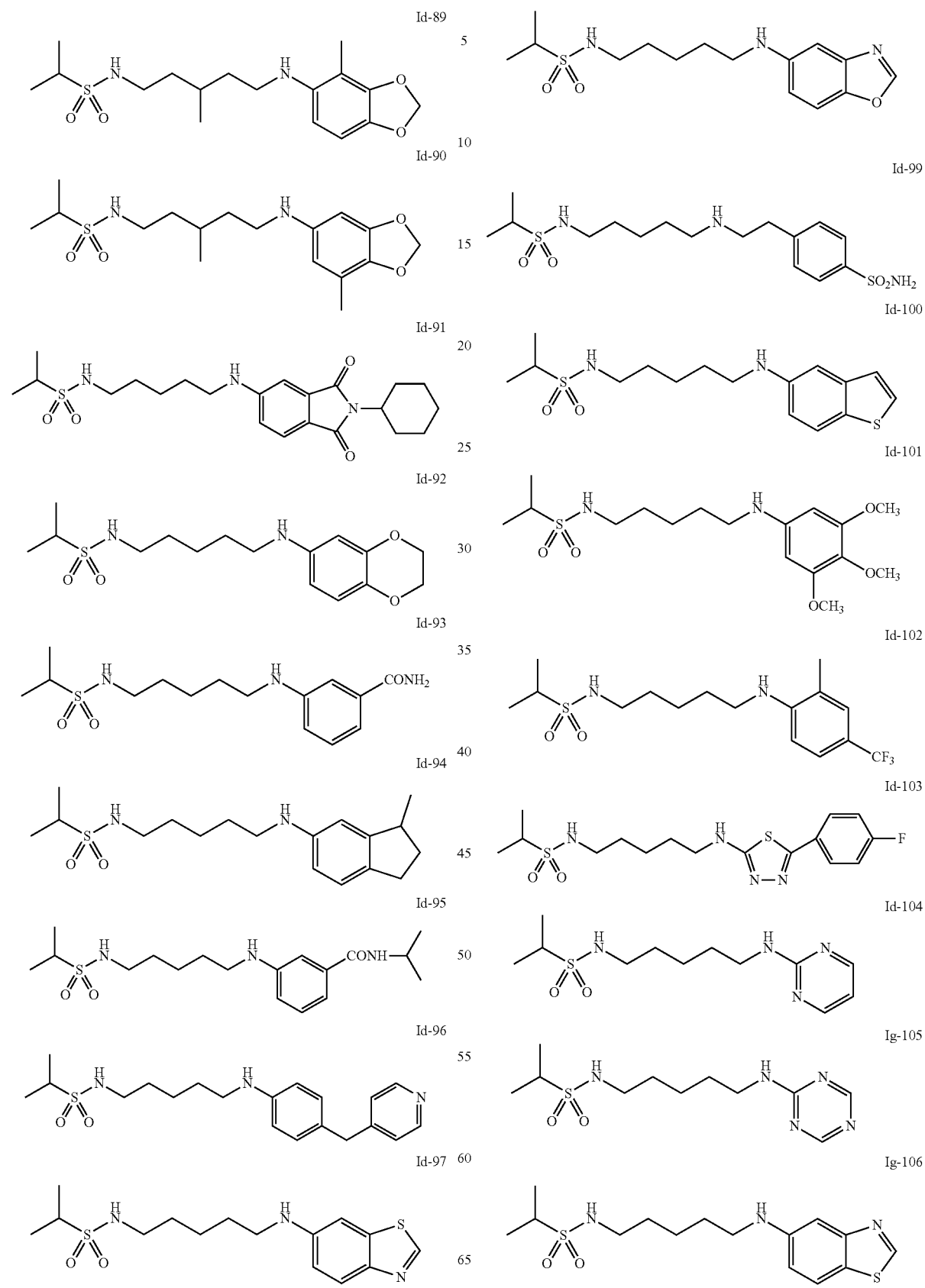

Ig-107
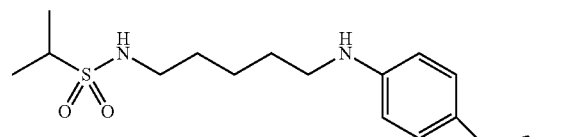
Ig-108
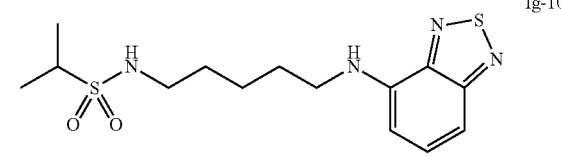
Ig-109
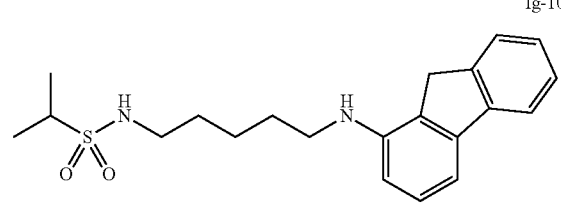
Ig-110
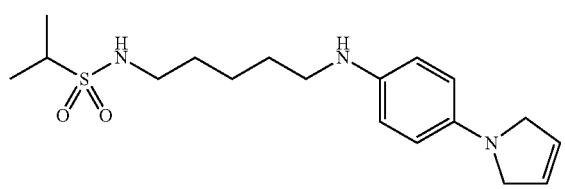
[Formula 140]
Ig-111
Ig-112
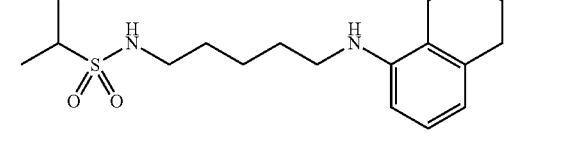
Ig-113
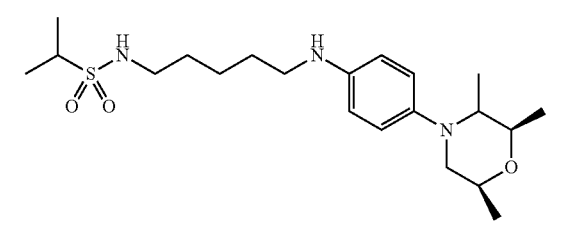
Ig-114
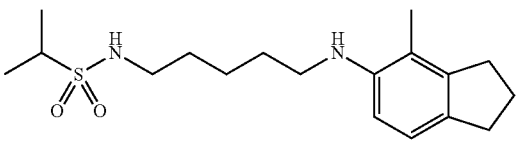
Ig-115
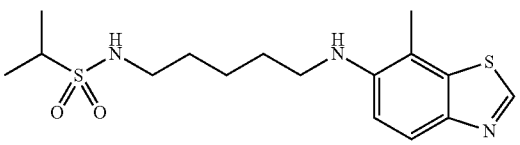
Ig-116
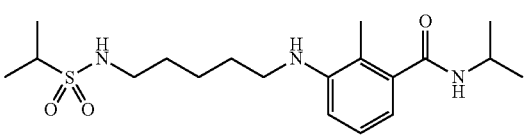
Ig-117
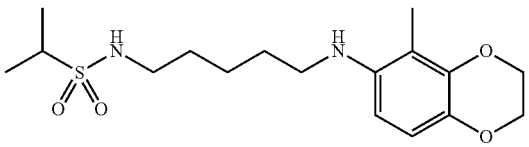
Ig-118
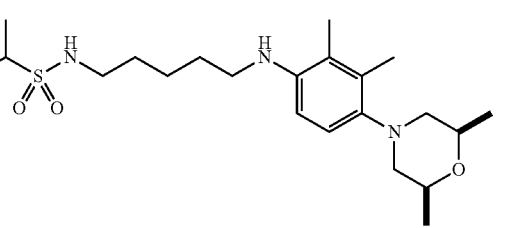
Ig-119
Ig-120
Ig-121
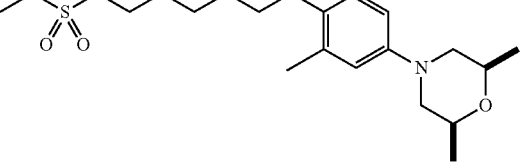

Ig-122
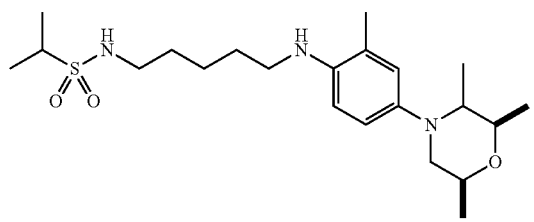
Ig-123
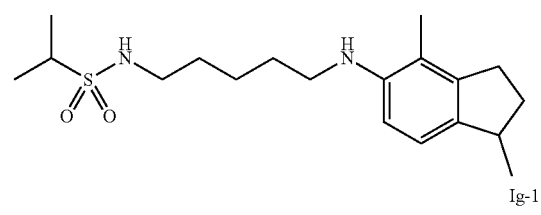
Ig-124
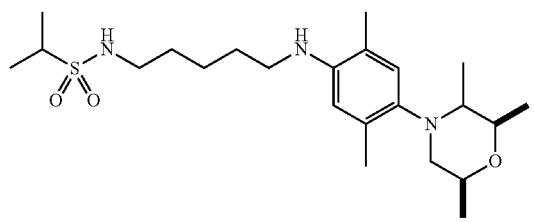
Ig-125
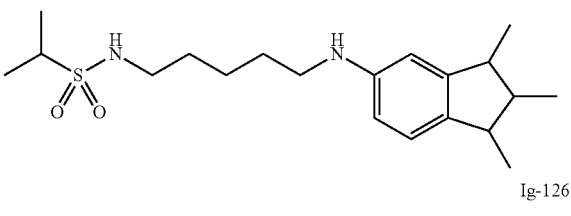
Ig-126
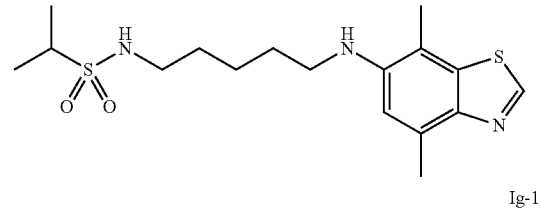
Ig-127
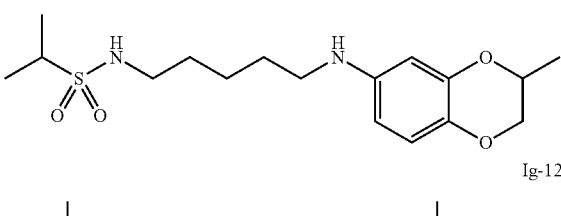
Ig-128
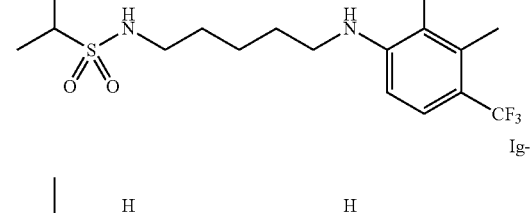
Ig-129
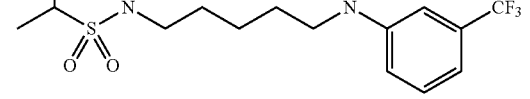
Ig-130
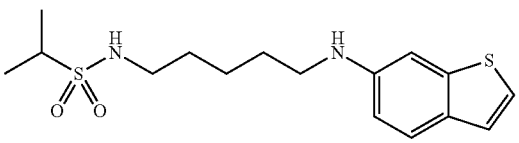
Ig-131
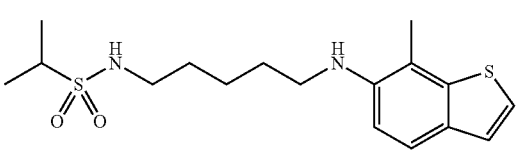
Ig-132
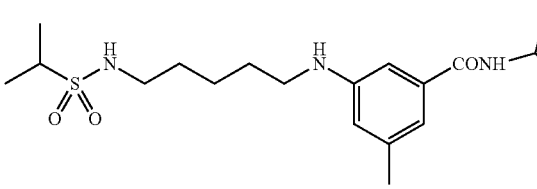
[Formula 141]
Id-133
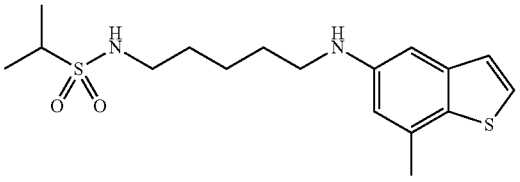
Id-134
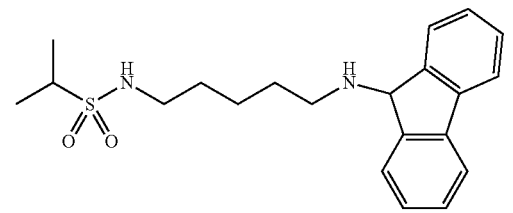
Id-135
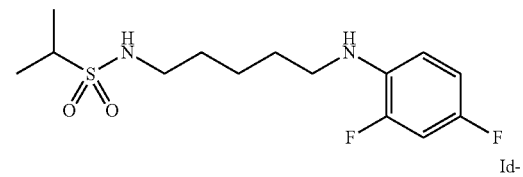
Id-136
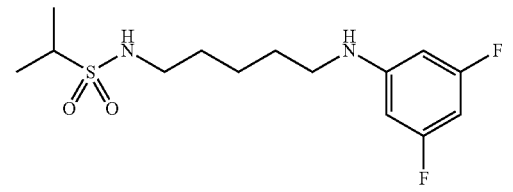

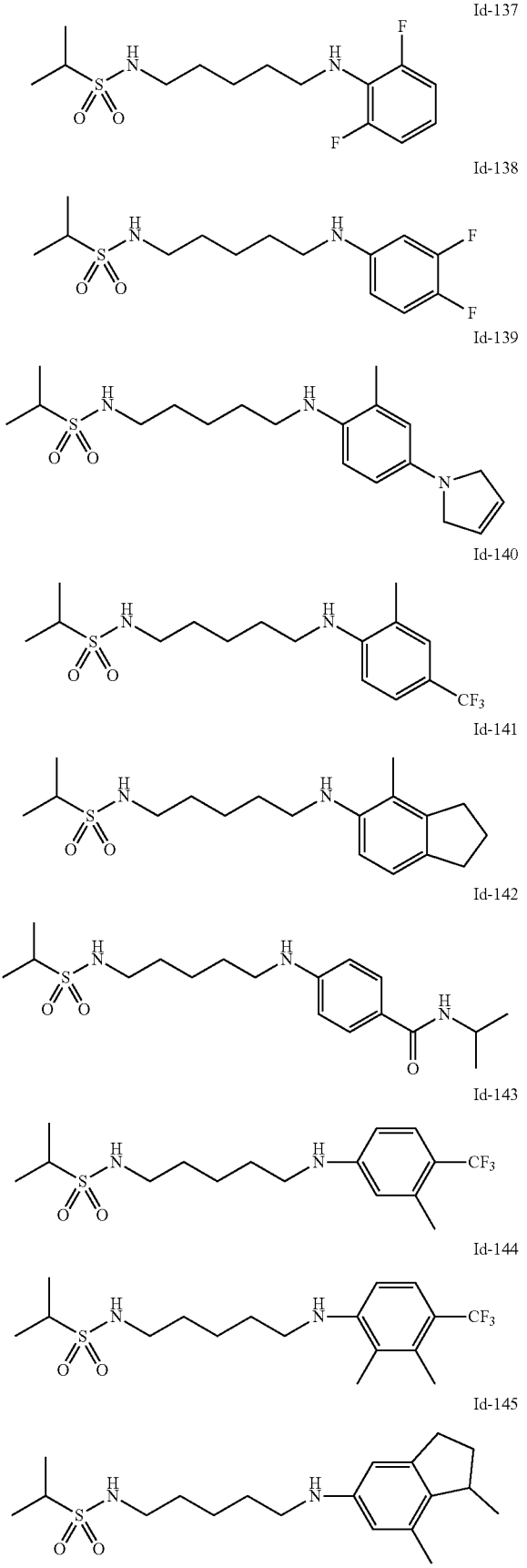
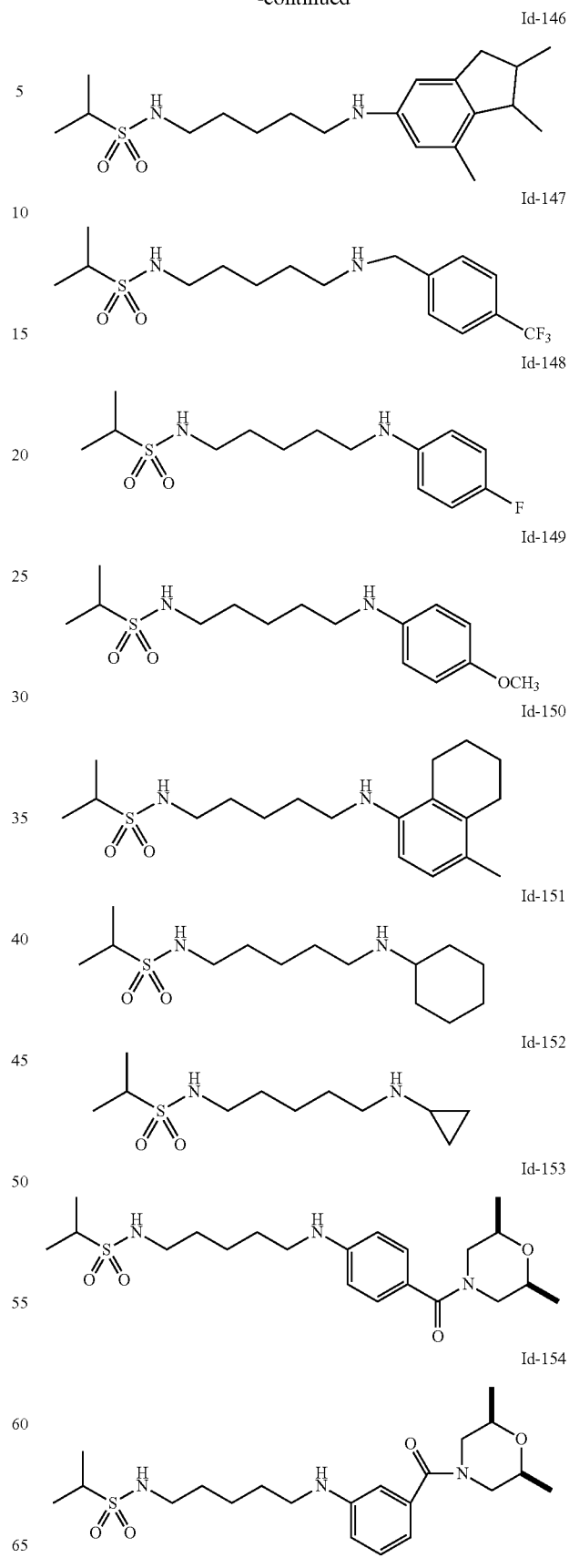

[Formula 142]
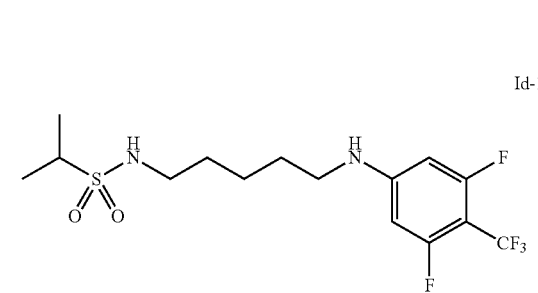
Id-155
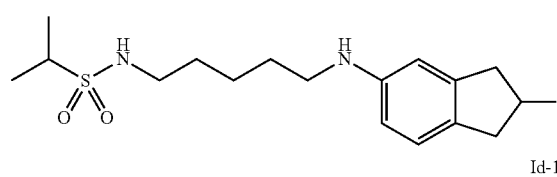
Id-156
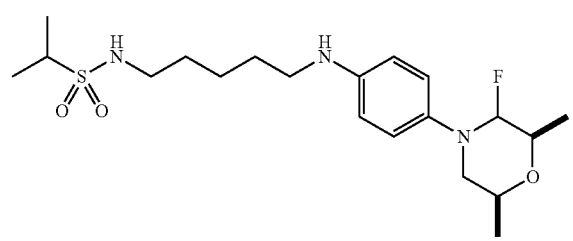
Id-157
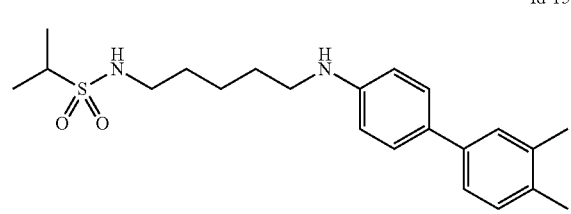
Id-158
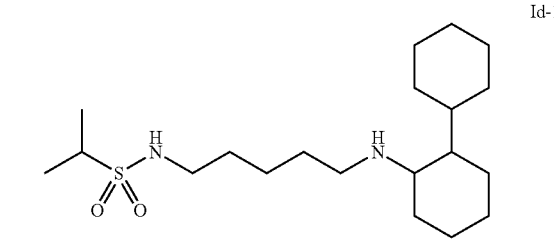
Id-159
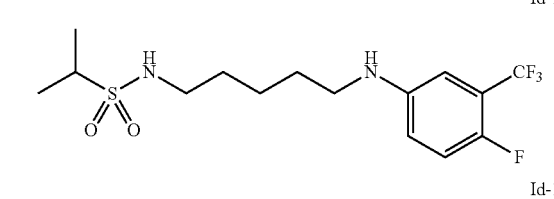
Id-160
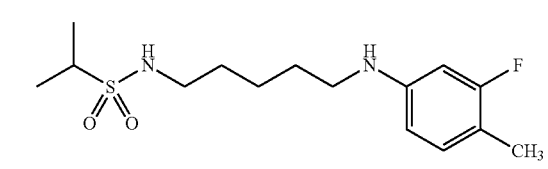
Id-161
-continued
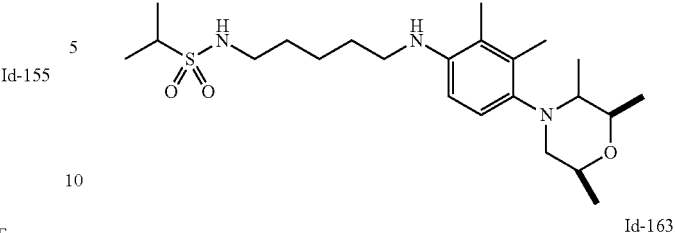
Id-162
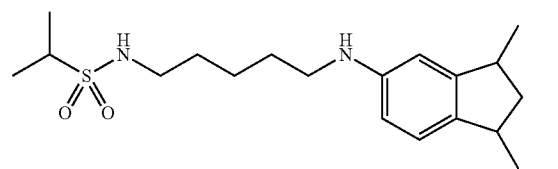
Id-163
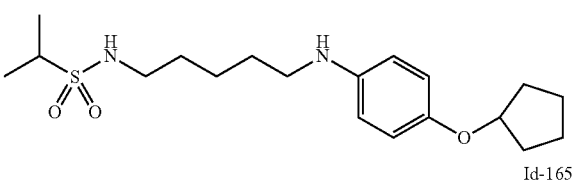
Id-164
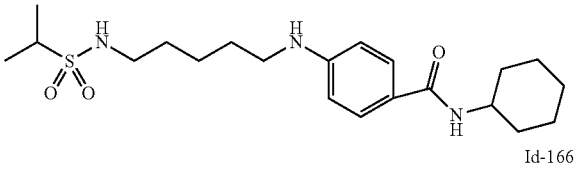
Id-165
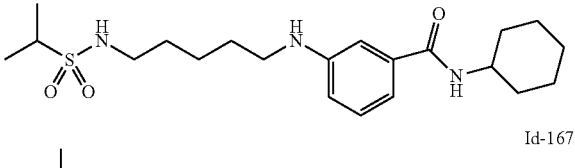
Id-166
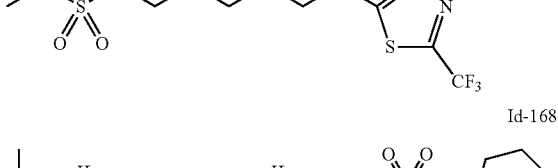
Id-167
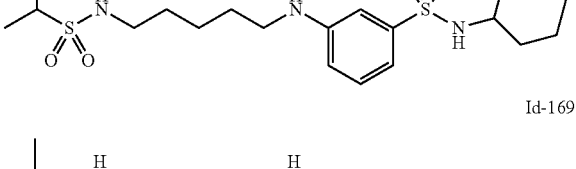
Id-168
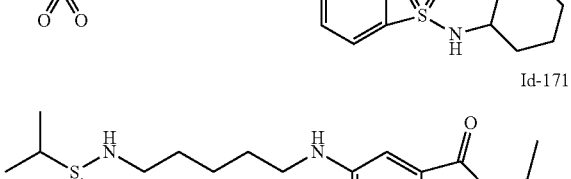
Id-169
Id-171

Id-172 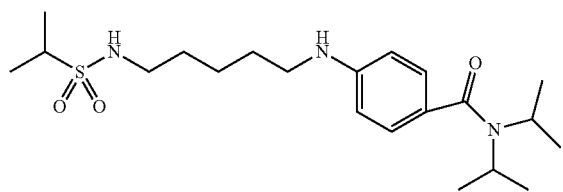
Id-179 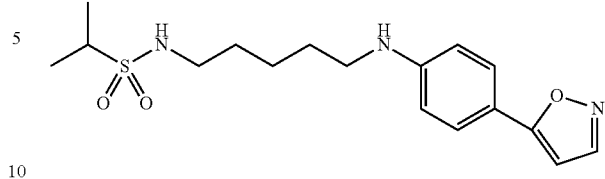
Id-173 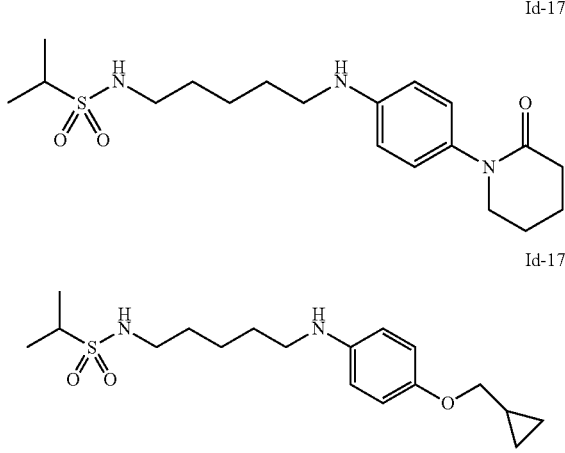
Id-180 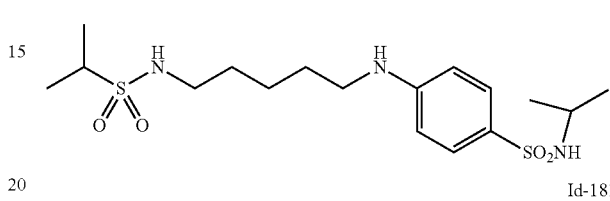
Id-174
Id-181 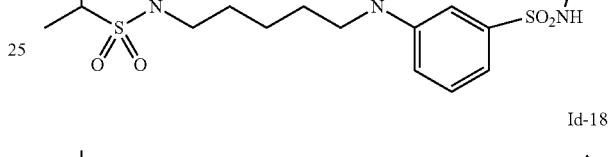
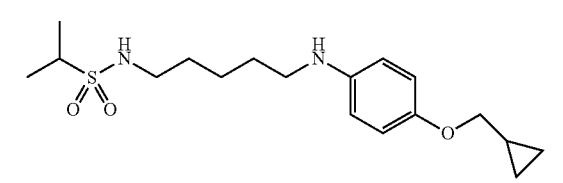
Id-182 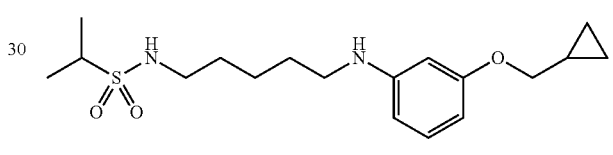
Id-175 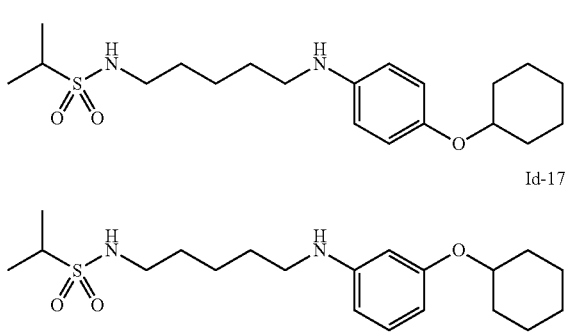
Id-183 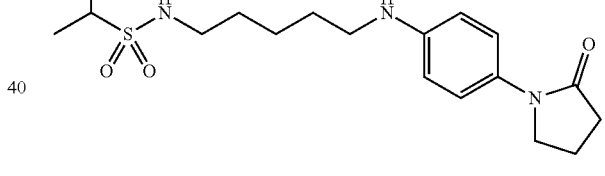
Id-176 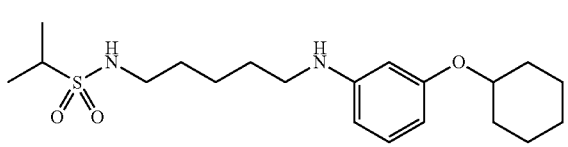
[Formula 143]
Id-177 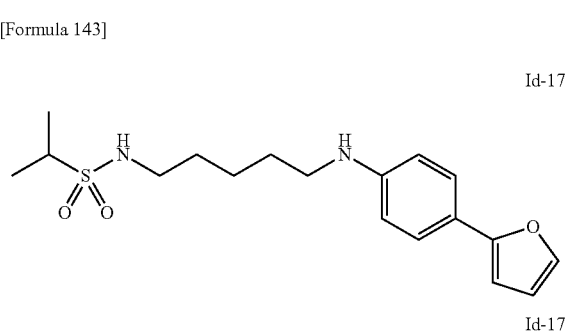
Id-184 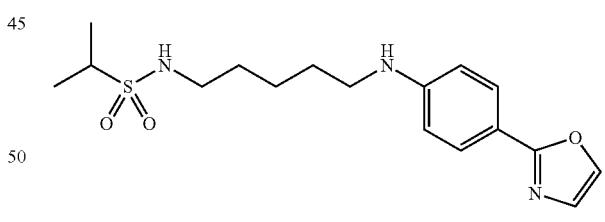
Id-178 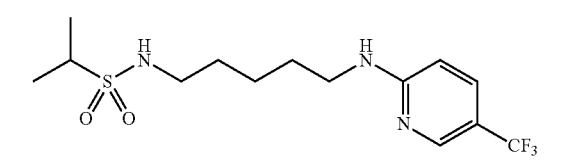
Id-185
Id-186 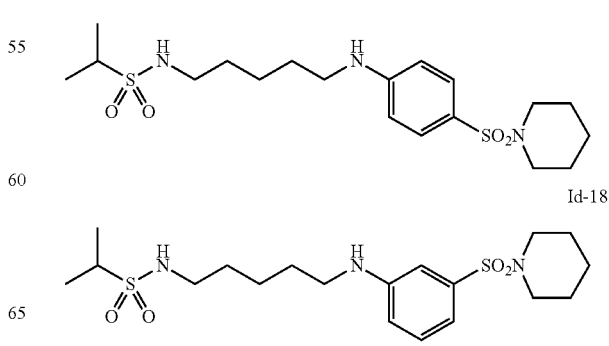

[Formula 144]

-continued

Id-203

Id-204

Id-205

Id-206

Id-207

Id-208

Id-209

-continued

Id-210

Id-211

Id-212

Id-213

Id-214

Id-215

Id-216

Id-219
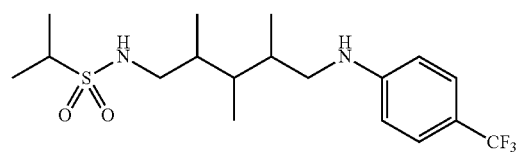
Id-220
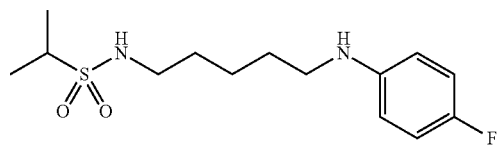
Id-221
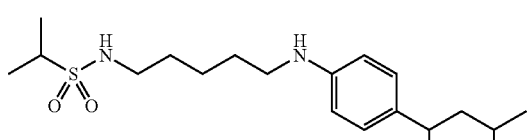
Id-222
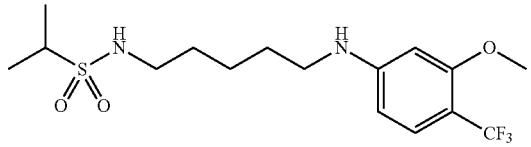
Id-223
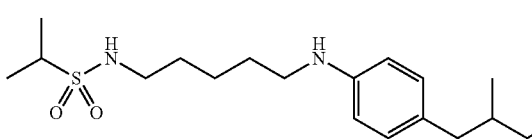
Id-224
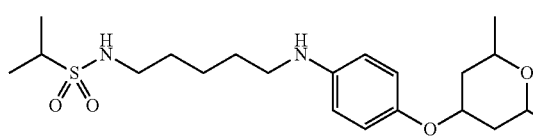
Id-225
Id-226
[Formula 145]
Ig-1
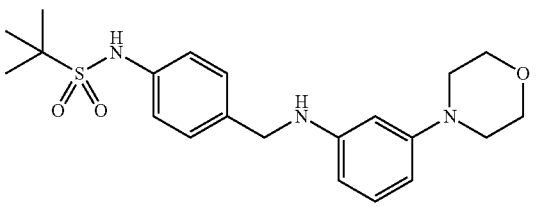
Ig-2
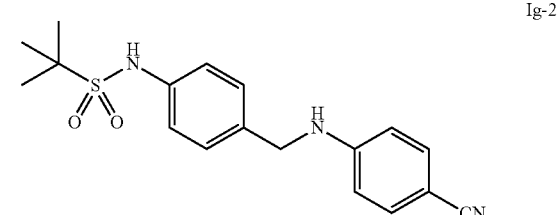
Ig-3
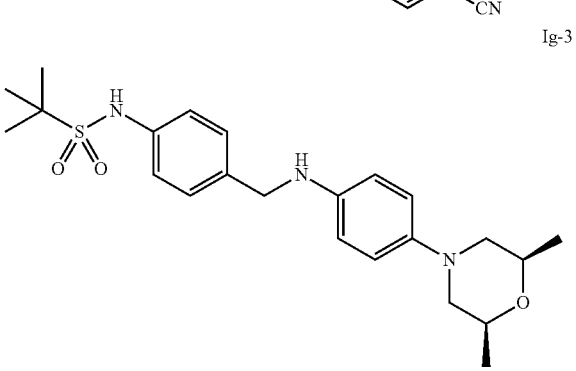
Ig-4
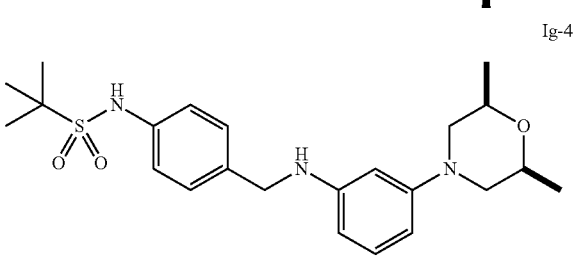
Ig-7
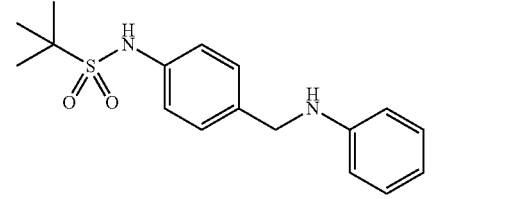
Ig-8
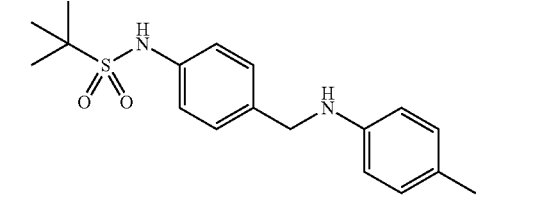

Ig-9
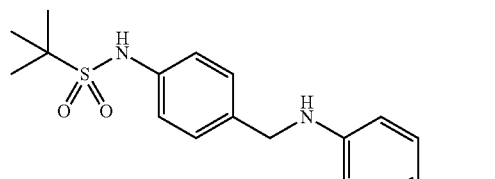
Ig-10
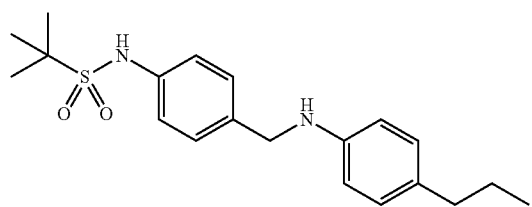
Ig-11
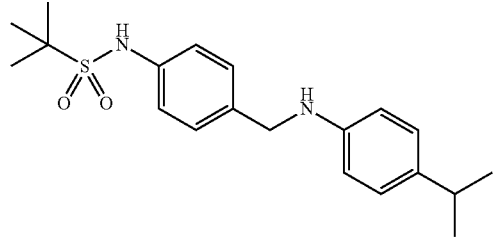
Ig-12
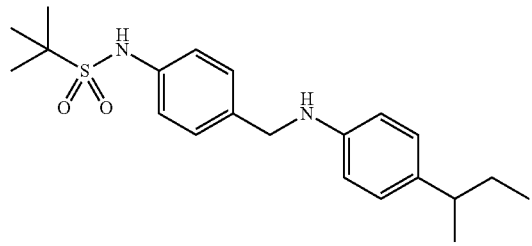
Ig-13
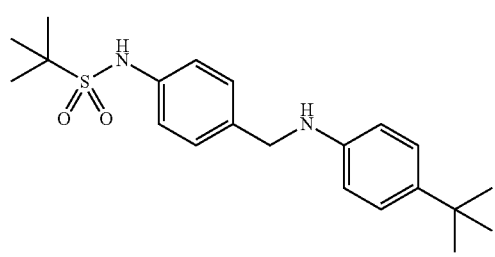
Ig-14
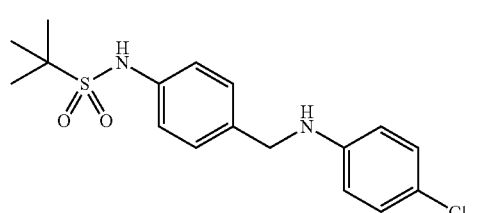
Ig-16
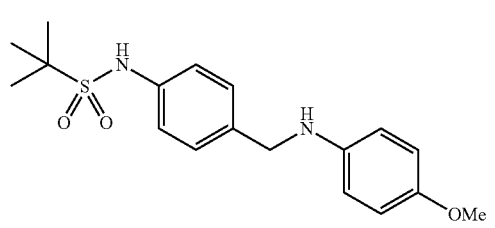
Ig-17
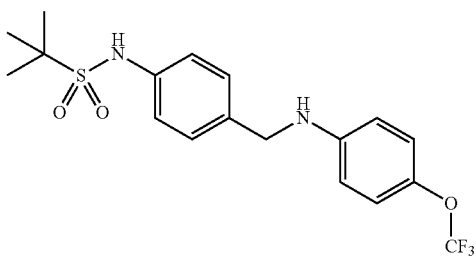
Ig-18
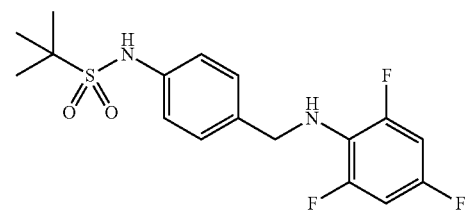
19
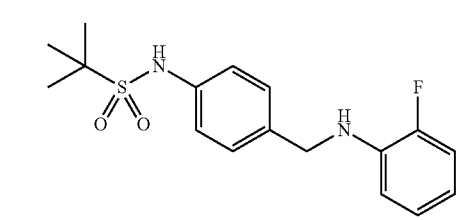
Ig-20
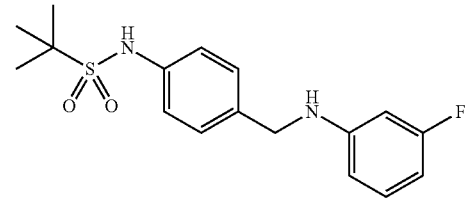
Ig-21
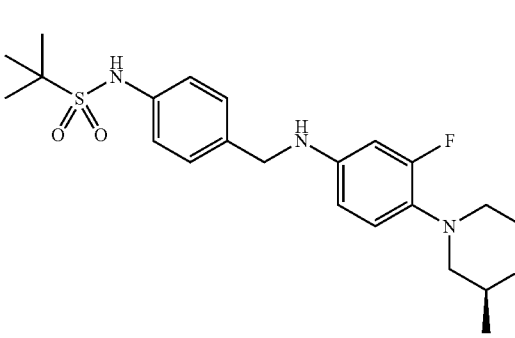
Ig-22
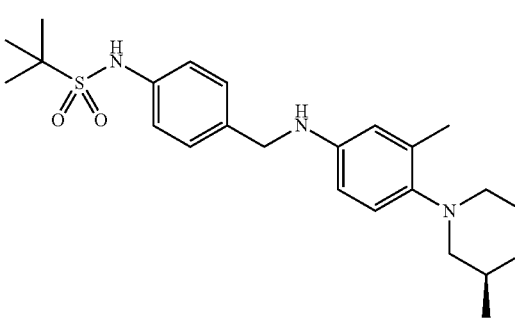

[Formula 146]
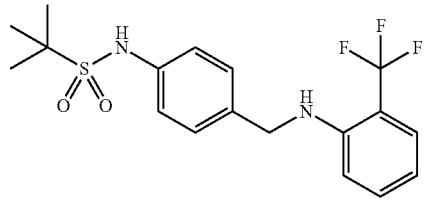
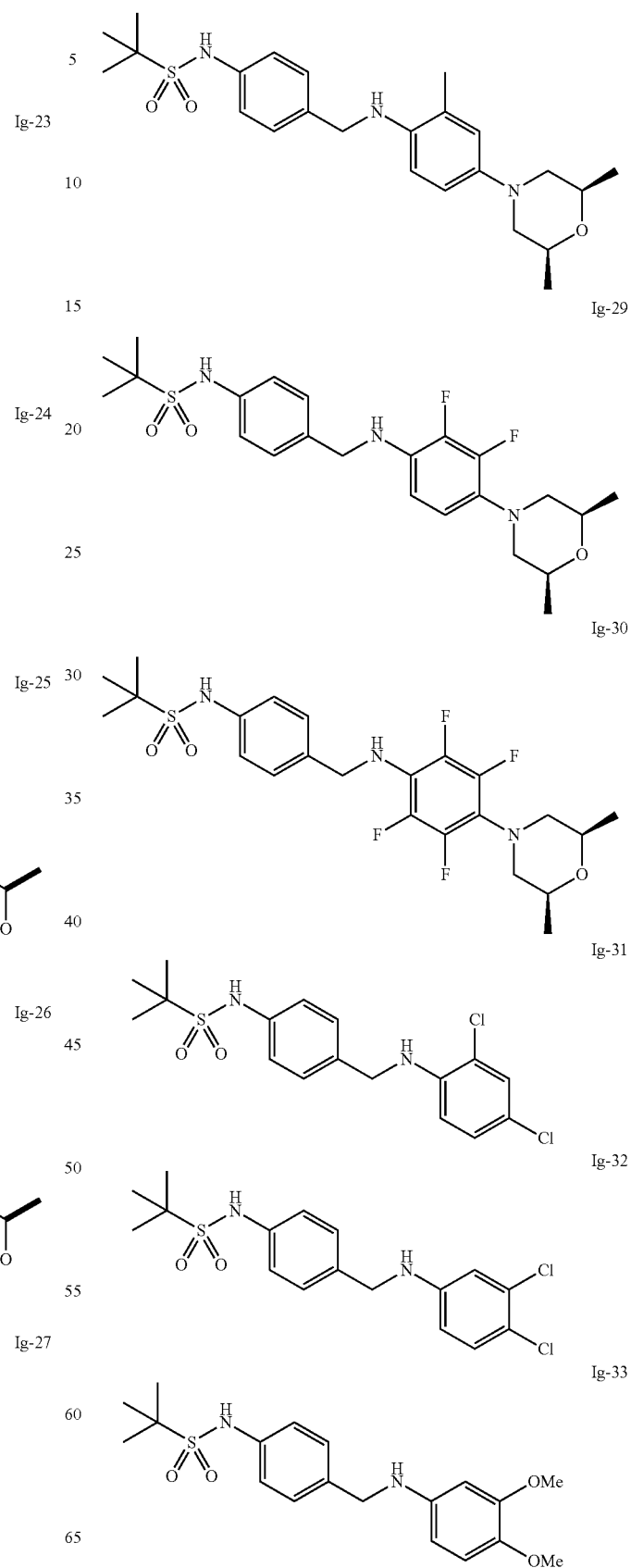

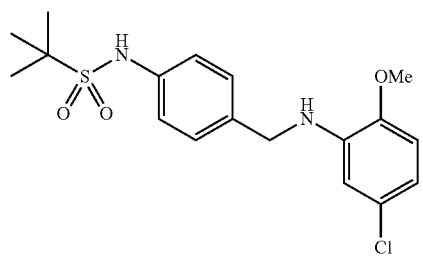
Ig-35
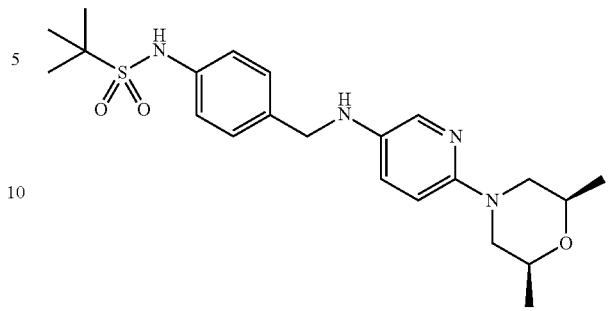
Ig-40
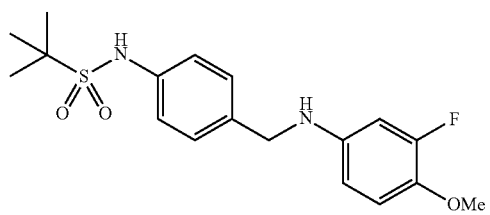
Ig-36
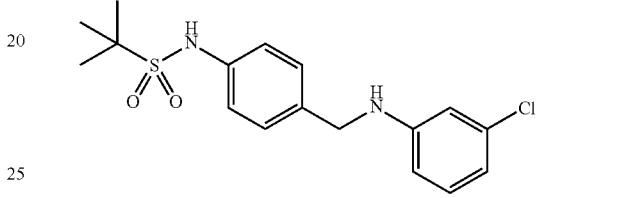
Ig-41
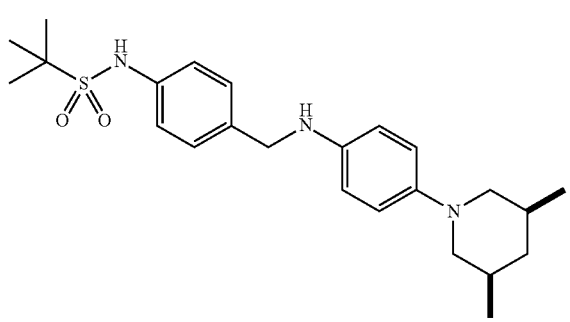
Ig-37
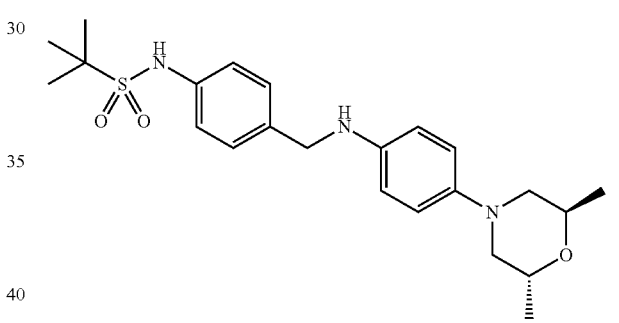
Ig-42
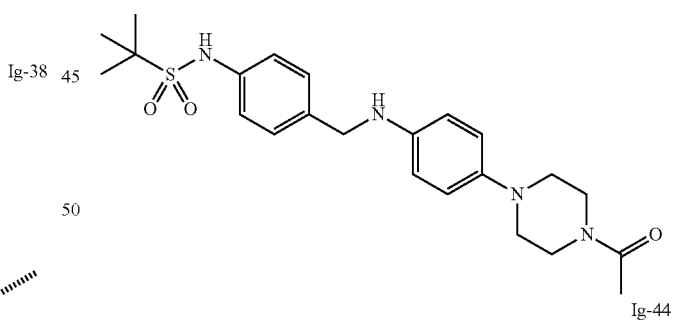
Ig-43
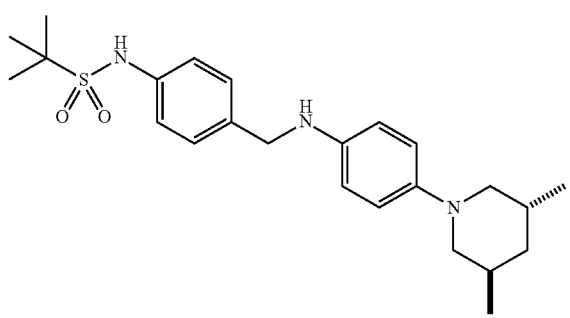
Ig-38
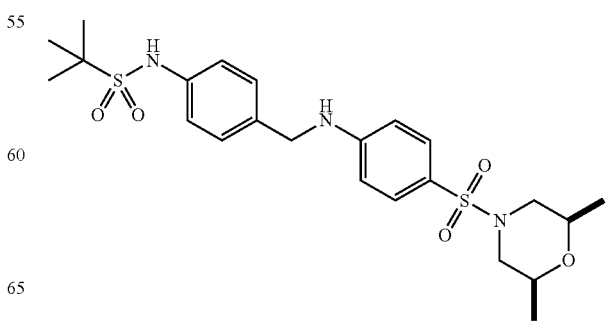
Ig-44
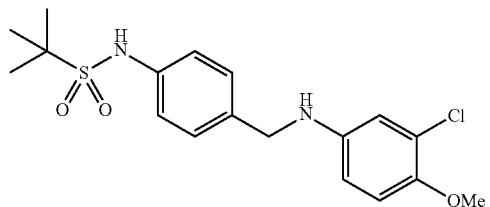
Ig-39

[Formula 147]
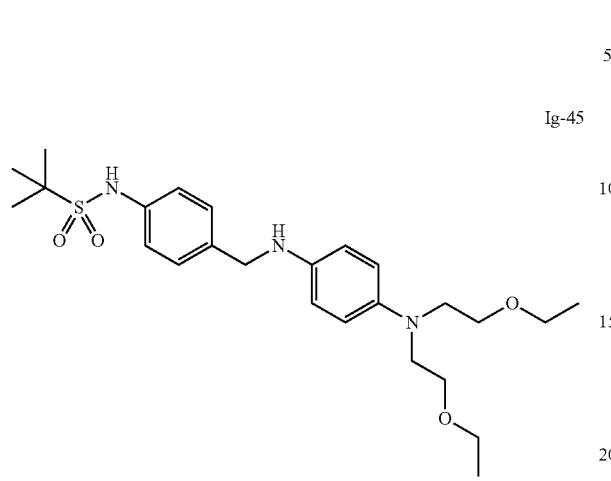
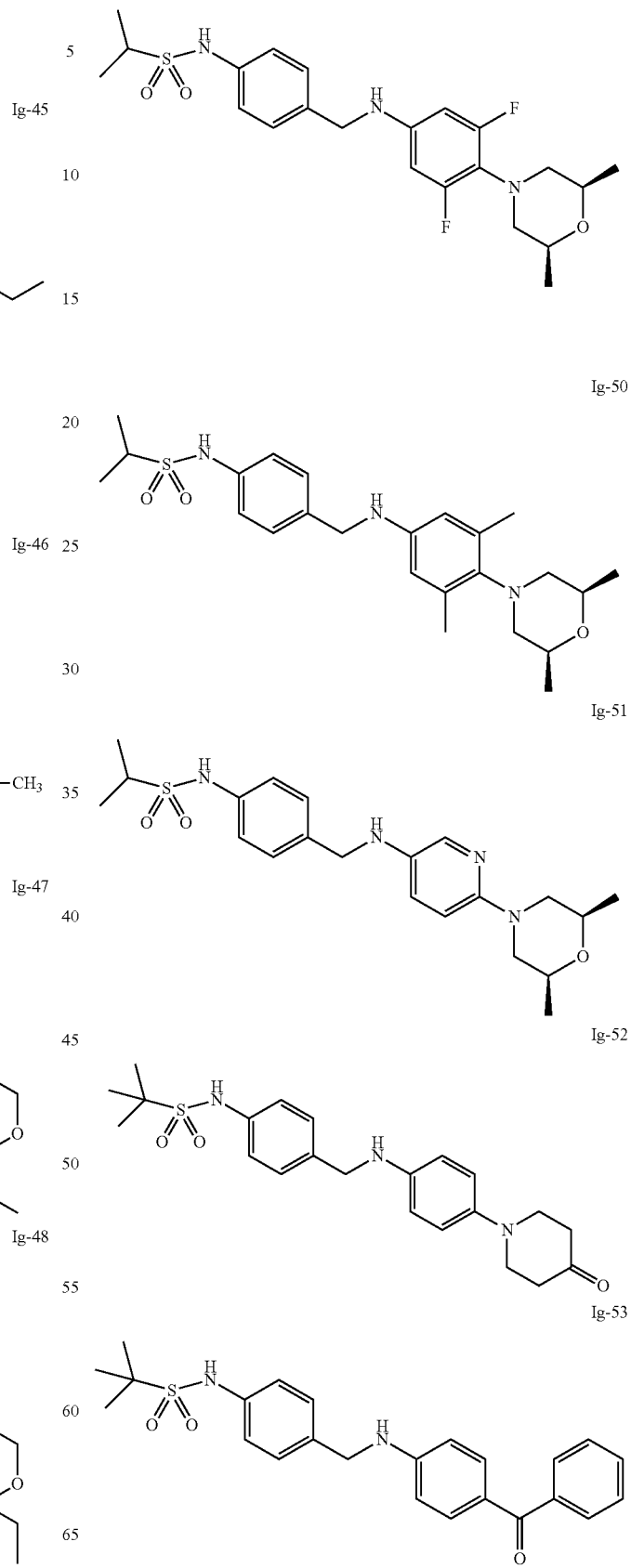

Ig-54
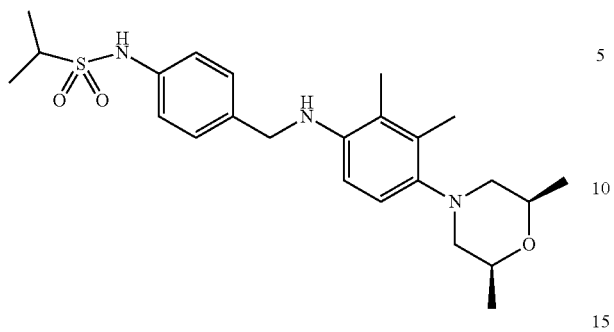
Ig-59
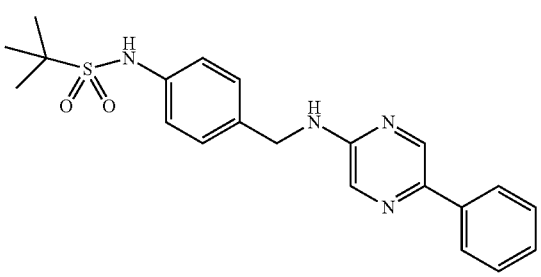
Ig-55
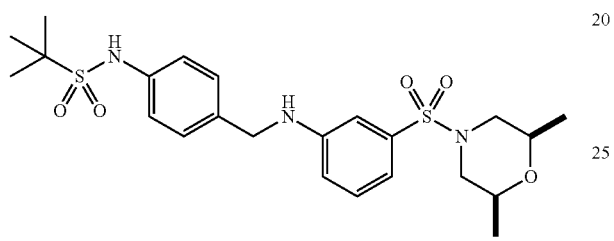
Ig-60
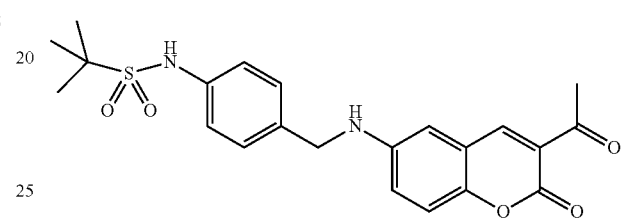
Ig-61
Ig-56
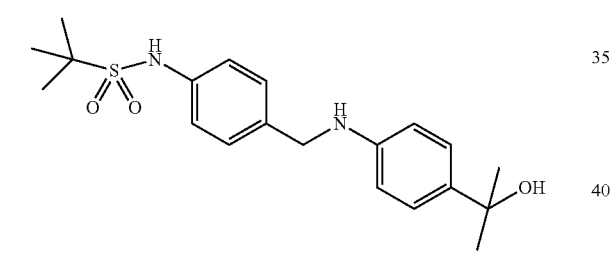
Ig-62
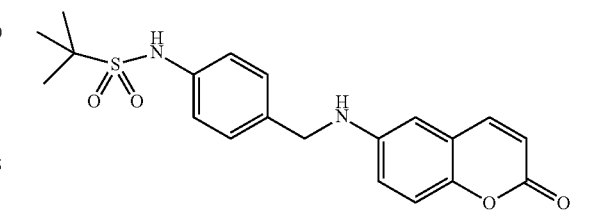
Ig-57
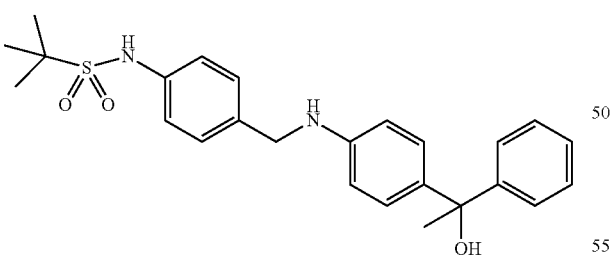
Ig-63
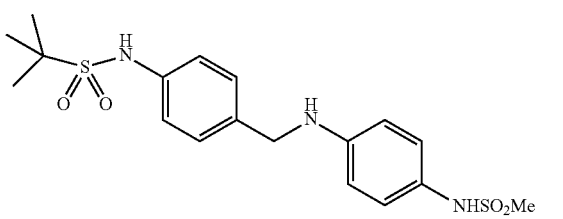
Ig-58
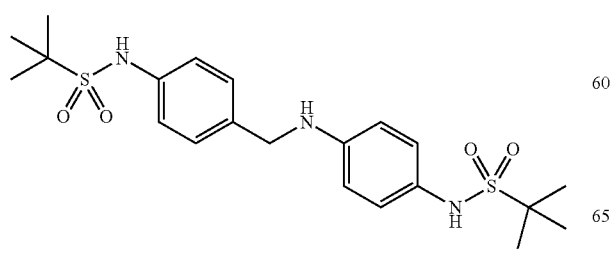
Ig-64
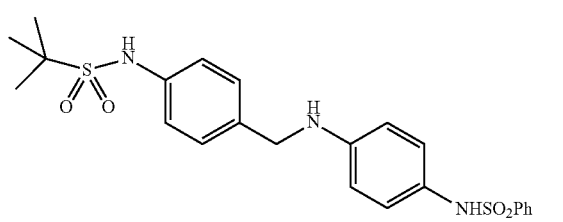

Ig-65
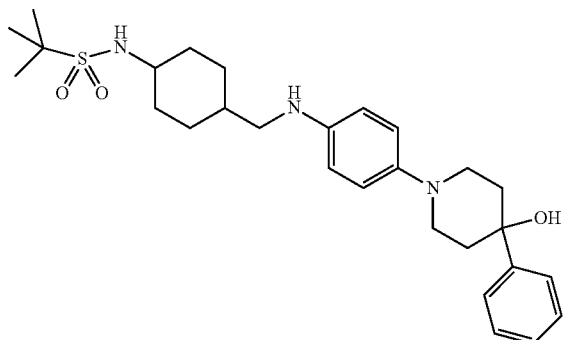
Ig-66
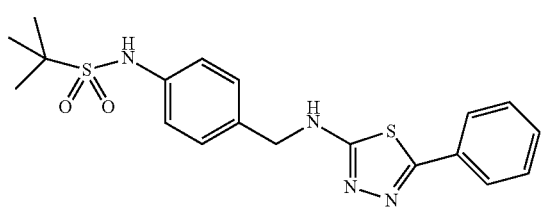
[Formula 148]
Ig-67
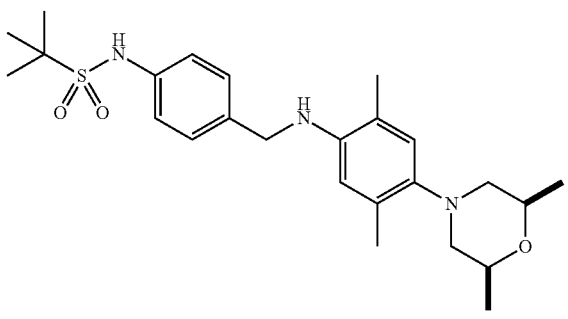
Ig-68
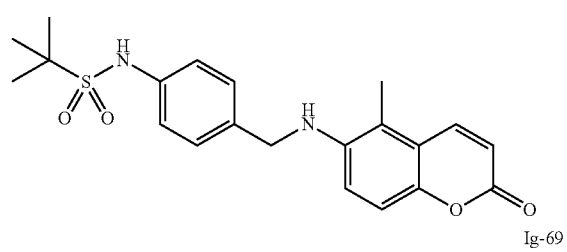
Ig-69
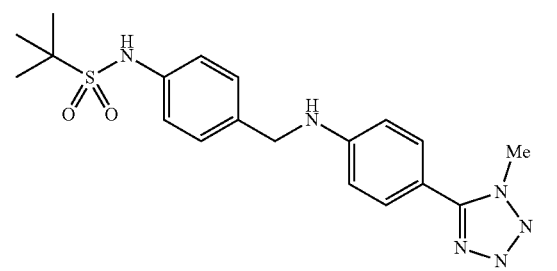
Ig-70
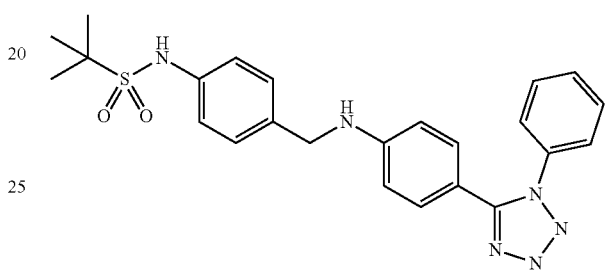
Ig-71
Ig-74
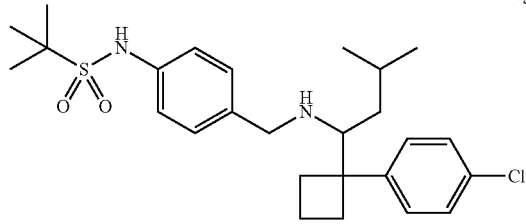
Ig-75
Ig-76
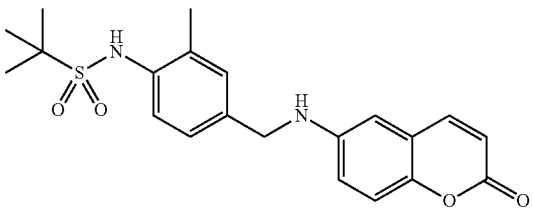

Ig-77
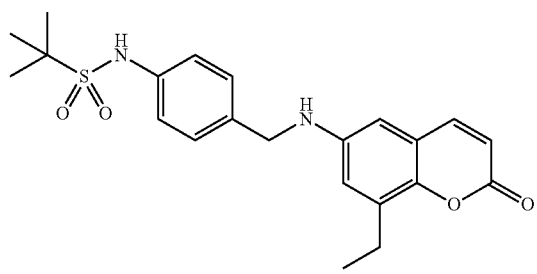
Ig-78
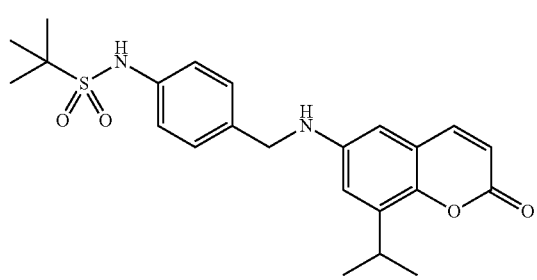
Ig-79
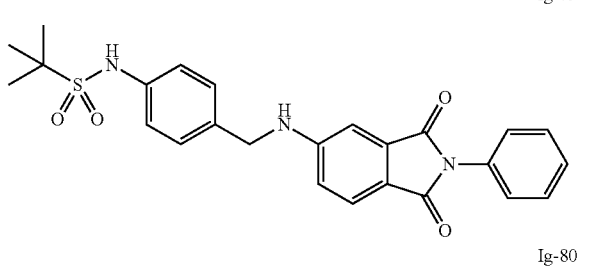
Ig-80
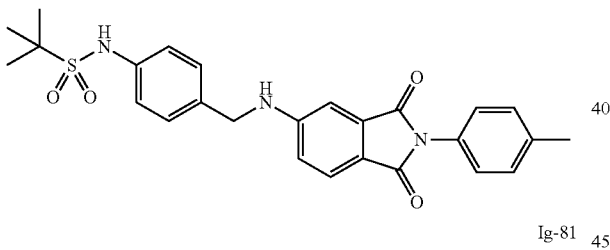
Ig-81
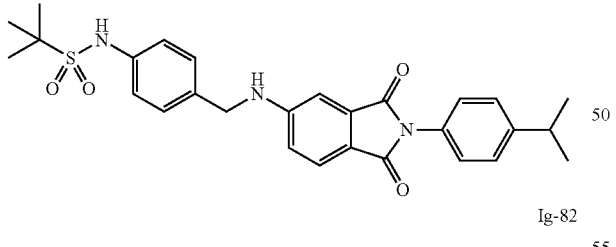
Ig-82
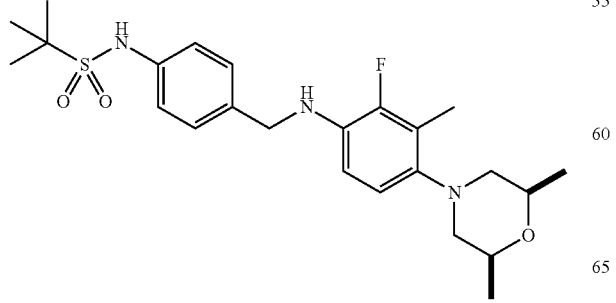
Ig-83
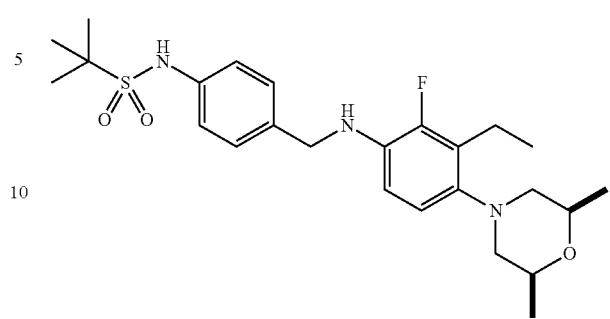
Ig-84
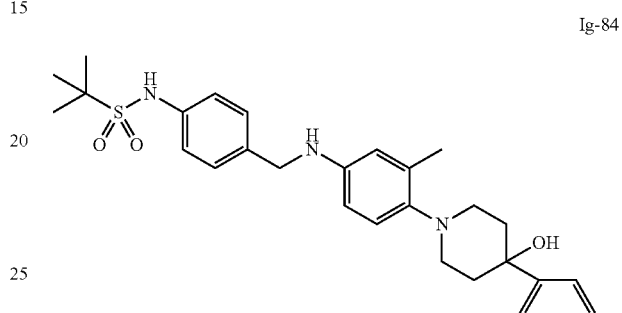
Ig-85
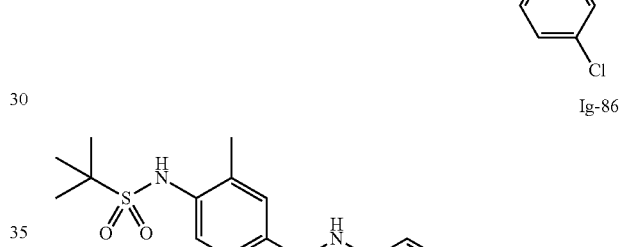
Ig-86
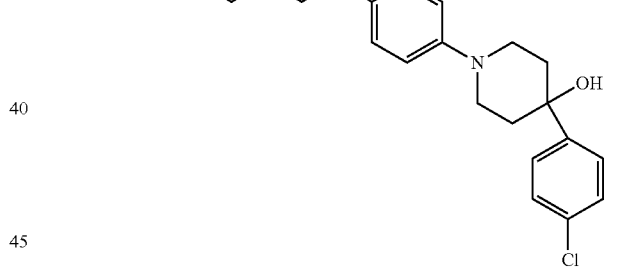
Ig-87
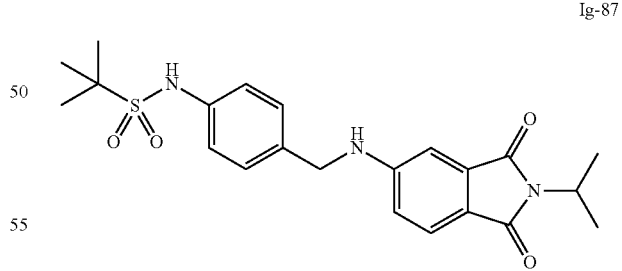

[Formula 149]
Ig-89
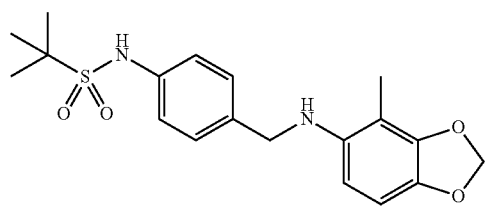
Ig-90
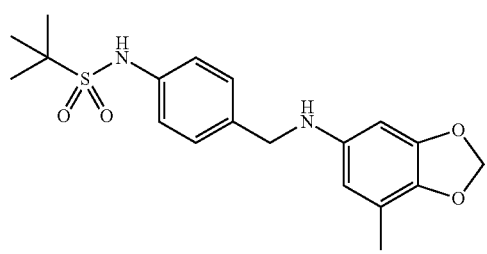
Ig-91
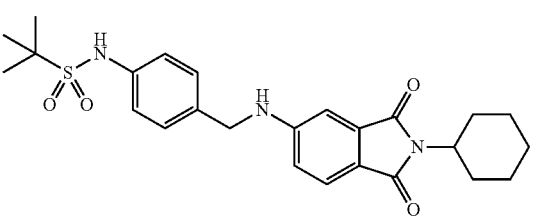
Ig-92
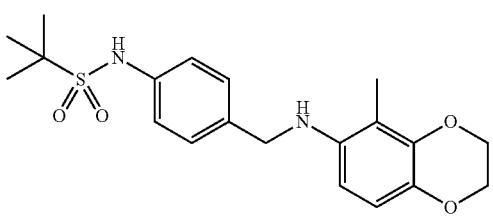
Ig-93
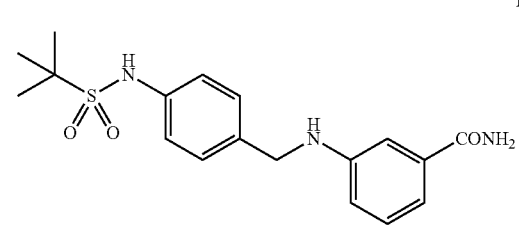
Ig-94
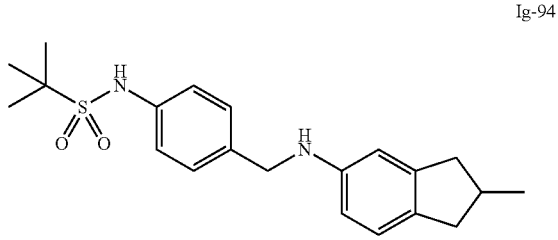
Ig-95
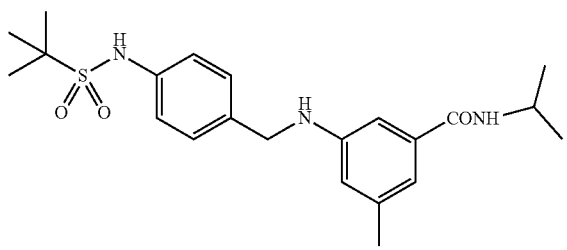
Ig-96
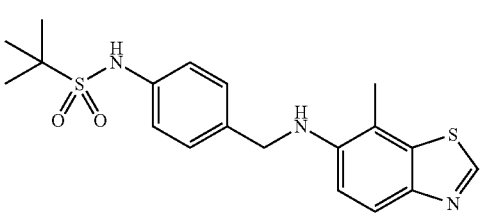
Ig-97
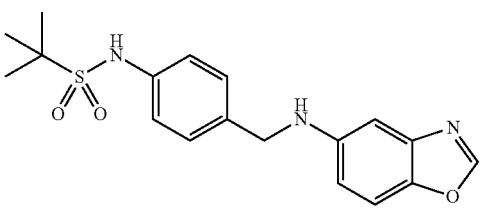
Ig-98
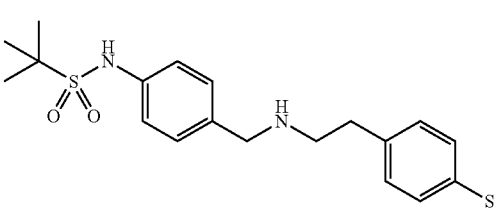
Ig-99
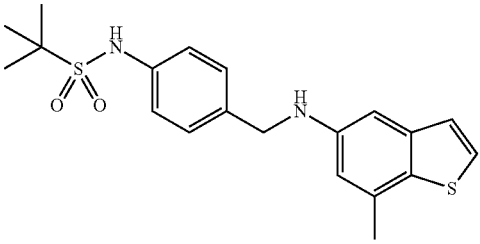
Ig-100

Ig-101
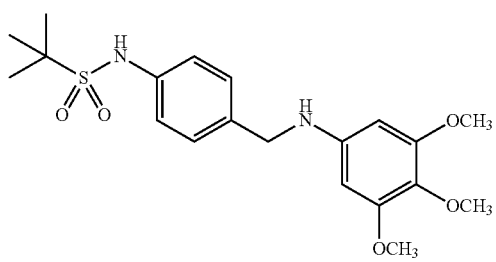
Ig-102
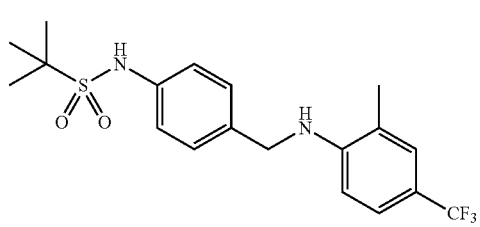
Ig-103
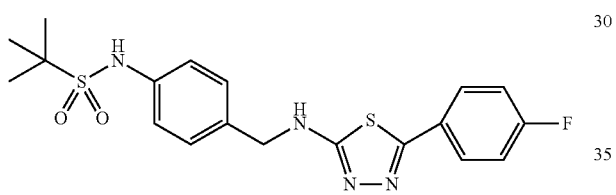
Ig-104
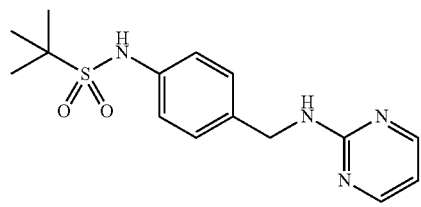
Ig-105
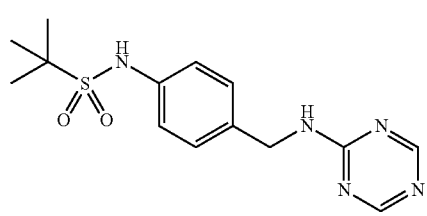
Ig-106
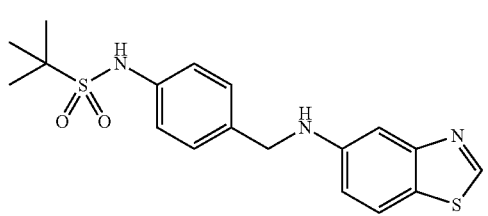
Ig-107
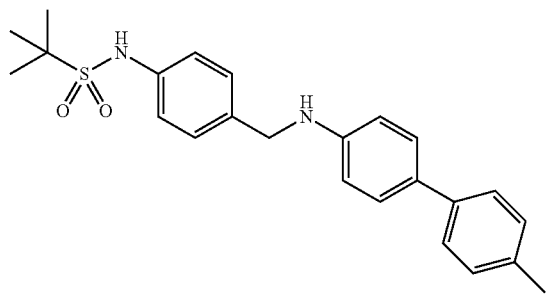
Ig-108
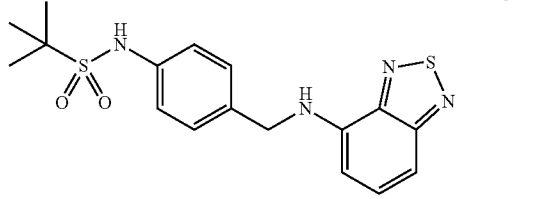
Ig-109
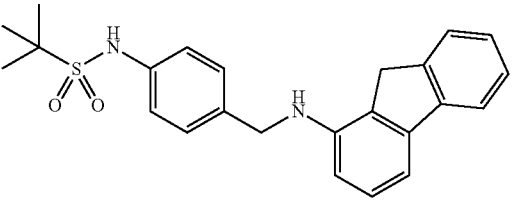
Ig-110
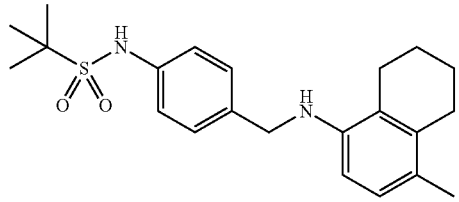
[Formula 150]
Ig-111

Ig-112
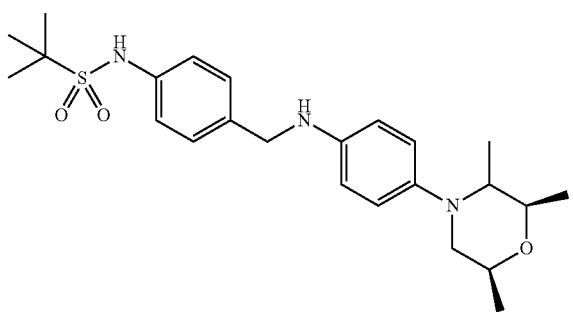
Ig-118
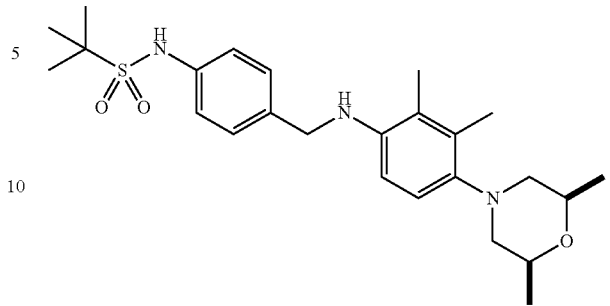
Ig-113
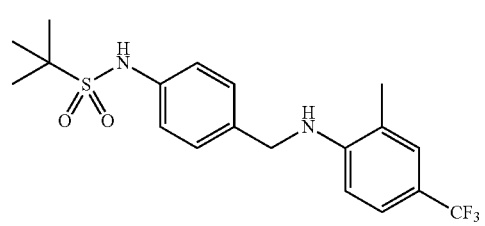
Ig-119
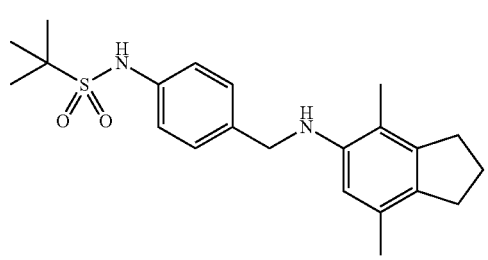
Ig-114
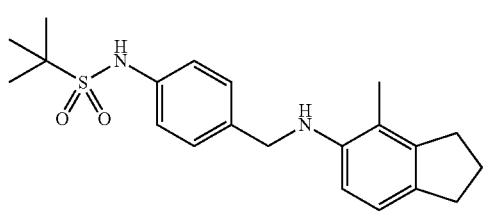
Ig-120
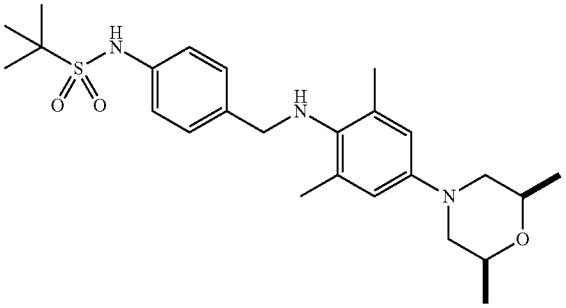
Ig-115
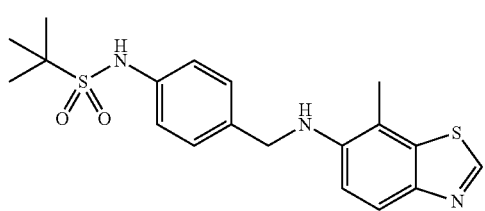
Ig-121
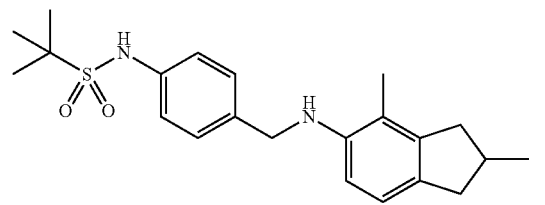
Ig-116
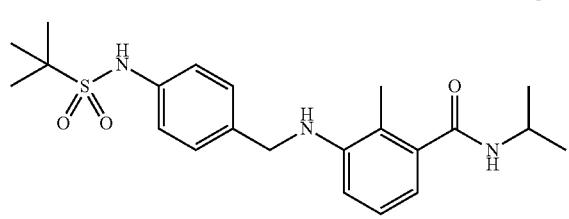
Ig-122
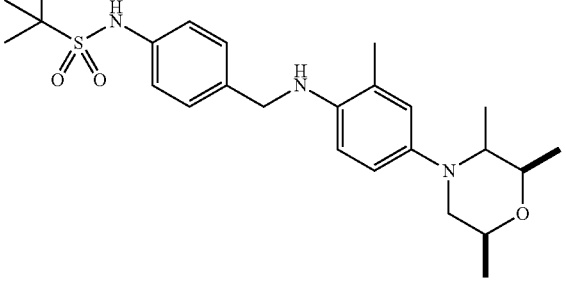
Ig-117
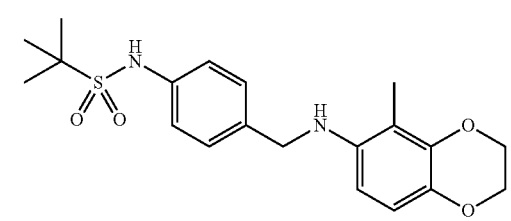

Ig-123
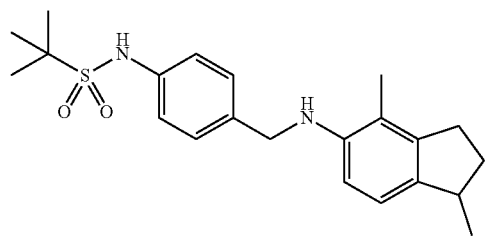
Ig-124
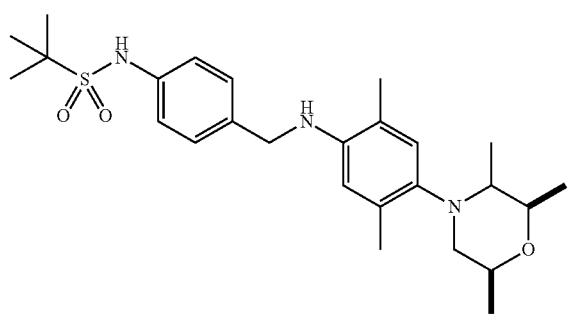
Ig-125
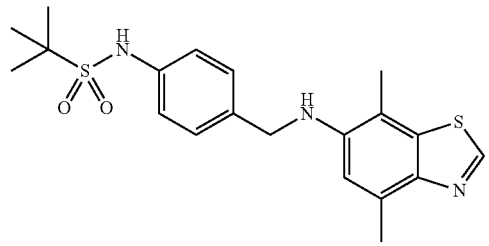
Ig-126
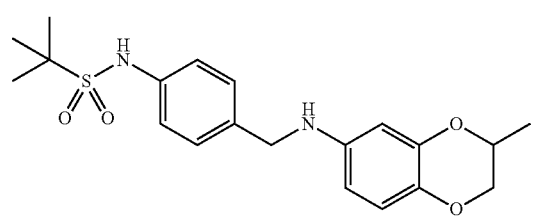
Ig-127
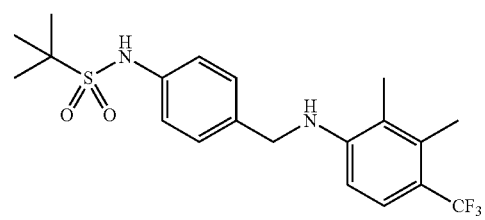
Ig-128
Ig-129
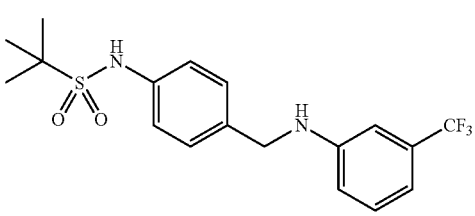
Ig-130
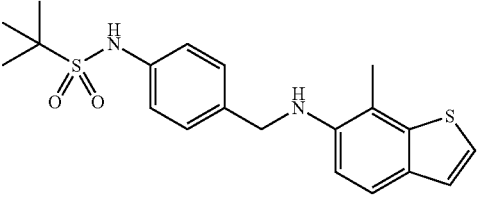
Ig-131
Ig-132
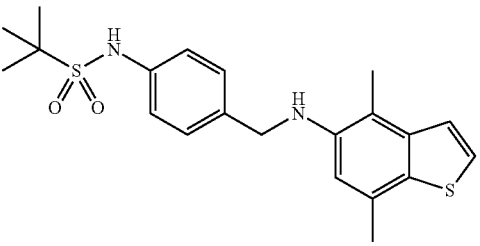
[Formula 151]
Ig-133
Ig-134
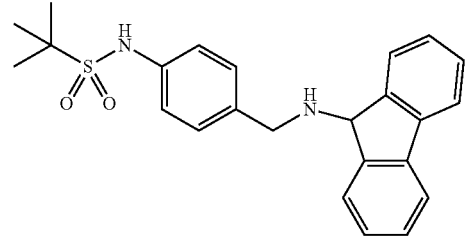

Ig-135 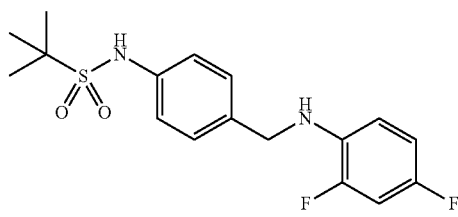
Ig-136 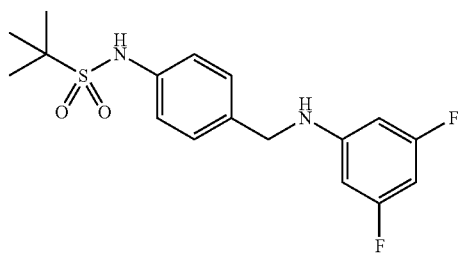
Ig-137 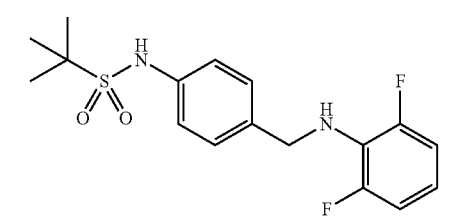
Ig-138 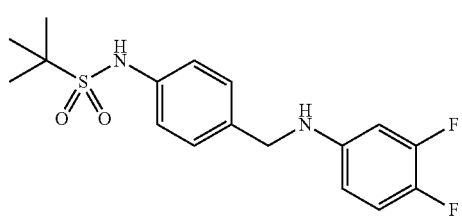
Ig-139 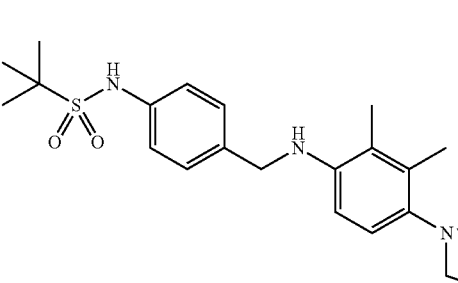
Ig-140 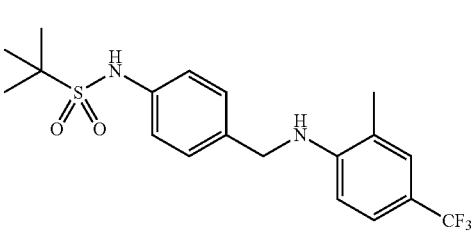
Ig-141 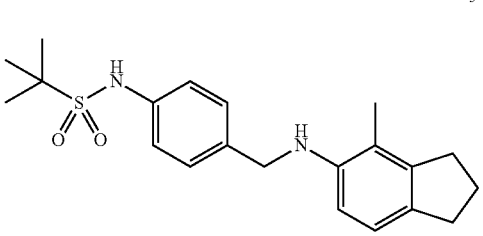
Ig-142 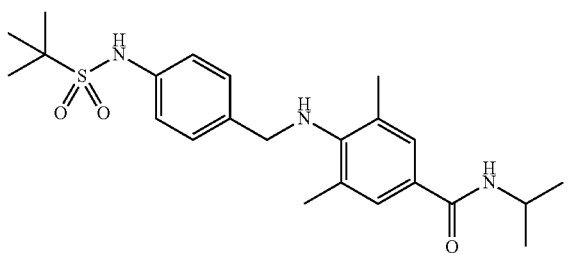
Ig-143 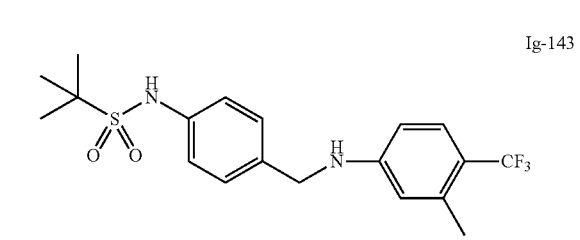
Ig-144 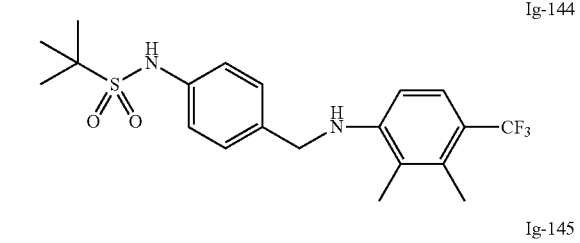
Ig-145 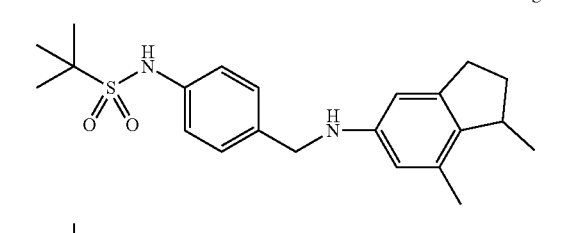
Ig-146 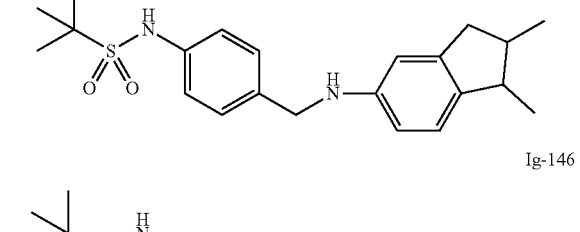
Ig-147 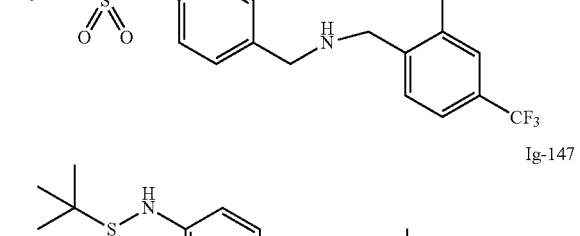
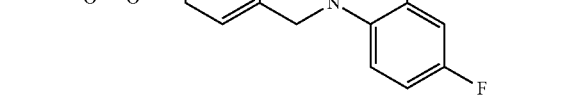

-continued
Ig-148
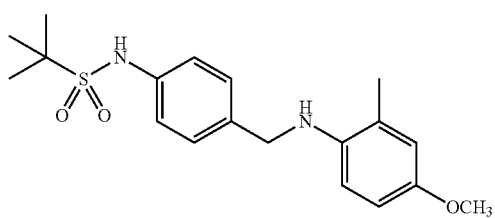
Ig-149
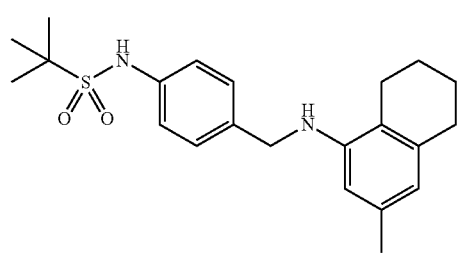
Ig-150
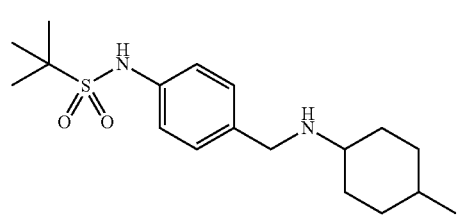
Ig-151
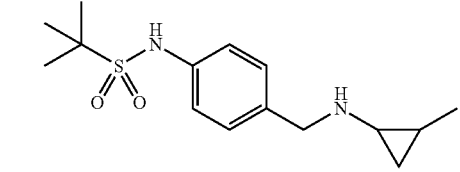
Ig-153
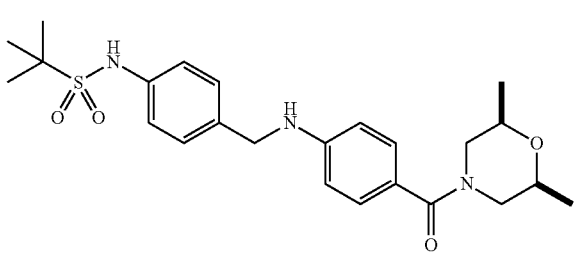
Ig-154
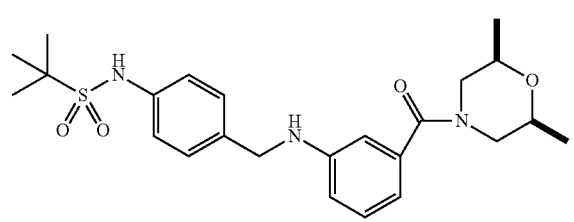
[Formula 152]
Ig-155
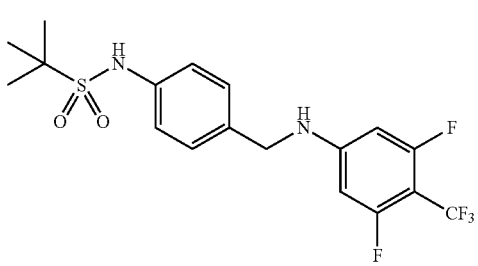
Ig-156
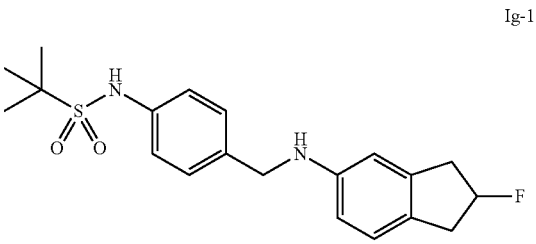
Ig-157
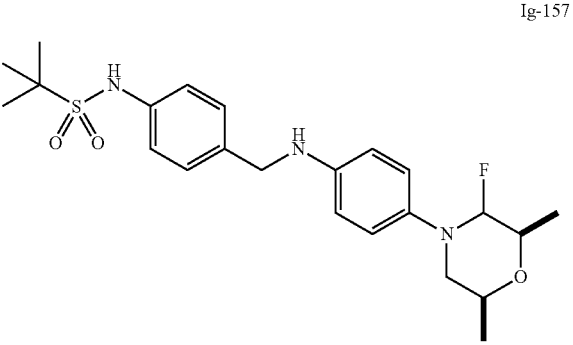 [SMILES: Cc1cc(CNc2ccc(N3C[C@@H](C)O[C@@H](C)C3)cc2)ccc1NS(=O)(=O)C(C)(C)C]
Ig-158
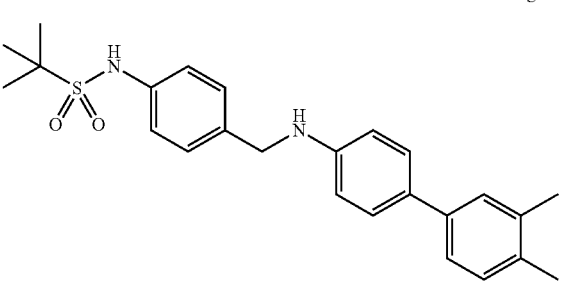
Ig-159
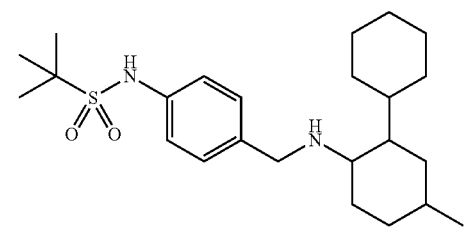
Ig-160
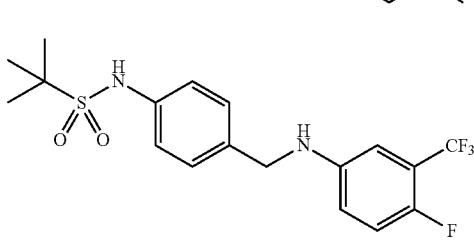

Ig-161
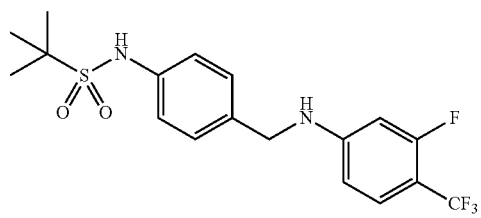
Ig-162
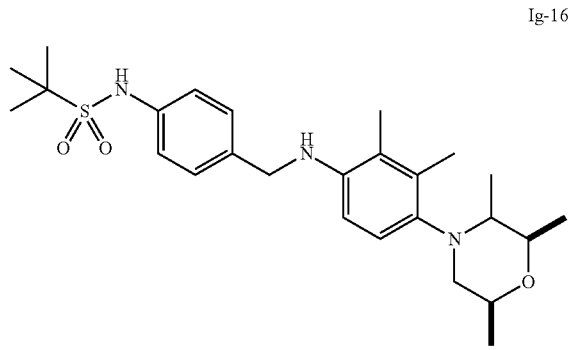
Ig-163
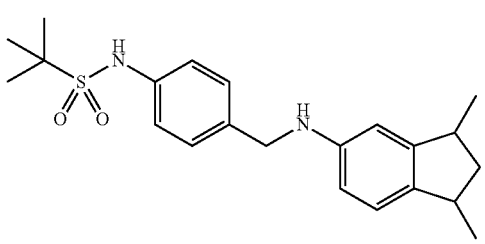
Ig-164
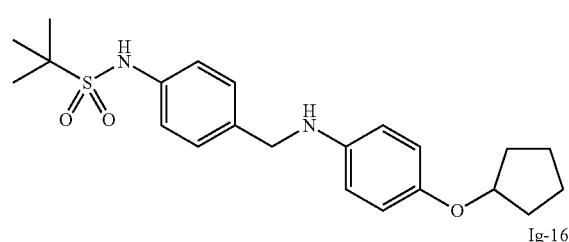
Ig-165
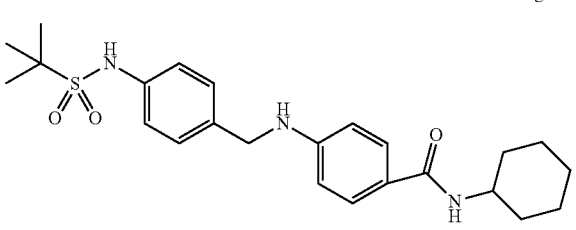
Ig-166
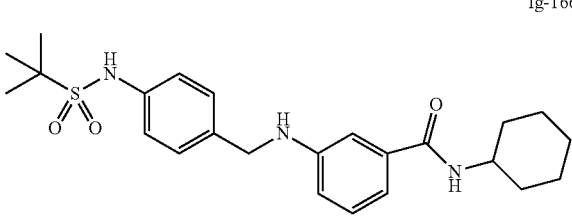
Ig-167
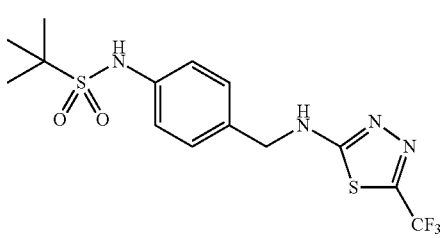
Ig-168
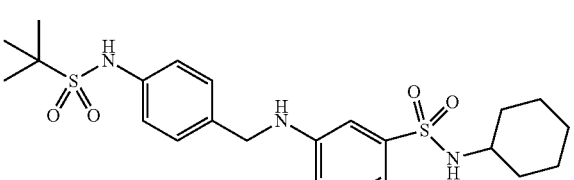
Ig-169
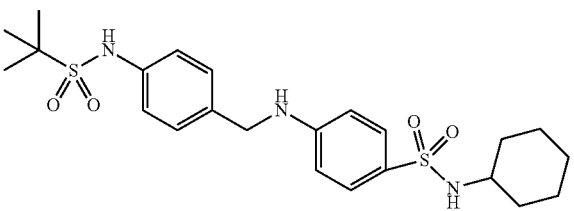
Ig-171
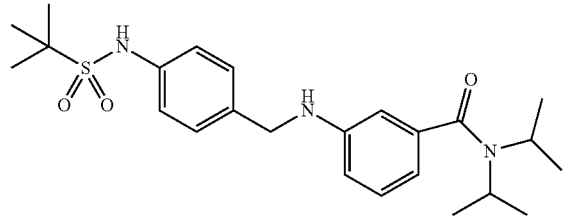
Ig-172
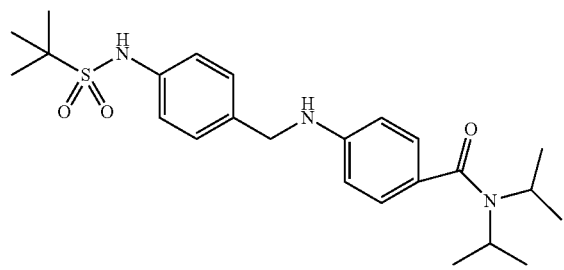
Ig-173
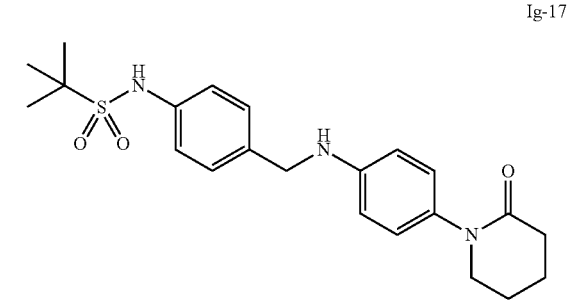

Ig-174
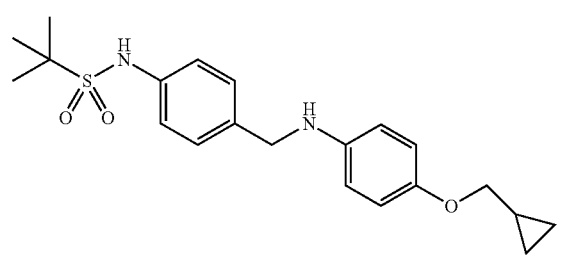
Ig-175
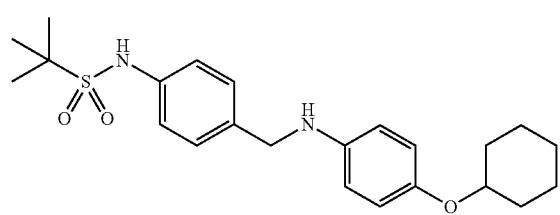
Ig-176
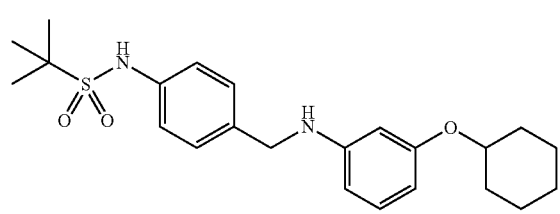
[Formula 153]
Ig-177
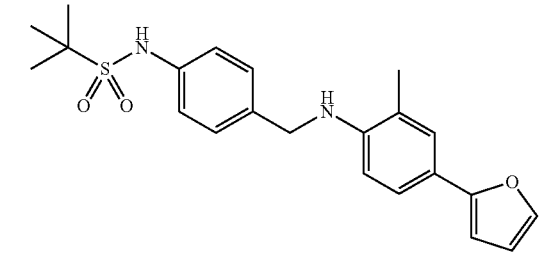
Ig-178
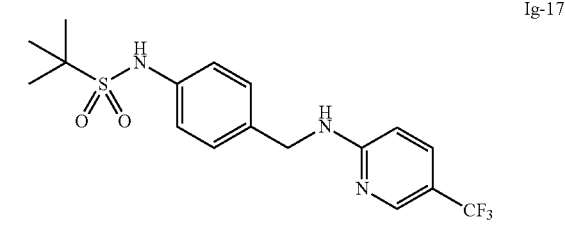
Ig-179
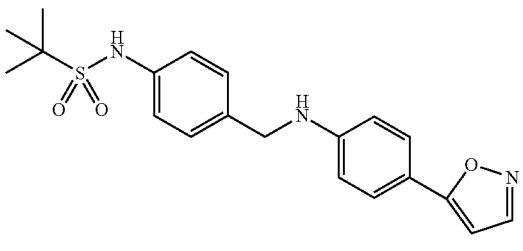
Ig-180
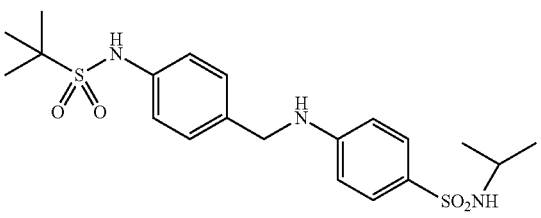
Ig-181
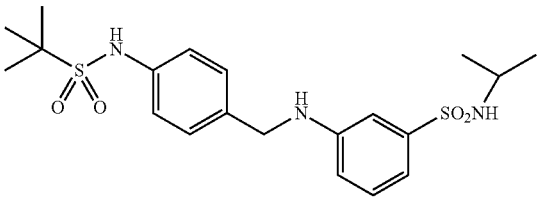
Ig-182
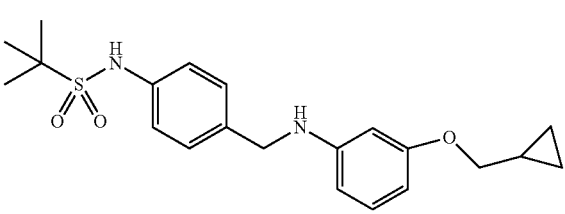
Ig-183
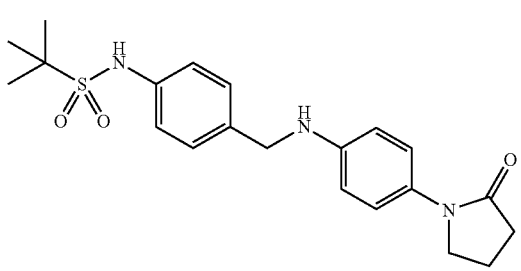
Ig-184
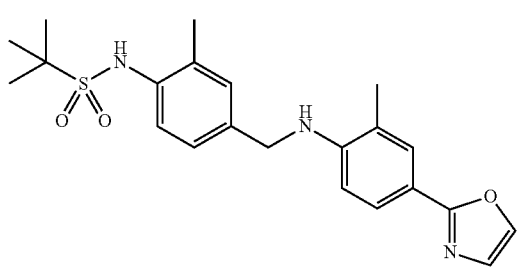

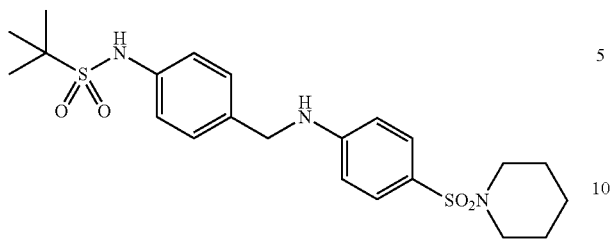
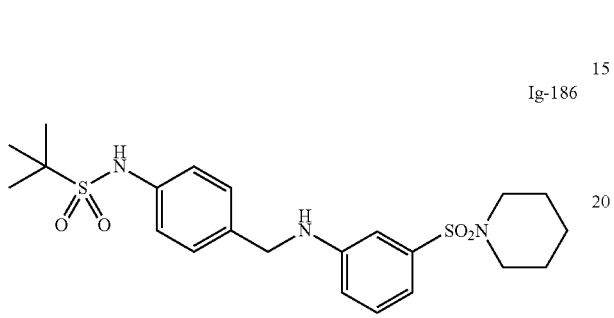
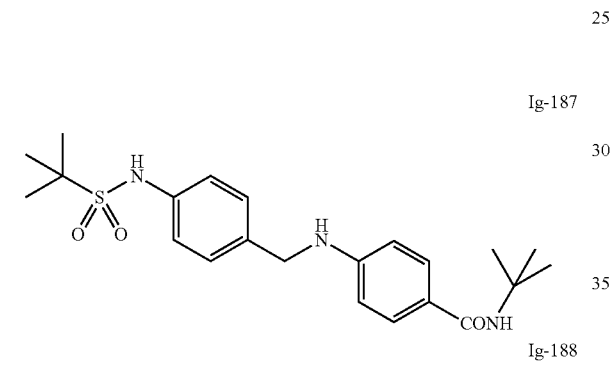
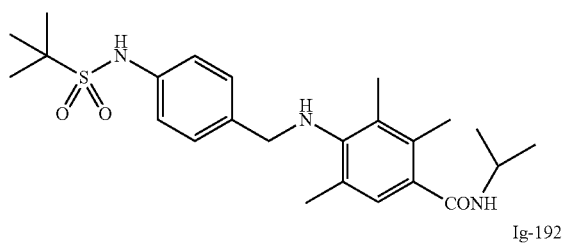

Ig-197
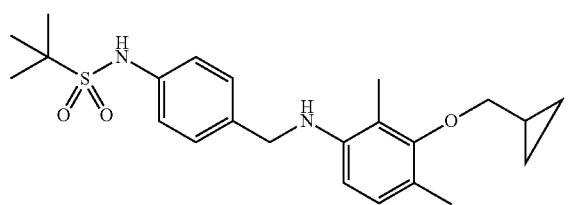
Ig-198
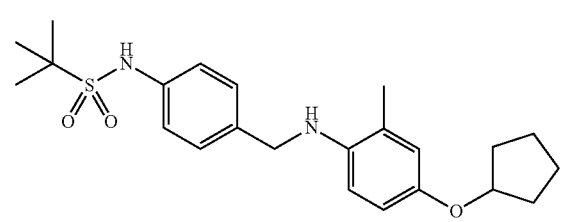
[Formula 154]
Ig-199
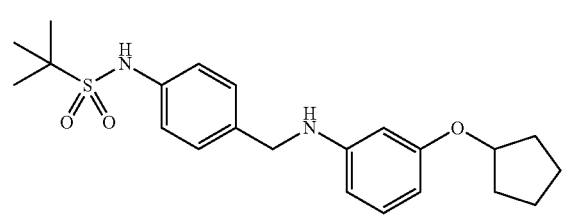
Ig-200
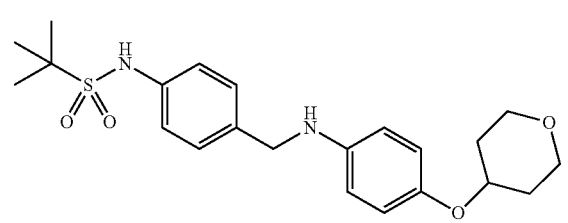
Ig-201
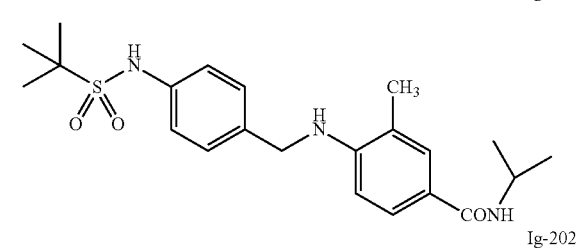
Ig-202
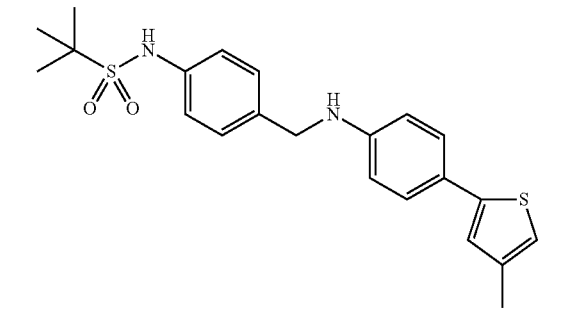
Ig-203
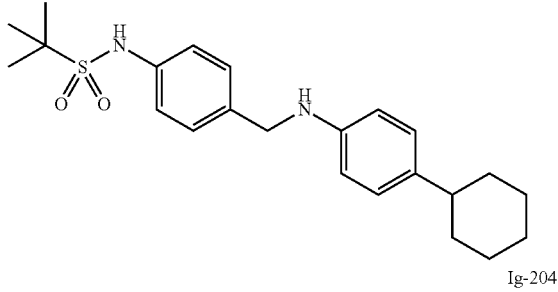
Ig-204
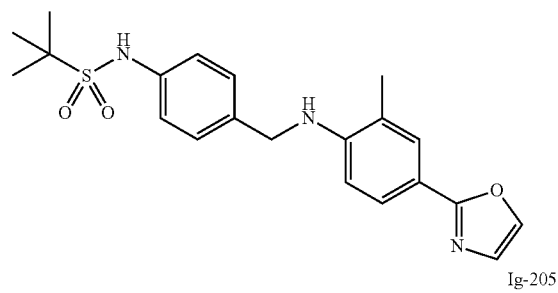
Ig-205
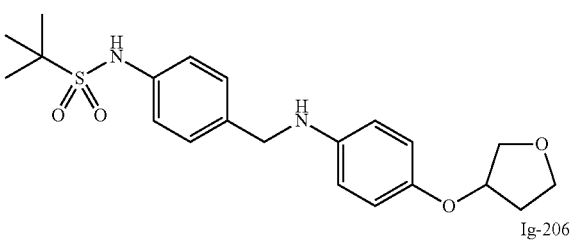
Ig-206
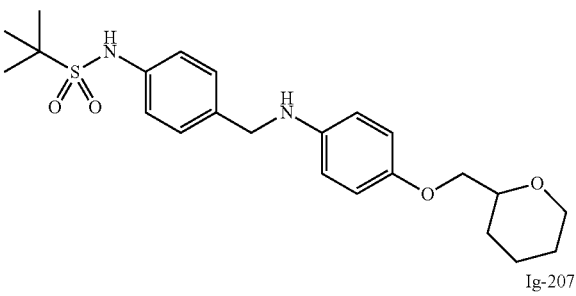
Ig-207
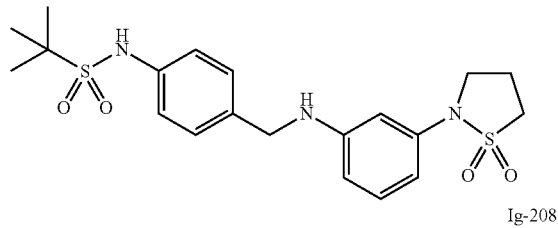
Ig-208
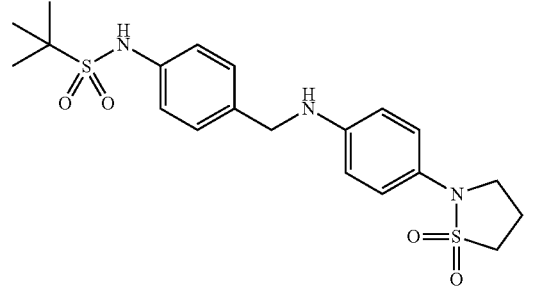

321
-continued
Ig-209
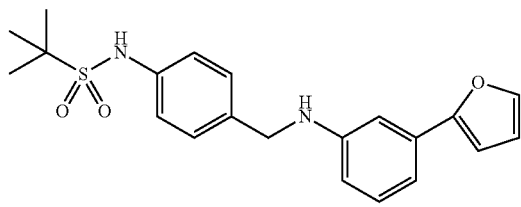
Ig-210
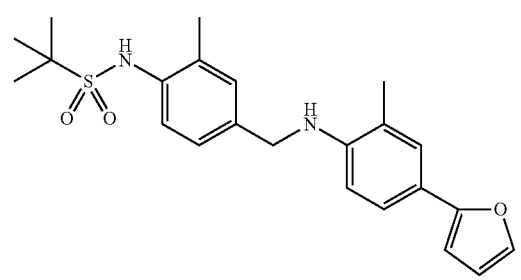
Ig-211
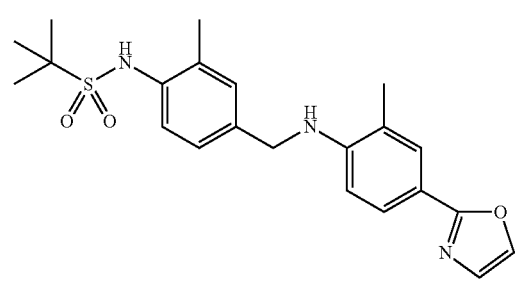
Ig-212
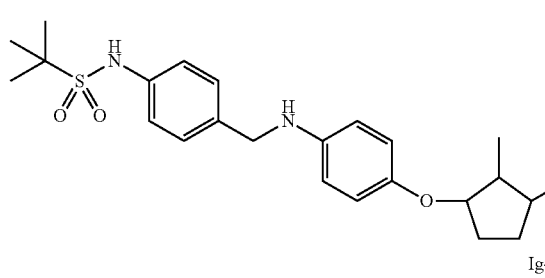
Ig-213
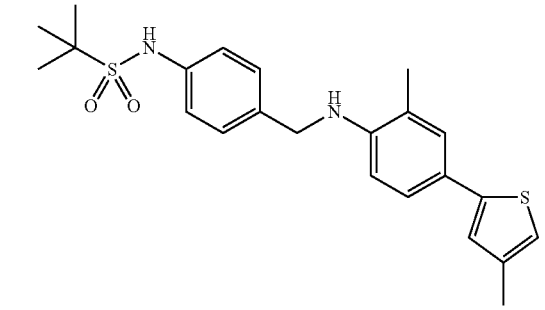
322
-continued
Ig-214
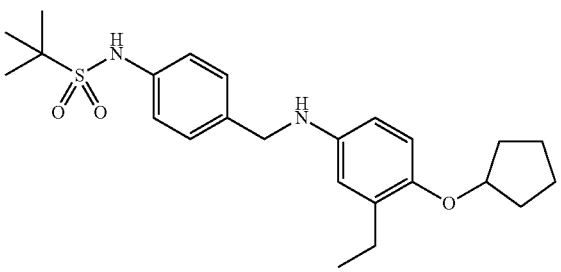
Ig-215
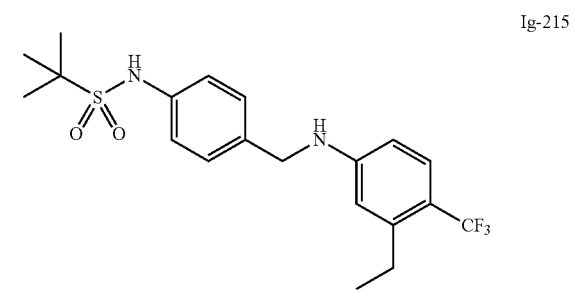
Ig-216
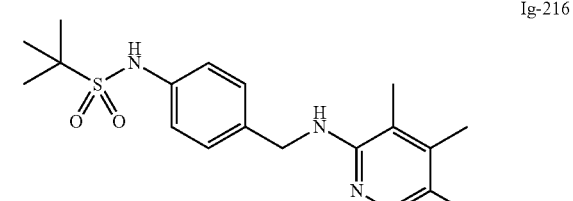
Ig-217
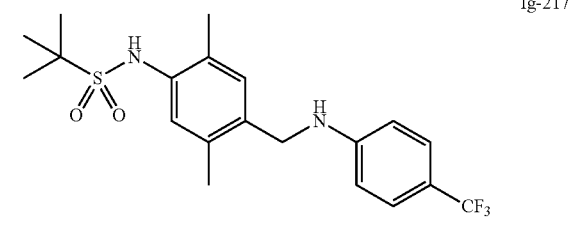
Ig-220
Ig-221
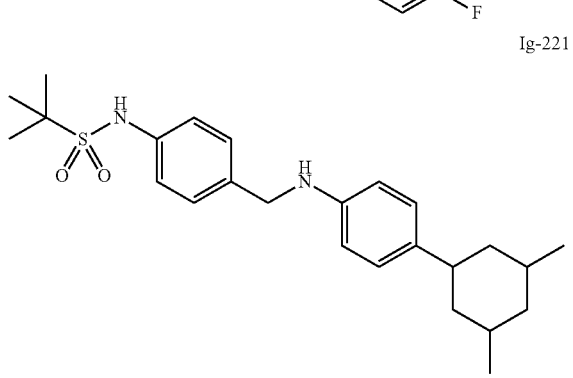

Ig-222
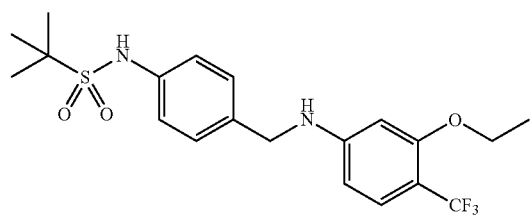
Ig-223
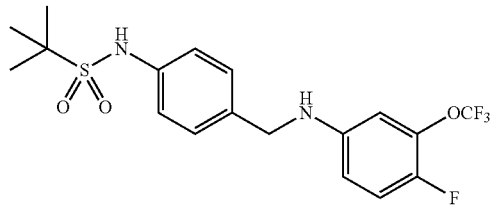
Ig-224
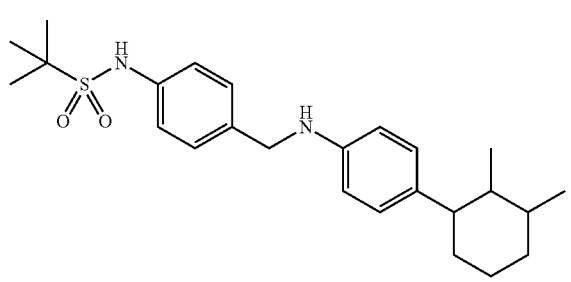
Ig-225
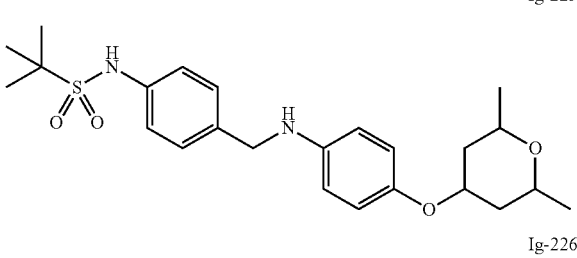
Ig-226
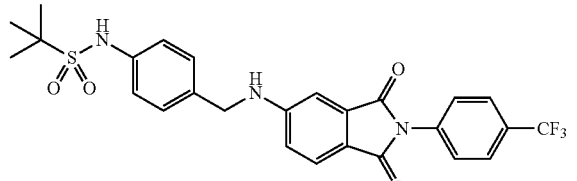
[Formula 155]
Ih-1
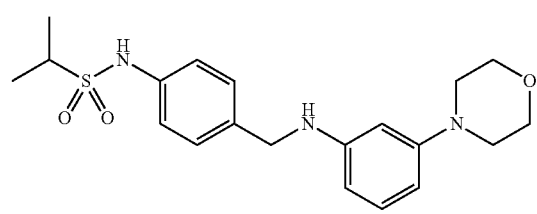
Ih-2
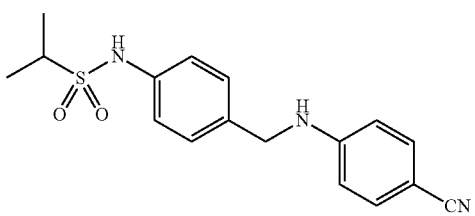
Ih-4
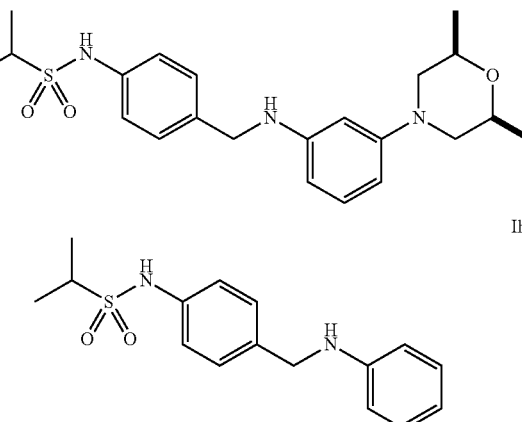
Ih-7
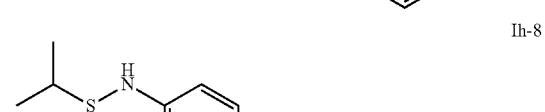
Ih-8
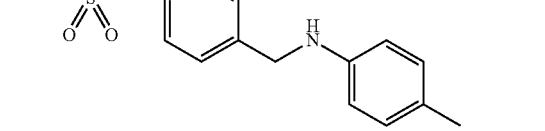
Ih-9
Ih-10
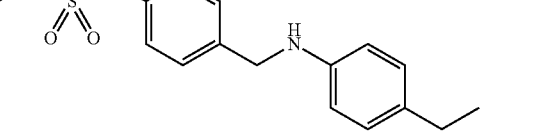
Ih-11

Ih-12
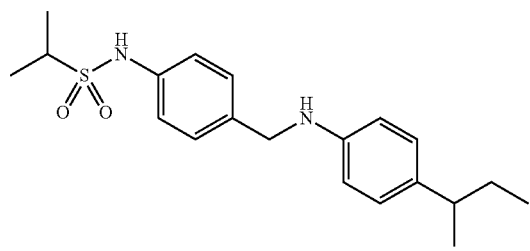
Ih-13
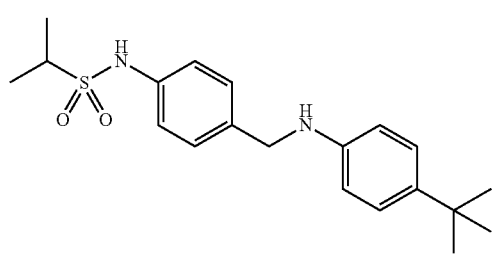
Ih-14
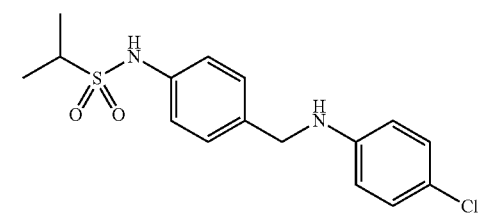
Ih-16
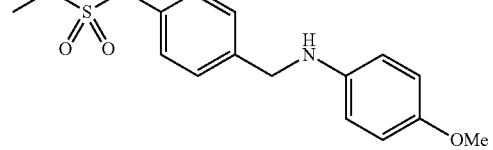
Ih-17
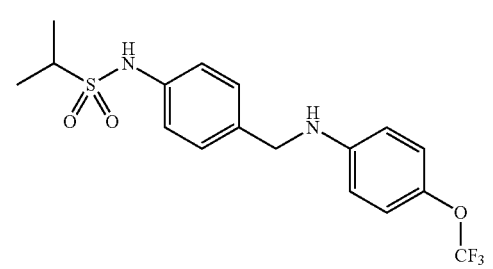
Ih-18
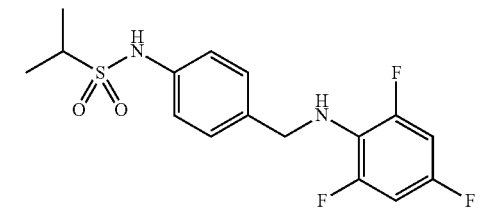
Ih-19
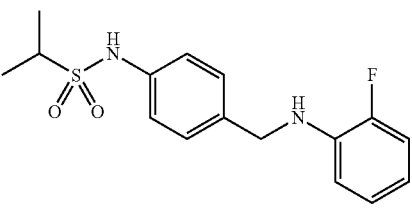
Ih-20
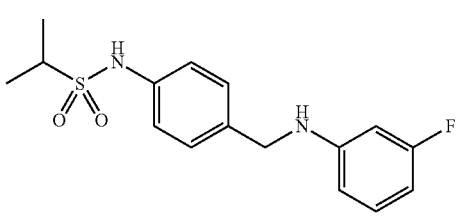
Ih-21
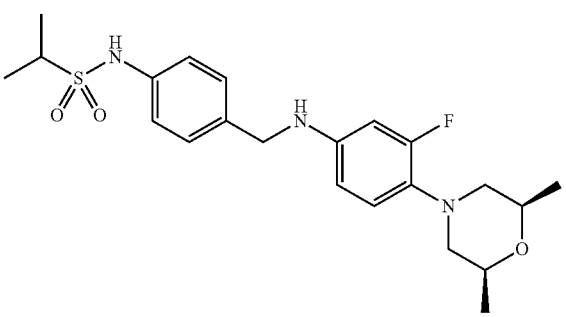
Ih-22
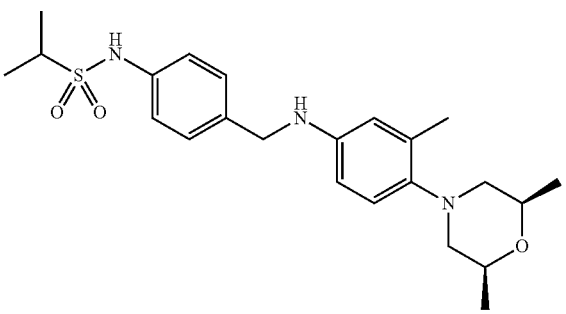
[Formula 156]
Ih-23
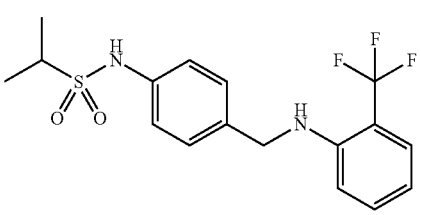
Ih-24

Ih-25
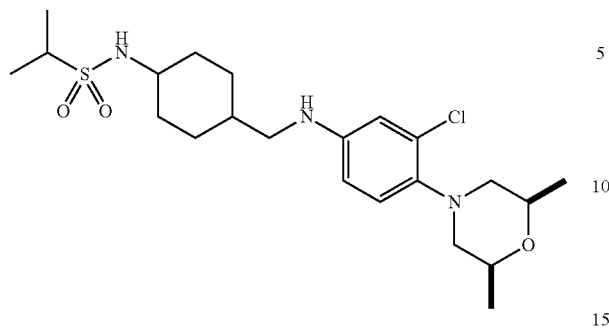
Ih-26
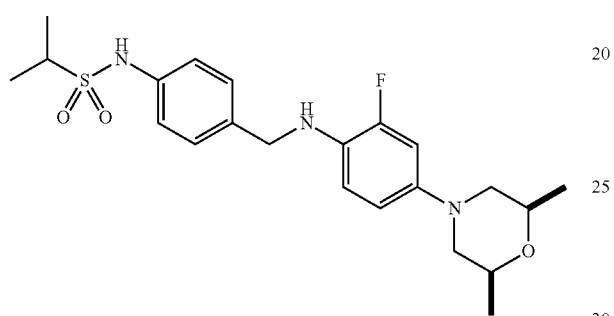
Ih-27
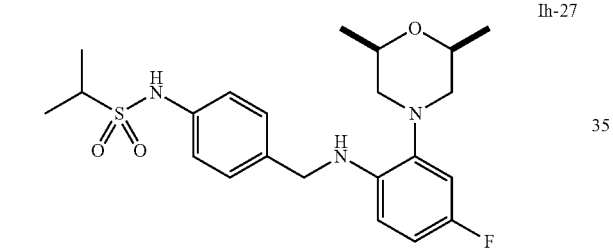
Ih-28
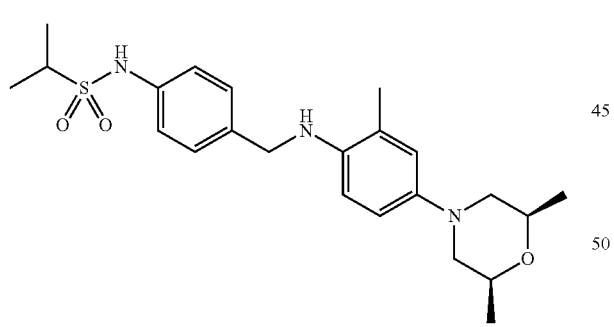
Ih-29
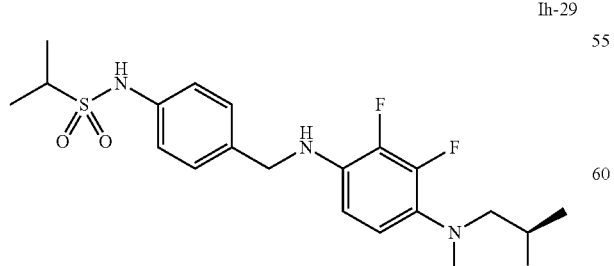
Ih-30
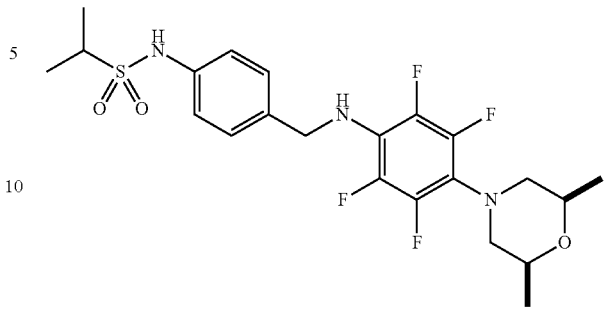
Ih-31
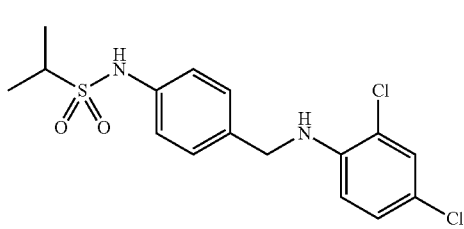
Ih-32
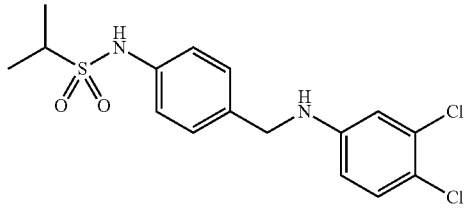
Ih-33
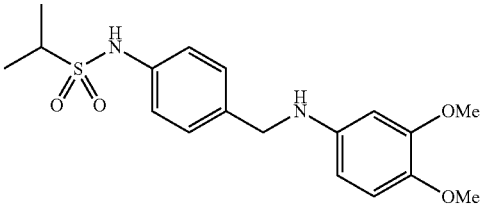
Ih-35
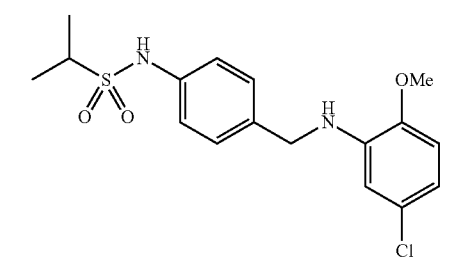
Ih-36

Ih-37
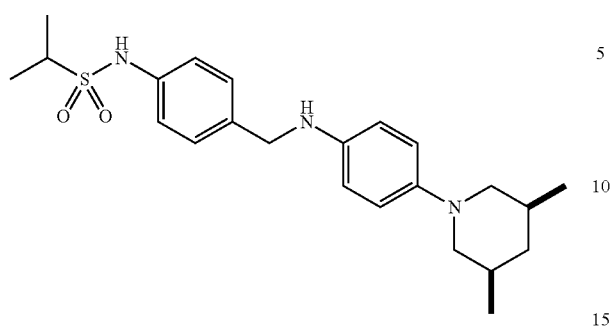
Ih-38
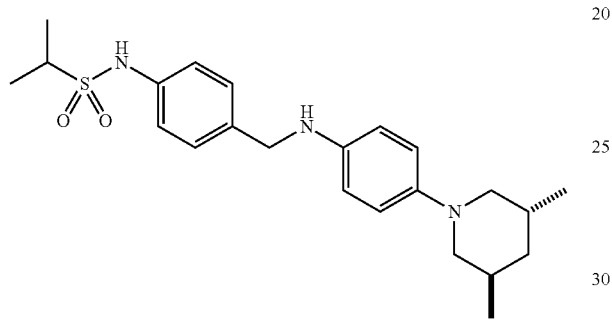
Ih-39
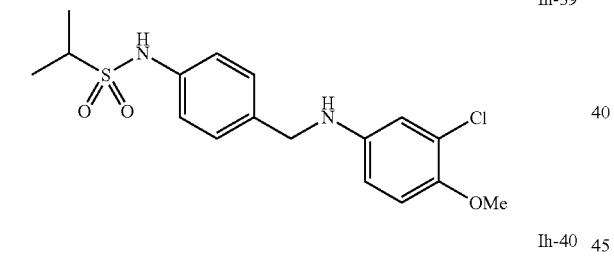
Ih-40
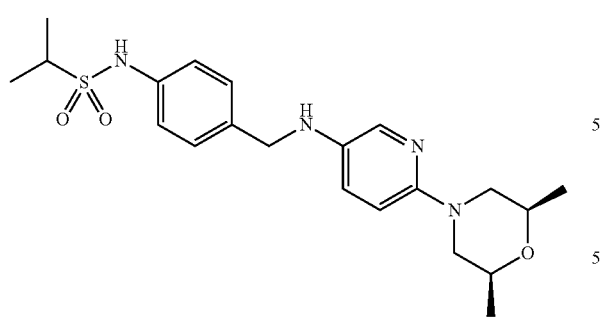
Ih-41
Ih-42
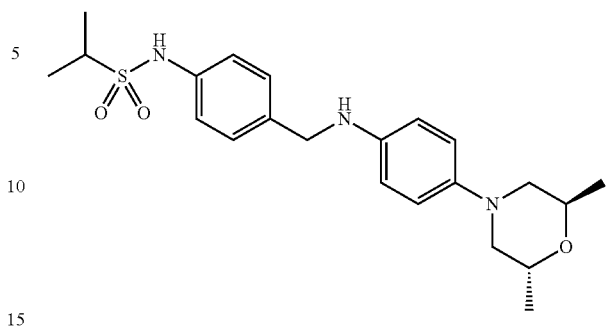
Ih-43
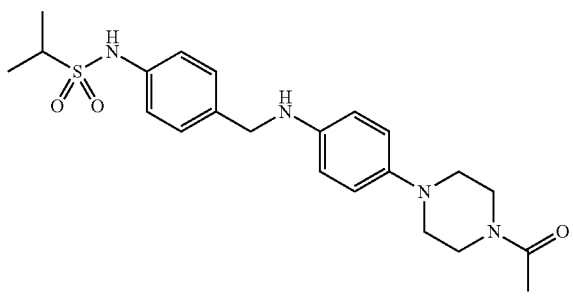
Ih-44
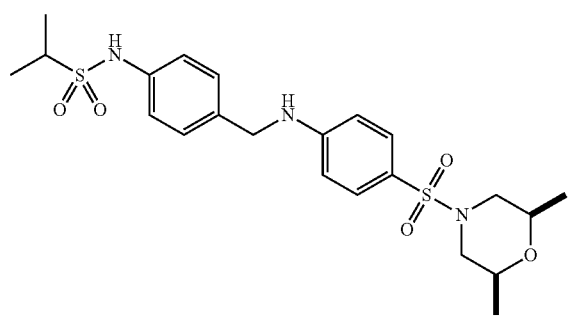
[Formula 157]
Ih-45
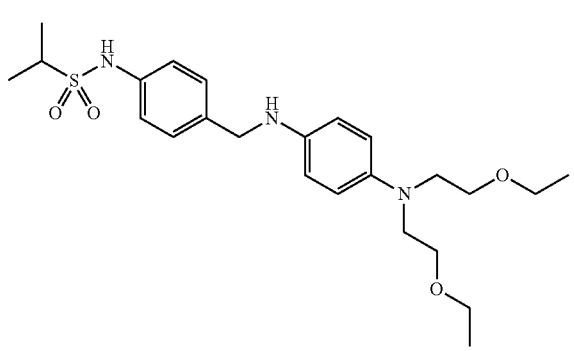

331
-continued
Ih-46
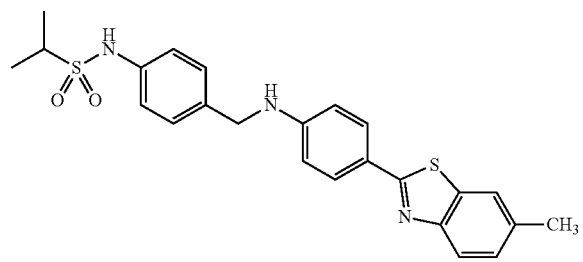
Ih-47
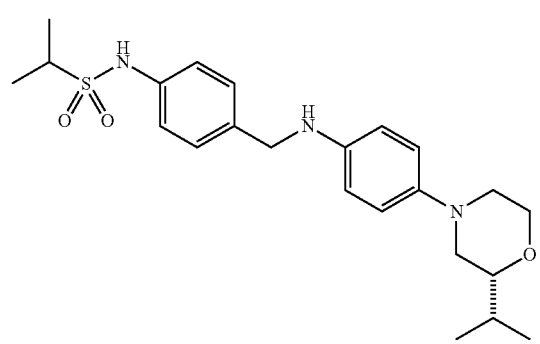
Ih-48
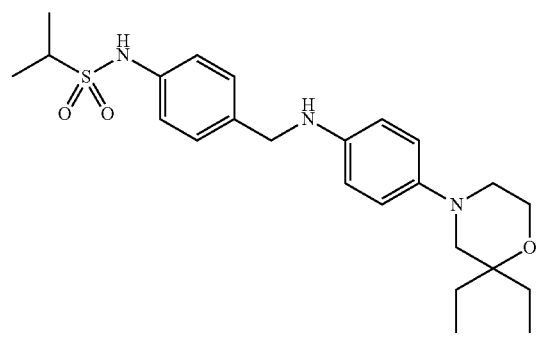
Ih-49
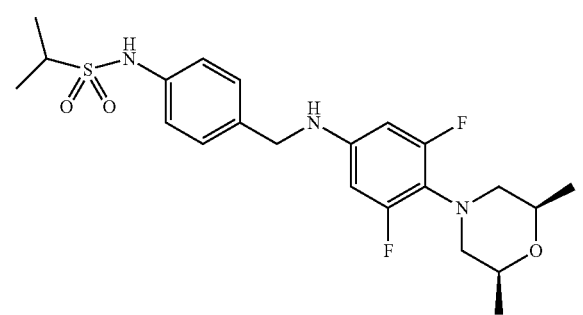
332
-continued
Ih-50
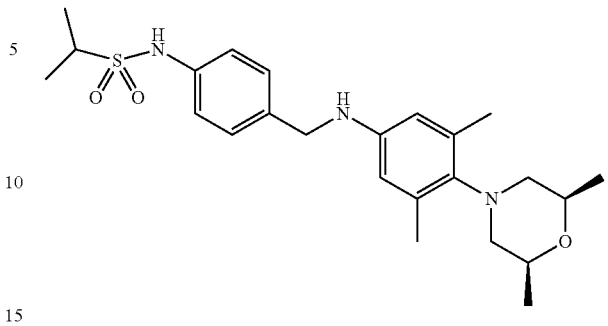
Ih-51
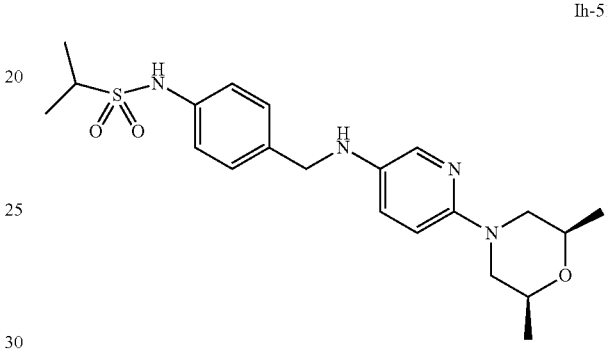
Ih-52
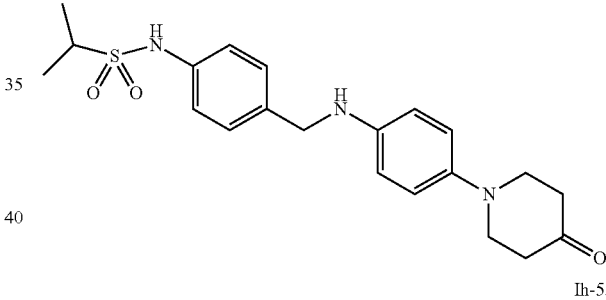
Ih-53
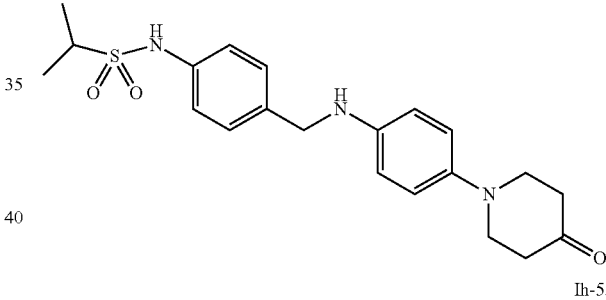
Ih-54
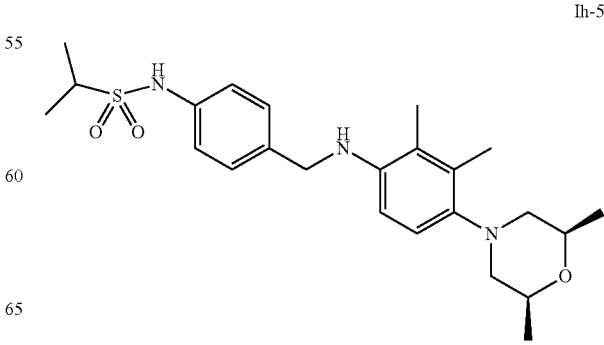

Ih-55
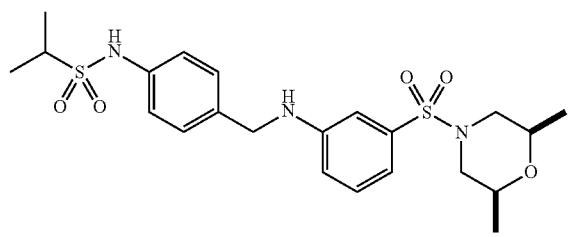
Ih-56
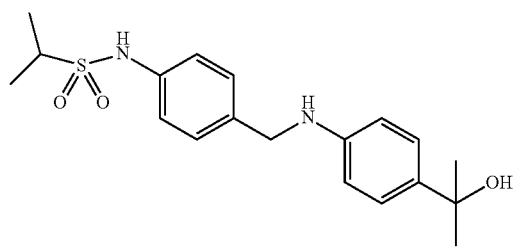
Ih-57
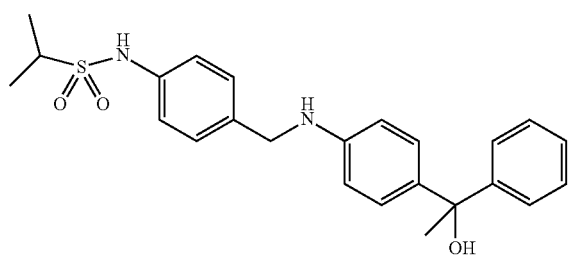
Ih-58
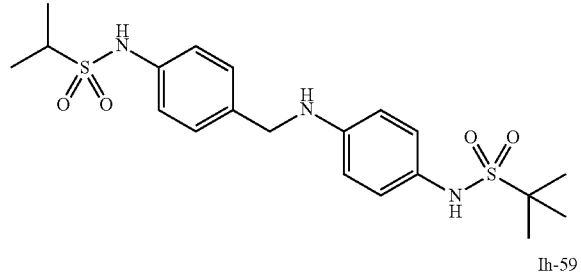
Ih-59
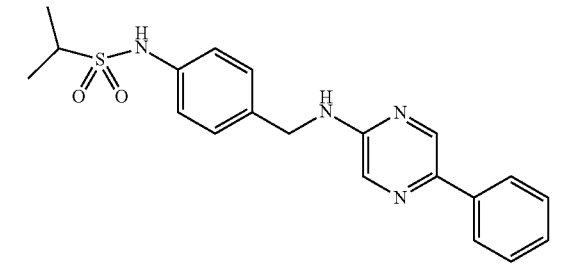
Ih-60
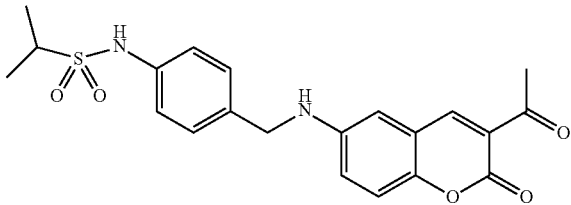
Ih-61
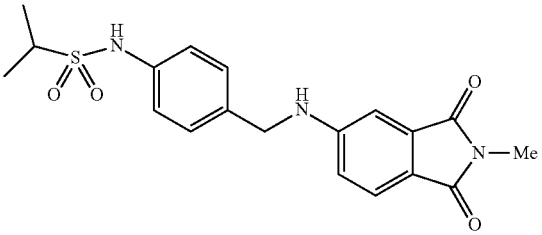
Ih-62
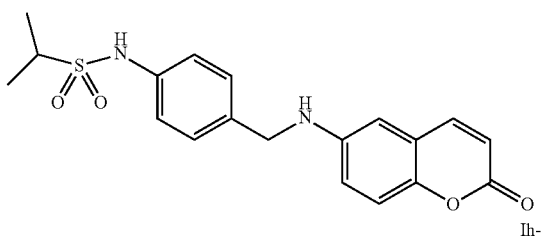
Ih-63
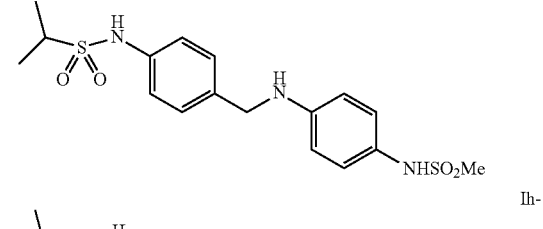
Ih-64
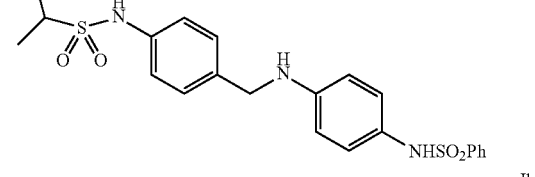
Ih-65
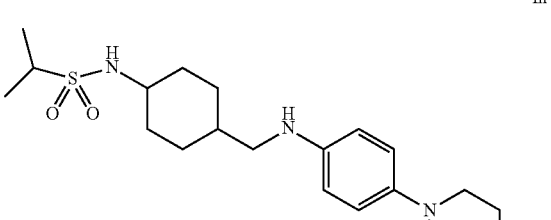
Ih-66

[Formula 158]
Ih-67
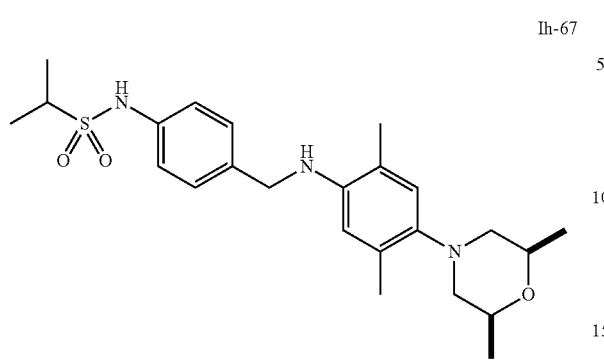
Ih-68
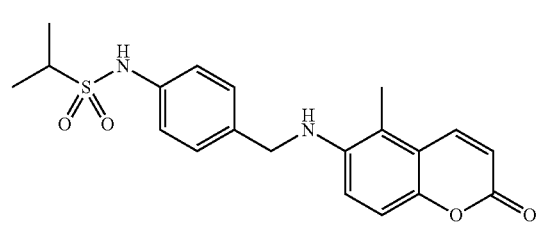
Ih-69
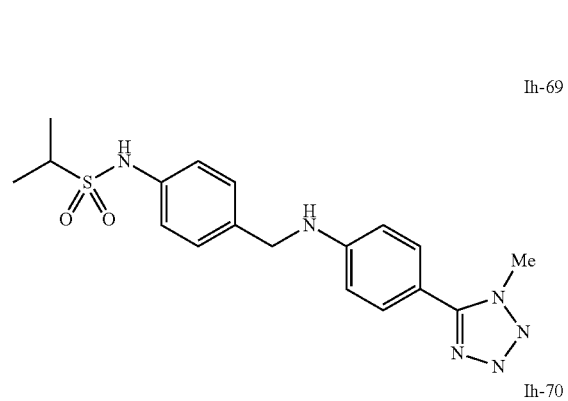
Ih-70
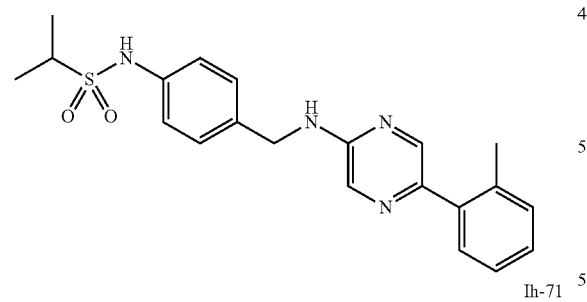
Ih-71
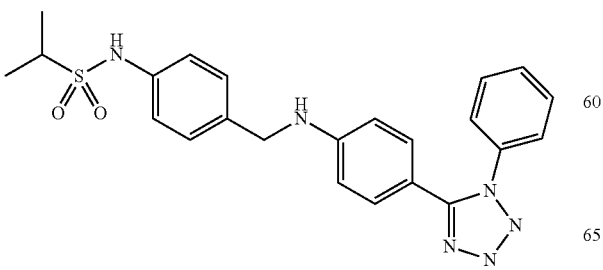
-continued
Ih-72
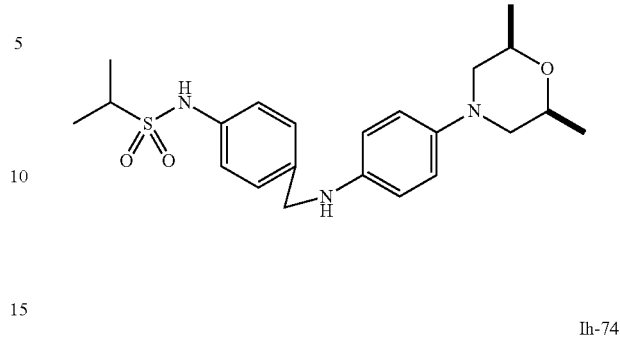
Ih-74
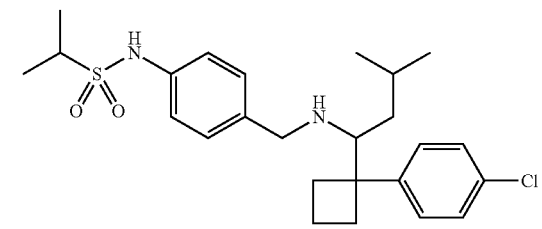
Ih-75
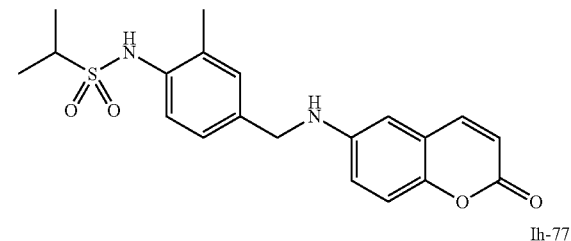
Ih-76
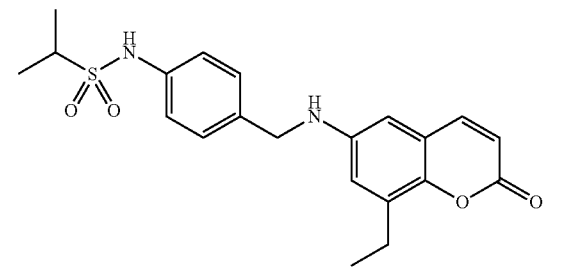
Ih-77

Ih-78
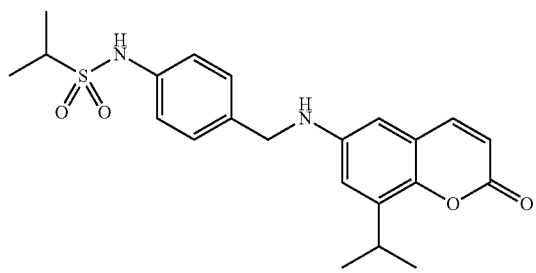
Ih-79
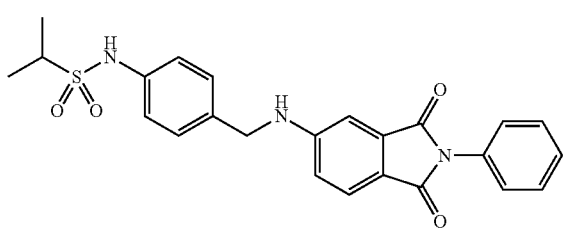
Ih-80
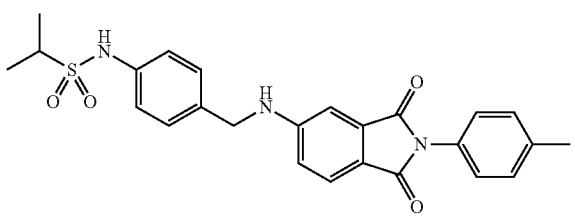
Ih-81
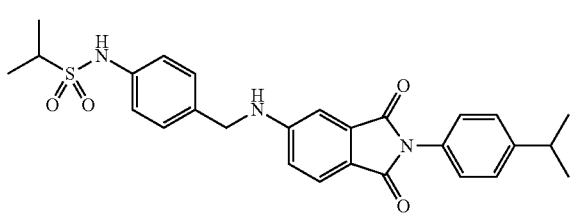
Ih-82
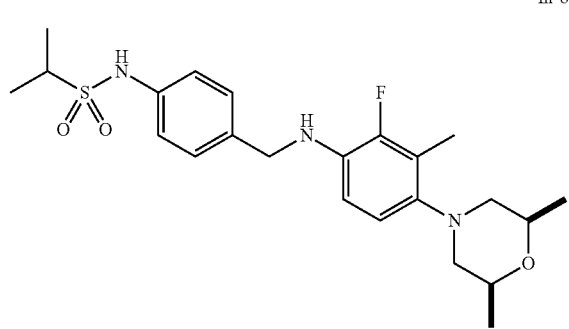
Ih-83
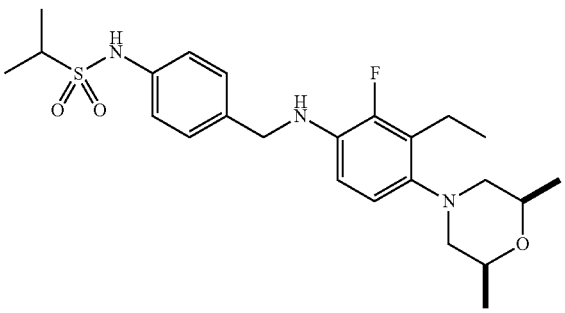
Ih-84
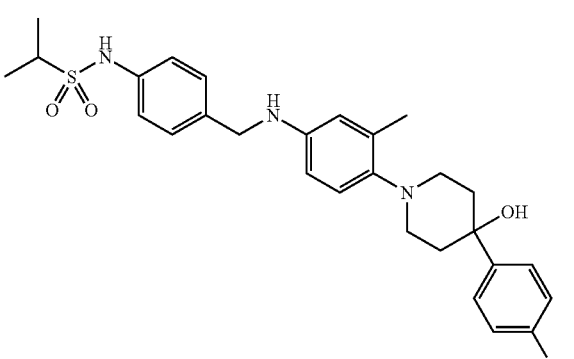
Ih-85
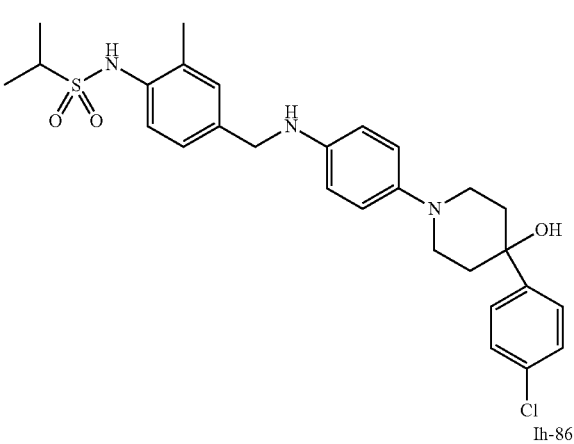
Ih-86
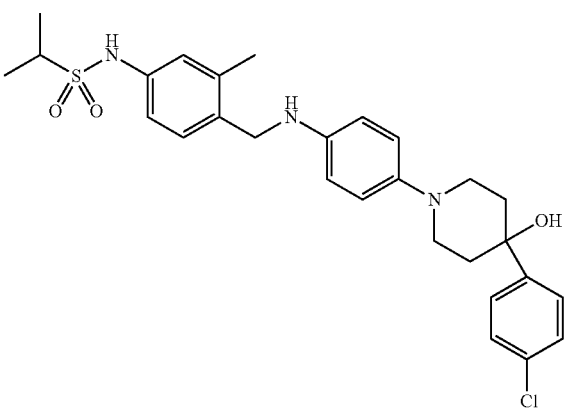

Ih-87
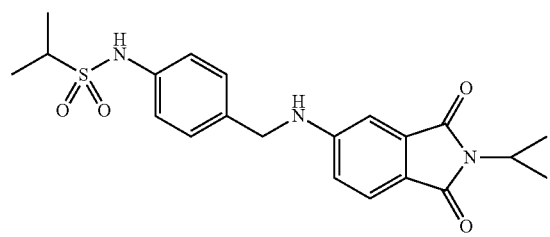
Ih-88
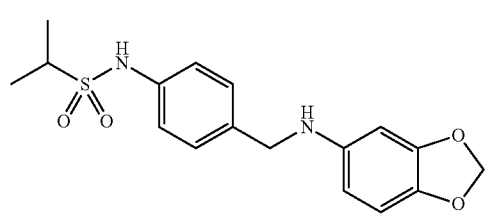
[Formula 159]
Ih-89
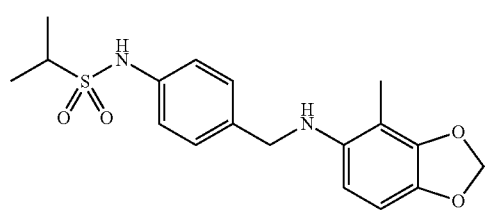
Ih-90
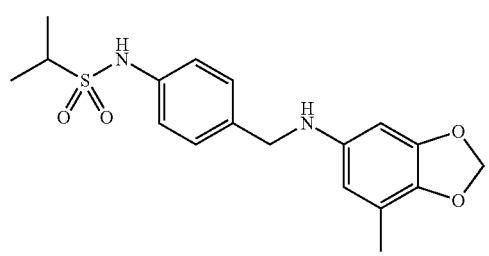
Ih-91
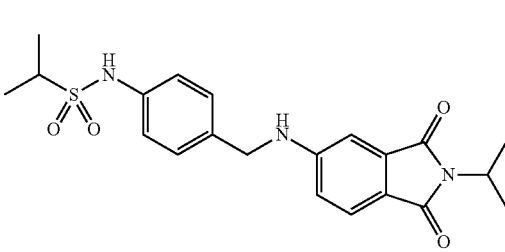
Ih-92
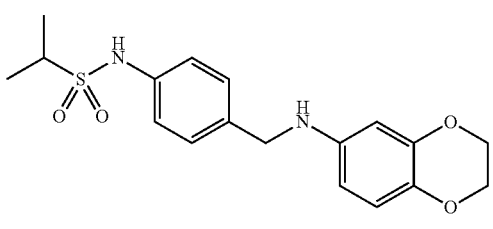
Ih-93
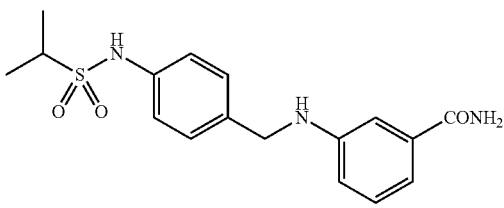
Ih-94
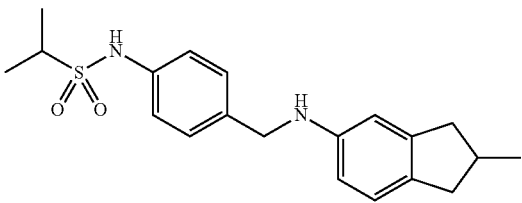
Ih-95
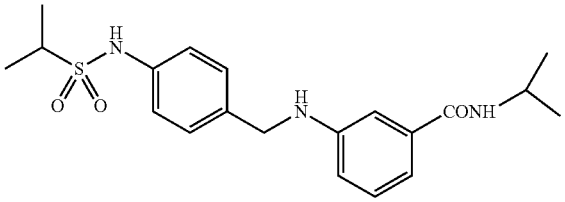
Ih-96
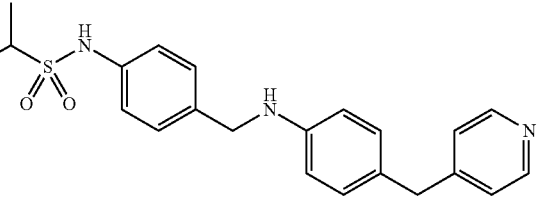
Ih-97
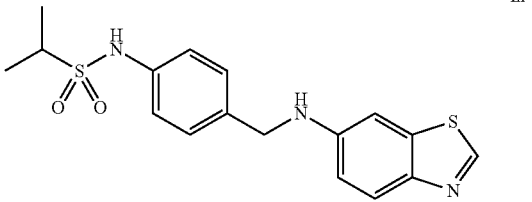
Ih-98
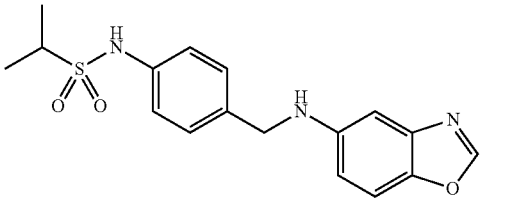
Ih-99
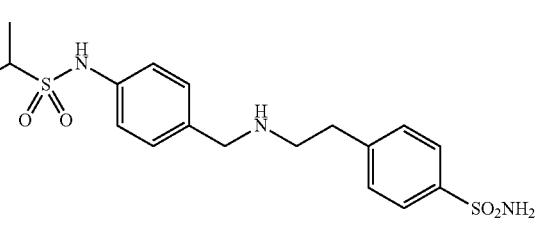

Ih-100
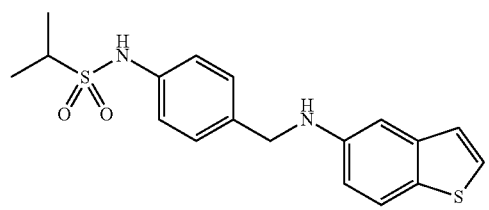
Ih-101
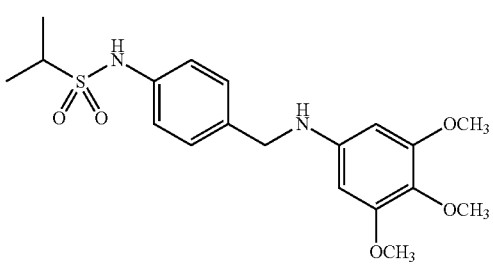
Ih-102
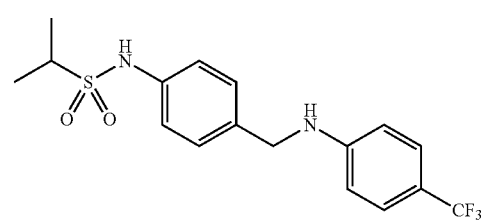
Ih-103
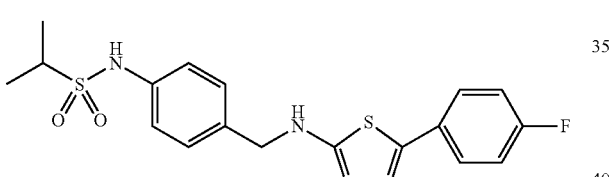
Ih-104
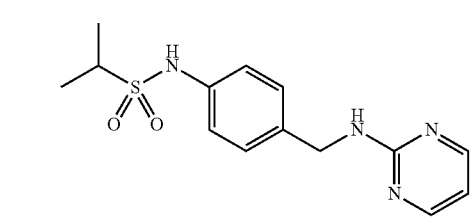
Ih-105
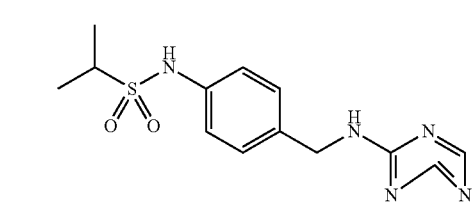
Ih-106
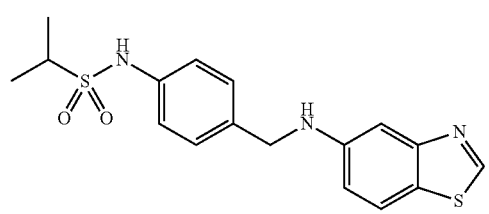
Ih-107
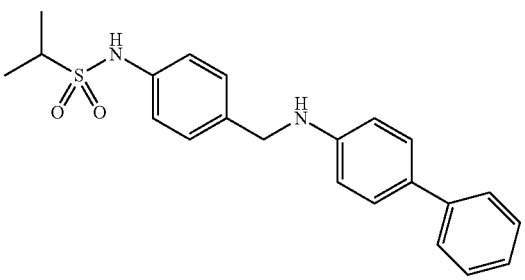
Ih-108
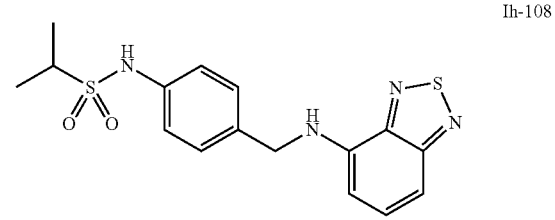
Ih-109
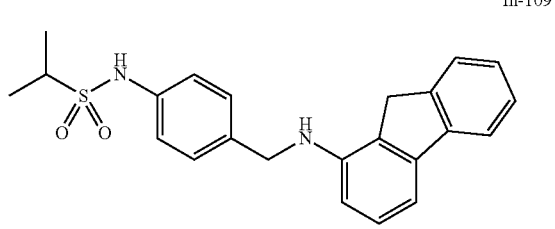
Ih-110
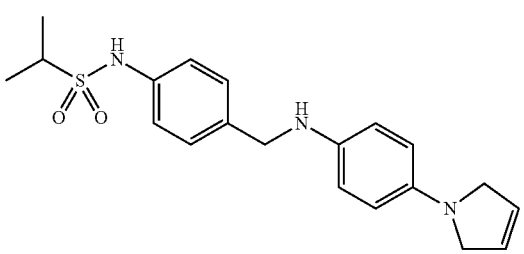
[Formula 160]
Ih-111
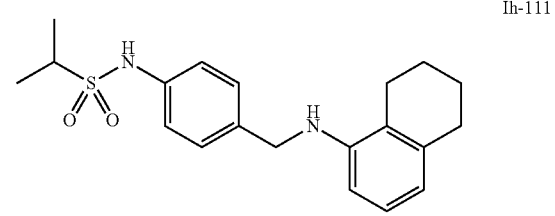

Ih-112
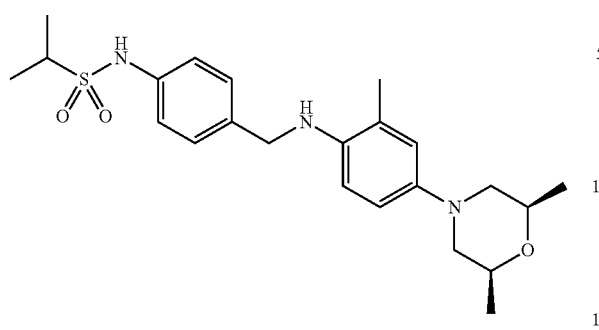
Ih-118
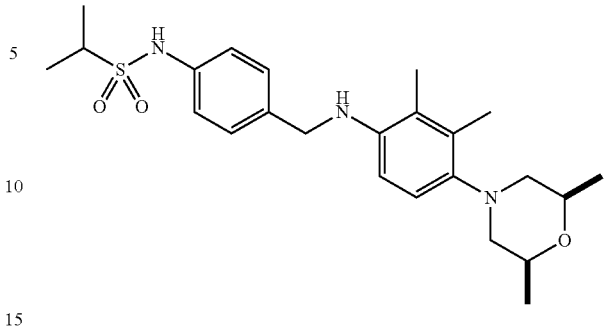
Ih-113
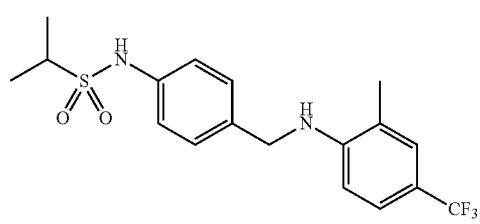
Ih-119
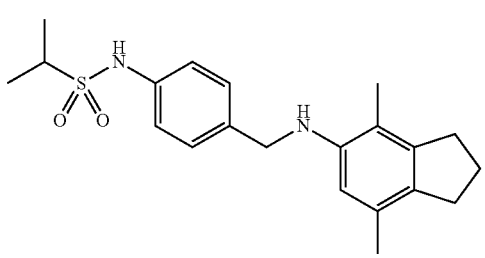
Ih-114
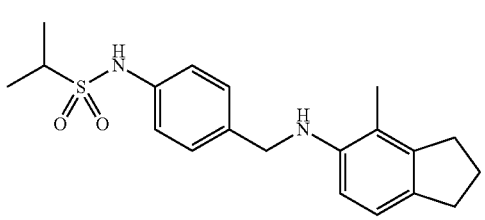
Ih-120
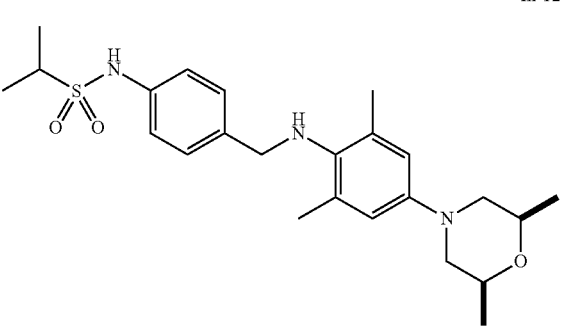
Ih-115
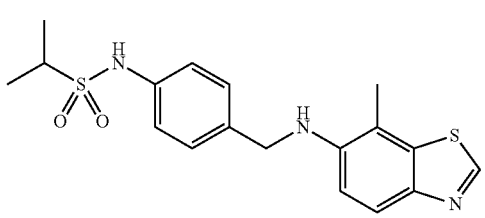
Ih-116
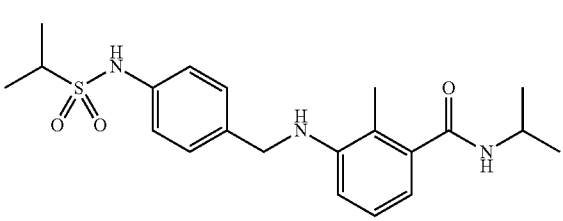
Ih-121
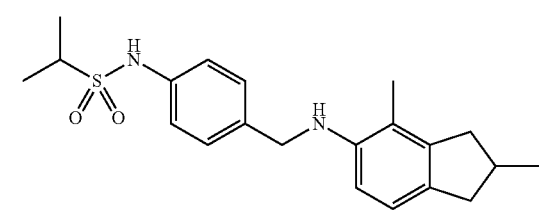
Ih-117
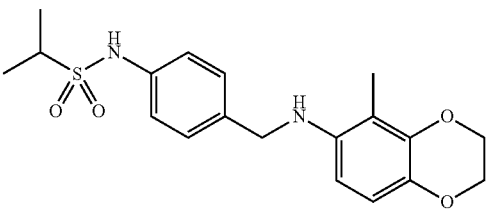
Ih-122
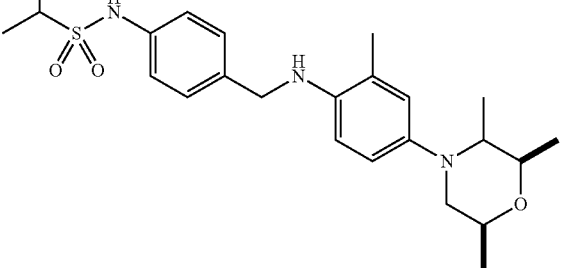

Ih-123
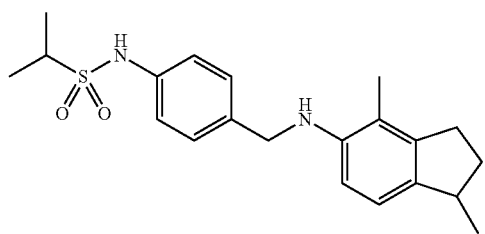
Ih-124
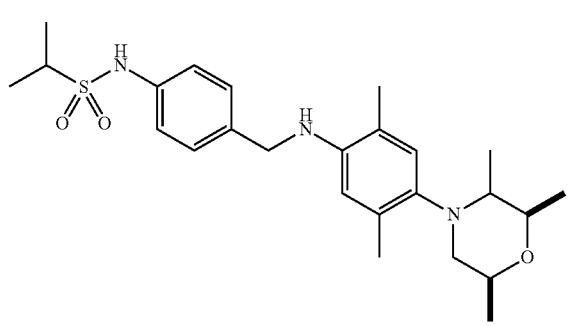
Ih-125
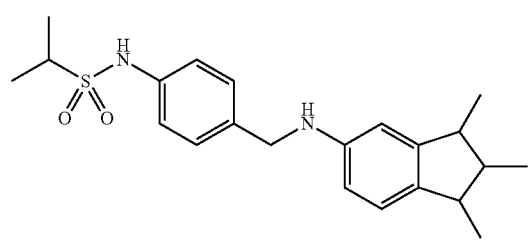
Ih-126
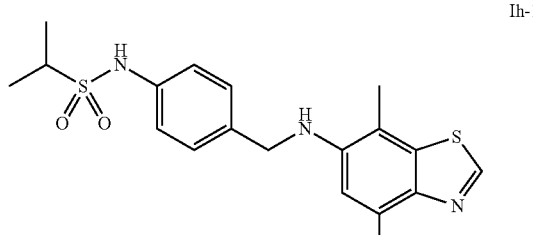
Ih-127
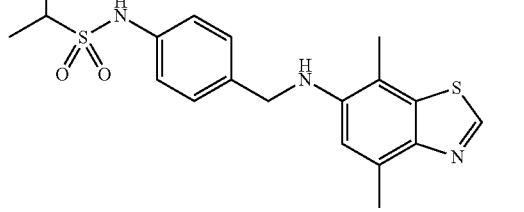
Ih-128
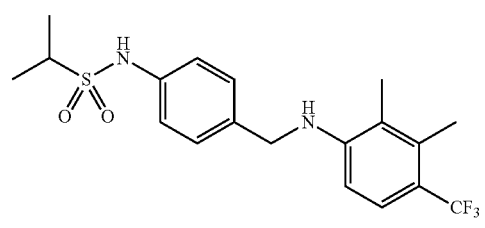
Ih-129
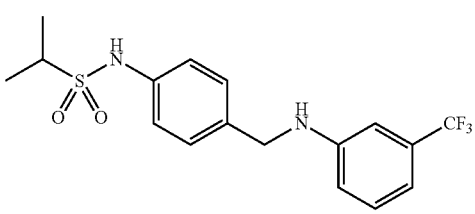
Ih-130
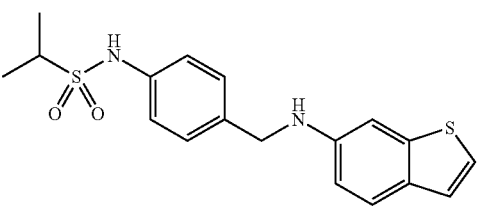
Ih-131
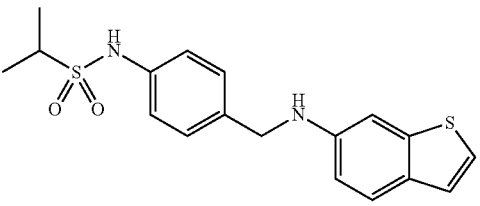
Ih-132
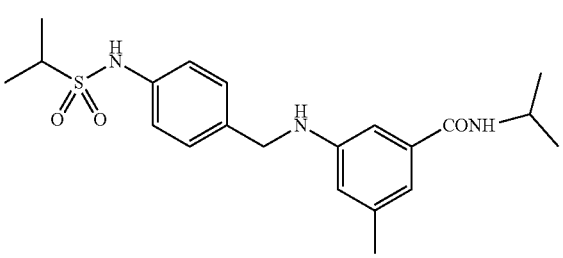
[Formula 161]
Ih-133
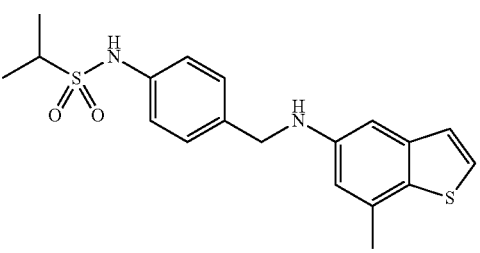
Ih-134
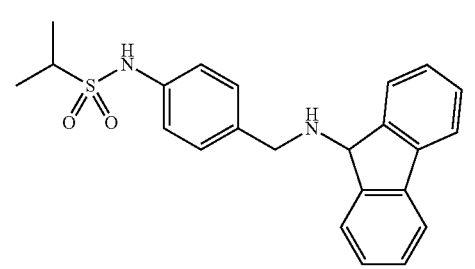

Ih-135
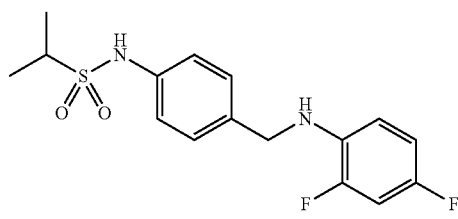
Ih-136
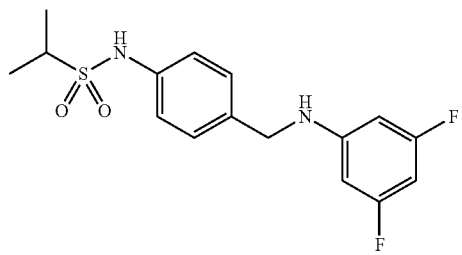
Ih-137
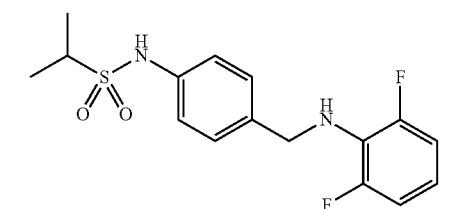
Ih-138
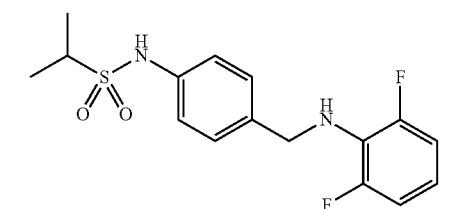
Ih-139
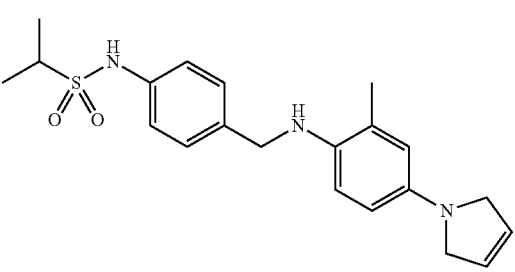
Ih-140
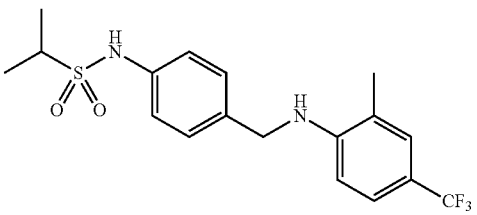
Ih-141
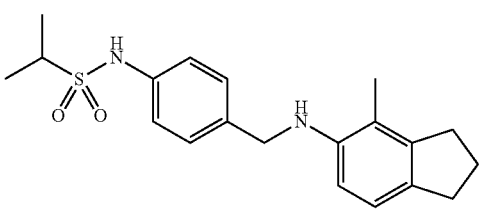
Ih-142
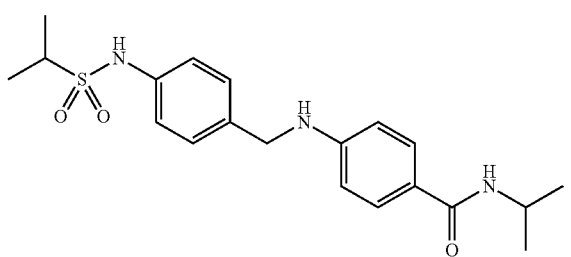
Ih-143
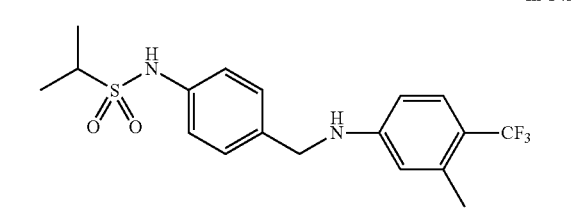
Ih-144
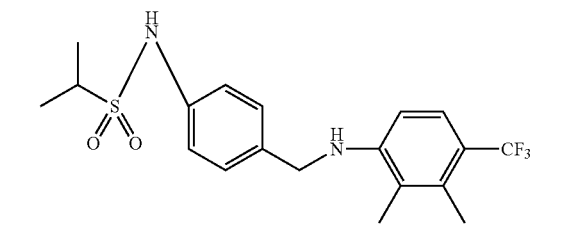
Ih-145
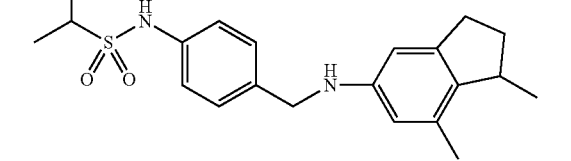
Ih-146
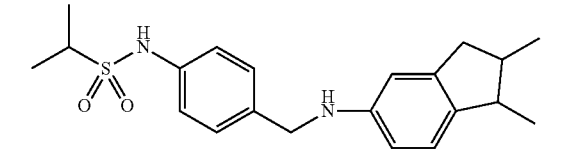
Ih-147
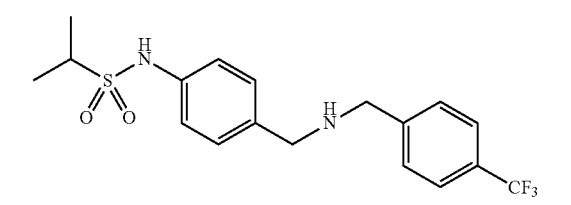
Ih-148
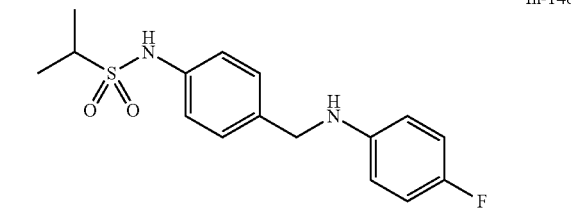

Ih-149
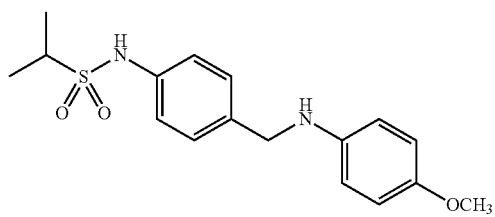
Ih-150
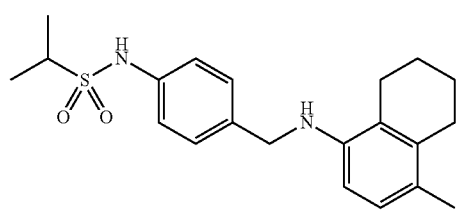
Ih-151
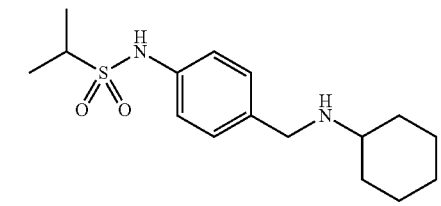
Ih-152
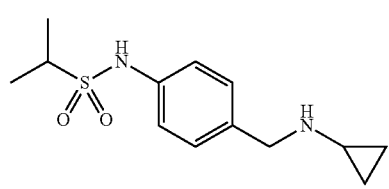
Ih-153
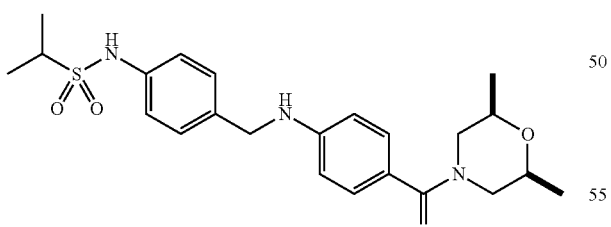
Ih-154
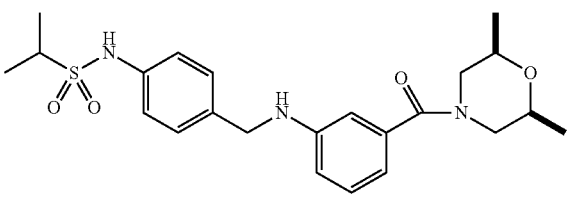
[Formula 162]
Ih-155
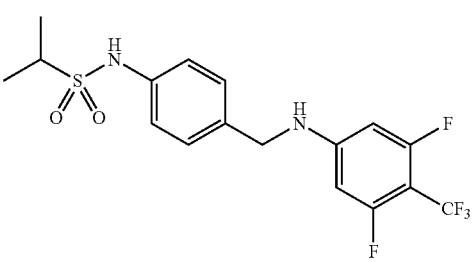
Ih-156
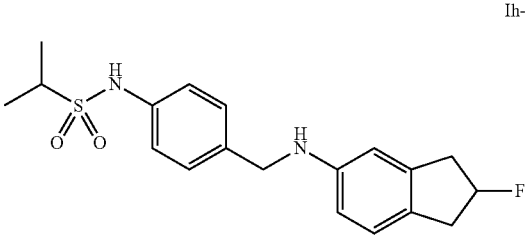
Ih-157
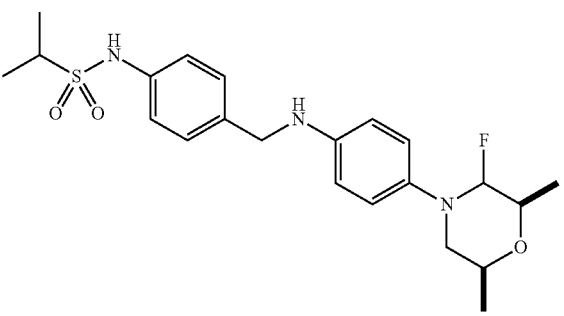
Ih-158
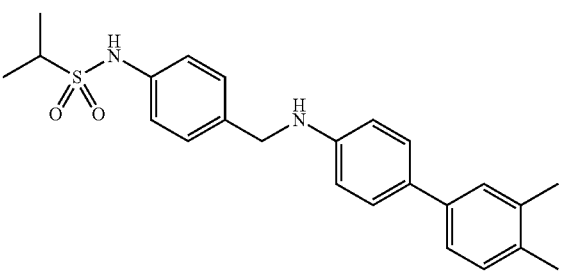
Ih-159
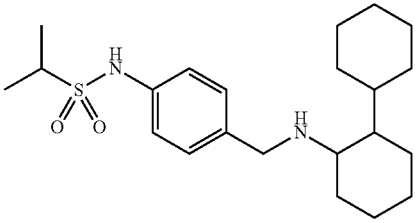
Ih-160
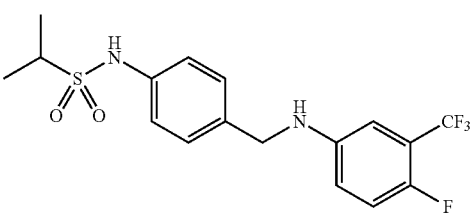

-continued
Ih-161
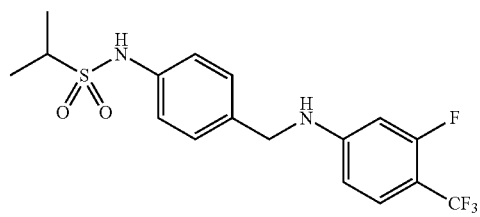
Ih-162
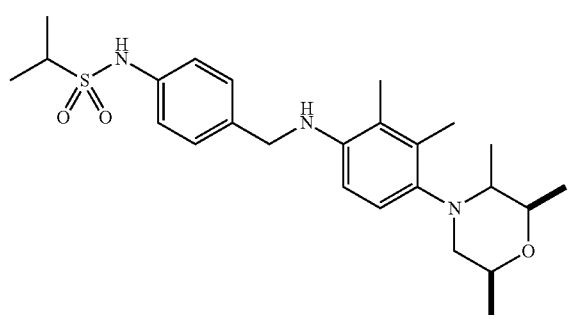
Ih-163
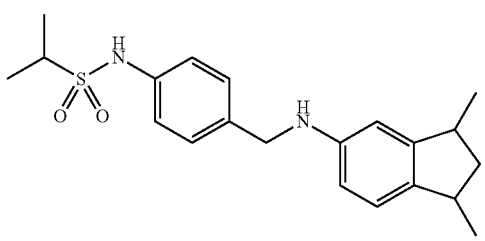
Ih-164
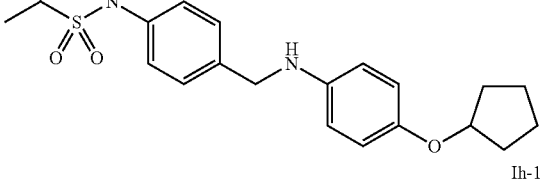
Ih-165
Ih-166
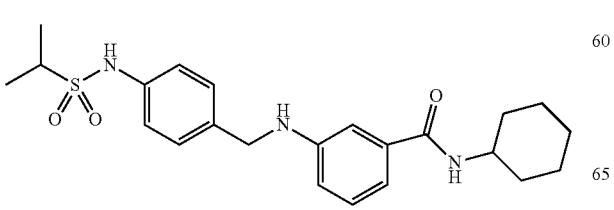
-continued
Ih-167
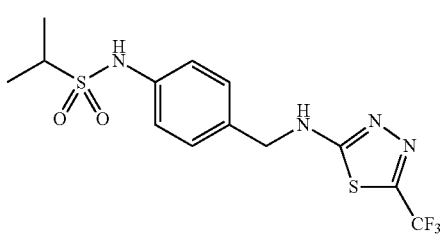
Ih-168
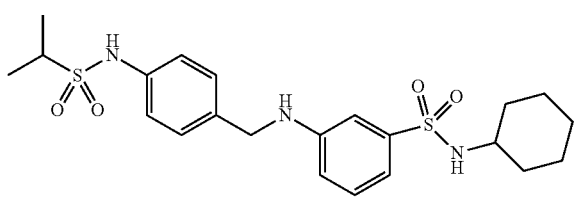
Ih-169
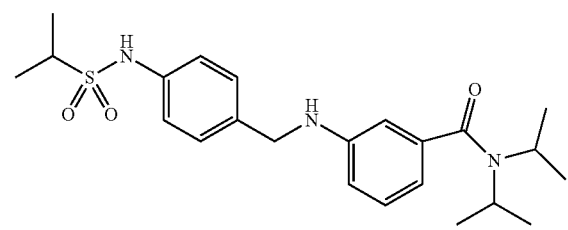
Ih-171
Ih-172
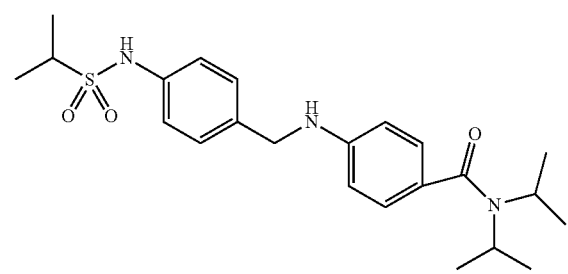
Ih-173
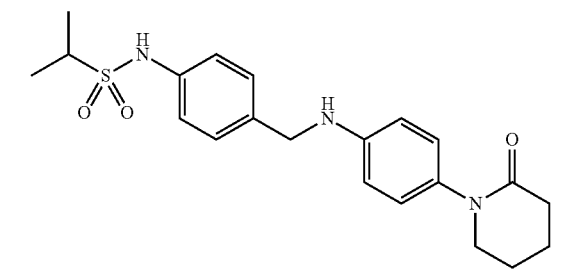

Ih-174
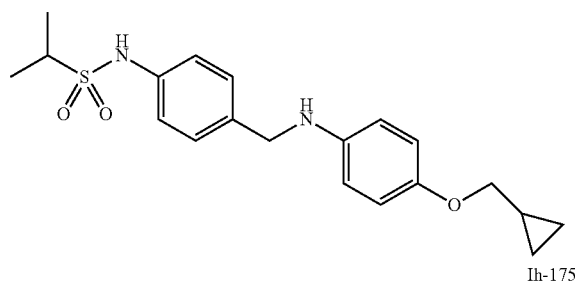
Ih-175
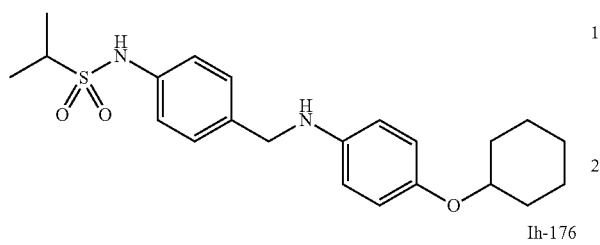
Ih-176
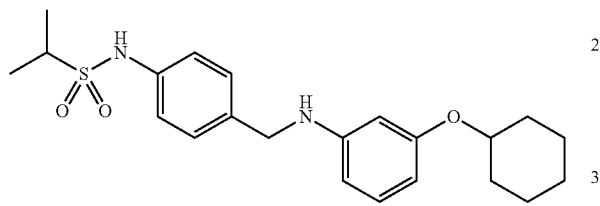
[Formula 163]
Ih-177
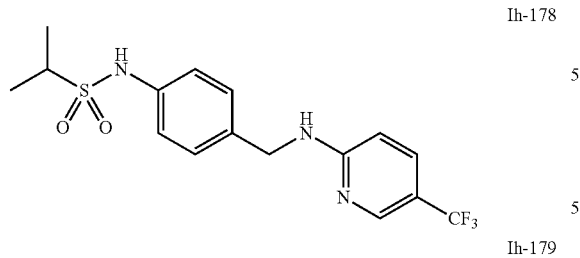
Ih-178
Ih-179
Ih-180
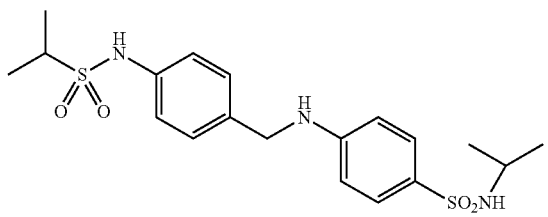
Ih-181
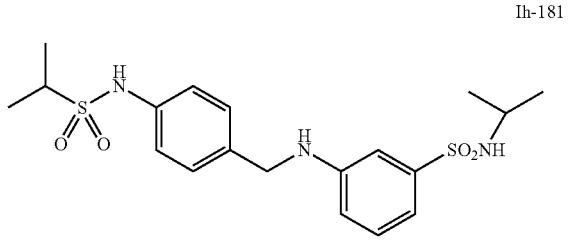
Ih-182
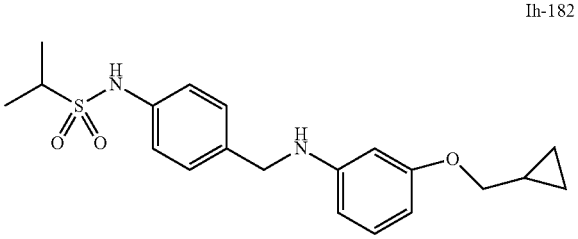
Ih-183
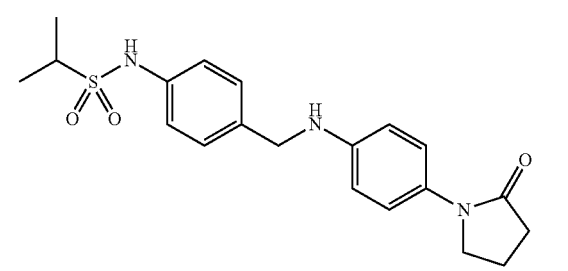
Ih-184
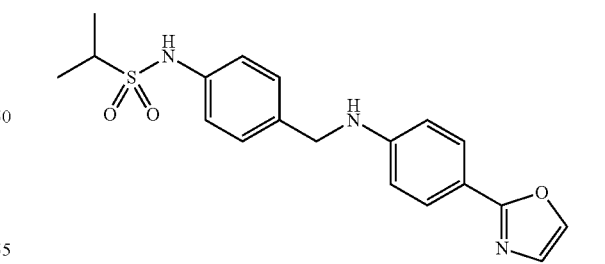
Ih-185
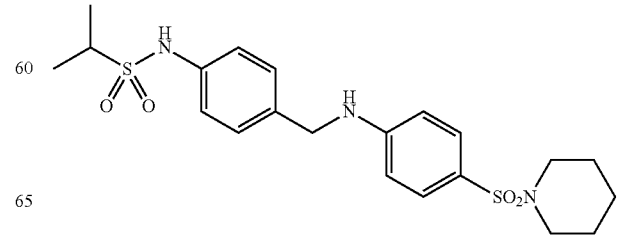

Ih-186
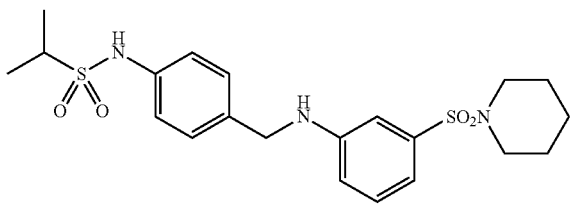
Ih-187
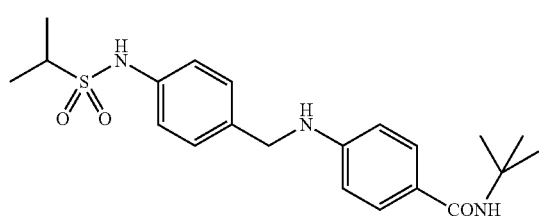
Ih-188
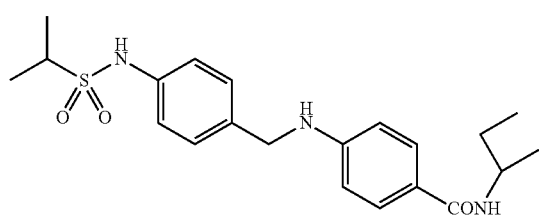
Ih-189
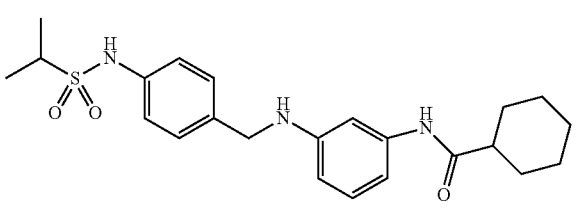
Ih-190
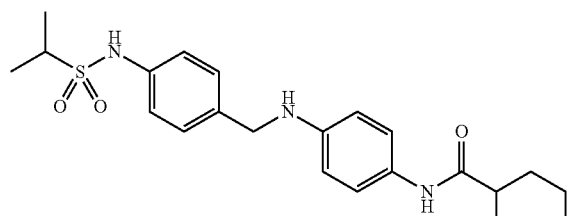
Ih-191
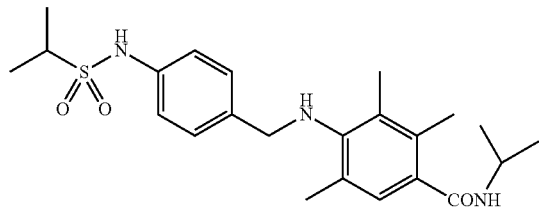
Ih-192
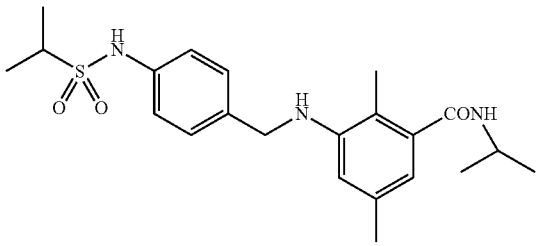
Ih-193
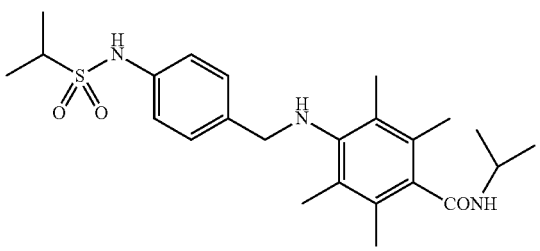
Ih-194
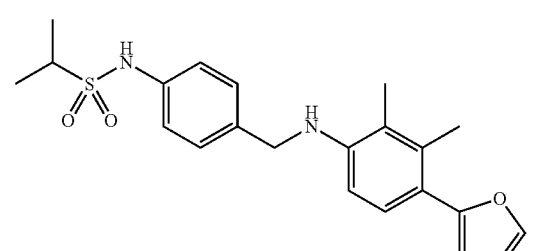
Ih-195
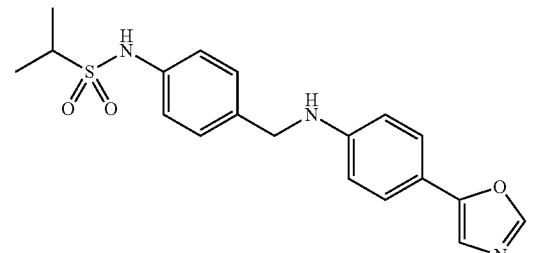
Ih-196
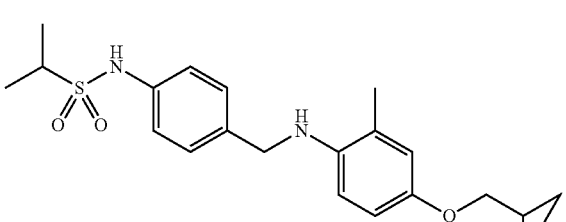
Ih-197
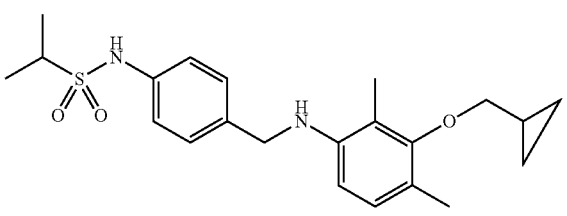

Ih-198
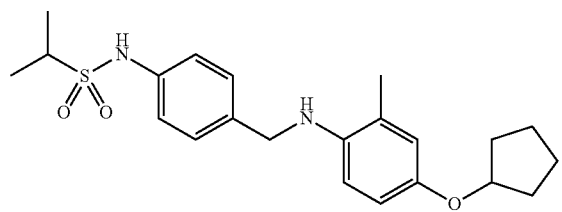
[Formula 164]
Ih-199
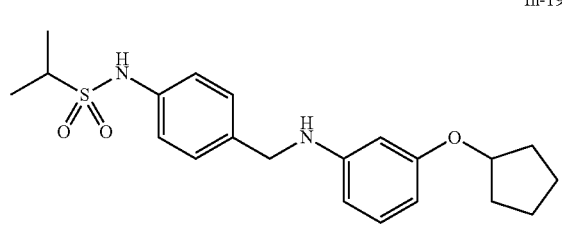
Ih-200
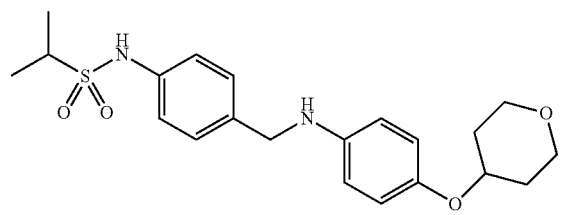
Ih-201
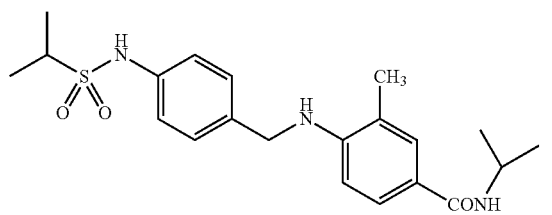
Ih-202
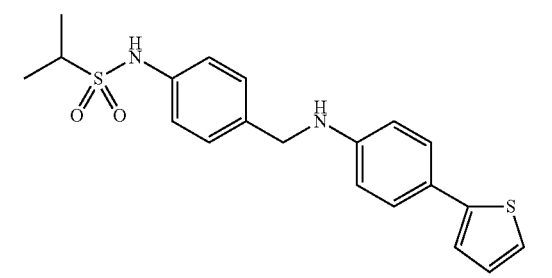
Ih-203
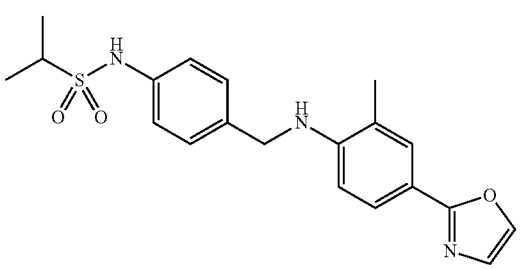
Ih-204
Ih-205
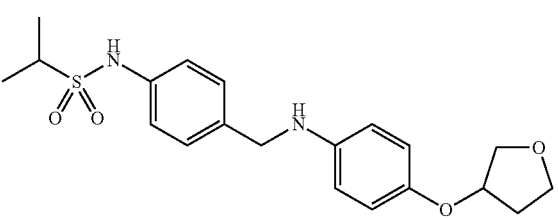
Ih-206
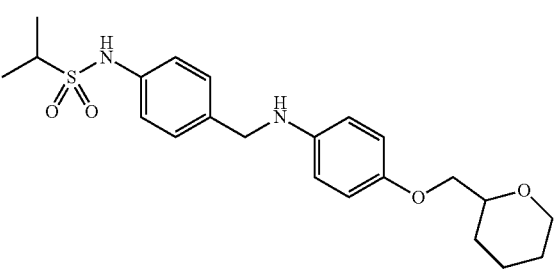
Ih-207
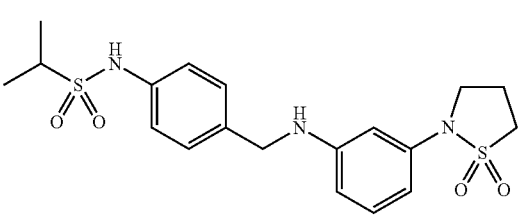

| 359 -continued | 360 -continued |
|---|---|
| Ih-208 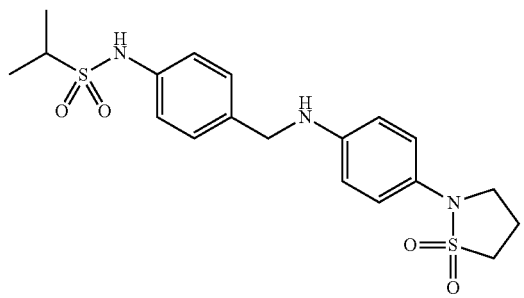 | Ih-213 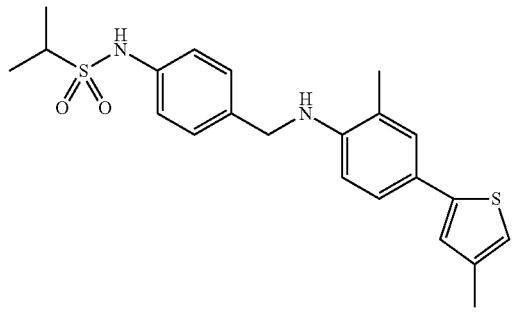 |
| Ih-209 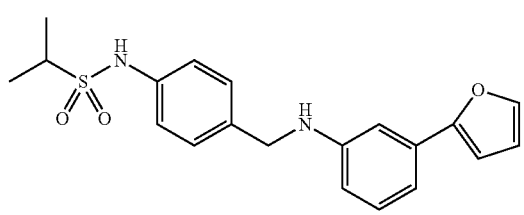 | Ih-214 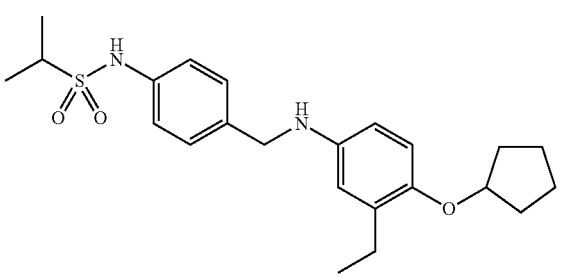 |
| Ih-210 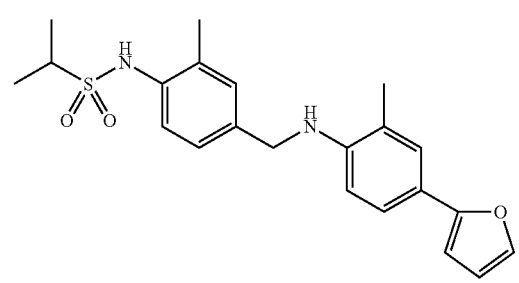 | Ih-215 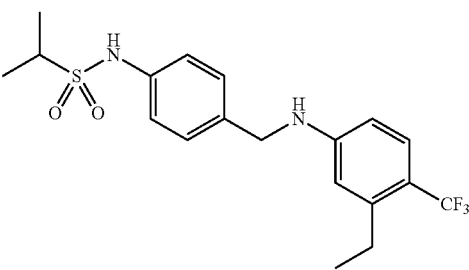 |
| Ih-211 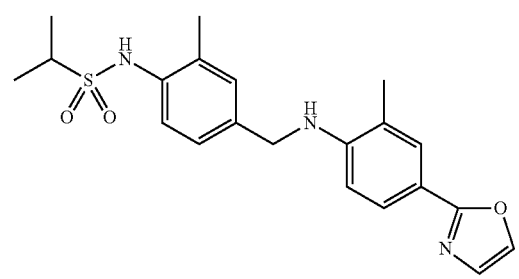 | Ih-216 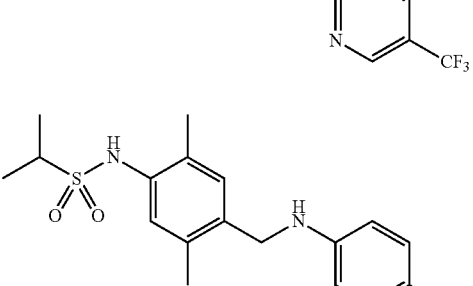 |
| Ih-212 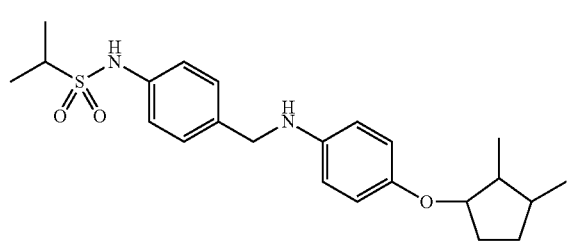 | Ih-219 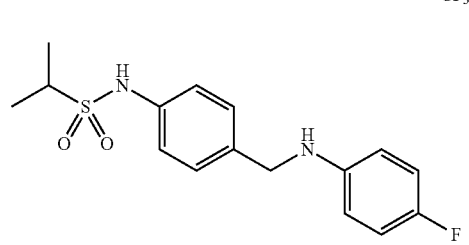 |
| | Ih-220 |

Ih-221
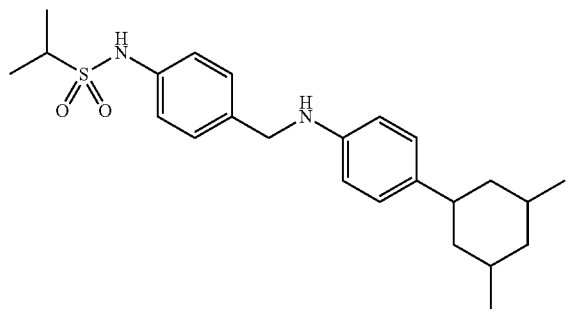
Compound I-72
[Formula 165]
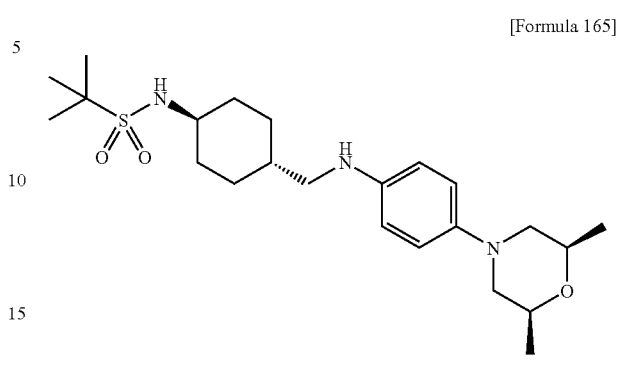
Ih-222
Ih-223
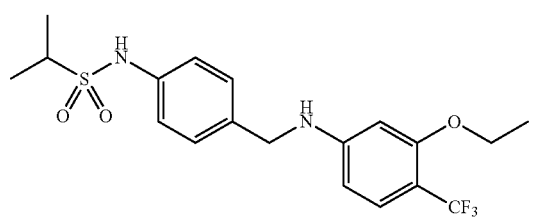
1H-NMR (DMSO-d6) δ: 0.90-1.05 (m, 2 H), 1.05-1.15 (m, 6H), 1.25 (s, 9H), 1.15-1.32 (m, 3H), 1.41 (m, 1H), 1.75-1.98 (m, 4H), 2.11 (m, 1H), 2.58-3.38 (m, 5H), 3.58-3.76 (m, 2H), 5.17 (m, 1H), 6.25-6.92 (m, 5H) Melting point: 147 to 149° C.
Compound Ia-140
[Formula 166]
Ih-224
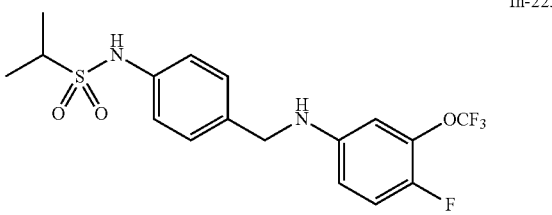
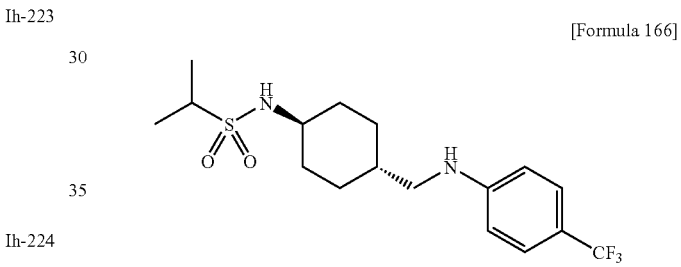
1H-NMR (CDCl3) δ: 1.02-1.20 (m, 2 H), 1.17-1.32 (m, 2H), 1.37 (d, 6H, J=6.9 Hz), 1.46-1.70 (m, 4H), 1.86-1.95 (m, 2H), 2.08-2.18 (m, 2H), 3.01 (d, 2H, J=6.9 Hz), 3.13 (m, 1H), 3.25 (m, 1H), 3.87 (d, 1H, J=8.4 Hz), 6.61(d, 2H, J=8.7 Hz), 7.39 (d, 2H, J=8.7 Hz)
Ih-225
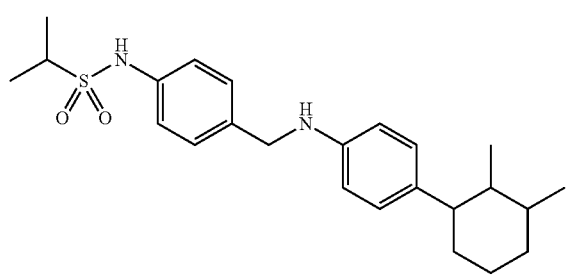
Compound Ia-141
[Formula 167]
Ih-226
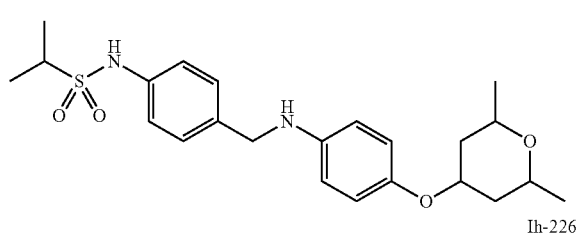
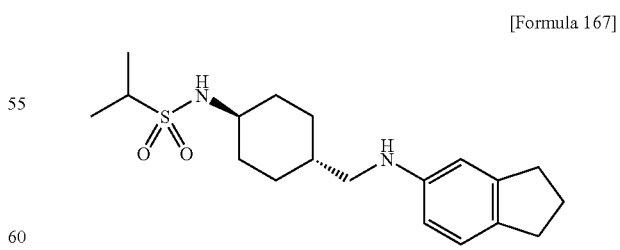
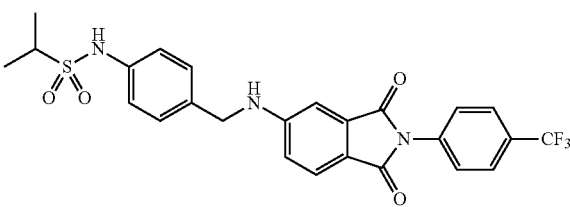
1H-NMR (CDCl3) δ: 1.00-1.30 (m, 4 H), 1.37 (d, 6H, J=6.9 Hz), 1.59 (m, 1H), 1.87-1.98 (m, 2H), 1.99-2.18 (m, 5H), 2.85 (q, 3H, J=7.5 Hz), 2.97 (d, 2H, J=6.9 Hz), 3.12 (m, 1H), 3.23 (m, 1H), 3.88 (d, 1H, J=8.1 Hz), 6.53 (d, 1H, J=7.8 Hz), 6.63 (brs, 1H), 7.04 (d, 1H, J=7.8 Hz) Mass: 351[M+H]

Compound Ia-178

[Formula 168]

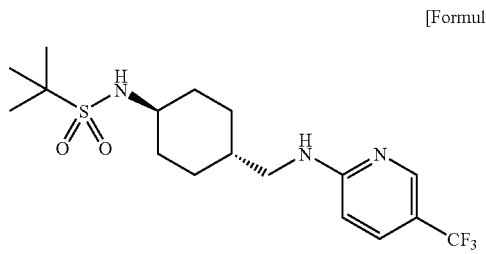

1H-NMR (CDCl3) δ: 1.08-1.36 (m, 4 H), 1.39 (s, 9H), 1.59 (m, 1H), 1.90-1.99 (m, 2H), 2.16-2.26 (m, 2H), 3.17-3.34 (m, 3H), 3.69 (d, 1H, J=9.3 Hz), 6.68 (d, 1H, J=9.3 Hz), 7.77 (dd, 1H, J=2.1 Hz and 9.3 Hz), 8.49 (brs, 1H) Mass:394[M+H]+

Compound Ib-138

[Formula 169]

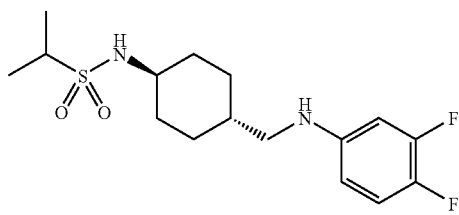

1H-NMR (CDCl3) δ: 1.02-1.34 (m, 4 H), 1.37 (d, 6H, J=6.6 Hz), 1.57 (m, 1H), 1.87-1.97 (m, 2H), 2.07-2.18 (m, 2H), 2.93 (d, 2H, J=6.6 Hz), 3.13 (m, 1H), 3.25 (m, 1H), 3.99 (d, 1H, J=8.4 Hz), 6.38 (m, 1H), 6.49 (brs, 1H), 6.97 (q, 1H, J=9.3 Hz) Mass:347[M+H]

Compound Ii-2

[Formula 170]

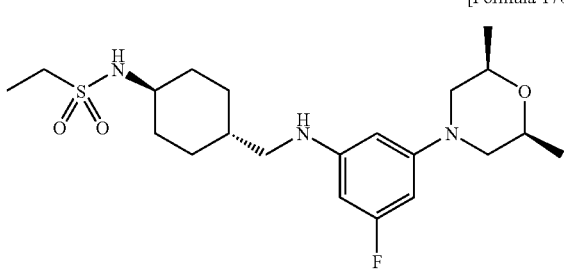

1H-NMR (DMSO-d6) δ: 0.91-1.06 (m, 2H), 1.12-1.28 (m, 1H), 1.31-1.47 (m, 1H), 1.75-1.94 (m, 4H), 2.19 (t, 2H, J=11.3 Hz), 2.79 (t, 2H, J=6.0 Hz), 2.93-3.08 (m, 1H), 2.97 (q, 2H, J=7.42 Hz), 3.46 (m, 2H), 3.57-3.69 (m, 2H), 5.71 (t, 1H, J=5.2 Hz), 5.77 (d, 1H, J=11.5 Hz), 5.88-5.96 (m, 2H), 7.01 (d, 1H, J=7.4 Hz).

Compound Ii-3

[Formula 171]

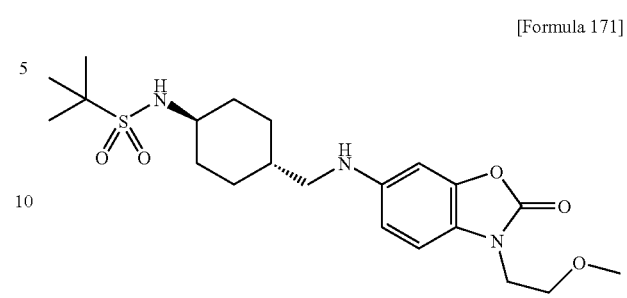

1H-NMR (DMSO-d6) δ: 0.90-1.07 (m, 2 H), 1.15-1.21 (m, 1H), 1.27 (s, 9H), 1.40-1.49 (m, 2H), 1.82 (d, 2H, J=11.6 Hz), 1.92 (d, 2H, J=11.6 Hz), 2.79-2.84 (m, 2H), 2.97-3.10 (m, 1H), 3.24 (s, 3H), 3.55-3.62 (m, 2H), 3.84-3.91 (m, 2H), 5.50-5.59 (m, 1H), 6.40 (d, 1H, J=8.0 Hz), 6.56 (s, 1H), 6.72 (d, 1H, J=8.4 Hz), 6.97 (d, 1H, J=8.4 Hz). Melting point: 166 to 168° C.

Compound Ii-4

[Formula 172]

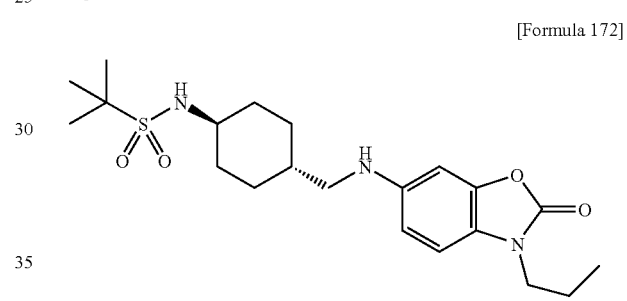

1H-NMR (DMSO-d6) δ: 0.87 (t, 3H, J=7.2 Hz), 0.93-1.06 (m, 2H), 1.13-1.21 (m, 1.26 (s, 9H), 1.37-1.49 (m, 2H), 1.61-1.72 (m, 2H), 1.82 (d, 2H, J=12.0 Hz), 1.91 (d, 2H, J=12.0 Hz), 2.78-2.84 (m, 2H), 2.97-3.08 (m, 1H), 3.61-3.71 (m, 2H), 5.52-5.60 (m, 1H), 6.40 (d, 1H, J=8.4 Hz), 6.56 (s, 1H), 6.73 (d, 1H, J=8.8 Hz), 6.97 (d, 1H, J=8.8 Hz). Melting point: 185 to 186° C.

Compound Ii-5

[Formula 173]

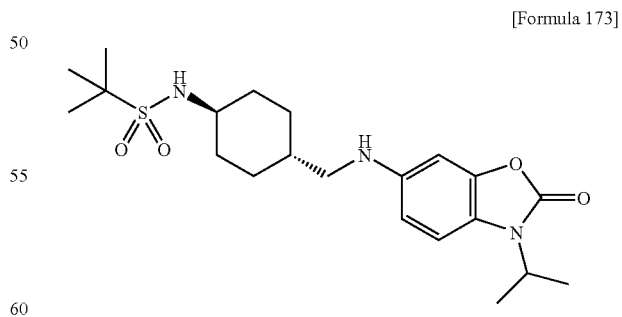

1H-NMR (DMSO-d6) δ: 0.90-1.05 (m, 2H), 1.26 (s, 9H), 1.28-1.31 (m, 1H), 1.35-1.47 (m, 8H), 1.81 (d, 2H, J=12.4 Hz), 1.91 (d, 2H, J=12.4 Hz), 2.77-2.84 (m, 2H), 2.96-3.07 (m, 1H), 4.30-4.42 (m, 1H), 5.51-5.64 (m, 1H), 6.39 (d, 1H, J=8.0 Hz), 6.55 (s, 1H), 6.72 (d, 1H, J=8.8 Hz), 7.07 (d, 1H, J=8.8 Hz). Melting point: 156 to 157° C.

Compound Ii-6

[Formula 174]

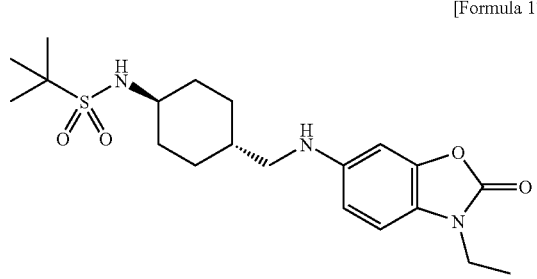

1H-NMR (DMSO-d6) δ: 0.91-1.07 (m, 2H), 1.19-1.25 (m, 4H), 1.26 (s, 9H), 1.38-1.49 (m, 2H), 1.82 (d, 2H, J=8.8 Hz), 1.91 (d, 2H, J=8.8 Hz), 2.79-2.84 (m, 2H), 2.97-3.07 (m, 1H), 3.69-3.80 (m, 2H), 5.51-5.63 (m, 1H), 6.41 (d, 1H, J=8.0 Hz), 6.56 (s, 1H), 6.72 (d, 1H, J=8.8 Hz), 6.97 (d, 1H, J=8.8 Hz). Melting point: 178 to 179° C.

Compound Ii-7

[Formula 175]

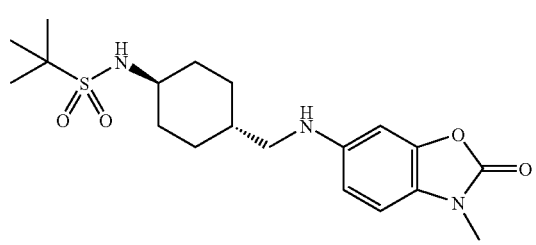

1H-NMR (DMSO-d6) δ: 0.92-1.07 (m, 2H), 1.19-1.22 (m, 1H), 1.26 (s, 9H), 1.38-1.48 (m, 2H), 1.82 (d, 2H, J=11.6 Hz), 1.91 (d, 2H, J=11.6 Hz), 2.79-2.84 (m, 2H), 2.95-3.09 (m, 1H), 3.25 (s, 3H), 5.52-5.60 (m, 1H), 6.41 (d, 1H, J=8.4 Hz), 6.56 (s, 1H), 6.72 (d, 1H, J=8.4 Hz), 6.92 (d, 1H, J=8.4 Hz). Melting point: 206 to 207° C.

Compound Ii-8

[Formula 176]

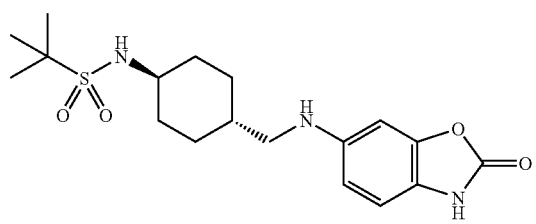

1H-NMR (DMSO-d6) δ: 0.91-1.05 (m, 2H), 1.16-1.24 (m, 1H), 1.26 (s, 9H), 1.37-1.47 (m, 2H), 1.81 (d, 2H, J=12.8 Hz), 1.90 (d, 2H, J=12.8 Hz), 2.75-2.81 (m, 2H), 2.96-3.08 (m, 1H), 5.45-5.52 (m, 1H), 6.33 (d, 1H, J=8.4 Hz), 6.50 (s, 1H), 6.68-6.80 (m, 2H), 11.02 (brs, 1H). Melting point: 213 to 214° C.

Compound Ii-9

[Formula 177]

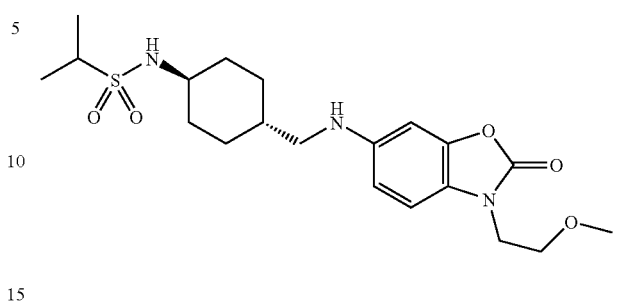

1H-NMR (DMSO-d6) δ: 0.91-1.08 (m, 2 H), 1.17-1.30 (m, 8H), 1.44 (brs, 1H), 1.82 (d, 2H, J=12.4 Hz), 1.89 (d, 2H, J=12.4 Hz), 2.78-2.82 (m, 2H), 2.97-3.15 (m, 2H), 3.23 (s, 3H), 3.55-3.62 (m, 2H), 3.83-3.90 (m, 2H), 5.52-5.59 (m, 1H), 6.40 (d, 1H, J=8.0 Hz), 6.55 (s, 1H), 6.92 (d, 1H, J=8.0 Hz), 6.97 (d, 1H, J=8.4 Hz). Melting point: 120 to 121° C.

Compound Ii-10

[Formula 178]

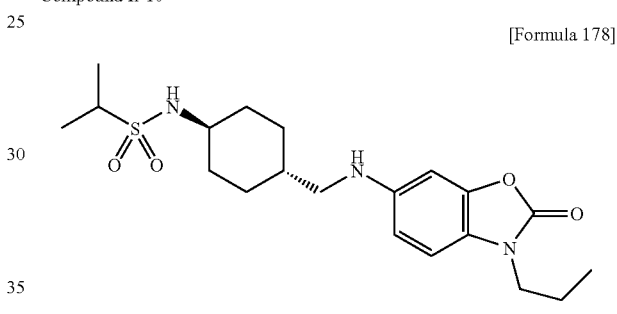

1H-NMR (DMSO-d6) δ: 0.88 (t, 3H, J=7.2 Hz), 0.93-1.08 (m, 2H), 1.17-1.30 (m, 8H), 1.44 (brs, 1H), 1.52-1.61 (m, 2H), 1.83 (d, 2H, J=12.0 Hz), 1.90 (d, 2H, J=12.0 Hz), 2.78-2.84 (m, 2H), 2.98-3.15 (m, 2H), 3.62-3.71 (m, 2H), 5.52-5.60 (m, 1H), 6.41 (d, 1H, J=8.4 Hz), 6.57 (s, 1H), 6.92 (d, 1H, J=8.0 Hz), 6.97 (d, 1H, J=8.4 Hz). Melting point: 144 to 145° C.

Compound Ii-11

[Formula 179]

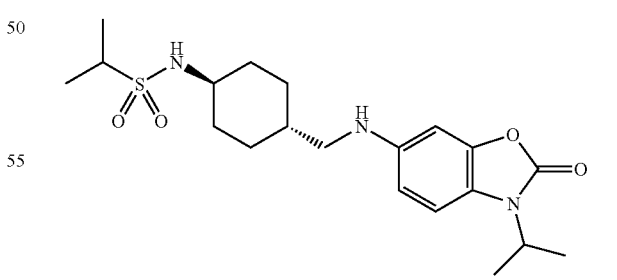

1H-NMR (DMSO-d6) δ: 0.90-1.08 (m, 2H), 1.15-1.30 (m, 8H), 1.33-1.50 (m, 7H), 1.82 (d, 2H, J=12.0 Hz), 1.89 (d, 2H, J=12.0 Hz), 2.78-2.86 (m, 2H), 2.96-3.14 (m, 2H), 4.30-4.45 (m, 1H), 5.50-5.61 (m, 1H), 6.40 (d, 1H, J=7.6 Hz), 6.55 (s, 1H), 6.92 (d, 1H, J=7.2 Hz), 7.07 (d, 1H, J=7.6 Hz). Melting point: 137 to 138° C.

Compound Ii-12

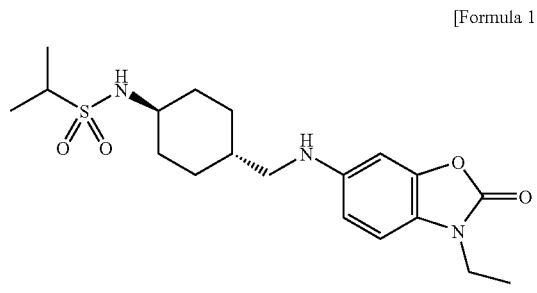

[Formula 180]

1H-NMR (DMSO-d6) δ: 0.92-1.07 (m, 2H), 1.14-1.30 (m, 1H), 1.36-1.50 (m, 1H), 1.82 (d, 2H, J=12.0 Hz), 1.89 (d, 2H, J=12.0 Hz), 2.78-2.85 (m, 2H), 2.97-3.15 (m, 2H), 3.69-3.79 (m, 2H), 5.52-5.60 (m, 1H), 6.41 (d, 1H, J=8.4 Hz), 6.56 (s, 1H), 6.92 (d, 1H, J=7.2 Hz), 6.98 (d, 1H, J=8.4 Hz). Melting point: 158 to 159° C.

Compound Ii-13

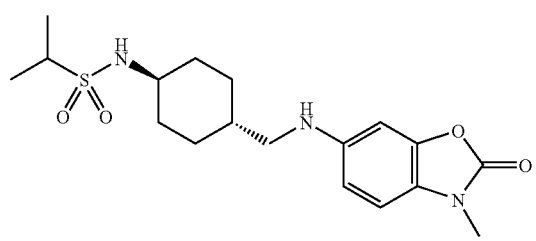

[Formula 181]

1H-NMR (DMSO-d6) δ: 0.90-1.06 (m, 2H), 1.12-1.30 (m, 8H), 1.34-1.51 (m, 1H), 1.82 (d, 2H, J=12.0 Hz), 1.88 (d, 2H, J=12.0 Hz), 2.77-2.83 (m, 2H), 2.95-3.12 (m, 2H), 3.25 (s, 3H), 5.51-5.59 (m, 1H), 6.41 (d, 1H, J=8.8 Hz), 6.56 (s, 1H), 6.86-6.97 (m, 2H). Melting point:157 to 158° C.

Compound Ii-14

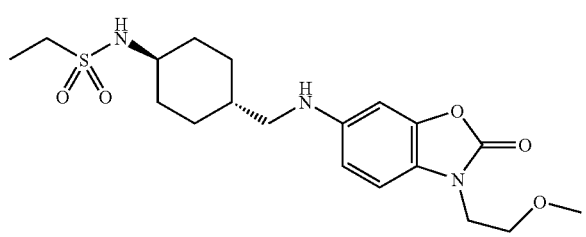

[Formula 182]

1H-NMR (DMSO-d6) δ: 0.91-1.08 (m, 2 H), 1.12-1.30 (m, 5H), 1.38-1.50 (m, 1H), 1.82 (d, 2H, J=12.0 Hz), 1.88 (d, 2H, J=12.0 Hz), 2.77-2.85 (m, 2H), 2.90-3.09 (m, 3H), 3.23 (s, 3H), 3.55-3.61 (m, 2H), 3.84-3.91 (m, 2H), 5.52-5.60 (m, 1H), 6.40 (d, 1H, J=8.4 Hz), 6.55 (s, 1H), 6.89-7.00 (m, 2H). Melting point:150 to 151° C.

Compound Ii-15

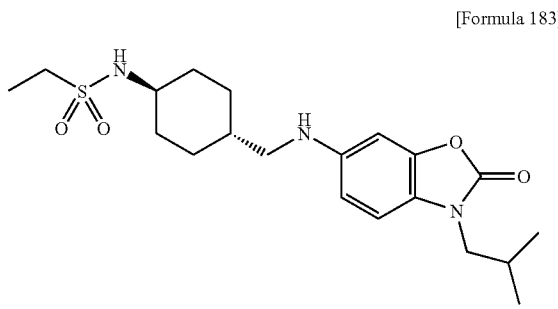

[Formula 183]

1H-NMR (DMSO-d6) δ: 0.88 (s, 3H), 0.90 (s, 3H), 0.92-1.08 (m, 2H), 1.12-1.30 (m, 5H), 1.35-1.51 (m, 1H), 1.83 (d, 2H, J=12.4 Hz), 1.89 (d, 2H, J=12.4 Hz), 2.00-2.16 (m, 1H), 2.77-2.84 (m, 2H), 2.90-3.10 (m, 3H), 3.42-3.55 (m, 2H), 5.50-5.65 (m, 1H), 6.40 (d, 1H, J=8.4 Hz), 6.56 (s, 1H), 6.88-7.01 (m, 2H) Melting point: 132 to 133° C.

Compound Ii-16

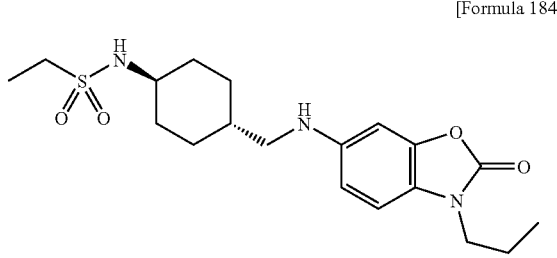

[Formula 184]

1H-NMR (DMSO-d6) δ: 0.87 (t, 3H, J=6.8 Hz), 0.90-1.08 (m, 2H), 1.10-1.28 (m, 5H), 1.35-1.50 (m, 1H), 1.59-1.72 (m, 2H), 1.82 (d, 2H, J=12.0 Hz), 1.89 (d, 2H, J=12.0 Hz), 2.77-2.85 (m, 2H), 2.90-3.09 (m, 3H), 3.61-3.71 (m, 2H), 5.52-5.61 (m, 1H), 6.40 (d, 1H, J=8.0 Hz), 6.56 (s, 1H), 6.97 (d, 2H, J=8.0 Hz). Melting point: 136 to 137° C.

Compound Ii-17

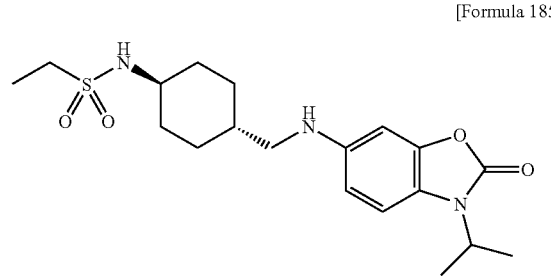

[Formula 185]

1H-NMR (DMSO-d6) δ: 0.92-1.06 (m, 2H), 1.12-1.28 (m, 5H), 1.33-1.50 (m, 7H), 1.81 (d, 2H, J=12.0 Hz), 1.88 (d, 2H, J=12.0 Hz), 2.78-2.84 (m, 2H), 2.90-3.08 (m, 3H), 4.28-4.44 (m, 1H), 5.49-5.79 (m, 1H), 6.39 (d, 1H, J=8.0 Hz), 6.55 (s, 1H), 6.97 (d, 1H, J=7.6 Hz), 7.07 (d, 1H, J=8.0 Hz). Melting point: 124 to 125° C.

Compound Ii-18

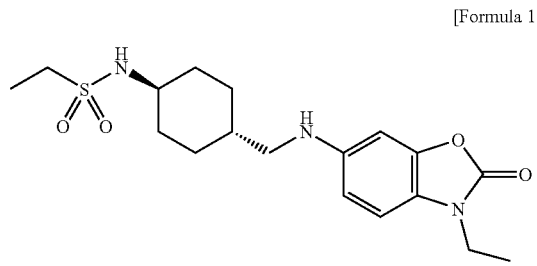

[Formula 186]

1H-NMR (DMSO-d6) δ: 0.90-1.07 (m, 2H), 1.12-1.29 (m, 8H), 1.36-1.51 (m, 1H), 1.82 (d, 2H, J=12.0 Hz), 1.89 (d, 2H, J=12.0 Hz), 2.78-2.86 (m, 2H), 2.90-3.09 (m, 3H), 3.68-3.80 (m, 2H), 5.51-5.61 (m, 1H), 6.41 (d, 1H, J=8.4 Hz), 6.57 (s, 1H), 6.97 (d, 2H, J=8.4 Hz). Melting point: 163 to 164° C.

Compound Ii-19

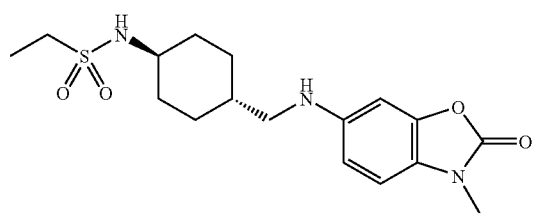

[Formula 187]

1H-NMR (DMSO-d6) δ: 0.89-1.08 (m, 2H), 1.11-1.30 (m, 5H), 1.35-1.51 (m, 1H), 1.82 (d, 2H, J=10.8 Hz), 1.89 (d, 2H, J=10.8 Hz), 2.75-2.88 (m, 2H), 2.89-3.10 (m, 3H), 3.25 (s, 3H), 5.48-5.60 (m, 1H), 6.42 (d, 1H, J=7.6 Hz), 6.56 (s, 1H), 6.92 (d, 1H, J=7.6 Hz), 6.98 (d, 1H, J=5.6 Hz). Melting point: 189 to 190° C.

Compound Ii-20

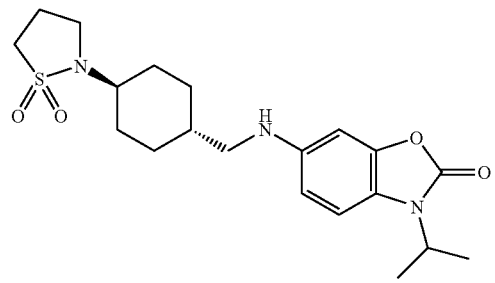

[Formula 188]

1H-NMR (DMSO-d6) δ: 0.95-1.13 (m, 2H), 1.31-1.59 (m, 10H), 1.73-1.92 (m, 4H), 2.12-2.26 (m, 2H), 2.84 (d, 2H, J=6.0 Hz), 3.07-3.30 (m, 4H), 4.30-4.46 (m, 1H), 5.64 (brs, 1H), 6.41 (d, 1H, J=8.4 Hz), 6.57 (s, 1H), 7.08 (d, 1H, J=8.4 Hz). Melting point: 165 to 166° C.

Compound Ii-21

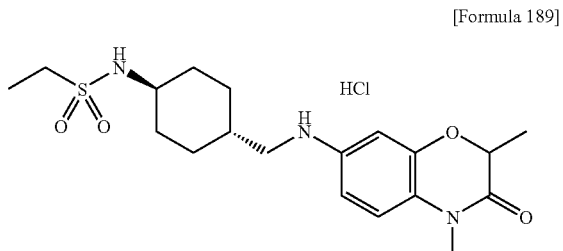

[Formula 189]

1H-NMR (DMSO-d6) δ: 0.86-1.25 (m, 10H), 1.40 (d, 3H, J=6.9 Hz), 1.52 (m, 1H), 1.82-1.93 (m, 4H), 2.95-3.00 (m, 5H), 3.63-3.91 (m, 2H), 4.61-4.68 (m, 1H), 6.73 (brs, 2H), 7.01 (d, 2H, J=7.8 Hz), 7.11 (d, 1H, J=8.1 Hz).

Compound Ii-22

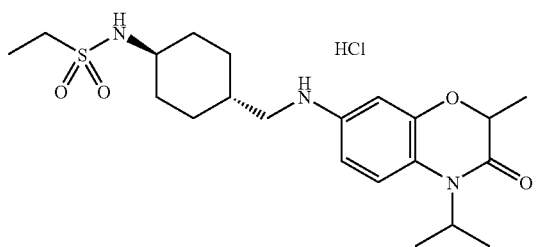

[Formula 190]

1H-NMR (DMSO-d6) δ: 0.98-1.10 (m, 2 H), 1.15-1.34 (m, 5H), 1.36-1.43 (m, 9H), 1.53 (m, 1H), 1.82.1-93 (m, 4H), 2.94-3.01 (m, 6H), 4.52 (m, 1H), 4.63 (m, 1H), 6.73 (brs, 2H), 7.02 (d, 1H, J=7.5 Hz), 7.21-7.25 (m, 1H).

Compound Ii-23

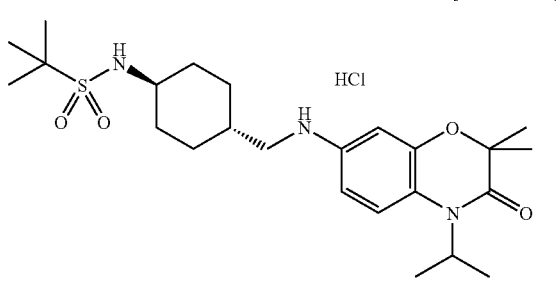

[Formula 191]

1H-NMR (DMSO-d6) δ: 0.86-1.04 (m, 4 H), 1.25 (s, 10H), 1.30 (s, 6H), 1.38 (s, 3H), 1.40 (s, 3H), 178-1.92 (m, 4H), 2.76-2.80 (m, 2H), 3.03 (m, 1H), 4.54-4.63 (m, 1H), 5.57 (m, 1H), 6.16 (s, 1H), 6.22 (d, 1H, J=8.4 Hz), 6.76 (d, 1H, J=8.4 Hz), 6.98 (d, 1H, J=8.4 Hz).

Compound Ii-24

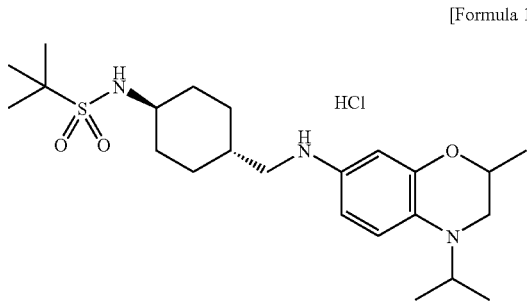

[Formula 192]

1H-NMR (DMSO-d6) δ: 0.98-1.11 (m, 5 H), 1.15-1.31 (m, 20H), 1.57 (m, 1H), 1.82.1-93 (m, 4H), 2.74-2.81 (m, 1H), 3.01-3.06 (m, 2H), 3.35 (m, 1H), 3.40 (m, 1H), 4.04-4.17 (m, 3H), 6.77 (d, 1H, J=9.0 Hz),

Compound Ii-25

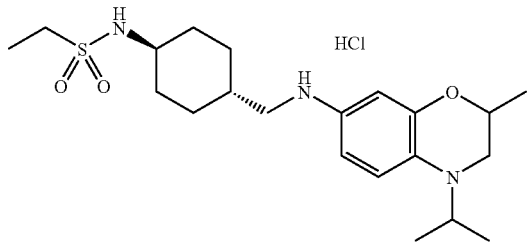

[Formula 193]

1H-NMR (DMSO-d6) δ: 0.98-1.20 (m, 13 H), 1.30 (d, 3H, J=3H), 1.59 (m, 1H), 1.81-1.91 (m, 4H), 2.73-2.83 (m, 1H), 2.94-3.04 (m, 4H), 3.35-3.45 (m, 2H), 4.08-4.19 (m, 3H), 6.88 (brs, 3H), 7.03 (d, 1H, J=8.4 Hz).

Compound Ii-26

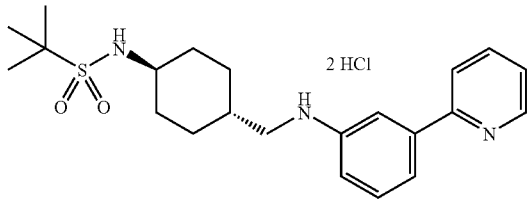

[Formula 194]

1H-NMR (DMSO-d6) δ: 1.02-1.10 (m, 2H), 1.19-1.32 (m, 2H), 1.26 (s, 9H), 1.55 (m, 1H), 1.86-1.93 (m, 4H), 3.01-3.04 (m, 3H), 6.76 (d, 1H, J=8.7 Hz), 7.03 (m, 1H), 7.37-7.43 (m, 3H), 7.76-7.80 (m, 1H), 8.20-8.23 (m, 1H), 8.34-8.40 (m, 1H), 8.78-8.79 (m, 1H)

Compound Ii-27

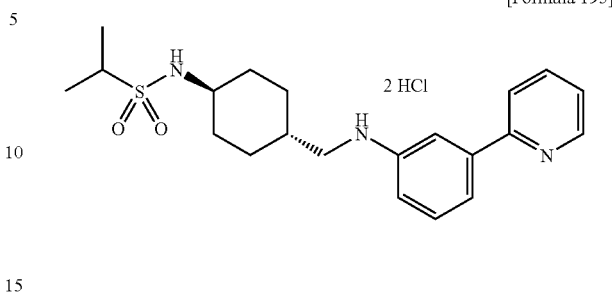

[Formula 195]

1H-NMR (DMSO-d6) δ: 1.03-1.10 (m, 2H), 1.20-1.30 (m, 2H), 1.21 (d, 6H, J=6.9 Hz), 1.53 (m, 1H), 1.88 (m, 4H), 2.99-3.15 (m, 3H), 7.33-7.35 (m, 3H), 7.71-7.75 (m, 1H), 8.16-8.18 (m, 1H), 829-8.32 (m, 1H), 8.76-8.78 (m, 1H)

Compound Ii-28

[Formula 196]

1H-NMR (DMSO-d6) δ: 1.04-1.11 (m, 2H), 1.15-1.28 (m, 2H), 1.19 (t, 3H, J=7.2 Hz), 1.59 (m, 1H), 1.87-1.91 (m, 4H), 2.93-3.08 (m, 2H), 2.97 (q, 2H, J=7.2 Hz), 3.06-3.08 (m, 2H), 7.01 (m, 1H), 7.17 (d, 1H, J=7.5 Hz), 7.43 (d, 1H, J=7.5 Hz), 7.50-7.57 (m, 2H), 7.80-7.84 (m, 1H), 8.25-8.27 (m, 1H), 8.39-8.44 (m, 1H), 8.80-8.82 (m, 1H)

Compound Ii-29

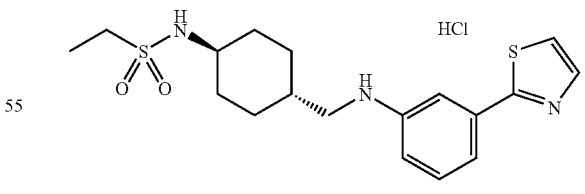

[Formula 197]

1H-NMR (DMSO-d6) δ: 0.99-1.10 (m, 2H), 1.15-1.28 (m, 2H), 1.19 (t, 3H, J=7.5 Hz), 1.52 (m, 1H), 1.84-1.91 (m, 4H), 2.94-3.01 (m, 5H), 6.88 (m, 1H), 7.00 (d, 1H, J=7.8 Hz), 7.26-7.28 (m, 2H), 7.38 (m, 1H), 7.76 (d, 1H, J=3.3. Hz), 7.90 (d, 1H, J=3.3 Hz)

Compound Ii-30

[Formula 198]

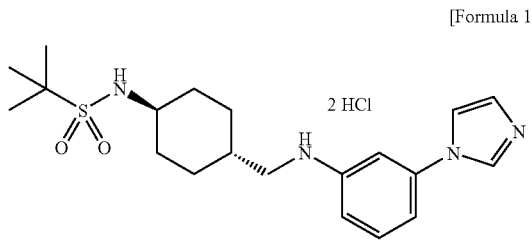

1H-NMR (DMSO-d6) δ: 0.93-1.08 (m, 2 H), 1.18-1.33 (m, 2H), 1.26 (s, 9H), 1.45 (m, 1H), 1.78-1.97 (m, 4H), 2.86-2.94 (m, 2H), 2.95-3.10 (m, 1H), 5.91 (m, 1H), 6.55 (d, 1H, J=7.6 Hz), 6.63-6.71 (m, 2H), 6.73 (d, 1H, J=8.0 Hz), 7.06 (s, 1H), 7.15 (t, 1H, J=8.0 Hz), 7.60 (s, 1H), 8.11 (s, 1H), 8.31 (s, 1H)

Compound Ii-31

[Formula 199]

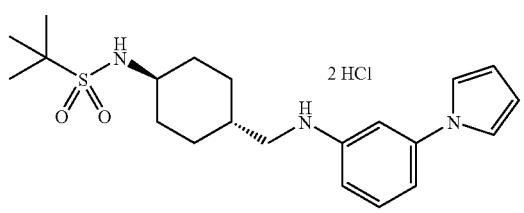

1H-NMR (DMSO-d6) δ: 0.93-1.08 (m, 2 H), 1.13-1.28 (m, 2H), 1.26 (s, 9H), 1.43 (m, 1H), 1.76-1.97 (m, 4H), 2.83-3.18 (m, 3H), 5.79 (m, 1H), 6.21 (s, 2H), 6.44 (d, 1H, J=6.8 Hz), 6.58-6.67 (m, 2H), 6.73 (d, 1H, J=8.0 Hz), 7.10 (t, 1H, J=8.0 Hz), 7.21 (s, 2H) Melting point: 205 to 206° C.

Compound Ii-32

[Formula 200]

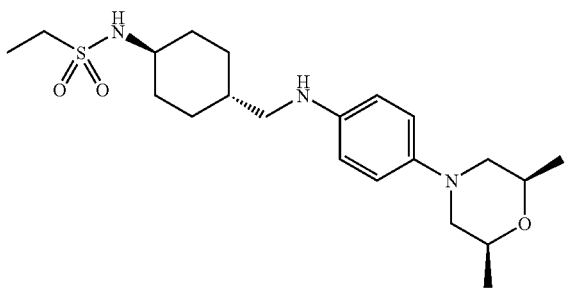

1H-NMR (DMSO-d6) δ: 0.90-1.05 (m, 2 H), 1.05-1.28 (m, 11H), 1.41 (m, 1H), 1.75-1.92 (m, 4 H), 2.11 (t, 2H, J=10.0 Hz), 2.73-2.82 (m, 2H), 2.91-3.08 (m, 3H), 3.24 (d, 2H, J=11.2 Hz), 3.62-3.72 (m, 2H), 5.07 (m, 1H), 6.47 (d, 2H, J=7.2 Hz), 6.72 (d, 2H, J=7.2 Hz), 6.97 (d, 1H, J=7.6 Hz) Melting point: 165 to 166° C.

Compound Ii-33

[Formula 201]

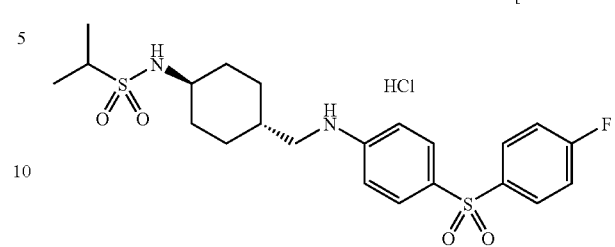

1H-NMR (DMSO-d6) δ: 0.91-1.06 (m, 2H), 1.15-1.26 (m, 8H), 1.33-1.48 (m, 1H), 1.71-1.93 (m, 4H), 2.88 (d, 2H, J=6.5 Hz), 2.93-3.15 (m, 2H), 5.70 (brs, 2H), 6.63 (d, 2H, J=9.1 Hz), 6.93-6.96 (m, 1H), 7.38-7.42 (m, 2H), 7.57 (d, 2H, J=9.1 Hz), 7.88-7.93 (m, 2H)

Compound Ii-34

[Formula 202]

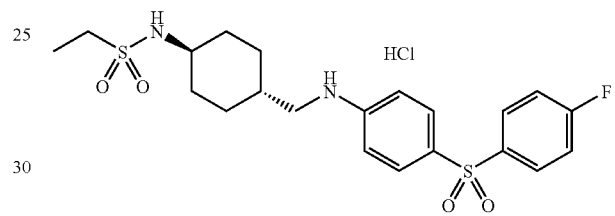

1H-NMR (DMSO-d6) δ: 0.98-1.02 (m, 2H), 1.16-1.18 (m, 5H), 1.42 (s, 1H), 1.75-1.91 (m, 4H), 2.88 (d, 2H, J=6.6 Hz), 2.96 (q, 3H, J=7.3 Hz), 6.63 (d, 2H, J=8.9 Hz), 6.99-7.02 (m, 1H), 7.38-7.41 (m, 2H), 7.57 (d, 2H, J=8.9 Hz), 7.89-7.92 (m, 2H).

Compound Ii-35

[Formula 203]

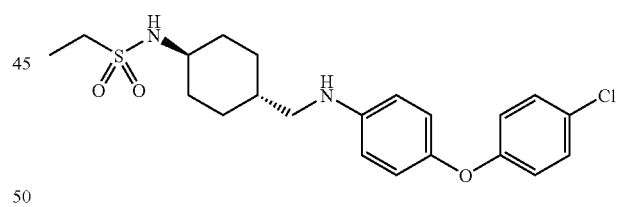

1H-NMR (DMSO-d6) δ: 0.90-1.52 (m, 5H), 1.19 (t, 3H, J=7.2 Hz), 1.75-1.96 (m, 4H), 2.50-3.10 (m, 3H), 2.62 (q, 2H, J=7.2 Hz), 5.55-5.70 (m, 1H), 6.57 (d, 2H, J=8.7 Hz), 6.80-7.04 (m, 4H), 7.01 (d, 1H, J=7.8 Hz), 7.34 (d, 2H, J=8.7 Hz)

Compound Ii-36

[Formula 204]

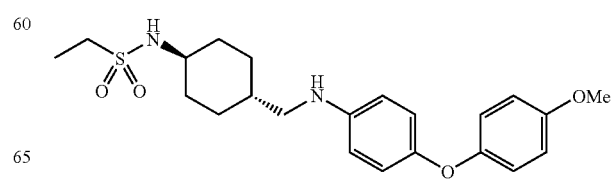

1H-NMR (DMSO-d6) δ: 0.90-1.50 (m, 5H), 1.19 (t, 3H, J=7.2 Hz), 1.75-1.95 (m, 4H), 2.70-3.10 (m, 3H), 2.97 (q, 2H, J=7.2 Hz), 3.70 (s, 3H), 5.40-5.50 (m, 1H), 6.53 (d, 2H, J=8.7 Hz), 6.74 (d, 2H, J=8.7 Hz), 6.78-6.90 (m, 4H), 6.99 (d, 1H, J=7.8 Hz)

Compound Ii-37

[Formula 205]

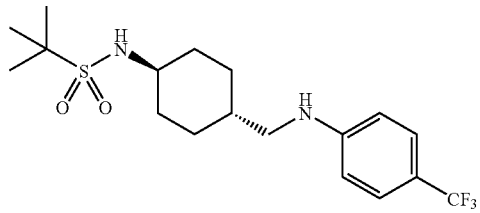

1H-NMR (CDCl3) δ: 1.02-1.32 (m, 4H), 139 (s, 9H), 1.58 (m, 1H), 1.86-1.96 (m, 2H), 2.12-2.22 (m, 2H), 3.02 (d, 2H, J=6.6 Hz), 3.25 (m, 1H), 3.67 (d, 1H, J=9.3 Hz), 6.67 (d, 2H, J=8.7 Hz), 7.41 (d, 2H, J=8.7 Hz) Mass:393[M+H]

Compound Ii-38

[Formula 206]

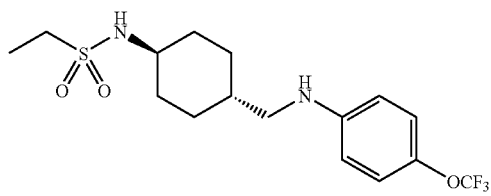

1H-NMR (DMSO-d6) δ: 0.93-1.07 (m, 2H), 1.17-1.26 (m, 2H), 1.19 (t, 3H, J=7.1 Hz), 1.43 (s, 1H), 1.77-1.85 (m, 2H), 1.85-1.94 (m, 2H), 2.82 (t, 1H, J=5.8 Hz), 2.98 (m, 1H), 2.97 (q, 2H, J=7.1 Hz), 5.87 (m, 1H), 6.56 (d, 2H, J=8.6 Hz), 6.98 (d, 1H, J=7.6 Hz), 7.02 (d, 2H, J=8.6 Hz).

Compound Ii-39

[Formula 207]

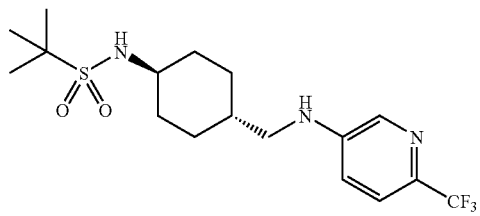

1H-NMR (DMSO-d6) δ: 0.98-1.10 (m, 2H), 1.19-1.35 (m, 2H), 1.29 (s, 9H), 1.46 (s, 1H), 1.73-1.98 (m, 4H), 2.93 (m, 1H), 3.04 (m, 1H), 6.60-6.69 (m, 2H), 6.75 (d, 1H, J=8.8 Hz), 6.97 (d, 1H, J=7.6 Hz), 7.49 (d, 1H, J=8.8 Hz), 8.05 (s, 1H).

Compound Ii-40

[Formula 208]

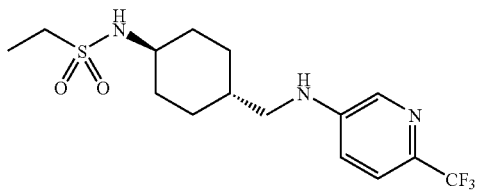

1H-NMR (DMSO-d6) δ: 0.96-1.09 (m, 2H), 1.16-1.29 (m, 2H), 1.19 (t, 3H, J=7.3 Hz), 1.45 (s, 1H), 1.76-1.94 (m, 4H), 1.76 (s, 2H), 2.93 (t, 2H, J=5.8 Hz), 2.97 (q, 2H, J=7.3 Hz), 6.66 (s, 1H), 6.94-7.01 (m, 2H), 7.49 (d, 1H, J=8.6 Hz), 8.04 (s, 1H).

Compound Ii-41

[Formula 209]

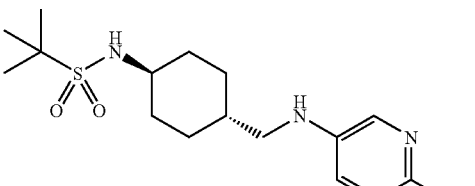

1H-NMR (DMSO-d6) δ: 0.91-1.05 (m, 2H), 1.17-1.33 (m, 2H), 1.26 (s, 9H), 1.35-1.48 (m, 1H), 1.76-1.86 (m, 2H), 1.86-1.95 (m, 2H), 2.76-2.82 (m, 1H), 2.96-3.08 (m, 1H), 3.71 (s, 3H), 5.21-5.30 (m, 1H), 6.57 (d, 1H, J=8.6 Hz), 6.73 (d, 1H, J=8.6 Hz), 7.02 (dd, 1H, J=8.6, 2.3 Hz), 7.44 (d, 1H, J=2.3 Hz).

Compound Ii-42

[Formula 210]

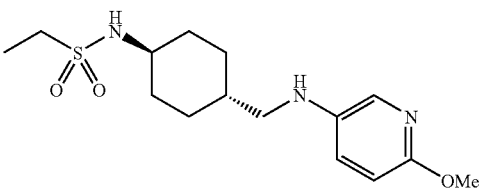

1H-NMR (DMSO-d6) δ: 0.98-1.01 (m, 2H), 1.18-1.28 (m, 2H), 1.19 (t, 3H, J=7.1 Hz), 1.42 (s, 1H), 1.76-1.85 (m, 2H), 1.85-1.93 (m, 2H), 2.79 (t, 2H, J=5.9 Hz), 2.97 (q, 2H, J=7.1 Hz), 3.02 (m, 1H), 3.71 (s, 3H), 5.26 (m, 1H), 6.58 (d, 1H, J=8.6 Hz), 6.98 (d, 2H, J=7.8 Hz), 7.02 (d, 2H, J=8.6 Hz), 7.44 (brs, 1H).

Compound Ii-43

[Formula 211]

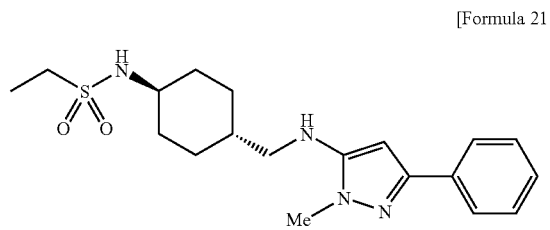

1H-NMR (DMSO-d6) δ: 0.98-1.06 (m, 2H), 1.16-1.25 (m, 2H), 1.18 (t, 3H, J=7.5 Hz), 1.51 (m, 1H), 1.83-1.91 (m, 4H), 2.85 (t, 2H, J=6.3 Hz), 2.97 (q, 2H, J=7.5 Hz), 3.04(m, 1H), 3.56 (s, 3H), 5.46 (t, 1H, J=6.3 Hz), 5.76 (s, 1H), 6.49 (d, 1H, J=7.8 Hz), 7.21 (t, 1H, J=7.5 Hz), 7.32 (t, 2H, J=7.5 Hz), 7.68 (d, 2H, J=7.5 Hz)

Compound Ii-44

[Formula 212]

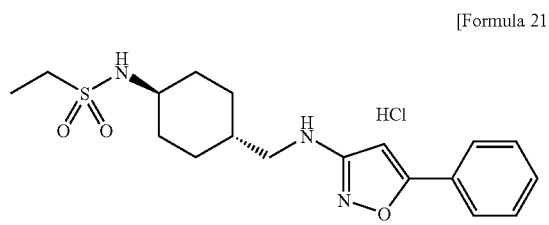

1H-NMR (DMSO-d6) δ: 0.96-1.05 (m, 2H), 1.18 (t, 3H, J=7.2 Hz), 1.24 (m, 2H), 1.48 (m, 1H), 1.76-1.91 (m, 4H), 2.91 (d, 2H, J=6.6 Hz), 2.97 (q, 2H, J=7.2 Hz), 6.35 (s, 1H), 6.99 (d, 1H, J=7.8 Hz), 7.46-7.49 (m, 3H), 7.73-7.76 (m, 2H)

Compound Ii-45

[Formula 213]

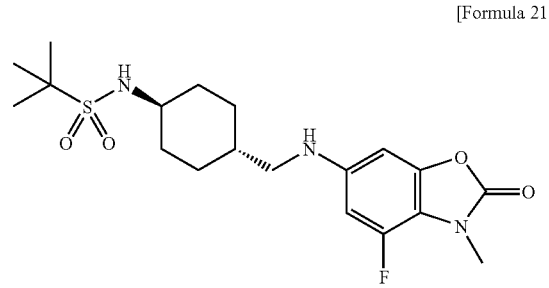

1H-NMR (DMSO-d6) δ: 0.92-1.08 (m, 2H), 1.15-1.22 (m, 1H), 1.26 (s, 9H), 1.37-1.51 (m, 2H), 1.81 (d, 2H, J=11.6 Hz), 1.91 (d, 2H, J=11.6 Hz), 2.76-2.86 (m, 2H), 2.97-3.08 (m, 1H), 3.35 (s, 3H), 5.82-5.91 (m, 1H), 6.26 (d, 1H, J=13.6 Hz), 6.39 (s, 1H), 6.73 (brs, 1H). Melting point: 215 to 216° C.

Compound Ii-46

[Formula 214]

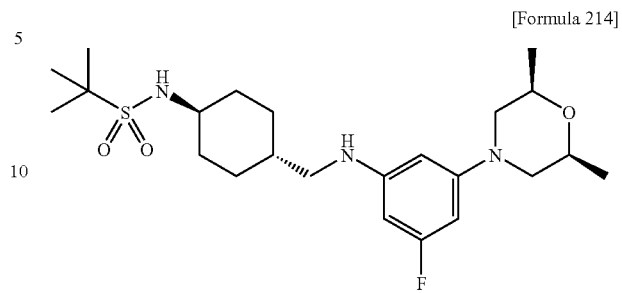

1H-NMR (CDCl3) δ: 1.02-1.32 (m, 4H), 1.24 (d, 6H, J=6.0 Hz), 1.39 (s, 9H), 1.54 (m, 1H), 1.84-1.94 (m, 2H), 2.12-2.22 (m, 2H), 2.39 (t, 2H, J=10.5 Hz), 2.94 (d, 2H, J=6.9 Hz), 3.24 (m, 1H), 3.38 (d, 1H, J=9.6 Hz), 3.61 (d, 1H, J=9.6 Hz), 3.72-4.00 (m, 2H), 5.83-5.94 (m, 1H), 5.96-6.10 (m, 2H).

Compound Ii-47

[Formula 215]

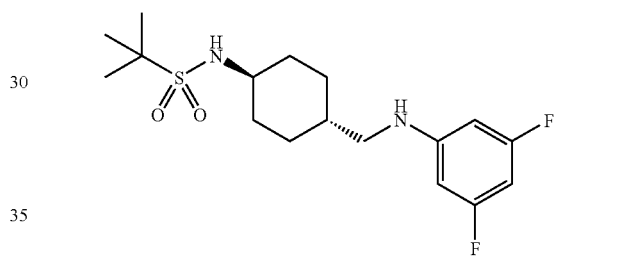

1H-NMR (DMSO-d6) δ: 0.91-1.07 (m, 2H), 1.16-1.34 (m, 11H), 1.40 (m, 1H), 1.79 (d, 2H, J=12.5 Hz), 1.90 (d, 2H, J=11.9 Hz), 2.82 (t, 2H, J=5.5 Hz), 3.01 (m, 1H), 6.12-6.18 (m, 3H), 6.30 (t, 1H, J=5.5 Hz), 6.76 (d, 1H, J=8.7 Hz).

Compound Ii-48

[Formula 216]

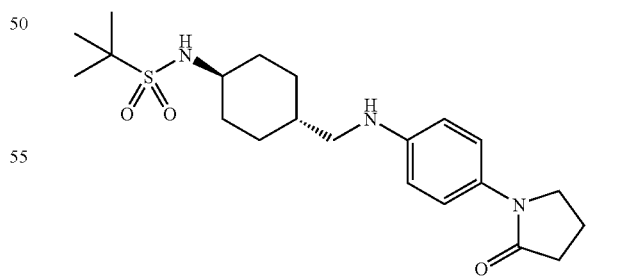

1H-NMR (CDCl3) δ: 1.00-1.28 (m, 4H), 1.39 (s, 9H), 1.56 (m, 1H), 1.91 (d, 2H, J=12.4 Hz), 2.08-2.21 (m, 4H), 2.58 (t, 2H, J=8.1 Hz), 2.97 (d, 2H, J=6.0 Hz), 3.23 (m, 1H), 3.70 (d, 1H, J=9.4 Hz), 3.80 (t, 2H, J=7.1 Hz), 6.66 (d, 2H, J=8.7 Hz), 7.36 (d, 2H, J=8.7 Hz).

Compound Ii-49

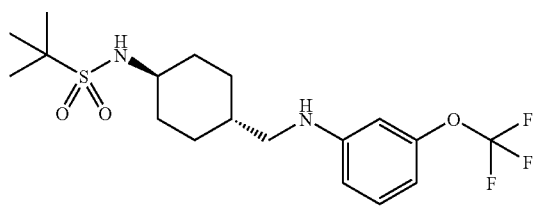

[Formula 217]

1H-NMR (DMSO-d6) δ: 0.92-1.06 (m, 2H), 1.17-1.33 (m, 11H), 1.41 (m, 1H), 1.80 (d, 2H, J=12.9 Hz), 1.90 (d, 2H, J=11.4 Hz), 2.82 (t, 2H, J=6.1 Hz), 3.01 (m, 1H), 6.07 (t, 1H, J=5.3 Hz), 6.34-6.43 (m, 2H), 6.51 (dd, 1H, J1=8.2 Hz, J2=1.8 Hz), 6.75 (d, 1H, J=8.5 Hz), 7.11 (t, 1H, 8.2 Hz).

Compound Ii-50

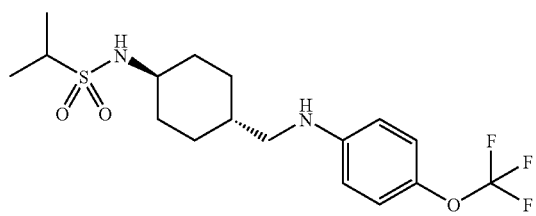

[Formula 218]

1H-NMR (DMSO-d6) δ: 0.92-1.08 (m, 2H), 1.14-1.31 (m, 8H), 1.43 (m, 1H), 1.76-1.94 (m, 4H), 2.82 (t, 2H, J=6.0 Hz), 2.95-3.16 (m, 2H), 5.90 (t, 1H, J=5.5 Hz), 6.56 (d, 2H, J=8.7 Hz), 6.95 (d, 1H, J=7.9 Hz), 7.03 (d, 2H, J=8.6 Hz).

Compound Ii-51

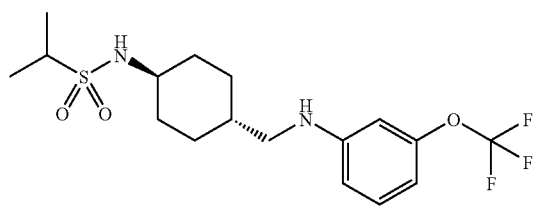

[Formula 219]

1H-NMR (DMSO-d6) δ: 0.90-1.08 (m, 2H), 1.13-1.31 (m, 8H), 1.42 (m, 1H), 1.76-1.94 (m, 4H), 2.83 (t, 2H, J=6.0 Hz), 2.95-3.16 (m, 2H), 6.07 (t, 1H, J=5.4 Hz), 6.36-6.46 (m, 2H), 6.53 (dd, 1H, J1=8.1 Hz, J2=1.9 Hz), 6.95 (d, 1H, J=7.9 Hz), 7.12 (d, 1H, J=8.1 Hz).

Compound Ii-52

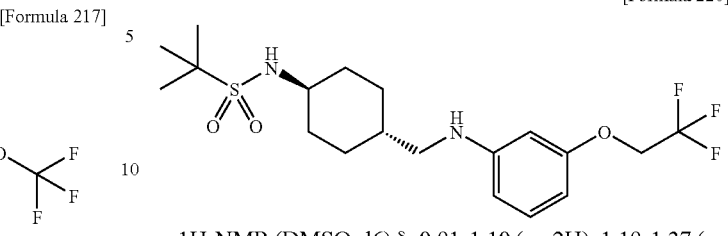

[Formula 220]

1H-NMR (DMSO-d6) δ: 0.91-1.10 (m, 2H), 1.19-1.37 (m, 11H), 1.45 (m, 1H), 1.78-1.90 (m, 4H), 2.84 (t, 2H, J=6.0 Hz), 3.04 (m, 1H), 4.64 (q, 2H, J=9.0 Hz), 5.73 (t, 1H, J=5.4 Hz), 6.13-6.21 (m, 2H), 6.26 (d, 1H, J=7.2 Hz), 6.78 (d, 1H, J=8.4 Hz), 6.99 (t, 1H, 8.0 Hz).

Compound Ii-53

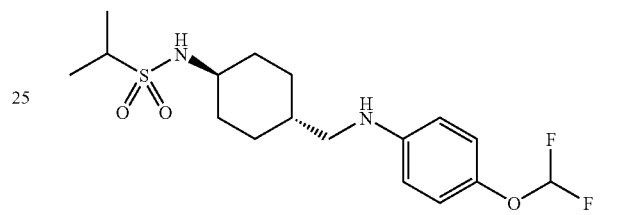

[Formula 221]

1H-NMR (DMSO-d6) δ: 0.90-1.06 (m, 2H), 1.13-1.30 (m, 8H), 1.42 (m, 1H), 1.75-1.93 (m, 4H), 2.80 (t, 2H, J=6.2 Hz), 2.93-3.16 (m, 2H), 5.66 (t, 1H, J=5.5 Hz), 6.53 (d, 2H, J=9.1 Hz), 6.89 (d, 2H, J=8.8 Hz), 6.92 (t, 1H, JH-F=75 Hz), 6.94 (d, 1H, J=8.0 Hz).

Compound Ii-54

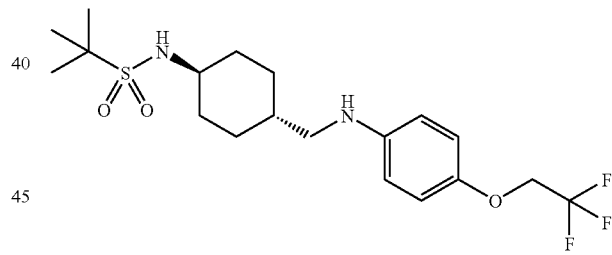

[Formula 222]

1H-NMR (DMSO-d6) δ: 0.88-1.05 (m, 2H), 1.14-1.32 (m, 11H), 1.41 (m, 1H), 1.75-1.94 (m, 4H), 2.77 (t, 2H, J=6.0 Hz), 3.01 (m, 1H), 4.54 (q, 2H, J=9.0 Hz), 5.33 (t, 1H, J=5.8 Hz), 6.49 (d, 2H, J=8.8 Hz), 6.75 (d, 1H, J=8.8 Hz), 6.80 (d, 2H, J=8.8 Hz).

Compound Ii-55

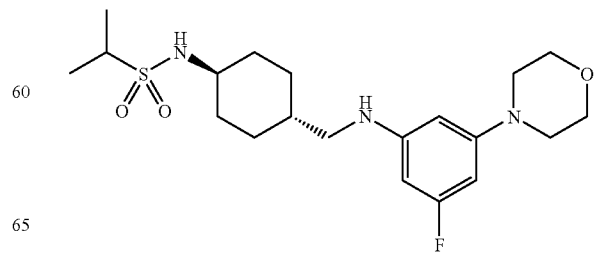

[Formula 223]

1H-NMR (DMSO-d6) δ: 0.90-1.06 (m, 2H), 1.14-1.31 (m, 8H), 1.40 (m, 1H), 1.74-1.93 (m, 4H), 2.79 (t, 2H, J=5.9 Hz), 2.94-3.15 (m, 6H), 3.69 (t, 4H, J=4.8 Hz), 5.70-5.94 (m, 4H), 6.94 (d, 1H, J=8.0 Hz).

Compound Ii-56

[Formula 224]

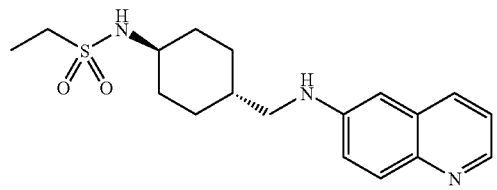

1H-NMR (DMSO-d6) δ: 0.98-1.14 (m, 2H), 1.15-1.32 (m, 5H), 1.54 (m, 1H), 1.83-1.96 (m, 4H), 2.89-3.10 (m, 5H), 6.17 (t, 1H, J=5.2 Hz), 6.63 (d, 1H, J=2.2 Hz), 7.02 (d, 1H, J=7.7 Hz), 7.21 (dd, 1H, J1=9.1 Hz, J2=2.5 Hz), 7.27 (dd, 1H, J1=8.2 Hz, J2=4.4 Hz), 7.67 (d, 1H, J=9.1 Hz), 7.97 (d, 1H, J=8.2 Hz), 8.45 (dd, 1H, J1=4.3 Hz, J2=1.5 Hz).

Compound Ii-57

[Formula 225]

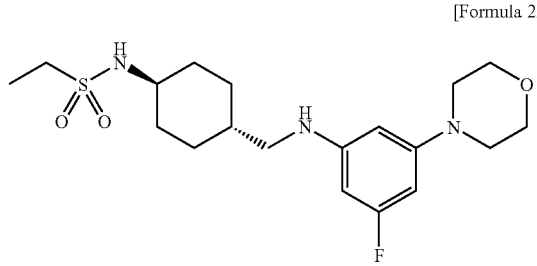

1H-NMR (DMSO-d6) δ: 0.97-1.14 (m, 2H), 1.17-1.34 (m, 8H), 1.54 (m, 1H), 1.83-1.96 (m, 4H), 2.94 (t, 2H, J=6.0 Hz), 2.99-3.18 (m, 2H), 6.17 (t, 1H, J=5.4 Hz), 6.63 (d, 1H, J=2.5 Hz), 6.96 (d, 1H, J=7.7 Hz), 7.21 (dd, 1H, J1=9.1 Hz, J2=2.5 Hz), 7.27 (dd, 1H, J1=8.2 Hz, J2=4.1 Hz), 7.67 (d, 1H, J=9.1 Hz), 7.97 (d, 1H, J=8.0 Hz), 8.45 (dd, 1H, J1=4.3 Hz, J2=1.5 Hz).

Compound Ii-58

[Formula 226]

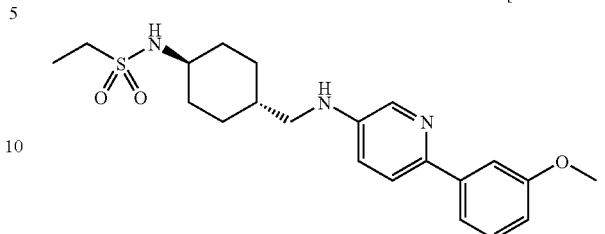

1H-NMR (DMSO-d6) δ: 0.90-1.07 (m, 2H), 1.12-1.29 (m, 5H), 1.40 (m, 1H), 1.74-1.93 (m, 4H), 2.80 (t, 2H, J=5.9 Hz), 2.92-3.07 (m, 7H), 3.69 (t, 4H, J=4.8 Hz), 5.69-5.95 (m, 4H), 6.99 (d, 1H, J=7.7 Hz).

Compound Ii-59

[Formula 227]

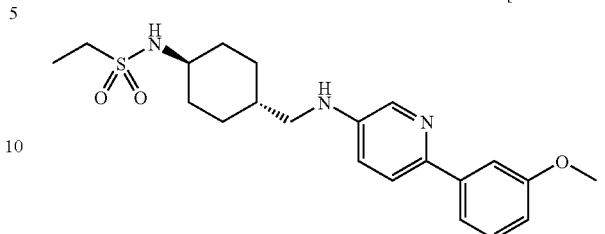

1H-NMR (DMSO-d6) δ: 0.94-1.11 (m, 2H), 1.14-1.30 (m, 5H), 1.47 (m, 1H), 1.78-1.95 (m, 4H), 2.88-3.09 (m, 5H), 3.80 (s, 3H), 6.09 (t, 1H, J=5.6 Hz), 6.81-6.86 (m, 1H), 6.96 (dd, 1H, J1=8.8 Hz, J2=2.8 Hz), 7.01 (d, 1H, J=7.4 Hz), 7.29 (t, 1H, J=8.0 Hz), 7.45-7.51 (m, 2H), 7.66 (d, 1H, J=8.5 Hz), 8.04 (d, 1H, J=2.8 Hz).

Compound Ii-60

[Formula 228]

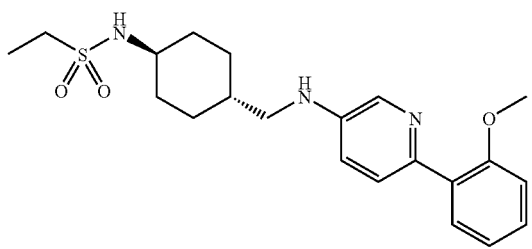

1H-NMR (DMSO-d6) δ: 1.03 (m, 2H), 1.19 (t, 2H, J=7.8 Hz), 1.21 (m, 2H), 1.46 (m, 1H), 1.76-1.95 (m, 4H), 2.90 (t, 2H, J=5.8 Hz), 2.97 (q, 2H, J=7.3 Hz), 3.03 (m, 1H), 3.80 (s, 3H), 5.95 (m, 1H), 6.90 (m, 1H), 6.98 (d, 1H, J=7.8 Hz), 6.98 (dd, 1H, J=7.8, 7.8 Hz), 7.06 (d, 1H, J=8.6 Hz), 7.26 (dd, 1H, J=7.8, 7.8 Hz), 7.61 (d, 1H, J=8.6 Hz), 7.69 (d, 1H, J=7.8 Hz), 8.03 (s, 1H).

Compound Ii-61

[Formula 229]

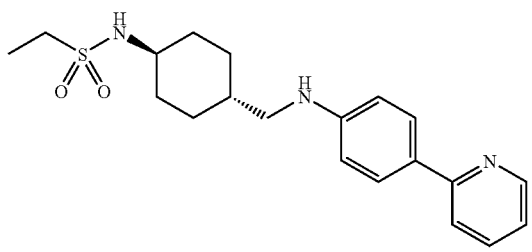

1H-NMR (DMSO-d6) δ: 0.96-1.09 (m, 2H), 1.18-1.29 (m, 2H), 1.19 (t, 3H, J=7.6 Hz), 1.47 (m, 1H), 1.87 (m, 5H), 2.90 (t, 2H, J=6.3 Hz), 2.97 (q, 2H, J=7.6 Hz), 3.02 (m, 1H), 5.98 (m, 1H), 6.63 (d, 2H, J=8.3 Hz), 6.98 (d, 1H, J=7.3 Hz), 7.14 (m, 1H), 7.73 (s, 2H), 7.83 (d, 2H, J=8.3 Hz), 8.52 (d, 1H, J=4.0 Hz).

Compound Ii-62

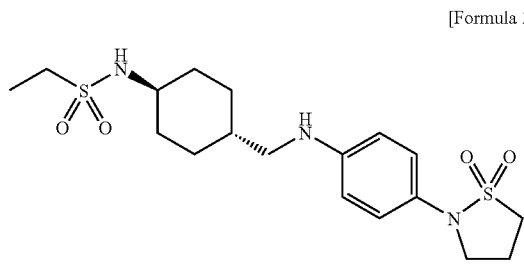

[Formula 230]

1H-NMR (DMSO-d6) δ: 0.98-1.01 (m, 2H), 1.20 (s, 9H), 1.20-1.37 (m, 2H), 1.42 (m, 1H), 1.76-1.96 (m, 4H), 2.28-2.37 (m, 2H), 2.75-2.85 (m, 2H), 3.02 (m, 1H), 3.36 (t, 2H, J=7.8 Hz), 3.57 (t, 2H, J=6.3 Hz), 5.66 (m, 1H), 6.54 (d, 2H, J=8.0 Hz), 6.73 (d, 1H, J=8.6 Hz), 7.00 (d, 1H, J=8.0 Hz).

Compound Ii-63

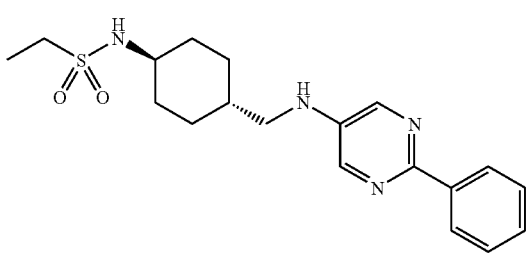

[Formula 231]

1H-NMR (DMSO-d6) δ: 0.96-1.14 (m, 2H), 1.14-1.32 (m, 2H), 1.19 (t, 3H, J=7.2 Hz), 1.50 (m, 1H), 1.76-1.96 (m, 4H), 2.91-3.10 (m, 3H), 2.97 (q, 2H, J=7.2 Hz), 6.28 (m, 1H), 7.02 (d, 1H, J=7.8 Hz), 7.32-7.46 (m, 3H), 8.20 (d, 1H, J=6.9 Hz), 8.22 (s, 2H).

Compound Ii-64

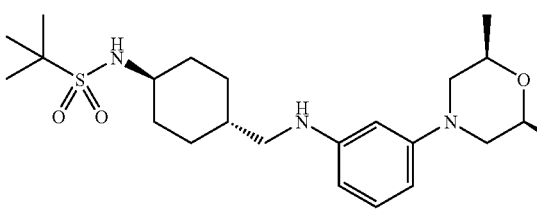

[Formula 232]

1H-NMR (DMSO-d6) δ: 1.03-1.15 (m, 2H), 1.18-1.29 (m, 2H), 1.24 (d, 6H, J=6.3 Hz), 1.52 (m, 1H), 1.86-1.94 (m, 2H), 2.10-2.19 (m, 2H), 2.40 (t, 2H, J=6.0 Hz), 2.95 (d, 2H, J=6.0 Hz), 3.23 (m, 1H), 3.40 (d, 2H, J=11.4 Hz), 3.75-3.85 (m, 2H), 3.86 (d, 1H, J=9.3 Hz), 6.14 (d, 1H, J=8.5 Hz), 6.15 (s, 1H), 6.29 (d, 1H, J=8.5 Hz), 7.06 (d, 1H, J=8.5 Hz).

Compound Ii-65

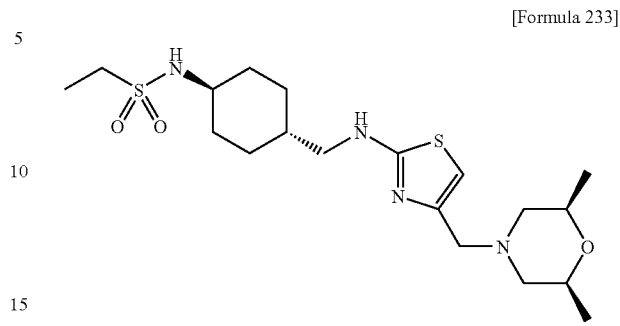

[Formula 233]

1H-NMR (CDCl3) δ:1.08-1.16 (m, 2H), 1.14 (d, 6H, J=6.8 Hz), 1.21-1.30 (m, 2H), 1.29 (s, 9H), 1.78 (t, 2H, J=10.6 Hz), 1.83-1.92 (m, 2H), 2.11-2.19 (m, 2H), 2.78 (d, 2H, J=10.6 Hz), 3.06 (s, 2H), 3.23 (m, 1H), 3.38 (s, 2H), 3.70-3.80 (m, 2H), 4.02 (d, 1H, J=9.9 Hz), 5.37 (s, 1H), 6.30 (s, 1H).

Compound Ii-66

[Formula 234]

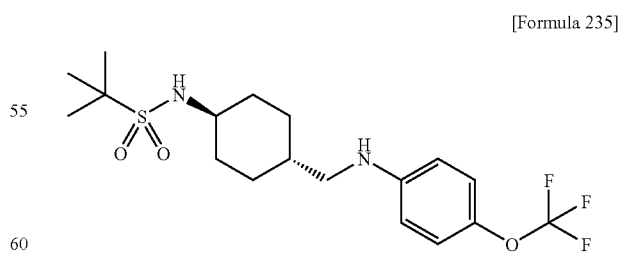

1H-NMR (DMSO-d6) δ: 1.01-1.12 (m, 2H), 1.20-1.34 (m, 2H), 1.27 (s, 9H), 1.54 (m, 1H), 1.82-1.99 (m, 4H), 2.91-2.98 (m, 2H), 3.06 (m, 1H), 6.17 (s, 1H), 6.63 (s, 1H), 6.78 (d, 1H, J=9.0 Hz), 7.20 (m, 1H), 7.27 (m, 1H), 7.77 (d, 1H, J=9.0 Hz), 7.98 (d, 1H, J=9.0 Hz), 8.54 (s, 1H).

Compound Ii-67

[Formula 235]

1H-NMR (DMSO-d6) δ: 0.92-1.06 (m, 2H), 1.20-1.32 (m, 2H), 1.26 (s, 9H), 1.42 (m, 1H), 1.78-1.88 (m, 2H), 1.88-1.96 (m, 2H), 2.78-2.86 (m, 2H), 3.02 (m, 1H), 5.89 (s, 1H), 6.56 (d, 1H, J=8.4 Hz), 6.76 (d, 1H, J=8.4 Hz), 7.02 (d, 1H, J=8.4 Hz).

Compound Ii-68

[Formula 236]

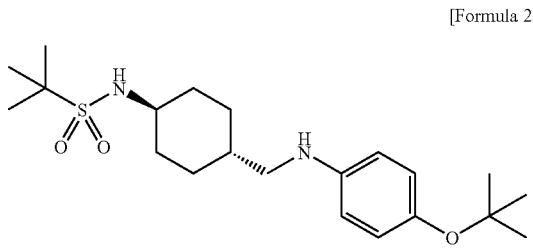

1H-NMR (DMSO-d6) δ: 0.92-1.05 (m, 2H), 1.19 (s, 9H), 1.20-1.32 (m, 2H), 1.26 (s, 9H), 1.42 (m, 1H), 1.80-1.96 (m, 4H), 2.77 (s, 2H), 3.04 (m, 1H), 5.29 (s, 1H), 6.44 (d, 1H, J=7.2 Hz), 6.68 (d, 1H, J=7.2 Hz), 6.75 (d, 1H, J=8.4 Hz).

Compound Ii-69

[Formula 237]

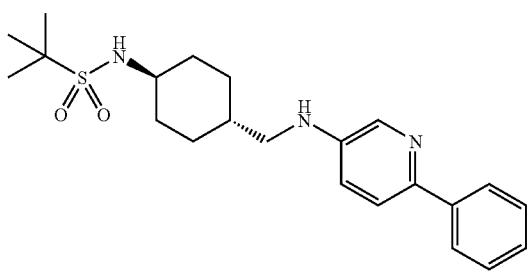

1H-NMR (DMSO-d6) δ: 0.95-1.10 (m, 2H), 1.20-1.32 (m, 2H), 1.26 (s, 9H), 1.47 (m, 1H), 1.80-1.88 (m, 2H), 1.88-1.95 (m, 2H), 2.88-2.95 (m, 2H), 3.02 (s, 1H), 6.07 (m, 1H), 6.77 (d, 1H, J=8.4 Hz), 6.97 (d, 1H, J=7.6 Hz), 7.26 (t, 1H, J=7.6 Hz), 7.35-7.42 (m, 2H), 7.46 (d, 1H, J=8.4 Hz), 7.91 (d, 1H, J=7.6 Hz), 8.04 (s, 1H).

Compound Ii-70

[Formula 238]

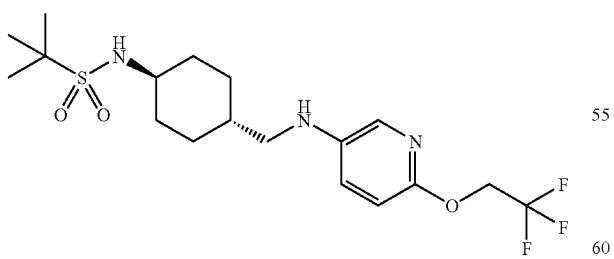

1H-NMR (DMSO-d6) δ: 0.93-1.05 (m, 2H), 1.10-1.32 (m, 2H), 1.26 (s, 9H), 1.42 (m, 1H), 1.78-1.86 (m, 2H), 1.86-1.95 (m, 2H), 2.78-2.83 (m, 2H), 3.03 (m, 1H), 4.80 (q, 2H, J=9.2 Hz), 5.48 (t, 1H, J=5.6 Hz), 6.69-6.76 (m, 2H), 7.08 (dd, 1H, J=8.8, 2.4 Hz), 7.45 (d, 1H, J=2.4 Hz).

Compound Ii-71

[Formula 239]

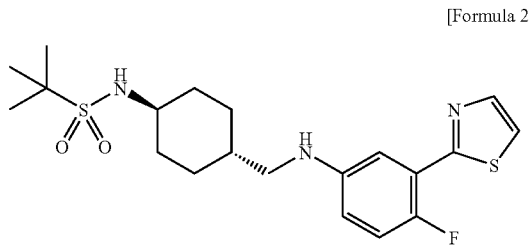

1H-NMR (DMSO-d6) δ: 0.96-1.10 (m, 2H), 1.20-1.32 (m, 2H), 1.27 (s, 9H), 1.82-1.88 (m, 2H), 1.88-1.97 (m, 2H), 2.83-2.88 (m, 2H), 3.04 (m, 1H), 5.82 (s, 1H), 6.69 (m, 1H), 6.76 (d, 1H, J=8.8 Hz), 7.12 (dd, 1H, J=9.2, 8.8 Hz), 7.37 (m, 1H), 7.87 (d, 1H, J=2.8 Hz), 7.99 (s, 1H).

Compound Ii-72

[Formula 240]

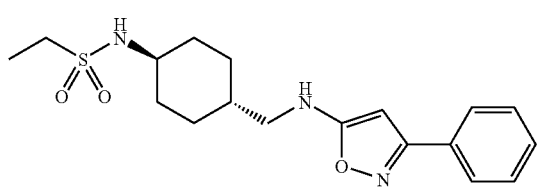

Compound Ii-73

[Formula 241]

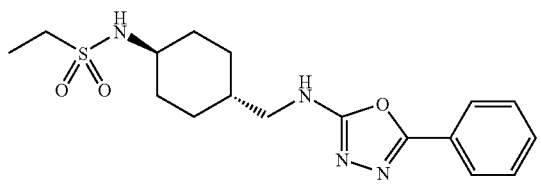

Compound Ii-74

[Formula 242]

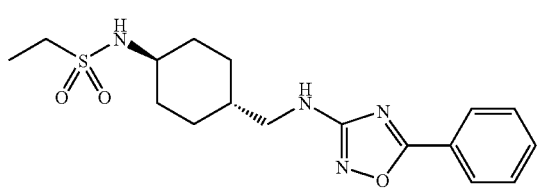

Compound Ii-75

[Formula 243]

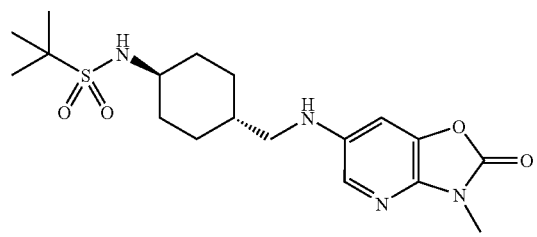

Compound Ii-76
[Formula 244]
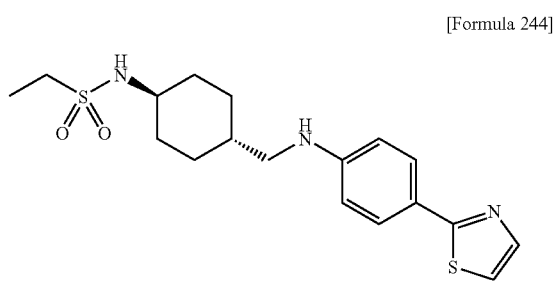
Compound Ii-77
[Formula 245]
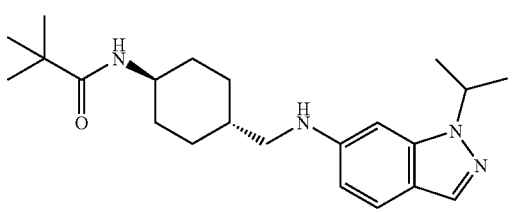
Compound Ii-78
[Formula 246]
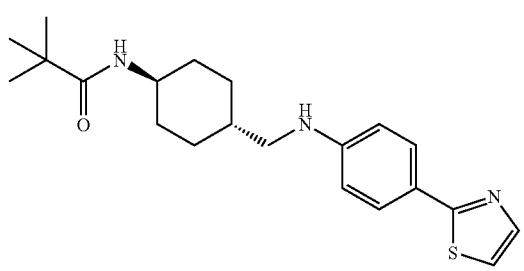
Compound Ii-79
[Formula 247]
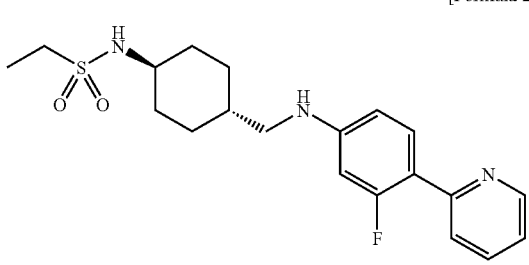
Compound Ii-80
[Formula 248]
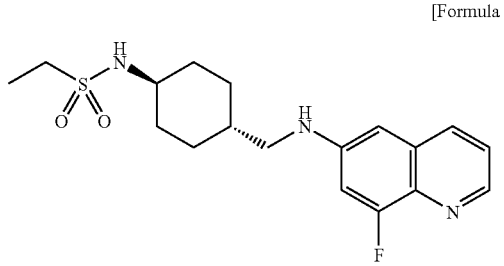
Compound Ii-81
[Formula 249]
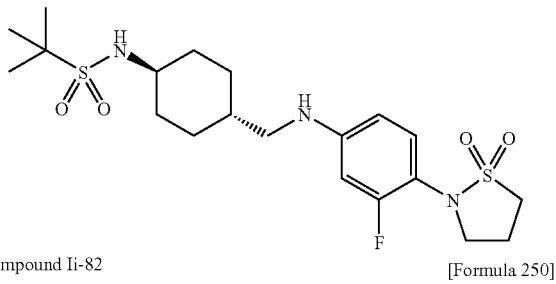
Compound Ii-82
[Formula 250]
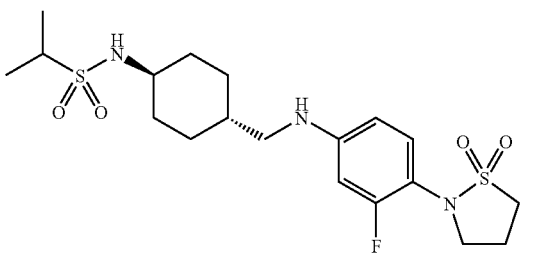
Compound Ii-83
[Formula 251]
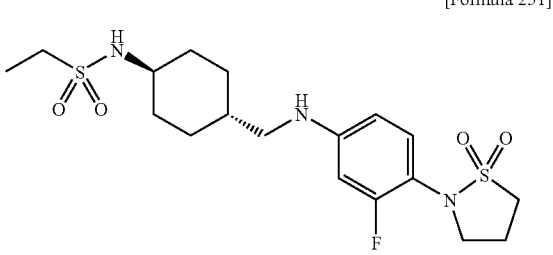
Compound Ii-84
[Formula 252]
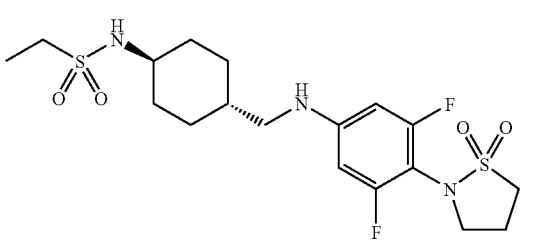
1H-NMR (DMSO-d6) δ: 0.91-1.08 (m, 2H), 1.14-1.30 (t, 3H, J=7.5 Hz), 1.41 (m, 1H), 1.73-1.94 (m, 4H), 2.34-2.46 (m, 2H), 2.85 (t, 2H, J=6.6 Hz), 2.97 (q, 2H, J=7.5 Hz), 3.00 (m, 1H), 3.25 (t, 2H, J=7.5 Hz), 3.53 (t, 2H, J=6.6 Hz), 6.27 (d, 2H, J=11.7 Hz), 6.52 (t, 1H, J=5.1 Hz), 7.00 (d, 1H, J=7.2 Hz).
Compound Ii-85
[Formula 253]
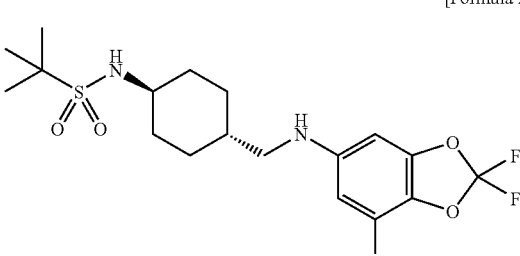

Compound Ii-86

[Formula 254]

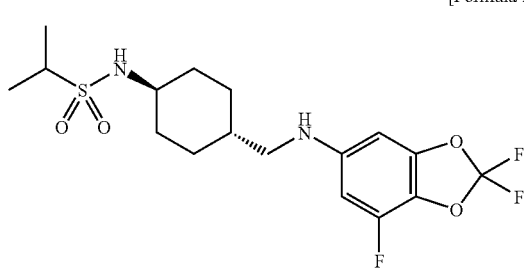

Compound Ii-87

[Formula 255]

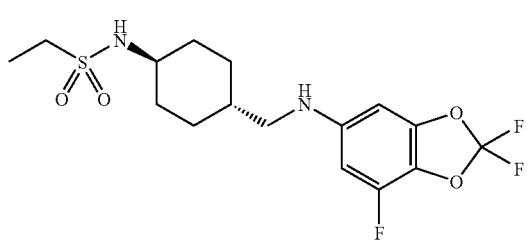

Compound Ii-88

[Formula 256]

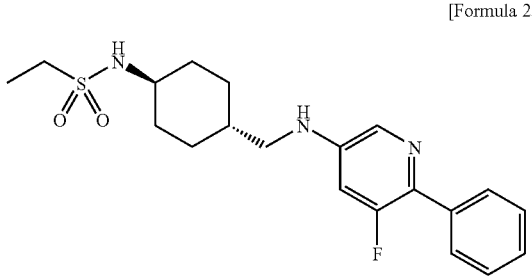

Compound Ii-89

[Formula 257]

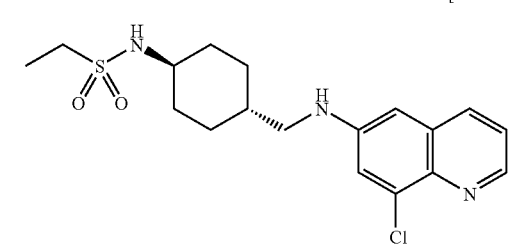

Compound Ii-90

[Formula 258]

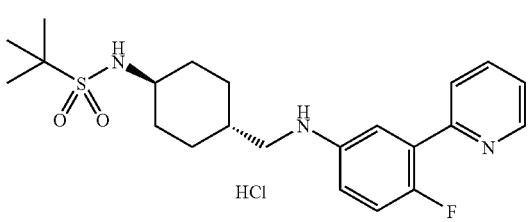

Compound Ii-91

[Formula 259]

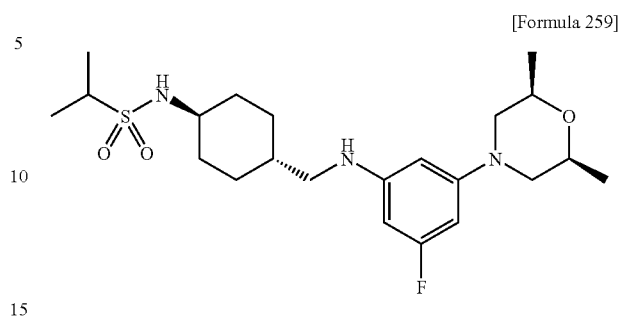

1H-NMR (DMSO-d6) δ: 0.92-1.05 (m, 2H), 1.13 (d, 6H, J=6.0 Hz), 1.18-1.30 (m, 2H), 1.21 (d, 6H, J=6.4 Hz), 1.40 (m, 1H), 1.76-1.83 (m, 2H), 1.83-1.93 (m, 2H), 2.19 (dd, 1H, J=11.2, 11.2 Hz), 2.76-2.82 (m, 2H), 3.01 (m, 1H), 3.09 (m, 1H), 3.45 (d, 2H, J=11.2 Hz), 3.58-3.69 (m, 2H), 5.67 (m, 1H), 5.77 (d, 1H, J=12.0 Hz), 5.90 (s, 1H), 5.91 (m, 1H), 6.91 (d, 1H, J=7.6 Hz).

Compound Ii-92

[Formula 260]

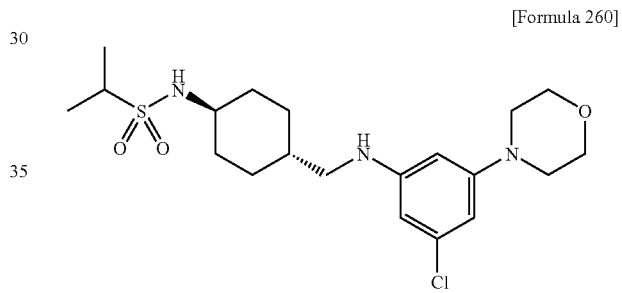

1H-NMR (DMSO-d6) δ: 0.90-1.07 (m, 2H), 1.14-1.30 (m, 2H), 1.21 (d, 6H, J=6.6 Hz), 1.32-1.46 (m, 1H), 1.75-1.92 (m, 4H), 2.78-2.83 (m, 2H), 2.95-3.18 (m, 6H), 3.66-3.72 (m, 4H), 5.75 (brs, 1H), 6.00 (s, 1H), 6.04 (s, 1H), 6.11 (s, 1H), 6.95 (d, 1H, J=9.0 Hz).

Compound Ii-93

[Formula 261]

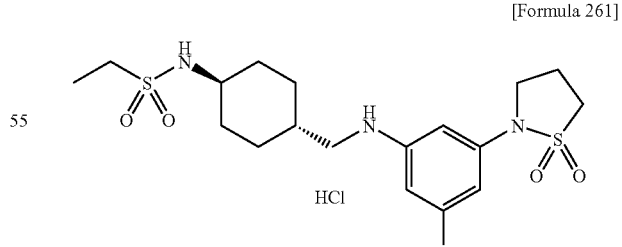

1H-NMR (DMSO-d6) δ: 0.90-1.08 (m, 2H), 1.13-1.27 (m, 5H), 1.42 (m, 1H), 1.74-1.93 (m, 4H), 2.30-2.40 (m, 2H), 2.81 (d, 2H, J=6.6 Hz), 2.97 (q, 2H, J=7.5 Hz), 3.00 (m, 1H), 3.49 (t, 2H, J=7.5 Hz), 3.66 (t, 2H, J=6.6 Hz), 5.00-5.50 (brs, 2H), 6.07-6.15 (m, 2H), 6.25 (s, 1H), 7.00 (d, 1H, J=6.6 Hz).

Compound Ii-94

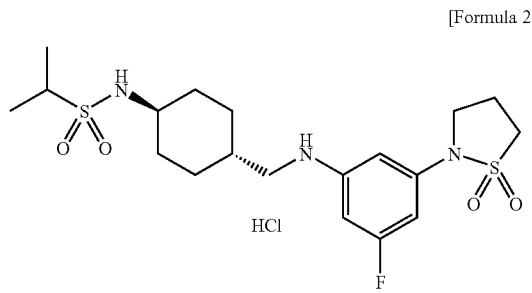

[Formula 262]

1H-NMR (DMSO-d6) δ: 0.92-1.07 (m, 2H), 1.15-1.32 (m, 5H), 1.21 (d, 6H, J=6.9 Hz), 1.42 (m, 1H), 1.74-1.93 (m, 4H), 2.30-2.42 (m, 2H), 2.81 (d, 2H, J=6.6 Hz), 2.92-3.18 (m, 2H), 3.49 (t, 2H, J=7.5 Hz), 3.66 (t, 2H, J=6.6 Hz), 4.70-5.30 (brs, 2H), 6.05-6.16 (m, 2H), 6.25 (s, 1H), 6.95 (d, 1H, J=8.1 Hz).

Compound Ii-95

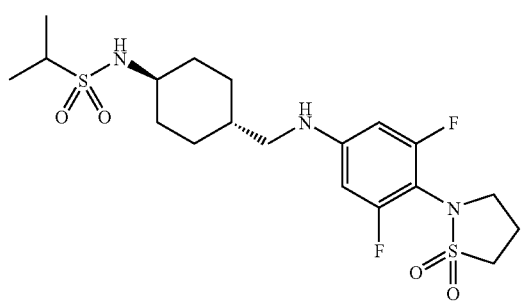

[Formula 263]

1H-NMR (DMSO-d6) δ: 0.90-1.06 (m, 2H), 1.16-1.31 (d, 6H, J=6.9 Hz), 1.40 (m, 1H), 1.73-1.94 (m, 4H), 2.34-2.46 (m, 2H), 2.84 (t, 2H, J=6.0 Hz), 2.94-3.16 (m, 2H), 3.28 (t, 2H, J=7.5 Hz), 3.53 (t, 2H, J=6.6 Hz), 6.27 (d, 2H, J=11.7 Hz), 6.52 (t, 1H, J=5.4 Hz), 6.94 (d, 1H, J=7.8 Hz).

Compound Ii-96

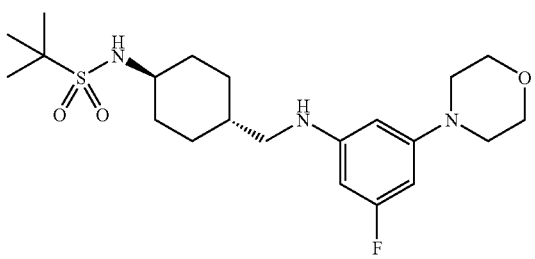

[Formula 264]

1H-NMR (DMSO-d6) δ: 0.91-1.04 (m, 2H), 1.20-1.32 (m, 2H), 1.26 (s, 9H), 1.40 (m, 1H), 1.76-1.95 (m, 4H), 2.77-2.83 (m, 2H), 2.99-3.04 (m, 5H), 3.67-3.72 (m, 4H), 5.71 (m, 1H), 5.79 (d, 1H, J=11.7 Hz), 5.89 (s, 1H), 5.90 (m, 1H), 6.72 (d, 1H, J=8.4 Hz).

Compound Ii-97

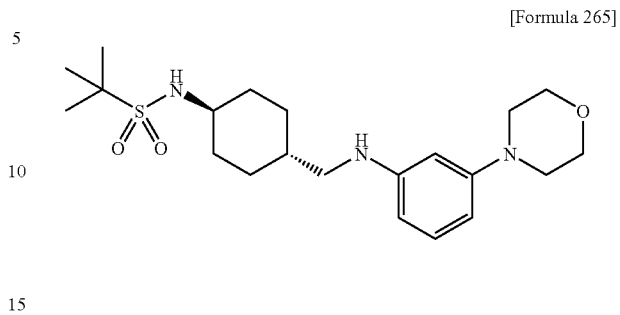

[Formula 265]

1H-NMR (DMSO-d6) δ: 0.92-1.03 (m, 2H), 1.20-1.32 (m, 2H), 1.26 (s, 9H), 1.41 (m, 1H), 1.77-1.93 (m, 4H), 2.78-2.83 (m, 2H), 2.97-3.05 (m, 5H), 3.68-3.72 (m, 4H), 5.36 (m, 1H), 6.04 (d, 1H, J=8.0 Hz), 6.10 (s, 1H), 6.11 (d, 1H, J=8.0 Hz), 6.72 (d, 1H, J=8.0 Hz), 6.89 (dd, 1H, J=8.0, 8.0 Hz).

Compound Ii-98

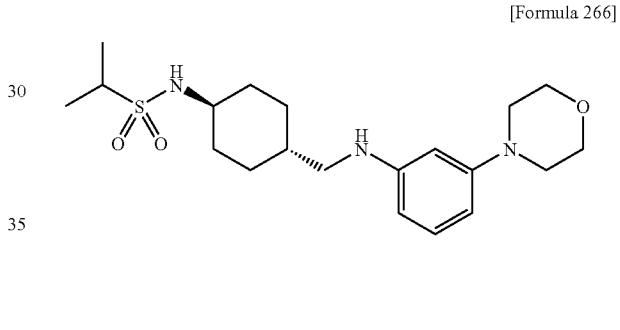

[Formula 266]

1H-NMR (DMSO-d6) δ: 0.92-1.04 (m, 2H), 1.17-1.29 (m, 2H), 1.21 (d, 6H, J=6.4 Hz), 1.41 (m, 1H), 1.75-1.92 (m, 4H), 2.77-2.83 (m, 2H), 2.95-3.05 (m, 5H), 3.09 (m, 1H), 3.67-3.72 (m, 4H), 5.36 (m, 1H), 6.04 (d, 1H, J=8.0 Hz), 6.10 (s, 1H), 6.11 (d, 1H, J=8.0 Hz), 6.89 (dd, 1H, J=8.0, 8.0 Hz), 6.92 (d, 1H, J=8.0 Hz).

Compound Ii-99

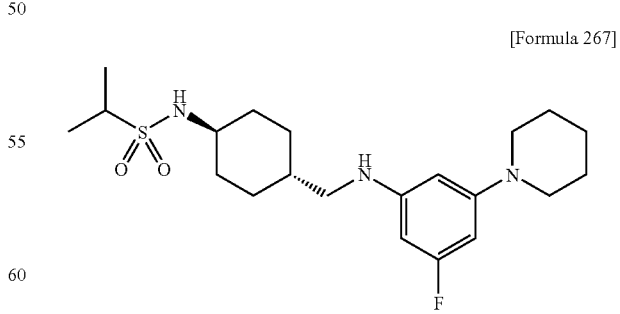

[Formula 267]

1H-NMR (DMSO-d6) δ: 0.90-1.06 (m, 2H), 1.15-1.31 (m, 2H), 1.21 (d, 6H, J=6.9 Hz), 1.39 (m, 1H), 1.47-1.62 (m, 6H), 1.74-1.94 (m, 4H), 2.78 (t, 2H, J=6.0 Hz), 2.93-3.16 (m, 6H), 5.64-5.76 (m, 2H), 5.83-5.92 (m, 2H), 6.94 (d, 1H, J=7.8 Hz).

Compound Ii-100

[Formula 268]

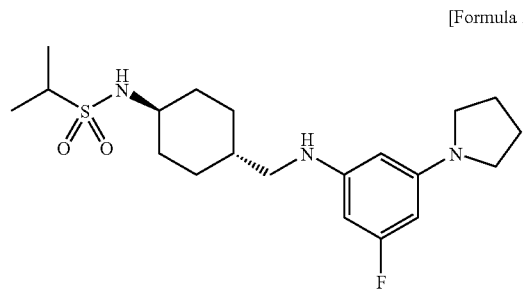

1H-NMR (DMSO-d6) δ: 0.90-1.06 (m, 2H), 1.15-1.30 (m, 2H), 1.21 (d, 6H, J=6.9 Hz), 1.40 (m, 1H), 1.74-1.96 (m, 8H), 2.79 (t, 2H, J=6.0 Hz), 2.93-3.18 (m, 6H), 5.48-5.67 (m, 4H), 6.94 (d, 1H, J=8.1 Hz).

Compound Ii-101

[Formula 269]

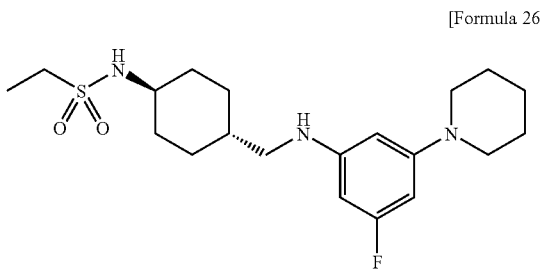

1H-NMR (DMSO-d6) δ: 0.90-1.06 (m, 2H), 1.13-1.29 (m, 2H), 1.18 (t, 3H, J=7.5 Hz), 1.39 (m, 1H), 1.47-1.62 (m, 6H), 1.75-1.94 (m, 4H), 2.79 (t, 2H, J=6.0 Hz), 2.97 (q, 2H, J=7.5 Hz), 3.03-3.10 (m, 4H), 5.64-5.75 (m, 2H), 5.83-5.91 (m, 2H), 7.00 (d, 1H, J=7.8 Hz).

Compound Ii-102

[Formula 270]

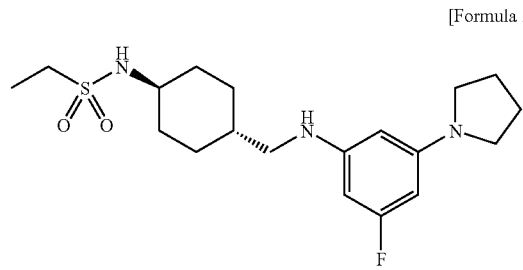

1H-NMR (DMSO-d6) δ: 0.90-1.07 (m, 2H), 1.13-1.29 (m, 2H), 1.18 (t, 3H, J=7.5 Hz), 1.41 (m, 1H), 1.74-1.96 (m, 8H), 2.79 (t, 2H, J=6.0 Hz), 2.97 (q, 2H, J=7.5 Hz), 3.00 (m, 1H), 3.09-3.19 (m, 4H), 5.46-5.66 (m, 4H), 6.99 (d, 1H, J=7.2 Hz).

Compound Ii-103

[Formula 271]

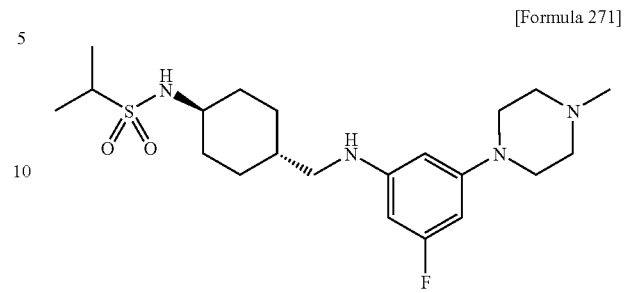

1H-NMR (DMSO-d6) δ: 0.91-1.03 (m, 2H), 1.16-1.29 (m, 2H), 1.21 (d, 6H, J=6.8 Hz), 1.40 (m, 1H), 1.75-1.92 (m, 4H), 2.20 (s, 3H), 2.35-2.43 (m, 4H), 2.75-2.82 (m, 2H), 2.88-3.13 (m, 6H), 5.67 (m, 1H), 5.76 (d, 1H, J=11.2 Hz), 5.82-5.92 (m, 2H), 6.91 (d, 1H, J=8.0 Hz).

Compound Ii-104

[Formula 272]

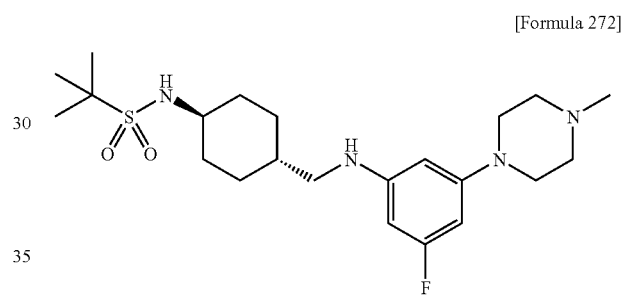

1H-NMR (DMSO-d6) δ: 0.92-1.02 (m, 2H), 1.19-1.32 (m, 2H), 1.26 (s, 9H), 1.39 (m, 1H), 1.75-1.95 (m, 4H), 2.19 (s, 3H), 2.38-2.42 (m, 4H), 2.77-2.83 (m, 5H), 2.98-3.09 (m, 5H), 5.67 (m, 1H), 5.76 (d, 1H, J=11.2 Hz), 5.88 (m, 1H), 5.88 (s, 1H), 6.72 (d, 1H, J=8.8 Hz).

Compound Ii-105

[Formula 273]

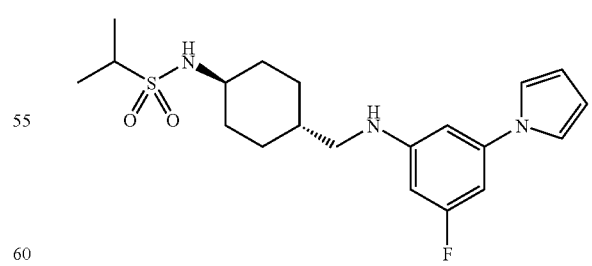

1H-NMR (DMSO-d6) δ: 0.95-1.09 (m, 2H), 1.18-1.31 (m, 2H), 1.22 (d, 6H, J=6.8 Hz), 1.44 (m, 1H), 1.78-1.93 (m, 4H), 2.87-2.92 (m, 2H), 3.03 (m, 1H), 3.10 (m, 1H), 6.13 (m, 1H), 6.21 (m, 1H), 6.22 (s, 2H), 6.51 (s, 1H), 6.52 (d, 1H, J=8.0 Hz), 6.92 (d, 1H, J=8.0 Hz), 7.26 (s, 2H).

Compound Ii-106

[Formula 274]

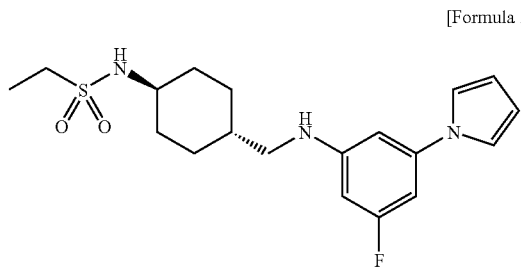

1H-NMR (DMSO-d6) δ: 0.97-1.08 (m, 2H), 1.17-1.29 (m, 5H), 1.40-1.68 (m, 3H), 1.80-1.92 (m, 2H), 2.90 (t, 2H, J=6.0 Hz), 2.94-3.06 (m, 3H), 6.12-6.22 (m, 4H), 6.50-6.54 (m, 2H), 6.94-7.00 (m, 1H), 7.26-7.27 (m, 2H).

Compound Ii-107

[Formula 275]

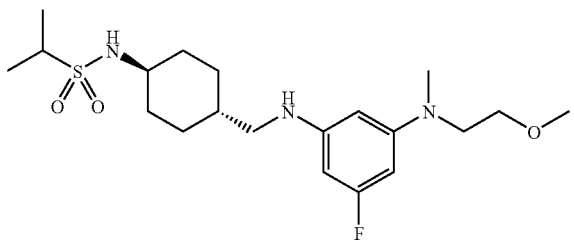

1H-NMR (DMSO-d6) δ: 0.91-1.03 (m, 2H), 1.16-1.29 (m, 2H), 1.21 (d, 6H, J=6.4 Hz), 1.40 (m, 1H), 1.74-1.92 (m, 4H), 2.75-2.81 (m, 2H), 2.84 (s, 3H), 3.00 (m, 1H), 3.09 (m, 1H), 3.25 (s, 3H), 3.35-3.47 (m, 4H), 5.59-5.67 (m, 4H), 6.91 (d, 1H, J=8.0 Hz).

Compound Ii-108

[Formula 276]

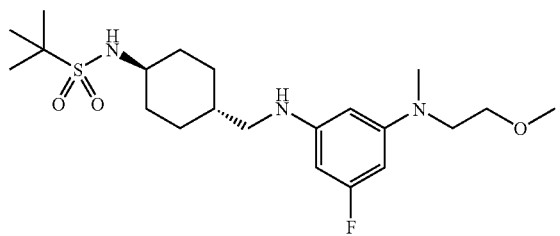

1H-NMR (DMSO-d6) δ: 0.92-1.03 (m, 2H), 1.18-1.32 (m, 2H), 1.26 (s, 9H), 1.40 (m, 1H), 1.75-1.94 (m, 4H), 2.75-2.81 (m, 2H), 2.83 (s, 3H), 3.01 (m, 1H), 3.25 (s, 3H), 3.34-3.47 (m, 4H), 5.58-5.70 (m, 4H), 6.72 (d, 1H, J=8.4 Hz).

Compound Ii-109

[Formula 277]

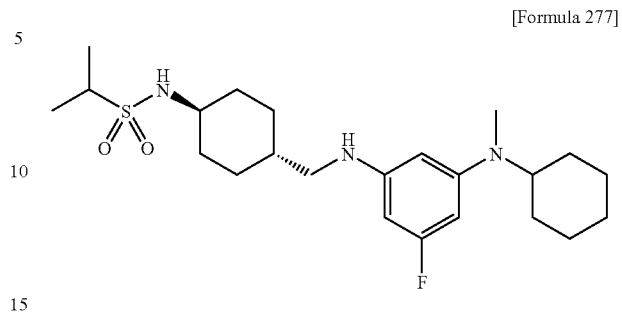

1H-NMR (DMSO-d6) δ: 0.90-1.51 (m, 10H), 1.21 (d, 6H, J=6.9 Hz), 1.56-1.67 (m, 3H), 1.71-1.93 (m, 6H), 2.64 (s, 3H), 2.78 (t, 2H, J=6.0 Hz), 2.93-3.17 (m, 2H), 3.44 (m, 1H), 5.56-5.77 (m, 4H), 6.94 (d, 1H, J=7.8 Hz).

Compound Ii-110

[Formula 278]

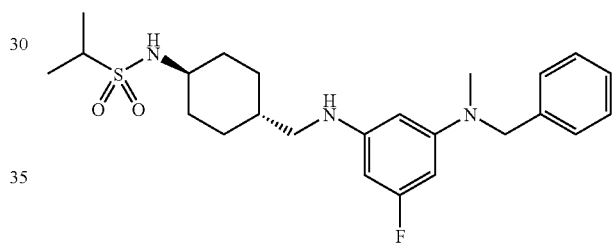

1H-NMR (DMSO-d6) δ: 0.83-1.01 (m, 2H), 1.00-1.40 (m, 3H), 1.21 (d, 6H, J=6.9 Hz), 1.68-1.91 (m, 4H), 2.73 (t, 2H, J=6.0 Hz), 2.90-3.15 (m, 2H), 2.95 (s, 3H), 4.48 (s, 2H), 5.60-5.72 (m, 4H), 6.94 (d, 1H, J=7.8 Hz), 7.15-7.35 (m, 5H).

Compound Ii-111

[Formula 279]

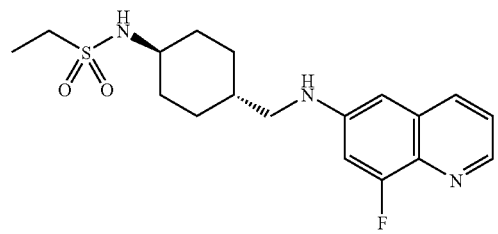

1H-NMR (DMSO-d6) δ: 0.97-1.14 (m, 2H), 1.14-1.33 (m, 5H), 1.45-1.61 (m, 1H), 1.81-1.96 (m, 4H), 2.90-3.10 (m, 5H), 6.34 (t, 1H, J=5.2 Hz), 6.51 (d, 1H, J=2.2 Hz), 6.99-7.07 (m, 2H), 7.36 (dd, 1H, J=8.2, 4.1 Hz), 8.02 (d, 1H, J=8.5 Hz), 8.48 (dd, 1H, J=4.1, 1.4 Hz).

Compound Ii-112

[Formula 280]

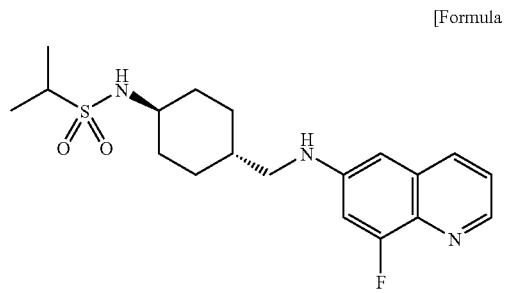

1H-NMR (DMSO-d6) δ: 0.97-1.13 (m, 2H), 1.17-1.34 (m, 8H), 1.45-1.59 (m, 1H), 1.81-1.99 (m, 4H), 2.94 (t, 2H, J=5.9 Hz), 2.99-3.21 (m, 2H), 6.33 (t, 1H, J=5.4 Hz), 6.51 (d, 1H, J=2.2 Hz), 6.96 (d, 1H, J=7.7 Hz), 7.02 (dd, 1H, J=13.5, 2.2 Hz), 7.36 (dd, 1H, J=8.2, 4.1 Hz), 8.02 (d, 1H, J=8.5 Hz), 8.48 (dd, 1H, J=4.1, 1.4 Hz).

Compound Ii-113

[Formula 281]

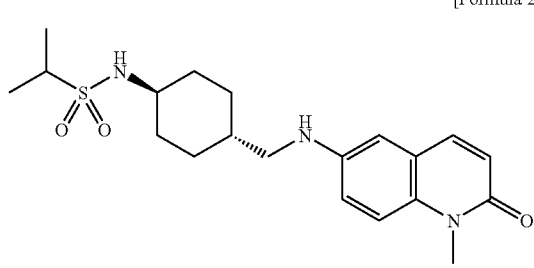

1H-NMR (DMSO-d6) δ: 0.93-1.13 (m, 2H), 1.15-1.34 (m, 8H), 1.39-1.57 (m, 1H), 1.79-1.95 (m, 4H), 2.87 (t, 2H, J=6.2 Hz), 2.94-3.16 (m, 2H), 3.54 (s, 3H), 5.66 (t, 1H, J=5.5 Hz), 6.49 (d, 1H, J=9.6 Hz), 6.73 (d, 1H, J=2.8 Hz), 6.91-7.02 (m, 2H), 7.29 (d, 1H, J=9.3 Hz), 7.72 (d, 1H, J=9.3 Hz).

Compound Ii-114

[Formula 282]

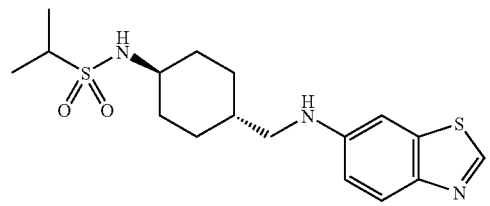

1H-NMR (DMSO-d6) δ: 0.93-1.10 (m, 2H), 1.14-1.33 (m, 8H), 1.41-1.56 (m, 1H), 1.79-1.94 (m, 4H), 2.89 (t, 2H, J=6.0 Hz), 2.95-3.16 (m, 2H), 6.00 (t, 1H, J=5.4 Hz), 6.84 (dd, 1H, J=8.8, 2.2 Hz), 6.95 (d, 1H, J=8.0 Hz), 7.07 (d, 1H, J=2.2 Hz), 7.72 (d, 1H, J=8.8 Hz), 8.86 (s, 1H).

Compound Ii-115

[Formula 283]

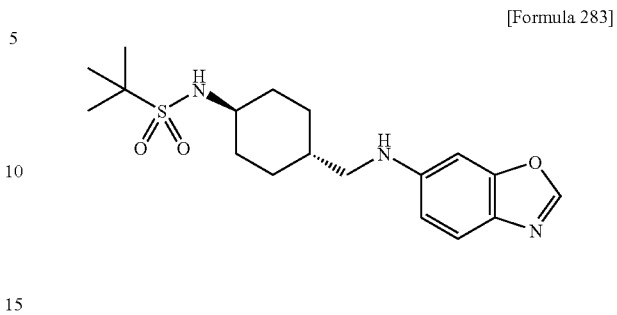

1H-NMR (DMSO-d6) δ: 0.94-1.06 (m, 4H), 1.26 (s, 9H), 1.40-1.51 (m, 1H), 1.84 (d, 2H, J=12.4 Hz), 1.91 (d, 2H, J=12.4 Hz), 2.85-2.90 (m, 2H), 2.97-3.06 (m, 1H), 5.93-5.99 (m, 1H), 6.63-6.79 (m, 3H), 7.40 (d, 1H, J=8.8 Hz), 8.32 (s, 1H).

Compound Ii-116

[Formula 284]

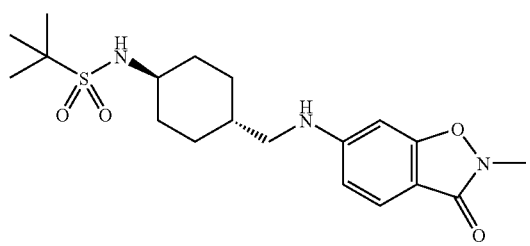

1H-NMR (DMSO-d6) δ: 0.95-1.07 (m, 4H), 1.26 (s, 9H), 1.39-1.47 (m, 1H), 1.80 (d, 2H, J=12.4 Hz), 1.91 (d, 2H, J=12.4 Hz), 2.87-2.93 (m, 2H), 2.98-3.06 (m, 1H), 3.37 (s, 3H), 6.27 (s, 1H), 6.55 (d, 1H, J=8.8 Hz), 6.73 (d, 1H, J=8.8 Hz), 6.80 (t, 1H, J=5.2 Hz), 7.32 (d, 1H, J=8.8 Hz).

Compound Ii-117

[Formula 285]

1H-NMR (DMSO-d6) δ: 0.94-1.08 (m, 4H), 1.20 (s, 3H), 1.22 (s, 3H), 1.39-1.51 (m, 1H), 1.80 (d, 2H, J=12.4 Hz), 1.88 (d, 2H, J=12.4 Hz), 2.87-2.94 (m, 2H), 2.97-3.07 (m, 1H), 3.08-3.14 (m, 1H), 3.37 (s, 3H), 6.27 (s, 1H), 6.55 (d, 1H, J=8.4 Hz), 6.82 (t, 1H, J=5.6 Hz), 6.94 (d, 1H, J=8.0 Hz), 7.32 (d, 1H, J=8.4 Hz).

Compound Ii-118

[Formula 286]

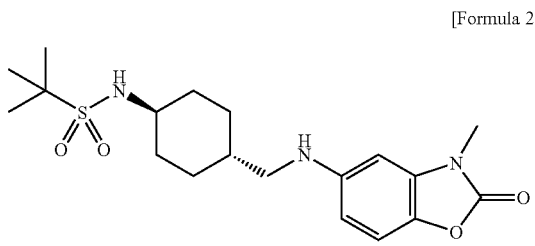

1H-NMR (DMSO-d6) δ: 0.92-1.06 (m, 4H), 1.26 (s, 9H), 1.38-1.50 (m, 1H), 1.83 (d, 2H, J=12.4 Hz), 1.90 (d, 2H, J=12.4 Hz), 2.80-2.86 (m, 2H), 2.96-3.06 (m, 1H), 3.26 (s, 3H), 5.58-5.65 (m, 1H), 6.27 (d, 1H, J=8.4 Hz), 6.38 (s, 1H), 6.75 (d, 1H, J=8.4 Hz), 6.99 (d, 1H, J=8.4 Hz).

Compound Ii-119

[Formula 287]

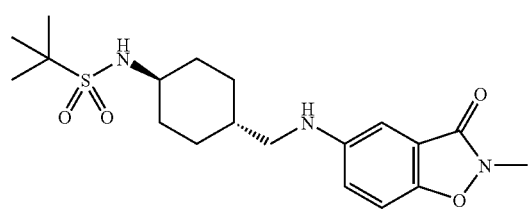

1H-NMR (DMSO-d6) δ: 0.94-1.06 (m, 4H), 1.26 (s, 9H), 1.39-1.50 (m, 1H), 1.84 (d, 2H, J=12.4 Hz), 1.90 (d, 2H, J=12.4 Hz), 2.81-2.89 (m, 2H), 2.96-3.07 (m, 1H), 3.51 (s, 3H), 5.79-5.84 (m, 1H), 6.60 (s, 1H), 6.75 (d, 1H, J=8.8 Hz), 7.03 (d, 1H, J=8.8 Hz), 7.19 (d, 1H, J=8.8 Hz).

Compound Ii-120

[Formula 288]

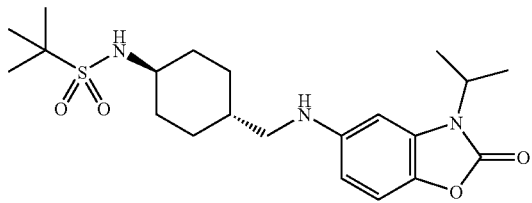

1H-NMR (DMSO-d6) δ: 0.93-1.10 (m, 4H), 1.26 (s, 9H), 1.37-1.40 (m, 1H), 1.42 (s, 3H), 1.44 (s, 3H), 1.83 (d, 2H, J=12.4 Hz), 1.91 (d, 2H, J=12.4 Hz), 2.79-2.96 (m, 2H), 2.97-3.07 (m, 1H), 4.33-4.46 (m, 1H), 5.50-5.59 (m, 1H), 6.25 (d, 1H, J=8.8 Hz), 6.57 (s, 1H), 6.75 (d, 1H, J=8.4 Hz), 7.00 (d, 1H, J=8.4 Hz).

Compound Ii-121

[Formula 289]

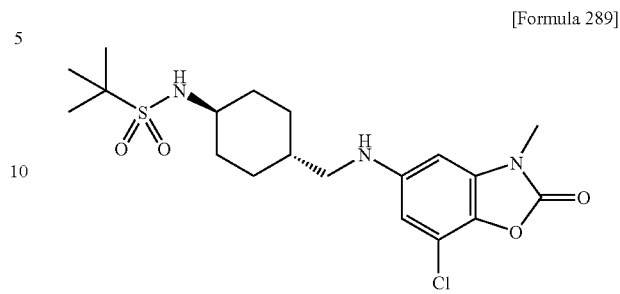

1H-NMR (DMSO-d6) δ: 0.90-1.06 (m, 4H), 1.26 (s, 9H), 1.36-1.49 (m, 1H), 1.82 (d, 2H, J=12.4 Hz), 1.90 (d, 2H, J=12.4 Hz), 2.80-2.87 (m, 2H), 2.95-3.97 (m, 1H), 3.27 (s, 3H), 5.85-5.92 (m, 1H), 6.33 (s, 1H), 6.36 (s, 1H), 6.75 (d, 1H, J=8.8 Hz).

Compound Ii-122

[Formula 290]

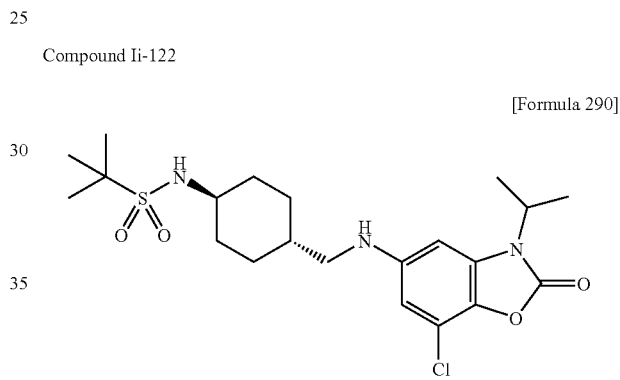

1H-NMR (DMSO-d6) δ: 0.92-1.08 (m, 4H), 1.26 (s, 9H), 1.38-1.41 (m, 1H), 1.42 (s, 3H), 1.43 (s, 3H), 1.82 (d, 2H, J=11.8 Hz), 1.90 (d, 2H, J=11.8 Hz), 2.83-2.88 (m, 2H), 2.98-3.06 (m, 1H), 4.33-4.47 (m, 1H), 6.35 (s, 1H), 6.54 (s, 1H), 6.76 (d, 1H, J=8.4 Hz), 8.32 (s, 1H).

Compound Ii-123

[Formula 291]

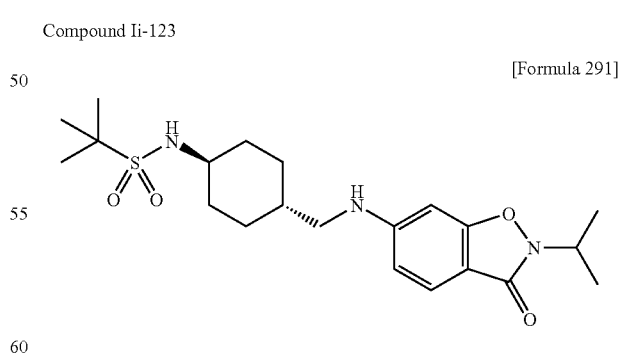

1H-NMR (DMSO-d6) δ: 0.93-1.06 (m, 4H), 1.22 (s, 3H), 1.24 (s, 3H), 1.26 (s, 9H), 1.39-1.50 (m, 1H), 1.81 (d, 2H, J=12.4 Hz), 1.90 (d, 2H, J=12.4 Hz), 2.87-2.93 (m, 2H), 2.96-3.07 (m, 1H), 4.39-4.47 (m, 1H), 6.30 (s, 1H), 6.54 (d, 1H, J=8.8 Hz), 6.77 (d, 1H, J=8.8 Hz), 6.86 (t, 1H, J=5.2 Hz), 7.32 (d, 1H, J=8.4 Hz).

Compound Ii-124

[Formula 292]

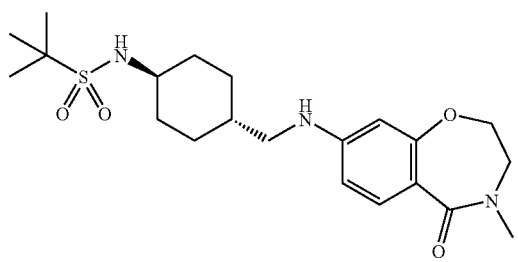

1H-NMR (DMSO-d6) δ: 0.90-1.05 (m, 4H), 1.26 (s, 9H), 1.36-1.51 (m, 1H), 1.79 (d, 2H, J=12.4 Hz), 1.90 (d, 2H, J=12.4 Hz), 2.80-2.86 (m, 2H), 3.01 (s, 3H), 3.02-3.05 (m, 1H), 3.49 (t, 2H, J=4.8 Hz), 4.26 (t, 2H, J=4.8 Hz), 6.02 (s, 1H), 6.20 (t, 1H, J=5.6 Hz), 6.31 (d, 1H, J=8.8 Hz), 6.74 (d, 1H, J=8.8 Hz), 7.43 (d, 1H, J=8.4 Hz).

Compound Ii-125

[Formula 293]

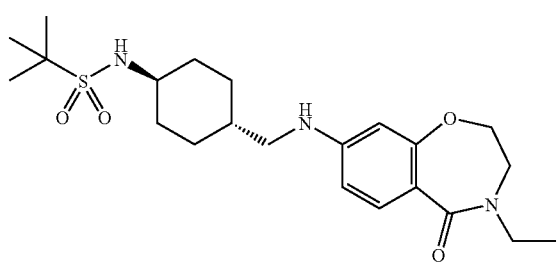

1H-NMR (DMSO-d6) δ: 0.92-1.02 (m, 4H), 1.08 (t, 3H, J=7.2 Hz), 1.25 (s, 9H), 1.35-1.42 (m, 1H), 1.79 (d, 2H, J=12.0 Hz), 1.90 (d, 2H, J=12.0 Hz), 2.80-2.86 (m, 2H), 2.96-3.05 (m, 1H), 3.42-3.51 (m, 4H), 4.20-4.26 (m, 2H), 6.03 (s, 1H), 6.20 (s, 1H), 6.31 (d, 1H, J=8.8 Hz), 6.75 (d, 1H, J=8.8 Hz), 7.42 (d, 1H, J=8.8 Hz).

Compound Ii-126

[Formula 294]

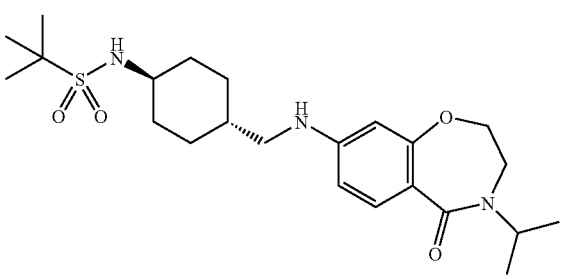

1H-NMR (DMSO-d6) δ: 0.92-1.02 (m, 4H), 1.09 (s, 3H), 1.11 (s, 3H), 1.25 (s, 9H), 1.43-1.55 (m, 1H), 1.80 (d, 2H, J=12.4 Hz), 1.91 (d, 2H, J=12.0 Hz), 2.84 (m, 2H), 2.97-3.08 (m, 1H), 3.37 (t, 2H, J=5.2 Hz), 4.18 (t, 2H, J=5.2 Hz), 4.71-4.80 (m, 1H), 6.05 (s, 1H), 6.19 (t, 1H, J=5.2 Hz), 6.32 (d, 1H, J=8.8 Hz), 6.74 (d, 1H, J=8.4 Hz), 7.18 (d, 1H, J=8.4 Hz).

Compound Ii-127

[Formula 295]

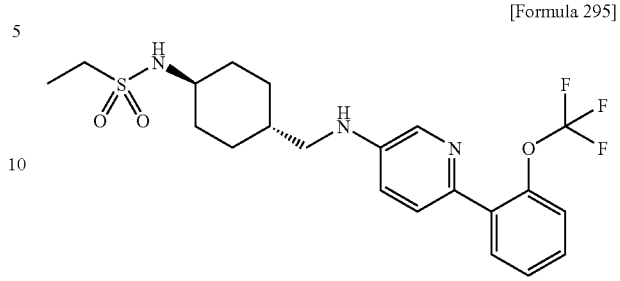

1H-NMR (DMSO-d6) δ: 0.94-1.12 (m, 2H), 1.14-1.39 (m, 5H), 1.34-1.56 (m, 1H), 1.70-1.97 (m, 4H), 2.87-3.10 (m, 5H), 6.17 (t, 1H, J=5.2 Hz), 6.94-7.06 (m, 2H), 7.35-7.47 (m, 4H), 7.75-7.80 (m, 1H), 8.07 (d, 1H, J=3.0 Hz).

Compound Ii-128

[Formula 296]

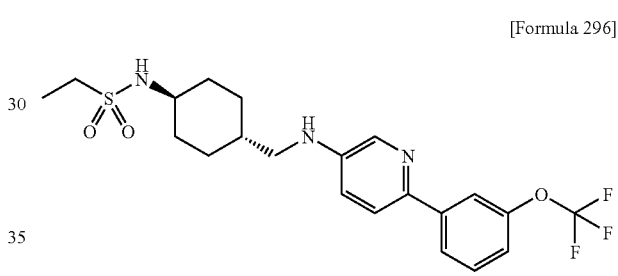

1H-NMR (DMSO-d6) δ: 0.96-1.12 (m, 2H), 1.14-1.31 (m, 5H), 1.31-1.55 (m, 1H), 1.70-1.96 (m, 4H), 2.89-3.09 (m, 5H), 6.24 (t, 1H, J=5.4 Hz), 6.94-7.05 (m, 2H), 7.24 (d, 1H, J=6.9 Hz), 7.52 (t, 1H, J=8.0 Hz), 7.75 (d, 1H, J=8.8 Hz), 7.88-7.97 (m, 2H), 8.07 (d, 1H, J=2.5 Hz).

Compound Ii-129

[Formula 297]

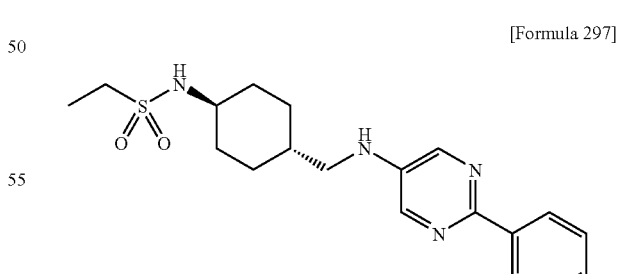

1H-NMR (DMSO-d6) δ: 0.98-1.12 (m, 2H), 1.18-1.30 (m, 2H), 1.19 (t, 3H, J=6.8 Hz), 1.48 (m, 1H), 1.79-1.95 (m, 4H), 2.92-3.09 (m, 3H), 2.97 (q, 2H, J=6.8 Hz), 6.27 (m, 1H), 7.01 (d, 1H, J=8.0 Hz), 7.39-7.47 (m, 2H), 7.56 (m, 1H), 8.18-8.25 (m, 2H), 8.23 (s, 2H).

Compound Ii-130

[Formula 298]

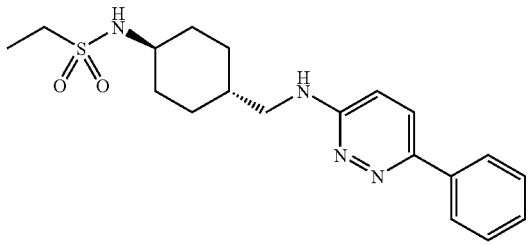

1H-NMR (DMSO-d6) δ: 0.96-1.12 (m, 2H), 1.15-1.30 (m, 2H), 1.18 (t, 3H, J=7.2 Hz), 1.45-1.64 (m, 1H), 1.78-1.96 (m, 4H), 2.97 (q, 2H, J=7.2 Hz), 2.95-3.15 (m, 1H), 3.22-3.28 (m, 2H), 6.89 (d, 1H, J=9.0 Hz), 6.94-7.02 (m, 2H), 7.38 (t, 1H, J=6.0 Hz), 7.46 (t, 2H, J=7.5 Hz), 7.78 (d, 1H, J=9.0 Hz), 7.96 (d, 2H, J=9.0 Hz).

Compound Ii-131

[Formula 299]

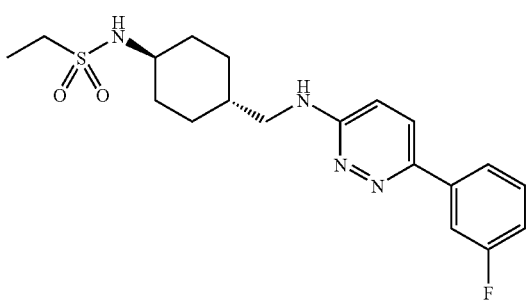

1H-NMR (DMSO-d6) δ: 0.96-1.12 (m, 2H), 1.15-1.30 (m, 2H), 1.18 (t, 3H, J=7.2 Hz), 1.48-1.62 (m, 1H), 1.78-1.96 (m, 4H), 2.98 (q, 2H, J=7.2 Hz), 2.94-3.10 (m, 1H), 3.22-3.28 (m, 2H), 6.89 (d, 1H, J=9.0 Hz), 7.02 (d, 1H, J=9.0 Hz), 7.10 (t, 1H, J=5.4 Hz), 7.22 (td, 1H, J=9.0, 3.0 Hz), 7.47-7.56 (m, 1H), 7.77-7.88 (m, 3H).

Compound Ii-132

[Formula 300]

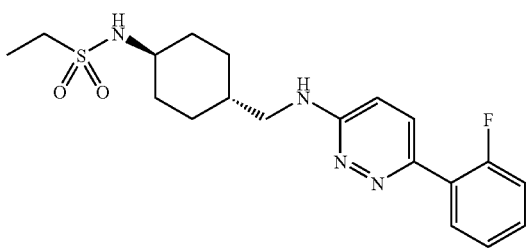

1H-NMR (DMSO-d6) δ: 0.96-1.13 (m, 2H), 1.15-1.32 (m, 2H), 1.19 (t, 3H, J=7.5 Hz), 1.48-1.65 (m, 1H), 1.78-1.96 (m, 4H), 2.98 (q, 2H, J=7.2 Hz), 2.94-3.12 (m, 1H), 3.22-3.28 (m, 2H), 6.89 (d, 1H, J=9.0 Hz), 7.01 (d, 1H, J=6.0 Hz), 7.09 (t, 1H, J=5.4 Hz), 7.27-7.35 (m, 2H), 7.42-7.50 (m, 1H), 7.57 (dd, 1H, J=9.0, 3.0 Hz), 7.86 (td, 1H, J=7.5, 3.0 Hz).

Compound Ii-133

[Formula 301]

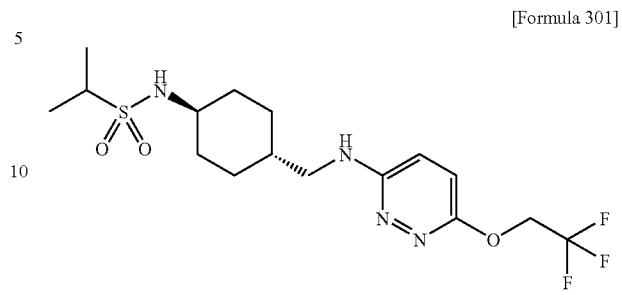

1H-NMR (DMSO-d6) δ: 0.92-1.08 (m, 2H), 1.15-1.30 (m, 2H), 1.21 (d, 6H, J=6.6 Hz), 1.42-1.58 (m, 1H), 1.72-1.94 (m, 4H), 2.95-3.20 (m, 4H), 4.89-4.98 (m, 2H), 6.65 (brs, 1H), 6.92 (d, 1H, J=9.0 Hz), 6.91-6.98 (m, 1H), 7.03 (d, 1H, J=9.0 Hz).

Compound Ii-134

[Formula 302]

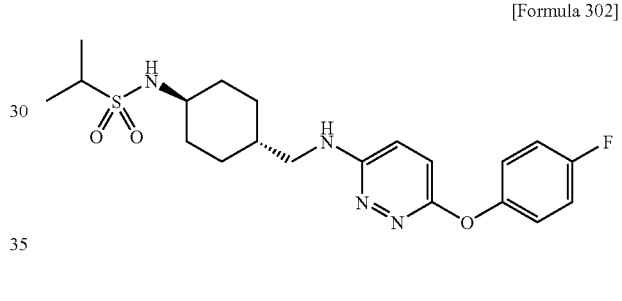

1H-NMR (DMSO-d6) δ: 0.90-1.08 (m, 2H), 1.15-1.30 (m, 2H), 1.21 (d, 6H, J=6.6 Hz), 1.42-1.58 (m, 1H), 1.72-1.94 (m, 4H), 2.92-3.20 (m, 4H), 6.74 (t, 1H, J=6.0 Hz), 6.94 (t, 1H, J=6.0 Hz), 6.97 (s, 1H), 7.08-7.24 (m, 5H).

Compound Ii-135

[Formula 303]

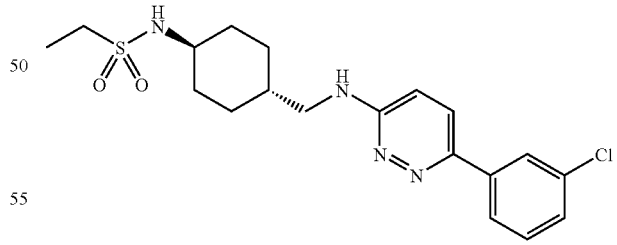

1H-NMR (DMSO-d6) δ: 0.95-1.10 (m, 2H), 1.12-1.30 (m, 2H), 1.19 (t, 3H, J=7.2 Hz), 1.48-1.60 (m, 1H), 1.76-1.94 (m, 4H), 2.92-3.10 (m, 1H), 2.97 (q, 2H, J=7.2 Hz), 3.18-3.30 (m, 2H), 6.89 (d, 1H, J=9.6 Hz), 7.02 (brs, 1H), 7.11 (t, 1H, J=5.4 Hz), 7.42-7.56 (m, 2H), 7.85 (d, 1H, J=9.6 Hz), 7.93 (d, 1H, J=7.5 Hz), 8.03 (s, 1H).

Compound Ii-136

[Formula 304]

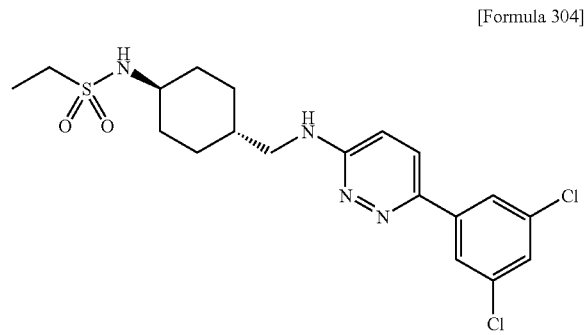

1H-NMR (DMSO-d6) δ: 0.98-1.12 (m, 2H), 1.13-1.30 (m, 2H), 1.18 (t, 3H, J=7.2 Hz), 1.48-1.62 (m, 1H), 1.78-1.96 (m, 4H), 2.92-3.12 (m, 1H), 2.97 (q, 2H, J=7.2 Hz), 3.22-3.32 (m, 2H), 6.89 (d, 1H, J=9.0 Hz), 7.01 (d, 1H, J=7.5 Hz), 7.20 (t, 1H, J=6.0 Hz), 7.62 (s, 1H), 7.91 (d, 1H, J=9.0 Hz), 8.02 (s, 2H).

Compound Ii-137

[Formula 305]

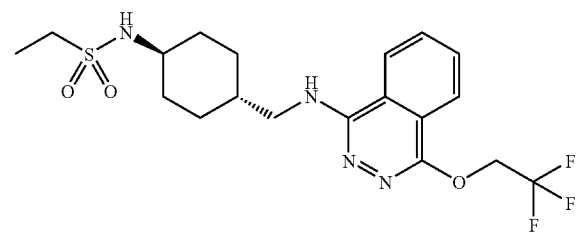

1H-NMR (DMSO-d6) δ: 0.95-1.12 (m, 2H), 1.13-1.30 (m, 2H), 1.18 (t, 3H, J=7.2 Hz), 1.65-1.95 (m, 5H), 2.93-3.12 (m, 1H), 2.97 (q, 2H, J=7.2 Hz), 3.25-3.40 (m, 2H), 5.07-5.16 (m, 2H), 7.01 (d, 1H, J=7.5 Hz), 7.25 (t, 1H, J=6.0 Hz), 7.92-8.03 (m, 3H), 8.33 (d, 1H, J=6.0 Hz).

Compound Ii-138

[Formula 306]

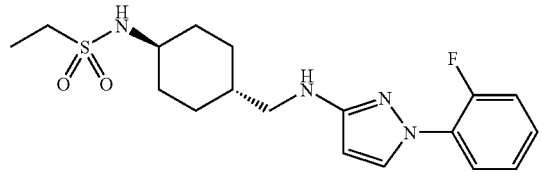

1H-NMR (DMSO-d6) δ: 0.91-1.26 (m, 4H), 1.19 (t, 3H, J=7.5 Hz), 1.36-1.43 (m, 1H), 1.78-1.90 (m, 4H), 2.90-3.07 (m, 3H), 2.96 (q, 2H, J=7.5 Hz), 5.69 (t, 1H, J=5.7 Hz), 5.81 (d, 1H, J=2.4 Hz), 7.00 (d, 1H, J=7.8 Hz), 7.16-7.39 (m, 3H), 7.73-7.79 (m, 1H), 7.86-7.88 (m, 1H).

Compound Ii-139

[Formula 307]

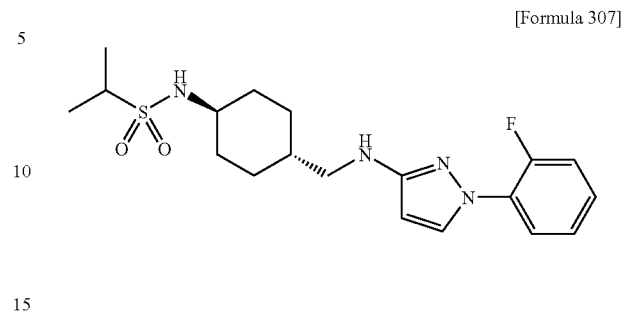

1H-NMR (DMSO-d6) δ: 0.90-1.06 (m, 4H), 1.20 (s, 3H), 1.22 (s, 3H), 1.40-1.52 (m, 1H), 1.81 (d, 2H, J=12.4 Hz), 1.88 (d, 2H, J=12.4 Hz), 2.90-2.98 (m, 2H), 2.99-3.13 (m, 2H), 5.68 (t, 1H, J=5.6 Hz), 5.81 (s, 1H), 6.93 (d, 1H, J=8.8 Hz), 7.16-7.40 (m, 3H), 7.76 (t, 1H, J=8.0 Hz), 7.87 (s, 1H).

Compound Ii-140

[Formula 308]

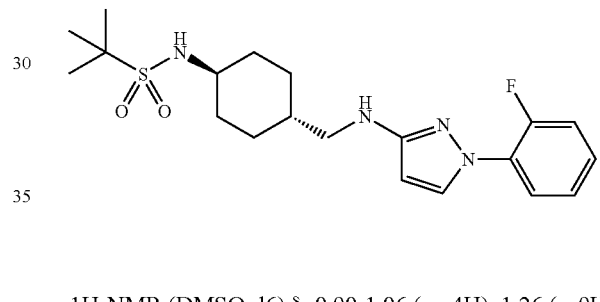

1H-NMR (DMSO-d6) δ: 0.90-1.06 (m, 4H), 1.26 (s, 9H), 1.40-1.49 (m, 1H), 1.82 (d, 2H, J=12.4 Hz), 1.91 (d, 2H, J=12.4 Hz), 2.90-2.99 (m, 2H), 3.01-3.06 (m, 1H), 5.67 (t, 1H, J=6.0 Hz), 5.81 (s, 1H), 6.74 (d, 1H, J=8.4 Hz), 7.14-7.40 (m, 3H), 7.76 (t, 1H, J=8.4 Hz), 7.87 (s, 1H).

Compound Ii-141

[Formula 309]

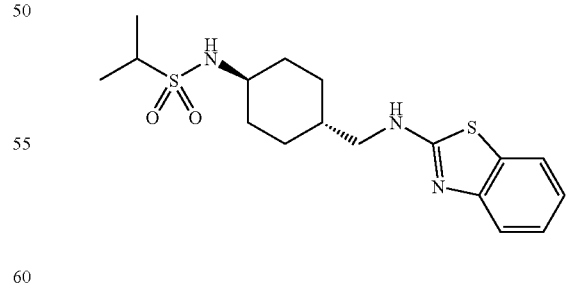

1H-NMR (DMSO-d6) δ: 0.97-1.06 (m, 2H), 1.18-1.27 (m, 2H), 1.21 (d, 6H, J=6.9 Hz), 1.45-1.59 (m, 1H), 1.76-1.81 (m, 2H), 1.87-1.91 (m, 2H), 2.97-3.09 (m, 1H), 3.10-3.13 (m, 1H), 3.17-3.22 (m, 2H), 6.94-7.02 (m, 2H), 6.98 (td, 1H, J=7.8, 1.2 Hz), 7.36 (dd, 1H, J=7.8, 0.6 Hz), 7.65 (dd, 1H, J=7.8, 0.6 Hz), 8.00-8.05 (m, 1H).

Compound Ii-142

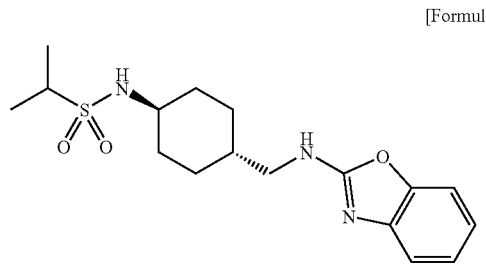

[Formula 310]

1H-NMR (DMSO-d6) δ: 0.96-1.04 (m, 2H), 1.18-1.28 (m, 2H), 1.20 (d, 6H, J=6.9 Hz), 1.43-1.59 (m, 1H), 1.74-1.79 (m, 2H), 1.85-1.90 (m, 2H), 2.92-3.07 (m, 1H), 3.09-3.18 (m, 3H), 6.92-6.99 (m, 2H), 7.10 (td, 1H, J=7.8, 1.2 Hz), 7.21 (dd, 1H, J=7.8, 0.6 Hz), 7.31 (dd, 1H, J=7.8, 0.6 Hz), 7.89-7.97 (m, 1H).

Compound Ii-143

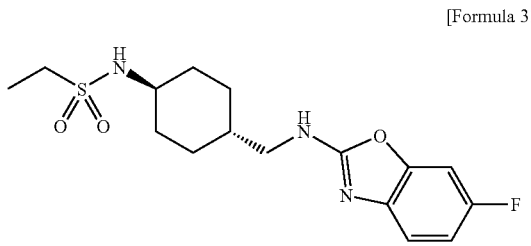

[Formula 311]

1H-NMR (DMSO-d6)δ: 0.97-1.07 (m, 2H), 1.17-1.23 (m, 2H), 1.18 (t, 3H, J=7.2 Hz), 1.42-1.57 (m, 1H), 1.73-1.78 (m, 2H), 1.86-1.90 (m, 2H), 2.93-3.02 (m, 1H), 2.97 (q, 2H, J=7.2 Hz), 3.11 (t, 2H, J=6.3 Hz), 6.91-7.02 (m, 2H), 7.19 (dd, 1H, J=8.4, 4.8 Hz), 7.34 (dd, 1H, J=9.3, 2.4 Hz), 8.00 (t, 1H, J=6.0 Hz).

Compound Ii-144

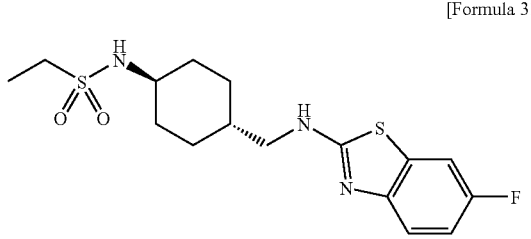

[Formula 312]

1H-NMR (DMSO-d6)δ: 0.97-1.08 (m, 2H), 1.16-1.24 (m, 2H), 1.18 (t, 3H, J=7.2 Hz), 1.42-1.59 (m, 1H), 1.74-1.80 (m, 2H), 1.85-1.90 (m, 2H), 2.92-3.03 (m, 1H), 2.97 (q, 2H, J=7.5 Hz), 3.18 (t, 2H, J=6.3 Hz), 6.99-7.07 (m, 2H), 7.33 (dd, 1H, J=9.0, 4.8 Hz), 7.58 (dd, 1H, J=8.7, 2.7 Hz), 8.00 (t, 1H, J=5.4 Hz).

Compound Ii-145

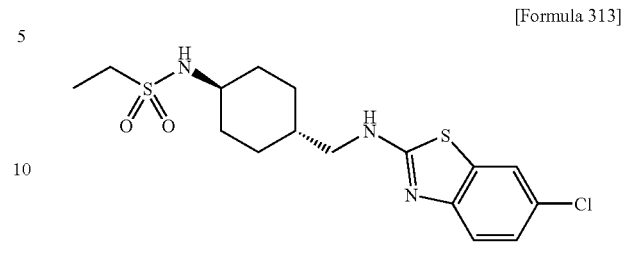

[Formula 313]

1H-NMR (DMSO-d6) δ: 0.97-1.09 (m, 2H), 1.17-1.23 (m, 2H), 1.18 (t, 3H, J=7.2 Hz), 1.43-1.59 (m, 1H), 1.72-1.81 (m, 2H), 1.85-1.92 (m, 2H), 2.95-3.06 (m, 1H), 2.97 (q, 2H, J=7.5 Hz), 3.19 (t, 2H, J=6.0 Hz), 7.01 (d, 1H, J=8.1 Hz), 7.20-7.23 (m, 1H), 7.33 (dd, 1H, J=8.7, 0.6 Hz), 7.58 (dd, 1H, J=2.1, 0.9 Hz), 8.11-8.18 (m, 1H).

Compound Ii-146

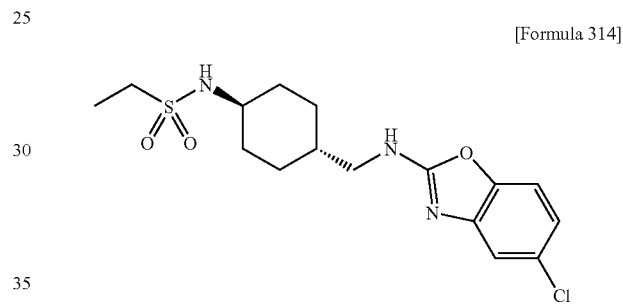

[Formula 314]

1H-NMR (DMSO-d6) δ: 0.98-1.06 (m, 2H), 1.15-1.21 (m, 2H), 1.18 (t, 3H, J=7.2 Hz), 1.42-1.58 (m, 1H), 1.70-1.81 (m, 2H), 1.82-1.96 (m, 2H), 2.93-3.00 (m, 3H), 3.13-3.19 (m, 2H), 6.98-7.02 (m, 2H), 7.26-7.27 (m, 1H), 7.32-7.35 (m, 1H), 8.18-8.21 (m, 1H).

Compound Ii-147

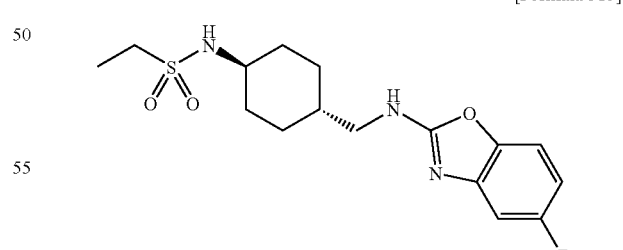

[Formula 315]

1H-NMR (DMSO-d6) δ: 0.98-1.04 (m, 2H), 1.16-1.23 (m, 2H), 1.18 (t, 3H, J=7.2 Hz), 1.43-1.59 (m, 1H), 1.73-1.78 (m, 2H), 1.86-1.89 (m, 2H), 2.93-3.00 (m, 3H), 3.11-3.15 (m, 2H), 6.72-6.79 (m, 1H), 7.00-7.08 (m, 2H), 7.29-7.34 (m, 1H), 8.13-8.16 (m, 1H).

Compound Ii-148

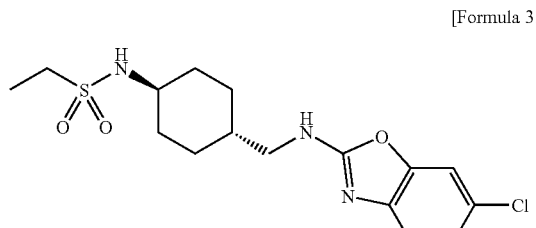

[Formula 316]

1H-NMR (DMSO-d6) δ: 0.94-1.06 (m, 2H), 1.15-1.26 (m, 2H), 1.18 (t, 3H, J=7.2 Hz), 1.45-1.58 (m, 1H), 1.72-1.80 (m, 2H), 1.84-1.92 (m, 2H), 2.96 (q, 2H, J=7.2 Hz), 2.96-3.05 (m, 1H), 3.09-3.16 (m, 2H), 6.99 (d, 1H, J=8.0 Hz), 7.13 (dd, 1H, J=8.0, 2.0 Hz), 7.20 (d, 1H, J=8.4 Hz), 7.49 (d, 1H, J=2.0 Hz), 8.11 (t, 1H, J=6.0 Hz).

Compound Ii-149

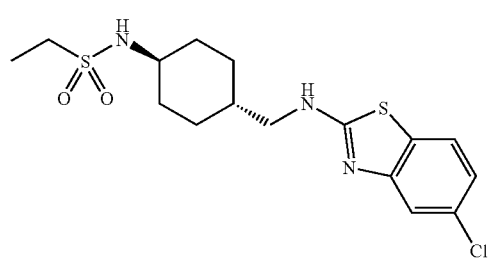

[Formula 317]

1H-NMR (DMSO-d6) δ: 0.96-1.08 (m, 2H), 1.12-1.24 (m, 2H), 1.18 (t, 3H, J=7.2 Hz), 1.43-1.59 (m, 1H), 1.74-1.80 (m, 2H), 1.86-1.91 (m, 2H), 2.93-3.01 (m, 3H), 3.17-3.22 (m, 2H), 7.00-7.05 (m, 2H), 7.37-7.39 (m, 1H), 7.65-7.68 (m, 1H), 8.22-8.26 (m, 1H).

Compound Ii-150

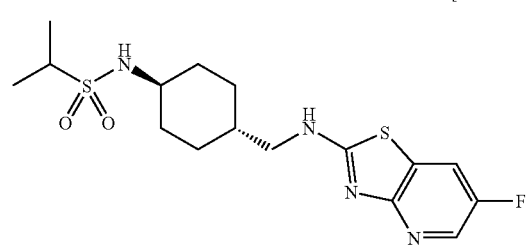

[Formula 318]

1H-NMR (DMSO-d6) δ: 0.98-1.08 (m, 2H), 1.15-1.29 (m, 2H), 1.21 (d, 6H, J=6.9 Hz), 1.44-1.60 (m, 1H), 1.74-1.80 (m, 2H), 1.86-1.91 (m, 2H), 2.95-3.17 (m, 2H), 3.21-3.27 (m, 2H), 6.95-6.98 (m, 1H), 8.10 (dd, 1H, J=8.4, 2.7 Hz), 8.19 (dd, 1H, J=3.0, 1.5 Hz), 8.44-8.47 (m, 1H).

Compound Ii-151

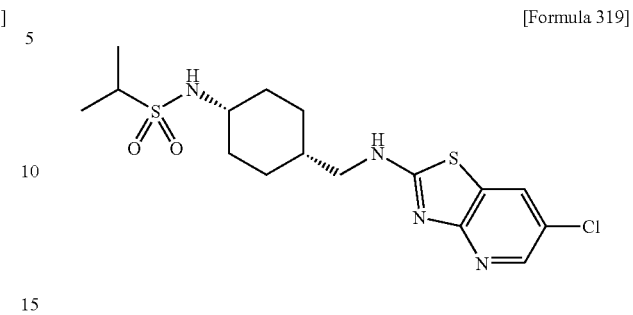

[Formula 319]

1H-NMR (DMSO-d6) δ: 0.99-1.04 (m, 2H), 1.15-1.23 (m, 2H), 1.21 (d, 6H, J=6.3 Hz), 1.43-1.59 (m, 1H), 1.73-1.81 (m, 2H), 1.85-1.91 (m, 2H), 2.97-3.18 (m, 2H), 3.21-3.29 (m, 2H), 6.95-6.98 (m, 1H), 8.20-8.23 (m, 2H), 8.58-8.61 (m, 1H).

Compound Ii-152

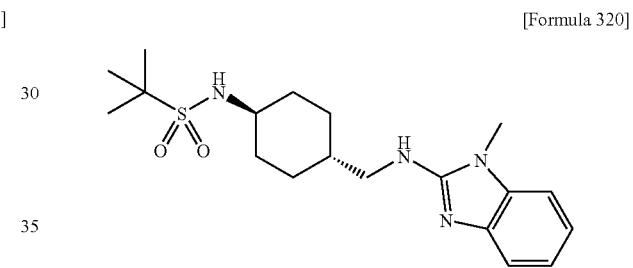

[Formula 320]

1H-NMR (DMSO-d6) δ: 0.96-1.04 (m, 2H), 1.15-1.26 (m, 2H), 1.25 (s, 9H), 1.56-1.62 (m, 1H), 1.78-1.83 (m, 2H), 1.87-1.93 (m, 2H), 2.98-3.08 (m, 1H), 3.17 (t, 2H, J=6.3 Hz), 3.48 (s, 3H), 6.47 (d, 2H, J=8.7 Hz), 6.89-6.96 (m, 2H), 7.11-7.19 (m, 2H).

Compound Ii-153

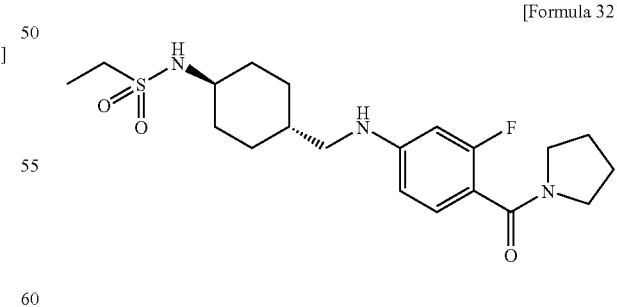

[Formula 321]

1H-NMR (DMSO-d6) δ: 0.95-1.04 (m, 2H), 1.13-1.30 (m, 2H), 1.18 (t, 3H, J=7.5 Hz), 1.41 (m, 1H), 1.71-1.94 (m, 4H), 2.80-2.89 (m, 2H), 2.92-3.10 (m, 2H), 2.97 (q, 2H, J=7.5 Hz), 3.21-3.30 (m, 2H), 6.25-6.35 (m, 2H), 6.39 (dd, 1H, J=8.4, 2.1 Hz), 7.01 (d, 1H, J=7.5 Hz), 7.01 (dd, 1H, J=8.4, 8.4 Hz).

Compound Ii-154
[Formula 322]
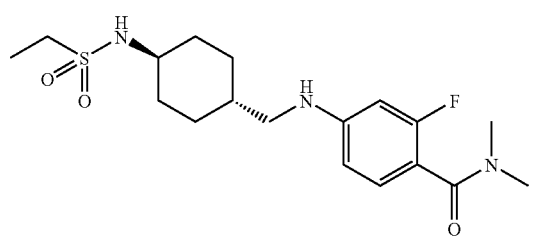
1H-NMR (DMSO-d6) δ: 0.91-1.09 (m, 2H), 1.16-1.28 (m, 2H), 1.18 (t, 3H, J=7.5 Hz), 1.42 (m, 1H), 1.74-1.95 (m, 4H), 2.80-3.16 (m, 9H), 2.97 (q, 2H, J=7.5 Hz), 6.24-6.36 (m, 2H), 6.30 (dd, 1H, J=8.4, 2.1 Hz), 7.10 (dd, 1H, J=8.4, 2.1 Hz), 7.05 (d, 1H, J=8.4 Hz).
Compound Ii-155
[Formula 323]
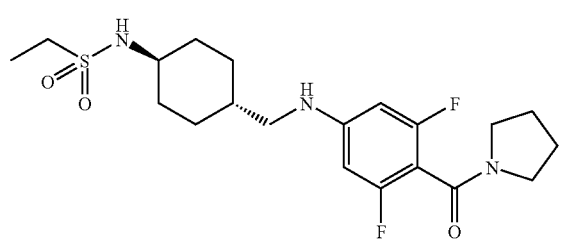
Compound Ii-156
[Formula 324]
Compound Ii-157
[Formula 325]
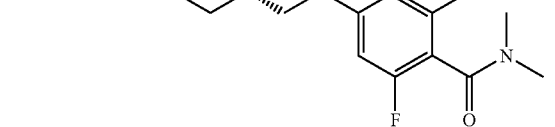
Compound Ii-158
[Formula 326]
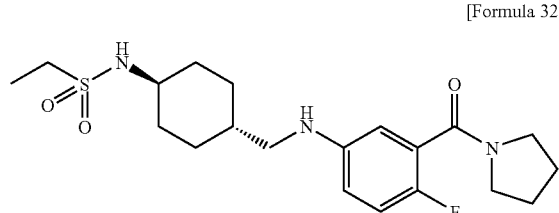
1H-NMR (DMSO-d6) δ: 0.91-1.07 (m, 2H), 1.10-1.30 (m, 5H), 1.41 (m, 1H), 1.76-1.94 (m, 4H), 2.74-2.83 (m, 2H), 2.83 (s, 3H), 2.90-3.08 (m, 3H), 2.96 (s, 3H), 5.68 (m, 1H), 6.39 (m, 1H), 6.58 (m, 1H), 6.95 (dd, 1H, J=8.4, 8.4 Hz), 7.00 (d, 1H, J=7.8 Hz).
Compound Ii-159
[Formula 327]
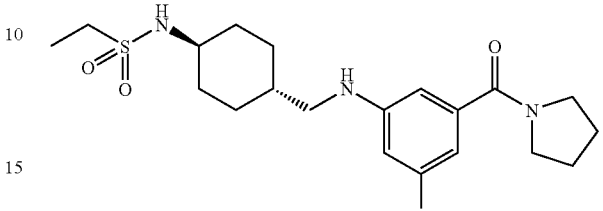
Compound Ii-160
[Formula 328]
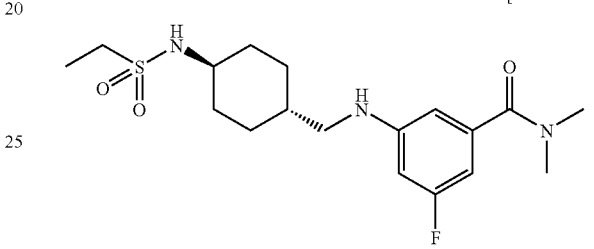
Compound Ii-161
[Formula 329]
Compound Ii-162
[Formula 330]
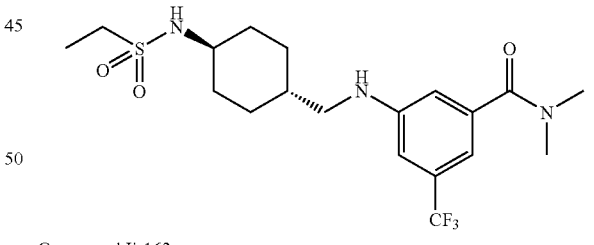
Compound Ii-163
[Formula 331]
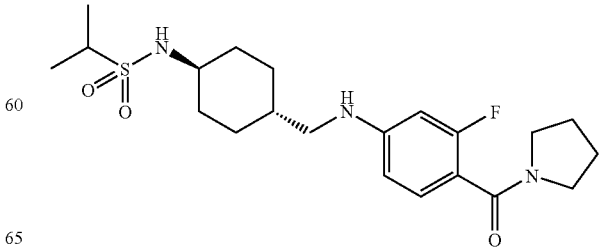

Compound Ii-164
[Formula 332]
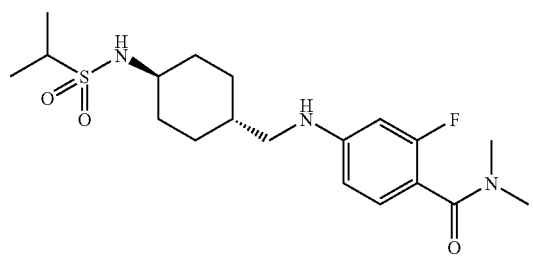
Compound Ii-165
[Formula 333]
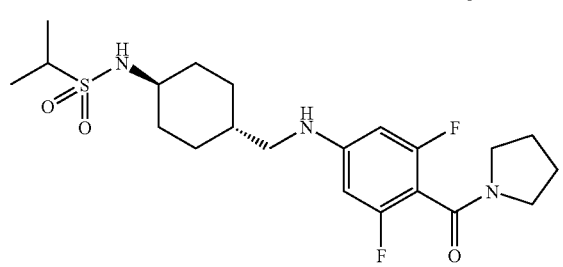
Compound Ii-166
[Formula 334]
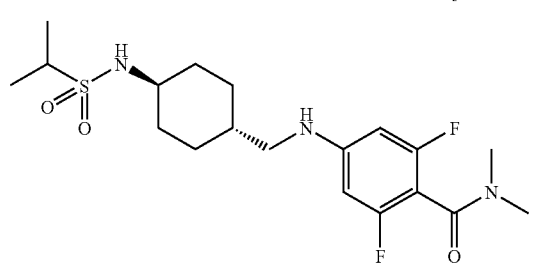
Compound Ii-167
[Formula 335]
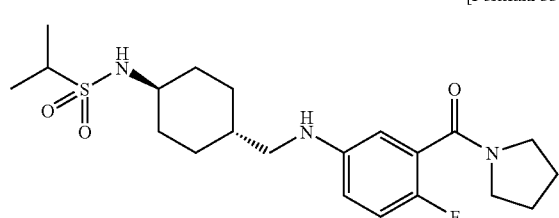
Compound Ii-168
[Formula 336]
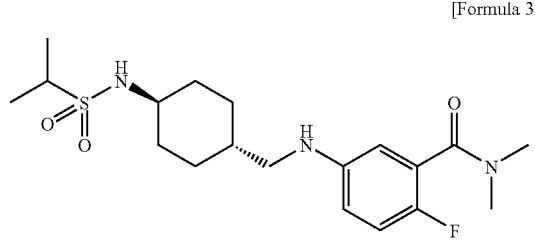
Compound Ii-169
[Formula 337]
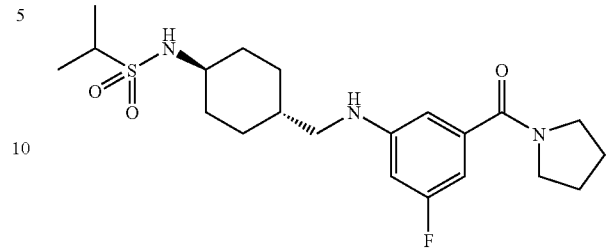
Compound Ii-170
[Formula 338]
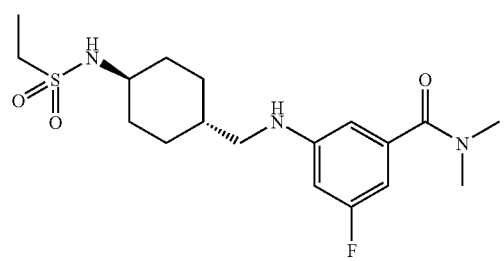
Compound Ii-171
[Formula 339]
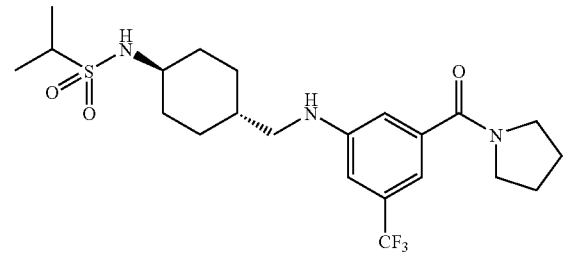
Compound Ii-172
[Formula 340]
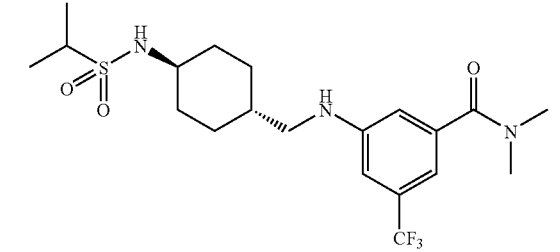
Compound Ii-173
[Formula 341]
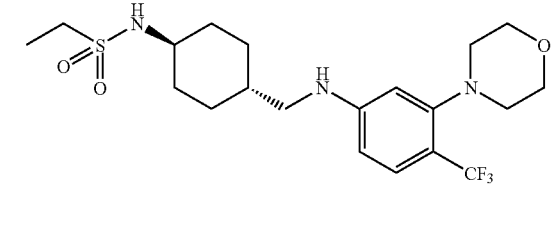
1H-NMR (DMSO-d6) δ: 0.95-1.08 (m, 2H), 1.15-1.28 (m, 2H), 1.19 (t, 3H, J=7.2 Hz), 1.43 (m, 1H), 1.76-1.85 (m, 2H), 1.85-1.93 (m, 2H), 2.76-2.82 (m, 2H), 2.88 (t, 2H, J=6.0 Hz), 2.97 (t, 2H, J=7.2 Hz), 3.00 (m, 1H), 3.64-3.70 (m, 4H), 6.33

(m, 1H), 6.37 (d, 1H, J=8.4 Hz), 6.56 (s, 1H), 7.00 (d, 1H, J=7.8 Hz), 7.28 (d, 1H, J=8.4 Hz).
Compound Ii-174
[Formula 342]
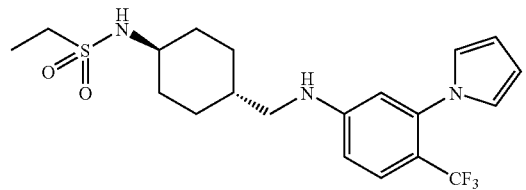
Compound Ii-175
[Formula 343]
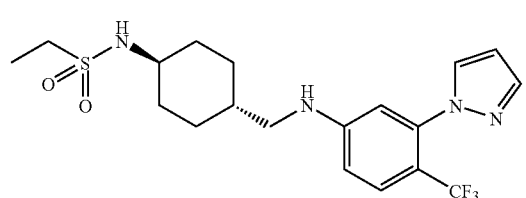
Compound Ii-176
[Formula 344]
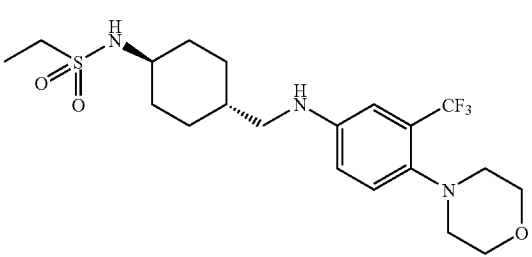
Compound Ii-177
[Formula 345]
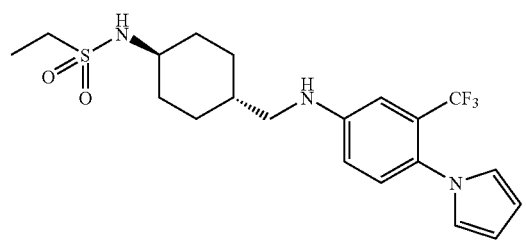
Compound Ii-178
[Formula 346]
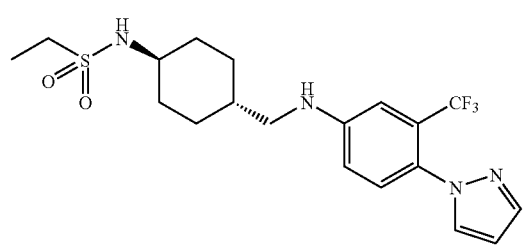
Compound Ii-179
[Formula 347]
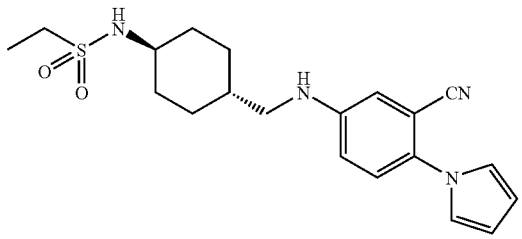
Compound Ii-180
[Formula 348]
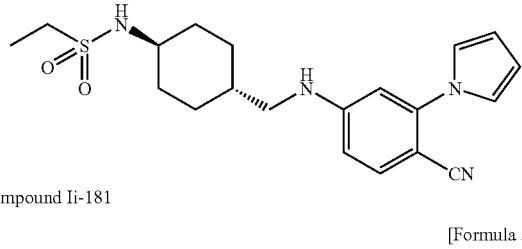
Compound Ii-181
[Formula 349]
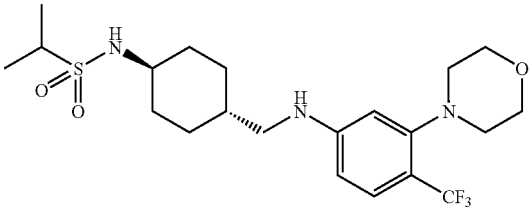
Compound Ii-182
[Formula 350]
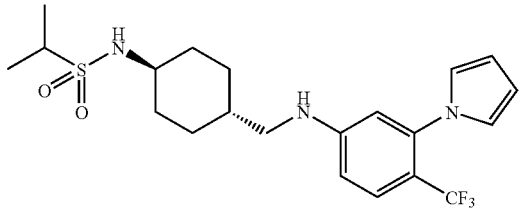
Compound Ii-183
[Formula 351]
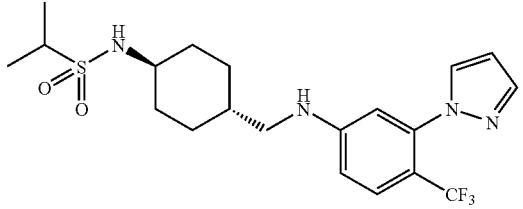
Compound Ii-184
[Formula 352]
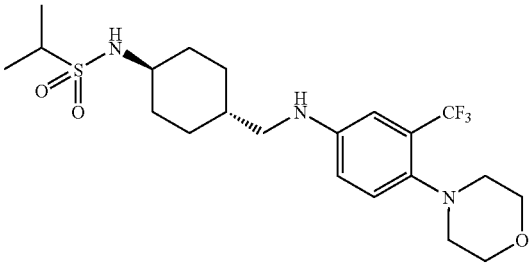

Compound Ii-185
[Formula 353]
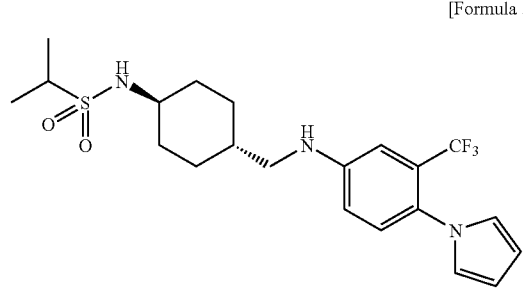
Compound Ii-186
[Formula 354]
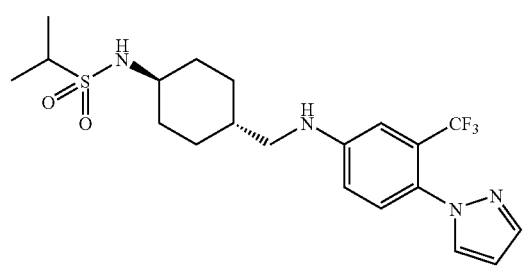
Compound Ii-187
[Formula 355]
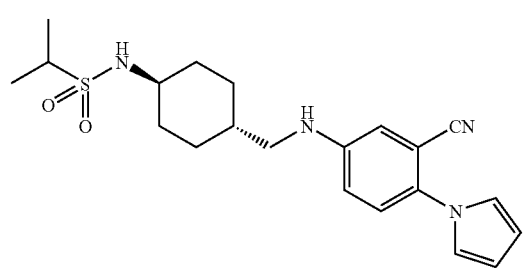
Compound Ii-188
[Formula 356]
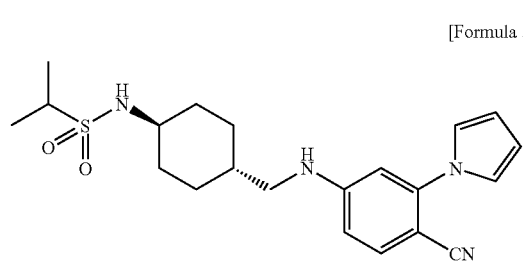
Compound Ii-189
[Formula 357]
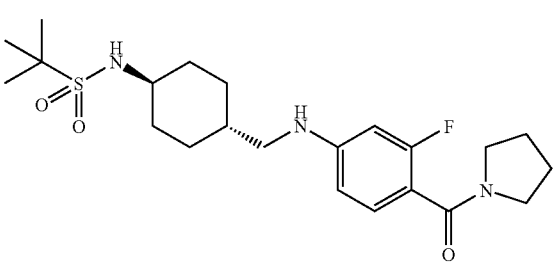
Compound Ii-190
[Formula 358]
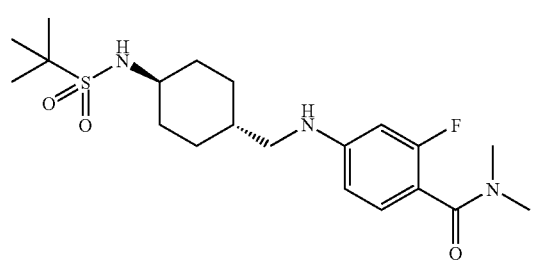
Compound Ii-191
[Formula 359]
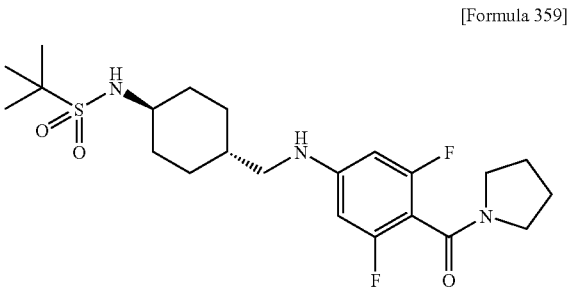
Compound Ii-192
[Formula 360]
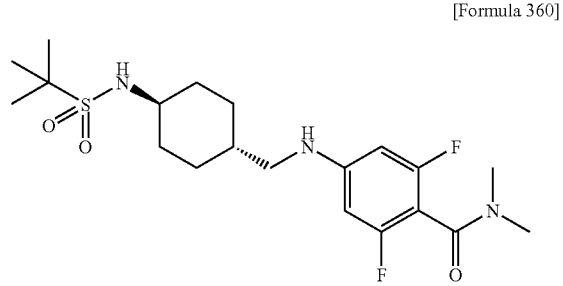
Compound Ii-193
[Formula 361]
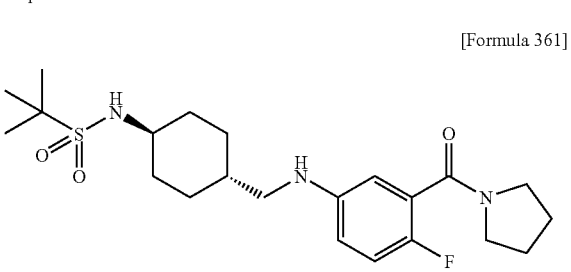
Compound Ii-194
[Formula 362]
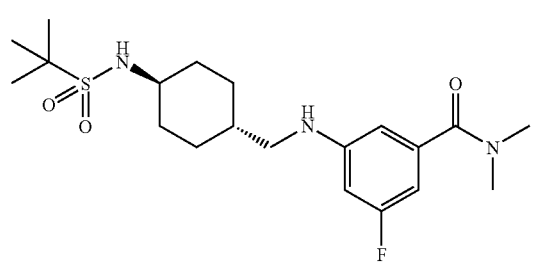

-continued
Compound Ii-195
[Formula 363]
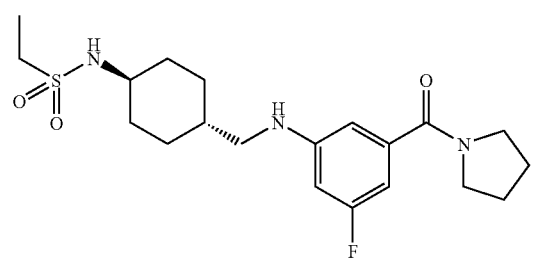
Compound Ii-196
[Formula 364]
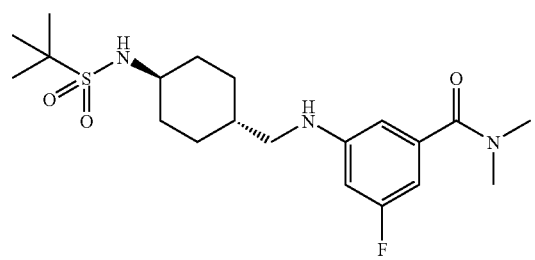
Compound Ii-197
[Formula 365]
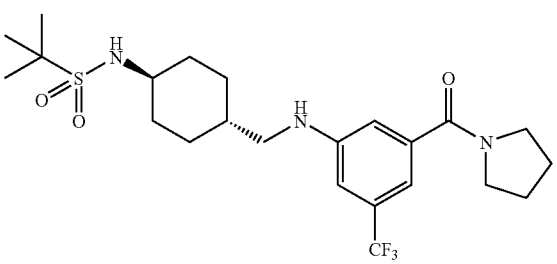
Compound Ii-198
[Formula 366]
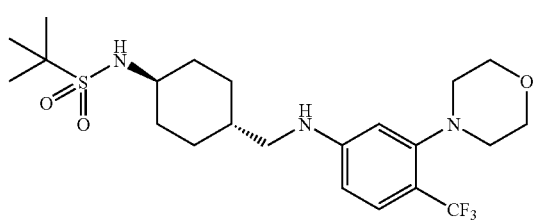
Compound Ii-199
[Formula 367]
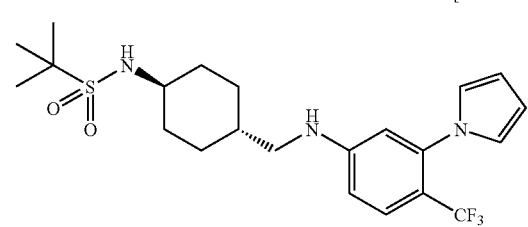
-continued
Compound Ii-200
[Formula 368]
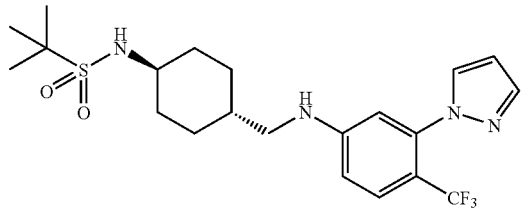
Compound Ii-201
[Formula 369]
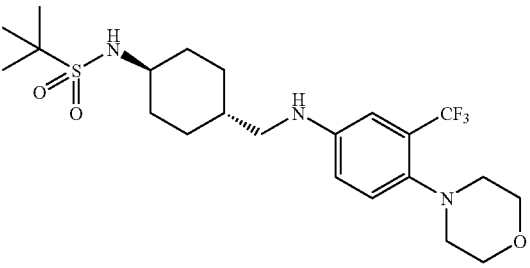
Compound Ii-202
[Formula 370]
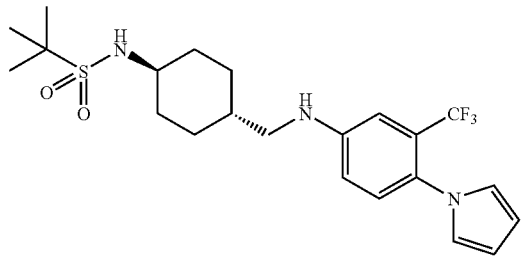
Compound Ii-203
[Formula 371]
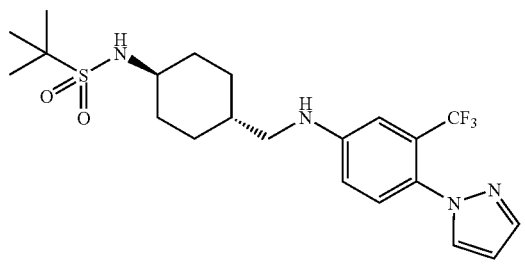
Compound Ii-204
[Formula 372]
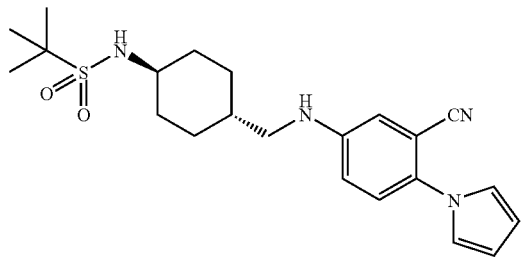

Compound Ii-205

[Formula 373]

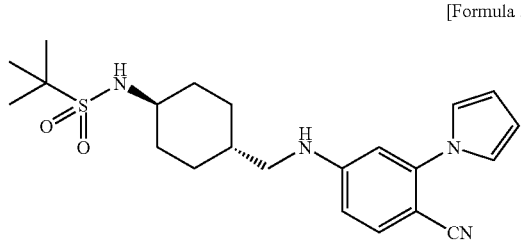

Compound Ii-206

[Formula 374]

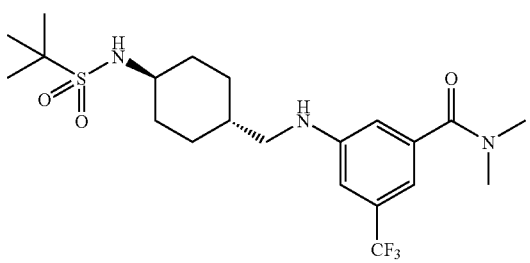

Compound Ij-2

[Formula 375]

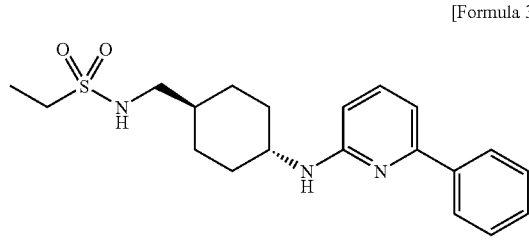

1H-NMR (DMSO-d6) δ: 0.98-1.24 (m, 4H), 1.19 (t, 3H, J=7.5 Hz), 1.40 (m, 1H), 1.78-1.88 (m, 2H), 2.02-2.14 (m, 2H), 2.80 (t, 2H, J=6.0 Hz), 2.86 (q, 2H, J=7.2 Hz), 3.64-3.82 (m, 1H), 6.40 (d, 2H, J=8.1 Hz), 7.01 (d, 2H, J=7.2 Hz), 7.32-7.50 (m, 4H), 7.99 (d, 2H, J=6.9 Hz)

Compound Ij-3

[Formula 376]

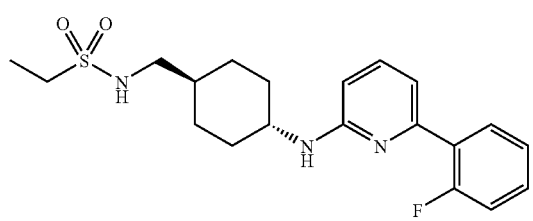

1H-NMR (DMSO-d6) δ: 0.96-1.26 (m, 4H), 1.18 (t, 3H, J=7.5 Hz), 1.40 (m, 1H), 1.78-1.88 (m, 2H), 2.02-2.14 (m, 2H), 2.78 (t, 2H, J=6.0 Hz), 2.98 (q, 2H, J=7.5 Hz), 3.60-3.78 (m, 1H), 6.40-6.50 (m, 2H), 6.85-6.92 (m, 1H), 6.97-7.03 (m, 1H), 7.22-7.35 (m, 2H), 7.36-7.46 (m, 2H), 7.88-7.96 (m, 1H)

Compound Ij-4

[Formula 377]

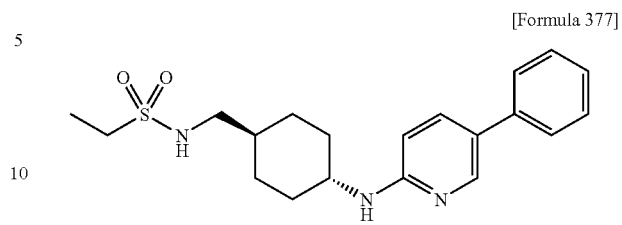

1H-NMR (DMSO-d6) δ: 0.92-1.24 (m, 4H), 1.19 (t, 3H, J=7.2 Hz), 1.38 (m, 1H), 1.78-1.88 (m, 2H), 1.96-2.06 (m, 2H), 2.78 (t, 2H, J=6.0 Hz), 2.98 (q, 2H, J=7.5 Hz), 3.60-3.78 (m, 1H), 6.50 (t, 1H, J=3.9 Hz), 6.53 (s, 1H), 7.00 (t, 1H, J=5.7 Hz), 7.25 (t, 1H, J=7.2 Hz), 7.34-7.45 (m, 2H), 7.55 (d, 2H, J=7.2 Hz), 7.67 (dd, 1H, J=8.7, 2.7 Hz), 8.29 (d, 1H, J=2.7 Hz)

Compound Ij-5

[Formula 378]

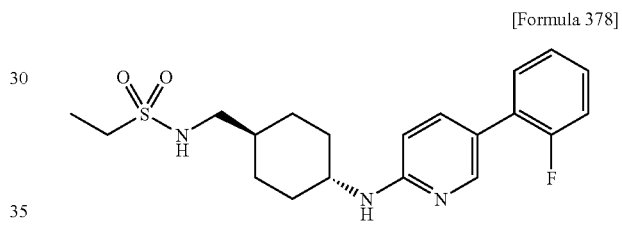

1H-NMR (DMSO-d6) δ: 0.92-1.24 (m, 4H), 1.19 (t, 3H, J=7.2 Hz), 1.38 (m, 1H), 1.78-1.88 (m, 2H), 1.96-2.06 (m, 2H), 2.78 (t, 2H, J=6.0 Hz), 2.98 (q, 2H, J=7.5 Hz), 3.60-3.78 (m, 1H), 6.52 (d, 1H, J=8.4 Hz), 6.60 (d, 1H, J=7.8 Hz), 7.01 (t, 1H, J=5.7 Hz), 7.20-7.36 (m, 3H), 7.46 (t, 1H, J=8.1 Hz), 7.55 (d, 1H, J=8.7 Hz), 8.15 (s, 1H)

Compound Ij-6

[Formula 379]

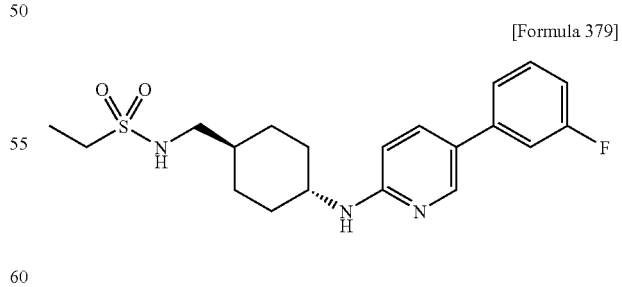

1H-NMR (DMSO-d6) δ: 0.92-1.24 (m, 4H), 1.19 (t, 3H, J=7.2 Hz), 1.40 (m, 1H), 1.78-1.88 (m, 2H), 1.96-2.06 (m, 2H), 2.78 (t, 2H, J=6.0 Hz), 2.98 (q, 2H, J=7.5 Hz), 3.60-3.78 (m, 1H), 6.51 (d, 1H, J=8.7 Hz), 6.60 (d, 1H, J=7.5 Hz), 7.01 (t, 1H, J=5.7 Hz), 7.02-7.12 (m, 1H), 7.36-7.48 (m, 3H), 7.71 (dd, 1H, J=8.7, 2.1 Hz), 8.33 (d, 1H, J=2.1 Hz)

Compound Ij-7

[Formula 380]

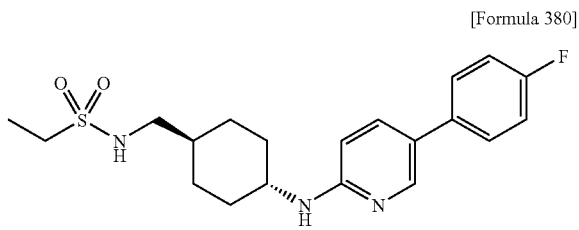

1H-NMR (DMSO-d6) δ: 0.92-1.24 (m, 4H), 1.19 (t, 3H, J=7.2 Hz), 1.40 (m, 1H), 1.78-1.88 (m, 2H), 1.96-2.06 (m, 2H), 2.78 (t, 2H, J=6.0 Hz), 2.98 (q, 2H, J=7.5 Hz), 3.60-3.78 (m, 1H), 6.50 (d, 2H, J=8.7 Hz), 6.99 (t, 1H, J=6.0 Hz), 7.16-7.26 (m, 2H), 7.52-7.68 (m, 3H), 8.25 (s, 1H)

Compound Ij-8

[Formula 381]

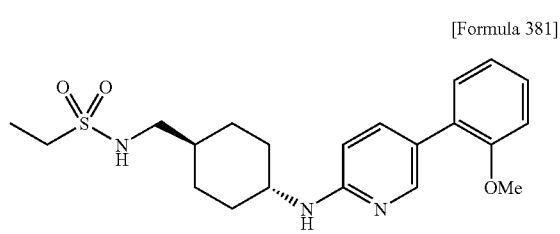

1H-NMR (CDCl3) δ: 1.15-1.26 (m, 4H), 1.40 (t, 3H, J=7.5 Hz), 1.55-1.58 (m, 1H), 1.93 (d, 2H, J=9.7 Hz), 2.23 (d, 2H, J=9.7 Hz), 3.01-3.11 (m, 4H), 3.56-3.61 (m, 1H), 3.84 (s, 3H), 4.34 (t, 1H, J=6.1 Hz), 4.83-4.86 (m, 1H), 6.46 (d, 1H, J=8.6 Hz), 6.99 (d, 1H, J=8.5 Hz), 7.05 (d, 1H, J=8.5 Hz), 7.29 (s, 1H), 7.30-7.34 (m, 1H), 7.69 (dd, 1H, J=8.7, 2.4 Hz), 8.25 (s, 1H).

Compound Ij-9

[Formula 382]

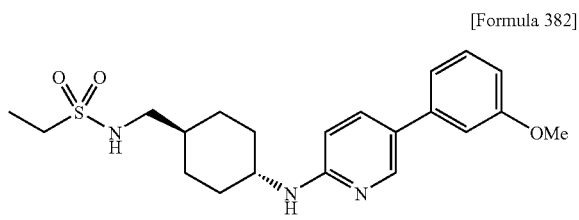

1H-NMR (CDCl3) δ: 1.16-1.24 (m, 4H), 1.40 (t, 3H, J=6.2 Hz), 1.55-1.59 (m, 1H), 1.94 (d, 2H, J=11.8 Hz), 2.23 (d, 2H, J=11.8 Hz), 3.03-3.09 (m, 4H), 3.58-3.62 (m, 1H), 3.88 (s, 3H), 4.29 (t, 1H, J=6.4 Hz), 4.85-4.89 (m, 1H), 6.49 (d, 1H, J=8.7 Hz), 6.88 (dd, 1H, J=8.7, 2.2 Hz), 7.04-7.06 (m, 1H), 7.10 (d, 1H, J=8.7 Hz), 7.36 (t, 1H, J=7.9 Hz), 7.70 (dd, 1H, J=8.7, 2.2 Hz), 8.32 (s, 1H).

Compound Ij-10

[Formula 383]

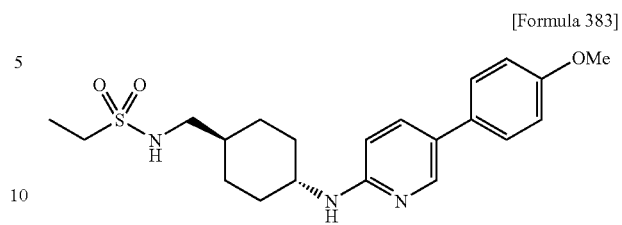

1H-NMR (CDCl3) δ: 1.19-1.30 (m, 4H), 1.41 (t, 3H, J=6.3 Hz), 1.56-1.59 (m, 1H), 1.94 (d, 2H, J=11.1 Hz), 2.23 (d, 2H, J=11.1 Hz), 3.01-3.11 (m, 4H), 3.57-3.61 (m, 1H), 3.87 (s, 3H), 4.27 (t, 1H, J=6.4 Hz), 4.98 (s, 1H), 6.50 (dd, 1H, J=8.7, 2.2 Hz), 6.99 (d, 2H, J=8.9 Hz), 7.43 (d, 2H, J=8.7 Hz), 7.68 (dd, 1H, J=8.7, 2.2 Hz), 8.25 (s, 1H).

Compound Ij-11

[Formula 384]

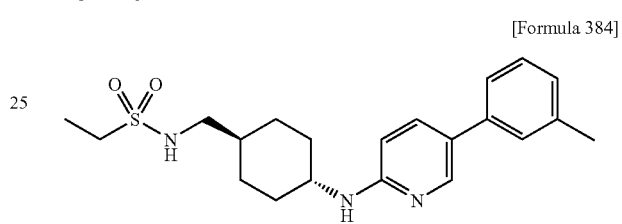

1H-NMR (DMSO-d6) δ: 0.93-1.08 (m, 2H), 1.09-1.25 (m, 5H), 1.39 (m, 1H), 1.75-1.86 (m, 2H), 1.95-2.07 (m, 2H), 2.34 (s, 3H), 2.78 (t, 2H, J=6.2 Hz), 2.98 (q, 2H, J=7.3 Hz), 3.65 (m, 1H), 6.45-6.53 (m, 2H), 7.01 (t, 1H, J=5.6 Hz), 7.07 (d, 1H, J=7.1 Hz), 7.23-7.38 (m, 3H), 7.64 (dd, 1H, J1=8.8 Hz, J2=2.5 Hz), 8.26 (d, 1H, J=2.5 Hz).

Compound Ij-12

[Formula 385]

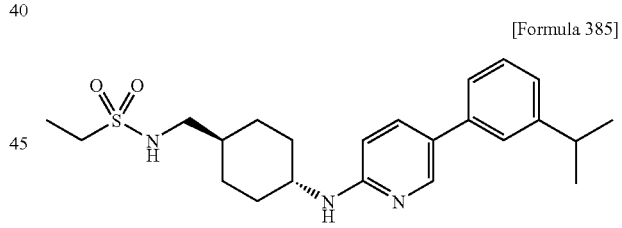

1H-NMR (DMSO-d6) δ: 0.93-1.08 (m, 2H), 1.09-1.27 (m, 11H), 1.39 (m, 1H), 1.76-1.87 (m, 2H), 1.96-2.06 (m, 2H), 2.78 (t, 2H, J=6.2 Hz), 2.84-3.03 (m, 3H), 3.66 (m, 1H), 6.45-6.54 (m, 2H), 7.01 (t, 1H, J=5.8 Hz), 7.13 (d, 1H, J=6.9 Hz), 7.27-7.41 (m, 3H), 7.66 (dd, 1H, J1=8.8 Hz, J2=2.5 Hz), 8.27 (d, 1H, J=2.2 Hz).

Compound Ij-13

[Formula 386]

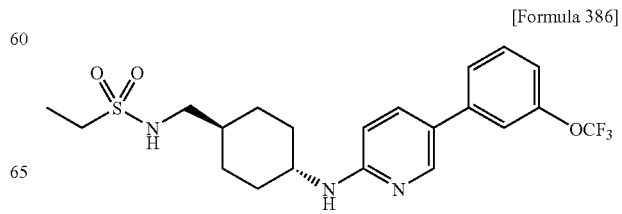

1H-NMR (DMSO-d6) δ: 0.92-1.09 (m, 2H), 1.09-1.25 (m, 5H), 1.39 (m, 1H), 1.76-1.85 (m, 2H), 1.95-2.06 (m, 2H), 2.78 (t, 2H, J=6.2 Hz), 2.98 (q, 2H, J=7.3 Hz), 3.68 (m, 1H), 6.52 (d, 1H, J=8.8 Hz), 6.66 (d, 1H, J=8.0 Hz), 7.02 (t, 1H, J=5.5 Hz), 7.23 (d, 1H, J=8.1 Hz), 7.49-7.55 (m, 2H), 7.62 (d, 1H, J1=8.5 Hz), 7.72 (dd, 1H, J1=8.8 Hz, J2=2.5 Hz), 8.35 (d, 1H, J=2.5 Hz).

Compound Ij-14

[Formula 387]

1H-NMR (DMSO-d6) δ: 0.92-1.22 (m, 4H), 1.22 (d, 6H, J=6.4 Hz), 1.39 (m, 1H), 1.76-1.86 (m, 2H), 1.95-2.03 (m, 2H), 2.81 (t, 2H, J=6.4 Hz), 3.10-3.20 (m, 1H), 3.60-3.75 (m, 1H), 6.65 (d, 1H, J=4.8 Hz), 6.70 (s, 1H), 6.88-6.98 (m, 2H), 8.16 (d, 1H, J=5.2 Hz).

Compound Ij-15

[Formula 388]

1H-NMR (CDCl3) δ: 1.02-1.28 (m, 4H), 1.38 (d, 6H, J=6.9 Hz), 1.52 (m, 1H), 1.85-1.94 (m, 2H), 2.11-2.21 (m, 2H), 3.01 (t, 2H, J=6.6 Hz), 3.10-3.25 (m, 1H), 3.38-3.54 (m, 1H), 4.22 (t, 1H, J=6.3 Hz), 4.58 (d, 1H, J=7.8 Hz), 6.34 (d, 1H, J=1.8 Hz), 6.53 (dd, 1H, J=5.4, 1.8 Hz), 7.93 (d, 1H, J=5.4 Hz).

Compound Ij-16

[Formula 389]

1H-NMR (CDCl3) δ: 1.03-1.28 (m, 4H), 1.37 (d, 6H, J=6.9 Hz), 1.52 (m, 1H), 1.84-1.93 (m, 2H), 2.11-2.21 (m, 2H), 3.01 (t, 2H, J=6.6 Hz), 3.09-3.24 (m, 1H), 3.40-3.54 (m, 1H), 4.26 (t, 1H, J=6.6 Hz), 4.44 (d, 1H, J=8.1 Hz), 6.29 (d, 1H, J=8.7 Hz), 7.33 (dd, 1H, J=8.7, 2.7 Hz), 7.99 (d, 1H, J=2.7 Hz).

Compound Ij-17

[Formula 390]

1H-NMR (DMSO-d6) δ: 0.92-1.22 (m, 4H), 1.21 (d, 6H, J=6.8 Hz), 1.36 (m, 1H), 1.76-1.84 (m, 2H), 1.92-2.00 (m, 2H), 2.80 (t, 2H, J=6.4 Hz), 3.08-3.18 (m, 1H), 3.45-3.56 (m, 1H), 6.36 (d, 1H, J=8.4 Hz), 6.43 (d, 1H, J=7.2 Hz), 6.75 (d, 1H, J=7.6 Hz), 6.94 (t, 1H, J=6.0 Hz), 7.33 (t, 1H, J=7.6 Hz).

Compound Ij-18

[Formula 391]

1H-NMR (DMSO-d6) δ: 0.98-1.24 (m, 4H), 1.22 (d, 6H, J=6.9 Hz), 1.40 (m, 1H), 1.78-1.88 (m, 2H), 2.04-2.14 (m, 2H), 2.83 (t, 2H, J=6.0 Hz), 3.10-3.22 (m, 1H), 3.64-3.82 (m, 1H), 6.40 (d, 2H, J=8.4 Hz), 6.95-7.05 (m, 2H), 7.35-7.50 (m, 4H), 7.99 (d, 2H, J=7.2 Hz)

Compound Ij-19

[Formula 392]

1H-NMR (CDCl3) δ: 1.22-1.38 (m, 4H), 1.38 (d, 6H, J=8.0 Hz), 1.54 (m, 1H), 1.86-1.95 (m, 2H), 2.18-2.26 (m, 2H), 3.03 (t, 2H, J=6.0 Hz), 3.12-3.22 (m, 1H), 3.52-3.64 (m, 1H), 4.16 (t, 1H, J=6.4 Hz), 4.82-4.92 (m, 1H), 6.46 (d, 1H, J=8.0 Hz), 7.10-7.20 (m, 2H), 7.23-7.33 (m, 1H), 7.37 (t, 1H, J=8.0 Hz), 7.65 (d, 1H, J=8.7 Hz), 8.24 (s, 1H).

Compound Ij-20

[Formula 393]

1H-NMR (CDCl3) δ: 1.22-1.38 (m, 4H), 1.39 (d, 6H, J=8.0 Hz), 1.54 (m, 1H), 1.86-1.95 (m, 2H), 2.18-2.26 (m, 2H), 3.03 (t, 2H, J=6.0 Hz), 3.12-3.22 (m, 1H), 3.52-3.64 (m, 1H), 4.16 (t, 1H, J=6.4 Hz), 4.78-4.88 (m, 1H), 6.46 (d, 1H, J=8.0 Hz), 6.98(t, 1H, J=5.7 Hz), 7.18 (d, 1H, J=8.0 Hz), 7.23-7.29 (m, 1H), 7.33-7.40 (m, 1H), 7.65 (d, 1H, J=8.7 Hz), 8.29 (s, 1H).

Compound Ij-21

[Formula 394]

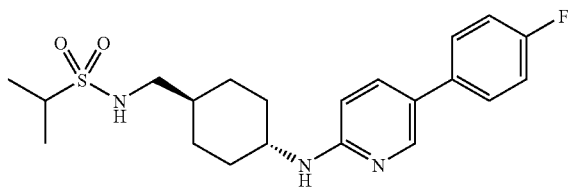

1H-NMR (CDCl3) δ: 1.10-1.30 (m, 4H), 1.38 (d, 6H, J=8.0 Hz), 1.54 (m, 1H), 1.86-1.95 (m, 2H), 2.18-2.26 (m, 2H), 3.03 (t, 2H, J=6.0 Hz), 3.13-3.22 (m, 1H), 3.52-3.64 (m, 1H), 4.15 (t, 1H, J=6.4 Hz), 4.78-4.88 (m, 1H), 6.46 (d, 1H, J=8.0 Hz), 7.07-7.14 (m, 2H), 7.40-7.46 (m, 2H), 7.62 (d, 1H, J=8.7 Hz), 8.23 (s, 1H).

Compound Ij-22

[Formula 395]

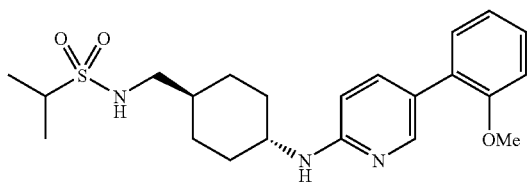

1H-NMR (DMSO-d6) δ: 0.95-1.25 (m, 4H), 1.22 (d, 6H, J=6.6 Hz), 1.25-1.50 (br, 1H), 1.81 (d, 2H, J=11.4 Hz), 2.00 (d, 2H, J=10.5 Hz), 2.81 (t, 2H, J=6.6 Hz), 3.05-3.22 (m, 1H), 3.58-3.80 (m, 1H), 3.76 (s, 3H), 6.49 (d, 2H, J=8.7 Hz), 6.50-6.70 (br, 1H), 6.95-7.10 (m, 3H), 7.20-7.32 (m, 2H), 7.51 (d, 1H, J=7.2 Hz), 8.05 (br, 1H). ESI(positive) 418.3 [M+H]+

Compound Ij-23

[Formula 396]

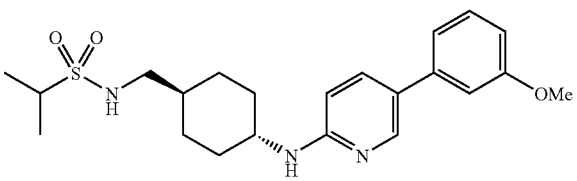

1H-NMR (DMSO-d6) δ: 0.95-1.32 (m, 4H), 1.22 (d, 6H, J=6.6 Hz), 1.25-1.55 (br, 1H), 1.82 (d, 2H, J=11.4 Hz), 2.01 (d, 2H, J=10.2 Hz), 2.81 (t, 2H, J=6.6 Hz), 3.05-3.22 (m, 1H), 3.58-3.78 (m, 1H), 3.80 (s, 3H), 6.59 (d, 2H, J=9.6 Hz), 6.85 (dd, 1H, J=8.4 Hz, 2.4 Hz), 6.99 (t, 3H, J=5.7 Hz), 7.05-7.18 (m, 2H), 7.32 (d, 1H, J=7.8 Hz), 7.76 (d, 1H, J=8.4 Hz), 8.27 (d, 1H, J=2.1 Hz). ESI(positive) 418.3 [M+H]+

Compound Ij-24

[Formula 397]

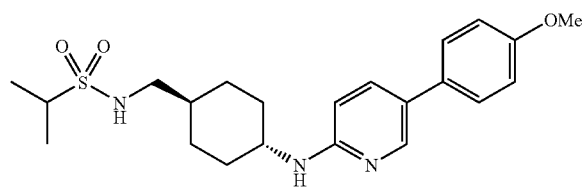

1H-NMR (DMSO-d6) δ: 0.92-1.25 (m, 4H), 1.22 (d, 6H, J=6.6 Hz), 1.28-1.48 (m, 1H), 1.81 (d, 2H, J=10.8 Hz), 2.00 (d, 2H, J=9.6 Hz), 2.81 (t, 2H, J=6.6 Hz), 3.08-3.22 (m, 1H), 3.58-3.74 (m, 1H), 3.77 (s, 3H), 6.51 (d, 2H, J=8.7 Hz), 6.97 (d, 2H, J=8.7 Hz), 6.98 (brs, 1H), 7.48 (d, 2H, J=8.7 Hz), 7.63 (dd, 1H, J=11.4 Hz, 2.4 Hz), 8.21 (d, 1H, J=2.4 Hz). ESI (positive) 418.3[M+H]+

Compound Ij-25

[Formula 398]

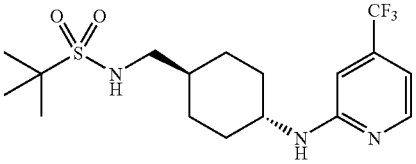

1H-NMR (DMSO-d6) δ: 0.92-1.22 (m, 4H), 1.27 (s, 9H), 1.38 (m, 1H), 1.78-1.88 (m, 2H), 1.95-2.05 (m, 2H), 2.88 (t, 2H, J=6.0 Hz), 3.60-3.80 (m, 1H), 6.65 (d, 1H, J=5.4 Hz), 6.70 (s, 1H), 6.87 (t, 1H, J=6.0 Hz), 6.94 (d, 1H, J=7.8 Hz), 8.16 (d, 1H, J=5.4 Hz)

Compound Ij-26

[Formula 399]

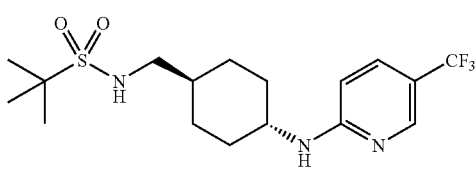

1H-NMR (DMSO-d6) δ: 0.92-1.22 (m, 4H), 1.27 (s, 9H), 1.38 (m, 1H), 1.78-1.88 (m, 2H), 1.94-2.04 (m, 2H), 2.88 (t, 2H, J=6.0 Hz), 3.60-3.80 (m, 1H), 6.53 (d, 1H, J=8.7 Hz), 6.87 (t, 1H, J=5.7 Hz), 7.19 (d, 1H, J=7.5 Hz), 7.59 (dd, 1H, J=9.0, 2.4 Hz), 8.26 (d, 1H, J=2.4 Hz)

Compound Ij-27

[Formula 400]

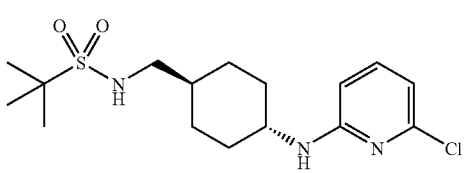

1H-NMR (DMSO-d6) δ: 0.92-1.22 (m, 4H), 1.26 (s, 9H), 1.38 (m, 1H), 1.76-1.86 (m, 2H), 1.92-2.02 (m, 2H), 2.88 (t,

2H, J=6.0 Hz), 3.40-3.60 (m, 1H), 6.36 (d, 1H, J=8.1 Hz), 6.43 (d, 1H, J=6.9 Hz), 6.80 (d, 1H, J=7.5 Hz), 6.86 (t, 1H, J=5.4 Hz), 7.34 (t, 1H, J=8.4 Hz)

Compound Ij-28

[Formula 401]

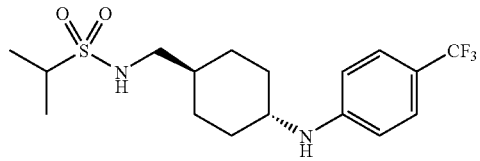

1H-NMR ((DMSO-d6) δ: 0.93-1.18 (m, 4H), 1.21 (d, 6H, J=6.9 Hz), 1.39 (m, 1H), 1.75-1.86 (m, 2H), 1.94-2.05 (m, 2H), 2.80 (t, 2H, J=6.0 Hz), 3.09-3.27 (m, 2H), 6.19 (d, 1H, J=8.1 Hz), 6.64 (d, 2H, J=8.7 Hz), 6.98 (t, 1H, J=6.0 Hz), 7.33 (d, 2H, J=8.7 Hz) Mass: 379 [M+H]+

Compound Ij-29

[Formula 402]

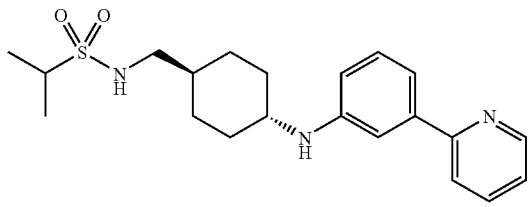

1H-NMR (DMSO-d6) δ: 0.93-1.18 (m, 4H), 1.22 (s, 3H), 1.24 (s, 3H), 1.32-1.49 (m, 2H), 1.82 (d, 2H, J=11.2 Hz), 2.04 (d, 2H, J=11.2 Hz), 2.75-2.87 (m, 2H), 3.07-3.28 (m, 2H), 6.64 (s, 1H), 6.96 (s, 1H), 7.10-7.22 (m, 2H), 7.25-7.39 (m, 2H), 7.77-7.90 (m, 2H), 8.63 (s, 1H). Melting point: 161 to 162° C.

Compound Ij-30

[Formula 403]

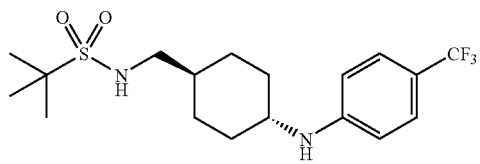

1H-NMR (DMSO-d6) δ: 0.92-1.22 (m, 4H), 1.27 (s, 9H), 1.37 (m, 1H), 1.76-1.86 (m, 2H), 1.94-2.05 (m, 2H), 2.88 (t, 2H, J=6.3 Hz), 3.19 (m, 1H), 6.19 (d, 1H, J=7.5 Hz), 6.64 (d, 2H, J=8.7 Hz), 6.88 (d, 1H, J=6.0 Hz), 7.33 (d, 2H, J=8.7 Hz) Mass:392 M+

Compound Ij-31

[Formula 404]

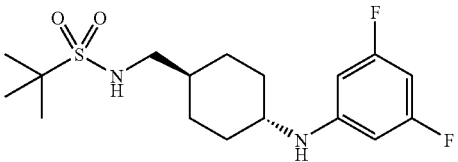

1H-NMR (DMSO-d6) δ: 0.92-1.16 (m, 4H), 1.26 (s, 9H), 1.36 (m, 1H), 1.72-1.83 (m, 2H), 1.92-2.02 (m, 2H), 2.87 (t, 2H, J=6.3 Hz), 3.12 (m, 1H), 6.09-6.23 (m, 4H), 6.87 (t, 1H, J=6.0 Hz) Mass:361[M+H]+

Compound Ij-32

[Formula 405]

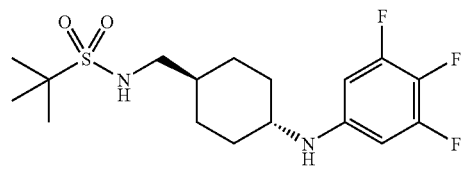

1H-NMR (CDCl3) δ: 1.00-1.20 (m, 4H), 1.40 (s, 9H), 1.42-1.64 (m, 2H), 1.84-1.95 (m, 2H), 2.09-2.20 (m, 2H), 3.07 (m, 1H), 3.07 (t, 2H, J=6.3 Hz), 3.90 (m, 1H), 6.10 (dd, 2H, J=9.6, 5.4 Hz).

Compound Ij-33

[Formula 406]

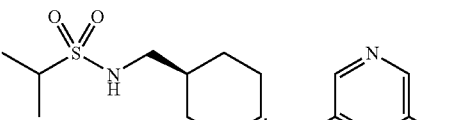

1H-NMR (DMSO-d6) δ: 0.93-1.21 (m, 5H), 1.28 (s, 9H), 1.33-1.46 (m, 1H), 1.82 (d, 2H, J=11.6 Hz), 2.04 (d, 2H, J=11.6 Hz), 2.86-2.95 (m, 2H), 3.03-3.29 (m, 1H), 6.59-6.71 (m, 1H), 6.80-6.92 (m, 1H), 7.09-7.21 (m, 2H), 7.27-7.37 (m, 2H), 7.77-7.88 (m, 2H), 8.58-8.67 (s, 1H). Melting point: 172 to 173° C.

Compound Ij-34

[Formula 407]

1H-NMR (DMSO-d6) δ: 0.96-1.08 (m, 2H), 1.12-1.24 (m, 2H), 1.21 (d, 6H, J=6.4 Hz), 1.38 (m, 1H), 1.76-1.86 (m, 2H), 1.92-2.00 (m, 2H), 2.80 (t, 2H, J=6.4 Hz), 3.10-3.20 (m, 1H), 3.48-3.60 (m, 1H), 6.95 (t, 1H, J=5.6 Hz), 7.41 (d, 1H, J=7.6 Hz), 7.63 (s, 1H), 7.82 (s, 1H).

Compound Ij-35

[Formula 408]

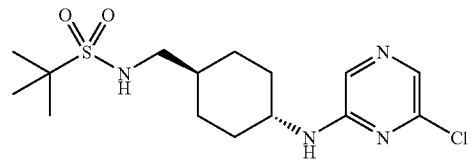

1H-NMR (DMSO-d6) δ: 0.96-1.26 (m, 4H), 1.27 (s, 9H), 1.38 (m, 1H), 1.78-1.88 (m, 2H), 1.92-2.02 (m, 2H), 2.88 (t, 2H, J=6.0 Hz), 3.48-3.62 (m, 1H), 6.87 (t, 1H, J=6.0 Hz), 7.45 (d, 1H, J=7.5 Hz), 7.63 (s, 1H), 7.82 (s, 1H)

Compound Ij-36

[Formula 409]

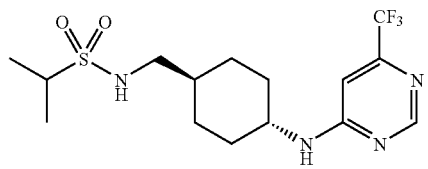

1H-NMR (DMSO-d6) δ: 0.96-1.06 (m, 2H), 1.12-1.20 (m, 2H), 1.21 (d, 6H, J=6.6 Hz), 1.39 (m, 1H), 1.78-1.84 (m, 2H), 1.95-1.99 (m, 2H), 2.81 (t, 2H, J=6.0 Hz), 3.10-3.20 (m, 1H), 3.74-3.88 (m, 1H), 6.80 (s, 1H), 6.98 (t, 1H, J=6.0 Hz), 7.93 (d, 2H, J=7.2 Hz), 8.53 (s, 1H).

Compound Ij-37

[Formula 410]

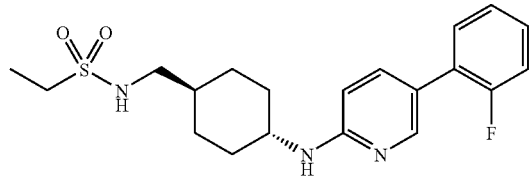

1H-NMR (DMSO-d6) δ: 0.96-1.30 (m, 4H), 1.19 (t, 3H, J=7.2 Hz), 1.42 (m, 1H), 1.78-1.88 (m, 2H), 2.04-2.16 (m, 2H), 2.80 (t, 2H, J=6.0 Hz), 2.99 (q, 2H, J=7.5 Hz), 3.72-3.90 (m, 1H), 6.85 (d, 1H, J=9.6 Hz), 6.93 (d, 1H, J=7.5 Hz), 7.04 (t, 1H, J=5.7 Hz), 7.26-7.38 (m, 2H), 7.40-7.52 (m, 1H), 7.57 (d, 1H, J=9.0 Hz), 7.85 (t, 1H, J=7.8 Hz)

Compound Ij-38

[Formula 411]

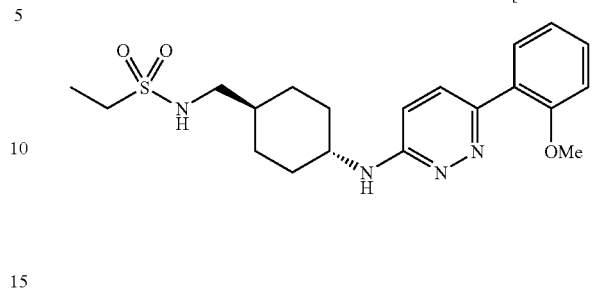

1H-NMR (DMSO-d6) δ: 0.96-1.30 (m, 4H), 1.19 (t, 3H, J=7.2 Hz), 1.42 (m, 1H), 1.78-1.88 (m, 2H), 2.04-2.16 (m, 2H), 2.80 (t, 2H, J=6.0 Hz), 2.99 (q, 2H, J=7.5 Hz), 3.72-3.90 (m, 1H), 3.80 (s, 3H), 6.72 (d, 1H, J=7.8 Hz), 6.77 (d, 1H, J=9.0 Hz), 6.98-7.10 (m, 2H), 7.12 (d, 1H, J=8.4 Hz), 7.38 (t, 1H, J=8.1 Hz), 7.56 (d, 1H, J=9.3 Hz), 7.61 (d, 1H, J=7.8 Hz)

Compound Ij-39

[Formula 412]

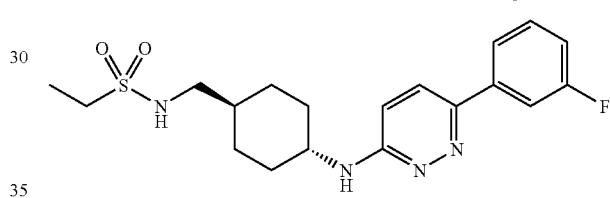

1H-NMR (DMSO-d6) δ: 0.96-1.30 (m, 4H), 1.19 (t, 3H, J=7.2 Hz), 1.42 (m, 1H), 1.78-1.88 (m, 2H), 2.04-2.16 (m, 2H), 2.80 (t, 2H, J=6.3 Hz), 2.99 (q, 2H, J=7.5 Hz), 3.72-3.90 (m, 1H), 6.85 (d, 1H, J=9.6 Hz), 6.92 (d, 1H, J=7.5 Hz), 7.04 (t, 1H, J=5.7 Hz), 7.21 (t, 1H, J=8.7 Hz), 7.46-7.56 (m, 1H), 7.75-7.88 (m, 3H)

Compound Ij-40

[Formula 413]

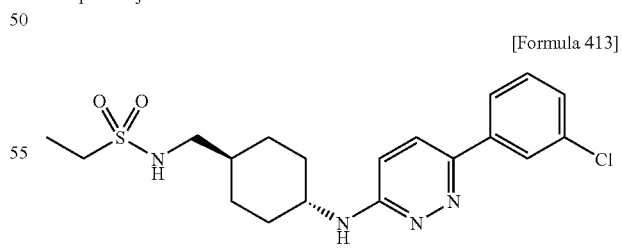

1H-NMR (DMSO-d6) δ: 0.96-1.10 (m, 2H), 1.19 (t, 3H, J=7.2 Hz), 1.15-1.26 (m, 2H), 1.42 (m, 1H), 1.78-1.88 (m, 2H), 2.04-2.14 (m, 2H), 2.80 (t, 2H, J=6.3 Hz), 2.99 (q, 2H, J=7.5 Hz), 3.76-3.87 (m, 1H), 6.85 (d, 1H, J=9.6 Hz), 6.91 (d, 1H, J=7.5 Hz), 7.01 (t, 1H, J=5.7 Hz), 7.42-7.52 (m, 2H), 7.83 (d, 1H, J=8.0 Hz), 7.93 (d, 1H, J=8.0 Hz), 8.02 (s, 1H).

Compound Ij-41

[Formula 414]

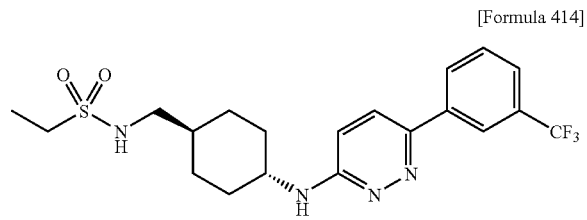

1H-NMR (DMSO-d6) δ: 0.96-1.30 (m, 4H), 1.20 (t, 3H, J=7.5 Hz), 1.42 (m, 1H), 1.78-1.88 (m, 2H), 2.04-2.16 (m, 2H), 2.80 (t, 2H, J=6.3 Hz), 2.99 (q, 2H, J=7.5 Hz), 3.76-3.90 (m, 1H), 6.88 (d, 1H, J=9.3 Hz), 6.97 (d, 1H, J=7.5 Hz), 7.03 (t, 1H, J=5.7 Hz), 7.67-7.77 (m, 2H), 7.92 (d, 1H, J=9.6 Hz), 8.26 (d, 1H, J=6.9 Hz), 8.33 (s, 1H)

Compound Ij-42

[Formula 415]

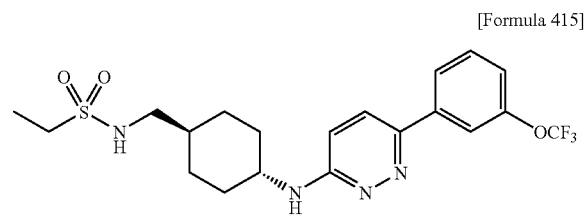

1H-NMR (DMSO-d6) δ: 0.93-1.10 (m, 2H), 1.20 (t, 3H, J=7.2 Hz), 1.22-1.28 (m, 1H), 1.35-1.50 (m, 2H), 1.84 (d, 2H, J=12.0 Hz), 2.08 (d, 2H, J=12.0 Hz), 2.63-2.76 (m, 2H), 2.91-3.03 (m, 2H), 3.75-3.90 (m, 1H), 6.86 (d, 1H, J=9.2 Hz), 6.93 (d, 1H, J=7.2 Hz), 6.98-7.07 (m, 1H), 7.36 (d, 1H, J=7.2 Hz), 7.59 (t, 1H, J=8.0 Hz), 7.85 (d, 1H, J=9.2 Hz), 7.91-8.02 (m, 2H). Melting point: 144 to 145° C.

Compound Ij-43

[Formula 416]

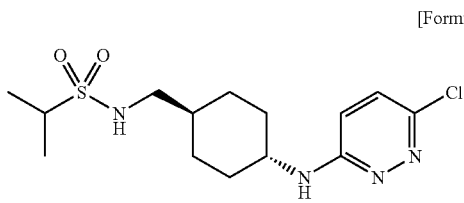

1H-NMR (DMSO-d6) δ: 0.94-1.06 (m, 2H), 1.10-1.24 (m, 2H), 1.21 (d, 6H, J=6.8 Hz), 1.39 (m, 1H), 1.76-1.86 (m, 2H), 1.98-2.06 (m, 2H), 2.81 (t, 2H, J=6.4 Hz), 3.10-3.20 (m, 1H), 3.62-3.74 (m, 1H), 6.84 (d, 1H, J=9.2 Hz), 6.88-6.98 (m, 2H), 7.31 (d, 1H, J=9.6 Hz).

Compound Ij-44

[Formula 417]

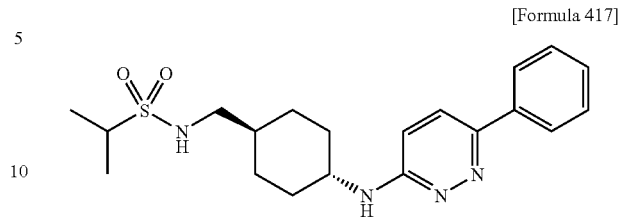

1H-NMR (DMSO-d6) δ: 0.94-1.26 (m, 4H), 1.20 (d, 6H, J=6.6 Hz), 1.40 (m, 1H), 1.78-1.88 (m, 2H), 2.04-2.16 (m, 2H), 2.81 (t, 2H, J=6.3 Hz), 3.06-3.20 (m, 1H), 3.72-3.90 (m, 1H), 6.75-6.88 (m, 2H), 6.97 (t, 1H, J=6.0 Hz), 7.30-7.48 (m, 3H), 7.76 (d, 1H, J=9.3 Hz), 7.94 (d, 2H, J=8.4 Hz)

Compound Ij-45

[Formula 418]

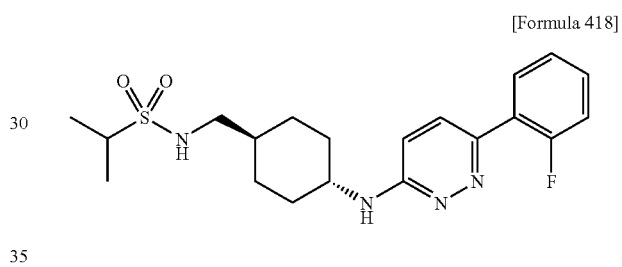

1H-NMR (DMSO-d6) δ: 0.96-1.28 (m, 4H), 1.22 (d, 6H, J=6.9 Hz), 1.42 (m, 1H), 1.78-1.88 (m, 2H), 2.04-2.16 (m, 2H), 2.83 (t, 2H, J=6.3 Hz), 3.10-3.22 (m, 1H), 3.74-3.92 (m, 1H), 6.85 (d, 1H, J=9.0 Hz), 6.91 (d, 1H, J=7.5 Hz), 6.98 (t, 1H, J=6.0 Hz), 7.25-7.36 (m, 2H), 7.40-7.50 (m, 1H), 7.57 (d, 1H, J=6.9 Hz), 7.85 (t, 1H, J=8.1 Hz)

Compound Ij-46

[Formula 419]

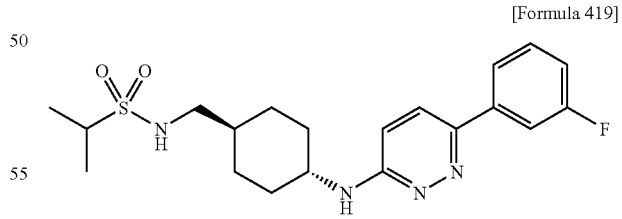

1H-NMR (DMSO-d6) δ: 0.96-1.28 (m, 4H), 1.22 (d, 6H, J=6.6 Hz), 1.42 (m, 1H), 1.78-1.88 (m, 2H), 2.04-2.16 (m, 2H), 2.83 (t, 2H, J=6.3 Hz), 3.10-3.22 (m, 1H), 3.74-3.92 (m, 1H), 6.85 (d, 1H, J=9.3 Hz), 6.90 (d, 1H, J=7.5 Hz), 6.98 (t, 1H, J=6.0 Hz), 7.21 (t, 1H, J=7.8 Hz), 7.46-7.56 (m, 1H), 7.75-7.86 (m, 3H)

Compound Ij-47

[Formula 420]

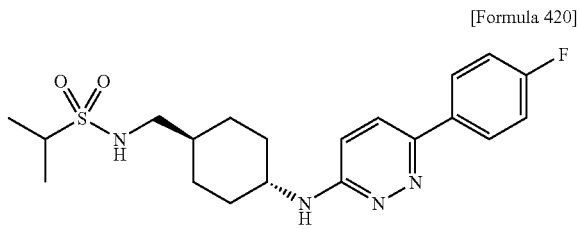

1H-NMR (DMSO-d6) δ: 0.96-1.28 (m, 4H), 1.22 (d, 6H, J=6.9 Hz), 1.42 (m, 1H), 1.78-1.88 (m, 2H), 2.04-2.16 (m, 2H), 2.83 (t, 2H, J=6.0 Hz), 3.10-3.22 (m, 1H), 3.74-3.92 (m, 1H), 6.81 (d, 1H, J=7.5 Hz), 6.84 (d, 1H, J=9.3 Hz), 6.98 (t, 1H, J=6.3 Hz), 7.25-7.35 (m, 2H), 7.77 (d, 1H, J=9.3 Hz), 7.96-8.06 (m, 2H)

Compound Ij-48

[Formula 421]

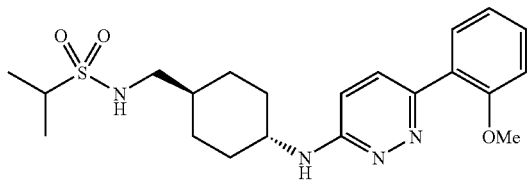

1H-NMR (DMSO-d6) δ: 0.96-1.28 (m, 4H), 1.22 (d, 6H, J=6.9 Hz), 1.42 (m, 1H), 1.78-1.88 (m, 2H), 2.04-2.16 (m, 2H), 2.83 (t, 2H, J=6.3 Hz), 3.10-3.22 (m, 1H), 3.74-3.92 (m, 1H), 3.80 (s, 3H), 6.71 (d, 1H, J=7.8 Hz), 6.76 (d, 1H, J=9.3 Hz), 6.98 (t, 1H, J=5.7 Hz), 7.05 (d, 1H, J=7.2 Hz), 7.12 (d, 1H, J=7.8 Hz), 7.38 (t, 1H, J=8.4 Hz), 7.56 (d, 1H, J=9.3 Hz), 7.62 (d, 1H, J=6.9 Hz)

Compound Ij-49

[Formula 422]

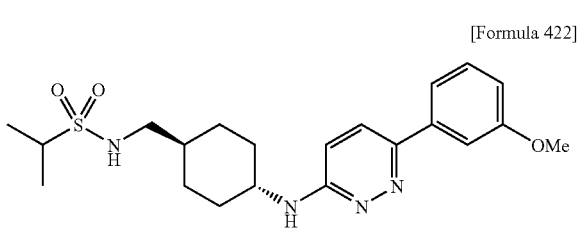

1H-NMR (DMSO-d6) δ: 0.96-1.28 (m, 4H), 1.22 (d, 6H, J=6.6 Hz), 1.42 (m, 1H), 1.78-1.88 (m, 2H), 2.04-2.16 (m, 2H), 2.83 (t, 2H, J=6.0 Hz), 3.10-3.22 (m, 1H), 3.74-3.92 (m, 1H), 3.82 (s, 3H), 6.78-6.88 (m, 2H), 6.92-7.04 (m, 2H), 7.37 (t, 1H, J=7.5 Hz), 7.46-7.58 (m, 2H), 7.79 (d, 1H, J=9.3 Hz)

Compound Ij-50

[Formula 423]

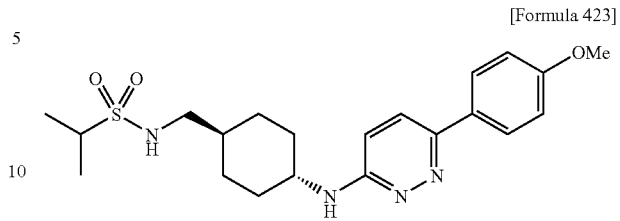

1H-NMR (DMSO-d6) δ: 0.96-1.28 (m, 4H), 1.22 (d, 6H, J=6.9 Hz), 1.42 (m, 1H), 1.78-1.88 (m, 2H), 2.04-2.16 (m, 2H), 2.83 (t, 2H, J=6.0 Hz), 3.10-3.22 (m, 1H), 3.74-3.92 (m, 1H), 3.80 (s, 3H), 6.70 (d, 1H, J=7.8 Hz), 6.82 (d, 1H, J=9.3 Hz), 6.95-7.05 (m, 3H), 7.72 (d, 1H, J=9.3 Hz), 7.90 (d, 2H, J=9.0 Hz).

Compound Ij-51

[Formula 424]

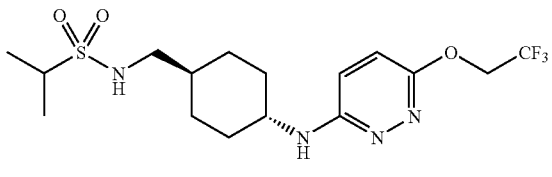

1H-NMR (DMSO-d6) δ: 0.92-1.05 (m, 2H), 1.07-1.20 (m, 2H), 1.22 (d, 6H, J=6.9 Hz), 1.39 (m, 1H), 1.76-1.85 (m, 2H), 2.02-2.10 (m, 2H), 2.81 (t, 2H, J=6.3 Hz), 3.09-3.20 (m, 1H), 3.57-3.68 (m, 1H), 4.89-4.98 (m, 2H), 6.47 (d, 1H, J=8.0 Hz), 6.88 (d, 1H, J=7.5 Hz), 6.96 (t, 1H, J=6.0 Hz), 7.02 (d, 1H, J=7.5 Hz).

Compound Ij-52

[Formula 425]

1H-NMR (DMSO-d6) δ: 0.92-1.05 (m, 2H), 1.07-1.20 (m, 2H), 1.22 (d, 6H, J=6.9 Hz), 1.39 (m, 1H), 1.52-1.74 (m, 6H), 1.77-1.85 (m, 2H), 1.87-1.97 (m, 2H), 2.02-2.09 (m, 2H), 2.81 (t, 2H, J=6.3 Hz), 3.09-3.20 (m, 1H), 3.55-3.65 (m, 1H), 5.25-5.32 (m, 1H), 6.19 (d, 1H, J=8.0 Hz), 6.77 (s, 2H), 6.95 (t, 1H, J=6.0 Hz).

Compound Ij-53

[Formula 426]

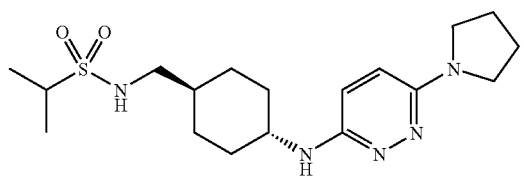

1H-NMR (DMSO-d6) δ: 0.92-1.15 (m, 4H), 1.21 (d, 6H, J=6.9 Hz), 1.38 (m, 1H), 1.77-1.85 (m, 2H), 1.88-1.95 (m, 4H), 2.02-2.09 (m, 2H), 2.80 (t, 2H, J=6.3 Hz), 3.09-3.20 (m, 1H), 3.25-3.35 (m, 4H), 3.55-3.65 (m, 1H), 5.80-5.85 (m, 1H), 6.72 (d, 1H, J=8.0 Hz), 6.80 (d, 1H, J=8.0 Hz), 6.96 (t, 1H, J=6.0 Hz).

Compound Ij-54

[Formula 427]

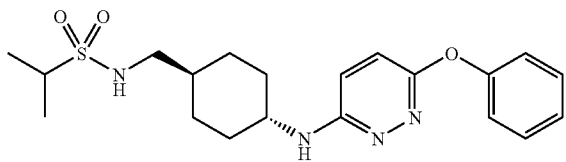

1H-NMR (DMSO-d6) δ: 0.92-1.20 (m, 4H), 1.21 (d, 6H, J=6.9 Hz), 1.38 (m, 1H), 1.77-1.85 (m, 2H), 2.02-2.09 (m, 2H), 2.80 (t, 2H, J=6.3 Hz), 3.09-3.20 (m, 1H), 3.58-3.65 (m, 1H), 6.56 (d, 1H, J=8.0 Hz), 6.90-6.98 (m, 2H), 7.03-7.10 (m, 3H), 7.15 (t, 1H, J=8.0 Hz), 6.38 (t, 2H, J=8.0 Hz).

Compound Ij-55

[Formula 428]

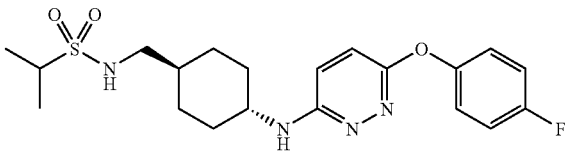

1H-NMR (DMSO-d6) δ: 0.92-1.20 (m, 4H), 1.21 (d, 6H, J=6.9 Hz), 1.38 (m, 1H), 1.77-1.85 (m, 2H), 2.02-2.09 (m, 2H), 2.80 (t, 2H, J=6.3 Hz), 3.09-3.20 (m, 1H), 3.58-3.65 (m, 1H), 6.55 (d, 1H, J=8.0 Hz), 6.90-6.98 (m, 2H), 7.05-7.15 (m, 3H), 7.21 (t, 2H, J=8.0 Hz).

Compound Ij-56

[Formula 429]

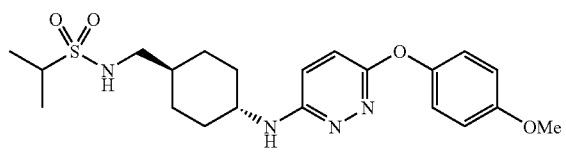

1H-NMR (DMSO-d6) δ: 0.92-1.20 (m, 4H), 1.21 (d, 6H, J=6.9 Hz), 1.38 (m, 1H), 1.77-1.85 (m, 2H), 2.02-2.09 (m, 2H), 2.80 (t, 2H, J=6.3 Hz), 3.09-3.20 (m, 1H), 3.58-3.65 (m, 1H), 3.75 (s, 3H), 6.49 (d, 1H, J=8.0 Hz), 6.87-6.98 (m, 4H), 7.00-7.07 (m, 3H).

Compound Ij-57

[Formula 430]

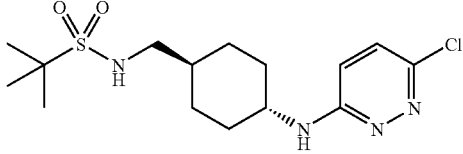

1H-NMR (DMSO-d6) δ: 0.96-1.28 (m, 4H), 1.27 (s, 9H), 1.40 (m, 1H), 1.78-1.88 (m, 2H), 2.00-2.10 (m, 2H), 2.88 (t, 2H, J=6.0 Hz), 3.60-3.76 (m, 1H), 6.82-6.92 (m, 2H), 6.96 (d, 1H, J=7.8 Hz), 7.32 (d, 1H, J=9.6 Hz).

Compound Ij-58

[Formula 431]

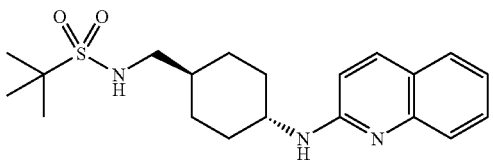

1H-NMR (DMSO-d6) δ: 0.99-1.28 (m, 4H), 1.21 (d, 6H, J=6.9 Hz), 1.39 (m, 1H), 1.78-1.86 (m, 2H), 2.04-2.10 (m, 2H), 2.82 (t, 2H, J=6.1 Hz), 3.06-3.20 (m, 1H), 3.80-3.96 (m, 1H), 6.71 (d, 1H, J=9.0 Hz), 6.76-6.86 (m, 1H), 6.90-6.98 (m, 1H), 7.10 (t, 1H, J=8.1 Hz), 7.39-7.50 (m, 2H), 7.56 (d, 1H, J=7.5 Hz), 7.78 (d, 1H, J=7.5 Hz).

Compound Ij-59

[Formula 432]

1H-NMR (DMSO-d6) δ: 0.99-1.28 (m, 4H), 1.27 (s, 9H), 1.40 (m, 1H), 1.80-1.85 (m, 2H), 2.04-2.09 (m, 2H), 2.91 (t, 2H, J=6.1 Hz), 3.80-3.96 (m, 1H), 6.70 (d, 1H, J=9.0 Hz), 6.81-6.87 (m, 2H), 7.10 (t, 1H, J=8.1 Hz), 7.39-7.44 (m, 2H), 7.56 (d, 1H, J=7.5 Hz), 7.79 (d, 1H, J=7.5 Hz).

Compound Ij-60

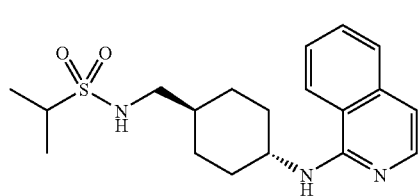

[Formula 433]

1H-NMR (DMSO-d6) δ: 0.97-1.09 (m, 2H), 1.23 (d, 6H, J=6.9 Hz), 1.31-1.50 (m, 2H), 1.82-1.87 (m, 2H), 2.01-2.05 (m, 2H), 2.83 (t, 2H, J=6.0 Hz), 3.11-3.20 (m, 1H), 4.00-4.18 (m, 1H), 6.83 (d, 1H, J=5.7 Hz), 6.90-7.06 (m, 2H), 7.45 (t, 1H, J=6.9 Hz), 7.59 (t, 1H, J=8.1 Hz), 7.67 (d, 1H, J=8.4 Hz), 7.83 (d, 1H, J=5.7 Hz), 8.27 (d, 1H, J=7.5 Hz).

Compound Ij-61

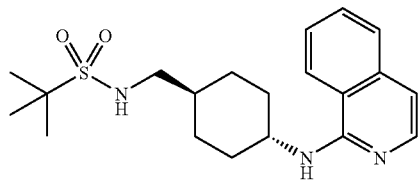

[Formula 434]

1H-NMR (DMSO-d6) δ: 0.96-1.09 (m, 2H), 1.28 (s, 9H), 1.29-1.50 (m, 2H), 1.82-1.87 (m, 2H), 2.01-2.05 (m, 2H), 2.91 (t, 2H, J=7.8 Hz), 4.00-4.18 (m, 1H), 6.82-6.89 (m, 2H), 6.97 (d, 1H, J=7.5 Hz), 7.45 (t, 1H, J=7.2 Hz), 7.59 (t, 1H, J=8.1 Hz), 7.67 (d, 1H, J=7.8 Hz), 7.84 (d, 1H, J=6.0 Hz), 8.27 (d, 1H, J=8.4 Hz).

Compound Ij-62

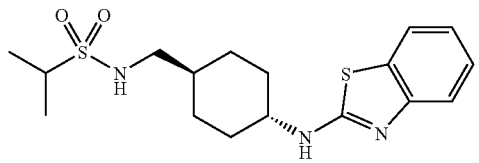

[Formula 435]

1H-NMR (DMSO-d6) δ: 0.96-1.14 (m, 2H), 1.18-1.30 (m, 2H), 1.22 (d, 6H, J=6.6 Hz), 1.40 (m, 1H), 1.78-1.88 (m, 2H), 2.04-2.14 (m, 2H), 2.81 (t, 2H, J=6.3 Hz), 3.10-3.20 (m, 1H), 3.58-3.70 (m, 1H), 6.95-7.03 (m, 2H), 7.20 (t, 1H, J=7.5 Hz), 7.37 (d, 1H, J=8.1 Hz), 7.64 (d, 1H, J=7.5 Hz), 7.92 (d, 1H, J=7.8 Hz).

Compound Ij-63

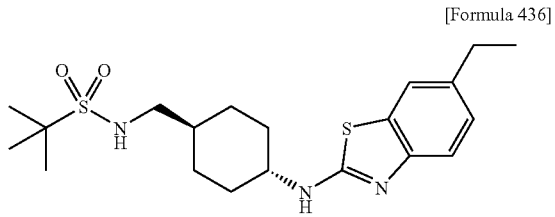

[Formula 436]

1H-NMR (DMSO-d6) δ: 1.00 (dd, 2H, J=24.8, 10.6 Hz), 1.15-1.22 (m, 2H), 1.18 (t, 3H, J=7.6 Hz), 1.27 (s, 9H), 1.34-1.40 (m, 1H), 1.81 (d, 2H, J=11.6 Hz), 2.07 (d, 2H, J=11.6 Hz), 2.60 (q, 2H, J=7.6 Hz), 2.89 (t, 2H, J=6.3 Hz), 3.52-3.63 (m, 1H), 6.87 (t, 1H, J=5.8 Hz), 7.04 (d, 1H, J=7.9 Hz), 7.27 (d, 1H, J=8.2 Hz), 7.47 (s, 1H), 7.80 (d, 1H, J=7.6 Hz).

Compound Ij-64

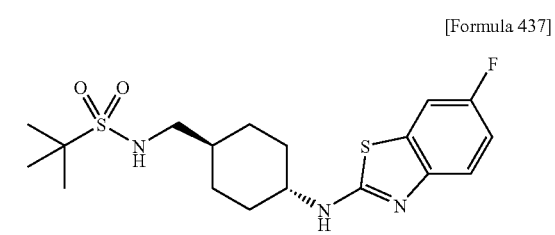

[Formula 437]

1H-NMR (DMSO-d6) δ: 0.92-1.10 (m, 2H), 1.12-1.25 (m, 2H), 1.27 (s, 9H), 1.37 (m, 1H), 1.76-1.84 (m, 2H), 2.02-2.12 (m, 2H), 2.89 (t, 2H, J=6.0 Hz), 3.50-3.66 (m, 1H), 6.87 (t, 1H, J=5.7 Hz), 7.03 (dd, 1H, J=8.7, 2.7 Hz), 7.32-7.37 (m, 1H), 7.58 (dd, 1H, J=8.7, 2.7 Hz), 7.92 (d, 1H, J=7.2 Hz).

Compound Ij-65

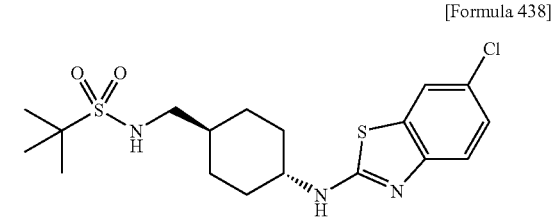

[Formula 438]

1H-NMR (DMSO-d6) δ: 1.01 (dd, 2H, J=24.6, 10.2 Hz), 1.21 (dd, 2H, J=24.6, 10.2 Hz), 1.27 (s, 9H), 1.34-1.40 (m, 1H), 1.82 (d, 2H, J=11.2 Hz), 2.08 (d, 2H, J=11.2 Hz), 2.89 (t, 2H, J=6.2 Hz), 3.59-3.65 (m, 1H), 6.87 (t, 1H, J=5.8 Hz), 7.21 (dd, 1H, J=8.6, 2.4 Hz), 7.34 (d, 1H, J=8.6 Hz), 7.77 (d, 1H, J=1.8 Hz), 8.06 (d, 1H, J=7.6 Hz).

Compound Ij-66

[Formula 439]

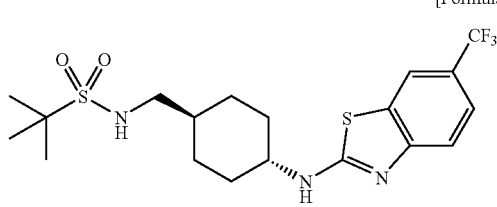

1H-NMR (CDCl3) δ: 1.09-1.46 (m, 4H), 1.41 (s, 9H), 1.54 (m, 1H), 1.90-2.00 (m, 2H), 2.24-2.34 (m, 2H), 3.09 (t, 2H, J=6.6 Hz), 3.46-3.60 (m, 1H), 3.99 (t, 1H, J=6.6 Hz), 6.58 (brs, 1H), 7.58(s, 2H), 7.85 (s, 1H).

Compound Ij-67

[Formula 440]

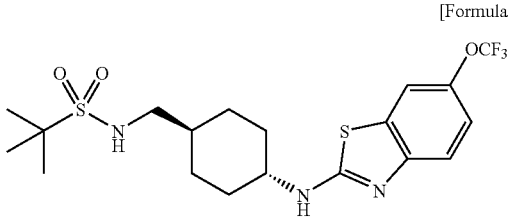

1H-NMR (DMSO-d6) δ: 0.90-1.30 (m, 4H), 1.27 (s, 9H), 1.30-1.48 (m, 1H), 1.82 (d, 2H, J=11.1 Hz), 2.08 (d, 2H, J=9.6 Hz), 2.89 (t, 2H, J=6.3 Hz), 3.55-3.70 (m, 1H), 6.87 (t, 1H, J=5.7 Hz), 7.17 (m, 1H), 7.41 (d, 1H, J=8.7 Hz), 7.77 (d, 1H, J=1.5 Hz), 8.10 (d, 1H, J=7.5 Hz). ESI(positive)m/z 466.2 [M+H]+

Compound Ij-68

[Formula 441]

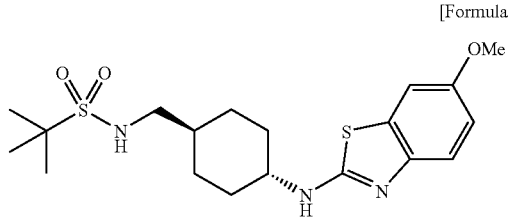

1H-NMR (DMSO-d6) δ: 0.90-1.28 (m, 4H), 1.25 (s, 9H), 1.32 (m, 1H), 1.76-1.82 (m, 2H), 2.00-2.10 (m, 2H), 2.87 (t, 2H, J=6.6 Hz), 3.50-3.62 (m, 1H), 3.71 (s, 3H), 6.77 (dd, 1H, J=8.7, 2.7 Hz), 6.84 (t, 1H, J=5.7 Hz), 7.22-7.28 (m, 2H), 7.66 (d, 1H, J=7.2 Hz).

Compound Ij-69

[Formula 442]

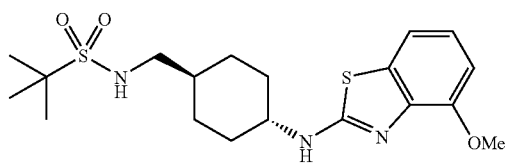

1H-NMR (DMSO-d6) δ: 0.94-1.10 (m, 2H), 1.12-1.25 (m, 2H), 1.27 (s, 9H), 1.37 (m, 1H), 1.76-1.84 (m, 2H), 2.02-2.12 (m, 2H), 2.90 (t, 2H, J=6.0 Hz), 3.52-3.68 (m, 1H), 3.84 (s, 3H), 6.82 (d, 1H, J=8.1 Hz), 6.88 (t, 1H, J=5.4 Hz), 6.95 (t, 1H, J=7.8 Hz), 7.23 (d, 1H, J=7.8 Hz), 7.83 (d, 1H, J=7.8 Hz).

Compound Ij-70

[Formula 443]

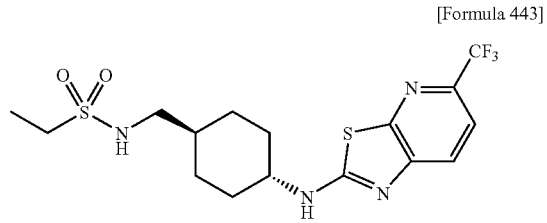

1H-NMR (DMSO-d6) δ: 0.98-1.10 (m, 2H), 1.19 (t, 3H, J=7.2 Hz), 1.17-1.32 (m, 2H), 1.40 (m, 1H), 1.76-1.88 (m, 2H), 2.04-2.14 (m, 2H), 2.79 (t, 2H, J=6.0 Hz), 2.98 (q, 2H, J=7.2 Hz), 3.60-3.78 (m, 1H), 7.03 (t, 1H, J=6.3 Hz), 7.45-7.54 (m, 2H), 8.10 (s, 1H), 8.34 (d, 1H, J=7.2 Hz).

Compound Ij-71

[Formula 444]

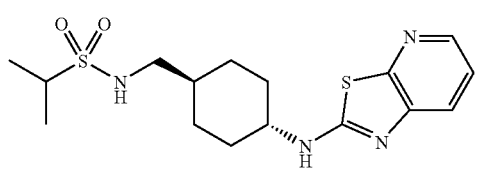

1H-NMR (DMSO-d6) δ: 1.01 (dd, 2H, J=26.1, 12.3 Hz), 1.16-1.22 (m, 2H), 1.22 (d, 6H, J=6.6 Hz), 1.35-1.41 (m, 1H), 1.70-1.77 (m, 1H), 1.82 (d, 2H, J=11.6 Hz), 2.08 (d, 2H, J=11.6 Hz), 2.81 (t, 2H, J=6.3 Hz), 3.66-3.72 (m, 1H), 6.99 (t, 1H, J=6.3 Hz), 7.23 (dd, 1H, J=8.1, 4.7 Hz), 7.66 (d, 1H, J=8.1 Hz), 8.07 (d, 1H, J=4.7 Hz), 8.26 (d, 1H, J=6.3 Hz).

Compound Ij-72

[Formula 445]

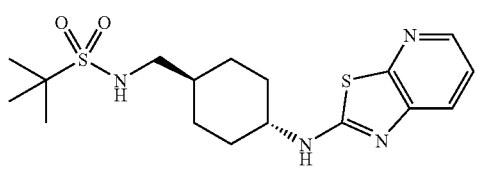

1H-NMR (DMSO-d6) δ: 1.01 (dd, 2H, J=24.8, 11.3 Hz), 1.18-1.23 (m, 2H), 1.27 (s, 9H), 1.36-1.39 (m, 1H), 1.82 (d, 2H, J=11.5 Hz), 2.08 (d, 2H, J=11.5 Hz), 2.89 (t, 2H, J=6.1 Hz), 3.65-3.73 (m, 1H), 6.87 (t, 1H, J=5.7 Hz), 7.23 (dd, 1H, J=8.1, 4.8 Hz), 7.66 (d, 1H, J=7.9 Hz), 8.07 (d, 1H, J=4.7 Hz), 8.26 (d, 1H, J=7.6 Hz).

Compound Ij-73

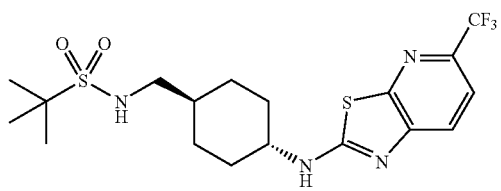

[Formula 446]

1H-NMR (CDCl3) δ: 1.09-1.46 (m, 4H), 1.41 (s, 9H), 1.55 (m, 1H), 1.92-2.02 (m, 2H), 2.24-2.34 (m, 2H), 3.09 (t, 2H, J=6.3 Hz), 3.58-3.72 (m, 1H), 3.98 (t, 1H, J=6.0 Hz), 6.30 (brs, 1H), 7.62(d, 1H, J=8.1 Hz), 7.77 (d, 1H, J=8.4 Hz).

Compound Ij-74

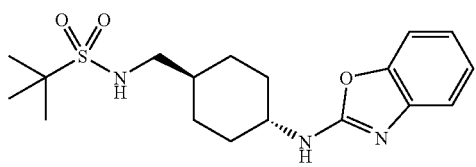

[Formula 447]

1H-NMR (DMSO-d6) δ: 0.90-1.08 (m, 2H), 1.12-1.40 (m, 3H), 1.25 (s, 9H), 1.76-1.86 (m, 2H), 1.98-2.10 (m, 2H), 2.87 (d, 2H, J=6.3 Hz), 3.40-3.56 (m, 1H), 6.85 (brs, 1H), 6.93 (t, 1H, J=7.5 Hz), 7.07 (t, 1H, J=7.5 Hz), 7.20 (d, 1H, J=7.5 Hz), 7.29 (d, 1H, J=7.8 Hz), 7.79 (brs, 1H).

Compound Ij-75

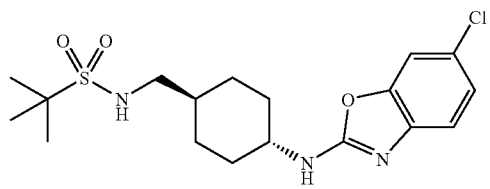

[Formula 448]

1H-NMR (CDCl3) δ: 1.08-1.26 (m, 2H), 1.36-1.60 (m, 3H), 1.40 (s, 9H), 1.92-2.02 (m, 2H), 2.22-2.32 (m, 2H), 3.08 (t, 2H, J=6.6 Hz), 3.68-3.80 (m, 1H), 4.03 (t, 1H, J=6.0 Hz), 7.06 (brs, 1H), 7.20-7.36(m, 3H).

Compound Ij-76

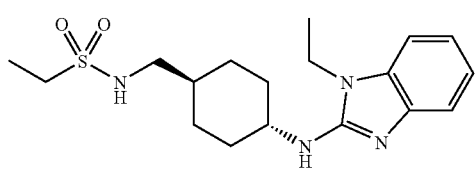

[Formula 449]

1H-NMR (DMSO-d6) δ: 1.02 (dd, 2H, J=25.2, 12.4 Hz), 1.17 (t, 3H, J=7.1 Hz), 1.20 (t, 3H, J=7.3 Hz), 1.26-1.35 (m, 2H), 1.37-1.42 (m, 1H), 1.83 (d, 2H, J=11.6 Hz), 2.05 (d, 2H, J=11.6 Hz), 2.80 (t, 2H, J=6.4 Hz), 2.99 (q, 2H, J=7.3 Hz), 3.65-3.72 (m, 1H), 4.01 (q, 2H, J=7.1 Hz), 6.32 (d, 1H, J=7.9 Hz), 6.86-6.94 (m, 2H), 7.01 (t, 1H, J=6.0 Hz), 7.12 (d, 1H, J=6.9 Hz), 7.17 (d, 1H, J=6.8 Hz).

Compound Ij-77

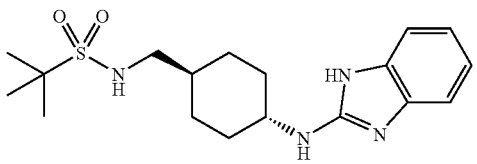

[Formula 450]

1H-NMR (DMSO-d6) δ: 1.02 (dd, 2H, J=24.8, 10.8 Hz), 1.19-1.21 (m, 2H), 1.30 (s, 9H), 1.37-1.41 (m, 1H), 1.84 (d, 2H, J=10.6 Hz), 2.06 (d, 2H, J=10.6 Hz), 2.92 (t, 2H, J=6.3 Hz), 3.50-3.52 (m, 1H), 6.42 (d, 1H, J=8.1 Hz), 6.83 (d, 1H, J=7.9 Hz), 6.88-6.92 (m, 2H), 7.11-7.14 (m, 2H), 10.58 (s, 1H).

Compound Ij-78

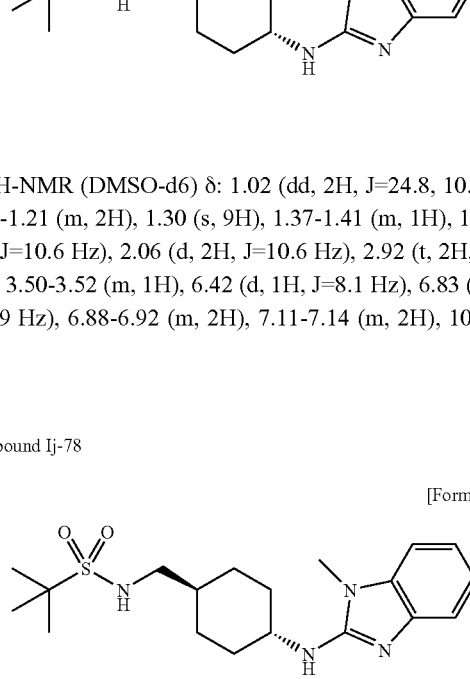

[Formula 451]

1H-NMR (DMSO-d6) δ: 0.97-1.05 (m, 2H), 1.20-1.26 (m, 2H), 1.28 (s, 9H), 1.34-1.38 (m, 1H), 1.84 (d, 2H, J=11.5 Hz), 2.07 (d, 2H, J=11.5 Hz), 2.90 (t, 2H, J=6.1 Hz), 3.47 (s, 3H), 3.63-3.69 (m, 1H), 6.34 (d, 1H, J=7.6 Hz), 6.87-6.93 (m, 3H), 7.11 (d, 1H, J=8.4 Hz), 7.17 (d, 1H, J=8.4 Hz).

Compound Ij-79

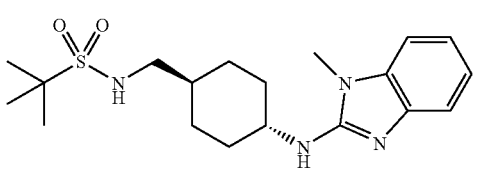

[Formula 452]

1H-NMR (DMSO-d6) δ: 1.03 (dd, 2H, J=23.6, 10.8 Hz), 1.18 (t, 3H, J=7.5 Hz), 1.25-1.34 (m, 2H), 1.29 (s, 9H), 1.37-1.40 (m, 1H), 1.86 (d, 2H, J=11.7 Hz), 2.07 (d, 2H, J=11.7 Hz), 2.92 (t, 2H, J=6.2 Hz), 3.67-3.73 (m, 1H), 4.03 (q, 2H, J=7.1 Hz), 6.34 (d, 1H, J=7.9 Hz), 6.87-6.96 (m, 3H), 7.14 (dd, 1H, J=8.1, 1.2 Hz), 7.19 (dd, 1H, J=8.1, 1.2 Hz).

Compound Ij-80

[Formula 453]

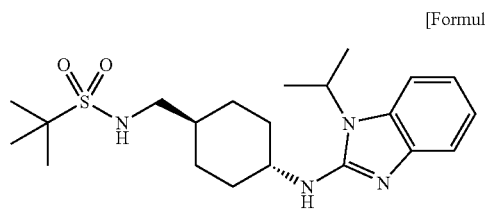

1H-NMR (DMSO-d6) δ: 1.00 (dd, 2H, J=23.2, 11.9 Hz), 1.19-1.25 (m, 2H), 1.28 (s, 9H), 1.33-1.38 (m, 1H), 1.45 (s, 3H), 1.47 (s, 3H), 1.83 (d, 2H, J=11.1 Hz), 2.07 (d, 2H, J=11.1 Hz), 2.90 (t, 2H, J=6.1 Hz), 3.62-3.70 (m, 1H), 4.57-4.66 (m, 1H), 6.21 (d, 1H, J=7.9 Hz), 6.82-6.94 (m, 3H), 7.18 (d, 1H, J=7.6 Hz), 7.31 (d, 1H, J=7.6 Hz).

Compound Ij-81

[Formula 454]

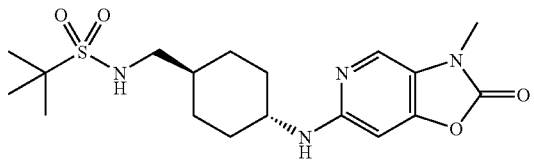

Compound Ij-82

[Formula 455]

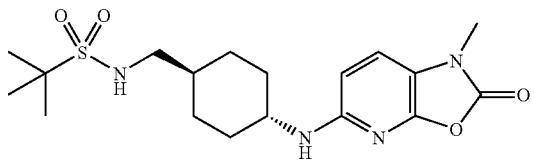

1H-NMR (DMSO-d6) δ: 0.90-1.19 (m, 4H), 1.28 (s, 9H), 1.32-1.45 (m, 1H), 1.80 (d, 2H, J=11.2 Hz), 1.98 (d, 2H, J=11.2 Hz), 2.84-2.93 (m, 2H), 3.26 (s, 3H), 3.40-3.53 (m, 1H), 6.29 (d, 1H, J=8.0 Hz), 6.38 (d, 1H, J=7.2 Hz), 6.86 (s, 1H), 7.33 (d, 1H, J=8.4 Hz).

Compound Ij-83

[Formula 456]

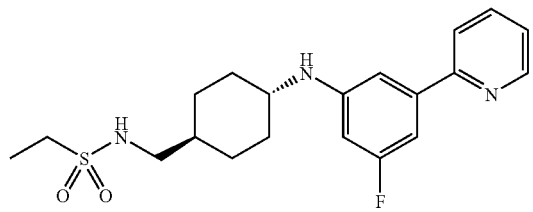

Compound Ij-84

[Formula 457]

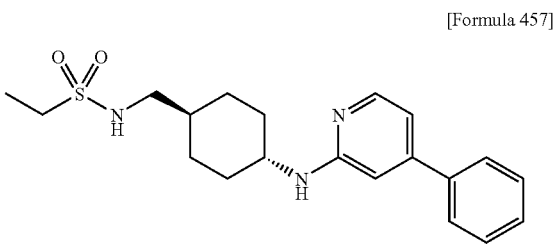

1H-NMR (DMSO-d6) δ: 0.92-1.20 (m, 4H), 1.18 (t, 3H, J=7.2 Hz), 1.40 (m, 1H), 1.75-1.85 (m, 2H), 1.96-2.06 (m, 2H), 2.78 (t, 2H, J=6.0 Hz), 2.98 (q, 2H, J=7.2 Hz), 3.60-3.78 (m, 1H), 6.38 (d, 1H, J=8.1 Hz), 6.67 (s, 1H), 6.72 (d, 1H, J=5.4 Hz), 7.00 (t, 1H, J=6.0 Hz), 7.36-7.54 (m, 3H), 7.62 (d, 2H, J=6.9 Hz), 8.00 (d, 1H, J=5.4 Hz)

Compound Ij-85

[Formula 458]

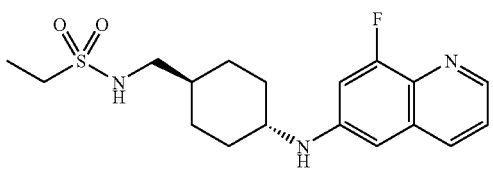

1H-NMR (DMSO-d6) δ: 1.00-1.20 (m, 4H), 1.20 (t, 3H, J=7.2 Hz), 1.43 (m, 1H), 1.80-1.88 (m, 2H), 2.03-2.13 (m, 2H), 2.81 (t, 3H, J=6.0 Hz), 3.00 (q, 2H, J=7.2 Hz), 3.26 (m, 1H), 6.17 (d, 1H, J=7.6 Hz), 6.57 (s, 1H), 6.96-7.07 (m, 2H), 7.35 (dd, 1H, J=8.4, 4.0 Hz), 8.02 (d, 1H, J=8.4 Hz), 8.47 (d, 1H, J=4.0 Hz).

Compound Ij-86

[Formula 459]

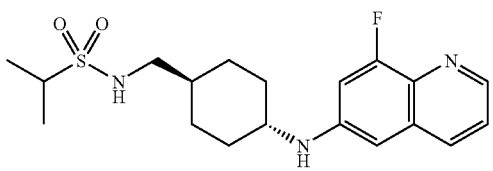

1H-NMR (DMSO-d6) δ: 1.00-1.24 (m, 4H), 1.23 (d, 6H, J=6.4 Hz), 1.42 (m, 1H), 1.80-1.88 (m, 2H), 2.03-2.12 (m, 2H), 2.79-2.87 (m, 2H), 3.16 (m, 1H), 3.27 (m, 1H), 6.17 (d, 1H, J=8.0 Hz), 6.57 (s, 1H), 6.99 (d, 1H, J=8.0 Hz), 7.01 (s, 1H), 7.35 (dd, 1H, J=8.0, 4.0 Hz), 8.02 (d, 1H, J=8.0 Hz), 8.47 (d, 1H, J=2.8 Hz).

Compound Ij-87

[Formula 460]

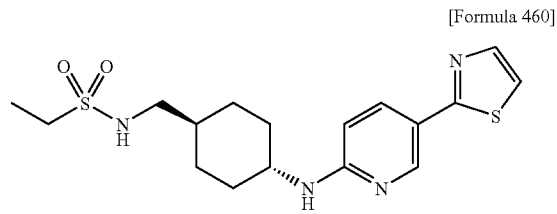

1H-NMR (DMSO-d6) δ: 0.95-1.08 (m, 2H), 1.11-1.25 (m, 2H), 1.20 (t, 3H, J=7.2 Hz), 1.40 (m, 1H), 1.76-1.86 (m, 2H), 1.97-2.04 (m, 2H), 2.73-2.82 (m, 2H), 2.99 (q, 2H, J=7.2 Hz), 3.70 (m, 1H), 6.53 (d, 1H, J=8.8 Hz), 6.53 (d, 1H, J=8.8 Hz), 7.01 (t, 1H, J=6.0 Hz), 7.58 (d, 1H, J=3.2 Hz), 7.79 (d, 1H, J=3.2 Hz), 7.86 (d, 1H, J=8.8 Hz), 8.55 (s, 1H).

Compound Ij-88

[Formula 461]

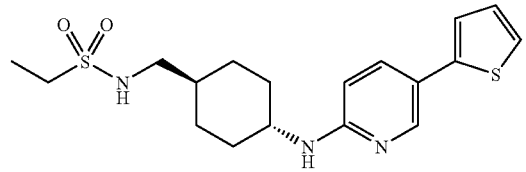

1H-NMR (DMSO-d6) δ: 0.92-1.07 (m, 2H), 1.09-1.20 (m, 2H), 1.19 (t, 6H, J=7.2 Hz), 1.39 (m, 1H), 1.75-1.83 (m, 2H), 1.95-2.03 (m, 2H), 2.74-2.81 (m, 2H), 2.98 (q, 2H, J=7.2 Hz), 3.66 (m, 1H), 6.48 (d, 1H, J=8.4 Hz), 6.60 (d, 1H, J=7.6 Hz), 7.00 (t, 1H, J=5.6 Hz), 7.06 (dd, 1H, J=4.8, 2.4 Hz), 7.25 (d, 1H, J=2.4 Hz), 7.37 (d, 1H, J=4.8 Hz), 7.60 (dd, 1H, J=8.4, 2.0 Hz), 8.26 (s, 1H).

Compound Ij-89

[Formula 462]

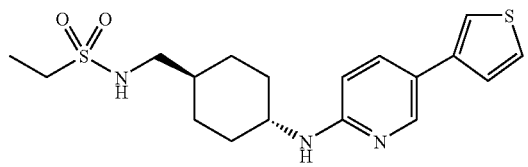

1H-NMR (DMSO-d6) δ: 0.93-1.07 (m, 2H), 1.10-1.20 (m, 2H), 1.19 (t, 3H, J=7.2 Hz), 1.39 (m, 1H), 1.76-1.84 (m, 2H), 1.96-2.04 (m, 2H), 2.73-2.81 (m, 2H), 2.98 (q, 2H, J=7.2 Hz), 3.65 (m, 1H), 6.41-6.50 (m, 2H), 7.01 (t, 1H, J=6.0 Hz), 7.44 (d, 1H, J=4.0 Hz), 7.58 (m, 1H), 7.59 (s, 1H), 7.68 (d, 1H, J=8.0 Hz), 8.34 (s, 1H).

Compound Ij-90

[Formula 463]

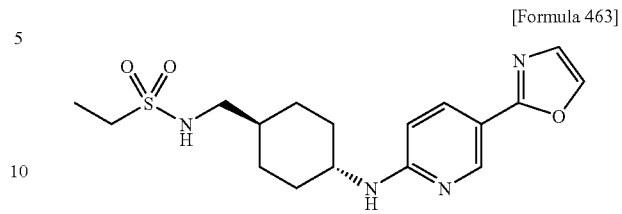

1H-NMR (DMSO-d6) δ: 0.95-1.08 (m, 2H), 1.12-1.25 (m, 2H), 1.19 (t, 3H, J=7.2 Hz), 1.39 (m, 1H), 1.76-1.86 (m, 2H), 1.94-2.03 (m, 2H), 2.75-2.82 (m, 2H), 2.98 (q, 2H, J=7.2 Hz), 3.71 (m, 1H), 6.54 (d, 1H, J=8.8 Hz), 6.98-7.07 (m, 2H), 7.25 (s, 1H), 7.85 (dd, 1H, J=8.8, 2.0 Hz), 8.07 (s, 1H), 8.56 (d, 1H, J=2.0 Hz).

Compound Ij-91

[Formula 464]

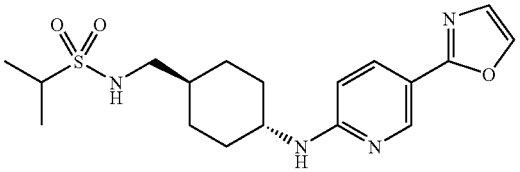

1H-NMR (DMSO-d6) δ: 0.93-1.07 (m, 2H), 1.11-1.22 (m, 2H), 1.21 (d, 6H, J=6.8 Hz), 1.38 (m, 1H), 1.77-1.85 (m, 2H), 1.95-2.03 (m, 2H), 2.77-2.83 (m, 2H), 3.14 (m, 1H), 3.72 (m, 1H), 6.53 (d, 1H, J=8.8 Hz), 6.97 (t, 1H, J=6.0 Hz), 7.02 (d, 1H, J=7.6 Hz), 7.25 (s, 1H), 7.84 (dd, 1H, J=8.8, 2.0 Hz), 8.06 (s, 1H), 8.56 (d, 1H, J=2.0 Hz).

Compound Ij-92

[Formula 465]

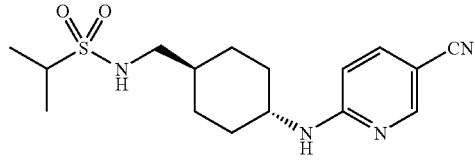

1H-NMR (DMSO-d6) δ: 0.92-1.03 (m, 2H), 1.11-1.23 (m, 2H), 1.21 (d, 6H, J=6.8 Hz), 1.37 (m, 1H), 1.75-1.83 (m, 2H), 1.91-1.99 (m, 2H), 2.36-2.42 (m, 2H), 3.12 (m, 1H), 3.70 (m, 1H), 6.49 (d, 1H, J=9.2 Hz), 6.97 (t, 1H, J=6.0 Hz), 7.47 (d, 1H, J=8.0 Hz), 7.62 (d, 1H, J=8.0 Hz), 8.36 (s, 1H).

Compound Ij-93

[Formula 466]

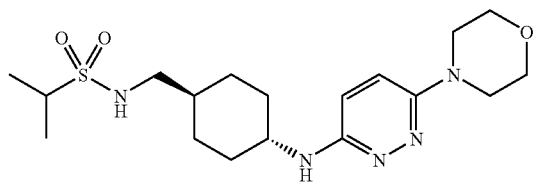

1H-NMR (DMSO-d6) δ: 0.95-1.13 (m, 4H), 1.23 (d, 6H, J=6.9 Hz), 1.31-1.44 (m, 1H), 1.78-1.82 (m, 2H), 2.03-2.06 (m, 2H), 2.76-2.82 (m, 2H), 3.10-3.19 (m, 1H), 3.20-3.25 (m, 4H), 3.58-3.65 (m, 1H), 3.69-3.74 (m, 4H), 6.04 (d, 1H, J=7.5 Hz), 6.72 (d, 1H, J=9.6 Hz), 6.95-6.99 (m, 1H), 7.10 (d, 1H, J=9.6 Hz).

Compound Ij-94

[Formula 467]

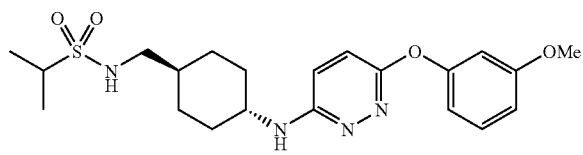

1H-NMR (DMSO-d6) δ: 0.96-1.42 (m, 5H), 1.22 (d, 6H, J=6.9 Hz), 1.79-1.83 (m, 2H), 2.03-2.07 (m, 2H), 2.80 (d, 2H, J=6.3 Hz), 3.10-3.19 (m, 1H), 3.54-3.70 (m, 1H), 3.74 (s, 3H), 6.57-6.64 (m, 3H), 6.72-6.75 (m, 1H), 6.90-7.09 (m, 3H), 7.24-7.30 (m, 1H).

Compound Ij-95

[Formula 468]

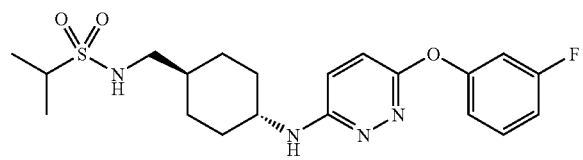

1H-NMR (DMSO-d6) δ: 0.93-1.04 (m, 2H), 1.10-1.18 (m, 2H), 1.21 (d, 6H, J=6.6 Hz), 1.34-1.44 (m, 1H), 1.78-1.87 (m, 2H), 2.02-2.12 (m, 2H), 2.77-2.84 (m, 2H), 3.10-3.20 (m, 1H), 3.52-3.70 (m, 1H), 6.64 (d, 1H, J=8.0 Hz), 6.88-7.06 (m, 5H), 7.12 (d, 1H, J=8.0 Hz), 7.37-7.46 (m, 1H).

Compound Ij-96

[Formula 469]

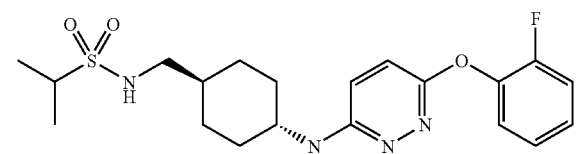

1H-NMR (DMSO-d6) δ: 0.90-1.04 (m, 2H), 1.05-1.18 (m, 2H), 1.21 (d, 6H, J=6.6 Hz), 1.33-1.43 (m, 1H), 1.75-1.84 (m, 2H), 1.98-2.08 (m, 2H), 2.76-2.84 (m, 2H), 3.08-3.18 (m, 1H), 3.52-3.64 (m, 1H), 6.55 (d, 1H, J=8.0 Hz), 6.91-7.00 (m, 2H), 7.15-7.38 (m, 5H).

Compound Ij-97

[Formula 470]

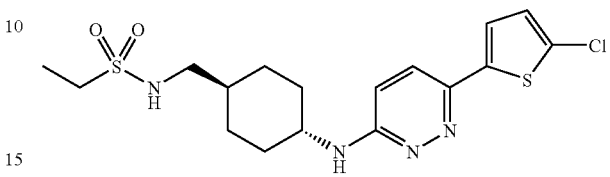

1H-NMR (DMSO-d6) δ: 0.96-1.08 (m, 2H), 1.12-1.25 (m, 2H), 1.19 (t, 3H, J=7.2 Hz), 1.35-1.47 (m, 1H), 1.78-1.87 (m, 2H), 2.02-2.10 (m, 2H), 2.78-2.83 (m, 2H), 2.98 (q, 2H, J=7.2 Hz), 3.70-3.82 (m, 1H), 6.82 (d, 1H, J=8.0 Hz), 6.93 (d, 1H, J=8.0 Hz), 7.01 (t, 1H, J=4.5 Hz), 7.13 (d, 1H, J=4.0 Hz), 7.43 (d, 1H, J=4.0 Hz), 7.76 (d, 1H, J=8.0 Hz).

Compound Ij-98

[Formula 471]

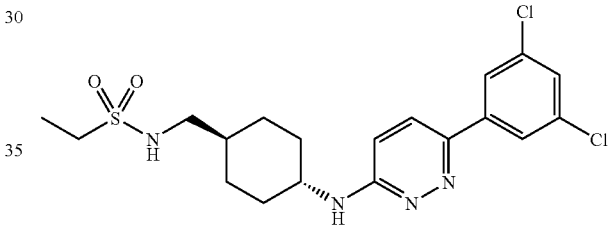

1H-NMR (DMSO-d6) δ: 0.97-1.10 (m, 2H), 1.17-1.28 (m, 2H), 1.19 (t, 3H, J=7.2 Hz), 1.37-1.49 (m, 1H), 1.80-1.88 (m, 2H), 2.04-2.12 (m, 2H), 2.77-2.83 (m, 2H), 2.99 (q, 2H, J=7.2 Hz), 3.76-3.88 (m, 1H), 6.85 (d, 1H, J=8.0 Hz), 6.99-7.05 (m, 2H), 7.61 (s, 1H), 7.90 (d, 1H, J=8.0 Hz), 8.02 (s, 2H).

Compound Ij-99

[Formula 472]

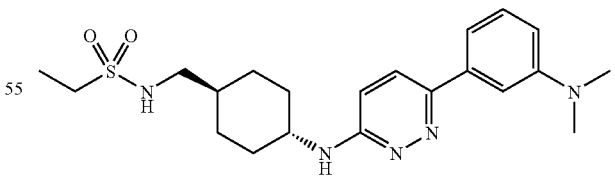

1H-NMR (DMSO-d6) δ: 0.98-1.10 (m, 2H), 1.14-1.26 (m, 2H), 1.19 (t, 3H, J=7.2 Hz), 1.37-1.48 (m, 1H), 1.80-1.88 (m, 2H), 2.04-2.13 (m, 2H), 2.77-2.83 (m, 2H), 2.96 (s, 6H), 2.99 (q, 2H, J=7.2 Hz), 3.76-3.86 (m, 1H), 6.72-6.78 (m, 2H), 6.82 (d, 1H, J=8.0 Hz), 7.02 (t, 1H, J=4.5 Hz), 7.18 (d, 1H, J=8.0 Hz), 7.26 (t, 1H, J=8.0 Hz), 7.34 (s, 1H), 7.74 (d, 1H, J=8.0 Hz).

Compound Ij-100

[Formula 473]

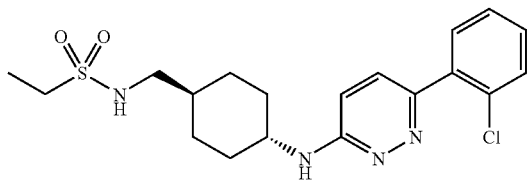

1H-NMR (DMSO-d6) δ: 0.98-1.10 (m, 2H), 1.16-1.27 (m, 2H), 1.19 (t, 3H, J=7.2 Hz), 1.37-1.48 (m, 1H), 1.80-1.88 (m, 2H), 2.04-2.13 (m, 2H), 2.77-2.83 (m, 2H), 2.99 (q, 2H, J=7.2 Hz), 3.76-3.86 (m, 1H), 6.83 (d, 1H, J=8.0 Hz), 6.89 (d, 1H, J=8.0 Hz), 7.02 (t, 1H, J=4.5 Hz), 7.42-7.50 (m, 3H), 7.53-7.59 (m, 2H).

Compound Ij-101

[Formula 474]

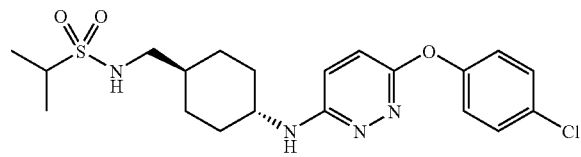

1H-NMR (DMSO-d6) δ: 0.92-1.05 (m, 2H), 1.08-1.20 (m, 2H), 1.21 (d, 6H, J=6.6 Hz), 1.36-1.43 (m, 1H), 1.76-1.84 (m, 2H), 2.02-2.09 (m, 2H), 2.77-2.83 (m, 2H), 3.10-3.20 (m, 1H), 3.56-3.68 (m, 1H), 6.62 (d, 1H, J=8.0 Hz), 6.93 (d, 1H, J=8.0 Hz), 6.98 (t, 1H, J=4.5 Hz), 7.10-7.15 (m, 3H), 7.43 (d, 2H, J=8.0 Hz).

Compound Ij-102

[Formula 475]

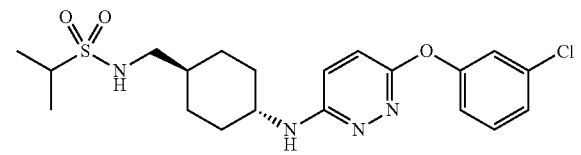

1H-NMR (DMSO-d6) δ: 0.92-1.05 (m, 2H), 1.08-1.20 (m, 2H), 1.21 (d, 6H, J=6.6 Hz), 1.36-1.43 (m, 1H), 1.76-1.84 (m, 2H), 2.02-2.09 (m, 2H), 2.77-2.83 (m, 2H), 3.10-3.20 (m, 1H), 3.57-3.68 (m, 1H), 6.65 (d, 1H, J=8.0 Hz), 6.94 (d, 1H, J=8.0 Hz), 6.97 (t, 1H, J=4.5 Hz), 7.06 (d, 1H, J=8.0 Hz), 7.13 (d, 1H, J=8.0 Hz), 7.18-7.26 (m, 2H), 7.41 (t, 1H, J=8.0 Hz).

Compound Ij-103

[Formula 476]

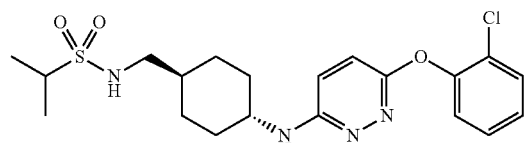

1H-NMR (DMSO-d6) δ: 0.88-1.04 (m, 2H), 1.05-1.20 (m, 2H), 1.21 (d, 6H, J=6.6 Hz), 1.33-1.43 (m, 1H), 1.77-1.82 (m, 2H), 2.00-2.07 (m, 2H), 2.76-2.82 (m, 2H), 3.08-3.20 (m, 1H), 3.52-3.64 (m, 1H), 6.57 (d, 1H, J=8.0 Hz), 6.92-7.00 (m, 2H), 7.17 (d, 1H, J=8.0 Hz), 7.23-7.28 (m, 2H), 7.38 (t, 1H, J=8.0 Hz), 7.56 (d, 1H, J=8.0 Hz).

Compound Ij-104

[Formula 477]

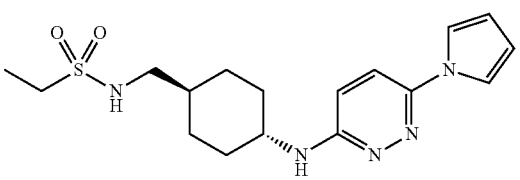

1H-NMR (DMSO-d6) δ: 0.96-1.08 (m, 2H), 1.12-1.24 (m, 2H), 1.19 (t, 3H, J=7.6 Hz), 1.35-1.46 (m, 1H), 1.78-1.86 (m, 2H), 2.04-2.12 (m, 2H), 2.76-2.82 (m, 2H), 2.98 (q, 2H, J=7.6 Hz), 3.67-3.78 (m, 1H), 6.27 (s, 2H), 6.71 (d, 1H, J=8.0 Hz), 6.93 (d, 1H, J=8.0 Hz), 7.02 (brs, 1H), 7.52 (s, 2H), 7.67 (d, 1H, J=8.0 Hz).

Compound Ij-105

[Formula 478]

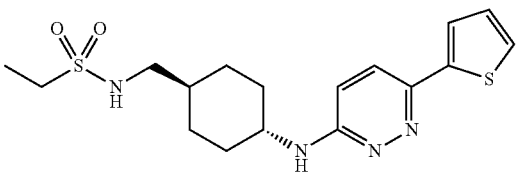

1H-NMR (DMSO-d6) δ: 0.96-1.08 (m, 2H), 1.13-1.25 (m, 2H), 1.19 (t, 3H, J=7.6 Hz), 1.35-1.46 (m, 1H), 1.78-1.87 (m, 2H), 2.04-2.12 (m, 2H), 2.76-2.83 (m, 2H), 2.99 (q, 2H, J=7.6 Hz), 3.72-3.82 (m, 1H), 6.82 (d, 1H, J=8.0 Hz), 6.85 (d, 1H, J=8.0 Hz), 7.03 (t, 1H, J=4.5 Hz), 7.12 (t, 1H, J=4.0 Hz), 7.51 (d, 1H, J=4.0 Hz), 7.56 (d, 1H, J=4.0 Hz), 7.76 (d, 1H, J=8.0 Hz).

Compound Ij-106

[Formula 479]

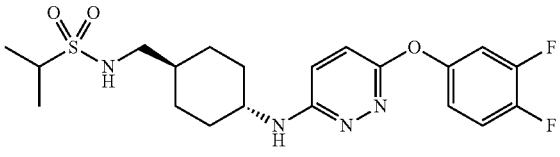

1H-NMR (DMSO-d6) δ: 0.88-1.02 (m, 2H), 1.07-1.20 (m, 2H), 1.21 (d, 6H, J=6.6 Hz), 1.33-1.45 (m, 1H), 1.76-1.85 (m, 2H), 2.02-2.08 (m, 2H), 2.76-2.83 (m, 2H), 3.10-3.20 (m, 1H), 3.57-3.67 (m, 1H), 6.63 (d, 1H, J=8.0 Hz), 6.92-7.00 (m, 3H), 7.13 (d, 1H, J=8.0 Hz), 7.29-7.36 (m, 1H), 7.42-7.50 (m, 1H).

Compound Ij-107

[Formula 480]

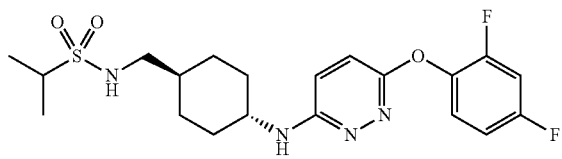

1H-NMR (DMSO-d6) δ: 0.88-1.02 (m, 2H), 1.07-1.20 (m, 2H), 1.21 (d, 6H, J=6.6 Hz), 1.33-1.43 (m, 1H), 1.75-1.83 (m, 2H), 1.98-2.06 (m, 2H), 2.76-2.83 (m, 2H), 3.08-3.18 (m, 1H), 3.52-3.63 (m, 1H), 6.57 (d, 1H, J=8.0 Hz), 6.93 (d, 1H, J=8.0 Hz), 6.97 (t, 1H, J=4.5 Hz), 7.12 (t, 1H, J=4.0 Hz), 7.19 (d, 1H, J=8.0 Hz), 7.33-7.47 (m, 2H).

Compound Ij-108

[Formula 481]

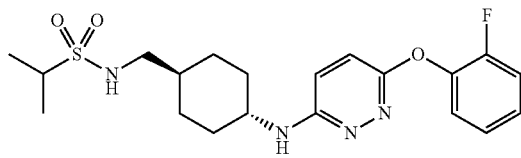

1H-NMR (DMSO-d6) δ: 0.88-1.02 (m, 2H), 1.07-1.20 (m, 2H), 1.21 (d, 6H, J=6.6 Hz), 1.33-1.43 (m, 1H), 1.75-1.83 (m, 2H), 1.98-2.07 (m, 2H), 2.76-2.83 (m, 2H), 3.08-3.18 (m, 1H), 3.54-3.63 (m, 1H), 6.63 (d, 1H, J=8.0 Hz), 6.93-7.00 (m, 2H), 7.14 (t, 1H, J=8.0 Hz), 7.20-7.37 (m, 3H).

Compound Ij-109

[Formula 482]

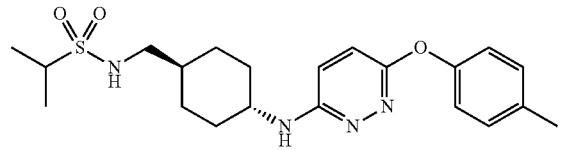

1H-NMR (DMSO-d6) δ: 0.82-1.05 (m, 2H), 1.05-1.20 (m, 2H), 1.21 (d, 6H, J=6.6 Hz), 1.32-1.43 (m, 1H), 1.76-1.83 (m, 2H), 2.00-2.08 (m, 2H), 2.29 (s, 3H), 2.76-2.83 (m, 2H), 3.08-3.18 (m, 1H), 3.56-3.66 (m, 1H), 6.55 (d, 1H, J=8.0 Hz), 6.90 (d, 1H, J=8.0 Hz), 6.93-7.00 (m, 3H), 7.05 (d, 1H, J=8.0 Hz), 7.17 (d, 2H, J=8.0 Hz).

Compound Ij-110

[Formula 483]

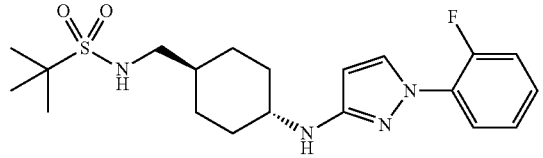

1H-NMR (DMSO-d6) δ: 0.91-1.19 (m, 4H), 1.28 (s, 9H), 1.32-1.43 (m, 1H), 1.80 (d, 2H, J=12.0 Hz), 2.07 (d, 2H, J=12.0 Hz), 2.88 (t, 2H, J=6.4 Hz), 3.16-3.27 (m, 1H), 5.47 (d, 1H, J=7.6 Hz), 5.80 (s, 1H), 6.83 (d, 1H, J=6.0 Hz), 7.15-7.40 (m, 3H), 7.75 (t, 1H, J=8.4 Hz), 7.86 (s, 1H).

Compound Ij-111

[Formula 484]

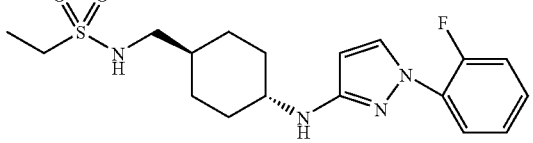

1H-NMR (DMSO-d6) δ: 0.91-1.19 (m, 4H), 1.21 (d, 6H, J=6.9 Hz), 1.32-1.43 (m, 1H), 1.76-1.82 (m, 2H), 2.02-2.12 (m, 2H), 2.77-2.83 (m, 2H), 3.08-3.27 (m, 2H), 5.48 (d, 1H, J=8.1 Hz), 5.80 (d, 1H, J=2.7 Hz), 6.95 (t, 1H, J=6.0 Hz), 7.15-7.39 (m, 3H), 7.75 (td, 1H, J=8.4, 1.8 Hz), 7.86 (t, 1H, J=2.7 Hz).

Compound Ij-112

[Formula 485]

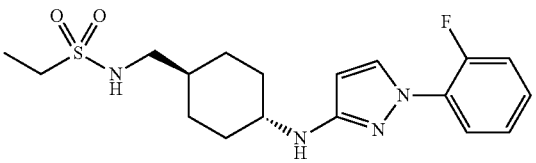

1H-NMR (DMSO-d6) δ: 0.91-1.19 (m, 4H), 1.18 (t, 3H, J=7.2 Hz), 1.30-1.45 (m, 1H), 1.76-1.82 (m, 2H), 2.02-2.12 (m, 2H), 2.77-2.83 (m, 2H), 2.98 (q, 2H, J=7.2 Hz) 3.10-3.30 (m, 1H), 5.48 (d, 1H, J=7.8 Hz), 5.80 (d, 1H, J=2.7 Hz), 6.99 (t, 1H, J=6.0 Hz), 7.15-7.40 (m, 3H), 7.75 (td, 1H, J=8.4, 1.8 Hz), 7.86 (t, 1H, J=2.7 Hz).

Compound Ij-113

[Formula 486]

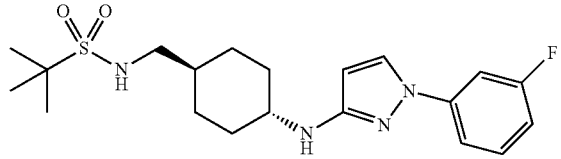

Compound Ij-114

[Formula 487]

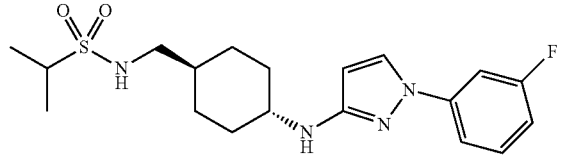

-continued

Compound Ij-115

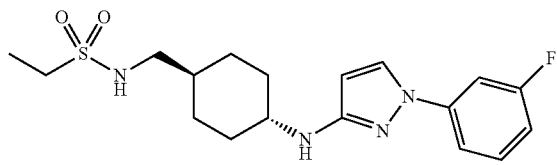

[Formula 488]

1H-NMR (DMSO-d6) δ: 0.92-1.19 (m, 4H), 1.19 (t, 3H, J=7.2 Hz), 1.30-1.45 (m, 1H), 1.76-1.84 (m, 2H), 2.02-2.12 (m, 2H), 2.74-2.82 (m, 2H), 2.98 (q, 2H, J=7.2 Hz) 3.15-3.30 (m, 1H), 5.53 (d, 1H, J=8.1 Hz), 5.80 (d, 1H, J=2.4 Hz), 6.92 (t, 1H, J=8.4 Hz), 7.01 (t, 1H, J=6.0 Hz), 7.37-7.43 (m, 3H), 8.21 (d, 1H, J=2.4 Hz).

Compound Ij-116

[Formula 489]

Compound Ij-117

[Formula 490]

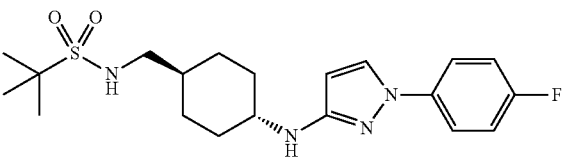

Compound Ij-118

[Formula 491]

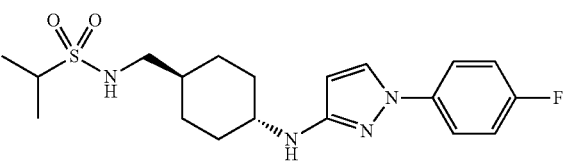

1H-NMR (DMSO-d6) δ: 0.92-1.19 (m, 4H), 1.19 (t, 3H, J=7.5 Hz), 1.30-1.45 (m, 1H), 1.75-1.86 (m, 2H), 2.02-2.12 (m, 2H), 2.74-2.83 (m, 2H), 2.97 (q, 2H, J=7.5 Hz) 3.13-3.30 (m, 1H), 5.38 (d, 1H, J=8.4 Hz), 5.75 (d, 1H, J=2.7 Hz), 6.99 (t, 1H, J=6.3 Hz), 7.18-7.28 (m, 2H), 7.63-7.70 (m, 2H), 8.11 (d, 1H, J=2.7 Hz).

Compound Ij-119

[Formula 492]

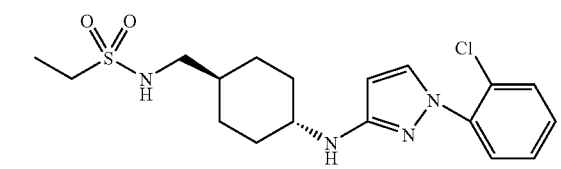

1H-NMR (DMSO-d6) δ: 0.88-1.19 (m, 4H), 1.18 (t, 3H, J=7.5 Hz), 1.28-1.45 (m, 1H), 1.73-1.83 (m, 2H), 2.02-2.13 (m, 2H), 2.73-2.81 (m, 2H), 2.95 (q, 2H, J=7.5 Hz) 3.12-3.30 (m, 1H), 5.36 (d, 1H, J=7.5 Hz), 5.76 (d, 1H, J=2.4 Hz), 6.98 (t, 1H, J=6.0 Hz), 7.30 (td, 1H, J=7.5, 1.8 Hz), 7.42 (td, 1H, J=7.8, 1.5 Hz), 7.53-7.60 (m, 2H), 7.84 (d, 1H, J=2.7 Hz).

Compound Ij-120

[Formula 493]

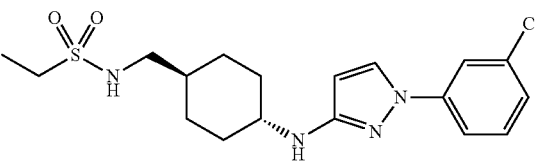

1H-NMR (DMSO-d6) δ: 0.92-1.19 (m, 4H), 1.19 (t, 3H, J=7.5 Hz), 1.30-1.45 (m, 1H), 1.74-1.84 (m, 2H), 2.02-2.10 (m, 2H), 2.75-2.82 (m, 2H), 2.97 (q, 2H, J=7.5 Hz) 3.20-3.30 (m, 1H), 5.52 (d, 1H, J=7.8 Hz), 5.80 (d, 1H, J=2.4 Hz), 6.99 (t, 1H, J=6.0 Hz), 7.13 (d, 1H, J=8.1 Hz), 7.40 (t, 1H, J=8.1 Hz), 7.62 (d, 1H, J=8.4 Hz), 7.72 (s, 1H), 8.22 (d, 1H, J=2.4 Hz).

Compound Ij-121

[Formula 494]

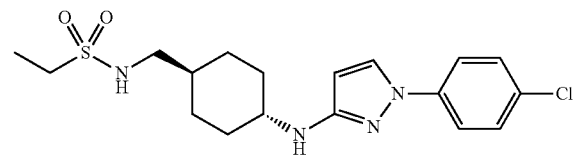

1H-NMR (DMSO-d6) δ: 0.92-1.19 (m, 4H), 1.19 (t, 3H, J=7.5 Hz), 1.30-1.45 (m, 1H), 1.74-1.84 (m, 2H), 2.02-2.12 (m, 2H), 2.75-2.82 (m, 2H), 2.98 (q, 2H, J=7.5 Hz) 3.15-3.30 (m, 1H), 5.47 (d, 1H, J=8.1 Hz), 5.78 (d, 1H, J=2.4 Hz), 7.00 (t, 1H, J=6.0 Hz), 7.43 (d, 2H, J=7.8 Hz), 7.67 (d, 2H, J=9.0 Hz), 8.17 (d, 1H, J=2.4 Hz).

Compound Ij-122

[Formula 495]

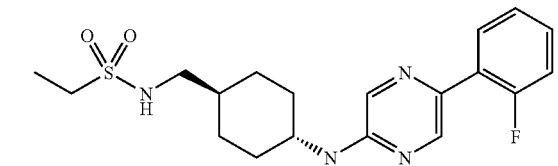

1H-NMR (DMSO-d6) δ: 0.94-1.07 (m, 4H), 1.19 (t, 3H, J=7.2 Hz), 1.32-1.50 (m, 1H), 1.81-1.84 (m, 2H), 1.99-2.07 (m, 2H), 2.77-2.81 (m, 2H), 2.98 (q, 2H, J=7.2 Hz), 3.60-3.77 (m, 1H), 7.01-7.05 (m, 1H), 7.22-7.40 (m, 4H), 7.81-7.87 (m, 1H), 8.02 (s, 1H), 8.36 (s, 1H).

Compound Ij-123

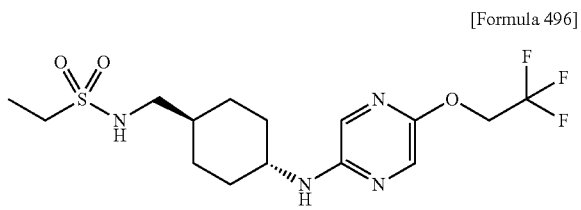

[Formula 496]

1H-NMR (DMSO-d6) δ: 0.95-1.12 (m, 4H), 1.18 (t, 3H, J=7.2 Hz), 1.32-1.50 (m, 1H), 1.77-1.81 (m, 2H), 1.96-1.99 (m, 2H), 2.74-2.78 (m, 2H), 2.97 (q, 2H, J=7.2 Hz), 3.54-3.70 (m, 1H), 4.81 (q, 2H, J=9.0 Hz), 6.50-6.53 (m, 1H), 6.99-7.03 (m, 1H), 7.50 (d, 1H, J=0.9 Hz) 7.83 (d, 1H, J=0.9 Hz).

Compound Ij-124

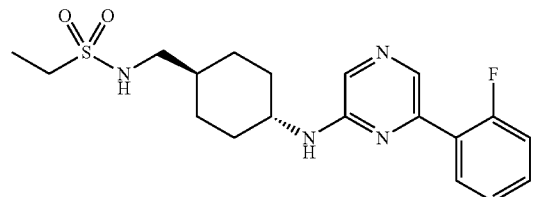

[Formula 497]

1H-NMR (DMSO-d6) δ: 0.95-1.23 (m, 4H), 1.19 (t, 3H, J=7.2 Hz), 1.32-1.50 (m, 1H), 1.77-1.81 (m, 2H), 2.03-2.07 (m, 2H), 2.74-2.80 (m, 2H), 2.97 (q, 2H, J=7.2 Hz), 3.61-3.73 (m, 1H), 7.00-7.04 (m, 1H), 7.09-7.12 (m, 1H), 7.29-7.37 (m, 2H), 7.45-7.52 (m, 1H), 7.88-7.94 (m, 2H), 8.04-8.05 (m, 1H).

Compound Ij-125

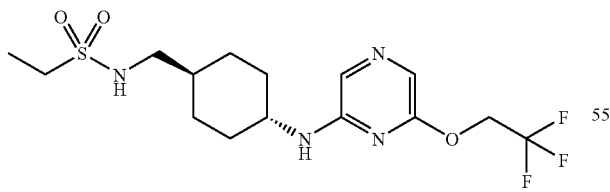

[Formula 498]

1H-NMR (DMSO-d6) δ: 0.94-1.14 (m, 4H), 1.19 (t, 3H, J=7.2 Hz), 1.32-1.50 (m, 1H), 1.79-1.83 (m, 2H), 1.97-2.03 (m, 2H), 2.76-2.81 (m, 2H), 2.98 (q, 2H, J=7.2 Hz), 3.50-3.63 (m, 1H), 4.43 (q, 2H, J=9.0 Hz), 7.00-7.04 (m, 1H), 7.13-7.15 (m, 1H), 7.35 (s, 1H) 7.55 (s, 1H).

Compound Ij-126

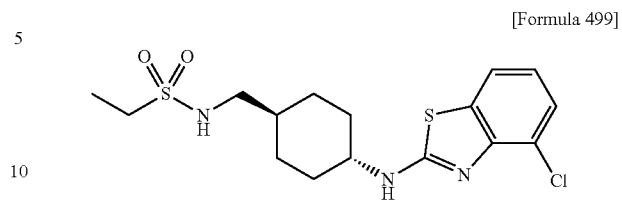

[Formula 499]

1H-NMR (DMSO-d6) δ: 1.02-1.08 (m, 2H), 1.17-1.29 (m, 2H), 1.19 (t, 3H, J=7.5 Hz), 1.36-1.43 (m, 1H), 1.79-1.85 (m, 2H), 2.05-2.11 (m, 2H), 2.79 (t, 2H, J=6.0 Hz), 2.99 (q, 2H, J=7.5 Hz), 3.53-3.62 (m, 1H), 6.98 (t, 1H, J=7.8 Hz), 7.03 (t, 1H, J=6.3 Hz), 7.28 (dd, 1H, J=7.5, 1.2 Hz), 7.63 (dd, 1H, J=7.5, 1.2 Hz), 8.28 (d, 1H, J=7.5 Hz).

Compound Ij-127

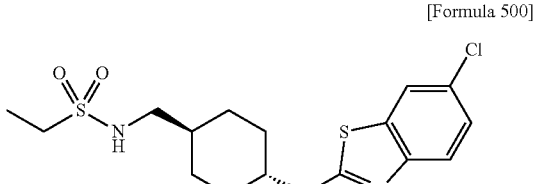

[Formula 500]

1H-NMR (DMSO-d6) δ: 0.97-1.05 (m, 2H), 1.18-1.24 (m, 2H), 1.16 (t, 3H, J=7.5 Hz), 1.34-1.41 (m, 1H), 1.77-1.81 (m, 2H), 2.02-2.08 (m, 2H), 2.76 (t, 2H, J=6.0 Hz), 2.96 (q, 2H, J=7.5 Hz), 3.55-3.64 (m, 1H), 7.00 (t, 1H, J=7.8 Hz), 7.18 (dd, 1H, J=8.4, 1.8 Hz), 7.32 (dd, 1H, J=8.4, 0.6 Hz), 7.74 (d, 1H, J=1.8 Hz), 8.04 (d, 1H, J=7.8 Hz).

Compound Ij-128

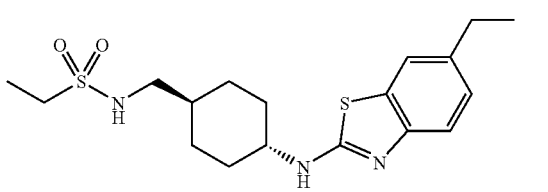

[Formula 501]

1H-NMR (DMSO-d6) δ: 0.98-1.07 (m, 2H), 1.15-1.26 (m, 8H), 1.32-1.43 (m, 1H), 1.78-1.84 (m, 2H), 1.98-2.09 (m, 2H), 2.60 (q, 2H, J=7.5 Hz), 2.78 (t, 2H, J=6.3 Hz), 2.96 (q, 2H, J=7.5 Hz), 3.55-3.64 (m, 1H), 6.98-7.05 (m, 2H), 7.27 (dd, 1H, J=7.8, 1.8 Hz), 7.47 (m, 1H), 7.84 (d, 1H, J=7.5 Hz).

Compound Ij-129

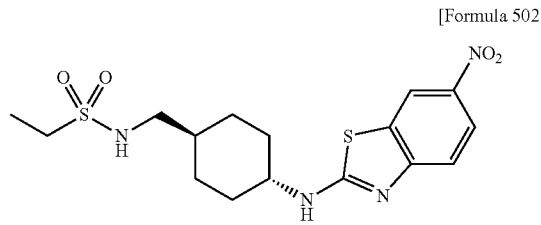

[Formula 502]

1H-NMR (DMSO-d6) δ: 0.92-1.15 (m, 2H), 1.15-1.35 (m, 2H), 1.19 (t, 3H, J=7.2 Hz), 1.33-1.48 (m, 1H), 1.78-1.88 (m, 2H), 2.04-2.16 (m, 2H), 2.78-2.84 (m, 2H), 2.97 (q, 2H, J=7.2 Hz), 3.62-3.80 (m, 1H), 7.02 (t, 1H, J=6.0 Hz), 7.45 (d, 1H, J=9.0 Hz), 8.09 (dd, 1H, J=9.0, 2.4 Hz), 8.68 (d, 1H, J=2.4 Hz), 8.70 (brs, 1H).

Compound Ij-130

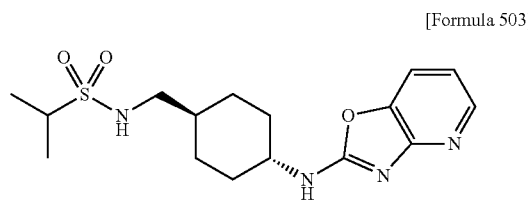

[Formula 503]

1H-NMR (DMSO-d6) δ: 0.88-1.10 (m, 2H), 1.15-1.46 (m, 3H), 1.21 (d, 6H, J=6.6 Hz), 1.78-1.88 (m, 2H), 1.98-2.08 (m, 2H), 2.76-2.86 (m, 2H), 3.10-3.20 (m, 1H), 3.46-3.62 (m, 1H), 6.91-6.96 (m, 1H), 7.01 (brs, 1H), 7.64 (d, 1H, J=7.8 Hz), 8.07 (d, 1H, J=5.1 Hz), 8.35 (d, 1H, J=7.8 Hz).

Compound Ij-131

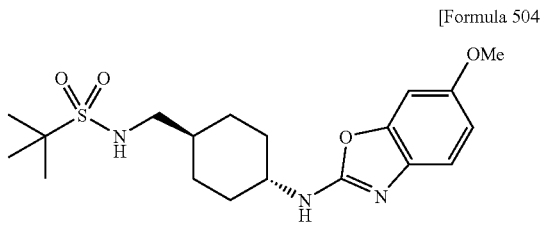

[Formula 504]

1H-NMR (DMSO-d6) δ: 0.92-1.05 (m, 2H), 1.15-1.30 (m, 2H), 1.27 (s, 9H), 1.30-1.43 (m, 1H), 1.77-1.86 (m, 2H), 1.98-2.08 (m, 2H), 2.86-2.92 (m, 2H), 3.35-3.50 (m, 1H), 3.73 (s, 3H), 6.69 (dd, 1H, J=8.4, 2.0 Hz), 6.86 (t, 1H, J=6.0 Hz), 7.01 (d, 1H, J=2.0 Hz), 7.10 (d, 1H, J=8.4 Hz), 7.62 (d, 1H, J=7.6 Hz).

Compound Ij-132

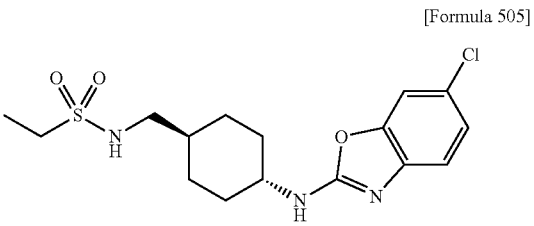

[Formula 505]

1H-NMR (DMSO-d6) δ: 0.92-1.08 (m, 2H), 1.15-1.33 (m, 2H), 1.19 (t, 3H, J=7.2 Hz), 1.33-1.42 (m, 1H), 1.76-1.86 (m, 2H), 1.98-2.08 (m, 2H), 2.76-2.82 (m, 2H), 2.97 (q, 2H, J=7.2 Hz), 3.40-3.58 (m, 1H), 7.01 (t, 1H, J=6.0 Hz), 7.13 (d, 1H, J=8.4 Hz), 7.20 (d, 1H, J=8.4 Hz), 7.49 (s, 1H), 8.01 (d, 1H, J=7.6 Hz).

Compound Ij-133

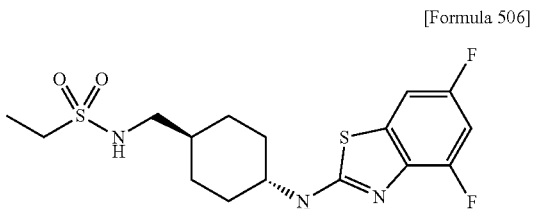

[Formula 506]

1H-NMR (DMSO-d6) δ: 0.96-1.10 (m, 2H), 1.16-1.28 (m, 2H), 1.19 (t, 3H, J=7.2 Hz), 1.33-1.46 (m, 1H), 1.78-1.85 (m, 2H), 2.04-2.12 (m, 2H), 2.76-2.82 (m, 2H), 2.98 (q, 2H, J=7.2 Hz), 3.55-3.70 (m, 1H), 7.01 (t, 1H, J=6.0 Hz), 7.12 (t, 1H, J=9.6 Hz), 7.48 (d, 1H, J=7.6 Hz), 8.13 (d, 1H, J=7.6 Hz).

Compound Ij-134

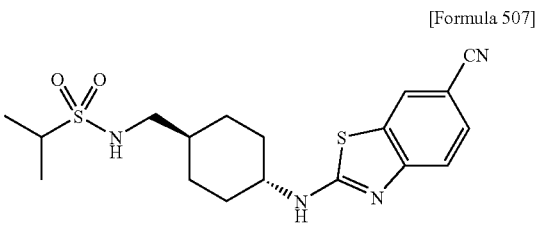

[Formula 507]

1H-NMR (DMSO-d6) δ: 0.98-1.08 (m, 2H), 1.15-1.26 (m, 2H), 1.21 (d, 6H, J=6.9 Hz), 1.33-1.42 (m, 1H), 1.39-1.84 (m, 2H), 2.05-2.09 (m, 2H), 2.81 (t, 2H, J=6.3 Hz), 3.10-3.20 (m, 1H), 3.61-3.75 (m, 1H), 6.98 (t, 1H, J=6.0 Hz), 7.45 (dd, 1H, J=7.5, 0.6 Hz), 7.60 (dd, 1H, J=8.4, 1.5 Hz), 8.17 (d, 1H, J=1.5 Hz), 8.50 (d, 1H, J=7.5 Hz).

Compound Ij-135

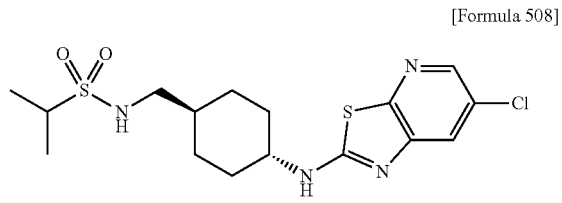
[Formula 508]

1H-NMR (DMSO-d6) δ: 0.98-1.08 (m, 2H), 1.15-1.25 (m, 2H), 1.21 (d, 6H, J=6.6 Hz), 1.35-1.44 (m, 1H), 1.80-1.84 (m, 2H), 2.05-2.08 (m, 2H), 2.81 (t, 2H, J=6.3 Hz), 3.10-3.19 (m, 1H), 3.62-3.78 (m, 1H), 6.98 (t, 1H, J=6.0 Hz), 7.79 (d, 1H, J=2.1 Hz), 8.10 (d, 1H, J=2.1, 1.5 Hz), 8.52 (d, 1H, J=6.9 Hz).

Compound Ij-136

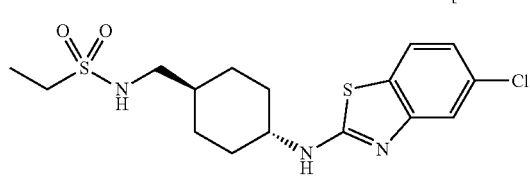
[Formula 509]

1H-NMR (DMSO-d6) δ: 0.97-1.08 (m, 2H), 1.17-1.24 (m, 2H), 1.19 (t, 3H, J=7.5 Hz), 1.33-1.41 (m, 1H), 1.78-1.83 (m, 2H), 2.04-2.08 (m, 2H), 2.78 (t, 2H, J=6.3 Hz), 2.98 (q, 2H, J=7.2 Hz), 3.56-3.67 (m, 1H), 7.00-7.04 (m, 2H), 7.39 (d, 1H, J=2.1 Hz), 7.66 (dd, 1H, J=8.4, 1.8 Hz), 8.14 (d, 1H, J=7.5 Hz).

Compound Ij-137

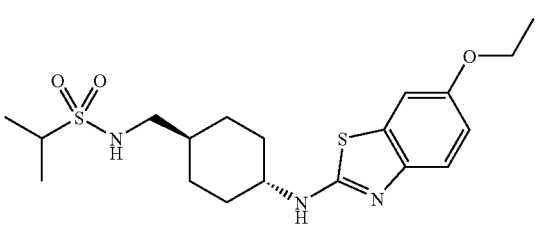
[Formula 510]

1H-NMR (DMSO-d6) δ: 0.96-1.10 (m, 2H), 1.12-1.28 (m, 2H), 1.21 (d, 6H, J=6.9 Hz), 1.31 (t, 3H, J=6.9 Hz), 1.33-1.46 (m, 1H), 1.76-1.85 (m, 2H), 2.02-2.16 (m, 2H), 2.78-2.84 (m, 2H), 3.10-3.22 (m, 1H), 3.50-3.64 (m, 1H), 3.98 (q, 2H, J=6.9 Hz), 6.78 (dd, 1H, J=8.7, 2.7 Hz), 6.98 (t, 1H, J=6.0 Hz), 7.23-7.27 (m, 2H), 7.68 (d, 1H, J=7.2 Hz).

Compound Ij-138

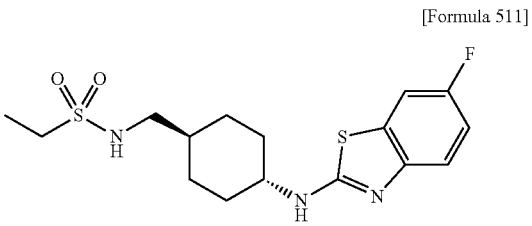
[Formula 511]

1H-NMR (DMSO-d6) δ: 0.94-1.08 (m, 2H), 1.14-1.26 (m, 2H), 1.19 (t, 3H, J=7.2 Hz), 1.33-1.45 (m, 1H), 1.77-1.86 (m, 2H), 2.03-2.12 (m, 2H), 2.76-2.82 (m, 2H), 2.98 (q, 2H, J=7.2 Hz), 3.52-3.68 (m, 1H), 6.97-7.06 (m, 2H), 7.34 (dd, 1H, J=8.4, 4.8 Hz), 7.56 (dd, 1H, J=8.4, 2.4 Hz), 7.91 (d, 1H, J=7.6 Hz).

Compound Ij-139

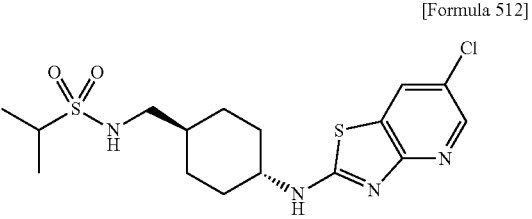
[Formula 512]

1H-NMR (DMSO-d6) δ: 0.96-1.12 (m, 2H), 1.16-1.32 (m, 2H), 1.21 (d, 6H, J=6.6 Hz), 1.32-1.46 (m, 1H), 1.78-1.86 (m, 2H), 2.02-2.16 (m, 2), 2.78-2.84 (m, 2H), 3.10-3.21 (m, 1H), 3.58-3.76 (m, 1H), 7.00 (t, 1H, J=6.0 Hz), 8.19-8.23 (m, 2H), 8.52 (d, 1H, J=6.9 Hz).

Compound Ij-140

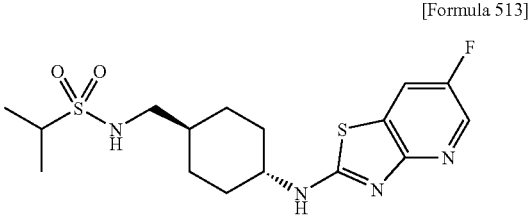
[Formula 513]

1H-NMR (DMSO-d6) δ: 0.96-1.12 (m, 2H), 1.12-1.30 (m, 2H), 1.21 (d, 6H, J=6.6 Hz), 1.32-1.46 (m, 1H), 1.78-1.86 (m, 2H), 2.02-2.16 (m, 2H), 2.78-2.84 (m, 2H), 3.10-3.20 (m, 1H), 3.58-3.78 (m, 1H), 7.01 (t, 1H, J=6.0 Hz), 8.08 (dd, 1H, J=8.4, 2.7 Hz), 8.19 (d, 1H, J=2.7 Hz), 8.38 (d, 1H, J=7.2 Hz).

Compound Ij-141

[Formula 514]

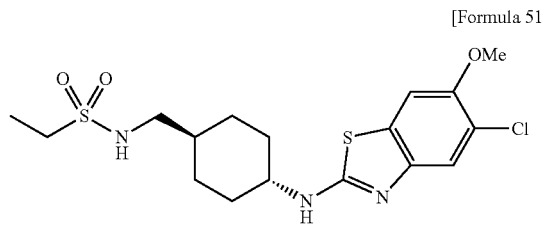

1H-NMR (DMSO-d6) δ: 0.97-1.08 (m, 2H), 1.15-1.22 (m, 5H), 1.34-1.42 (m, 1H), 1.78-1.83 (m, 2H), 2.04-2.08 (m, 2H), 2.78 (t, 2H, J=6.0 Hz), 2.98 (q, 2H, J=7.2 Hz), 3.53-3.62 (m, 1H), 3.81 (s, 1H), 7.02 (t, 1H, J=6.3 Hz), 7.41 (s, 1H), 7.53 (s, 1H), 7.88 (d, 1H, J=7.5 Hz).

Compound Ij-142

[Formula 515]

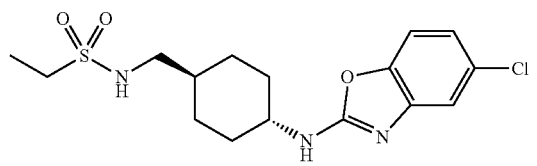

1H-NMR (DMSO-d6) δ: 0.94-1.06 (m, 2H), 1.17-1.30 (m, 2H), 1.18 (t, 3H, J=7.5 Hz), 1.32-1.41 (m, 1H), 1.79-1.84 (m, 2H), 2.01-2.05 (m, 2H), 2.77 (t, 2H, J=6.0 Hz), 2.98 (q, 2H, J=7.2 Hz), 3.41-3.58 (m, 1H), 6.97 (dd, 1H, J=8.4, 2.4 Hz), 6.99-7.03 (m, 1H), 7.27 (d, 1H, J=2.4 Hz), 7.34 (dd, 1H, J=8.4, 0.3 Hz), 8.07-8.14 (m, 1H).

Compound Ij-143

[Formula 516]

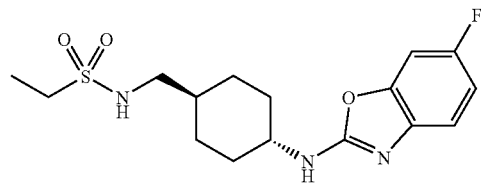

1H-NMR (DMSO-d6) δ: 0.94-1.08 (m, 2H), 1.16-1.33 (m, 2H), 1.19 (t, 3H, J=7.2 Hz), 1.33-1.45 (m, 1H), 1.77-1.86 (m, 2H), 2.00-2.08 (m, 2H), 2.74-2.82 (m, 2H), 2.98 (q, 2H, J=7.2 Hz), 3.38-3.54 (m, 1H), 6.90-7.00 (m, 1H), 7.02 (t, 1H, J=4.5 Hz), 7.19 (dd, 1H, J=8.4, 5.1 Hz), 7.33 (dd, 1H, J=8.4, 2.7 Hz), 7.88 (d, 1H, J=7.8 Hz).

Compound Ij-144

[Formula 517]

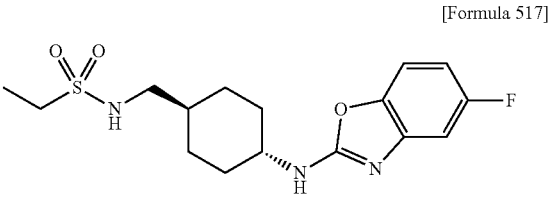

1H-NMR (DMSO-d6) δ: 0.94-1.06 (m, 2H), 1.19-1.29 (m, 2H), 1.18 (t, 3H, J=7.2 Hz), 1.31-1.41 (m, 1H), 1.79-1.84 (m, 2H), 2.01-2.05 (m, 2H), 2.77 (t, 2H, J=6.0 Hz), 2.98 (q, 2H, J=6.9 Hz), 3.41-3.57 (m, 1H), 6.71-6.79 (m, 1H), 7.06-7.08 (m, 2H), 7.31 (dd, 1H, J=8.7, 4.8 Hz), 8.03 (d, 1H, J=7.8 Hz).

Compound Ij-145

[Formula 518]

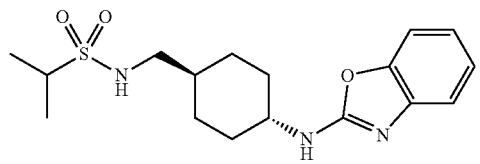

1H-NMR (DMSO-d6) δ: 0.95-1.16 (m, 2H), 1.18-1.44 (m, 3H), 1.21 (d, 6H, J=6.6 Hz), 1.78-1.86 (m, 2H), 2.02-2.12 (m, 2H), 2.78-2.84 (m, 2H), 3.10-3.20 (m, 1H), 3.40-3.58 (m, 1H), 6.95 (t, 1H, J=7.8 Hz), 7.01 (brs, 1H), 7.09 (t, 1H, J=6.9 Hz), 7.22 (d, 1H, J=6.6 Hz), 7.31 (d, 1H, J=7.8 Hz), 7.83 (d, 1H, J=7.8 Hz).

Compound Ij-146

[Formula 519]

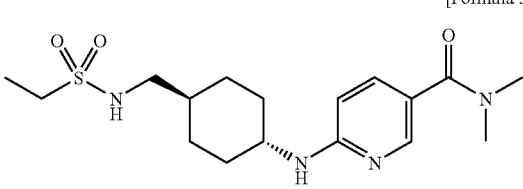

Compound Ij-147

[Formula 520]

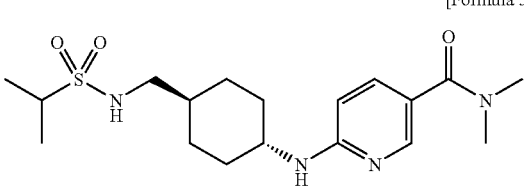

Compound Ij-148

{Formula 521]

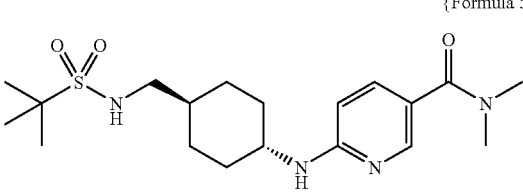

Experiment 1 Transportability Through the Blood-brain Barrier and Potential for Drug-drug Interactions Through P-gp Transportability of the compounds of the present invention through the blood-brain barrier (blood-brain partition coefficient; Kp) in mice (Jcl; C57BL/6J mice, ♂, 7 weeks) was defined from the difference in concentration of the compounds between in plasma and in brain after intravenous administration of the compounds (0.5 mg/2 mL/kg). The brain Kp value of Compound (I-72) ($Kp_{Cont.}$) was 1.29 showing high transportability through the blood-brain barrier.

To examine the potential for drug-drug interactions through P-gp in vivo, the Kp values of compounds of the present invention with ($Kp_{CSA}$) or without ($Kp_{Cont.}$) cyclosporin A (20 mg/kg), a P-gp inhibitor, were calculated. The $Kp_{CSA}$ value of Compound (I-72) was 1.14, and the calculated $Kp_{CSA}/Kp_{Cont.}$ ratio was 0.9. The result indicate that Compound (I-72) has no significant potential for drug-drug interactions through P-gp in mice.

On the other hand the potential for drug-drug interactions through P-gp of amide compound B which has similar structure of Compound (I-72) was also examined in mice. The $Kp_{Cont.}$ and $Kp_{CSA}$ were 0.04 and 0.84, respectively. The $Kp_{CSA}/Kp_{Cont.}$ ratio was more than 1.0 (i.e. 20.5), indicating that the compound is effectively excreted through P-gp from the brain to vessels, and that significant drug-drug interactions through P-gp could be induced in mice.

Compound B

[Formula 522]

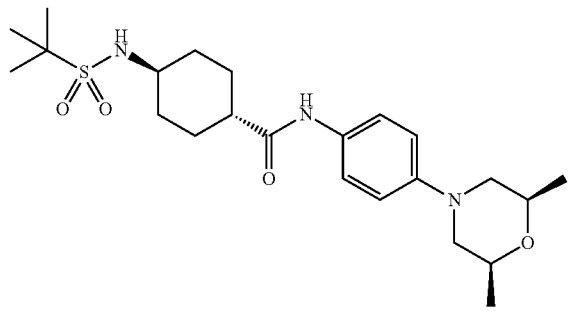

Experiment 3 Inhibitory Effect on cAMP Production in CHO Cells

CHO cells expressing human NPY Y5 receptor were incubated in the presence of 2.5 mM isobutylmethylxanthine (SIGMA) at 37° C. for 20 min. After the incubation the compound of the present invention was added, and then the mixture was incubated for 5 min. Next, 50 nM NPY and 10 µM forskolin (SIGMA) were added, and the mixture was incubated for 30 min. After termination of the reaction by adding 1N HCl, the amount of cAMP in the supernatant was determined with an EIA kit (Amersham LIFE SCIENCE). The inhibitory activity of NPY against forskolin stimulated cAMP production was expressed as 100% and the 50% inhibitory concentration ($IC_{50}$ value) of the compound of the present invention against the NPY activity was calculated.

Experiment 4

Using the membranes prepared from Y1-expression cells (human neuroblastoma, SK-N-MC) and the membranes prepared from Y2-expression cells (human neuroblastoma, SMS-KAN), the experiment was carried out in a similar way as Experiment 2 to determine the affinity of the compounds for NPY Y1 and NPY Y2 receptor. The results showed that the compounds of the present invention had no significant affinity for their receptors, indicating high selectivity for NPY Y5 receptor.

Experiment 5

Under diethylether anesthesia the skull of male C57BL/6J mice (12-14 week old, 25-30 g) was exposed by making an incision about 1-cm long from external occipital crest to nasal dorsum, and drilled in the 1-mm lateral position to the left following 1-mm posterior from bregma. After recovery from anesthesia mice were dosed with either 0.5% hydroxypropylmethyl cellulose solution (Shin-Etsu Chemical Co., Ltd) or the compounds of the present invention suspended in the 0.5% hydroxypropylmethyl cellulose solution. At one hour after the treatment, each animal received a NPY Y5 receptor specific agonist, [$cPP^{1-7}$, $NPY^{19-23}$, $Ala^{31}$, $Aib^{32}$, $Gln^{34}$]-hPancreatic Polypeptide (0.1 nmol/1.5 µL/mouse) through the skull opening using a canula. Residual food was measured at 2 and 4 hours after the treatment, and the difference in food intake between the compounds-treated mice and 0.5% hydroxypropylmethyl cellulose solution-treated mice was calculated. The compound at 6 mg/kg caused a significant reduction in food intake of mice compared to the treatment with 0.5% hydroxymethylpropylmethyl cellulose solution.

FORMULATION EXAMPLE

The following Formulation Examples are only exemplified and not intended to limit the scope of the present invention.

Formulation Example 1

Tablets

| | |
|---|---|
| Compound (I-1) | 15 mg |
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

All of the above ingredients except for calcium stearate are uniformly mixed. Then the mixture was crushed, granulated and dried to obtain a suitable size of granules. Next, calcium stearate was added to the granules. Finally, tableting was performed under a compression force.

Formulation Example 2

Capsules

| | |
|---|---|
| Compound (I-2) | 10 mg |
| Magnesium stearate | 10 mg |
| Lactose | 80 mg |

The above ingredients were mixed uniformly to obtain powders or fine granules, and then the obtained mixture was filled in capsules.

Formulation Example 3

Granules

| | |
|---|---|
| Compound (I-3) | 30 g |
| Lactose | 265 g |
| Magnesium Stearate | 5 g |

After the above ingredients are mixed uniformly, the mixture was compressed. The compressed matters were crushed, granulated and sieved to obtain suitable size of granules.

Industrial Applicability

As shown in the above Experiments, the compounds of the present invention have a NPY Y5 receptor antagonistic activity. Therefore, the compounds of the present invention are very useful as an anti-obesity and anorectic agent.

The invention claimed is:

1. A compound of formula (I):

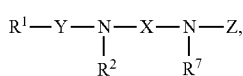

wherein
$R^1$ is optionally substituted lower alkyl,
Y is $-S(O)_2-$,
$R^2$ is hydrogen or optionally substituted lower alkyl,
$R^7$ is hydrogen or optionally substituted lower alkyl,
X is a group of formula:

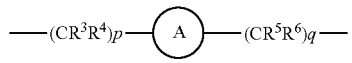

wherein each of $R^5$ and $R^6$ is hydrogen, a group of formula:

is optionally substituted C6 cycloalkylene, p is 0, and q is 1 or 2,

Z is optionally substituted carbocyclyl or optionally substituted heterocyclyl, and the optionally substituted heterocyclyl has heterocyclyl selected from the group consisting of pyrrolyl, imidazolyl, pyrazolyl, triazolyl, triazinyl, tetrazolyl, isoxazolyl, oxazolyl, oxadiazolyl, isothiazolyl, thiadiazolyl, furyl, thienyl, indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazoropyridyl, imidazothiazolyl, pyrazinopyridazinyl, tetrahydroquinolyl, tetrahydrobenzothienyl, oxazolopyridyl, thiazolopyridyl, benzoxazolinonyl, benzisoxazolinonyl, benzoxazinonyl, benzoxyazepinonyl, oxazolopyridinonyl, benzodioxolyl, dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, tetrahydrofuryl, tetrahydropyranyl, tetrahydrothiazolyl and tetrahydroisothiazolyl, or a pharmaceutically acceptable salt thereof.

2. The compound according to claim 1, wherein Z is optionally substituted phenyl, optionally substituted indanyl, optionally substituted pyrazolyl, optionally substituted isoxazolyl, optionally substituted oxadiazolyl or optionally substituted fused heterocycle consisting of two rings.

3. The compound according to claim 1, wherein Z is optionally substituted quinolyl, optionally substituted benzothiazolyl, optionally substituted benzoxazolyl, optionally substituted isoquinolyl, optionally substituted benzopyridazinyl, optionally substituted benzimidazolyl, optionally substituted thiazolopyridyl, optionally substituted benzisoxazolinonyl, optionally substituted benzoxazolinonyl, optionally substituted benzoxazinonyl or optionally substituted benzoxyazepinonyl.

4. A pharmaceutical composition comprising the compound according to claim 1 as an active ingredient.

5. A pharmaceutical composition comprising the compound according to claim 2 as an active ingredient.

6. A pharmaceutical composition comprising the compound according to claim 3 as an active ingredient.

7. The pharmaceutically acceptable salt according to claim 1, wherein Z is optionally substituted phenyl, optionally substituted indanyl, optionally substituted pyrazolyl, optionally substituted isoxazolyl, optionally substituted oxadiazolyl or optionally substituted fused heterocycle consisting of two rings.

8. The pharmaceutically acceptable salt according to claim 1, wherein Z is optionally substituted quinolyl, optionally substituted benzothiazolyl, optionally substituted benzoxazolyl, optionally substituted isoquinolyl, optionally substituted benzopyridazinyl, optionally substituted benzimidazolyl, optionally substituted thiazolopyridyl, optionally substituted benzisoxazolinonyl, optionally substituted benzoxazolinonyl, optionally substituted benzoxazinonyl or optionally substituted benzoxyazepinonyl.

9. A pharmaceutical composition comprising the pharmaceutically acceptable salt according to claim 1 as an active ingredient.

10. A pharmaceutical composition comprising the pharmaceutically acceptable salt according to claim 7 as an active ingredient.

11. A pharmaceutical composition comprising the pharmaceutically acceptable salt according to claim 8 as an active ingredient.

12. The compound according to claim 1, wherein in the formula (I), the group of formula:

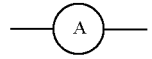

is optionally substituted 1,4-cyclohexanediyl,
or a pharmaceutically acceptable salt thereof.

* * * * *